US010414727B2

(12) United States Patent
O'Neill et al.

(10) Patent No.: US 10,414,727 B2
(45) Date of Patent: Sep. 17, 2019

(54) PHENYL AMINO PIPERIDINE MTORC INHIBITORS AND USES THEREOF

(71) Applicant: Navitor Pharmaceuticals, Inc., Cambridge, MA (US)

(72) Inventors: David John O'Neill, Arlington, MA (US); Eddine Saiah, Brookline, MA (US); Seong Woo Anthony Kang, Somerville, MA (US); Andrew Brearley, Abingdon (GB); Jonathan Bentley, Abingdon (GB)

(73) Assignee: Navitor Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/807,293

(22) Filed: Nov. 8, 2017

(65) Prior Publication Data

US 2018/0127370 A1    May 10, 2018

Related U.S. Application Data

(60) Provisional application No. 62/419,008, filed on Nov. 8, 2016.

(51) Int. Cl.
| | | |
|---|---|---|
| *A61P 11/00* | (2006.01) | |
| *C07D 205/04* | (2006.01) | |
| *C07D 207/14* | (2006.01) | |
| *C07D 209/52* | (2006.01) | |
| *C07D 211/58* | (2006.01) | |
| *C07D 223/12* | (2006.01) | |
| *C07D 401/12* | (2006.01) | |
| *C07D 401/14* | (2006.01) | |
| *C07D 413/14* | (2006.01) | |
| *C07D 471/04* | (2006.01) | |

(52) U.S. Cl.
CPC ............ *C07D 211/58* (2013.01); *A61P 11/00* (2018.01); *C07D 205/04* (2013.01); *C07D 207/14* (2013.01); *C07D 209/52* (2013.01); *C07D 223/12* (2013.01); *C07D 401/12* (2013.01); *C07D 401/14* (2013.01); *C07D 413/14* (2013.01); *C07D 471/04* (2013.01)

(58) Field of Classification Search
CPC .. C07D 211/58; C07D 205/04; C07D 207/14; C07D 209/52; C07D 223/12; C07D 401/12; C07D 401/14; C07D 413/14; C07D 471/04; A61P 11/00
USPC ...................................................... 514/210.2
See application file for complete search history.

(56) References Cited

U.S. PATENT DOCUMENTS

| | | | |
|---|---|---|---|
| 5,639,600 A | 6/1997 | McGrath et al. | |
| 6,552,065 B2 | 4/2003 | Remiszewski et al. | |
| 7,087,648 B1 | 8/2006 | McGrath | |
| 7,390,799 B2 | 6/2008 | Bruncko et al. | |
| 8,138,347 B2 | 3/2012 | Knight et al. | |
| 2010/0273764 A1 | 10/2010 | Andrews et al. | |
| 2011/0183998 A1 | 7/2011 | Zoller et al. | |
| 2013/0210831 A1* | 8/2013 | Su ................... | C07D 487/04 514/252.02 |
| 2015/0087673 A1* | 3/2015 | Hitoshi ............. | A61K 31/4427 514/316 |
| 2015/0296787 A1* | 10/2015 | Gauvry ............. | C07D 403/12 514/210.2 |
| 2015/0362483 A1 | 12/2015 | Blackman et al. | |
| 2016/0251335 A1* | 9/2016 | Gauvry ............. | C07D 401/14 514/210.2 |

FOREIGN PATENT DOCUMENTS

| | | | | |
|---|---|---|---|---|
| WO | 2001042246 | 6/2001 | | |
| WO | 2002088112 | 11/2002 | | |
| WO | 2003063794 | 8/2003 | | |
| WO | 2004019973 | 3/2004 | | |
| WO | 2004089925 | 10/2004 | | |
| WO | 2004106328 | 12/2004 | | |
| WO | 2005007623 | 1/2005 | | |
| WO | 2005113554 | 12/2005 | | |
| WO | 2006078846 | 7/2006 | | |
| WO | 2006122806 | 11/2006 | | |
| WO | 2007016176 | 2/2007 | | |
| WO | 2007044729 | 4/2007 | | |
| WO | 2007053452 | 5/2007 | | |
| WO | 2007070514 | 6/2007 | | |
| WO | 2007084786 | 7/2007 | | |
| WO | 2007129161 | 11/2007 | | |
| WO | 2008039218 | 4/2008 | | |
| WO | 2008109943 | 9/2008 | | |
| WO | 2008118802 | 10/2008 | | |
| WO | 2009114512 | 9/2009 | | |
| WO | 2011090760 | 7/2011 | | |
| WO | WO-2018089433 A1 * | 5/2018 | ........... | C07D 213/81 |
| WO | WO-2018089499 A1 * | 5/2018 | | |

OTHER PUBLICATIONS

Nishimura; J. Med. Chem., 2011, 54 (13), pp. 4735-4751. (Year: 2011).*
Chemical Abstracts, STN Registry Database, records for: RN 1955481-65-8, RN 1954998-46-9, RN 1952608-74-0, RN 1952605-87-6, RN 1946928-95-5, RN 1946909-02-9 and RN 1946485-62-6; entered into the database Jul. 6, 2016 through Jul. 19, 2016. (Year: 2016).*
Zheng Mol Cell Pharmacol. 2015, 7(2), 15-20. (Year: 2015).*
Written Opinion of the International Searching Authority, Application PCT/US2017/060647, dated Feb. 6, 2018. (Year: 2018).*
Chemical Abstracts STN Registry Database, record for RN 773151-41-0, Entered into STN on Nov. 1, 2004. (Year: 2004).*
Awad et al., "Altered TFEB-mediated lysosomal biogenesis in Gaucher disease iPSC-derived neuronal cells," Human Molecular Genetics, vol. 24, No. 20, Oct. 2015 (pp. 5775-5788).

(Continued)

*Primary Examiner* — Daniel R Carcanague
(74) *Attorney, Agent, or Firm* — Andrea L. C. Reid; Dechert LLP

(57) ABSTRACT

The present invention provides compounds, compositions thereof, and methods of using the same.

17 Claims, No Drawings

(56) References Cited

OTHER PUBLICATIONS

Bonne et al., "Emery—Dreifuss muscular dystrophy, laminopathies, and other nuclear envelopathies," Handbook of Clinical Neurology, vol. 113, No Month Listed 2013 (pp. 1367-1376).
Chen et al., "Rapamycin ameliorates kidney fibrosis by inhibiting the activation of mTOR signaling in interstitial macrophages and myofibroblasts," PLoS One, vol. 7, No. 3, Mar. 2012 (14 pages).
Choo et al., "Rapamycin differentially inhibits S6Ks and 4E-BP1 to mediate cell-type-specific repression of mRNA translation," Proceedings of the National Academy of Sciences, USA, vol. 105, No. 45, Nov. 2008 (pp. 17414-17419).
Cortes et al., "Polyglutamine-expanded androgen receptor interferes with TFEB to elicit autophagy defects in SBMA," Nature Neuroscience, vol. 17, No. 9, Sep. 2014 (pp. 1180-1189).
Decressac et al., "TFEB-mediated autophagy rescues midbrain dopamine neurons from α-synuclein toxicity," Proceedings of the National Academy of Sciences, USA, vol. 110, No. 19, May 2013 (pp. E1817-1826).
Feldman et al., "Active-Site Inhibitors of mTOR Target Rapamycin-Resistant Outputs of mTORC1 and mTORC2," PLoS One, vol. 7, No. 2, Feb. 2009 (13 pages).
Fok et al., "Combined treatment of rapamycin and dietary restriction has a larger effect on the transcriptome and metabolome of liver," Aging Cell, vol. 13, No. 2, Apr. 2014 (pp. 311-319).
Franz et al., "Molecular Therapies for Tuberous Sclerosis and Neurofibromatosis," Current Neurology and Neuroscience Reports, vol. 12, No. 3, Jun. 2012 (pp. 294-301).
Garcia-Martinez et al., "Ku-0063794 is a specific inhibitor of the mammalian target of rapamycin (mTOR)," Biochemical Journal, vol. 421, No. 1, Jun. 2009 (pp. 29-42).
Gould et al., "The glucose transporter family: structure, function and tissue-specific expression," The Biochemical Journal, vol. 295, Oct. 1993 (pp. 329-341).
Howell et al., "A growing role for mTOR in promoting anabolic metabolism," Biochemical Society Transactions, vol. 41, No. 4, Aug. 2013 (pp. 906-912).
Hua et al., "Rapamycin inhibition of eosinophil differentiation attenuates allergic airway inflammation in mice," Respirology, vol. 20, No. 7, Oct. 2015 (pp. 1055-1065).
Ilagen et al., "Emerging role of mTOR in the response to cancer therapeutics," Trends Cancer, vol. 2, No. 5, May 2016 (pp. 241-251).
Jacinto et al., "Mammalian TOR complex 2 controls the actin cytoskeleton and is rapamycin insensitive," Nature Cell Biology, vol. 6, No. 11, Nov. 2004 (pp. 1122-1128).
Jiang et al., "Rheb/mTORC1 Signaling Promotes Kidney Fibroblast Activation and Fibrosis," Journal of the American Society of Nephrology, vol. 24, No. 7, Jul. 2013 (pp. 1114-1126).
Johnson et al., "MTOR inhibition alleviates mitochondrial disease in a mouse model of Leigh syndrome," Science, vol. 342, No. 6165, 2013 (pp. 1524-1528).
Kaeberlin, "mTOR Inhibition: From Aging to Autism and Beyond," Scientifica, vol. 2013, Oct. 2013 (17 pages).
Kim et al., "Nutrient Regulation of the mTOR Complex 1 Signaling Pathway," Molecules and Cells, vol. 35, No. 6, Jun. 2013 (pp. 463-473).
Laberge et al., "MTOR regulates the pro-tumorigenic senescence-associated secretory phenotype by promoting IL1A translation," Nature Cell Biology, vol. 17, No. 8, Aug. 2015 (pp. 1049-1061).
Lamming et al., "Rapamycin-induced insulin resistance is mediated by mTORC2 loss and uncoupled from longevity," Science, vol. 335, Mar. 2012 (pp. 1638-1643).
Laplante et al., "mTOR signaling in growth control and disease," Cell, vol. 149, No. 2, Apr. 2012 (pp. 274-293).
Laval et al., "Metabolic adaptation of neutrophils in cystic fibrosis airways involves distinct shifts in nutrient transporter axpression," Journal of Immunology, vol. 190, No. 12, Jun. 2013 (pp. 6043-6050).

Liu et al., "Characterization of Torin2, an ATP-competitive inhibitor of mTOR, ATM, and ATR," Cancer Research, vol. 13, No. 8, Apr. 2013 (pp. 2574-2586).
Liu et al., "Kinome-wide Selectivity Profiling of ATP-competitive Mammalian Target of Rapamycin (mTOR) Inhibitors and Characterization of Their Binding Kinetics," Journal of Biological Chemistry, vol. 287, No. 13, Mar. 2012 (pp. 9742-9752).
Liu et al., "Rapamycin reduces renal hypoxia, interstitial inflammation and fibrosis in a rat model of unilateral ureteral obstruction," Clinical and Investigative Medicine, vol. 37, No. 3, Jun. 2014 (pp. E142-E153).
Medina et al., "Transcriptional Activation of Lysosomal Exocytosis Promotes Cellular Clearance," Developmental Cell, vol. 21, No. 3, Sep. 2011 (pp. 421-430).
Mercer et al., "Exploration of a potent PI3 kinase/mTOR inhibitor as a novel anti-fibrotic agent in IPF," Thorax, vol. 71, No. 8, Aug. 2016 (pp. 701-711).
Mitra et al., "Dual mTOR Inhibition Is Required to Prevent TGF-β-Mediated Fibrosis: Implications for Scleroderma," Journal of Investigative Dermatology, vol. 135, No. 11, Nov. 2015 (pp. 2873-2876).
Nacarelli et al., "Mitochondrial stress induces cellular senescence in an mTORC1-dependent manner," Free Radical Biology and Medicine, vol. 95, Jun. 2016 (pp. 133-154).
Pastore et al, "Gene transfer of master autophagy regulator TFEB results in clearance of toxic protein and correction of hepatic disease in alpha-1-anti-trypsin deficiency," EMBO Molecular Medicine, vol. 5, No. 3, Mar. 2013 (pp. 397-412).
Patel et al., "Autophagy in Idiopathic Pulmonary Fibrosis," PLoS One, vol. 7, No. 7, Jul. 2012 (9 pages).
Polito et al., "Selective clearance of aberrant tau proteins and rescue of neurotoxicity by transcription factor EB," EMBO Molecular Medicine, vol. 6, No. 9, Sep. 2014 (pp. 1142-1160).
Puri et al., "Autophagy modulation as a potential therapeutic target for liver diseases," Journal of Clinical and Experimental Hepatology, vol. 4, No. 1, Mar. 2014 (pp. 51-59).
Ramos et al., "Rapamycin Reverses Elevated mTORC1 Signaling in Lamin A/C—Deficient Mice, Rescues Cardiac and Skeletal Muscle Function, and Extends Survival," Science Translational Medicine, vol. 4, No. 144, Jul. 2012 (11 pages).
Sarbassov et al., "Prolonged rapamycin treatment inhibits mTORC2 assembly and AKT/PKB," Molecular Cell, vol. 22, No. 2, Apr. 2006 (pp. 159-168).
Sarbassov et al., "Rictor, a novel binding partner of mTOR, defines a rapamycin-insensitive and raptor-independent pathway that regulates the cytoskeleton," Current Biology, vol. 14, No. 14, Jul. 2004 (pp. 1296-1302).
Sardiello, "Transcription factor EB: from master coordinator of lysosomal pathways to candidate therapeutic target in degenerative storage diseases," Annals of the New York Academy of Sciences, vol. 1371, No. 1, 2016 (pp. 3-14).
Shum et al., "Pharmacological inhibition of S6K1 increases glucose metabolism and Akt signalling in vitro and in diet-induced obese mice," Diabetologia, vol. 59, No. 3, Mar. 2016 (pp. 592-603).
Spampanato et al., "Transcription factor EB (TFEB) is a new therapeutic target for Pompe disease," EMBO Molecular Medicine, vol. 5, No. 5, May 2013 (pp. 691-706).
Syed et al., "Keloid disease can be inhibited by antagonizing excessive mTOR signaling with a novel dual TORC1/2 inhibitor," The American Journal of Pathology, vol. 181, No. 5, Nov. 2012 (pp. 1642-1658).
Taveira-DaSilva et al., "Clinical features, epidemiology, and therapy of lymphangioleiomyomatosis," Journal of Clinical Epidemiology, vol. 7, Apr. 2015 (pp. 249-257).
Thoreen et al., "An ATP-competitive mammalian target of rapamycin inhibitor reveals rapamycin-resistant functions of rnTORC1," Journal of Biological Chemistry, vol. 284, No. 12, Mar. 2009 (pp. 8023-8032).
Tsunemi et al., "PGC-1a rescues Huntington's disease proteotoxicity by preventing oxidative stress and promoting TFEB function," Science Translational Medicine, vol. 4, No. 142, Jul. 2012 (28 pages).

(56) References Cited

OTHER PUBLICATIONS

Varin et al., "Dual mTORC1/2 inhibition induces anti-proliferative effect in NF1-associated plexiform neurofibroma and malignant peripheral nerve sheath tumor cells," Oncotarget, vol. 7, No. 24, Jan. 2016 (pp. 35753-35767).

Wander et al., "Next-generation mTOR inhibitors in clinical oncology: how pathway complexity informs therapeutic strategy," The Journal of Clinical Investigation, vol. 121, Apr. 2011 (pp. 1231-1241).

Wu et al., "Rapamycin attenuates unilateral ureteral obstruction-induced renal fibrosis," Kidney International, vol. 69, No. 11, Jun. 2006 (pp. 2029-2036).

Yano et al., "Clinical impact of myocardial mTORC1 activation in nonischemic dilated cardiomyopathy," Journal of Molecular and Cellular Cardiology, vol. 91, Feb. 2016 (pp. 6-9).

Yu et al., "Rapamycin and Dietary Restriction Induce Metabolically Distinctive Changes in Mouse Liver," Journals of Gerontolology: Biological Sciences, vol. 70, No. 4, Apr. 2015 (pp. 410-420).

International Search Report and Written Opinion issued by the United States Patent and Trademark Office as International Searching Authority for International Application No. PCT/US2017/060647, dated Feb. 16, 2018 (11 pages).

\* cited by examiner

PHENYL AMINO PIPERIDINE MTORC INHIBITORS AND USES THEREOF

TECHNICAL FIELD OF THE INVENTION

The present invention relates to compounds and methods useful for modulating mTORC1 activity. The invention also provides pharmaceutically acceptable compositions comprising provided compounds of the present invention and methods of using such compositions in the treatment of various disorders.

BACKGROUND OF THE INVENTION

The mechanistic target of rapamycin (mTOR) signaling pathway integrates both intracellular and extracellular signals and serves as a central regulator of cell metabolism, growth, proliferation and survival. Discoveries that have been made over the last decade show that the mTOR pathway is activated during various cellular processes (e.g. tumor formation and angiogenesis, insulin resistance, adipogenesis and T-lymphocyte activation) and is deregulated in human diseases such as cancer and type 2 diabetes. These observations have attracted broad scientific and clinical interest in mTOR. This is highlighted by the growing use of mTOR inhibitors [rapamycin and its analogues (rapalogues)] in pathological settings, including the treatment of solid tumors, organ transplantation, coronary restenosis and rheumatoid arthritis.

In particular, mTOR complex 1 (mTORC1) positively regulates cell growth and proliferation by promoting many anabolic processes, including biosynthesis of proteins, lipids and organelles, and by limiting catabolic processes such as autophagy. Much of the knowledge about mTORC1 function comes from the use of the bacterial macrolide rapamycin. Upon entering the cell, rapamycin binds to FK506-binding protein of 12 kDa (FKBP12) and interacts with the FKBP12-rapamycin binding domain (FRB) of mTOR, thus inhibiting mTORC1 functions (reviewed by Guertin and Sabatini, 2007). In contrast to its effect on mTORC1, FKBP12-rapamycin cannot physically interact with or acutely inhibit mTOR complex 2 (mTORC2)(Jacinto et al., 2004; Sarbassov et al., 2004). On the basis of these observations, mTORC1 and mTORC2 have been respectively characterized as the rapamycin-sensitive and rapamycin-insensitive complexes. However, this paradigm might not be entirely accurate, as chronic rapamycin treatment can, in some cases, inhibit mTORC2 activity by blocking its assembly (Sarbassov et al., 2006). In addition, recent reports suggest that important mTORC1 functions are resistant to inhibition by rapamycin (Choo et al., 2008; Feldman et al., 2009; Garcia-Martinez et al., 2009; Thoreen et al., 2009). Therefore, selective inhibition of mTORC1 would enable the treatment of diseases that involve dysregulation of protein synthesis and cellular metabolism. Furthermore, this detailed understanding of regulating mTORC1 activation pathways will permit the discovery of new strategies for regulating abnormal disease processes by modulating mTORC1 activity across its spectrum of function.

Many diseases are associated with abnormal cellular responses triggered by events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

The mechanistic target of rapamycin complex 1 (mTORC1) is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., (2013) Biochemical Society transactions 41, 906-912; Kim et al., (2013) Molecules and cells 35, 463-473; Laplante and Sabatini, (2012) Cell 149, 274-293). Accordingly, there remains a need to find protein kinase inhibitors useful as therapeutic agents.

Additionally, Glucose Transporters (GLUT) are a family of membrane proteins (GLUT1, 2, 3, 4, and 5) that facilitate the transport of glucose and other hexoses across cell membranes. The transport of glucose into cells is one of the most important cellular transport events because of the role in maintaining normal cellular respiration and metabolism (Gould and Holman, (1993) Biochem J., 295, 329-341). Dysfunction or dysregulation of glucose transporters may contribute to, or directly result in, disease states because of the central role the transporters play in cellular homeostasis and metabolism. For example, mutations in the GLUT1 gene are responsible for the rare autosomal disorder De Vivo disease, which is characterized by impaired glucose transport into the brain. Relatedly, elevated levels of GLUT1 in neutrophils has been found to contribute to the inflammatory response in cystic fibrosis (CF) patients (Laval et al., (2013) J. Immunol, 190(12), 6043-50). GLUT inhibition may normalize cellular metabolism and response in affected cells, including immune cells such as neutrophils. Therefore, GLUT inhibition would enable the treatment of cystic fibrosis, as well as autoimmune diseases characterized by abnormal GLUT expression or activity.

SUMMARY OF THE INVENTION

It has now been found that compounds of this invention, and pharmaceutically acceptable compositions thereof, are effective as inhibitors mTORC1 inhibitors. Such compounds have the general Formula I:

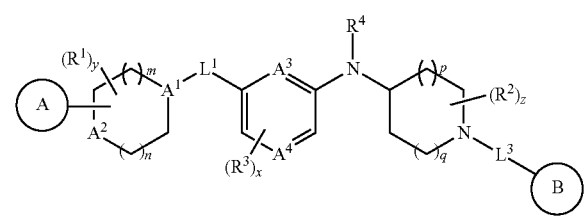

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with mTORC1. Such diseases, disorders, or conditions include those described herein.

DETAILED DESCRIPTION OF CERTAIN EMBODIMENTS

1. General Description of Certain Embodiments of the Invention

In certain embodiments, the present invention provides a compound of Formula I:

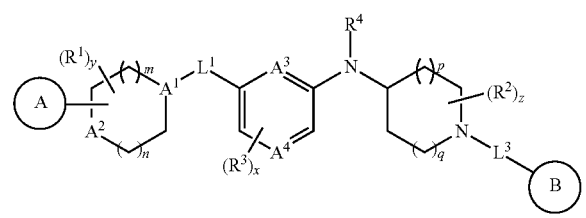

I or a pharmaceutically acceptable salt thereof, wherein:
$A^1$ is N or CH;
$A^2$ is N(Ring A) or N—$R^1$;
$A^3$ is C(R') or N;
$A^4$ is CH or N;
R' is H, $C_{1-6}$ aliphatic, or halogen;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
each of m, n, p, q, and x is independently 0, 1, or 2;
each of y and z is independently 0, 1, 2, 3 or 4;
each of $R^1$ and $R^2$ is independently R, or:
  two $R^1$ groups are optionally taken together to form =O;
  two $R^2$ groups are optionally taken together to form =O;
  two $R^1$ groups are optionally taken together to form a covalent bond or a bivalent $C_{1-4}$ alkylene chain; or
  two $R^2$ groups are optionally taken together to form a covalent bond or a bivalent $C_{1-4}$ alkylene chain;
  an $R^1$ group and Ring A are optionally taken together with their intervening atoms to form a 5-8 membered fused ring having 0-2 heteroatoms independently selected from nitrogen, oxygen or sulfur; or
  an $R^2$ group and Ring B are optionally taken together with their intervening atoms to form a 5-8 membered fused ring having 0-2 heteroatoms independently selected from nitrogen, oxygen or sulfur;
each of $R^3$ is independently R, halogen, —OR, —CN, or two $R^3$ groups are optionally taken together with their intervening atoms to form a 5-8 membered partially unsaturated or aryl fused ring having 0-2 heteroatoms independently selected from nitrogen, oxygen, or sulfur;
$R^4$ is hydrogen or an optionally substituted $C_{1-6}$ aliphatic group;
Ring A is absent or an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur;
Ring B is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur; and
$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, or —S(O)$_2$—.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}R^\circ$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}(CH_2)_{0-1}$-pyridyl which may be substituted with $R^\circ$; $-NO_2$; $-CN$; $-N_3$; $-(CH_2)_{0-4}$ N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$S(O)$_2$R°; —S(O)$_2$NR°$_2$; —S(O)(NR°)R°; —S(O)$_2$N=C(NR°$_2$)$_2$; —(CH$_2$)$_{0-4}$S(O)R; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in mTORC1 activity between a sample comprising a compound of the present invention, or composition thereof, and mTORC1, and an equivalent sample comprising mTORC1 in the absence of said compound, or composition thereof.

3. Description of Exemplary Embodiments

As described above, in certain embodiments, the present invention provides a compound of Formula I:

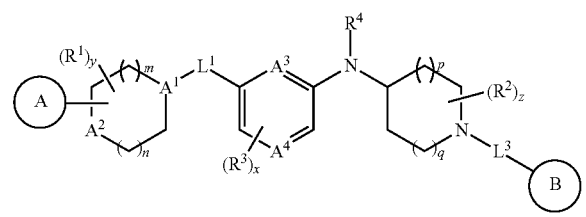

I or a pharmaceutically acceptable salt thereof, wherein:
$A^1$ is N or CH;
$A^2$ is N(Ring A) or N—$R^1$;
$A^3$ is C(R') or N;
$A^4$ is CH or N;
R' is H, $C_{1-6}$ aliphatic, or halogen;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
each of m, n, p, q, and x is independently 0, 1, or 2;
each of y and z is independently 0, 1, 2, 3 or 4;
each of $R^1$ and $R^2$ is independently R, or:
  two $R^1$ groups are optionally taken together to form =O;
  two $R^2$ groups are optionally taken together to form =O;
  two $R^1$ groups are optionally taken together to form a covalent bond or a bivalent $C_{1-4}$ alkylene chain; or
  two $R^2$ groups are optionally taken together to form a covalent bond or a bivalent $C_{1-4}$ alkylene chain;
  an $R^1$ group and Ring A are optionally taken together with their intervening atoms to form a 5-8 membered fused ring having 0-2 heteroatoms independently selected from nitrogen, oxygen or sulfur; or
  an $R^2$ group and Ring B are optionally taken together with their intervening atoms to form a 5-8 membered fused ring having 0-2 heteroatoms independently selected from nitrogen, oxygen or sulfur;
each of $R^3$ is independently R, halogen, —OR, —CN, or two $R^3$ groups are optionally taken together with their intervening atoms to form a 5-8 membered partially unsaturated or aryl fused ring having 0-2 heteroatoms independently selected from nitrogen, oxygen, or sulfur;
$R^4$ is hydrogen or an optionally substituted $C_{1-6}$ aliphatic group;
Ring A is absent or an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur;
Ring B is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur; and
$L^1$ is a covalent bond or a $C_1$-3 bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, or —S(O)$_2$—.

As defined above and described herein, $A^1$ is N or CH. In some embodiments, $A^1$ is N. In some embodiments, $A^1$ is CH.

In some embodiments, $A^1$ is selected from those depicted in Table 1, below.

As defined above and described herein, $A^2$ is N(Ring A) or N—$R^1$.

In some embodiments, $A^2$ is N(Ring A). In some embodiments, $A^2$ is N—$R^1$. In some embodiments, $A^2$ is NH. In some embodiments, $A^2$ is NC(O)OC(CH$_3$)$_3$. In some embodiments, $A^2$ is NCH(CH$_3$)$_2$. In some embodiments, $A^2$ is NCH$_2$CF$_3$.

In some embodiments, $A^2$ is selected from those depicted in Table 1, below.

As defined above and described herein, each of m, and n is independently 0, 1, or 2. In some embodiments, m is 0. In some embodiments, n is 0. In some embodiments, m is 1. In some embodiments, n is 1. In some embodiments, m is 2. In some embodiments, n is 2.

As defined above and described herein, each of p, q and x is independently 0, 1, or 2. In some embodiments, p is 0. In some embodiments, q is 0. In some embodiments, x is 0. In some embodiments, p is 1. In some embodiments, q is 1. In some embodiments, x is 1. In some embodiments, p is 2. In some embodiments, q is 2. In some embodiments, x is 2.

As defined above and described herein, each of y and z is independently 0, 1, 2, 3 or 4. In some embodiments, y is 0. In some embodiments, z is 0. In some embodiments, y is 1. In some embodiments, z is 1. In some embodiments, y is 2. In some embodiments, z is 2. In some embodiments, y is 3. In some embodiments, z is 3. In some embodiments, y is 4. In some embodiments, z is 4.

As defined above and described herein, $A^3$ is C(R') or N. In some embodiments, $A^3$ is C(R'). In some embodiments, $A^3$ is N.

In some embodiments, $A^3$ is CH. In some embodiments, $A^3$ is CCH$_3$. In some embodiments, $A^3$ is CF.

In some embodiments, $A^3$ selected from those depicted in Table 1, below.

As defined above and described herein, $A^4$ is CH or N. In some embodiments, $A^4$ is CH. In some embodiments, $A^4$ is N.

In some embodiments, $A^4$ is selected from those depicted in Table 1, below.

As defined above and described herein, each of $R^1$ and $R^2$ is independently R, or: two $R^1$ groups are optionally taken together to form =O; two $R^2$ groups are optionally taken together to form =O; two $R^1$ groups are optionally taken together to form a covalent bond or a bivalent $C_{1-4}$ alkylene chain; two $R^2$ groups are optionally taken together to form a covalent bond or a bivalent $C_{1-4}$ alkylene chain; an $R^1$ group and Ring A are optionally taken together with their intervening atoms to form a 5-8 membered fused ring having 0-2 heteroatoms independently selected from nitrogen, oxygen, or sulfur; or an $R^2$ group and Ring B are optionally taken together with their intervening atoms to form a 5-8 membered fused ring having 0-2 heteroatoms independently selected from nitrogen, oxygen, or sulfur.

In some embodiments, each $R^1$ is hydrogen. In some embodiments $R^1$ is methyl. In some embodiments, $R^1$ is —CH$_2$OH. In some embodiments, two $R^1$ groups are optionally taken together to form =O. In some embodiments, two $R^1$ groups are optionally taken together to form a covalent bond. In some embodiments, two $R^1$ groups are optionally taken together to form a bivalent $C_{1-4}$ alkylene chain. In some embodiments, a $R^1$ group and Ring A are optionally taken together to form a 5-8 membered fused ring having 0-2 heteroatoms independently selected from nitrogen, oxygen, or sulfur.

In some embodiments $R^1$ is

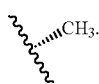

In some embodiments $R^1$ is

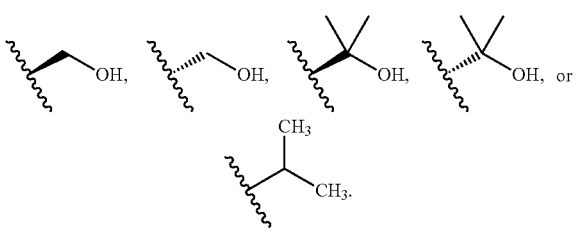

In some embodiments $R^1$ is

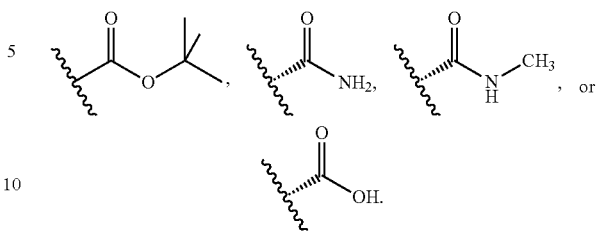

In some embodiments, each $R^2$ is hydrogen. In some embodiments, $R^2$ is methyl. In some embodiments, $R^2$ is —CH$_2$OH. In some embodiments, two $R^2$ groups are optionally taken together to form =O. In some embodiments, two $R^2$ groups are optionally taken together to form a covalent bond. In some embodiments, two $R^2$ groups are optionally taken together to form a bivalent $C_{1-4}$ alkylene chain. In some embodiments, a $R^2$ group and Ring B are optionally taken together to form a 5-8 membered fused ring having 0-2 heteroatoms independently selected from nitrogen, oxygen, or sulfur.

In some embodiments, each of $R^1$ and $R^2$ is independently selected from those depicted in Table 1, below.

As defined above and described herein, each of $R^3$ is independently R, halogen, —OR, —CN, or two $R^3$ groups are optionally taken together with their intervening atoms to form a 5-8 membered fused ring having 0-2 heteroatoms independently selected from nitrogen, oxygen, or sulfur. In some embodiments, $R^3$ is R. In some embodiments, $R^3$ is halogen. In some embodiments, $R^3$ is —OR. In some embodiments, $R^3$ is —CN. In some embodiments, two $R^3$ groups are optionally taken together to form a 5-8 membered fused ring having 0-2 heteroatoms independently selected from nitrogen, oxygen or sulfur.

In some embodiments, $R^3$ is methyl. In some embodiments, $R^3$ is fluoro. In some embodiments, $R^3$ is chloro. In some embodiments, $R^3$ is —OCH$_3$.

In some embodiments, each of $R^3$ is selected from those depicted in Table 1, below.

As defined above and described herein, $R^4$ is hydrogen or an optionally substituted $C_{1-6}$ aliphatic group. In some embodiments, $R^4$ is hydrogen. In some embodiments, $R^4$ is methyl. In some embodiments, $R^4$ is ethyl. In some embodiments, $R^4$ is

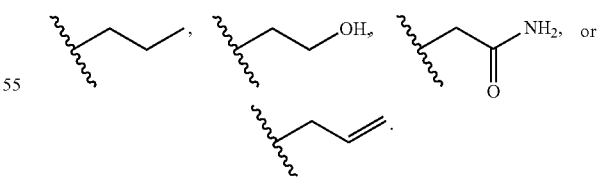

As defined above and described herein, Ring A is absent or an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur.

In some embodiments, Ring A is
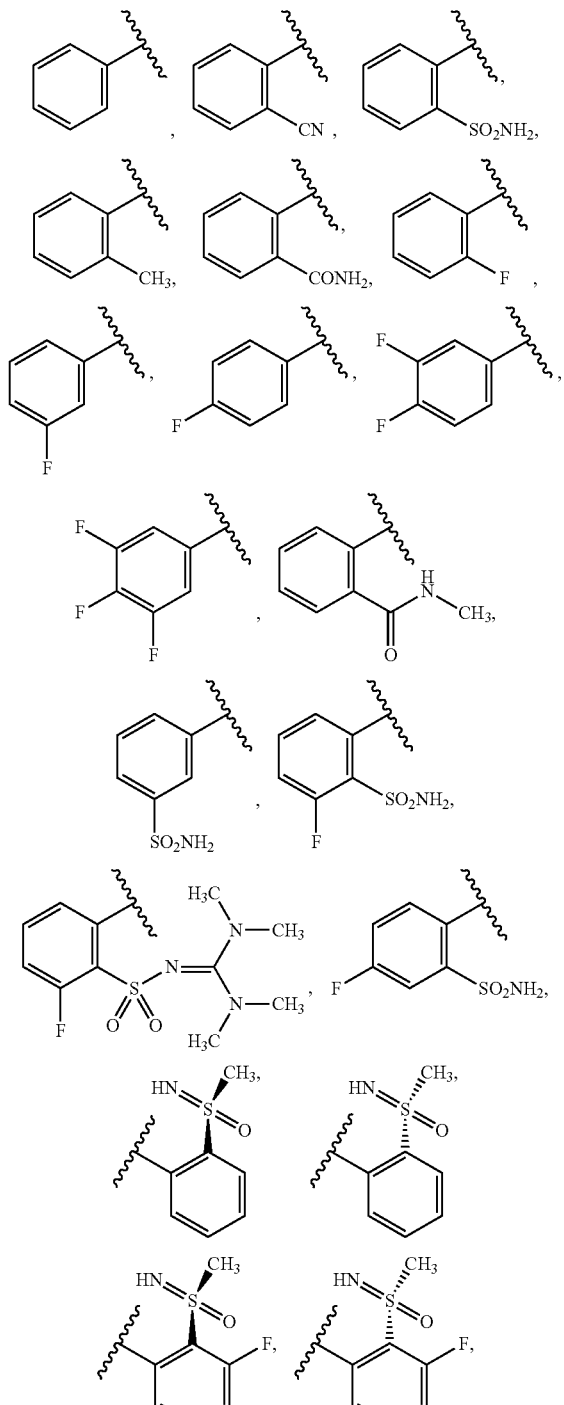
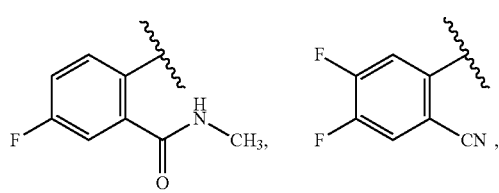
-continued
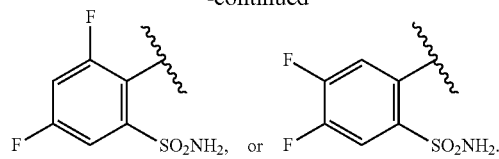
In some embodiments, Ring A is
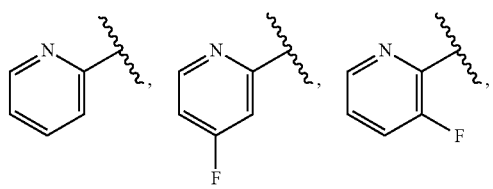
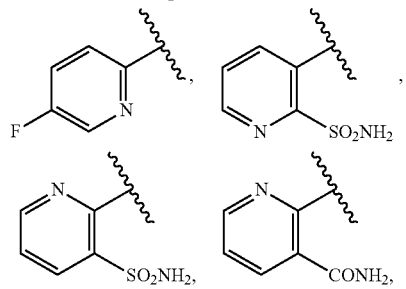
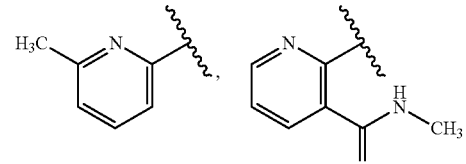
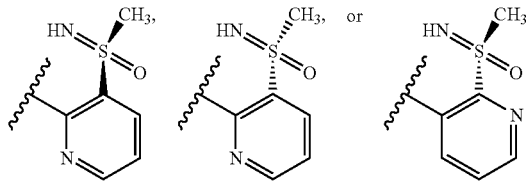
In some embodiments, Ring A is
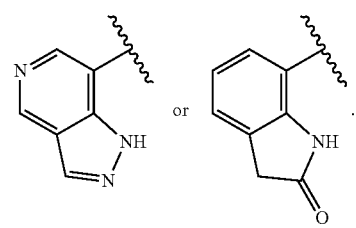 [SMILES: *c1cncc2cn[nH]c12 ; *c1cccc2c1NC(=O)C2]
In some embodiments, Ring A is
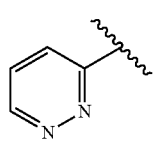

or

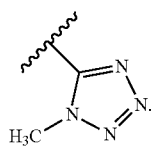

In some embodiments, Ring A is

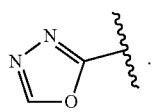

In some embodiments, Ring A is selected from those depicted in Table 1, below.

As defined above and described herein, Ring B is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur.

In some embodiments, Ring B is

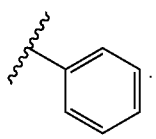 [SMILES: *c1ccccc1]

In some embodiments, Ring B is

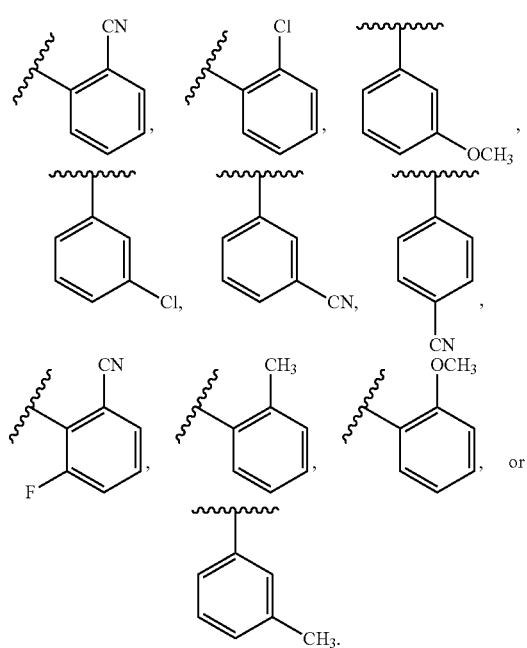

In some embodiments, Ring B is

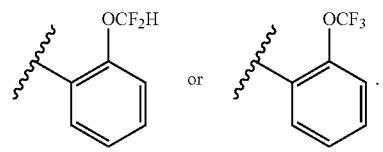

In some embodiments, Ring B is,

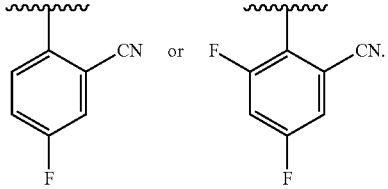 [SMILES: *c1ccc(F)cc1C#N ; "or" ; *c1c(F)cc(F)cc1C#N]

In some embodiments, Ring B is

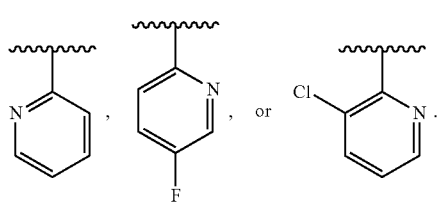

In some embodiments, Ring B is

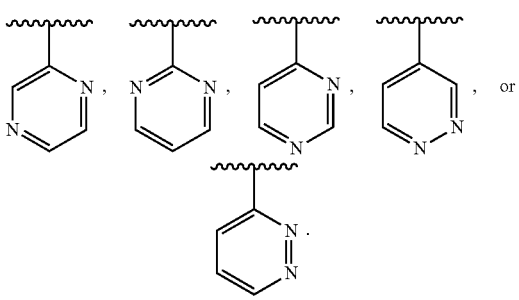

In some embodiments, Ring B is selected from those depicted in Table 1, below.

As defined above and described herein, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, or —S(O)$_2$—.

In some embodiments, $L^1$ is a covalent bond. In some embodiments, $L^1$ is

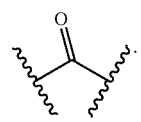 [SMILES: *C(*)=O]

In some embodiments, L¹ is

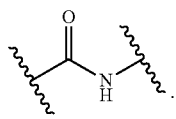

In some embodiments, L¹ is

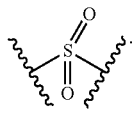

In some embodiments, L¹ is selected from those depicted in Table 1, below.

In some embodiments, the present invention provides a compound of Formulae II:

II

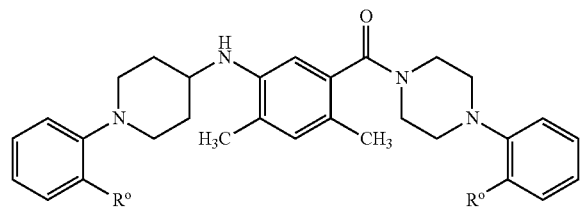

or a pharmaceutically acceptable salt thereof, wherein each phenyl ring is substituted in the ortho position with a suitable monovalent substituent as described herein.

Exemplary compounds of the invention are set forth in Table 1, below.

Table 1. Exemplary Compounds

I-1

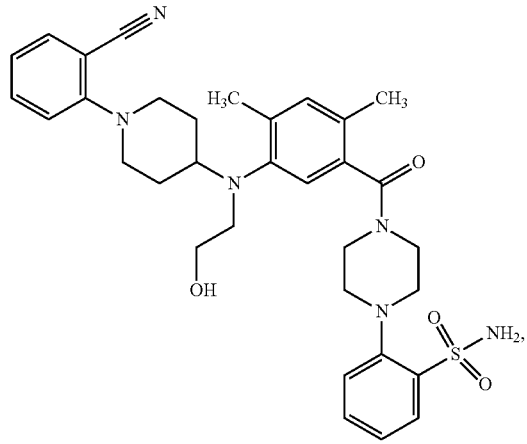

I-2

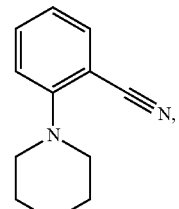
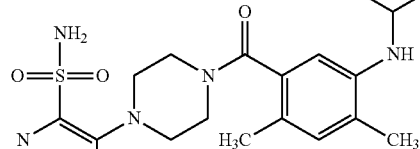

I-3

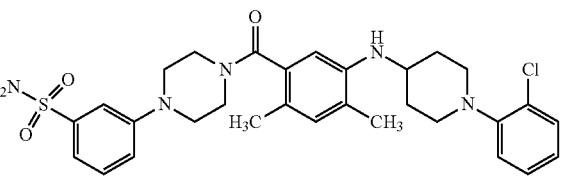

I-4

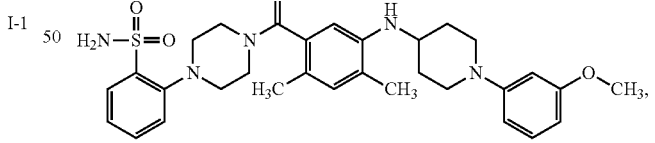

I-5

(I-5 structure)

I-6

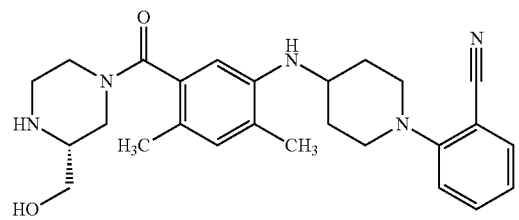

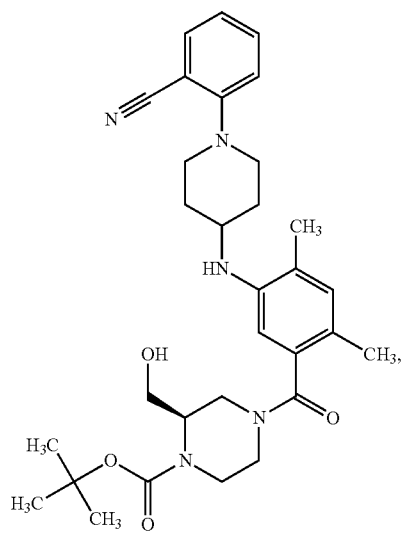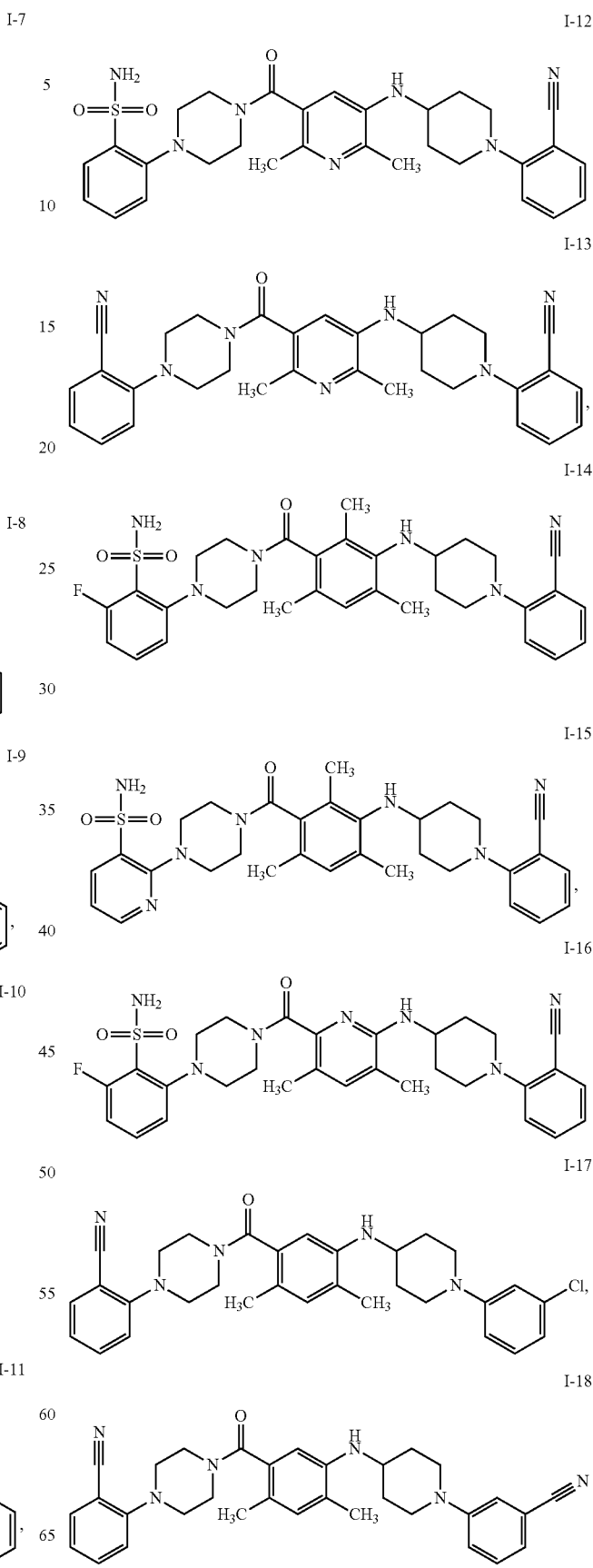

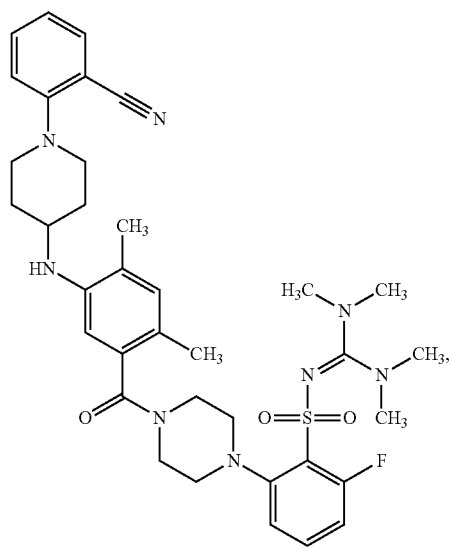
I-19
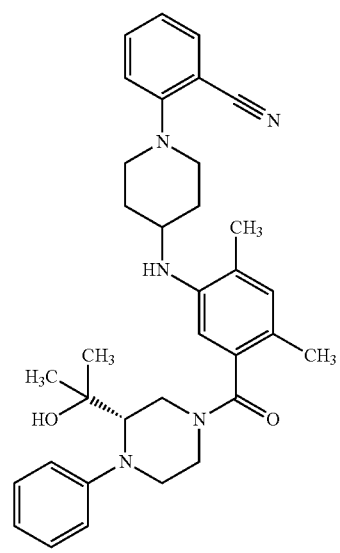
I-20
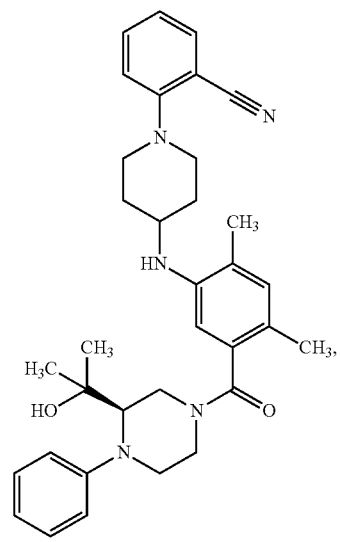
I-21
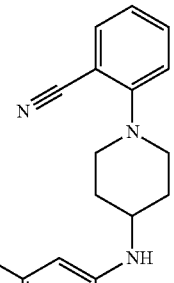
I-22
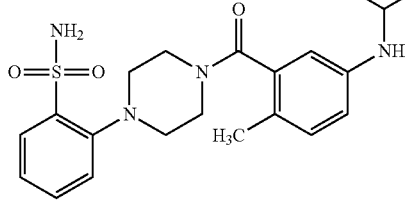
I-23
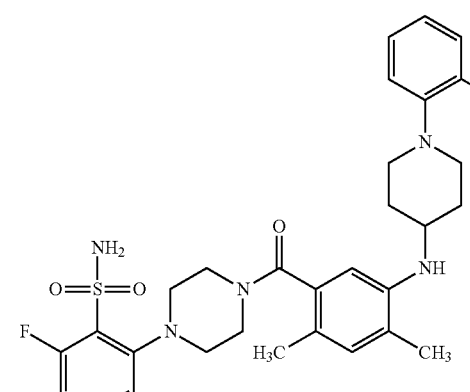
I-24
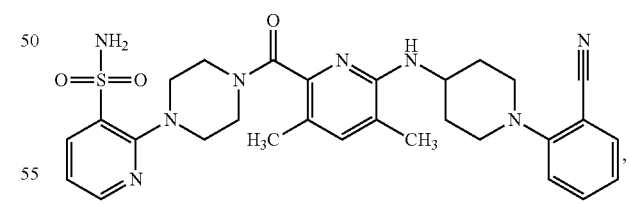
I-25
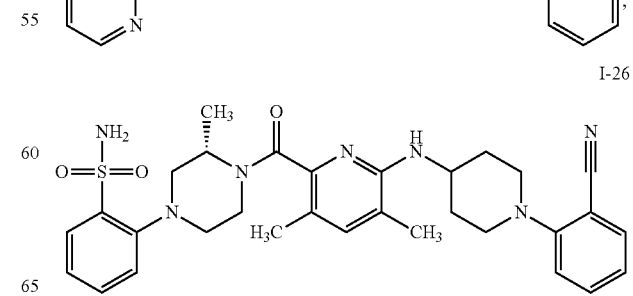
I-26

I-27
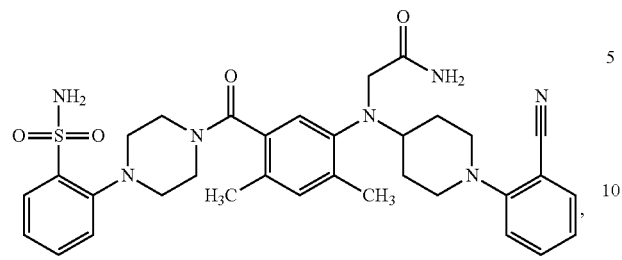
I-28
I-30
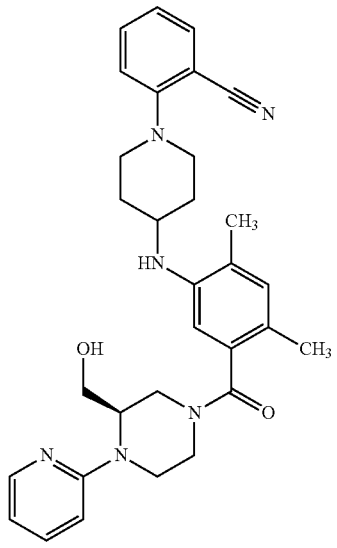
I-29
I-31
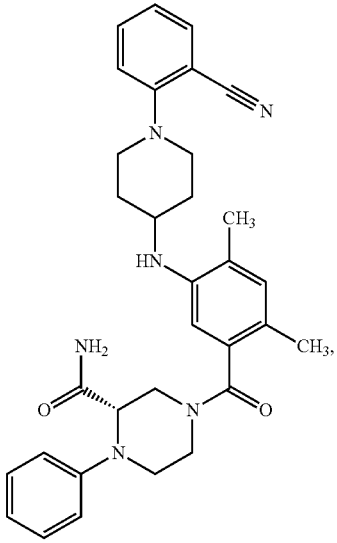

I-32 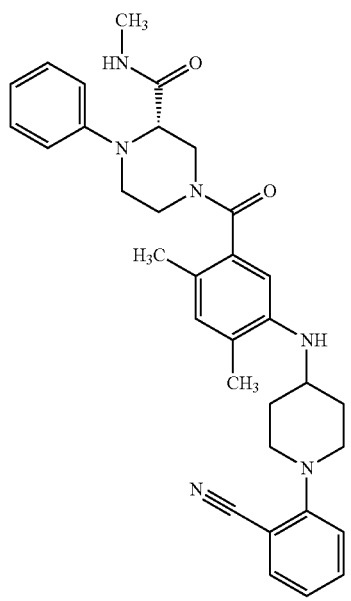
I-36 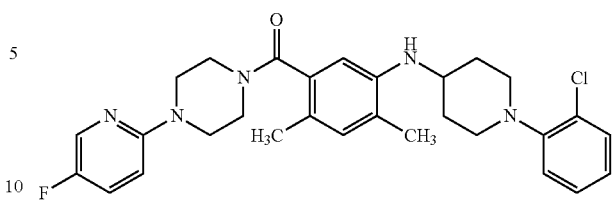
I-37
I-33 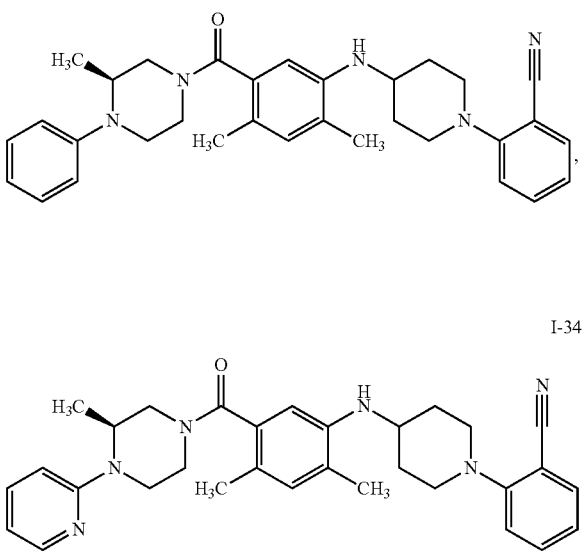
I-38 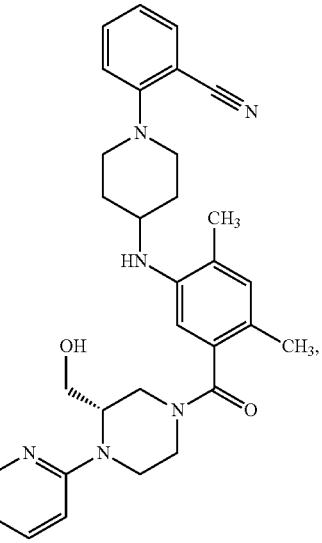
I-34
I-35 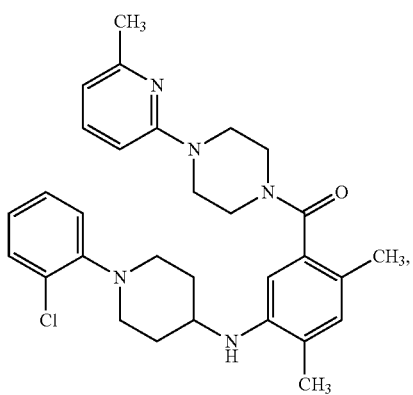
I-39 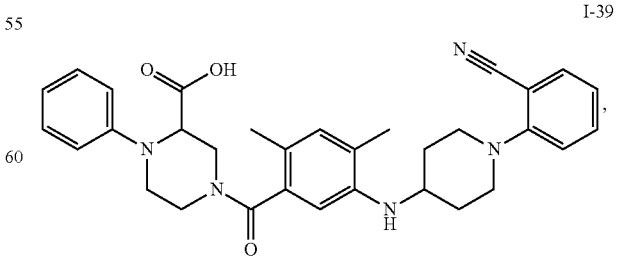

I-40
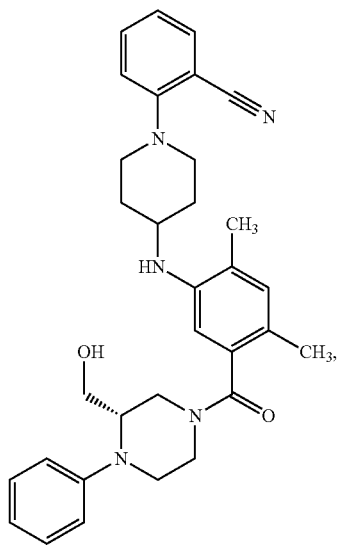
I-43
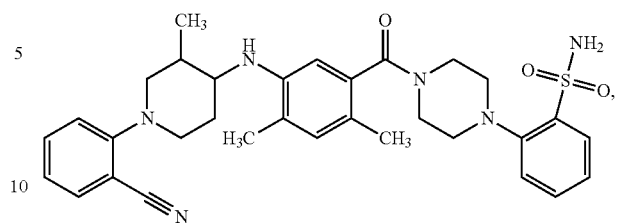
I-44
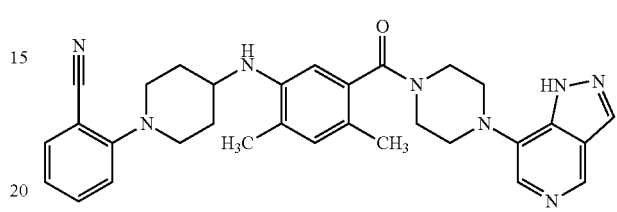
I-45
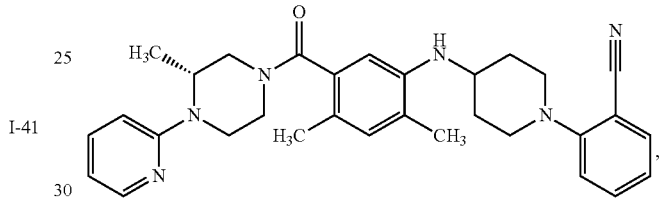
I-41
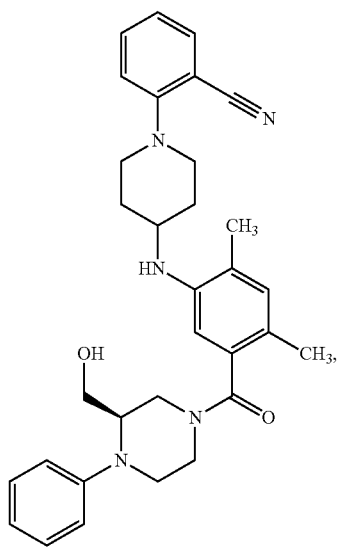
I-46
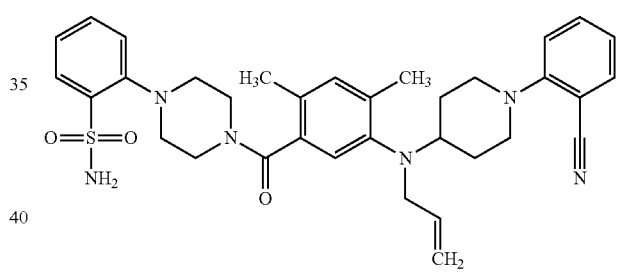
I-47
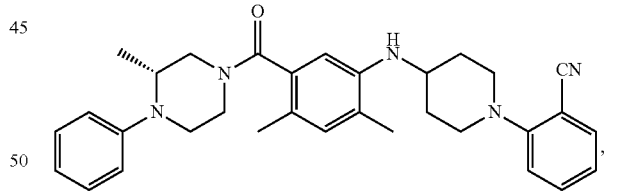
I-48
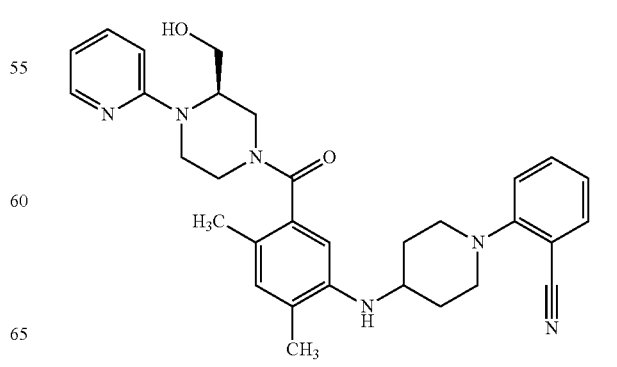
I-42
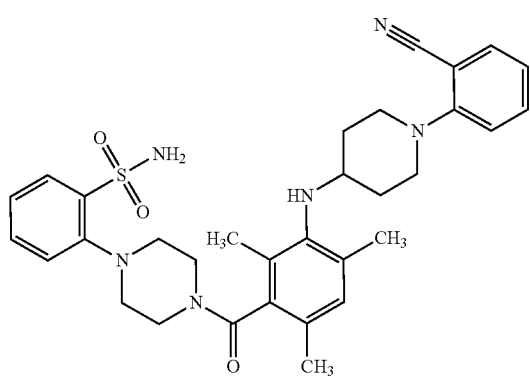

-continued
I-49
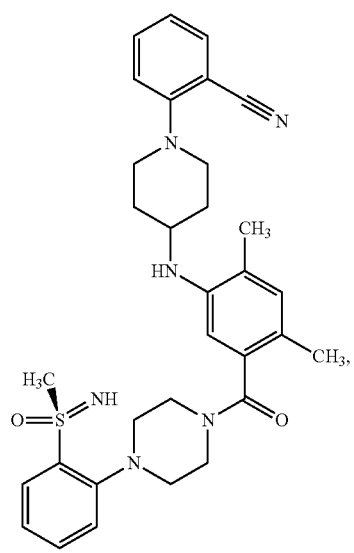
I-50
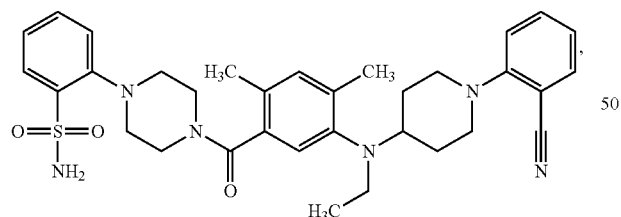
I-51
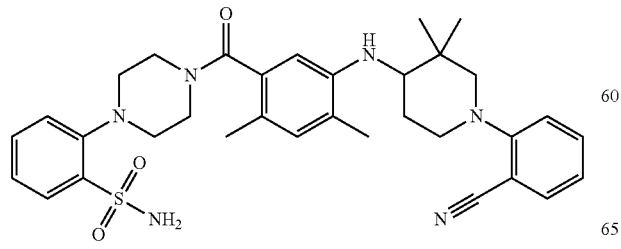
I-52
-continued
I-53
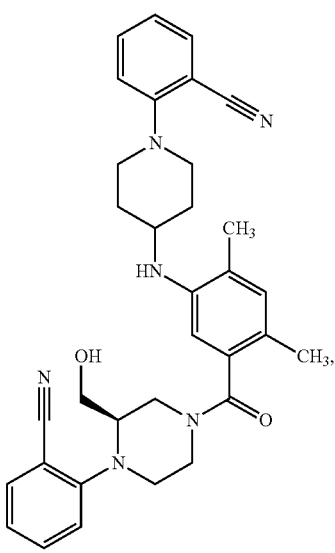
I-54
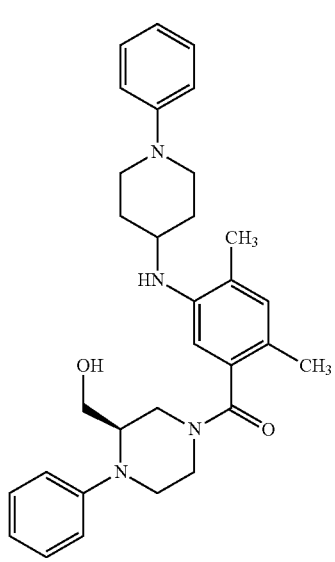
I-55
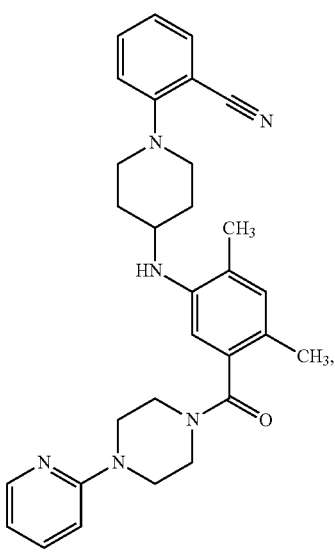

-continued
I-56
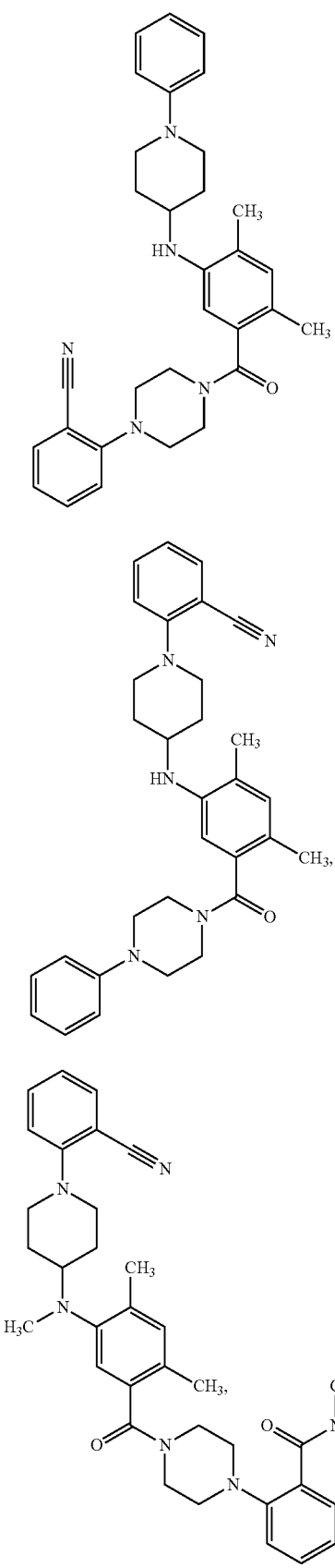
I-57
I-58
-continued
I-59
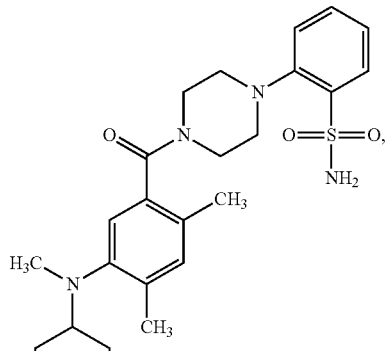
I-60
I-61

I-62
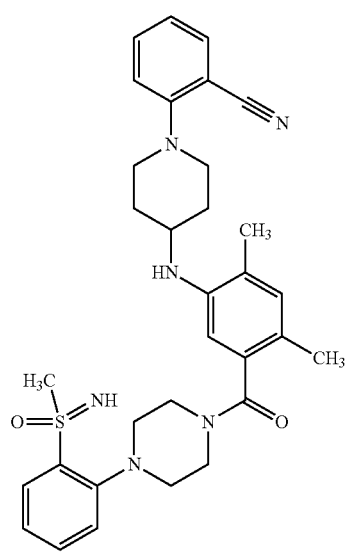
I-63
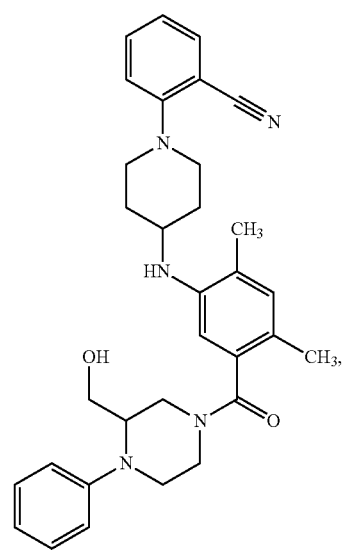
I-64
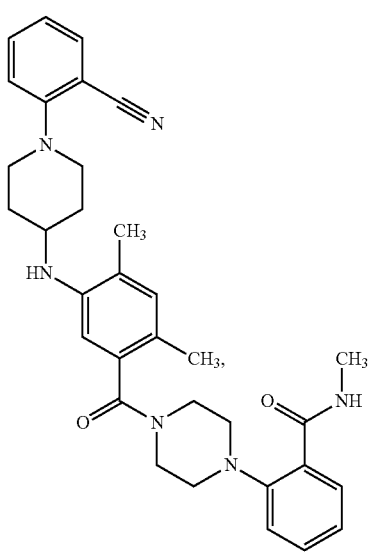
I-65
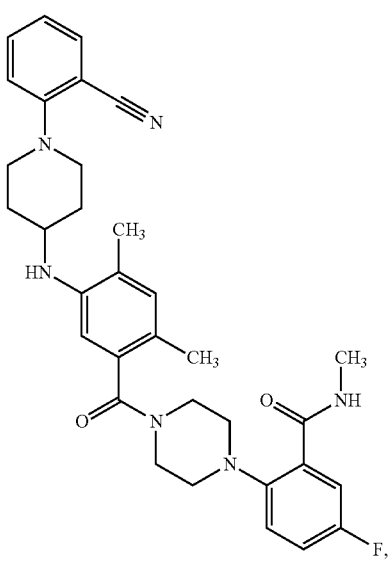
I-66
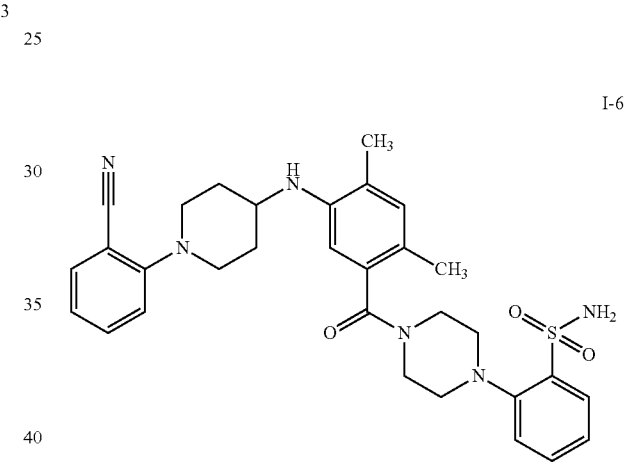
I-67
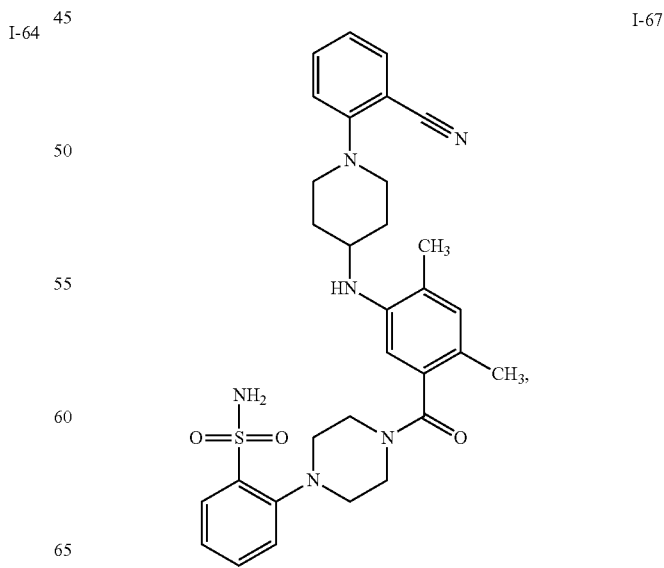

35
-continued
I-68
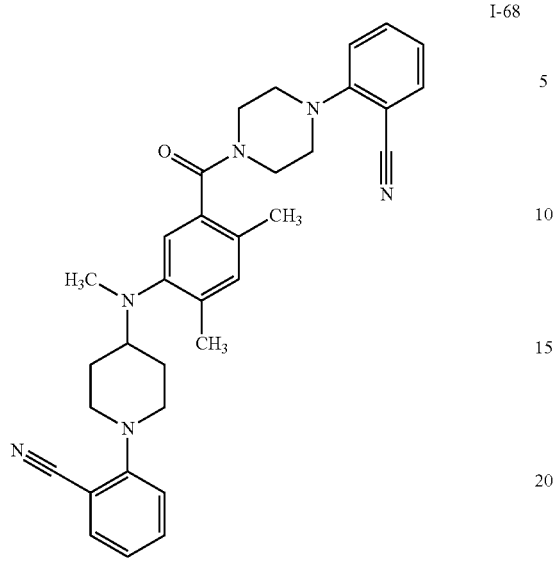
I-69
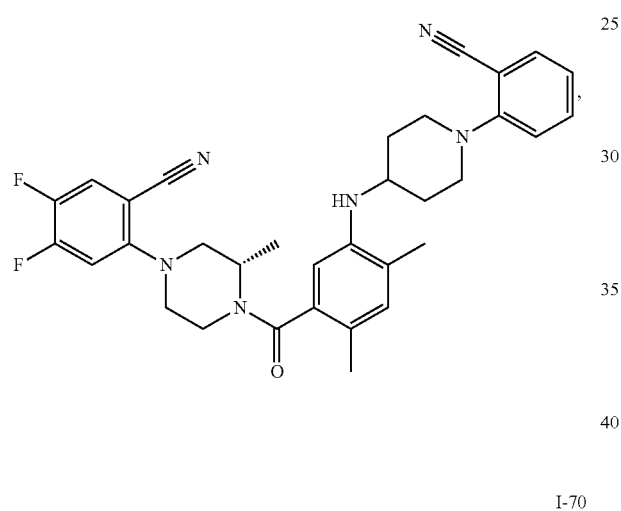
I-70
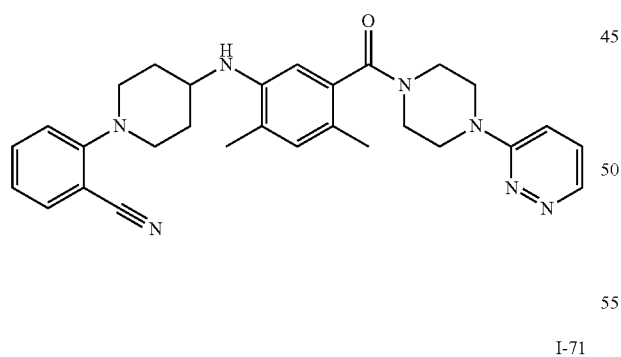
I-71
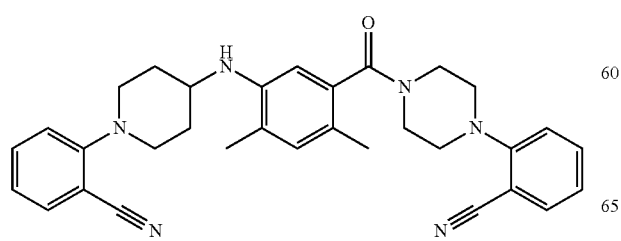
36
-continued
I-72
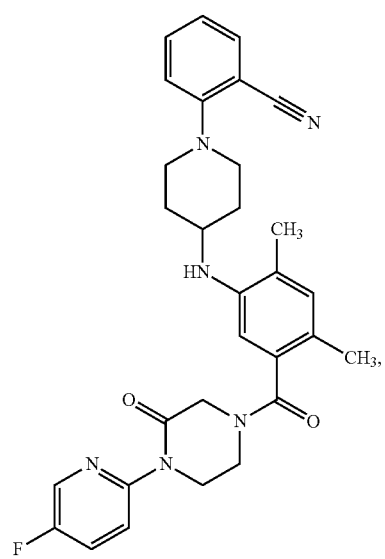
I-73
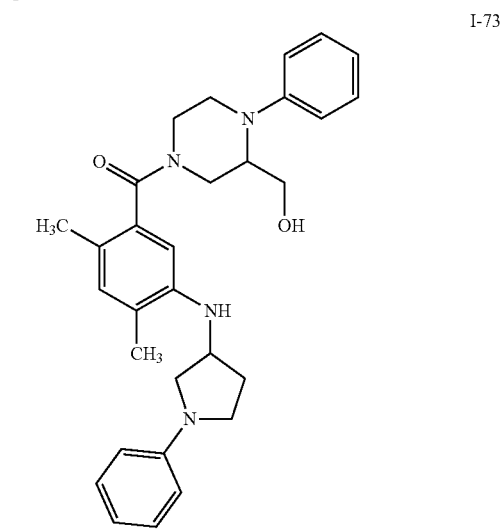
I-74
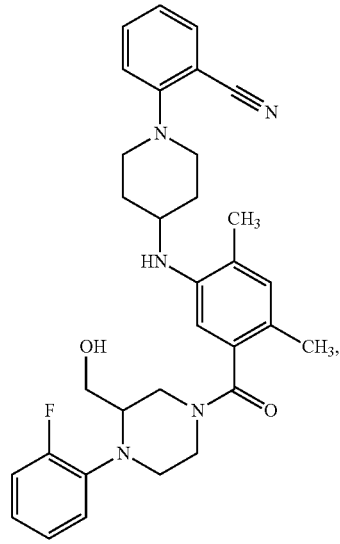

I-75
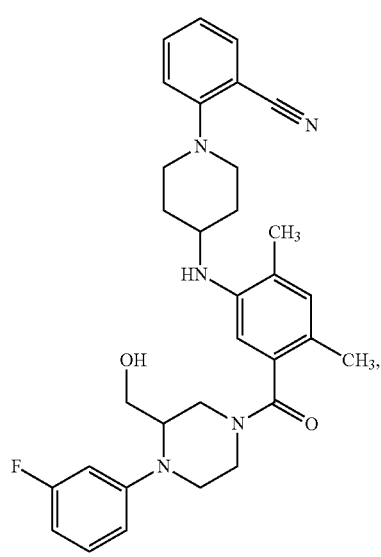
I-76
I-77
I-78
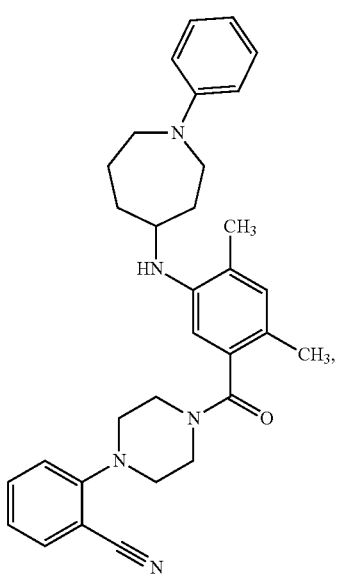
I-79
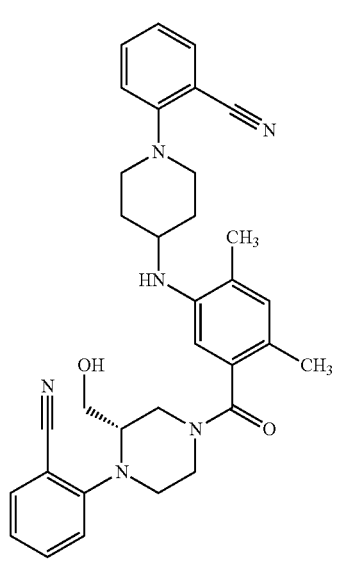

-continued
I-80
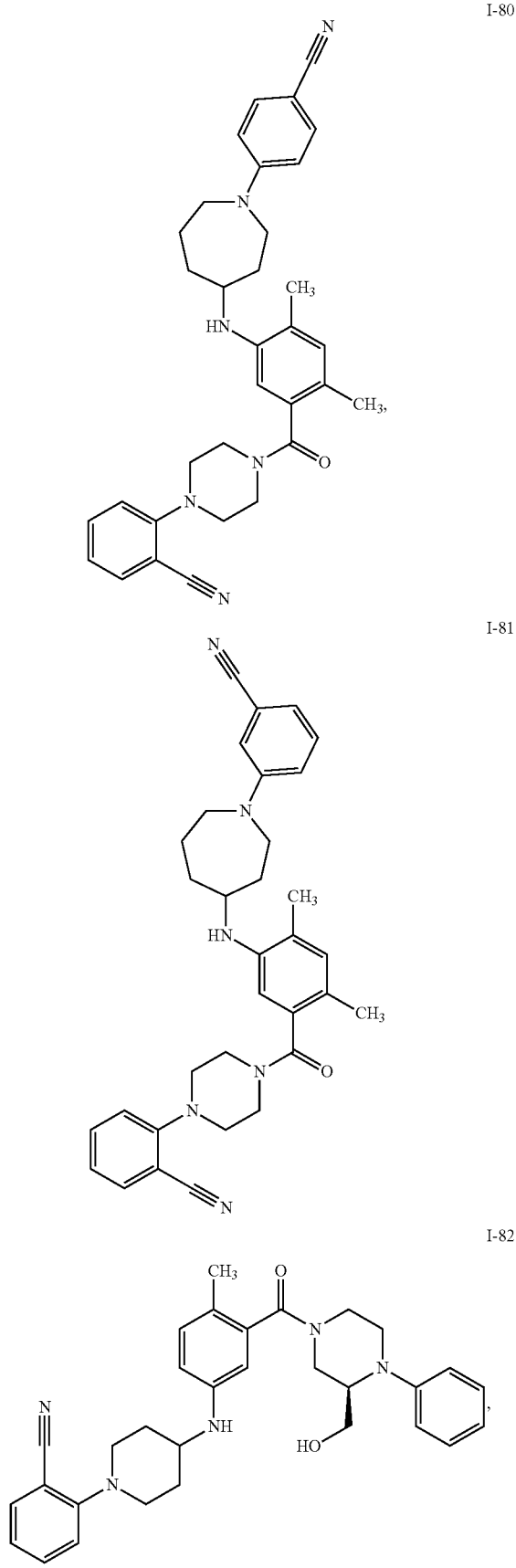
I-81
I-82
-continued
I-83
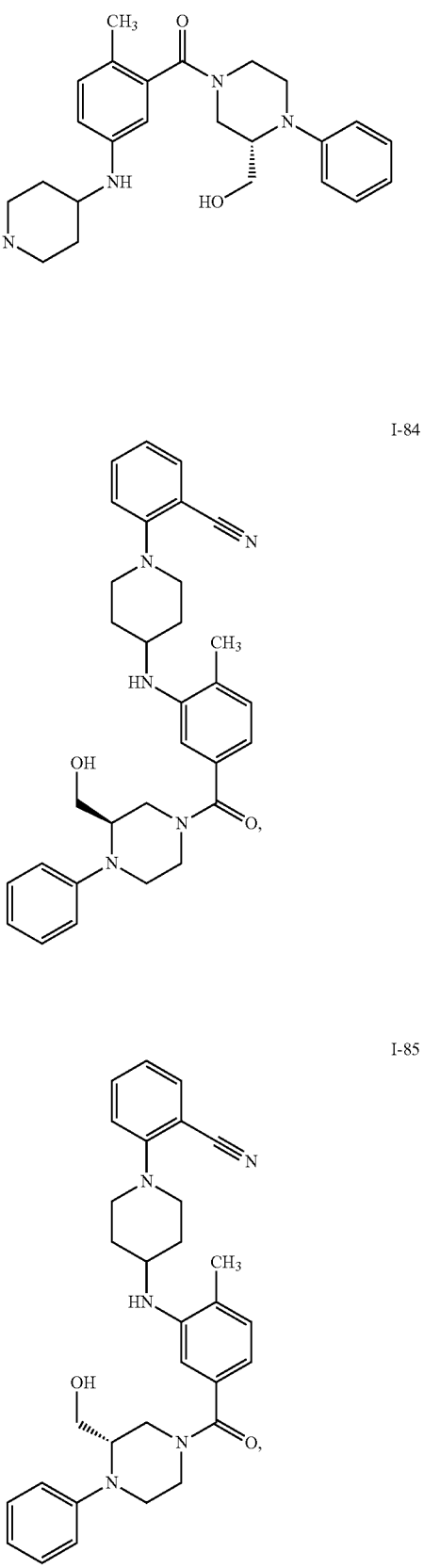
I-84
I-85

-continued
I-86
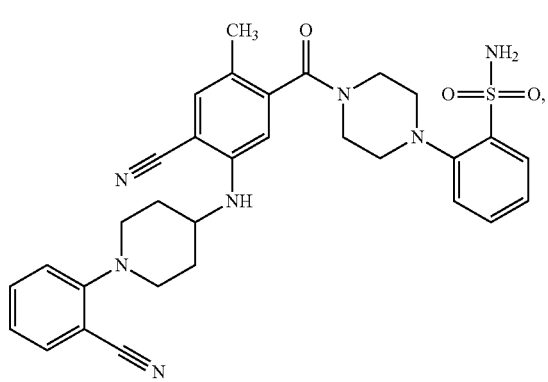
I-89
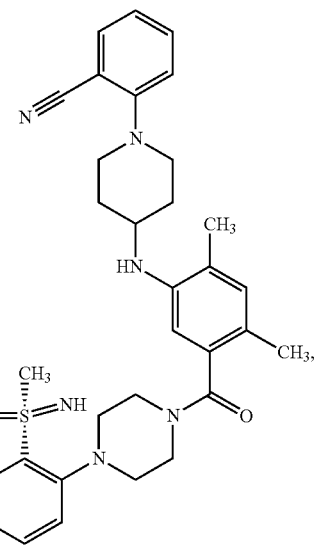
I-87
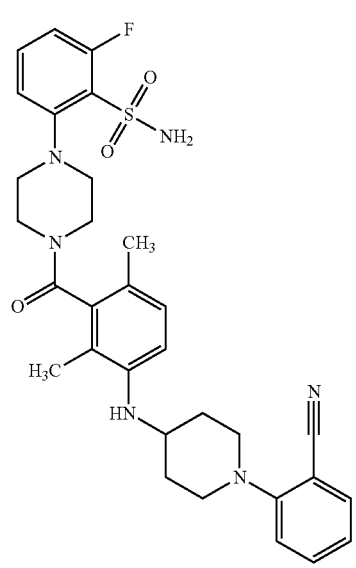
I-90
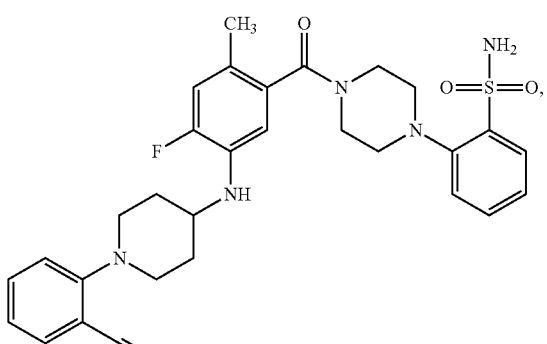
I-88
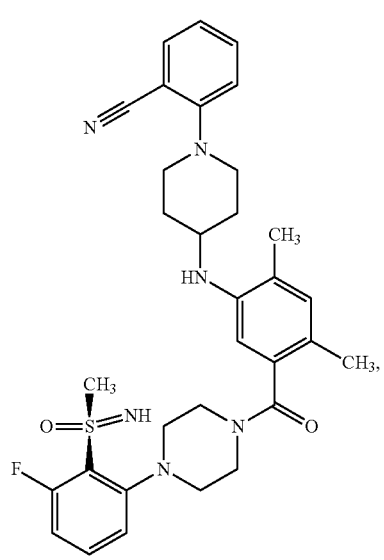
I-91
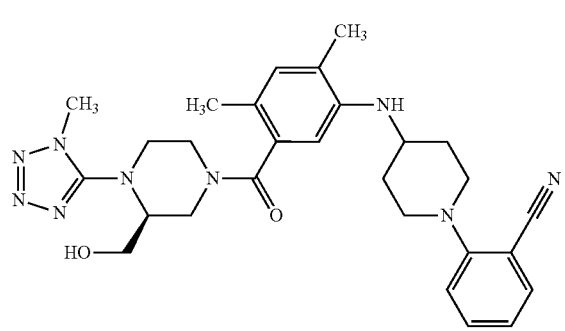

I-92
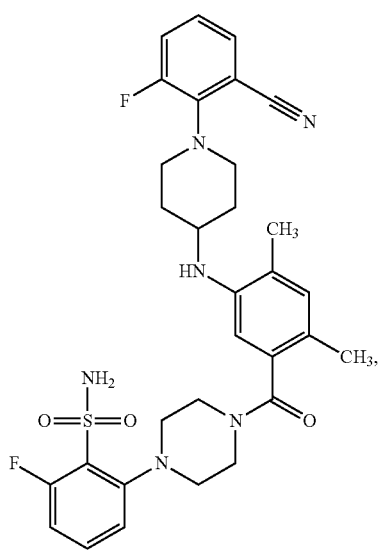
I-93
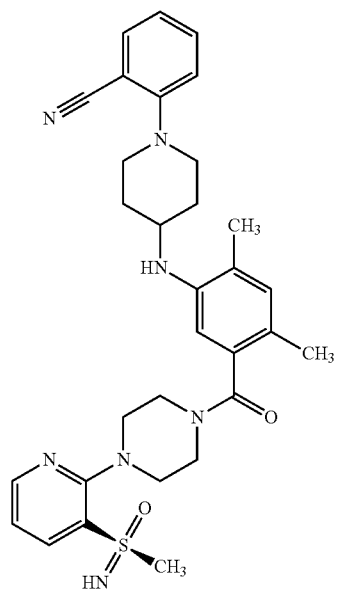
I-94
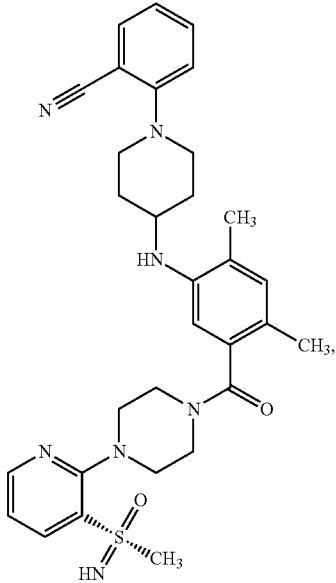
I-95
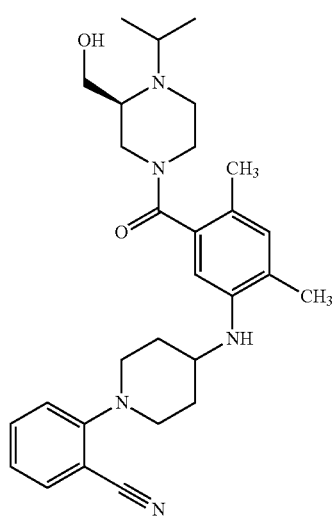
I-96
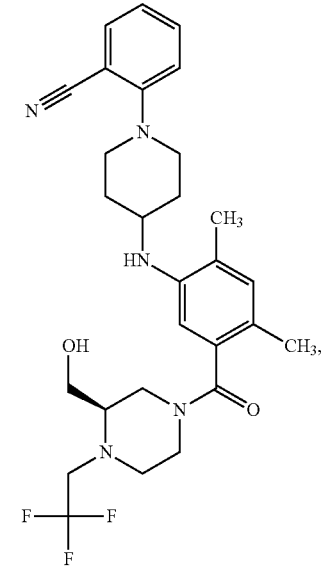

I-97
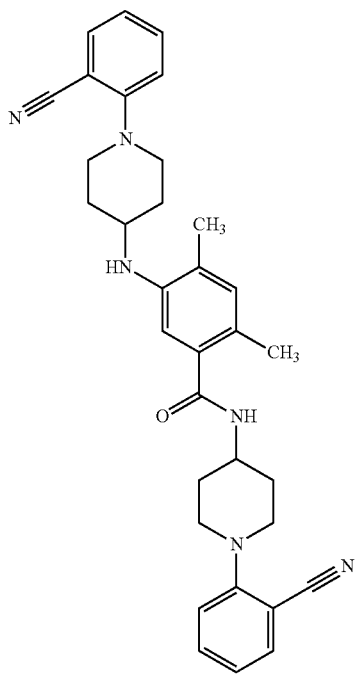
I-98
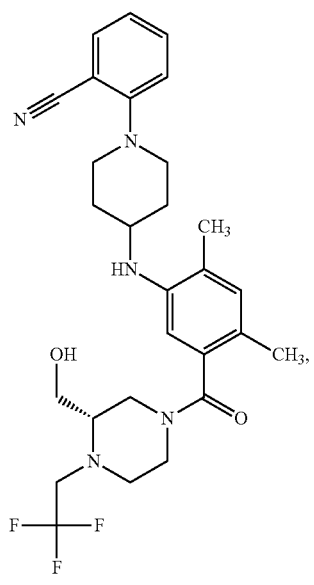
I-99
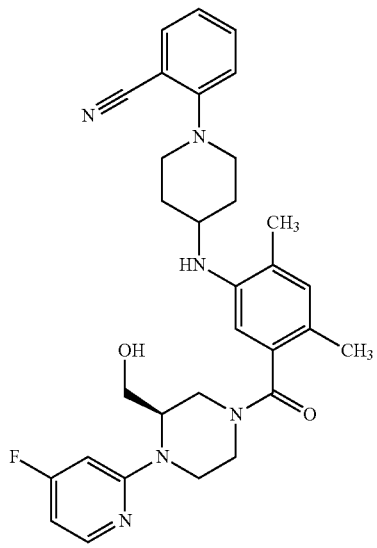
I-100
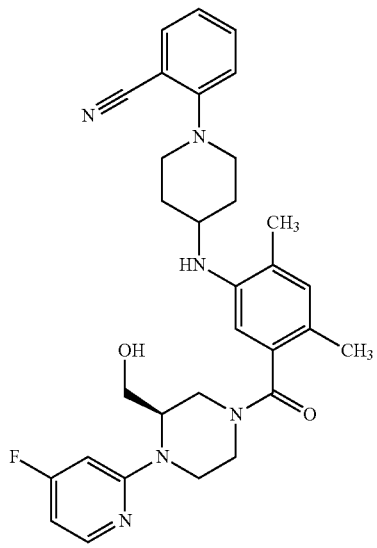
I-101
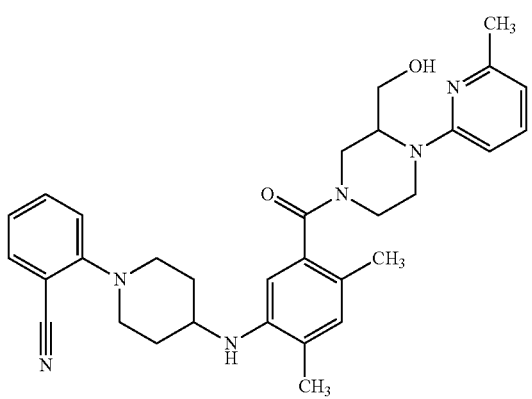

-continued
I-102
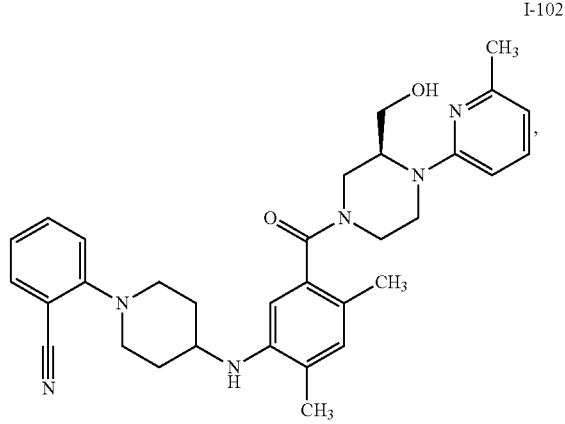
I-103
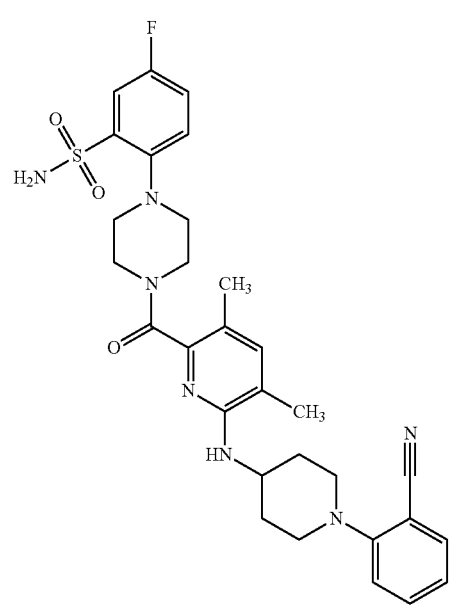
I-104
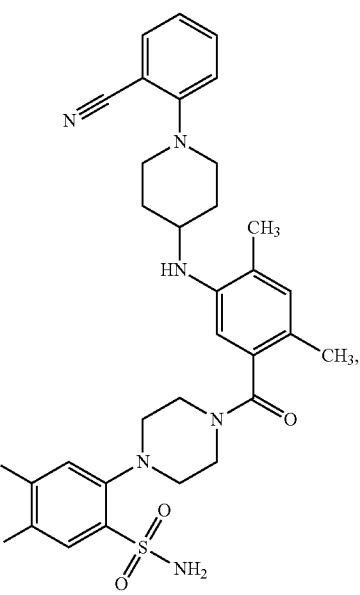
-continued
I-105
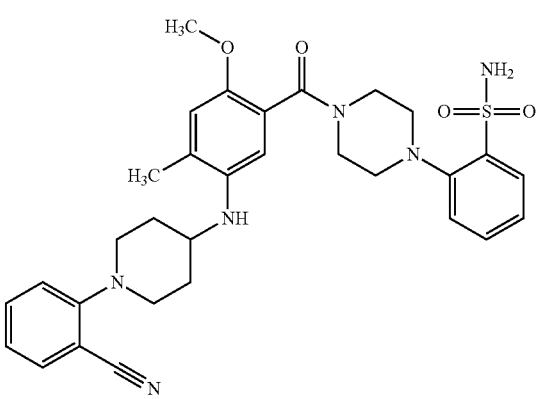
I-106
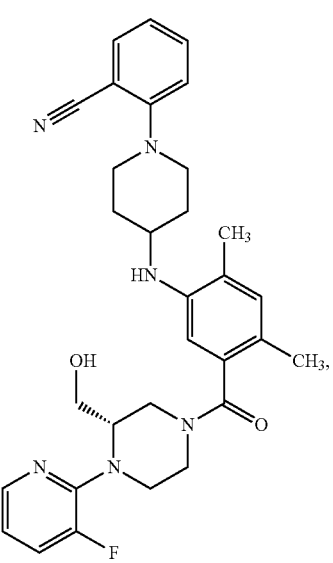
I-107
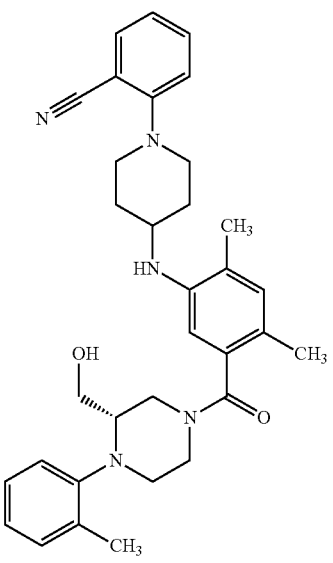

-continued
I-108
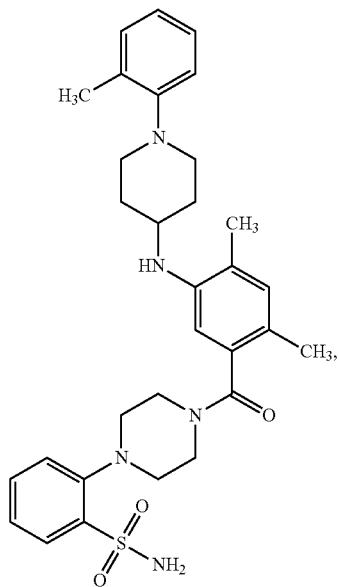
I-109
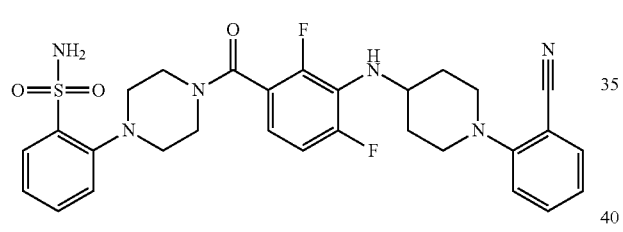
I-110
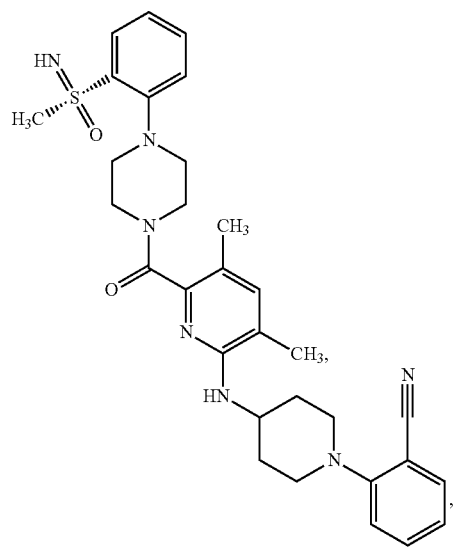
-continued
I-111
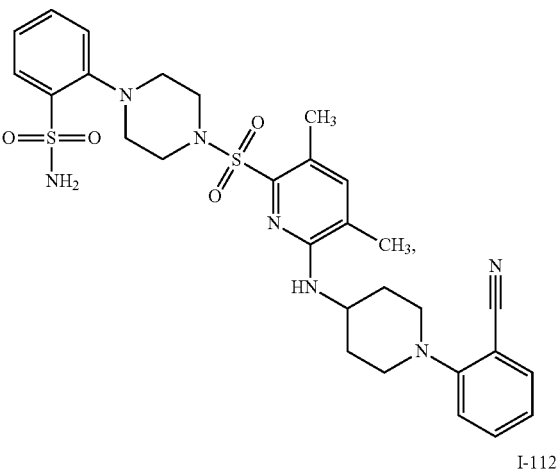
I-112
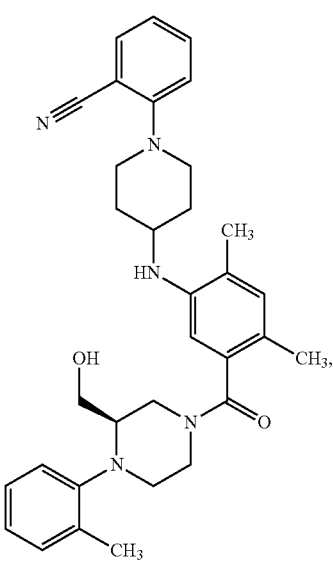
I-113
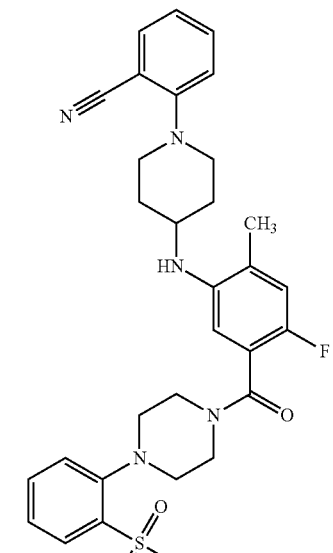

I-114
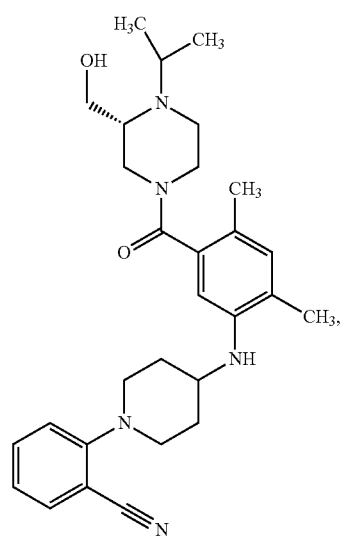
I-115
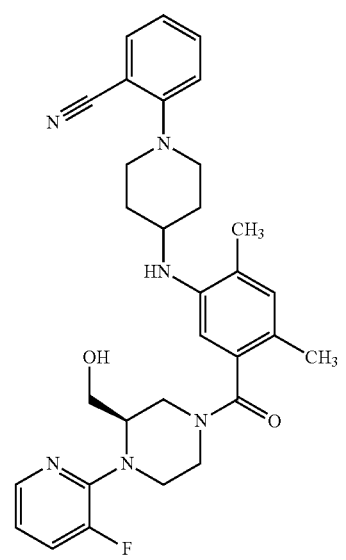
I-116
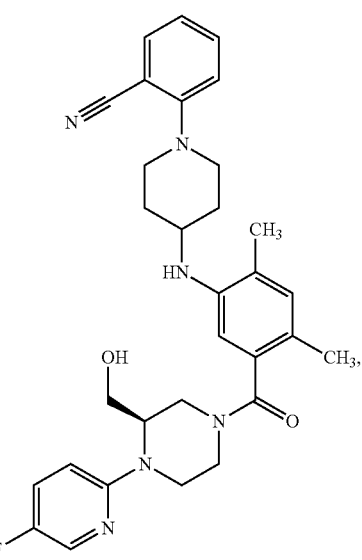
I-117
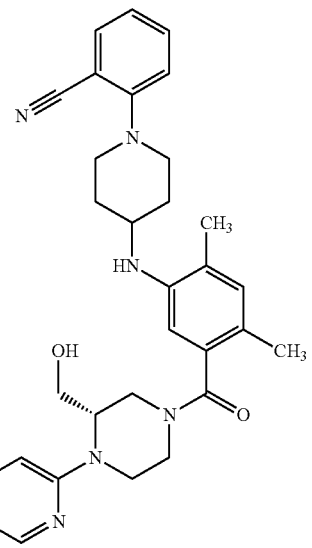
I-118
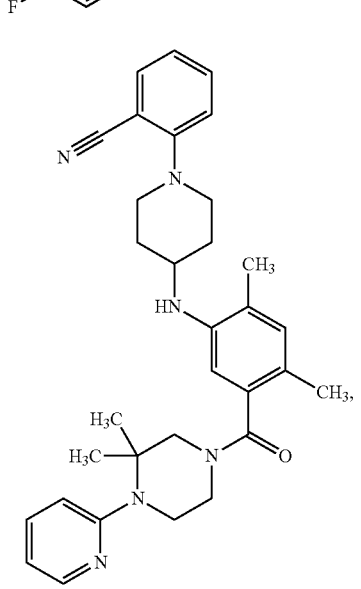
I-119
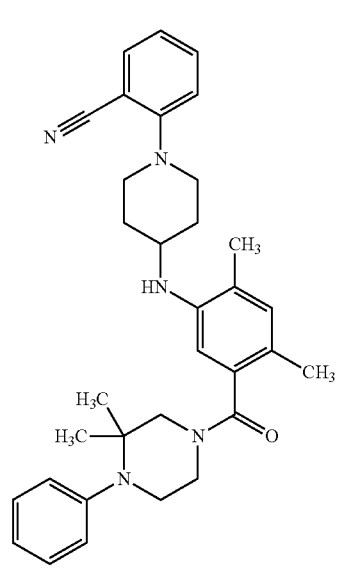

-continued
I-120
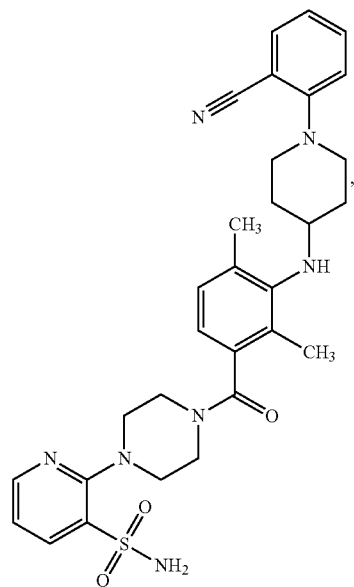
I-121
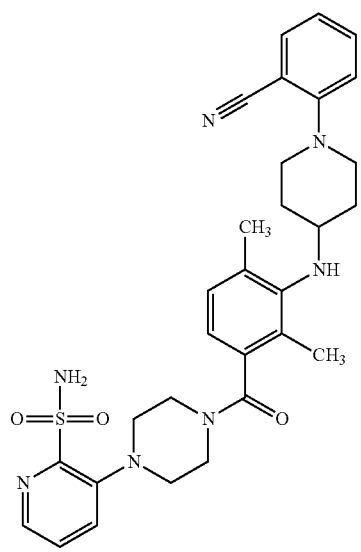
I-122
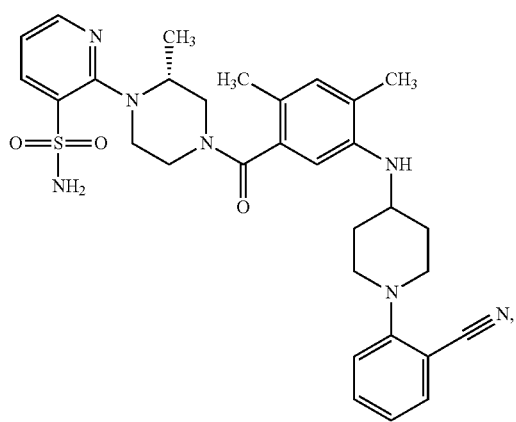
-continued
I-123
I-124
I-125

I-126
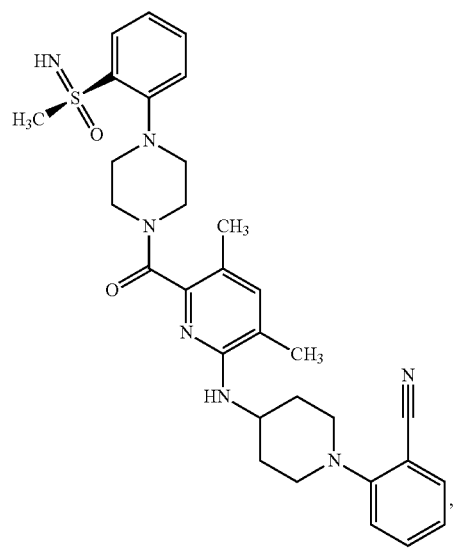
I-127
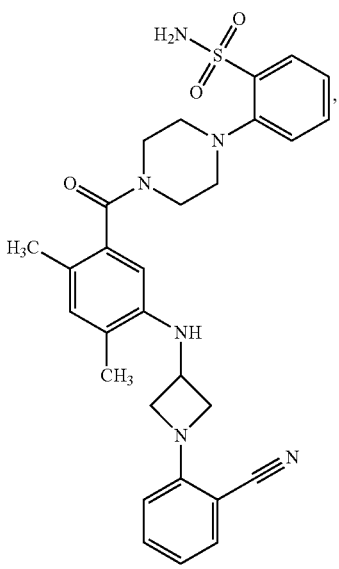
I-128
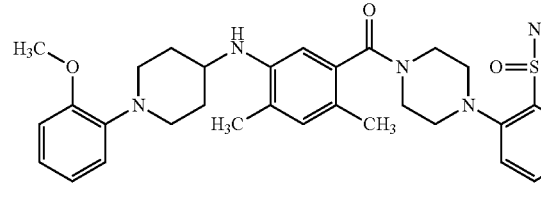
I-129
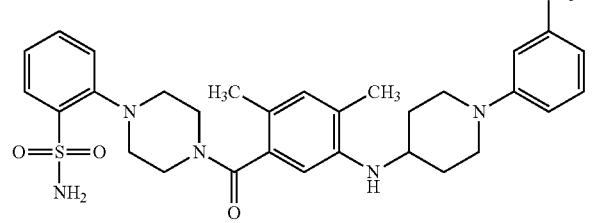
I-130
I-131
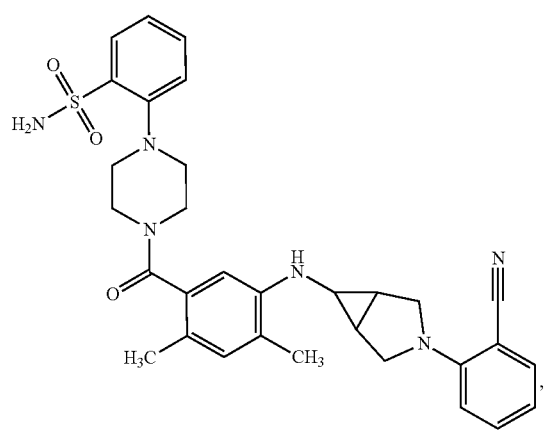
I-132
I-133
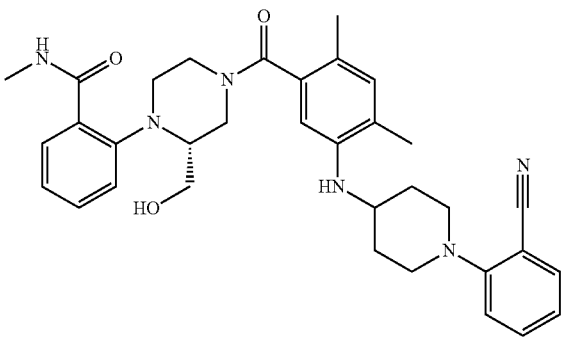

I-134
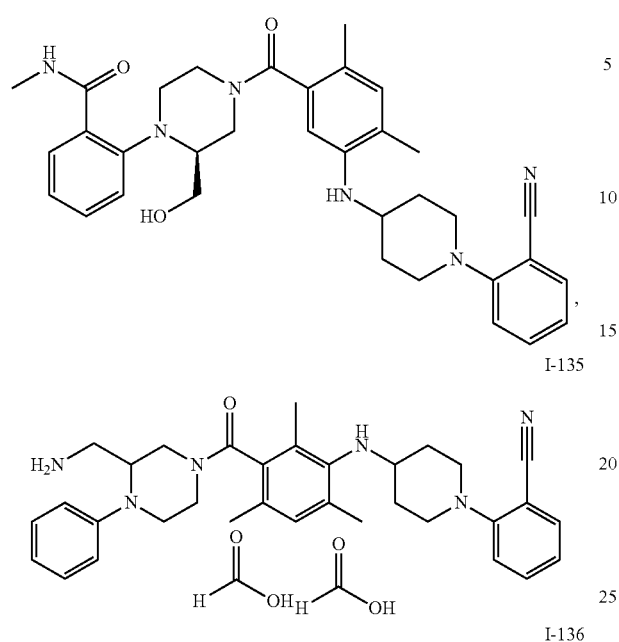
I-135
I-136
I-137
I-138
I-139
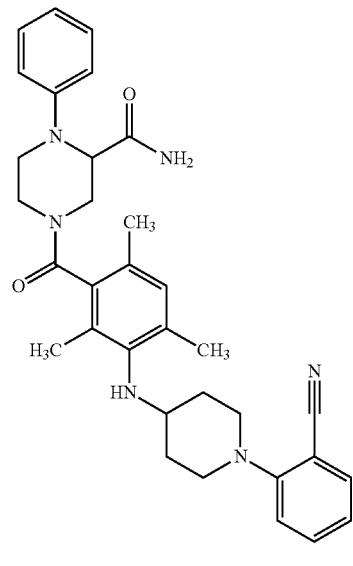
I-140
I-141

I-142
I-143
I-144
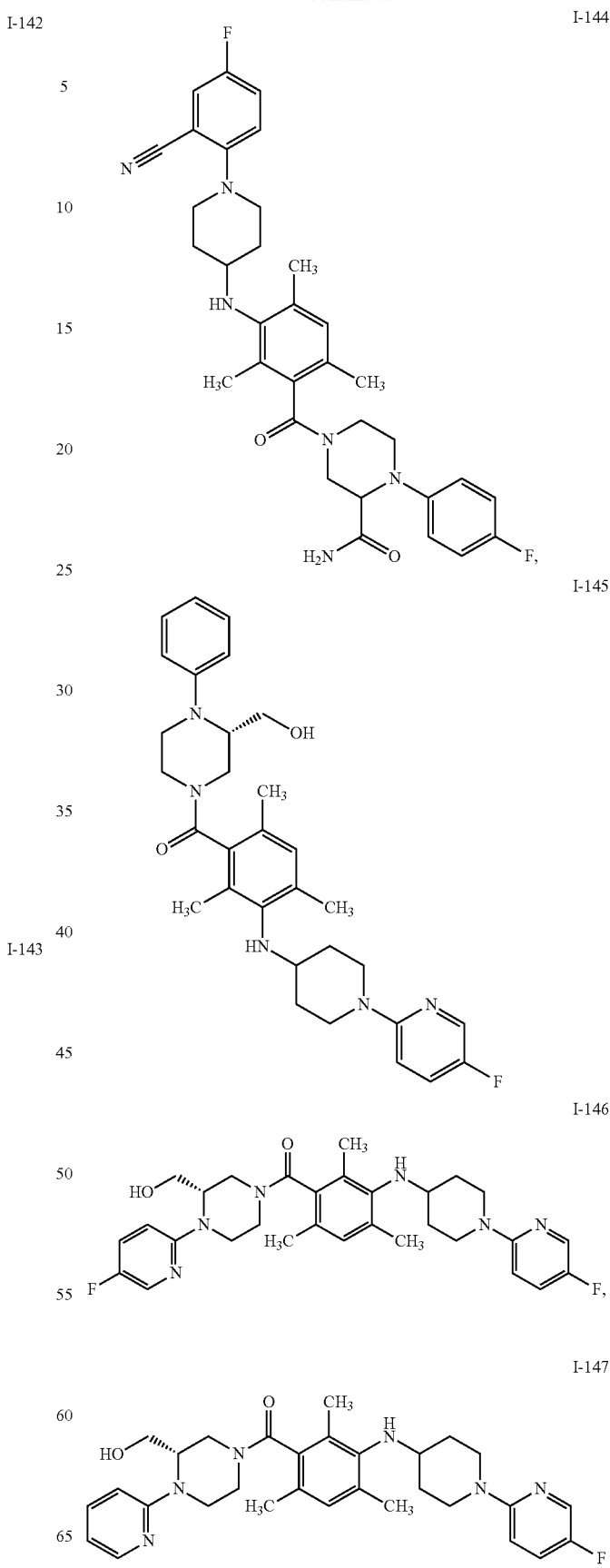
I-145
I-146
I-147

-continued
I-148
I-149
I-150
I-151
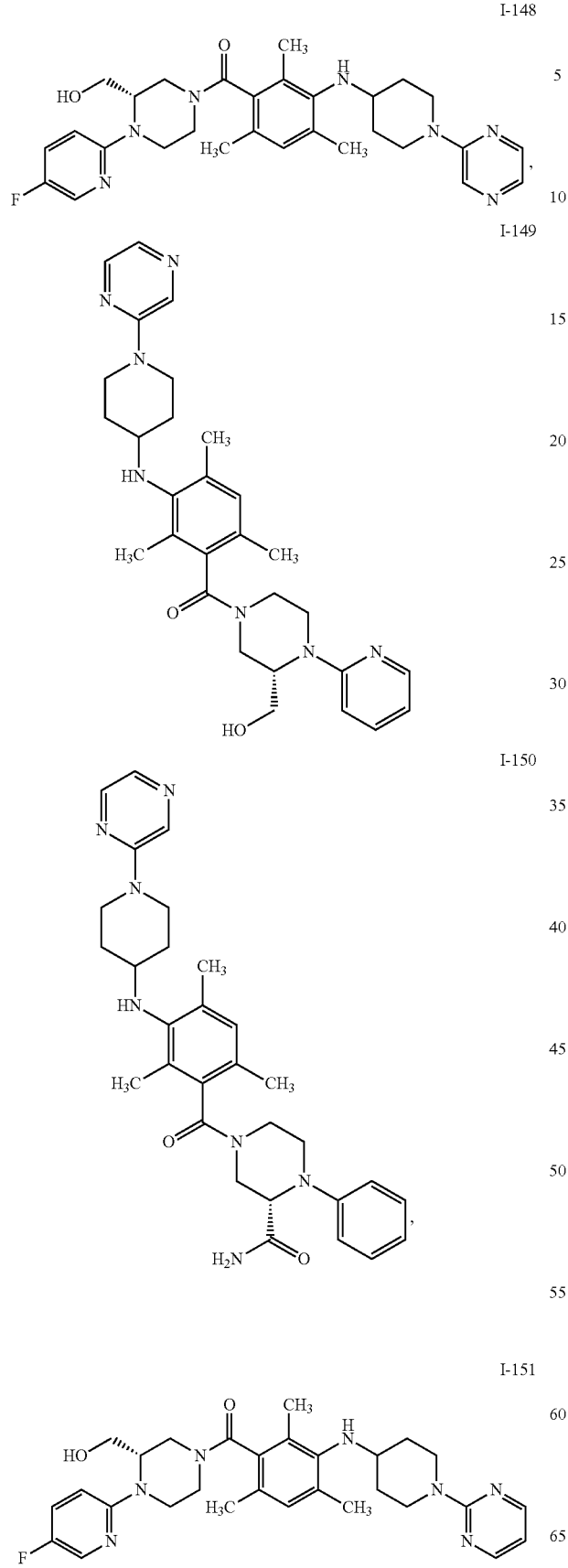
-continued
I-152
I-153
I-154
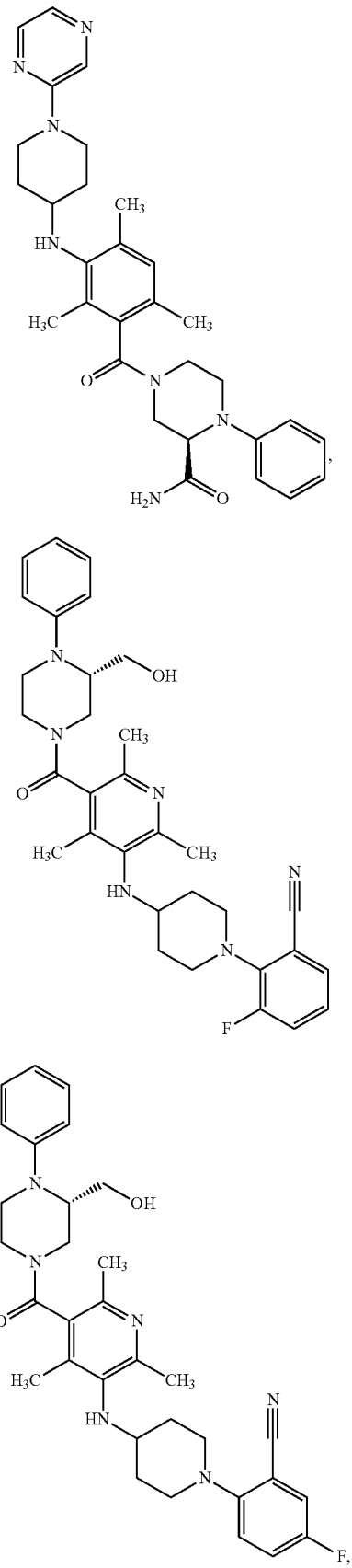

I-155
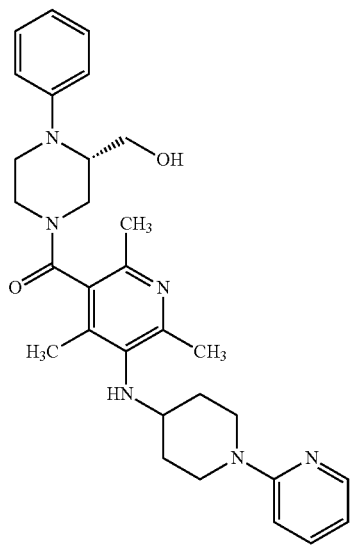
I-156
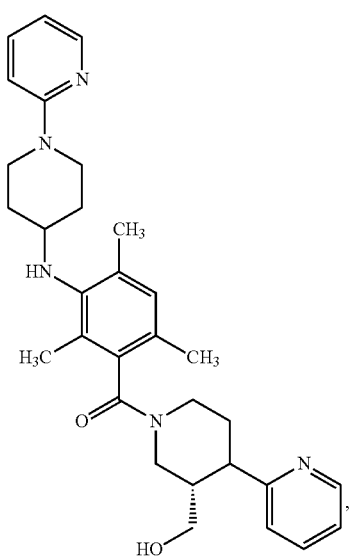
I-157
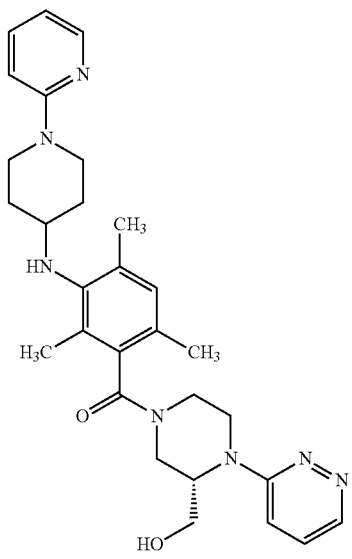
I-158
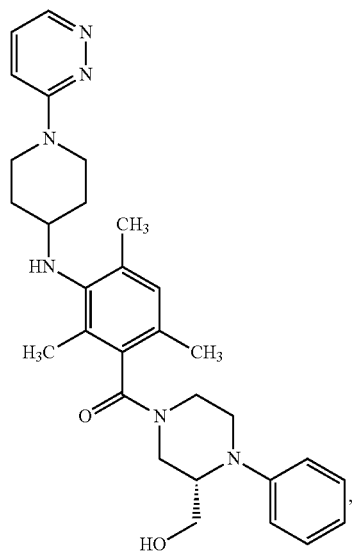
I-159
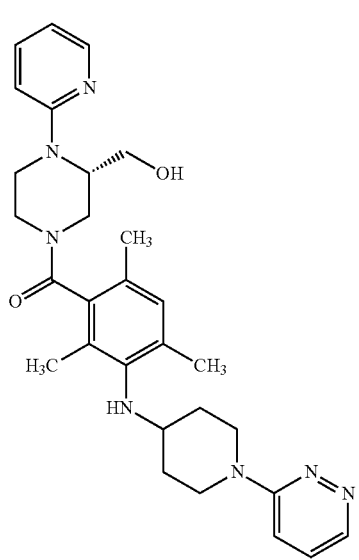
I-160
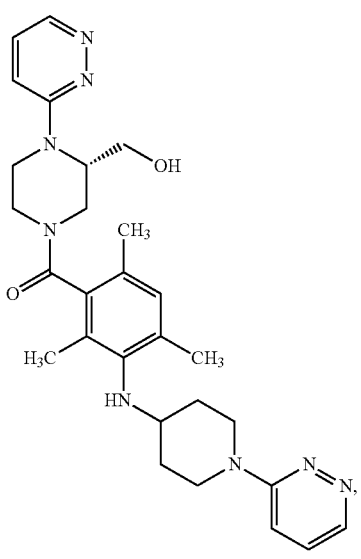

I-161
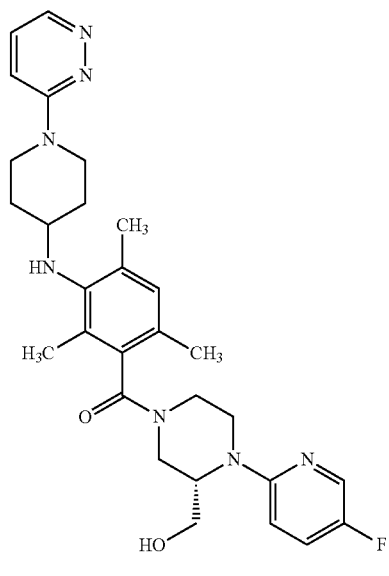
I-162
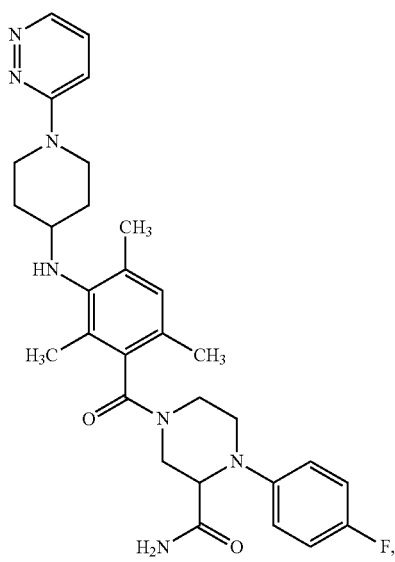
I-163
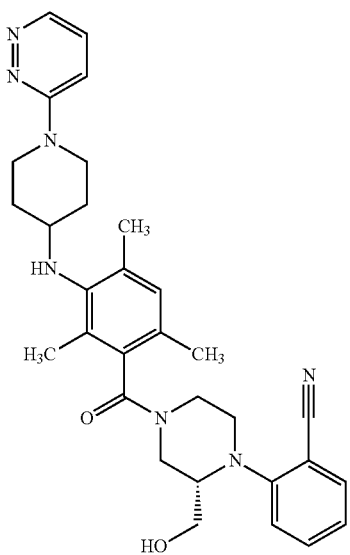
I-164
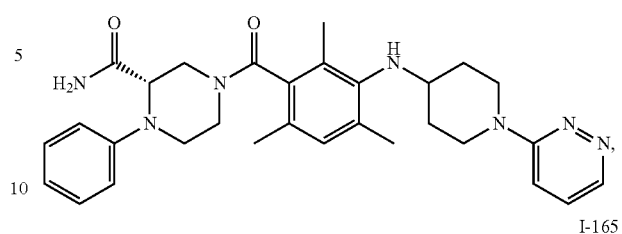
I-165
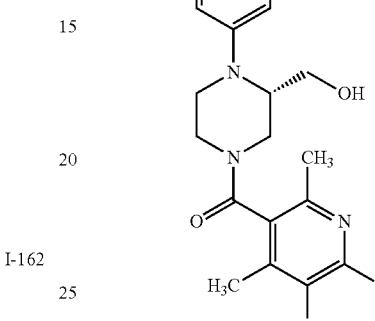
I-166
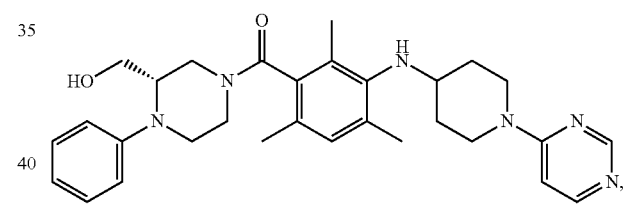
I-167
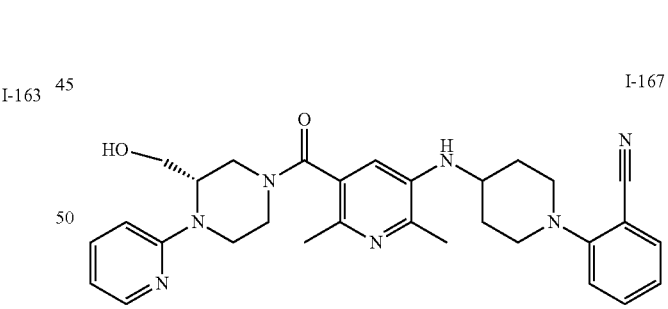
I-168
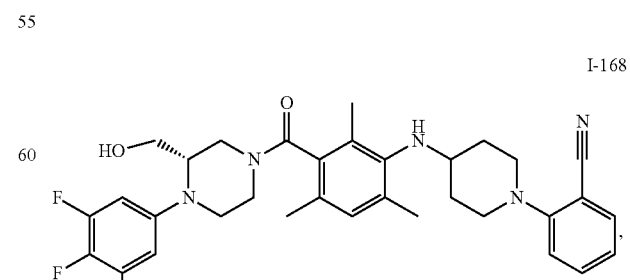

I-169
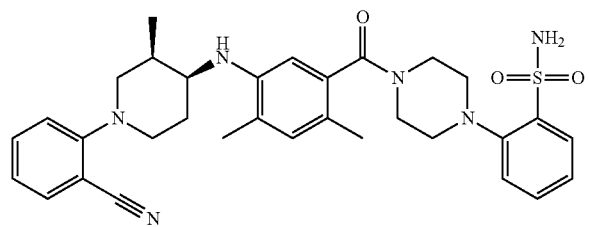
I-170
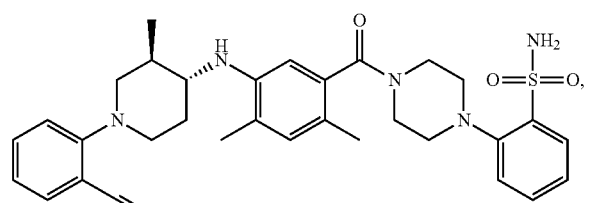
I-171
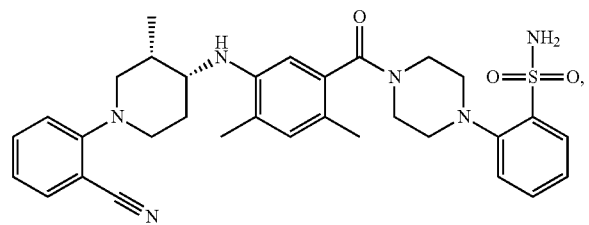
I-172
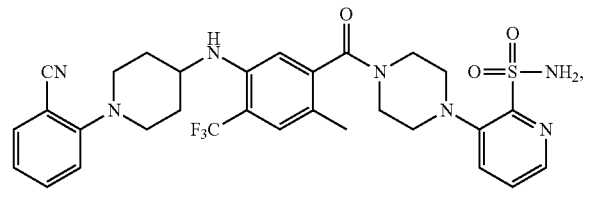
I-173
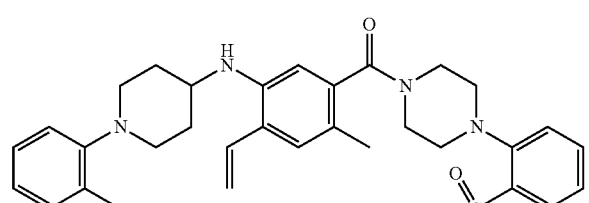
I-174
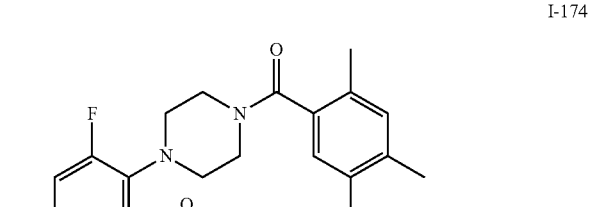
I-175
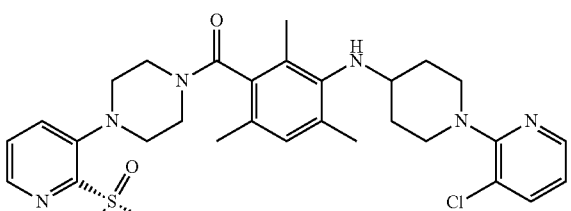
I-176
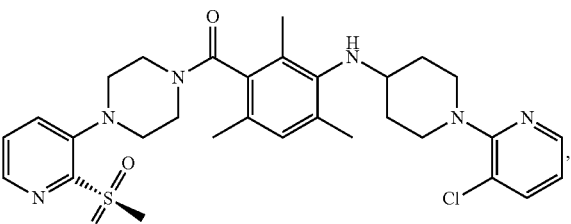
I-177
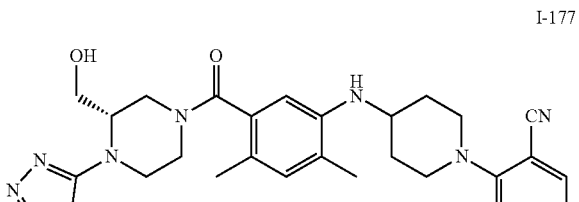
I-178
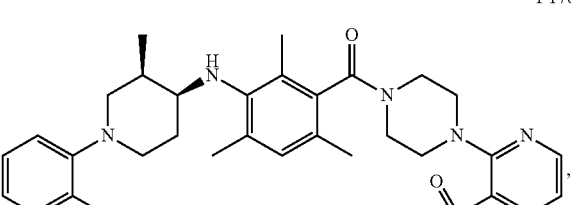
I-179
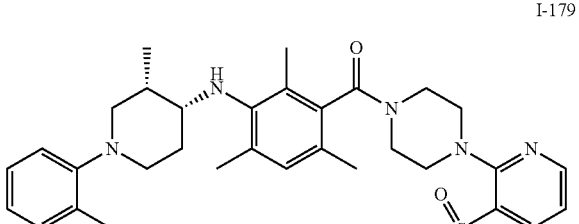
I-180
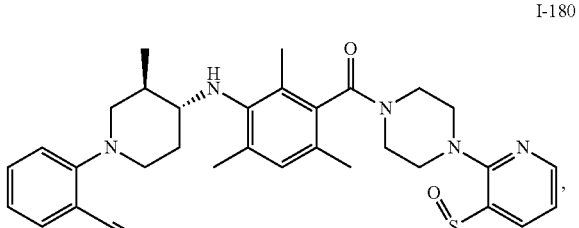

I-181
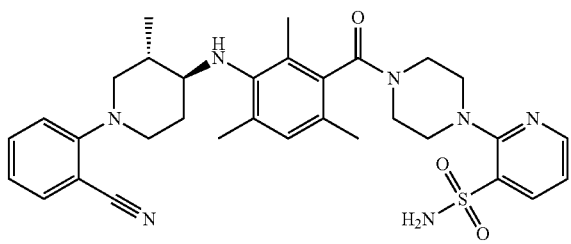
I-182
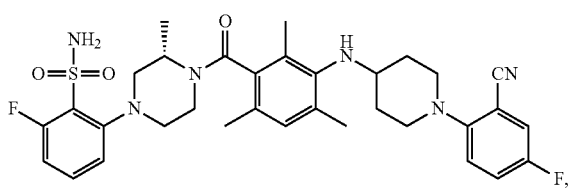
I-183
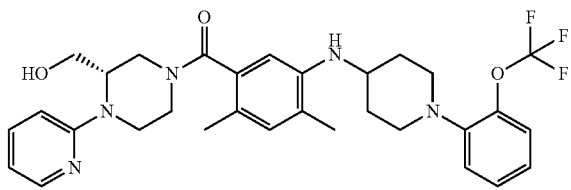
I-184
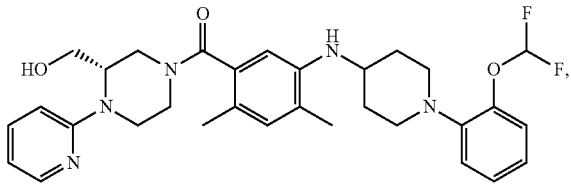
I-185
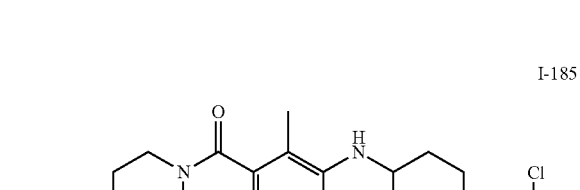
I-186
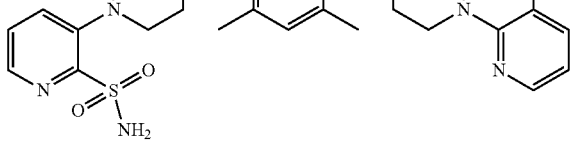
I-187
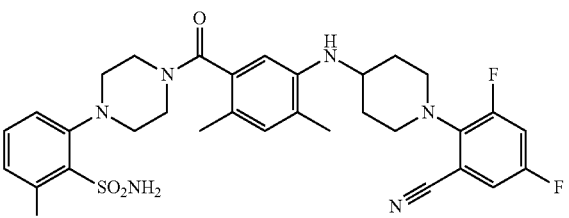
I-188
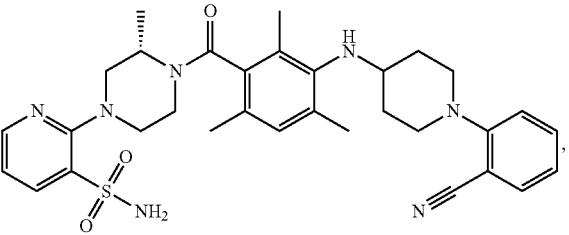
I-189
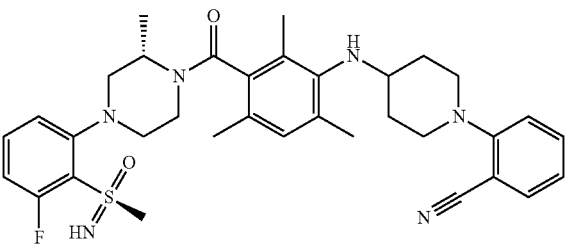
I-190
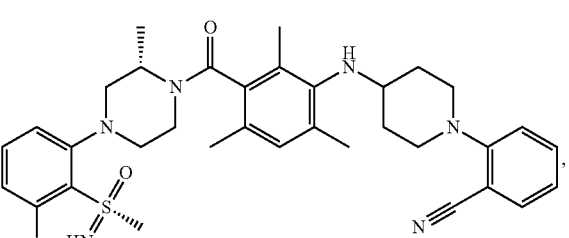
I-191
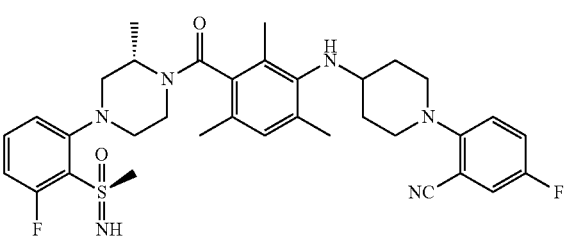
I-192
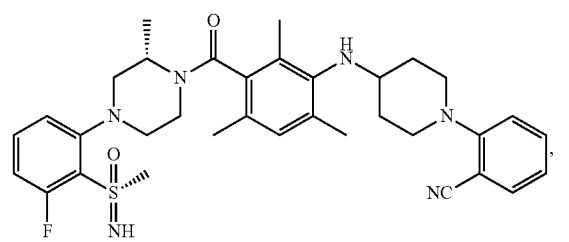

-continued

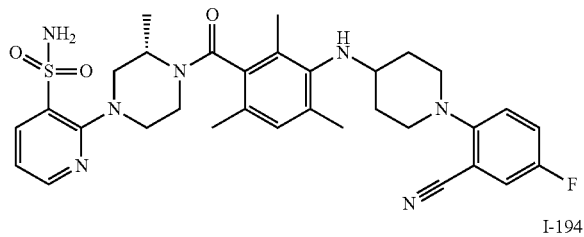
I-193

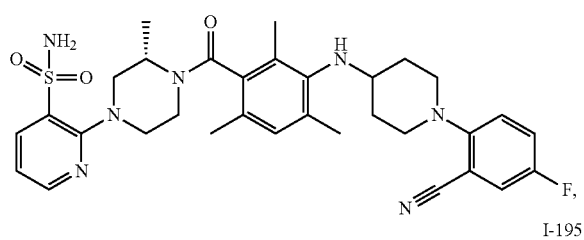
I-194

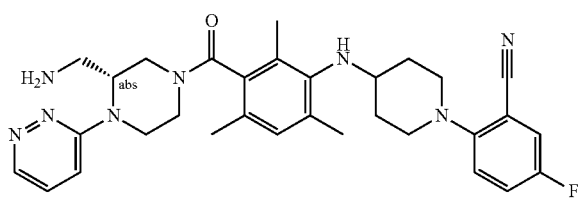
I-195

In some embodiments, the present invention provides a compound set forth in Table 1, above, or a pharmaceutically acceptable salt thereof. It will be appreciated that the present invention also provides a compound set forth in Table 1, above, as a racemic mixture, or a pharmaceutically acceptable salt thereof.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit mTORC1, in a biological sample or in a patient. In certain embodiments, the amount of compound in compositions of this invention is such that is effective to measurably inhibit mTORC1, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of mTORC1.

The activity of a compound utilized in this invention as an inhibitor of mTORC1, may be assayed in vitro, in vivo or in a cell line. In vitro assays include assays that determine the inhibition of mTORC1. Detailed conditions for assaying a compound utilized in this invention as an inhibitor of mTORC1 are well known to one of ordinary skill in the art. Such methods are described in detail by Liu et al., *Cancer Research*, 73(8), Apr. 15, 2013 and Liu et al., *J. Biological Chemistry*, vol 287, no. 13, pp 9742-9752 (2012).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of mTORC1 and are therefore useful for treating one or more disorders associated with activity of mTORC1. Thus, in certain embodiments, the present invention provides a method for treating an mTORC1-mediated disorder comprising the step of administering to a patient in need thereof a compound of the present invention, or pharmaceutically acceptable composition thereof.

As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role. In certain embodiments, an mTORC1-mediated disorder, disease, and/or condition is selected from those described by Matt Kaeberlin, *Scientifica*, vol. 2013, Article ID 849186.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of mTORC1 or an increased expression or activity of a mTORC1 relative to normal tissues or to other cancers of the same tissues; methods known in the art and described herein can be used to identify those cancers. In some embodiments, the methods include obtaining a sample comprising cells of the cancer, determining the mTORC1 activity in the sample, and administering a treatment as described herein (e.g., a provided inhibitor of mTORC1). In some embodiments, the cancer is one that is shown herein to have increased levels of mTORC1 activity In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by inhibiting mTORC1 activity. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Fibrotic Diseases

Idiopathic Pulmonary Fibrosis (IPF). The PI3K pathway is activated in fibrotic foci, the cardinal lesions in IPF. mTOR kinase inhibitor GSK2126458 reduces PI3K pathway signaling and functional responses in IPF-derived lung fibroblasts and mTOR inhibition reduces collagen expression in models of IPF patients. In the bleomycin model of pulmonary fibrosis, rapamycin treatment is antifibrotic, and rapamycin also decreases expression of α-smooth muscle actin and fibronectin by fibroblasts in vitro.

In some embodiments, the method of inhibiting mTORC1 activity is used to treat idiopathic pulmonary fibrosis (IPF). (See Thorax. 2016, 71(8), pp. 701-11; PLoS One. 2012, 7(7)). Accordingly, in some embodiments, the present invention provides a method of treating idiopathic pulmonary fibrosis (IPF), in a patient in need thereof, comprising the step of administering to said patient a provided compound or pharmaceutically acceptable salt thereof.

Kidney Fibrosis. mTORC1 is activated in myofibroblasts, a major pathogenic cell type in kidney fibrosis. Inhibition of mTOR with rapamycin in a murine model of kidney fibrosis (UUO), attenuated expression of markers of fibrosis and tubulointerstitial damage.

In some embodiments, the method of inhibiting mTORC1 activity is used to treat kidney fibrosis. (See J Am Soc Nephrol 2013, 24, pp. 1114-1126; Kidney International 2006, 69, pp. 2029-2036; PLoS 2012, 7, Issue 3, e33626; Clin Invest Med 2014, Vol 37, no 3, E142). Accordingly, in some embodiments, the present invention provides a method of treating kidney fibrosis, in a patient in need thereof, comprising the step of administering to said patient a provided compound or pharmaceutically acceptable salt thereof.

In some embodiments, the method of inhibiting mTORC1 activity is used to treat scleroderma. (See J Invest Dermatol. 2015 November; 135(11): 2873-6). Accordingly, in some embodiments, the present invention provides a method of treating scleroderma, in a patient in need thereof, comprising the step of administering to said patient a provided compound or pharmaceutically acceptable salt thereof.

In some embodiments, the method of inhibiting mTORC1 activity is used to treat hypertrophic scarring and keloid disease. (See Am J Pathol. 2012 November; 181(5): 1642-58). Accordingly, in some embodiments, the present invention provides a method of treating hypertrophic scarring and keloid disease, in a patient in need thereof, comprising the step of administering to said patient a provided compound or pharmaceutically acceptable salt thereof.

In some embodiments, the method of inhibiting mTORC1 activity is used to treat cardiac fibrosis. (See J Mol Cell Cardiol. 2016 February; 91: 6-9). Accordingly, in some embodiments, the present invention provides a method of treating cardiac fibrosis, in a patient in need thereof, comprising the step of administering to said patient a provided compound or pharmaceutically acceptable salt thereof.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Other Disorders

Other disorders include lysosomal storage diseases, including but not limited to Pompe disease, Gaucher disease, mucopolysaccharidosis, multiple sulfatase deficiency; neurodegenerative diseases such as Parkinson's disease, Alzheimer's disease, Huntington's disease, alpha1-antitrypsin deficiency, and spinal bulbar muscular atrophy. The present invention provides compounds that were shown to cause translocation of TFEB to the nucleus. TFEB translocation to the nucleus promotes exocytosis and/or cellular clearance of accumulating substrates in the above-mentioned diseases.

In some embodiments, the method of inhibiting mTORC1 activity is used to treat asthma. (See Respirology 2015 October; 20(7): 1055-65). Accordingly, in some embodiments, the present invention provides a method of treating asthma, in a patient in need thereof, comprising the step of administering to said patient a provided compound or pharmaceutically acceptable salt thereof.

In some embodiments, the method of inhibiting mTORC1 activity is used to treat a lysosomal storage disease. (See Annals of the New York Academy of Sciences, 2016, Volume 1371, Issue 1, pp. 3-14; Hum Mol Genet. 2015, 24(20), pp. 5775-88; EMBO Mol Med. 2013, 5(5), pp. 691-706; Medina, D. L., et al., Dev Cell. 2011 Sep. 13, 21(3), pp. 421-30). Accordingly, in some embodiments, the present invention provides a method of treating a lysosomal storage disease, in a patient in need thereof, comprising the step of administering to said patient a provided compound or pharmaceutically acceptable salt thereof.

In some embodiments, the method of inhibiting mTORC1 activity is used to treat Parkinson's disease. (See Proc Natl Acad Sci USA. 2013, 110(19):E1817-26). Accordingly, in some embodiments, the present invention provides a method of treating Parkinson's disease, in a patient in need thereof, comprising the step of administering to said patient a provided compound or pharmaceutically acceptable salt thereof.

In some embodiments, the method of inhibiting mTORC1 activity is used to treat Alzheimer's disease. (See EMBO Mol Med. 2014, 6(9), pp. 1142-60). Accordingly, in some embodiments, the present invention provides a method of treating Alzheimer's disease, in a patient in need thereof, comprising the step of administering to said patient a provided compound or pharmaceutically acceptable salt thereof.

In some embodiments, the method of inhibiting mTORC1 activity is used to treat Huntington's disease. (See Sci Transl Med. 2012, 4(142):142ra97). Accordingly, in some embodiments, the present invention provides a method of treating Huntingtons's disease, in a patient in need thereof, comprising the step of administering to said patient a provided compound or pharmaceutically acceptable salt thereof.

In some embodiments, the method of inhibiting mTORC1 activity is used to treat alpha1-anti-trypsin deficiency. (See EMBO Mol Med. 2013, 5(3), pp. 397-412). Accordingly, in some embodiments, the present invention provides a method of treating alpha1-anti-trypsin deficiency, in a patient in need thereof, comprising the step of administering to said patient a provided compound or pharmaceutically acceptable salt thereof.

In some embodiments, the method of inhibiting mTORC1 activity is used to treat spinal bulbar muscular atrophy. (See Nat Neurosci. 2014, 17(9), pp. 1180-9). Accordingly, in some embodiments, the present invention provides a method of treating spinal bulbar muscular atrophy, in a patient in need thereof, comprising the step of administering to said patient a provided compound or pharmaceutically acceptable salt thereof.

The present invention provides compounds that are inhibitors of mTORC1 activity and were shown to selectively inhibit mTORC1 over mTORC2 as measured by pS6K inhibition (a measure of mTORC1 activity) and pAKT activation (a measure of mTORC2 activity). In some embodiments, a provided compound inhibits mTORC1 selectively over mTORC2. In some embodiments, a provided compound does not measurably inhibit mTORC2. In some embodiments, a provided compound has a pAKT activation $IC_{50}$ of >10 µM. In some embodiments, a provided compound inhibits mTORC1 with >10-fold selectivity over mTORC2. In some embodiments, a provided compound inhibits mTORC1 with >20-fold selectivity over mTORC2. In some embodiments, a provided compound inhibits mTORC1 with >50-fold selectivity over mTORC2. In some embodiments, a provided compound inhibits mTORC1 with >100-fold selectivity over mTORC2. In some embodiments, a provided compound inhibits mTORC1 with >150-fold selectivity over mTORC2. In some embodiments, a provided compound inhibits mTORC1 with >200-fold selectivity over mTORC2. In some embodiments, a provided compound inhibits mTORC1 with >500-fold selectivity over mTORC2. In some embodiments, a provided compound inhibits mTORC1 with >1,000-fold selectivity over mTORC2. Accordingly, in some embodiments, the present invention provides a method of treating a disorder associate with mTORC1 comprising administering to patient a compound that inhibits mTORC1 wherein said compound does not inhibit mTORC2. Such compounds may be employed for indications where rapamycin and rapalogs demonstrated a benefit either in animal models or in a human disease setting. Such indications include:

Treatment of Metabolic Disease (Obesity and Insulin Resistance in Type 2 Diabetes). Inhibition of mTORC1 pathway leads to extension of life span in yeast, fly and mouse, and caloric restriction improves longevity and insulin sensitivity. The underlying mechanism has been proposed to function by regulation of mTORC1 activation. Rapamycin-induced insulin resistance has been shown to be mediated by inhibition of mTORC2 and selective mTORC1 inhibitor is predicted to improve insulin sensitivity and glucose homeostasis.

In some embodiments, the method of inhibiting mTORC1 activity is used to treat metabolic disease (obesity and insulin resistance in type 2 diabetes). (See J Gerontol A Biol Sci Med Sci 2015, 70 (4), pp. 410-20; Aging Cell 2014, 13 (2), pp. 311-9; Diabetologia 2016, 59(3), pp. 592-603; Science 2012, 335, pp. 1638-1643). Accordingly, in some embodiments, the present invention provides a method of treating metabolic disease (obesity and insulin resistance in type 2 diabetes), in a patient in need thereof, comprising the step of administering to said patient a provided compound or pharmaceutically acceptable salt thereof.

Neurofibromatosis. Neurofibromatosis type 1 (NF1) is caused by mutations in the NF1 gene. Its protein product, neurofibromin, functions as a tumor suppressor and ultimately produces constitutive upregulation of mTOR. mTOR inhibitors have been shown to reduce tumor size and induce anti-proliferative effect in NF1-associated plexiform neurofibroma.

In some embodiments, the method of inhibiting mTORC1 activity is used to treat neurofibromatosis. (See Curr Neurol Neurosci Rep. 2012 Jun. 12(3), pp. 294-301; Oncotarget. 2016 Jan. 31). Accordingly, in some embodiments, the present invention provides a method of treating neurofibromatosis, in a patient in need thereof, comprising the step of administering to said patient a provided compound or pharmaceutically acceptable salt thereof.

Cardiomyopathy and skeletal muscle dystrophy, Emery-Dreifuss muscular dystrophy model (LMNA$^{-/-}$). Mutations in LMNA result in several human diseases including limb-girdle muscular dystrophy (LGMD1B), Emery-Dreifuss muscular dystrophy (EDMD2/3), dilated cardiomyopathy (DCM) and conduction-system disease (CMD1A), lipodystrophy, Charcot-Marie-Tooth disease, and Hutchinson-Gilford progeria syndrome (HGPS). Lmna$^{-/-}$ mice have elevated mTORC1 activity and short-term treatment with rapamycin in Lmna$^{-/-}$ mice results in reduced mTORC1 signaling, improved cardiac and skeletal muscle function and enhanced survival by ~50%.

In some embodiments, the method of inhibiting mTORC1 activity is used to treat cardiomyopathy and skeletal muscle dystrophy. (See Sci Transl Med. 2012, 4(144):144ra103; Handb Clin Neurol. 2013, 113, pp. 1367-76). Accordingly, in some embodiments, the present invention provides a method of treating cardiomyopathy and skeletal muscle dystrophy, in a patient in need thereof, comprising the step of administering to said patient a provided compound or pharmaceutically acceptable salt thereof.

Leigh syndrome. Ndufs4 knockout (KO) mice are used as a model of Leigh syndrome and exhibit hyperactivation of mTORC1 and metabolic defects. Treatment of Ndufs4 KO mice with rapamycin extended lifespan, improve metabolic and neurological defect associated with this disease.

In some embodiments, the method of inhibiting mTORC1 activity is used to treat Leigh syndrome. (See Science 2013, 342(6165), pp. 1524-8). Accordingly, in some embodiments, the present invention provides a method of treating Leigh syndrome, in a patient in need thereof, comprising the step of administering to said patient a provided compound or pharmaceutically acceptable salt thereof.

Oncology. Inhibition of mTOR with rapalogs has been shown to have antitumor activity in murine cancer models and in cancer patients. Examples of sensitive cancer types include, but are not limited to, hepatocellular carcinoma, breast cancers, mantle cell lymphomas, lung carcinoma, tuberous sclerosis and lymphangioleiomyomatosis.

In some embodiments, the method of inhibiting mTORC1 activity is used to treat cancer and oncologic disorders. (See Trends Cancer 2016; In press). Accordingly, in some embodiments, the present invention provides a method of treating cancer and oncologic disorders, in a patient in need thereof, comprising the step of administering to said patient a provided compound or pharmaceutically acceptable salt thereof.

Non-alcoholic steatohepatitis (NASH). The present invention provides inhibitors that induce autophagy to clear degraded cytoplasmic proteins, and NASH disease is characterized by lipid deposits, inflammation and fibrosis in the liver. The inhibition of mTORC1 pathway induce autophagy and down regulate SREBP-1 to decrease lipid biosynthesis to reduce lipid storage.

In some embodiments, the method of inhibiting mTORC1 activity is used to treat non-alcoholic steatohepatitis (NASH). (See J Clin Exp Hepatol 2014; 4(1), pp. 51-9). Accordingly, in some embodiments, the present invention provides a method of treating non-alcoholic steatohepatitis (NASH), in a patient in need thereof, comprising the step of administering to said patient a provided compound or pharmaceutically acceptable salt thereof.

Tuberous sclerosis (TSC) and lymphangioleiomyomatosis (LAM). Failure in the regulation of mTOR is critical to the pathogenesis of the inherited disorder tuberous sclerosis complex (TSC) and the related lung disease, lymphangioleiomyomatosis (LAM). Both diseases are caused by mutations of TSC1 or TSC2 leading to inappropriate activity of signaling downstream of mTORC1. TSC patients develop nonmalignant tumors in many organs, including the brain, while LAM patients, mostly women, accumulate abnormal, muscle-like cells in certain organs or tissues, especially the lungs, lymph nodes, and kidneys. The rapalogs, Everolimus and Sirolimus, are currently approved for the treatment of both TSC and LAM, respectively, by the US FDA.

In some embodiments, the method of inhibiting mTORC1 activity is used to treat tuberous sclerosis and lymphangioleiomyomatosis. (See J. Clin. Invest. 2011, 121, pp. 1231-1241; J. Clin Epidemiol. 2015, 7, pp. 249-57). Accordingly, in some embodiments, the present invention provides a method of treating tuberous sclerosis and lymphangioleiomyomatosis, in a patient in need thereof, comprising the step of administering to said patient a provided compound or pharmaceutically acceptable salt thereof.

Senescence and diseases of aging. Rapamycin suppresses the mammalian TORC1 complex, which regulates translation, and extends lifespan in diverse species, including mice. Rapamycin was shown to inhibit the pro-inflammatory phenotype of senescent cells. As senescent cells accumulate with age, the senescence-associated secretory phenotype (SASP) can disrupt tissues and contribute to age-related pathologies, including cancer. Inhibition of mTOR suppressed the secretion of inflammatory cytokines by senescent cells. Rapamycin reduced cytokine levels including IL6 and suppressed translation of the membrane-bound cytokine IL1A. Reduced IL1A diminishes NF-κB transcriptional activity, which controls the SASP. Thus, mTORC1 inhibitors might ameliorate age-related pathologies, including late-life cancer, by suppressing senescence-associated inflammation.

In some embodiments, the method of inhibiting mTORC1 activity is used to treat senescence and diseases of aging. (See Nature Cell Biology 17, 2015, pp. 1049-1061; Free Radic Biol Med. 2016 June; 95:133-54). Accordingly, in some embodiments, the present invention provides a method of treating senescence and diseases of aging, in a patient in need thereof, comprising the step of administering to said patient a provided compound or pharmaceutically acceptable salt thereof.

Additional therapeutic indications where mTORC inhibition may be beneficial are: cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis.

In some embodiments, the method of inhibiting mTORC1 activity is used to treat cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis. Accordingly, in some embodiments, the present invention provides a method of treating cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis, in a patient in need thereof, comprising the step of administering to said patient a provided compound or pharmaceutically acceptable salt thereof.

In some embodiments, the present invention is an inhibitor of members of the glucose transporter (GLUT) family. In some embodiments, the present invention is a pan-glucose inhibitor, inhibiting GLUT subtypes 1, 2, 3, 4, and 5. In some embodiments, the present invention is an inhibitor of one or more GLUT subtypes, individually or severally.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In other embodiments, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

List of common abbreviations used in the experimental section.

4A MS: 4 Å molecular sieves
AcOH: acetic acid
Anhyd: anhydrous
aq: aqueous
$BH_3$-THF: borane tetrahydrofuran complex
BINAP: (2,2'-bis(diphenylphosphino)-1,1'-binaphthyl)
Bn: benzyl
Boc: tert-butoxycarbonyl
$(Boc)_2O$: di-tert-butyl dicarbonate
BrettPhos: 2-(Dicyclohexylphosphino)3,6-dimethoxy-2',4',6'-triisopropyl-1,1'-biphenyl
CbzCl: benzyl chloroformate
Cbz-OSU: N-(Benzyloxycarbonyloxy)succinimide
CHIRAL-HPLC: chiral high performance liquid chromatography
CMBP: (cyanomethylene)tributylphosphorane
Conc.: concentrated
CuCN: copper cyanide
d: days
DAST: diethylaminosulfur trifluoride
DavePhos: 2-Dicyclohexylphosphino-2'-(N,N-dimethylamino)biphenyl
dba: dibenzylideneacetone DBU: 1,8-diazobicyclo[5.4.0]undec-7-ene
DCE: 1,2-dichloroethane
DCM: dichloromethane
DEA: diethylamine
DIBAL-H: diisobutylaluminium hydride
DIPEA: N,N-diisopropylethylamine
DMA: N,N-dimethylacetamide
DMAP: 4-dimethylaminopyridine
DMF: N,N-dimethylformamide
DMPU: 1,3-dimethyl-3,4,5,6-tetrahydro-2-pyrimidinone
DMSO: dimethyl sulfoxide
DPPA: diphenylphosphoryl azide
dppf: 1,1'-bis(diphenylphosphino)ferrocene
EA: ethyl acetate
EDCI: 1-(3-dimethylaminopropyl)-3-ethylcarbodiimide hydrochloride
EDTA: ethylenediaminetetraacetic acid
ee: enantiomeric excess
ESI: electrospray ionization
Et$_3$N: triethylamine
Et$_2$O: diethyl ether
EtOAc: ethyl acetate
EtOH: ethanol
Fmoc: fluorenylmethyloxycarbonyl
Fmoc-OSu: N-(9-fluorenylmethoxycarbonyloxy)succinimide
h: hours
HATU: N,N,N',N'-tetramethyl-O-(7-azabenzotriazol-1-yl)uranium hexafluorophosphate
HOBT: Hydroxybenzotriazole
HPLC: high performance liquid chromatography
HCl: hydrochloric acid
IBX: 2-iodoxybenzoic acid
IPA: isopropyl alcohol
JackiePhos: 2-{Bis[3,5-bis(trifluoromethyl)phenyl]phosphino}-3,6-dimethoxy 2',4',6'-triisopropyl-1,1'-biphenyl, Bis(3,5-bis(trifluoromethyl)phenyl)(2',4',6'-triisopropyl-3,6-dimethoxybiphenyl-2-yl)phosphine
LDA: lithium diisopropylamide
M: molar
mCPBA: meta-chloroperoxybenzoic acid
Me: methyl
MeCN: acetonitrile
MeOH: methanol
MgO: magnesium oxide
min: minutes
mL: milliliters
mM: millimolar
mmol: millimoles
MOM: methoxymethyl
MsCl: Mesyl Chloride
MTBE: methyl tert-butyl ether
NMP: N-methyl-2-pyrrolidone
n-BuLi: n-butyl lithium
NBS: N-bromosuccinimide
NIS: N-iodosuccinimide
NMO: 4-methylmorpholine N-oxide
NMP: N-methylpyrrolidine
NMR: Nuclear Magnetic Resonance
° C.: degrees Celsius
PBS: phosphate buffered saline
Pd/C: palladium on carbon
Pd$_2$(dba)$_3$: tris(dibenzylideneacetone)dipalladium(0)
PE: petroleum ether
prep-HPLC: preparative high performance liquid chromatography
P(o-tol)$_3$: tri(o-tolyl)phosphine
PTFE: polytetrafluoroethylene
Rel: relative
rt: room temperature
RuPhos: 2-dicyclohexylphosphino-2',6'-diisopropoxybiphenyl
sat: saturated
SFC: supercritical fluid chromatography
SGC: silica gel chromatography
STAB: sodium triacetoxyborohydride
TBAB: Tetra-n-butylammonium bromide
TBAF: Tetra-n-butylammonium fluoride
TBSCl: tert-Butyldimethylsilyl chloride
tBuOK: potassium tert-butoxide
tBuONa: sodium tert-butoxide
TEA: triethylamine
TEBAC: Benzyltriethylammonium chloride
Tf: trifluoromethanesulfonate
TfAA: trifluoromethanesulfonic anhydride
TFA: trifluoracetic acid
TIPS: triisopropylsilyl
TLC: thin layer chromatography
THF: tetrahydrofuran
TMSCN: trimethylsilyl cyanide
pTSA: para-toluenesulfonic acid
TsOH: p-Toluenesulfonic acid
XantPhos: 4,5-Bis(diphenylphosphino)-9,9-dimethylxanthene
XPhos: 2-Dicyclohexylphosphino-2',4',6'-triisopropylbiphenyl LCMS Methods Samples were analyzed by LCMS using the following methods:
Method A: SunFire™ C18, 4.6*50 mm, 3.5 um column Xbridge C18 3.5 μm4.6×50 mm column. The elution system used was a gradient of 5%-95% over 1.5 min at 2 ml/min and the solvent was acetonitrile/0.01% aqueous TFA.
Method B: Xbridge C18 3.5 μm4.6×50 mm column, the elution system used was a gradient of 5%-95% over 1.5 min at 2 ml/min and the solvent was acetonitrile/10 mM ammonium acetate aqueous solution.
Samples were also analyzed using the following LCMS methods:

TABLE 2

| | LCMS Method 1 - | |
|---|---|---|
| Column | Kinetex Core-Shell C18 Part No. 00B-4601-AN 2.1 × 50 mm, 5 μm | |
| Column Temp | 40° C. | |
| Mobile Phase | A, Water + 0.1% Formic acid B, Acetonitrile + 0.1% Formic acid | |
| | Time (mins) | % organic |
| Gradient | 0.00 | 5 |
| | 1.20 | 100 |
| | 1.30 | 100 |
| | 1.31 | 5 |
| Flow rate | 1.2 ml/min | |
| Injection Vol | 3 μl | |
| | Detection | |
| Signal | UV 215 | |
| PDA Spectrum | Range: 210-420 nm step: 1 nm (Not MS14 this has single wavelength detector) | |
| MSD Signal settings | Scan Pos (Shimadzu): 100-1000 Scan Pos (MS14): 130-850 Scan Pos (MS11): 150-850 | |

TABLE 3

LCMS Method 2 -

| | |
|---|---|
| Column | Supelco Ascentis Express<br>Part No. 53802-U<br>2.1 × 30 mm, 2.7 μm |
| Column Temp | 40° C. |
| Mobile Phase | A, Water + 0.1% Formic acid<br>B, Acetonitrile + 0.1% Formic acid |

| | Time (mins) | % organic |
|---|---|---|
| Gradient | 0 | 5 |
| | 1.5 | 100 |
| | 1.6 | 100 |
| | 1.61 | 5 |

| | |
|---|---|
| Flow rate | 1 ml/min |
| Injection Vol | 3 μl |
| Detection | |
| Signal | UV 215 |
| PDA Spectrum | Range: 210-420 nm step: 1 nm<br>(Not MS14 this has single wavelength detector) |
| MSD Signal settings | Scan Pos (Shimadzu): 100-1000<br>Scan Pos (MS14): 130-850<br>Scan Pos (MS11): 150-850 |

TABLE 4

LCMS Method 3 -

| | |
|---|---|
| Column | Waters Atlantis dC18<br>Part No. 186001291<br>2.1 × 50 mm, 3 μm |
| Column Temp | 40° C. |
| Mobile Phase | A, Water + 0.1% Formic acid<br>B, Acetonitrile + 0.1% Formic acid |

| | Time (mins) | % organic |
|---|---|---|
| Gradient | 0.00 | 5 |
| | 2.50 | 100 |
| | 2.70 | 100 |
| | 2.71 | 5 |
| | 3.50 | 5 |

| | |
|---|---|
| Flow rate | 1 ml/min |
| Injection Vol | 3 μl |
| Detection | |
| Signal | UV 215 |
| PDA Spectrum | Range: 210-420 nm step: 1 nm<br>(Not MS14 this has single wavelength detector) |
| MSD Signal settings | Scan Pos (MS14): 130-850 |

TABLE 5

LCMS Method 4 -

| | |
|---|---|
| Column | Phenomenex Gemini-NX C18<br>00B-4453-B0<br>2.0 × 50 mm, 3 um |
| Column Temp | 40° C. |
| Mobile Phase | A, 2 mM amm. bicarbonate, buffered to pH 10<br>B, Acetonitrile |

| | Time (mins) | % organic |
|---|---|---|
| Gradient | 0.00 | 1 |
| | 1.80 | 100 |
| | 2.10 | 100 |
| | 2.30 | 1 |
| | 3.50 | 1 |

TABLE 5-continued

LCMS Method 4 -

| | |
|---|---|
| Flow rate | 1 ml/min |
| Injection Vol | 3 μl |
| Detection | |
| Signal | UV 215 |
| PDA Spectrum | Range: 210-420 nm step: 1 nm<br>(Not MS14 this has single wavelength detector) |
| MSD Signal settings | Scan Pos (MS10): 150-850<br>Scan Pos (MS14): 130-850 |

TABLE 6

LCMS Method 5 -

| | |
|---|---|
| Column | Waters Atlantis dC18<br>Part No. 186001295<br>2.1 × 100 mm, 3 μm |
| Column Temp | 40° C. |
| Mobile Phase | A, Water + 0.1% Formic acid<br>B, Acetonitrile + 0.1% Formic acid |

| | Time (mins) | % organic |
|---|---|---|
| Gradient | 0.00 | 5 |
| | 5.00 | 100 |
| | 5.40 | 100 |
| | 5.42 | 5 |
| | 7.00 | 5 |

| | |
|---|---|
| Flow rate | 0.6 ml/min |
| Injection Vol | 3 μl |
| Detection | |
| Signal | UV 215 |
| PDA Spectrum | Range: 210-420 nm step: 1 nm |
| MSD Signal settings | Scan Pos (Shimadzu): 100-1000<br>Scan Pos (MS11): 150-850 |

TABLE 7

LCMS Method 6 -

| | |
|---|---|
| Column | Phenomenex Gemini-NX C18<br>Part No. 00D-4453-B0<br>2.0 × 100 mm, 3 μm column |
| Column Temp | 40° C. |
| Mobile Phase | A, 2 mM amm. bicarbonate, buffered to pH 10<br>B, Acetonitrile |

| | Time (mins) | % organic |
|---|---|---|
| Gradient | 0.00 | 5 |
| | 5.50 | 100 |
| | 5.90 | 100 |
| | 5.92 | 5 |
| | 7.00 | 5 |

| | |
|---|---|
| Flow rate | 0.5 ml/min |
| Injection Vol | 3 μl |
| Detection | |
| Signal | UV 215 |
| PDA Spectrum | Range: 210-420 nm step: 1 nm<br>(Not MS14 this has single wavelength detector) |
| MSD Signal settings | Scan Pos (MS10): 150-850<br>Scan Pos (MS14): 130-850 |

TABLE 8

| | LCMS Method 7 - | |
|---|---|---|
| Column | Phenomenex Kinetix-XB C18 Part No. 00D-4498-AN 2.1 × 100 mm, 1.7 µm | |
| Column Temp | 40° C. | |
| Mobile Phase | A, Water + 0.1% Formic acid B, Acetonitrile + 0.1% Formic acid | |
| | Time (mins) | % organic |
| Gradient | 0.00 | 5 |
| | 5.30 | 100 |
| | 5.80 | 100 |
| | 5.82 | 5 |
| | 7.00 | 5 |
| Flow rate | 0.6 ml/min | |
| Injection Vol | 1 µl | |
| | Detection | |
| Signal | UV 215 | |
| PDA Spectrum | Range: 200-400 nm step: 1 nm | |
| MSD Signal settings | Scan Pos: 150-850 | |

TABLE 9

| | LCMS Method 8 - | |
|---|---|---|
| Column | Waters SymmetryShield RP8 Part No. WAT094257 2.1 × 50 mm, 3.5 µm | |
| Column Temp | 40° C. | |
| Mobile Phase | A, Water + 0.1% Formic acid B, Acetonitrile + 0.1% Formic acid | |
| | Time (mins) | % organic |
| Gradient | 0.00 | 5 |
| | 2.20 | 100 |
| | 2.70 | 100 |
| | 2.71 | 5 |
| Flow rate | 1 ml/min | |
| Injection Vol | 3 µl | |
| | Detection | |
| Signal | UV 215 | |
| PDA Spectrum | Range: 210-420 nm step: 1 nm | |
| MSD Signal settings | Scan Pos: 100-1000 | |

TABLE 10

| | LCMS Method 9 - | |
|---|---|---|
| Column | Phenomenex Gemini-NX C18 Part No. 00D-4453-B0 2.0 × 100 mm, 3 µm column | |
| Column Temp | 40° C. | |
| Mobile Phase | A, 2 mM amm. bicarbonate, buffered to pH 10 B, Acetonitrile | |
| | Time (mins) | % organic |
| Gradient | 0.00 | 5 |
| | 5.50 | 100 |
| | 5.90 | 100 |
| | 5.92 | 5 |
| | 7.00 | 5 |
| Flow rate | 0.6 ml/min | |
| Injection Vol | 3 µl | |

TABLE 10-continued

| | LCMS Method 9 - | |
|---|---|---|
| | Detection | |
| Signal | UV 215 | |
| PDA Spectrum | Range: 210-420 nm step: 1 nm (Not MS14 this has single wavelength detector) | |
| MSD Signal settings | Scan Pos (MS10): 150-850 Scan Pos (MS14): 130-850 | |

Purification Methods

Samples were purified via preparative HPLC using the following methods: Method C: the crude samples were dissolved in DMF otherwise noted before purified. Boston C18 21*250 mm 10 µm column. The mobile phase was acetonitrile/0.01% aqueous TFA (or 0.01% aqueous HCl). Method D: the crude samples were dissolved in DMF otherwise noted before purified. Boston C18 21*250 mm 10 µm column. The mobile phase was acetonitrile/10 mM ammonium acetate aqueous solution.

Samples were also purified via preparative HPLC using the following methods:

TABLE 11

| | Generic UV-Directed High pH prep method | |
|---|---|---|
| Column | Waters Xbridge C18 Part no. 186003930 30 × 100 mm, 10 um | |
| Column Temp | Room temperature | |
| Mobile Phase | A, Water + 0.2% Ammonium hydroxide B, Acetonitrile + 0.2% Ammonium hydroxide | |
| | Time (mins) | % organic |
| Gradient | 0 | 10 |
| | 0.55 | 10 |
| | 14.44 | 95 |
| | 16.55 | 95 |
| | 16.75 | 10 |
| Flow rate | 40 ml/min | |
| Injection Vol | 1500 µl | |
| | Detection | |
| Signal | UV 215 | |

TABLE 12

| | Generic UV-Directed low pH prep method | |
|---|---|---|
| Column | Waters Sunfire C18 Part no. 186003971 30 × 100 mm, 10 um | |
| Column Temp | Room temperature | |
| Mobile Phase | A, Water + 0.1% Formic acid B, Acetonitrile + 0.1% Formic acid | |
| | Time (mins) | % organic |
| Gradient | 0 | 10 |
| | 0.55 | 10 |
| | 14.44 | 95 |
| | 16.55 | 95 |
| | 16.75 | 10 |
| Flow rate | 40 ml/min | |
| Injection Vol | 1500 µl | |
| | Detection | |
| Signal | UV 215 | |

Amide Coupling using HATU Generic Method A.

A solution of amine (1.0 eq), acid (1.2 eq), HATU (1.05 eq) and DIPEA (3.0 eq) were dissolved in DMF and stirred at rt for 17 h. The mixture was extracted with EtOAc, the organic layer was concentrated. The residue was purified by column chromatography or prep-HPLC to obtain the target compounds.

Amide Coupling using EDCI/HOBT Generic Method B.

The acid (1.2 eq) was dissolved in DMF, and then EDCI (2.0 eq) and HOBT (1.5 eq) were added and stirred at rt for 1 h. Then corresponding amine (1.0 eq) was added. The mixture was stirred at rt for 18 h. The solution was purified via preparative HPLC to obtain the target compounds.

INTERMEDIATES

[Intermediate 1]—5-{[1-(2-Cyanophenyl)piperidin-4-yl]amino}-2,4-dimethylbenzoic

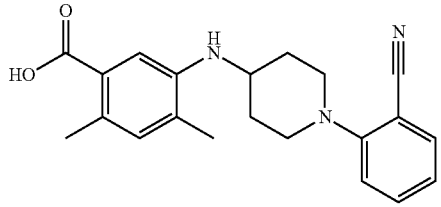 [SMILES: Cc1cc(C)c(C(=O)O)cc1NC1CCN(c2ccccc2C#N)CC1]

Methyl 5-{[1-(2-cyanophenyl)piperidin-4-yl]amino}-2,4-dimethylbenzoate [Intermediate 5] (87%, 2.5 g, 6.0 mmol) was suspended in 4:1 methanol/water (20 ml). 2M. aq. LiOH (12 ml) was added and the reaction was heated at 65° C. for 2 h. The reaction was concentrated in vacuo. The concentrated aqueous solution was diluted with water (30 ml), acidified to pH 5 and extracted with EtOAc (4×30 ml). The combined organics were washed with sat aq NaHCO$_3$ (30 ml) and concentrated in vacuo to give 2.3 g of the crude product as a pale yellow solid. The solid was purified via flash column chromatography (gradient from 0% to 10% MeOH in DCM). The fractions containing product were combined and concentrated in vacuo to afford the title compound as a cream solid (1.70 g, 81%). $^1$H NMR (250 MHz, DMSO-d6) δ 12.41 (s, 1H), 7.68 (dd, J=7.7, 1.5 Hz, 1H), 7.64-7.53 (m, 1H), 7.19 (d, J=8.2 Hz, 1H), 7.11 (s, 1H), 7.07 (t, J=7.5 Hz, 1H), 6.90 (s, 1H), 4.55 (s, 1H), 3.52 (d, J=12.4 Hz, 3H), 2.98 (t, J=11.0 Hz, 2H), 2.35 (s, 3H), 2.12 (s, 3H), 2.10-2.00 (m, 2H), 1.71 (d, J=10.5 Hz, 2H). LCMS Method 2—Tr=1.25 min (ES+) (M+H)+ 350.2.

[Intermediate 2]—Methyl 5-amino-2,4-dimethylbenzoate

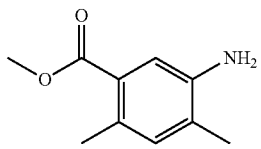

Methyl 2,4-dimethyl-5-nitrobenzoate (2 g, 9.56 mmol) was suspended in a mixture of 4:1 ethanol/water (60 ml) then ammonium chloride (0.56 g, 10.52 mmol) and iron powder (1.87 g, 33.46 mmol) were added and the reaction was stirred at 80° C. for 1 h. The mixture was cooled to rt and filtered through Celite using EtOAc. The filtrate was concentrated in vacuo to yield crude title compound as a cream solid (2.171 g, 127%). $^1$H NMR (250 MHz, DMSO-d6) δ 7.15 (s, 1H), 6.85 (s, 1H), 4.89 (s, 2H), 3.76 (s, 3H), 2.32 (s, 3H), 2.06 (s, 3H). LCMS Method 2—Tr=0.88 min (ES+) (M+H)+ 180.0.

[Intermediate 3]—2-(4-Hydroxypiperidin-1-yl)benzonitrile

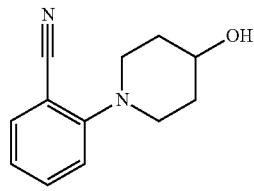 [SMILES: N#Cc1ccccc1N1CCC(O)CC1]

A suspension of 2-fluorobenzonitrile (1.00 g, 8.257 mmol), piperidin-4-ol (1.25 g, 12.39 mmol) and K$_2$CO$_3$ (2.28 g, 16.51 mmol) in DMF (10 ml) was heated at 130° C. for 18 h. The cooled reaction mixture was diluted with water (30 ml) and EtOAc (30 ml) then the phases were separated. The aqueous phase was extracted with EtOAc (3×30 ml) and the combined organics were washed with brine (3×20 ml), dried (MgSO$_4$) and filtered. The filtrate was concentrated in vacuo to yield the title compound as a brown viscous oil (1.80 g, 97%). $^1$H NMR (500 MHz, Chloroform-d) δ 7.54 (dd, J=7.7, 1.5 Hz, 1H), 7.49-7.42 (m, 1H), 7.01 (d, J=8.3 Hz, 1H), 6.97 (t, J=7.5 Hz, 1H), 3.90 (tt, J=8.0, 3.9 Hz, 1H), 3.46 (dt, J=10.4, 4.2 Hz, 2H), 3.01 (ddd, J=12.1, 9.0, 3.0 Hz, 2H), 2.07 (ddt, J=12.3, 6.3, 3.2 Hz, 2H), 1.80 (dtd, J=12.6, 8.6, 3.6 Hz, 2H). LCMS Method 3—Tr=1.39 min (ES+) (M+H)+ 203

[Intermediate 4]—2-(4-Oxopiperidin-1-yl)benzonitrile

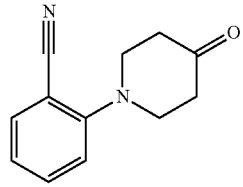 [SMILES: N#Cc1ccccc1N1CCC(=O)CC1]

To a solution of 2-(4-hydroxypiperidin-1-yl)benzonitrile [Intermediate 3] (300 mg, 1.48 mmol) in DCM (5 ml) at 0° C. was added Dess-Martin periodinane (944 mg, 2.23 mmol) and the reaction was stirred at rt for 2 h. 2M. aq. NaOH (10 ml) was added to the reaction mixture with stirring for 10 min. DCM (10 ml) was added and the phases separated. The aqueous phase was extracted with DCM (3×15 ml) and the combined organic extracts were washed with brine (30 ml) and then concentrated in vacuo to yield the title compound as a brown viscous oil (300 mg, 72%). $^1$H NMR (500 MHz, Chloroform-d) δ 7.61 (dd, J=7.7, 1.6 Hz, 1H), 7.54-7.49 (m, 1H), 7.09-7.04 (m, 2H), 3.52 (t, J=6.1 Hz, 4H), 2.69 (t, J=6.1 Hz, 4H). LCMS Method 4—Tr=1.49 min (ES+) (M+H)+ 201.

[Intermediate 5]—Methyl 5-{[1-(2-cyanophenyl)piperidin-4-yl]amino}-2,4-dimethylbenzoate

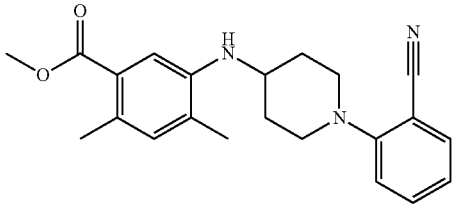 [SMILES: COC(=O)c1cc(NC2CCN(c3ccccc3C#N)CC2)c(C)cc1C]

Methyl 5-amino-2,4-dimethylbenzoate [Intermediate 2] (2.1 g, 11.7 mmol and 2-(4-oxopiperidin-1-yl)benzonitrile [Intermediate 4] (2.84 g, 12.9 mmol) were suspended in DCM (40 ml) and stirred at rt for 30 min. NaBH(OAc)$_3$ (2.48 g, 11.7 mmol) was then added and the reaction was stirred for 30 min. Further NaBH(OAc)$_3$ (3.73 g, 17.6 mmol) was then added and the reaction was stirred overnight. 2-(4-Oxopiperidin-1-yl)benzonitrile (91%, 0.88 g, 4 mmol) and NaBH(OAc)$_3$ (2.00 g, 9.4 mmol) were added and the reaction stirred for 1 h. The reaction mixture was diluted with water (40 ml). The organics were separated and the aqueous phase extracted with DCM (40 ml). The combined organics were concentrated in vacuo to give a brown oil. The oil was purified via flash column chromatography using gradients from 0% to 100% EtOAc in heptane followed by 0% to 100% MeOH in EtOAc. The fractions containing product were combined and concentrated in vacuo to afford the title compound as a pale yellow solid (2.5 g, 52%). $^1$H NMR (250 MHz, DMSO-d6) δ 7.68 (dd, J=7.7, 1.6 Hz, 1H), 7.59 (ddd, J=9.0, 7.5, 1.7 Hz, 1H), 7.23-7.16 (m, 1H), 7.11-7.02 (m, 2H), 6.93 (s, 1H), 6.85 (s, OH), 4.61 (d, J=8.1 Hz, 1H), 3.79 (s, 3H), 3.58-3.39 (m, 3H), 2.98 (t, J=10.9 Hz, 2H), 2.34 (s, 3H), 2.13 (s, 4H), 2.01 (d, J=9.3 Hz, 1H), 1.82-1.62 (m, 2H). LCMS Method 2—Tr=1.96 min (ES+) (M+H)+ 364.

[Intermediate 6]—tert-Butyl (2S)-4-(2-cyano-4,5-difluorophenyl)-2-methylpiperazine-1-carboxylate

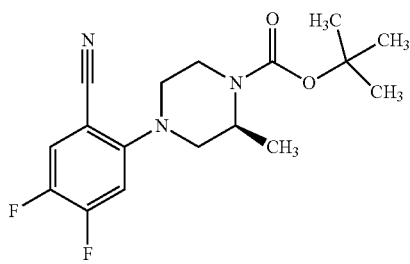 [SMILES: C[C@H]1CN(c2cc(F)c(F)cc2C#N)CCN1C(=O)OC(C)(C)C]

2-Bromo-4,5-difluorobenzonitrile (1.0 g, 4.59 mmol), tert-butyl (2S)-2-methylpiperazine-1-carboxylate (0.96 g, 4.82 mmol), Pd$_2$(dba)$_3$ (0.21 g, 0.23 mmol), XantPhos (0.27 g, 0.46 mmol) and sodium tert-butoxide (1.32 g, 13.76 mmol) were suspended in 1,4-dioxane (20 ml) (degassed with nitrogen for 5 minutes) then the reaction was heated at 100° C. for 6 h. The reaction was cooled then filtered through Celite, using DCM. The filtrate was concentrated in vacuo then the residue was partitioned between DCM (50 ml) and water (30 ml) and the organics were separated, dried over Na$_2$SO$_4$, filtered and concentrated in vacuo. The residue was purified via flash column chromatography using gradients of 0% to 100% EtOAc in heptane followed by 0% to 100% MeOH in EtOAc, then the fractions containing product were concentrated in vacuo to yield the title compound as a pale yellow oil which crystallized on standing (548 mg, 35%). $^1$H NMR (500 MHz, DMSO-d6) 8.04 (dd, J=10.4, 8.8 Hz, 1H), 7.32 (dd, J=12.7, 7.2 Hz, 1H), 4.24 (s, 1H), 3.84 (d, J=13.2 Hz, 1H), 3.32 (d, J=2.1 Hz, 2H), 3.16 (t, J=11.4 Hz, 1H), 2.90 (dd, J=12.1, 3.7 Hz, 1H), 2.78 (td, J=11.9, 3.4 Hz, 1H), 1.42 (s, 9H), 1.27 (d, J=6.7 Hz, 3H). LCMS Method 2—Tr=1.28 min (ES+) (M+H$^+$) 360.1

[Intermediate 7]—4,5-Difluoro-2-[(3S)-3-methylpiperazin-1-yl]benzonitrile

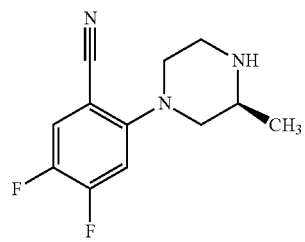 [SMILES: C[C@H]1CN(c2cc(F)c(F)cc2C#N)CCN1]

tert-Butyl (2S)-4-(2-cyano-4,5-difluorophenyl)-2-methylpiperazine-1-carboxylate [Intermediate 6] (400 mg, 1.19 mmol) was dissolved in trifluoroacetic acid (20% in DCM) (2.5 ml) then the reaction was agitated at ambient temperature for 4 h then concentrated in vacuo. The residue was partitioned between DCM (15 ml) and sat. aq. NaHCO$_3$(15 ml) then the organics were dried over Na$_2$SO$_4$, filtered and concentrated in vacuo to yield the title compound as a pale yellow crystalline solid (258 mg, 92%). $^1$H NMR (500 MHz, DMSO-d6) δ 7.99 (dd, J=10.4, 8.8 Hz, 1H), 7.27 (dd, J=12.9, 7.2 Hz, 1H), 3.34 (s, 1H), 3.04-2.96 (m, 1H), 2.94-2.80 (m, 2H), 2.76 (td, J=11.3, 2.5 Hz, 1H), 2.53-2.51 (m, 1H), 2.48-2.42 (m, 1H), 1.02 (d, J=6.4 Hz, 3H). LCMS Method 2—Tr=0.70 min (ES+) (M+H$^+$) 238.45.

[Intermediate 8]—Methyl 5-{[1-(2-cyanophenyl)piperidin-4-yl](methyl)amino}-2,4-dimethylbenzoate

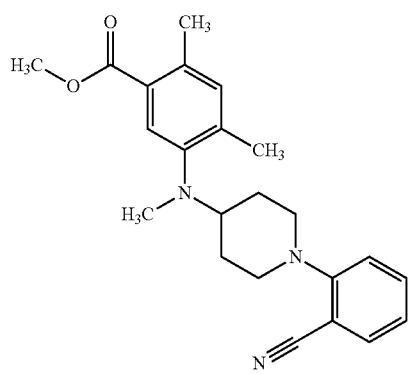 [SMILES: COC(=O)c1cc(N(C)C2CCN(c3ccccc3C#N)CC2)c(C)cc1C]

To a suspension of methyl 5-{[1-(2-cyanophenyl)piperidin-4-yl]amino}-2,4-dimethylbenzoate (60 mg, 0.165 mmol) [Intermediate 5] and potassium carbonate (27 mg, 0.198 mmol) in DMF (1 mL) was added methyl iodide (10 uL, 0.165 mmol) and the reaction mixture stirred at 70° C. for 3 h. After 3 h, methyl iodide (10 uL, 0.165 mmol) and potassium carbonate (27 mg, 0.198 mmol) were added and the reaction mixture heated at 90° C. for 3 h. After 3 h, the reaction mixture was cooled to rt and partitioned between water (5 mL) and ethyl acetate (5 mL). The aqueous was extracted into ethyl acetate (3×5 mL) and the combined organic extracted washed with brine (2×10 mL) and concentrated in vacuo to afford the title compound as a yellow viscous oil (50 mg, 66%). $^1$H NMR (500 MHz, Chloroform-d) δ 7.68 (s, 1H), 7.54 (dd, J=8.1, 1.6 Hz, 1H), 7.49-7.41 (m, 1H), 7.07 (s, 1H), 6.99-6.96 (m, 2H), 3.88 (s, 3H), 3.62-3.57 (m, 2H), 2.95-2.90 (m, 1H), 2.79 (td, J=11.7, 2.5 Hz, 2H), 2.69 (s, 3H), 2.53 (s, 3H), 2.32 (d, J=2.6 Hz, 3H), 1.97-1.84 (m, 4H). LCMS Method 1—Tr=2.21 min (ES+) (M+H)+ 378.

[Intermediate 9]—5-{[1-(2-Cyanophenyl)piperidin-4-yl](methyl)amino}-2,4-dimethylbenzoic Acid

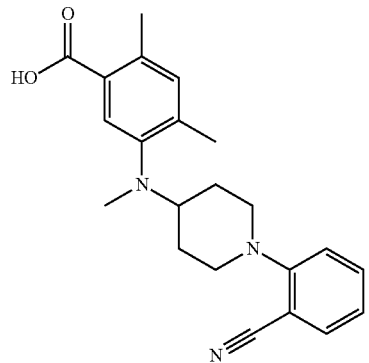 [SMILES: Cc1cc(C)c(N(C)C2CCN(c3ccccc3C#N)CC2)cc1C(=O)O]

To a suspension of methyl 5-{[1-(2-cyanophenyl)piperidin-4-yl](methyl)amino}-2,4-dimethylbenzoate (50 mg, 0.132 mmol) [Intermediate 8] and lithium hydroxide monohydrate (56 mg, 1.325 mmol) in methanol/water (3:1, 10 mL) was heated at 50° C. for 4 h. After 4 h, the reaction mixture was cooled to rt and the methanol removed in vacuo. The resultant suspension was diluted with water (5 mL) and then acidified to pH ~1 using 4M. aq, HCl (~5 mL). The solution was diluted with ethyl acetate (20 mL) and the phases separated. The aqueous was extracted into ethyl acetate (2×10 mL) and the combined organic extracts were washed with brine (20 mL), dried (MgSO$_4$) and filtered. The filtrate was concentrated in vacuo to afford the title compound as off-white solid (45 mg, 75%).

1H NMR (500 MHz, Chloroform-d) δ 8.06-7.89 (m, 1H), 7.54 (dd, J=7.7, 1.6 Hz, 1H), 7.49-7.44 (m, 1H), 7.23 (s, 1H), 7.06-6.96 (m, 2H), 3.71-3.40 (m, 3H), 3.38-2.91 (m, 3H), 2.91-2.81 (m, 2H), 2.81-2.66 (m, 2H), 2.66-2.56 (m, 3H), 2.42-2.11 (m, 3H), 2.08-1.94 (m, 3H). LCMS Method 1—Tr=1.80 min (ES+) (M+H)+ 368.

[Intermediate 10]—1-Fluoro-2-methanesulfinylbenzene

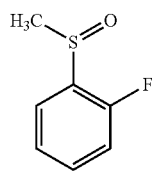

1-Fluoro-2-(methylsulfanyl)benzene (5 g, 35.16 mmol) was suspended in THF (10 ml) at 0° C. then mCPBA (6.7 g, 38.7 mmol) was added portionwise and the reaction was stirred at rt for 18 h. The reaction was partitioned between aq. sodium bisulfite (10%, 20 ml) and DCM (20 ml). The aqueous layer was extracted with DCM (3×20 ml). The organics were combined and concentrated in vacuo to afford a white solid. The white solid was partitioned between 2M. aq. NaOH (30 ml) and DCM (30 ml). The organics were washed with 2M. aq. NaOH (2×20 ml), brine (30 ml), dried (MgSO$_4$), filtered and concentrated in vacuo to afford the title compound as a yellow oil (5.0 g, 69%). $^1$H NMR (500 MHz, Chloroform-d) δ 7.84-7.77 (m, 1H), 7.48-7.42 (m, 1H), 7.35 (t, J=7.0 Hz, 1H), 7.08 (t, J=8.7 Hz, 1H), 2.80-2.76 (m, 3H). LCMS Method 3—Tr=0.82 min (ES+) (M+H)+ 159.

[Intermediate 11]—tert-Butyl N-[(2-fluorophenyl)(methyl)oxo-λ$^6$-sulfanylidene]carbamate

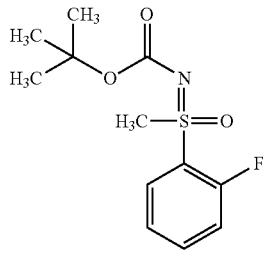 [SMILES: CC(C)(C)OC(=O)N=S(C)(=O)c1ccccc1F]

1-Fluoro-2-methanesulfinylbenzene [Intermediate 10] (5 g, 31.6 mmol), tert-butyl carbamate (7.4 g, 63.2 mmol), magnesium oxide (5.1 g, 126.4 mmol) and rhodium (II) acetate (419 mg, 0.95 mmol) were suspended in DCM (20 ml). (Diacetoxyiodo)benzene (20.4 g, 63.2 mmol) was added portionwise and the reaction was stirred at rt for 18 h. The reaction was filtered and the filtrate was concentrated in vacuo. The residue was purified by flash column chromatography eluting with EtOAc in heptane (0% with a gradient towards 100%). The fractions containing product were combined and concentrated in vacuo to afford the title compound as a pale yellow oil (6.5 g, 60%). $^1$H NMR (250 MHz, Chloroform-d) δ 8.12-7.87 (m, 1H), 7.74-7.60 (m, 1H), 7.42-7.33 (m, 1H), 7.30-7.19 (m, 1H), 3.40-3.31 (m, 3H), 1.37-1.30 (m, 9H). LCMS Method 4—Tr=2.14 min (ES+) (M+H)+ 274.

[Intermediate 12]—tert-Butyl N-[methyl(oxo)[2-(piperazin-1-yl)phenyl]-λ6-sulfanylidene]carbamate tert-Butyl N-[(2-fluorophenyl)(methyl)oxo-λ⁶-sulfanylidene]carbamate [Intermediate 11] (6.5 g, 19.0 mmol) and piperazine (6.55 g, 76.1 mmol) were heated neat in a pressure tube at 110° C. for 18 h. The reaction mixture was cooled to rt and then dissolved in water (20 ml) and EtOAc (20 ml). The phases were separated and the aqueous phase was extracted with EtOAc (3×20 ml). The combined organics were washed with brine (2×30 ml) and then concentrated in vacuo to afford a viscous pale brown oil. The crude material was purified by flash column chromatography eluting first with EtOAc in heptane (0% with gradient towards 100%), then methanol in EtOAc, (0% with gradient towards 100%). The fractions containing product were combined and concentrated in vacuo to afford a pale yellow viscous oil. DCM (5 ml) was added and the mixture was sonication. The solid that formed was removed via filtration and the filtrate was concentrated in vacuo to give a clear pale yellow viscous oil. The material was dried in a vacuum oven to afford the title compound as a pale yellow glass (4.5 g, 68%). ¹H NMR (500 MHz, Chloroform-d) δ 8.14 (dd, J=8.0, 1.5 Hz, 1H), 7.64 (td, J=7.9, 1.5 Hz, 1H), 7.45 (dd, J=8.0, 0.9 Hz, 1H), 7.42-7.37 (m, 1H), 3.56 (s, 3H), 3.16-3.07 (m, 4H), 3.07-3.01 (m, 2H), 2.92-2.81 (m, 2H), 1.39 (s, 9H). LCMS Method 2—Tr=0.77 min (ES+) (M+H)+ 340.

[Intermediate 13]—tert-Butyl N-({2-[4-(5-{[1-(2-cyanophenyl)piperidin-4-yl]amino}-2,4-dimethylbenzoyl)piperazin-1-yl]phenyl}(methyl)oxo-λ-sulfanylidene)carbamate

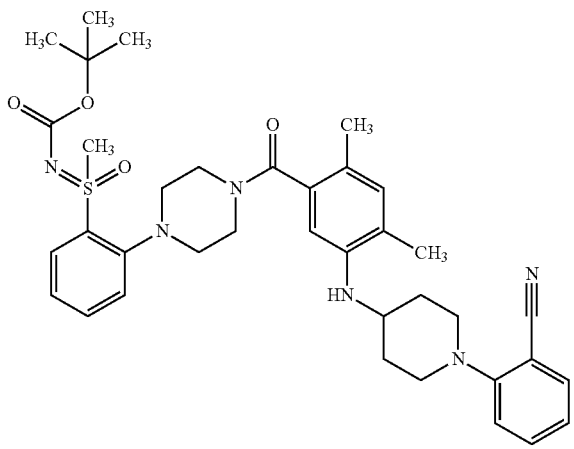 [SMILES: Cc1cc(C)c(C(=O)N2CCN(c3ccccc3S(C)(=O)=NC(=O)OC(C)(C)C)CC2)cc1NC1CCN(c2ccccc2C#N)CC1]

The title compound was synthesized from 5-{[1-(2-cyanophenyl)piperidin-4-yl](methyl)amino}-2,4-dimethylbenzoic acid [Intermediate 1] (259 mg, 0.742 mmol) and tert-butyl N-[(2-fluorophenyl)(methyl)oxo-λ⁶-sulfanylidene]carbamate [Intermediate 12] (350 mg, 0.928 mmol) using the method described above for Example 1 to afford the title compound as an off-white glass (440 mg, 71%). ¹H NMR (250 MHz, Chloroform-d) δ 8.15 (d, J=8.0 Hz, 1H), 7.75-7.60 (m, 1H), 7.59-7.37 (m, 4H), 7.11-6.97 (m, 2H), 6.92 (s, 1H), 6.48 (s, 1H), 3.69-2.33 (m, 16H), 2.32-2.06 (m, 8H), 1.89-1.63 (m, 2H), 1.38 (s, 9H). LCMS Method 4—Tr=1.94 min (ES+) (M+H)+ 671.

[Intermediate 14]—2-(Piperazin-1-yl)benzamide

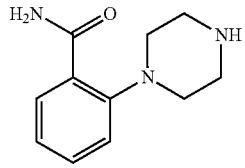

Prepared via the method of Lagu et al. Journal of Medicinal Chemistry (1999) 42, 23, 4794-4803.

[Intermediate 15]—Methyl 5-hydroxy-2-methylbenzoate

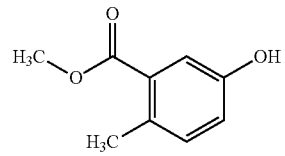

To a solution of 5-hydroxy-2-methylbenzoic acid (750 mg, 4.93 mmol) in methanol (20 ml) at rt was dropwise added acetyl chloride (1.94 g, 24.65 mmol) and the reaction was heated at 80° C. for 2 h. The reaction mixture was cooled to rt and then concentrated in vacuo to afford the title compound as a brown solid (750 mg, 91%). ¹H NMR (250 MHz, Chloroform-d) δ 7.41 (d, J=2.8 Hz, 1H), 7.10 (d, J=8.3 Hz, 1H), 6.91 (dd, J=8.3, 2.8 Hz, 1H), 3.88 (s, 3H), 2.50 (s, 3H). LCMS Method 2—Tr=0.94 min (ES+) (M+H)+ 166.9.

[Intermediate 16]—tert-Butyl 4-[2-(methylsulfanyl)pyridin-3-yl]piperazine-1-carboxylate

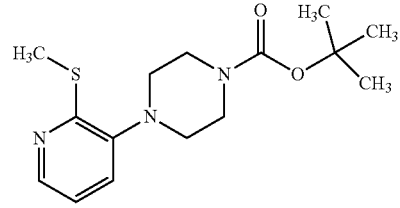 [SMILES: CSc1ncccc1N1CCN(C(=O)OC(C)(C)C)CC1]

tert-Butyl piperazine-1-carboxylate (456 mg, 2.45 mmol), 3-bromo-2-(methylsulfanyl)pyridine (500 mg, 2.45 mmol) and cesium carbonate (1.20 g, 3.68 mmol) were suspended in anhydrous toluene (5 ml). Nitrogen was bubbled through the reaction for 20 min. Pd₂(dba)₃ (22 mg, 0.024 mmol) and (±)-BINAP (38 mg, 0.061) were added and the reaction mixture bubbled with nitrogen for 10 min; the pressure tube was sealed and heated at 110° C. overnight. The reaction mixture was cooled to rt and filtered through a sintered glass funnel, the solid was extracted with EtOAc (~10 ml). The filtrate was concentrated in vacuo to afford a brown oily liquid. The crude material was purified by flash column chromatography eluting with EtOAc in heptane (0% with gradient towards 100%). The product-containing fractions were combined and concentrated in vacuo to afford to the title compound as a viscous brownish-yellow oil (660 mg, 84%). ¹H NMR (500 MHz, Chloroform-d) δ 8.09 (dd, J=4.8, 1.6 Hz, 1H), 7.39 (dd, J=7.7, 1.4 Hz, 1H), 6.96 (dd, J=7.7, 4.8 Hz, 1H), 3.63-3.56 (m, 4H), 3.22-3.16 (m, 4H), 2.43 (s, 3H), 1.48 (s, 9H). LCMS Method 4—Tr=1.82 min (ES+) (M+H)+ 310.

[Intermediate 17]—tert-Butyl 4-(2-methanesulfinylpyridin-3-yl)piperazine-1-carboxylate

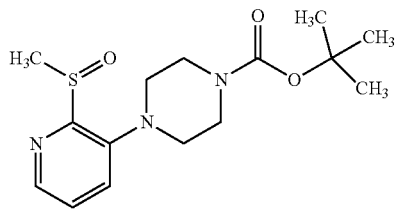 [SMILES: CS(=O)c1ncccc1N1CCN(C(=O)OC(C)(C)C)CC1]

tert-Butyl 4-[2-(methylsulfanyl)pyridin-3-yl]piperazine-1-carboxylate [Intermediate 16] (650 mg, 2.10 mmol) was suspended in THF (6 ml) at 0° C. then mCPBA (399 mg, 2.31 mmol) was added portionwise and the reaction was stirred at rt overnight. The reaction mixture was diluted with aq. sodium bisulfite (10%, 20 ml) and DCM (30 ml) and the phases separated. The aqueous layer was extracted with DCM (3×20 ml). The organics were combined and washed with brine (30 ml), dried (MgSO₄) and filtered. The filtrate was concentrated in vacuo and the residue was purified by flash column chromatography eluting with EtOAc in heptane (0% with gradient towards 100%). The fractions containing product were combined and concentrated in vacuo to afford the title compound as a yellow oil (360 mg, 44%). ¹H NMR (250 MHz, Chloroform-d) δ 8.39 (dd, J=4.8, 1.8 Hz, 1H), 8.24 (dd, J=7.7, 1.8 Hz, 1H), 7.20 (dd, J=7.7, 4.9 Hz, 1H), 3.67-3.34 (m, 6H), 3.20-3.02 (m, 2H), 2.81 (s, 3H), 1.48 (s, 9H). LCMS Method 4—Tr=1.51 min (ES+) (M+H)+ 326.

[Intermediate 18]—tert-butyl 4-{2-[methyl(oxo)[(trifluoroacetyl)imino]-λ-sulfanyl]pyridin-3-yl}piperazine-1-carboxylate

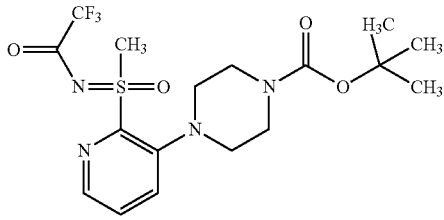 [SMILES: CC(C)(C)OC(=O)N1CCN(c2cccnc2S(C)(=O)=NC(=O)C(F)(F)F)CC1]

To a suspension of tert-butyl 4-(2-methanesulfinylpyridin-3-yl)piperazine-1-carboxylate [Intermediate 17](1.60 g, 4.92 mmol), trifluoroacetamide (1.11 g, 9.83 mmol), magnesium oxide (793 mg, 19.67 mmol) and rhodium(II)acetate (65 mg, 0.147 mmol) in DCM (10 mL) was added portionwise bis(acetyloxy)(phenyl)-lambda~3~-iodane (3.17 g, 9.83 mmol) and the reaction mixture stirred at rt overnight. The solids were filtered off and extracted with DCM (~10 mL). The filtrate was concentrated in vacuo and the crude product obtained. The crude product was purified by flash column chromatography eluting with ethyl acetate in heptane (0% with gradient towards 100%). The product rich fractions were combined and concentrated in vacuo to afford to the title compound as a yellow oil (400 mg, 15%). ¹H NMR (500 MHz, Chloroform-d) δ 8.41 (dd, J=4.5, 1.4 Hz, 1H), 7.72 (dd, J=8.2, 1.4 Hz, 1H), 7.59 (dd, J=8.2, 4.4 Hz, 1H), 3.73 (s, 3H), 3.66-3.61 (m, 4H), 3.12-3.07 (m, 4H), 1.48 (s, 9H). LCMS Method 4—Tr=1.81 min (ES+) (M+H)+ 437.

[Intermediate 19] 1-(2-chloropyridin-3-yl)piperazine

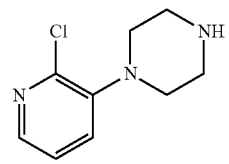 [SMILES: Clc1ncccc1N1CCNCC1]

A suspension of tert-butyl 4-{2-[methyl(oxo)[(trifluoroacetyl)imino]-λ-sulfanyl]pyridin-3-yl}piperazine-1-carboxylate [Intermediate 18] (400 mg, 0.928 mmol) in DCM (10 mL) was added 4M HCl in dioxane (5 mL) and the reaction mixture stirred at rt for 1 h. After 1 h, the reaction mixture was concentrated in vacuo and the crude material was dissolved in DCM (1 mL) and loaded onto an SCX-2 column. DCM/MeOH (50:50, 30 mL) was washed through the column first and this fraction discarded. Secondly, 7N NH₃ in MeOH (30 mL) was eluted through the column and this fraction concentrated in vacuo to afford the title compound as a yellow viscous oil (190 mg, 42%).

[Intermediate 20] 2-{4-[(tert-butoxy)carbonyl]piperazin-1-yl}-5-fluorobenzoic Acid

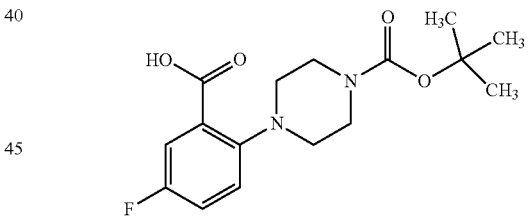

5-fluoro-2-(piperazin-1-yl)benzoic acid (500 mg, 2.23 mmol), di-tert-butyl dicarbonate (535 mg, 2.45 mmol) and sodium hydrogen carbonate (562 mg, 6.69 mmol) were suspended in THF (8 ml) and stirred at rt for 1 h. The mixture was concentrated under reduced pressure. The residue obtained was partitioned between DCM (30 ml) and water (30 ml). The organic layer was separated and the aqueous phase extracted with DCM (2×30 ml). The organics were combined, washed with brine (30 ml) and concentrated in vacuo to yield a yellow oil. The oil was then purified by flash column chromatography eluting with a gradient from 0-100% EtOAc in heptane followed by 0-100% MeOH in EtOAc. The product containing fractions were combined and concentrated in vacuo to afford the title compound as a white solid (269 mg, 37%). ¹H NMR (250 MHz, DMSO-d6) δ 7.76-7.62 (m, 2H), 7.50 (td, J=8.4, 3.2 Hz, 1H), 3.56-3.47 (m, 4H), 3.06-2.97 (m, 4H), 1.43 (s, 9H). LCMS method 1—Tr=1.12 min (ES+) (M+H)+ 269.0.

[Intermediate 21]—tert-Butyl 4-[4-fluoro-2-(methylcarbamoyl)phenyl]piperazine-1-carboxylate

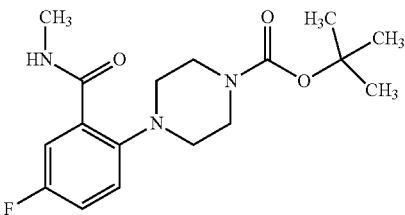 [SMILES: CNC(=O)c1cc(F)ccc1N1CCN(C(=O)OC(C)(C)C)CC1]

2-{4-[(tert-Butoxy)carbonyl]piperazin-1-yl}-5-fluorobenzoic acid [Intermediate 20](269 mg, 0.83 mmol) and DIPEA (520.05 µl, 2.99 mmol) were dissolved in DCM (8 ml) and placed under nitrogen atmosphere. The reaction mixture was cooled 0° C. and thionyl chloride (73 µl, 1 mmol) was added. The mixture was stirred was warmed to rt and stirred for 1 h. The reaction mixture was cooled to 0° C. and methylamine hydrochloride (115 mg, 1.7 mmol) was added. The reaction was warmed to rt and stirred for 1 h. The mixture was concentrated under reduced pressure. The resultant residue was partitioned between DCM (20 ml) and water (20 ml). The aqueous phase was extracted with DCM (2×20 ml). The organic layers were combined, washed with aq. 5 mM. aq. NaOH (30 ml) and concentrated in vacuo to yield a brown oil. The oil was purified flash column chromatography eluting with gradient from 0-100% EtOAc in heptane followed by 0-100% MeOH in EtOAc. The product containing fractions were combined and concentrated in vacuo to afford the title compound as a brown oil (273 mg, 52%). $^1$H NMR (250 MHz, Chloroform-d) δ 9.69 (s, 1H), 7.96-7.85 (m, 1H), 7.21-7.04 (m, 2H), 3.64-3.54 (m, 4H), 3.01 (dd, J=4.9, 0.7 Hz, 3H), 2.96-2.86 (m, 4H), 1.49 (d, J=0.7 Hz, 9H). LCMS Method 1—Tr=1.21 min (ES+) (M+H)+ 338.0.

[Intermediate 22]—5-Fluoro-N-methyl-2-(piperazin-1-yl)benzamide dihydrochloride

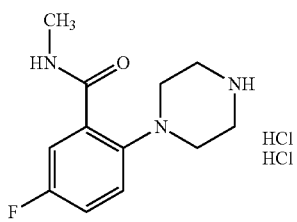 [SMILES: CNC(=O)c1cc(F)ccc1N1CCNCC1 ; Cl ; Cl]

tert-Butyl 4-[4-fluoro-2-(methylcarbamoyl)phenyl]piperazine-1-carboxylate [Intermediate 21] (273 mg, 0.81 mmol) was suspended in 4M HCl in Dioxane (4 ml) and stirred at rt for 2 h. The reaction mixture was concentrated under in vacuo to afford the title compound as a beige solid (259 mg, 99%). $^1$H NMR (250 MHz, Methanol-d4) δ 7.41 (dd, J=9.0, 3.0 Hz, 1H), 7.37-7.17 (m, 2H), 3.40 (dd, J=6.4, 3.6 Hz, 4H), 3.25 (dd, J=6.4, 3.6 Hz, 4H), 2.96 (s, 3H). LCMS Method 4—Tr=1.38 min (ES+) (M+H)+ 238.1.

[Intermediate 23]—tert-Butyl 4-[2-(methylcarbamoyl)phenyl]piperazine-1-carboxylate

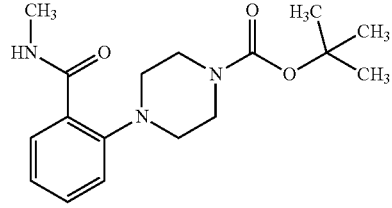 [SMILES: CNC(=O)c1ccccc1N1CCN(C(=O)OC(C)(C)C)CC1]

2-{4-[(tert-Butoxy)carbonyl]piperazin-1-yl}benzoic acid (626 mg, 1.98 mmol) and DIPEA (1.2 ml, 7.14 mmol) were suspended in DCM (10 ml). A solution of thionyl chloride (173 µl, 2.38 mmol) in DCM (5 ml) was then added dropwise to the stirred reaction mixture at 0° C. The reaction was warmed to rt and stirred for 1 h. The reaction mixture was cooled to 0° C. and methylamine hydrochloride (121 mg, 1.79 mmol) was added. The reaction mixture was warmed to rt and stirred for 16 h. The reaction mixture was concentrated in vacuo to yield an oil. The oil was partitioned between DCM (30 ml) and aq. NaHCO$_3$ (30 ml). The aqueous phase extracted with DCM (2×30 ml). The organics layers were combined and washed with aq. 0.1M NaOH (2×50 ml), dried over MgSO$_4$ and concentrated in vacuo to afford the title compound as a brown solid (286 mg, 55%). $^1$H NMR (250 MHz, Chloroform-d) δ 9.32 (s, 1H), 8.14 (dd, J=7.8, 1.7 Hz, 1H), 7.42 (td, J=7.8, 1.7 Hz, 1H), 7.25-7.17 (m, 1H), 7.13 (d, J=8.0 Hz, 1H), 3.64-3.54 (m, 4H), 3.00 (d, J=4.9 Hz, 3H), 2.98-2.90 (m, 4H), 1.49 (s, 9H). LCMS Method 1—Tr=1.16 min (ES+) (M+H)+ 320.0.

[Intermediate 24]—N-Methyl-2-(piperazin-1-yl)benzamide di-hydrochloride

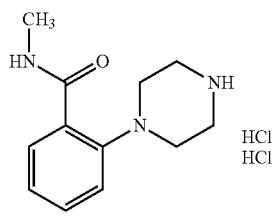 [SMILES: CNC(=O)c1ccccc1N1CCNCC1 ; Cl ; Cl]

tert-Butyl 4-[2-(methylcarbamoyl)phenyl]piperazine-1-carboxylate [Intermediate 23] (143 mg, 0.45 mmol) was suspended in 4M HCl in Dioxane (2 ml) and stirred at rt for 2 h. The reaction mixture was concentrated in vacuo to afford the title compound as a beige solid (124 mg, 93%). $^1$H NMR (250 MHz, Methanol-d4) δ 7.77 (dd, J=7.7, 1.5 Hz, 1H), 7.65-7.56 (m, 1H), 7.47 (dd, J=8.2, 1.0 Hz, 1H), 7.36 (td, J=7.6, 1.2 Hz, 1H), 3.50 (s, 8H), 2.99 (s, 3H). LCMS Method 10—Tr=0.38 min (ES+) (M+H)+ 220.1.

[Intermediate 25]—(1-Phenylpiperazin-2-yl)methanol

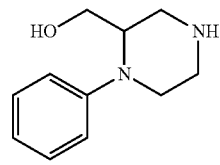 [SMILES: OCC1CNCCN1c1ccccc1]

1-Phenylpiperazine-2-carboxylic acid dihydrochloride (250 mg, 0.9 mmol) was suspended in anhydrous tetrahydrofuran (5 ml) under nitrogen. The reaction was cooled to 0° C. and 4M lithium aluminum hydride in Et$_2$O (672 μl) was added slowly. The reaction was stirred at rt for 2 h. The reaction was diluted with DCM (15 ml) and sat. aq. NH$_4$Cl (30 ml) was added dropwise to the stirring reaction mixture. The biphasic suspension was filtered, then the organics were separated and concentrated in vacuo to yield the title compound as a tan oil (179 mg, 100%). $^1$H NMR (500 MHz, DMSO-d6) δ 7.17 (ddt, J=9.7, 7.3, 2.0 Hz, 2H), 6.84 (d, J=8.0 Hz, 2H), 6.67 (t, J=7.2 Hz, 1H), 3.74 (t, J=9.8 Hz, 1H), 3.21 (dt, J=6.4, 4.3 Hz, 2H), 3.14 (d, J=12.0 Hz, 1H), 3.02 (dd, J=6.0, 4.0 Hz, 1H), 2.94 (d, J=11.7 Hz, 1H), 2.82 (ddt, J=11.6, 7.8, 3.4 Hz, 2H), 2.74 (dd, J=11.7, 3.3 Hz, 1H), 2.66 (td, J=11.6, 3.5 Hz, 1H).

[Intermediate 26]—tert-Butyl 4-(3-sulfamoylpyridin-2-yl)piperazine-1-carboxylate

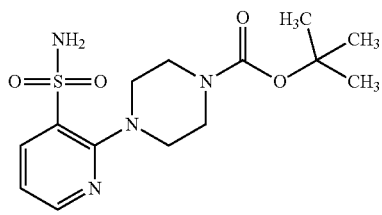 [SMILES: CC(C)(C)OC(=O)N1CCN(c2ncccc2S(N)(=O)=O)CC1]

2-Chloropyridine-3-sulfonamide (250 mg, 1.3 mmol), tert-butyl piperazine-1-carboxylate (290 mg, 1.56 mmol) and potassium carbonate (215 mg, 1.56 mmol) were suspended in DMF (5 ml). The mixture was then heated via microwave irradiation at 130° C. for 3 h. The mixture was concentrated in vacuo the resultant residue was partitioned between DCM (20 ml) and water (20 ml). The aqueous phase was extracted with DCM (2×20 ml). The organic layers were combined and the solvents removed under reduced pressure. The residue obtained was purified flash column chromatography eluting with gradient from 0-100% EtOAc in heptane followed by 0-100% MeOH in EtOAc. The product containing fractions were combined and concentrated in vacuo to give a clear oil. The oil was purified flash column chromatography eluting with gradient from 0% MeOH to 10% MeOH in DCM. The product containing fractions were concentrated in vacuo to afford the title compound as a white solid (259 mg, 58%). $^1$H NMR (250 MHz, DMSO-d6) δ 8.48 (dd, J=4.7, 1.8 Hz, 1H), 8.22 (dd, J=7.8, 1.8 Hz, 1H), 7.34-7.21 (m, 3H), 3.57-3.44 (m, 4H), 3.23-3.10 (m, 4H), 1.42 (s, 9H). LCMS Method 1—Tr=1.77 min (ES+) (M+H)+ 343.0.

[Intermediate 27]—2-(Piperazin-1-yl)pyridine-3-sulfonamide

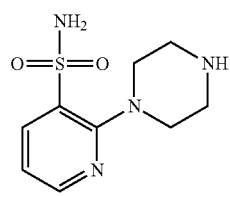 [SMILES: NS(=O)(=O)c1cccnc1N1CCNCC1]

tert-Butyl 4-(3-sulfamoylpyridin-2-yl)piperazine-1-carboxylate [Intermediate 26] (259 mg, 0.76 mmol) was suspended in 4M HCl in Dioxane (4 ml) and stirred at rt overnight. The reaction was concentrated in vacuo and the residue was loaded onto a Biotage SCX-2 column (10 g) and washed with 1:1 DCM/MeOH (40 ml). The product was then eluted with 7N NH$_3$ in MeOH (40 ml) and concentrated in vacuo to afford the title compound as a white solid (181 mg, 82%). $^1$H NMR (250 MHz, Chloroform-d) δ 7.84 (s, 1H), 7.54 (dd, J=8.0, 1.6 Hz, 1H), 7.50-7.40 (m, 1H), 7.11 (s, 1H), 7.01-6.92 (m, 2H), 3.67-3.53 (m, 2H), 2.99-2.87 (m, 1H), 2.87-2.73 (m, 2H), 2.70 (s, 3H), 2.59 (s, 3H), 2.34 (s, 3H), 1.98-1.82 (m, 4H). LCMS Method 4—Tr=1.03 min (ES+) (M+H)+ 243.1.

[Intermediate 28]—Methyl 2,4-dimethyl-5-[(1-phenylpiperidin-4-yl)amino]benzoate

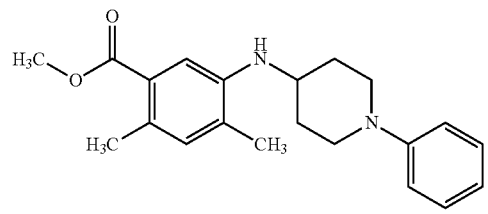 [SMILES: COC(=O)c1cc(NC2CCN(c3ccccc3)CC2)c(C)cc1C]

Methyl 5-amino-2,4-dimethylbenzoate (300 mg, 1.67 mmol) and 1-phenylpiperidin-4-one (324 mg, 1.76 mmol) were suspended in DCM (10 ml) and stirred at rt for 1 h. NaBH(OAc)$_3$ (887 mg, 4.18 mmol) was added and the reaction was stirred for 1 hr. 1-phenylpiperidin-4-one (50 mg, 0.27 mmol) was added and the reaction was stirred for 17 h. The mixture was diluted with DCM (20 ml) and water (20 ml). The aqueous phase extracted with DCM (2×20 ml). The organic layers were combined and reduced in vacuo. The residue obtained was then purified flash column chromatography eluting with gradient from 0-100% EtOAc in heptane followed by 0-100% MeOH in EtOAc. The product containing fractions were combined and concentrated in vacuo to afford the title compound as a white solid (518 mg, 91%). $^1$H NMR (250 MHz, DMSO-d6) δ 7.20 (dd, J=8.7, 7.2 Hz, 2H), 7.08 (s, 1H), 6.96 (s, 1H), 6.93 (s, 2H), 6.74 (t, J=7.2 Hz, 1H), 4.51 (d, J=8.1 Hz, 1H), 3.79 (s, 3H), 3.76-3.65 (m, 2H), 3.53-3.36 (m, 1H), 2.94-2.77 (m, 2H), 2.34 (s, 3H), 2.10 (s, 3H), 2.03-1.89 (m, 2H), 1.58 (d, J=11.7 Hz, 2H). LCMS Method 1—Tr=1.22 min (ES+) (M+H)+ 339.1.

[Intermediate 29]—2,4-Dimethyl-5-[(1-phenylpiperidin-4-yl)amino]benzoic Acid

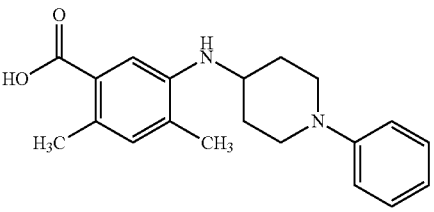 [SMILES: Cc1cc(C)c(C(=O)O)cc1NC1CCN(c2ccccc2)CC1]

To a stirred suspension of methyl 2,4-dimethyl-5-[(1-phenylpiperidin-4-yl)amino]benzoate [Intermediate 28] (518 mg, 1.53 mmol) in (4:1) Methanol/Water (5 ml) was added aq. 2M LiOH (3.0 ml). The reaction mixture was then heated at 65° C. for 3 h. The mixture was concentrated in vacuo, then partitioned between DCM (20 ml) and water (20 ml). The aqueous phase was extracted with DCM (3×20 ml). The organic layers were combined and reduced in vacuo to afford the title compound as a pink solid (490 mg, 99%). $^1$H NMR (250 MHz, Chloroform-d) δ 7.37 (s, 1H), 7.31 (s, 1H), 7.25 (s, 1H), 7.06-6.94 (m, 3H), 6.87 (t, J=7.3 Hz, 1H), 3.74-3.51 (m, 3H), 3.08-2.90 (m, 2H), 2.53 (s, 3H), 2.23 (d, J=10.1 Hz, 2H), 2.16 (s, 3H), 1.75-1.56 (m, 2H). LCMS Method 1—Tr=1.08 min (ES+) (M+H)+ 325.0.

[Intermediate 30]—2-(Piperazin-1-yl)pyridine-3-carboxamide

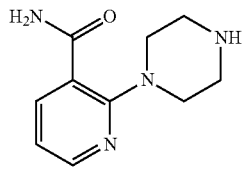 [SMILES: NC(=O)c1cccnc1N1CCNCC1]

2-(piperazin-1-yl)pyridine-3-carbonitrile (250 mg, 1.33 mmol) was suspended in conc. sulfuric acid (5 ml) and stirred at 100° C. for 19 h. The reaction mixture was then diluted with water (30 ml), basified to pH 14 with aq. sat. NaOH and extracted with chloroform/isopropanol (9:1, 3×30 ml). The combined organics were concentrated under reduced pressure to afford the title compound as a tan solid (128 mg, 47%). $^1$H NMR (500 MHz, Chloroform-d) δ 8.55 (s, 1H), 8.40 (dd, J=4.8, 2.0 Hz, 1H), 8.31 (dd, J=7.6, 2.0 Hz, 1H), 7.09 (dd, J=7.6, 4.8 Hz, 1H), 5.90 (s, 1H), 3.22-3.16 (m, 4H), 3.07-3.01 (m, 4H). LCMS Method 4—Tr=1.03 min (ES+) (M+H)+207.4.

[Intermediate 31]—5-Iodo-2,4-dimethylbenzoic Acid

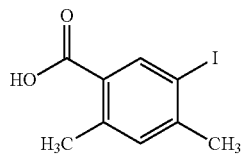

2,4-Dimethylbenzoic acid (25 g, 166 mmol), sodium periodate (17.8 g, 83 mmol) and Iodine (46.5 g, 183 mmol) were suspended in glacial acetic acid (188 ml). Sulfuric acid (1.3 ml, 25 mmol) was added and the reaction was heated at 110° C. for 6 h. The reaction mixture was added slowly to water (1.2 L) and the residuals washed in with a further 300 ml water. Aq. sat. Na$_2$S$_2$O$_3$ (1 L) was added to the aqueous suspension. The suspension was agitated for 20 mins. The suspension was filtered to give a white solid. The solid was triturated with EtOAc (250 ml×2), and filtered to afford the title compound as a pale solid (25.6 g, 56%). $^1$H NMR (500 MHz, DMSO-d6) δ 8.19 (s, 1H), 7.27 (s, 1H), 2.44 (s, 3H), 2.36 (s, 3H). LCMS Method 2—Tr=1.14 min.

[Intermediate 32]—methyl 5-iodo-2,4-dimethylbenzoate

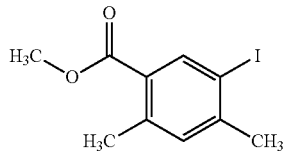

5-Iodo-2,4-dimethylbenzoic acid [Intermediate 31] (10 g, 36 mmol) was suspended in methanol (100 ml) then sulfuric acid (1.9 ml, 36.2 mmol) was added and the reaction was stirred at 80° C. for 2 h. The reaction was concentrated in vacuo then the residue was taken up in DCM (50 ml). Aq. sat. NaHCO$_3$ (50 ml) was added followed by water (25 ml) and the reaction was agitated for 10 mins. The biphasic suspension was filtered and the organic layer was separated, dried Na$_2$SO$_4$, filtered and concentrated in vacuo to afford the title compound as a pale yellow crystallized solid (4.1 g, 39%). $^1$H NMR (500 MHz, DMSO-d6) δ 8.19 (s, 1H), 7.31 (s, 1H), 3.81 (s, 3H), 2.43 (s, 3H), 2.37 (s, 3H). LCMS Method 2—Tr=1.35 min (ES+) (M+H)+ 290.8.

[Intermediate 33]—[4-(2,4-Dimethyl-5-nitrobenzoyl)-1-phenylpiperazin-2-yl]methanol

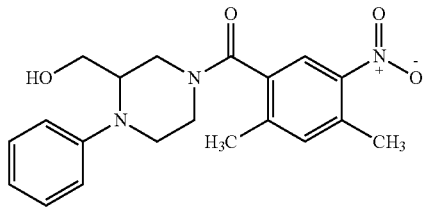

2,4-Dimethyl-5-nitrobenzoic acid (120 mg, 0.61 mmol), DIPEA (321 μl, 1.84 mmol) and HATU (280 mg, 0.74 mmol) were suspended in DMF (2 ml) and stirred at rt for 20 min. (1-Phenylpiperazin-2-yl)methanol [Intermediate 25] (166 mg, 0.61 mmol) in DMF (2 ml) was then added and the mixture was stirred for 72 h. The reaction mixture was concentrated in vacuo. The resultant residue was partitioned between DCM (20 ml) and water (20 ml). The aqueous phase was extracted with DCM (20 ml). The organic layers were combined and reduced in vacuo to give an orange oil. The oil was purified by flash column chromatography eluting with gradient from 0-100% EtOAc in heptane followed by 0-100% MeOH in EtOAc. The product containing fractions were reduced in vacuo to give a yellow oil. The oil was further purified by flash column chromatography eluting with gradient from 0% to 50% EtOAc in heptane. The product containing fractions were combined and concentrated in vacuo to afford the title compound as a yellow solid (162 mg, 71%). $^1$H NMR (250 MHz, Chloroform-d) δ 7.95-7.86 (m, 1H), 7.34-7.26 (m, 2H), 7.25-7.19 (m, 1H), 6.91 (d, J=7.8 Hz, 3H), 4.74 (d, J=13.3 Hz, 1H), 3.76-3.54 (m, 3H), 3.53-3.34 (m, 3H), 3.32-2.91 (m, 2H), 2.66-2.58 (m, 3H), 2.45-2.35 (m, 3H). LCMS Method 10—Tr=1.18 min (ES+) (M+H)+ 370.1.

115

[Intermediate 34]—[4-(5-Amino-2,4-dimethylbenzoyl)-1-phenylpiperazin-2-yl]methanol

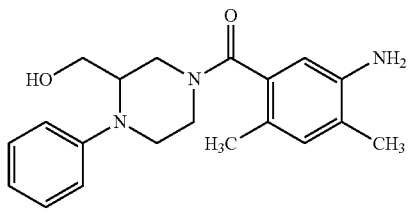 [SMILES: Cc1cc(C)c(C(=O)N2CCN(c3ccccc3)C(CO)C2)cc1N]

To a suspension of [4-(2,4-dimethyl-5-nitrobenzoyl)-1-phenylpiperazin-2-yl]methanol [Intermediate 33] (162 mg, 0.44 mmol) in ethanol/water (5:1, 6 ml) was added iron powder (86 mg, 1.53 mmol) and ammonium chloride (26 mg, 0.48 mmol). The mixture was heated at 80° C. for 16 h. The reaction mixture was cooled to rt, then filtered through Celite. The filtrate was concentrated under reduced pressure to afford the title compound as an off-white solid (143 mg, 93%). $^1$H NMR (250 MHz, DMSO-d6) δ 7.26-7.14 (m, 2H), 6.91 (s, 1H), 6.88 (s, 1H), 6.84-6.68 (m, 2H), 6.42 (d, J=6.2 Hz, 1H), 4.91-4.46 (m, 4H), 4.17-3.38 (m, 4H), 3.25-3.02 (m, 2H), 3.01-2.76 (m, 1H), 2.08-1.99 (m, 6H). LCMS Method 1—Tr=0.95 min (ES+) (M+H)+ 340.2.

[Intermediate 35]—tert-Butyl 3-(2-methoxy-2-oxoethyl)-4-phenylpiperazine-1-carboxylate

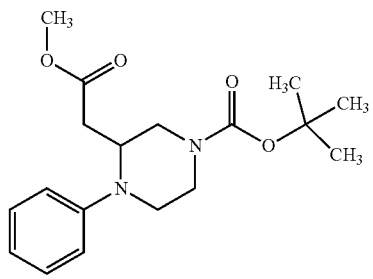 [SMILES: COC(=O)CC1CN(C(=O)OC(C)(C)C)CCN1c1ccccc1]

tert-Butyl 3-(2-methoxy-2-oxoethyl)piperazine-1-carboxylate (100 mg, 0.39 mmol), bromobenzene (41 µl, 0.39 mmol), DavePhos (15 mg, 0.04 mmol), Pd$_2$(dba)$_3$ (18 mg, 0.02 mmol) and cesium carbonate (252 mg, 0.77 mmol) were suspended in de-gassed anhydrous toluene (5 ml) and the mixture was stirred at 100° C. for 22 h. The reaction mixture was cooled to rt, then filtered through Celite, washing with EtOAc (20 ml). The filtrate was concentrated in vacuo to give a brown oil. The oil was purified by flash column chromatography eluting with gradient from 0-100% EtOAc in heptane followed by 0-100% MeOH in EtOAc. The product containing fractions were combined and concentrated in vacuo to afford the title compound as a yellow oil (59 mg, 46%). $^1$H NMR (250 MHz, Chloroform-d) δ 7.32-7.26 (m, 1H), 7.26-7.22 (m, 1H), 6.87 (dd, J=15.0, 7.7 Hz, 3H), 4.35-4.11 (m, 2H), 4.09-3.99 (m, 1H), 3.60 (s, 3H), 3.35-3.18 (m, 2H), 3.13-2.94 (m, 2H), 2.67-2.51 (m, 1H), 2.41-2.25 (m, 1H), 1.47 (s, 9H). LCMS Method 4—Tr=1.86 min (ES+) (M+H)+ 335.3.

116

[Intermediate 36]—2-(1-Phenylpiperazin-2-yl)ethan-1-ol

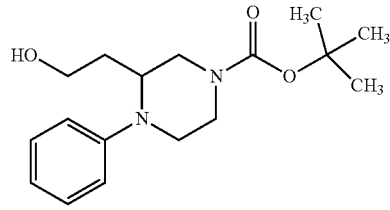 [SMILES: CC(C)(C)OC(=O)N1CCN(c2ccccc2)C(CCO)C1]

tert-Butyl 3-(2-methoxy-2-oxoethyl)-4-phenylpiperazine-1-carboxylate [Intermediate 35] (89 mg, 0.27 mmol) was suspended in anhydrous THF (5 ml) and stirred under nitrogen at 0° C. 2.4 M Lithium aluminum hydride in THF (0.33 ml) was added dropwise to the reaction mixture and stirred for 10 min at 0° C., then warmed to rt and stirred 3 h. The reaction mixture was diluted with DCM (3 ml) and cooled to 0° C. sat. aq. NH$_4$Cl (10 ml) was added and the mixture was stirred for 10 min, then warmed to rt. The reaction mixture was partitioned between DCM (10 ml) and water (10 ml). The aqueous phase was extracted with DCM (20 ml) and the organic phases were combined and reduced in vacuo to afford the title compound as a yellow oil (81 mg, 27%). LCMS Method 4—Tr=1.68 min (ES+) (M+H)+ 307.2. [Intermediate 37]-2-(1-Phenylpiperazin-2-yl)ethan-1-ol dihydrochloride

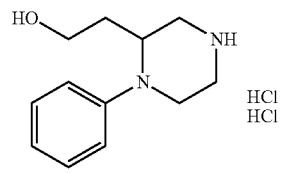

tert-Butyl 3-(2-hydroxyethyl)-4-phenylpiperazine-1-carboxylate [Intermediate 36] (81 mg, 0.13 mmol) was suspended in 4M HCl in Dioxane (0.63 ml) and stirred at rt for 16 h. The reaction mixture was concentrated in vacuo to afford the title compound as a brown solid (105 mg, 100%). LCMS Method 4—Tr=1.36 min (ES+) (M+H)+ 207.3.

[Intermediate 38]—2-[4-(5-Amino-2,4-dimethylbenzoyl)piperazin-1-yl]benzonitrile

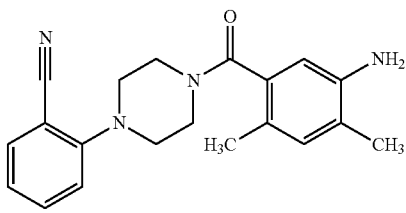

The title compound was synthesized from 2-(piperazin-1-yl)benzonitrile (403 mg, 2.15 mmol) and 2,4-dimethyl-5-nitrobenzoic acid (400 mg, 2.05 mmol) using the method described above for Intermediate 33 & 34 to afford the title compound as a white foamy solid (723 mg, 100%). $^1$H NMR (250 MHz, Chloroform-d) δ 7.58 (dd, J=7.7, 1.6 Hz, 1H), 7.51 (td, J=8.2, 1.6 Hz, 1H), 7.12-6.97 (m, 2H), 6.90 (s, 1H), 6.51 (s, 1H), 6.51 (s, 1H), 4.07-3.33 (m, 6H), 3.24 (d, J=4.7 Hz, 2H), 3.09 (d, J=4.6 Hz, 2H), 2.18 (s, 3H), 2.15 (s, 3H). LCMS Method 1—Tr=1.08 min (ES+) (M+H)+ 334.8.

[Intermediate 39]—1-Phenylazepan-4-one

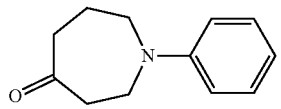 [SMILES: O=C1CCCN(c2ccccc2)CC1]

Azepan-4-one hydrochloride (250 mg, 1.67 mmol), phenylboronic acid (407 mg, 3.34 mmol), copper (II) acetate (303 mg, 1.67 mmol) and pyridine (405 µl, 5.01 mmol) were suspended in anhydrous DCM (10 ml). 4 Å molecular sieves (450 mg) were added and the mixture was stirred at rt with air bubbled through the mixture for 1 hr. The reaction was stirred for 16 h at rt, then 9 h at 40° C. The mixture was filtered through Celite and the filtrate was partitioned between water (30 ml) and DCM (20 ml). The aqueous phase was extracted with DCM (2×20 ml). The organics were combined and concentrated in vacuo to give a brown oil. The oil was purified by flash column chromatography eluting with gradient from 0-100% EtOAc in heptane. The product containing fractions were combined and concentrated in vacuo to afford the title compound as a white solid (98 mg, 31%). $^1$H NMR (250 MHz, Chloroform-d) δ 7.26-7.17 (m, 2H), 6.77-6.67 (m, 3H), 3.81-3.71 (m, 2H), 3.69-3.59 (m, 2H), 2.79-2.70 (m, 2H), 2.68-2.60 (m, 2H), 1.95-1.83 (m, 2H). LCMS Method 4—Tr=1.64 min (ES+) (M+H)+ 190.2.

[Intermediate 40]—[2-(Piperazin-1-yl)phenyl]methanol

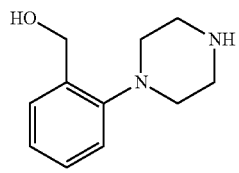

2-(Piperazin-1-yl)benzoic acid (80 mg, 0.39 mmol) was suspended in anhydrous THF (5 ml) under nitrogen atmosphere at 0° C. 2.4M Lithium aluminum hydride in THF (485 µl) was added dropwise to the reaction mixture. The reaction mixture was warmer to rt and stirred for 3 h. The reaction was cooled to 0° C., diluted with DCM (5 ml) and quenched with sat. aq. NH$_4$Cl (10 ml). The biphasic solution was stirred for 5 min and warmed to rt. 2M aq. NaOH (20 ml) was added. The organic layer was separated and the aqueous phase extracted with DCM (2×20 ml). The combined organics were concentrated in vacuo to afford the title compound as a yellow oil (74 mg, 87%). $^1$H NMR (250 MHz, Chloroform-d) δ 7.32-7.26 (m, 1H), 7.25-7.07 (m, 3H), 4.81 (s, 2H), 3.06 (dd, J=6.1, 2.8 Hz, 4H), 2.96 (dd, J=6.3, 2.9 Hz, 4H). LCMS Method 4—Tr=1.30 min (ES+) (M+H)+ 193.3.

[Intermediate 41]—tert-butyl 3-(hydroxymethyl)-4-(pyrazin-2-yl)piperazine-1-carboxylate

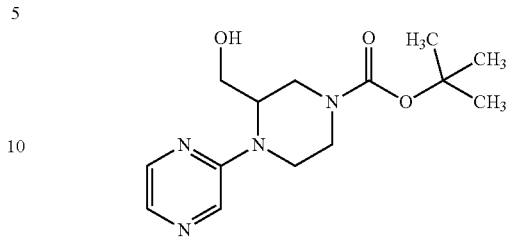

2-Chloropyrazine (250 mg, 2.18 mmol), tert-butyl 3-(hydroxymethyl)piperazine-1-carboxylate (495 mg, 2.29 mmol), (+/−) BINAP (14 mg, 0.02 mmol), Pd(OAc)$_2$ (25 mg, 0.11 mmol) and cesium carbonate (1.4 g, 4.4 mmol) were suspended in anhydrous de-gassed toluene (10 ml). The mixture was de-gassed with nitrogen for 5 minutes then sealed under a nitrogen atmosphere and stirred at 100° C. for 18 h. The reaction mixture was cooled to rt and filtered through Celite, washing with EtOAc. The filtrate was concentrated in vacuo. The resultant orange oil was purified by flash column chromatography eluting with gradient from 0-100% EtOAc in heptane followed by 0-100% MeOH in EtOAc. The product containing fractions were combined and concentrated in vacuo to give a yellow oil. The oil was purified by preparative HPLC [UV-Directed High pH prep method]. The fractions containing product were combined and concentrated in vacuo to yield the title compound as a clear gel (170 mg, 25%). $^1$H NMR (250 MHz, Chloroform-d) δ 8.17-8.12 (m, 1H), 8.06-7.99 (m, 1H), 7.86 (d, J=2.6 Hz, 1H), 4.54-4.42 (m, 1H), 4.35-3.90 (m, 3H), 3.78-3.59 (m, 2H), 3.18 (s, 4H), 1.49 (s, 9H). LCMS Method 1—Tr=1.03 min (ES+) (M+H)+ 295.3

[Intermediate 42]—[1-(Pyrazin-2-yl)piperazin-2-yl]methanol Dihydrochloride

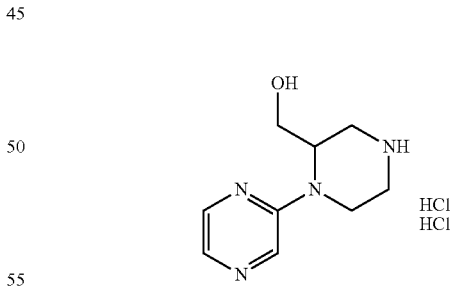

tert-Butyl 3-(hydroxymethyl)-4-(pyrazin-2-yl)piperazine-1-carboxylate [Intermediate 41] (170 mg, 0.54 mmol) was suspended in 4M HCl in Dioxane (3 ml) and stirred at rt for 1 h. The reaction mixture was concentrated in vacuo to afford the title compound as a yellow solid (159 mg, 94%). $^1$H NMR (250 MHz, DMSO-d6) δ 9.90-9.63 (m, 1H), 9.29-8.94 (m, 1H), 8.38 (d, J=1.4 Hz, 1H), 8.16 (dd, J=2.7, 1.4 Hz, 1H), 7.88 (d, J=2.7 Hz, 1H), 4.64-4.52 (m, 2H), 4.46-4.31 (m, 1H), 3.86-3.63 (m, 2H), 3.52-2.88 (m, 6H). LCMS Method 4—Tr=1.10 min (ES+) (M+H)+ 195.2.

[Intermediate 43]—5-Hydroxy-2,4-dimethylbenzoic Acid

Prepared by the method of Adediran Cabaret et al. Journal of Organic Chemistry (1999)64, 3, 713-720.

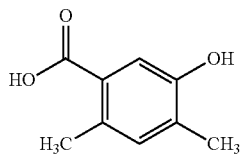

To a stirred solution of methyl 5-amino-2,4-dimethylbenzoate (250 mg, 1.39 mmol) in 20% sulfuric acid (aq) (10 ml) at 0° C. was added a solution of $NaNO_2$ (115 mg, 1.67 mmol) in water (5 ml). Conc sulfuric acid (8 ml) was then added. The resultant solution was then added to boiling 50% aq sulfuric acid (30 ml) at 100° C. The reaction mixture was stirred for 10 min then poured over ice and extracted with EtOAc. The organics were concentrated in vacuo then purified via flash column chromatography using 9:1 DCM/MeOH. The fractions containing product were combined and the solvent removed in vacuo to yield the title compound (151 mg, 65%). $^1$H NMR (250 MHz, Methanol-d4) δ 7.36 (s, 1H), 6.98 (s, 1H), 2.46 (s, 3H), 2.21 (s, 3H).

[Intermediate 44]—2-[4-(5-Hydroxy-2,4-dimethylbenzoyl)piperazin-1-yl]benzonitrile

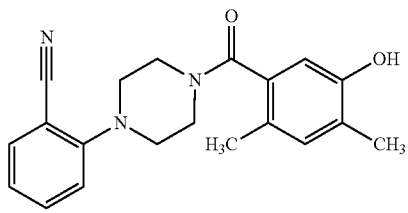 [SMILES: Cc1cc(C)c(C(=O)N2CCN(c3ccccc3C#N)CC2)cc1O]

5-Hydroxy-2,4-dimethylbenzoic acid [Intermediate 43] (151 mg, 0.91 mmol) and HATU (414 mg, 1.09 mmol) were suspended in DMF (5 ml) and stirred at rt for 20 min. 2-(Piperazin-1-yl)benzonitrile (187 mg, 1 mmol) and DIPEA (475 µl, 2.7 mmol) were then added and the reaction was stirred for 16 h. The reaction was concentrated in vacuo. The residue was partitioned between DCM (20 ml) and water (20 ml) then the organics were separated and the aqueous phase extracted with DCM (2×20 ml). The combined organics were concentrated in vacuo then the residue was purified via flash column chromatography (gradient of 0-100% EtOAc in heptane followed by 0-100% MeOH in EtOAc). The fractions containing product were combined and concentrated in vacuo to give a yellow solid. The solid was then loaded onto the UV Direct High pH preparative HPLC system. The fractions containing product were collected and the solvents removed in vacuo to yield the title compound as a yellow solid (56 mg, 18%). $^1$H NMR (250 MHz, Chloroform-d) δ 7.59 (dd, J=7.7, 1.5 Hz, 1H), 7.56-7.47 (m, 1H), 7.07 (t, J=7.2 Hz, 1H), 7.01 (s, 1H), 6.89 (s, 1H), 6.64-6.56 (m, 2H), 4.02 (d, J=40.6 Hz, 2H), 3.48 (t, J=4.9 Hz, 2H), 3.32-3.17 (m, 2H), 3.13-3.01 (m, 2H), 2.19 (s, 3H), 2.15 (s, 3H). LCMS Method 8—Tr=1.61 min (ES+) (M+H)+ 336.2.

Intermediate 45]—3-(4-Oxoazepan-1-yl)benzonitrile

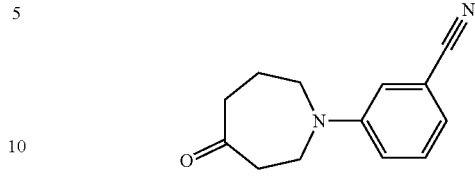

Azepan-4-one hydrochloride (125 mg, 0.84 mmol), (3-cyanophenyl)boronic acid (24 mg, 1.67 mmol), copper (II) acetate (152 mg, 0.84 mmol), pyridine (202 µl, 2.51 mmol) and 4 Å molecular sieves (500 mg) were suspended in anhydrous DCM (10 ml). The reaction mixture was stirred at 40° C. for 18 h. The reaction mixture was cooled to rt and filtered through Celite. The filtrate was concentrated in vacuo to give a brown oil. The oil was purified by flash column chromatography eluting with gradient from 0-100% EtOAc in heptane followed by 0-100% MeOH in EtOAc. The product containing fractions were combined and reduced in vacuo to afford the title compound as a white solid (54 mg, 30%). $^1$H NMR (250 MHz, Chloroform-d) δ 7.32-7.23 (m, 1H), 6.99-6.92 (m, 1H), 6.91-6.83 (m, 2H), 3.83-3.71 (m, 2H), 3.70-3.56 (m, 2H), 2.78-2.62 (m, 4H), 1.95-1.79 (m, 2H). LCMS Method 4—Tr=1.58 min (ES+) (M+H)+ 215.2.

[Intermediate 46]—4-(4-Oxoazepan-1-yl)benzonitrile

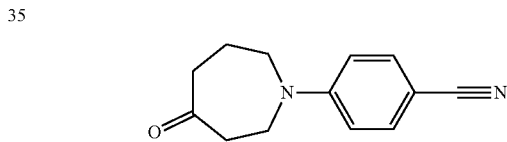

The title compound was synthesized from (4-cyanophenyl)boronic acid (245 mg, 1.67 mmol) using the method described above for Intermediate 45 to afford the title compound as a white solid (124 mg, 69%). $^1$H NMR (250 MHz, Chloroform-d) δ 7.46 (d, J=9.0 Hz, 2H), 6.66 (d, J=9.0 Hz, 2H), 3.86-3.75 (m, 2H), 3.73-3.63 (m, 2H), 2.79-2.60 (m, 4H), 1.95-1.81 (m, 2H). LCMS Method 4—Tr=1.55 min (ES+) (M+H)+ 215.

[Intermediate 47]—Methyl 5-{[1-(2-cyanophenyl)piperidin-4-yl]amino}-2-methylbenzoate

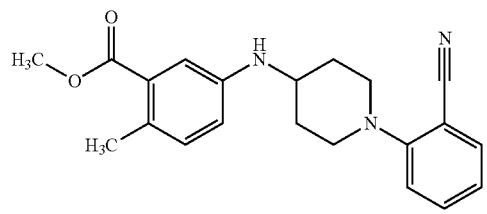 [SMILES: COC(=O)c1cc(NC2CCN(c3ccccc3C#N)CC2)ccc1C]

2-(4-Oxopiperidin-1-yl)benzonitrile [Intermediate 4] (200 mg, 1 mmol) was dissolved in dichloromethane (2.5 ml) then methyl 3-amino-4-methylbenzoate (165 mg, 1 mmol) was added and the reaction was stirred for 10 mins at ambient temperature. NaBH(OAc)$_3$ (423.39 mg, 2 mmol) was then added and the reaction was stirred for a further 18 h. The reaction was partitioned between DCM (2.5 ml) and water (3 ml) then the reaction was stirred until no further gas evolution was observed. The organic layer was separated via filtration through a PTFE fritted tube and concentrated in vacuo. The residue obtained was purified via flash column chromatography using a gradient of EtOAc (0% to 100%) in heptane. The fractions containing product were combined and concentrated in vacuo to afford the title compound as a clear gel (329 mg, 94%). LCMS Method 2—Tr=1.24 min (ES+) (M+H$^+$) 350.1.

[Intermediate 48]—5-{[1-(2-Cyanophenyl)piperidin-4-yl]amino}-2-methylbenzoic Acid

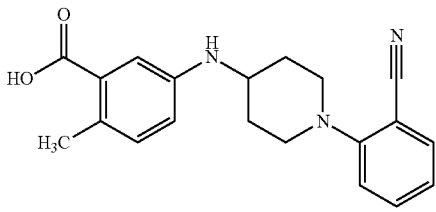 [SMILES: Cc1ccc(NC2CCN(c3ccccc3C#N)CC2)cc1C(=O)O]

Methyl 5-{[1-(2-cyanophenyl)piperidin-4-yl]amino}-2-methylbenzoate [Intermediate 47] (329 mg, 0.94 mmol) was dissolved in THF (5 ml) then LiOH (2M aq, 941.52 µl) was added and the reaction was heated to 65° C. for 4 h. Further additions of 2M. aq. LiOH (2×1.0 ml) and the addition of MeOH (0.5 ml) were required to push the reaction to completion. Addition of an equivolume of 2M. aq, hydrochloric acid (2.94 ml), followed by the addition of DCM (15 ml) and water (10 ml) then the reaction was stirred for 5 minutes. The organics were separated via filtration through a PTFE fritted tube and concentrated in vacuo to afford the title compound as a yellow powdery solid (254 mg, 72%). LCMS Method 2—Tr=1.11 min (ES+) (M+H$^+$) 336.1.

[Intermediate 49]—4-[(tert-Butoxy)carbonyl]-1-phenylpiperazine-2-carboxylic Acid

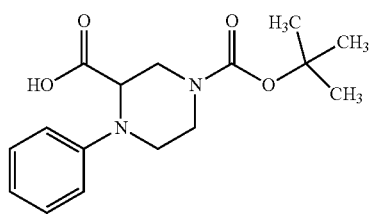 [SMILES: CC(C)(C)OC(=O)N1CCN(c2ccccc2)C(C(=O)O)C1]

1-Phenylpiperazine-2-carboxylic acid dihydrochloride (1.0 g, 3.58 mmol) was suspended in 1,4-dioxane (20 ml) then DIPEA (2.0 ml, 11.46 mmol) was added followed by the addition of di-tert-butyl dicarbonate (860 mg, 3.94 mmol) and the reaction was stirred at rt for 2 h. The reaction was concentrated in vacuo then the residue was partitioned between DCM (20 ml) and water (10 ml) then the organics were separated, dried over Na$_2$SO$_4$, filtered and concentrated in vacuo. The residue obtained was purified via flash column chromatography eluting with a gradients of EtOAc (0% to 100%) in heptane followed by MeOH (0% to 100%) in EtOAc. Two peaks were noted with the desired mass; the relevant fractions for both peaks were combined and concentrated in vacuo to give two crops of the title compound. The first crop was a white crystalline solid (513 mg, 47%). LCMS Method 2—Tr=1.08 min (ES+) (M+H$^+$) 307.1.

[Intermediate 50]—1-Phenylpiperazine-2-carboxamide Hydrochloride

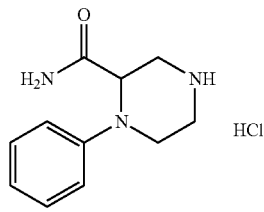 [SMILES: NC(=O)C1CNCCN1c1ccccc1 ; Cl]

4-[(tert-Butoxy)carbonyl]-1-phenylpiperazine-2-carboxylic acid (263 mg, 0.86 mmol) and HATU (392 mg, 1.03 mmol) were suspended in 1,4-dioxane (5 ml) then the reaction mixture was stirred for 1 h. Ammonium carbonate (99 mg, 1.03 mmol) was added and the reaction stirred at rt for 2 h. Further ammonium carbonate (99 mg, 1.03 mmol) was added then the reaction was stirred for 5 h. The reaction was then diluted with DCM (30 ml) and water (15 ml) then the reaction was briefly stirred and the organics were separated and concentrated in vacuo. The resulting residue was taken up in 1,4-dioxane then 4M hydrochloric acid in 1,4-dioxane (2.5 ml) was added The reaction was agitated for 18 h. Further 4M hydrochloric acid in 1,4-dioxane (2.5 ml) was added then the reaction mixture was agitated for a 6 h before concentration in vacuo to yield the title compound as a pale tan solid (192 mg, 93%). $^1$H NMR (500 MHz, DMSO-d6) δ 9.41 (s, 1H), 8.44 (s, 1H), 7.58 (s, 1H), 7.42 (s, 1H), 7.25 (dd, J=8.7, 7.3 Hz, 2H), 6.97 (d, J=8.0 Hz, 2H), 6.83 (t, J=7.3 Hz, 1H), 4.56-4.50 (m, 1H), 3.58-3.50 (m, 3H), 3.23 (d, J=11.8 Hz, 2H), 3.06 (d, J=10.0 Hz, 1H).

[Intermediate 51]—Methyl 3-{[1-(2-cyanophenyl)piperidin-4-yl]amino}-4-methylbenzoate

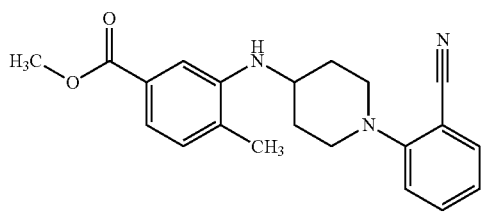 [SMILES: COC(=O)c1ccc(C)c(NC2CCN(c3ccccc3C#N)CC2)c1]

Prepared analogously to the method of methyl 5-{[1-(2-cyanophenyl)piperidin-4-yl]amino}-2-methylbenzoate [Intermediate 47] from 2-(4-oxopiperidin-1-yl)benzonitrile [Intermediate 4] (200 mg, 1 mmol) and methyl 5-amino-2-methylbenzoate (165 mg, 1 mmol) to yield the title compound as a clear gel (257 mg, 52%). LCMS Method 2—Tr=1.29 min (ES+) (M+H$^+$) 350.1.

[Intermediate 52]—3-{[1-(2-Cyanophenyl)piperidin-4-yl]amino}-4-methylbenzoic Acid

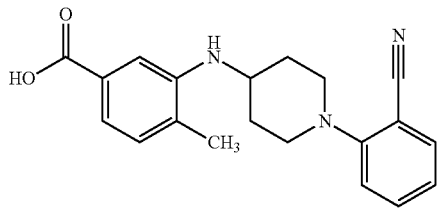 [SMILES: Cc1ccc(C(=O)O)cc1NC1CCN(c2ccccc2C#N)CC1]

Prepared analogously to the method of 5-{[1-(2-cyanophenyl)piperidin-4-yl]amino}-2-methylbenzoic acid [Intermediate 48] from Methyl 3-{[1-(2-cyanophenyl)piperidin-4-yl]amino}-4-methylbenzoate (329 mg, 0.94 mmol) to yield the title compound as a yellow powdery solid (218 mg, 72%). LCMS Method 2—Tr=1.14 min (ES+) (M+H$^+$) 336.1.

[Intermediate 53]—1-tert-Butyl 3-methyl (3R)-4-phenylpiperazine-1,3-dicarboxylate

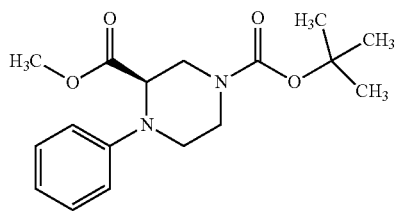 [SMILES: COC(=O)[C@H]1CN(C(=O)OC(C)(C)C)CCN1c1ccccc1]

Bromobenzene (125 mg, 0.8 mmol), 1-tert-butyl 3-methyl (3R)-piperazine-1,3-dicarboxylate (213.94 mg, 0.88 mmol), Pd$_2$(dba)$_3$.CHCl$_3$ (8.24 mg, 0.01 mmol), RuPhos (9.29 mg, 0.02 mmol) and Cs$_2$CO$_3$ (324.24 mg, 1 mmol) were suspended in anhydrous toluene (2.5 ml). The sealed reaction was heated at 110° C. for 18 h. The reaction was partitioned between DCM (5 ml) and water (5 ml) then the organics were separated and concentrated in vacuo. The residue was purified via flash column chromatography using a gradient of 0% to 100% EtOAc in heptane then 0% to 100% MeOH in EtOAc. Fractions containing product were combined and concentrated in vacuo to yield the title compound as a yellow glassy solid (51 mg, 13%). LCMS Method 2—Tr=1.21 min (ES+) (M+H$^+$) 321.0.

[Intermediate 54] 2-[(2R)-1-phenylpiperazin-2-yl]propan-2-ol

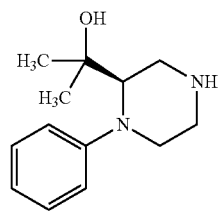 [SMILES: CC(C)(O)[C@H]1CNCCN1c1ccccc1]

1-tert-Butyl 3-methyl (3R)-4-phenylpiperazine-1,3-dicarboxylate (51 mg, 0.16 mmol) was dissolved in anhydrous tetrahydrofuran (2.5 ml) then 3M methyl magnesium bromide in Et$_2$O (111 µl, 0.33 mmol) was added and the reaction was stirred at rt for 18 h. The reaction was partitioned between DCM (5 ml) and water (5 ml) then the organics were separated and concentrated in vacuo. The residue was dissolved in DCM (2 ml) and the solution was retreated with 3M methyl magnesium bromide in Et$_2$O (300 µl, 0.9 mmol) and agitated for a further 3 h. The reaction was partitioned between DCM (5 ml) and water (5 ml) then the organics were separated and concentrated in vacuo. The residue was dissolved in DCM (4 ml) and TFA (1 ml) was added and stirred at rt for 6 h. The reaction was diluted with further DCM (5 ml) and sat. aq. NaHCO$_3$ (5 ml), then agitated for 5 minutes. The organics were separated and concentrated in vacuo to yield the crude title compound as a brown gel (28 mg, 44%). LCMS Method 2—Tr=0.80 min (ES+) (M+H$^+$) 221.15.

[Intermediate 55]—1-tert-Butyl 3-methyl (3S)-4-phenylpiperazine-1,3-dicarboxylate

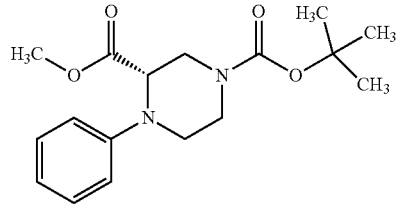 [SMILES: COC(=O)[C@@H]1CN(C(=O)OC(C)(C)C)CCN1c1ccccc1]

Prepared analogously to the method of 1-tert-butyl 3-methyl (3R)-4-phenylpiperazine-1,3-dicarboxylate [Intermediate 53] from 1-tert-butyl 3-methyl (3S)-piperazine-1,3-dicarboxylate (214 mg, 0.88 mmol) to yield the title compound as a yellow glass (45 mg, 16%). LCMS Method 2—Tr=1.21 min (ES+) (M+H$^+$) 321.0

[Intermediate 56]—2-[(2S)-1-phenylpiperazin-2-yl]propan-2-ol

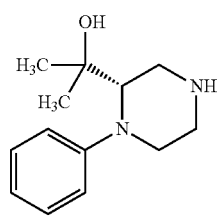 [SMILES: CC(C)(O)[C@@H]1CNCCN1c1ccccc1]

Prepared analogously to the method of [Intermediate 54] from 1-tert-butyl 3-methyl (3S)-4-phenylpiperazine-1,3-dicarboxylate (45 mg, 0.14 mmol) to yield the crude title compound as a brown gel (29 mg, 58%). LCMS Method 2—Tr=0.79 min (ES+) (M+H$^+$) 221.15.

[Intermediate 57]—tert-Butyl 3-(hydroxymethyl)-4-[2-(methylcarbamoyl)phenyl]piperazine-1-carboxylate

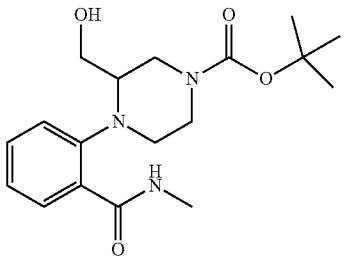 [SMILES: CNC(=O)c1ccccc1N1CCN(C(=O)OC(C)(C)C)CC1CO]

To a pressure tube of tert-butyl 3-(hydroxymethyl)piperazine-1-carboxylate (216 mg, 1 mmol), 2-iodo-N-methyl benzamide (261 mg, 1 mmol), 2,3-butylene glycol (180 mg, 2 mmol) and potassium phosphate (425 mg, 2 mmol) in isopropanol (2 mL). The reaction mixture was purged with nitrogen 5 mins and CuI (20 mg, 0.1 mmol) was added. The reaction was stirred at 92° C. for 4 h. After cooling to rt, the reaction mixture was partitioned between MBTE (10 mL) and water (4 mL). The aqueous layer was extracted with MBTE (2×4 mL). The combined organic phases were dried (Na$_2$SO$_4$), filtered and reduced in vacuo to yield a pale brown gum. The crude material was purified by preparative HPLC [UV-Directed High pH prep method]. The product containing fractions were reduced in vacuo to afford the title compound as colorless gum (73.1 mg, 20%). $^1$H NMR (500 MHz, Chloroform-d) δ 9.19 (s, 1H), 8.22 (dd, J=7.8, 1.9 Hz, 1H), 8.06 (s, 1H), 8.04 (s, 0.8H), 7.50-7.36 (m, 1.8H), 7.29-7.22 (m, 2.6H), 7.11-7.00 (m, 0.8H), 7.00-6.91 (m, 1H), 4.72 (hept, J=6.1 Hz, 0.8H), 4.14-3.94 (m, 1H), 3.94-3.75 (m, 1H), 3.61-3.44 (m, 2H), 3.43-3.30 (m, 1H), 3.29-3.14 (m, 2H), 3.04 (dt, J=12.0, 3.6 Hz, 1H), 3.00 (s, 1.2H), 2.99 (s, 1.2H), 2.99 (s, 1.5H), 2.98 (s, 1.5H), 2.82 (t, J=9.3 Hz, 1H), j 1.50 (s, 9H), 2.16 (s, 1H), 1.42 (d, J=6.1 Hz, 4.8H). LCMS Method 5—Tr=1.20 min (ES+) (M+H$^+$) 350.

[Intermediate 58]—2-[2-(hydroxymethyl)piperazin-1-yl]-N-methylbenzamide Dihydrochloride

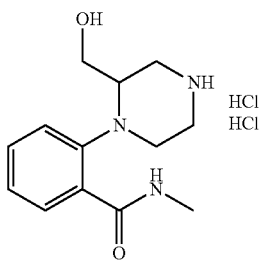

tert-Butyl 3-(hydroxymethyl)-4-[2-(methylcarbamoyl)phenyl]piperazine-1-carboxylate [Intermediate 57] (36.4 mg, 0.104 mmol) was dissolved in dioxane (1 mL). To stirred reaction mixture was added 4M HCl in dioxane (1 mL). The reaction mixture was stirred at rt for 2 h. The reaction mixture was reduced to yield the tile compound white solid (33 mg, 99%)

[Intermediate 59]—tert-Butyl 4-(2-cyanophenyl)-3-(hydroxymethyl)piperazine-1-carboxylate

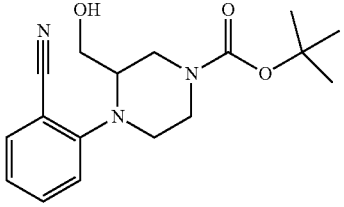 [SMILES: CC(C)(C)OC(=O)N1CCN(c2ccccc2C#N)C(CO)C1]

To a pressure tube of tert-butyl 3-(hydroxymethyl)piperazine-1-carboxylate (227 mg, 1.05 mmol), 2-iodobenzonitrile (229 mg, 1 mmol), ethylene glycol (124 mg, 2 mmol) and K$_3$PO$_4$ (425 mg, 2 mmol) in isopropanol (2 ml) purged with nitrogen for 5 mins, copper iodide (20 mg, 0.1 mmol) was added. The reaction was heated to 90° C. overnight. After cooling to ambient temperature MBTE (4 ml) and water (2 ml) were added to the reaction mixture. The aqueous layer was extracted with MBTE (2×4 ml). The combined organic phases were washed with brine and dried over Na$_2$SO$_4$. The solvent was concentrated in vacuo and the residue purified by flash column chromatography on silica gel (cyclohexane—50% MBTE) to yield the title compound as a colorless gum (60.4 mg, 18%). LCMS Method 2—Tr=1.12 min, (ES+) (M+H$^+$-$^t$Bu) 262, (M+Na$^+$) 340. $^1$H NMR (500 MHz, Chloroform-d) δ 7.64-7.57 (m, 1H), 7.54-7.47 (m, 1H), 7.12-7.04 (m, 2H), 4.19-3.99 (m, 1H), 3.99-3.92 (m, 1H), 3.92-3.80 (m, 1H), 3.80-3.68 (m, 1H), 3.68-3.45 (m, 2H), 3.46-3.39 (m, 1H), 3.38-3.28 (m, 1H), 3.08 (dt, J=11.8, 3.3 Hz, 1H), 1.52 (s, 9H).

[Intermediate 60]—tert-Butyl 3-(hydroxymethyl)-4-(pyridin-2-yl)piperazine-1-carboxylate

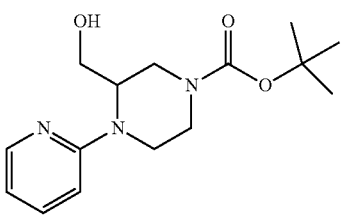 [SMILES: CC(C)(C)OC(=O)N1CCN(c2ccccn2)C(CO)C1]

To a pressure tube; tert-butyl 3-(hydroxymethyl)piperazine-1-carboxylate (681 mg, 3.15 mmol), 2-iodopyridine (615 mg, 3 mmol), ethylene glycol (372 mg, 6 mmol) and potassium phosphate (1.28 g, 6 mmol) in isopropanol (6 ml) purged with nitrogen 5 mins were added then CuI (60 mg, 0.3 mmol) was added. The reaction was stirred and heated to 90° C. overnight. After cooling to ambient temperature MBTE (4 ml) and water (2 ml) were then added to the reaction mixture. The organic layer was extracted with MBTE (2×4 ml). The combined organic phases were washed with brine and dried over Na$_2$SO$_4$. The solvent was concentrated in vacuo giving 918 mg of a green oil. Purified by flash column chromatography on silica gel using gradient 0% to 100% MBTE in DCM. The product containing fractions were combined and reduced in vacuo to yield the title compound as a colorless gum (143 mg, 9%).

Found by 1H NMR to be a ~3:5 mixture of the title product and 2-(pyridine-2-yloxy)ethan-1-ol. Used the crude product for the next stage. $^1$H NMR (500 MHz, Chloroform-d) δ 8.20-8.10 (m, 1.6H), 7.68-7.58 (m, 1H), 7.57-7.47 (m, 0.6H), 6.97-6.89 (m, 1H), 6.87-6.80 (m, 1H), 6.72-6.61 (m, 1.2H), 4.72-4.35 (m, 2.6H), 4.32-3.62 (m, 7H), 3.24 (d, J=7.7 Hz, 2H), 1.51 (s, 5.4H). LCMS Method 2—Tr=0.98 min, (ES+) (M+H$^+$) 294.

[Intermediate 61]—[1-(Pyridin-2-yl)piperazin-2-yl]methanol Dihydrochloride

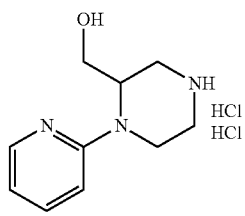

tert-Butyl 3-(hydroxymethyl)-4-(pyridin-2-yl)piperazine-1-carboxylate [Intermediate 60] (80 mg, 0.27 mmol) was dissolved in MeOH (3 ml) then 12N. aq. HCl (1 ml) was added. The reaction was stirred overnight. The reaction was evaporated to dryness below 30° C., to yield the title compound as a colorless gum (152 mg, 100%).

Found by 1H NMR to be a ~3:5 mixture of the title product and 2-(pyridine-2-yloxy)ethan-1-ol. Used as the mixture in the next step. $^1$H NMR (500 MHz, DMSO-d6) δ 10.03-9.59 (s, 0.6H), 9.50-9.15 (m, 0.6H), 8.16 (dd, J=5.1, 1.3 Hz, 1H), 8.08 (dd, J=6.0, 1.4 Hz, 0.6H), 8.05-7.94 (m, 0.6H), 7.75 (ddd, J=8.9, 7.1, 2.0 Hz, 1H), 7.44-7.33 (m, 0.6H), 7.05-6.94 (m, 1.6H), 6.91-6.82 (m, 1H), 4.69-4.64 (m, 0.6H), 4.38-4.30 (m, 0.6H), 4.30-4.24 (m, 12H), 4.03-3.88 (m, 0.6H), 3.76-3.67 (m, 0.6H), 3.73-3.67 (m, 2H), 3.62-3.51 (m, 0.6H), 3.48-3.44 (m, 0.6H), 3.39-3.30 (m, 0.6H), 3.30-3.20 (m, 0.6H), 3.16-3.04 (m, 0.6H).

[Intermediate 62]—tert-Butyl 4-(3-fluoro-2-sulfamoylphenyl)piperazine-1-carboxylate

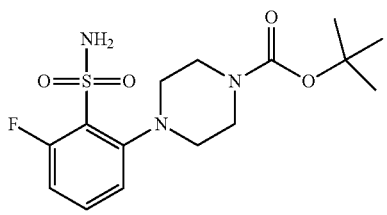 [SMILES: CC(C)(C)OC(=O)N1CCN(c2cccc(F)c2S(N)(=O)=O)CC1]

A mixture of 2,6-difluorobenzene-1-sulfonamide (1.00 g, 5.18 mmol), tert-butyl piperazine-1-carboxylate (0.96 g, 5.18 mmol) and DIPEA (1.35 ml, 7.77 mmol) in 1,4-dioxane (10 ml) was heated at 110° C. for 3 h. The reaction mixture was evaporated and the residue purified by flash column chromatography on a 50 g silica Biotage cartridge using a gradient of 0-45% MBTE in DCM to yield the title compound as a crystalline solid. (796 mg, 39%). LCMS Method 2—Tr=1.13 mins, (ES+) (M+H$^+$) 360.

[Intermediate 63]—tert-Butyl 4-(5-fluoropyridin-2-yl)-3-oxopiperazine-1-carboxylate

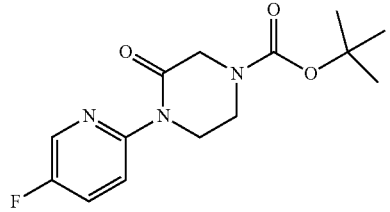 [SMILES: CC(C)(C)OC(=O)N1CCN(c2ccc(F)cn2)C(=O)C1]

Sodium hydride (144 mg, 6 mmol) was added to a stirred solution of tert-butyl 3-oxopiperazine-1-carboxylate (1.00 g, 5 mmol) in anhydrous DMF (8 ml) at 0-20° C. The reaction was then heated at 55° C. for 30 minutes and then allowed to cool. 2,5-Difluoropyridine (0.575 g, 5 mmol) was added and the mixture was stirred at 20° C. for 10 minutes then warmed to 60° C. for 20 h. The solution was diluted with DCM (40 ml), filtered through Celite, solids washed well with DCM and the filtrate was reduced in vacuo to yield the crude product. The crude product was purified via column chromatography (25 g silica) eluted with a gradient of 0-100% DCM in MBTE. The product containing fraction were combined and reduced in vacuo to yield the title compound as a pale brown gum. (254 mg, 17%). $^1$H NMR (500 MHz, Chloroform-d) δ 8.28 (d, J=3.0 Hz, 1H), 8.10-7.95 (m, 1H), 7.47 (ddd, J=9.1, 7.6, 3.0 Hz, 1H), 4.30 (s, 2H), 4.17-4.06 (m, 2H), 3.87-3.71 (m, 2H), 1.52 (s, 9H). LCMS Method 2—Tr=1.07 mins, (ES+) (M+H$^+$) 296.

[Intermediate 64]—tert-Butyl 4-(2-fluorophenyl)-3-(hydroxymethyl)piperazine-1-carboxylate

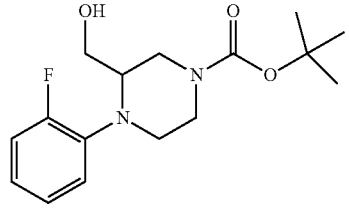 [SMILES: CC(C)(C)OC(=O)N1CCN(c2ccccc2F)C(CO)C1]

Prepared analogously to the method of tert-Butyl 4-(2-cyanophenyl)-3-(hydroxymethyl)piperazine-1-carboxylate [Intermediate 59] from tert-butyl 3-(hydroxymethyl)piperazine-1-carboxylate (216 mg, 1 mmol) and 1-fluoro-2-iodobenzene (222 mg, 1 mmol) to yield the title compound as a colorless solid (194 mg, 63%). $^1$H NMR (500 MHz, Chloroform-d) δ 7.12-6.93 (m, 4H), 4.09-3.69 (m, 2H), 3.69-3.33 (m, 5H), 3.33-3.22 (m, 1H), 3.02 (s, 1H), 1.49 (s, 9H). LCMS Method 2—Tr=1.17 mins, (ES+) (M+H$^+$) 311.

[Intermediate 65]—tert-Butyl 4-(3-fluorophenyl)-3-(hydroxymethyl)piperazine-1-carboxylate

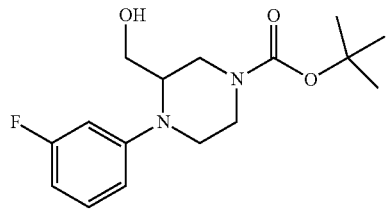 [SMILES: CC(C)(C)OC(=O)N1CCN(c2cccc(F)c2)C(CO)C1]

Prepared analogously to the method of tert-Butyl 4-(2-cyanophenyl)-3-(hydroxymethyl)piperazine-1-carboxylate [Intermediate 59] from tert-butyl 3-(hydroxymethyl)piperazine-1-carboxylate (216 mg, 1 mmol) and 1-fluoro-3-iodobenzene (222 mg, 1 mmol) to yield the title compound as a colorless solid (181 mg, 58%). $^1$H NMR (500 MHz, Chloroform-d) δ 7.23-7.14 (m, 1H), 6.69-6.62 (m, 1H), 6.61-6.45 (m, 2H), 4.49-3.75 (m, 3H), 3.75-3.24 (m, 3H), 3.20-2.94 (m, 3H), 2.69 (s, 1H), 1.49 (s, 9H).

LCMS Method 2—Tr=1.18 mins, (ES+) (M+H$^+$) 310.

[Intermediate 66]—tert-Butyl 4-(4-fluorophenyl)-3-(hydroxymethyl)piperazine-1-carboxylate

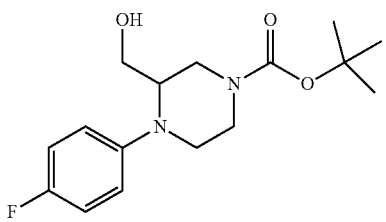 [SMILES: CC(C)(C)OC(=O)N1CCN(c2ccc(F)cc2)C(CO)C1]

Prepared analogously to the method of tert-Butyl 4-(2-cyanophenyl)-3-(hydroxymethyl)piperazine-1-carboxylate [Intermediate 59] from tert-butyl 3-(hydroxymethyl)piperazine-1-carboxylate (216 mg, 1 mmol) and 1-fluoro-4-iodobenzene (205 mg, 1 mmol) to yield the title compound as a colorless solid (200 mg, 64%). $^1$H NMR (500 MHz, Chloroform-d) δ 7.02-6.93 (m, 2H), 6.93-6.77 (m, 2H), 4.37-3.94 (m, 1H), 3.90 (dtd, J=13.2, 3.7, 1.6 Hz, 1H), 3.82-3.23 (m, 4H), 3.28 (ddd, J=13.4, 9.6, 4.2 Hz, 1H), 3.10 (d, J=13.2 Hz, 2H), 2.55 (br. s, 0.5H), 1.49 (s, 9H). LCMS Method 2—Tr=1.13 mins, (ES+) (M+H$^+$) 311.

[Intermediate 67]—tert-Butyl N-[1-(5-fluoro-2-pyridyl)-4-piperidyl]carbamate

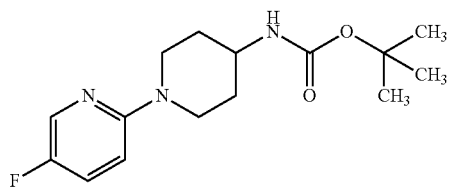 [SMILES: CC(C)(C)OC(=O)NC1CCN(c2ccc(F)cn2)CC1]

2,5-Difluoropyridine (250 mg, 2.17 mmol), tert-butyl N-(4-piperidyl)carbamate (478 mg, 2.39 mmol) and K$_2$CO$_3$ (300 mg, 2.17 mmol) were suspended in DMF (2.5 ml) then the sealed reaction was heated at 110° C. for 18 hours. The reaction mixture was diluted with 4:1 EtOAc/heptane (10 ml) and water (10 ml). The organic layer was separated, dried (Na$_2$SO$_4$) and concentrated in vacuo to yield the title compound as a yellow crystalline solid (433 mg, 61%). $^1$H NMR (500 MHz, Chloroform-d) 8.02 (d, J=3.1 Hz, 1H), 7.22 (ddd, J=9.2, 7.8, 3.1 Hz, 1H), 6.61 (dd, J=9.2, 3.3 Hz, 1H), 4.49 (s, 1H), 4.11-4.02 (m, 2H), 3.65 (s, 1H), 2.98-2.89 (m, 2H), 2.01 (d, J=10.5 Hz, 2H), 1.44 (s, 11H). LCMS Method 1—Tr=1.09 min (ES$^+$) (M+H$^+$) 296.

[Intermediate 68]—1-(5-Fluoro-2-pyridyl)piperidin-4-amine

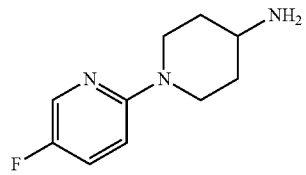 [SMILES: NC1CCN(c2ccc(F)cn2)CC1]

tert-Butyl N-[1-(5-fluoro-2-pyridyl)-4-piperidyl]carbamate [Intermediate 67] (5.0 g, 17.1 mmol) was dissolved in 50% TFA in DCM (30 ml) and stirred at ambient temperature for 16 hours. The reaction was concentrated in vacuo. The residue was dissolved in the minimum volume of (1:1) MeOH/DCM. A glass column was charged with MP-TsOH (33 g, 103 mmol) then the solution of crude product was loaded under gravity. The resin was washed sequentially with DCM (200 ml), MeOH (200 ml), DCM (200 ml) and MeOH (200 ml). The washings were discarded. The product was then eluted with 7N NH$_3$ in MeOH (400 ml). The NH$_3$ rinsing's were concentrated in vacuo to give the title compound as a beige solid (3.22 g, 93% yield). $^1$H NMR (500 MHz, Chloroform-d) δ 8.02 (d, J=3.1 Hz, 1H), 7.22 (ddd, J=9.2, 7.8, 3.1 Hz, 1H), 6.62 (dd, J=9.3, 3.3 Hz, 1H), 4.11 (dt, J=13.2, 2.9 Hz, 2H), 2.93-2.81 (m, 3H), 1.94-1.84 (m, 2H), 1.44-1.31 (m, 4H). LCMS Method 5—Tr=0.65 min (ES$^+$) (M+H$^+$) 196.

[Intermediate 69]—tert-Butyl 3-[[1-(5-fluoro-2-pyridyl)-4-piperidyl]amino]-2,4,6-trimethyl-benzoate

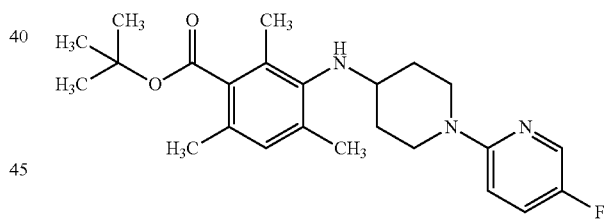

1-(5-Fluoro-2-pyridyl)piperidin-4-amine [Intermediate 68] (1 g, 5.12 mmol), tert-butyl 3-bromo-2,4,6-trimethylbenzoate (1.53 g, 5.12 mmol), (±)-BINAP (0.8 g, 1.28 mmol), NaO$^t$Bu (0.98 g, 10.24 mmol) and Pd$_2$(dba)$_3$ (0.47 g, 0.51 mmol) were suspended in toluene (5 ml). The reaction was purged with nitrogen gas for 5 minutes then sealed and heated at 100° C. for 16 hours. The reaction was filtered through celite and concentrated in vacuo. The crude residue was partitioned between EtOAc (25 ml) and water (25 ml) the organic layer was separated, washed with brine (10 ml), dried (Na2SO4), filtered and concentrated in vacuo. The crude product was purified via flash column chromatography eluting with a gradient from 0-100% EtOAc in heptane followed by 0-100% MeOH in EtOAc. The product containing fractions were combined and concentrated in vacuo to yield the title compound as a brown oil (1.09 g, 51%). $^1$H NMR (500 MHz, Chloroform-d) δ 8.04 (d, J=3.1 Hz, 1H), 7.23 (ddd, J=9.2, 7.8, 3.1 Hz, 1H), 6.83 (s, 1H), 6.62 (dd, J=9.2, 3.3 Hz, 1H), 4.17 (d, J=13.3 Hz, 2H), 3.04 (tt, J=11.0, 3.9 Hz, 1H), 2.80 (td, J=13.2, 2.4 Hz, 3H), 2.27-2.20 (m, 10H), 2.04-1.94 (m, 2H), 1.60 (s, 11H), 1.44 (qd, J=12.3, 4.1 Hz, 2H). LCMS Method 5—Tr=4.13 min (ES⁺) (M+H⁺) 414.

[Intermediate 70]—3-[[1-(5-Fluoro-2-pyridyl)-4-piperidyl]amino]-2,4,6-trimethyl-benzoic Acid

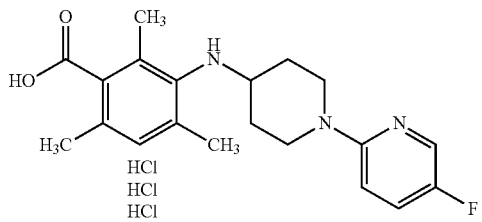 [SMILES: Cc1cc(C)c(C(=O)O)c(C)c1NC1CCN(c2ccc(F)cn2)CC1]

A solution of tert-butyl 3-[[1-(5-fluoro-2-pyridyl)-4-piperidyl]amino]-2,4,6-trimethyl-benzoate [Intermediate 69] (1.09 g, 2.64 mmol) was dissolved in 4M HCl in dioxane (26 ml). The reaction mixture was stirred at ambient temperature for 16 hours. The precipitate was isolated via filtration and washed with Et₂O to yield the title compound as a pale yellow solid (1.80 g, 99%). ¹H NMR (500 MHz, Deuterium Oxide) δ 8.00 (ddd, J=10.1, 7.2, 2.9 Hz, 1H), 7.94 (t, J=2.7 Hz, 1H), 7.40 (dd, J=10.2, 4.1 Hz, 1H), 7.25 (s, 1H), 4.25 (d, J=14.2 Hz, 2H), 3.91 (tt, J=11.9, 4.1 Hz, 1H), 3.76 (s, 4H), 3.30 (t, J=12.3 Hz, 2H), 2.46 (s, 3H), 2.41 (s, 3H), 2.34-2.25 (m, 5H), 2.06 (qd, J=12.5, 4.3 Hz, 2H). LCMS Method 5—Tr=2.19 min (ES⁺) (M+H⁺) 358.2

[Intermediate 71]—(2S)-4-[(tert-Butoxy)carbonyl]-1-phenylpiperazine-2-carboxylic Acid

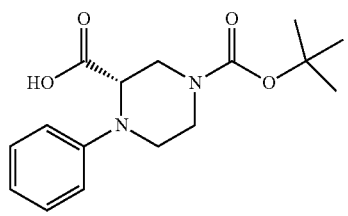 [SMILES: CC(C)(C)OC(=O)N1CCN(c2ccccc2)[C@H](C(=O)O)C1]

1-tert-Butyl 3-methyl (3S)-4-phenylpiperazine-1,3-dicarboxylate [Intermediate 55](90%, 2.1 g, 5.9 mmol) was suspended in MeOH (14 ml) then 2M aq. LiOH (6 ml) was added. The reaction mixture was sonicated and THF (5 ml) was added. The solution was stirred for 16 hours at ambient temperature. The mixture was concentrated in vacuo. The resultant residue was taken up in DCM (20 ml) and partitioned with water (20 ml). The aqueous phase was acidified to pH 4 with aq. HCl and the organic layer was then separated and concentrated in vacuo to afford the title compound as a white solid (1.7 g, 86%). ¹H NMR (250 MHz, Chloroform-d) δ 7.32-7.26 (m, 1H), 7.25-7.20 (m, 1H), 6.91-6.79 (m, 3H), 4.51 (d, J=13.3 Hz, 1H), 4.40-4.32 (m, 1H), 4.09-3.96 (m, 1H), 3.58-3.27 (m, 3H), 3.23-3.04 (m, 1H), 1.40 (s, 9H). LCMS Method 1—Tr=1.17 min, (ES+) (M+H⁺) 307.1.

[Intermediate 72]—tert-Butyl (3S)-3-carbamoyl-4-phenylpiperazine-1-carboxylate

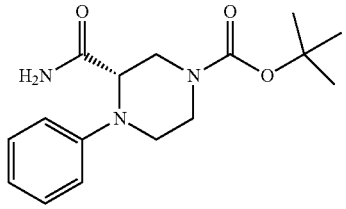 [SMILES: CC(C)(C)OC(=O)N1CCN(c2ccccc2)[C@H](C(N)=O)C1]

(2S)-4-[(tert-Butoxy)carbonyl]-1-phenylpiperazine-2-carboxylic acid [Intermediate 71] (91%, 1.7 g, 5.05 mmol), ammonium carbonate (0.68 g, 7.07 mmol), HATU (2.3 g, 6.06 mmol) and DiPEA (2.05 ml, 11.8 mmol) were suspended in DMF (12 ml) and stirred at ambient temperature for 16 hours. The reaction mixture was concentrated in vacuo. The resultant residue was partitioned between DCM (30 ml) and water (30 ml). The organic layer was separated and the aqueous phase extracted with DCM (2×15 ml). The organics were combined and concentrated in vacuo to give the crude product. The crude product was purified via flash column chromatography eluting with a gradient from 0-100% EtOAc in heptane followed by 0-100% MeOH in EtOAc. The fractions containing product were concentrated in vacuo to yield the title compound as a red solid (1.25 g, 81%). ¹H NMR (250 MHz, Chloroform-d) δ 7.35-7.26 (m, 2H), 6.98-6.84 (m, 3H), 6.41 (s, 1H), 5.55 (s, 1H), 4.15 (dd, J=13.1, 4.5 Hz, 1H), 4.09-3.98 (m, 1H), 3.76-3.56 (m, 3H), 3.55-3.29 (m, 2H), 1.47 (s, 9H). LCMS Method 3—Tr=1.62 min, (ES+) (M+H⁺) 306.1.

[Intermediate 73]—(2S)-1-Phenylpiperazine-2-carboxamide

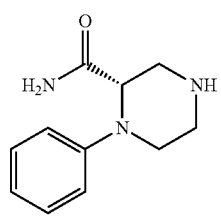 [SMILES: NC(=O)[C@@H]1CNCCN1c1ccccc1]

tert-Butyl (3S)-3-carbamoyl-4-phenylpiperazine-1-carboxylate [Intermediate 72] (1.25 g, 4.08 mmol) was suspended in 4M HCl in dioxane (15 ml) and the reaction mixture was stirred at ambient temperature for 1 hour. 2M HCl in 1,4-dioxane (10 ml) was added and the mixture stirred for 4 hours. The reaction mixture was concentrated in vacuo. The resultant residue was loaded onto a Biotage SCX-2 column and washed with DCM/MeOH (100 ml), then eluted with 7N NH₃ in MeOH (100 ml). The eluate was collected and concentrated in vacuo to afford the title compound as a beige solid (821 mg, 98%). ¹H NMR (250 MHz, DMSO-d6) δ 7.35 (s, 1H), 7.27-7.11 (m, 3H), 6.96-6.86 (m, 2H), 6.77 (t, J=7.2 Hz, 1H), 4.35-4.22 (m, 1H), 3.47-3.40 (m, 3H), 3.17 (s, 1H), 3.13-3.00 (m, 2H), 2.97-2.80 (m, 1H). LCMS Method 3—Tr=1.25 min, (ES+) (M+H⁺) 206.2.

[Intermediate 74]—1-tert-Butyl 3-methyl (3S)-4-(4-fluorophenyl)piperazine-1,3-dicarboxylate

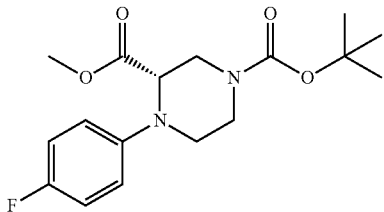 [SMILES: COC(=O)[C@@H]1CN(C(=O)OC(C)(C)C)CCN1c1ccc(F)cc1]

1-tert-Butyl 3-methyl (3S)-piperazine-1,3-dicarboxylate (10 g, 40.9 mmol), (4-fluorophenyl)boronic acid (11.5 g, 82.1 mmol), copper(II) acetate (7.44 g, 40.9 mmol) and pyridine (6.67 ml, 82.6 mmol) were suspended in anhydrous 1,2-dichloroethane (300 ml) and the mixture was stirred at ambient temperature for 72 hours. A continuous airflow was bubbled through the reaction and the mixture stirred for 44 hours at ambient temperature. The airflow was removed and the reaction stirred at 45° C. for 20 hours, then cooled to ambient temperature. The mixture was filtered through celite, washed with DCM. The filtrate was concentrated in vacuo and the green oil obtained was purified via flash column chromatography eluting with gradient from 0-100% EtOAc in heptane followed by 0-100% MeOH in EtOAc. The product containing fractions were combined and concentrated in vacuo to afford the title compound as a yellow oil (4.29 g, 29%). $^1$H NMR (500 MHz, Chloroform-d) δ 6.98-6.92 (m, 2H), 6.85-6.80 (m, 2H), 4.47 (d, J=12.7 Hz, 1H), 4.27 (s, 1H), 4.21-3.92 (m, 1H), 3.64 (s, 3H), 3.60-3.47 (m, 1H), 3.37 (d, J=10.6 Hz, 1H), 3.27-2.99 (m, 2H), 1.46 (s, 9H). LCMS Method 3 Tr=1.88 min, (ES+) (M+H$^+$) 339.1.

[Intermediate 75]—(2S)-4-[(tert-Butoxy)carbonyl]-1-(4-fluorophenyl)piperazine-2-carboxylic Acid

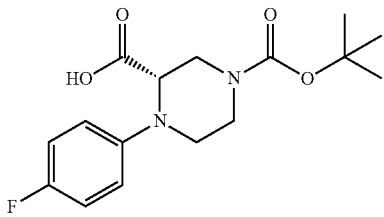 [SMILES: CC(C)(C)OC(=O)N1CCN(c2ccc(F)cc2)[C@H](C(=O)O)C1]

1-tert-Butyl 3-methyl (3 S)-4-(4-fluorophenyl)piperazine-1,3-dicarboxylate [Intermediate 74] (93%, 4.29 g, 11.78 mmol) was suspended in MeOH (40 ml) and 2M aq. LiOH (12 ml). The mixture was stirred at ambient temperature for 75 hours. The MeOH was removed in vacuo and the aqueous suspension was acidified to pH 4 with 2M. aq. HCl and extracted with DCM (2×20 ml). The organics were combined and concentrated in vacuo to afford the title compound as a yellow solid (4.07 g, 99%). $^1$H NMR (250 MHz, Chloroform-d) δ 6.98-6.87 (m, 2H), 6.84-6.73 (m, 2H), 4.44 (d, J=13.0 Hz, 1H), 4.18 (s, 1H), 4.03 (d, J=11.8 Hz, 1H), 3.58-3.00 (m, 4H), 1.38 (s, 9H). LCMS Method 3—Tr=1.25 min, (ES+) (M+H+) 325.2.

[Intermediate 76]—tert-Butyl (3S)-3-carbamoyl-4-(4-fluorophenyl)piperazine-1-carboxylate

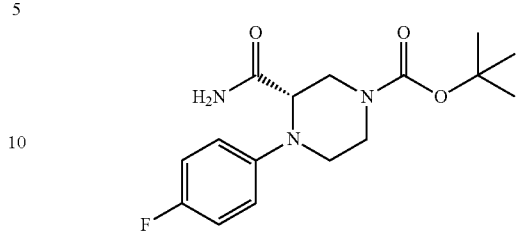

(2S)-4-[(tert-Butoxy)carbonyl]-1-(4-fluorophenyl)piperazine-2-carboxylic acid [Intermediate 75] (93%, 4.07 g, 11.7 mmol), HATU (5.32 g, 14.0 mmol), DiPEA (5.08 ml, 29.1 mmol) and ammonium carbonate (1.57 g, 16.3 mmol) were suspended in 1,4-dioxane (40 ml) and DMF (10 ml). The mixture was stirred at ambient temperature for 1 hour. The mixture was concentrated in vacuo. The resultant residue was partitioned between DCM (40 ml) and water (40 ml). The organic layer was separated and the aqueous phase extracted with DCM (2×20 ml). The organic layers were combined and the solvents removed in vacuo. The solid obtained was purified via flash column chromatography using gradients of 0 to 100% EtOAc in heptane, followed by 0 to 100% MeOH in EtOAc. The product containing fractions were combined and concentrated in vacuo to afford the title compound as a white solid (1.61 g, 38%). $^1$H NMR (500 MHz, DMSO-d6) δ 7.44 (s, 1H), 7.10-7.07 (m, 1H), 7.06-7.01 (m, 2H), 6.81-6.75 (m, 2H), 4.11 (s, 1H), 4.04-3.99 (m, 1H), 3.76 (s, 1H), 3.57-3.47 (m, 1H), 3.45-3.37 (m, 1H), 3.30-3.26 (m, 1H), 3.16 (s, 1H), 1.39 (s, 9H). LCMS Method 3—Tr=1.62 min, (ES+) (M+H$^+$) 324.2.

[Intermediate 77]—(2S)-1-(4-Fluorophenyl)piperazine-2-carboxamide

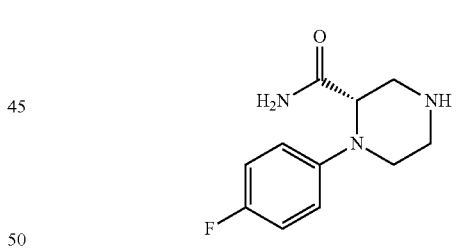

tert-Butyl (3 S)-3-carbamoyl-4-(4-fluorophenyl)piperazine-1-carboxylate [Intermediate 76] (89%, 1.61 g, 4.44 mmol) was suspended in 4M HCl in dioxane (15 ml). 1,4-dioxane (10 ml) was added and the mixture was stirred for 1 hour at ambient temperature. 4M HCl in dioxane (5 ml) was added and the mixture was stirred for 18 hours. The reaction mixture was concentrated in vacuo. The resultant beige solid was taken up in MeOH and loaded onto a Biotage SCX-2 Column. The column was washed with MeOH (60 ml), then eluted with 7N NH$_3$ in MeOH (60 ml). The eluate was concentrated in vacuo to afford the title compound as a brown solid (910 mg, 92%). $^1$H NMR (250 MHz, Chloroform-d) δ 7.06-6.86 (m, 4H), 6.35 (s, 1H), 5.49 (s, 1H), 3.92 (t, J=4.6 Hz, 1H), 3.38-3.15 (m, 3H), 3.13-2.93 (m, 3H). LCMS Method 3—Tr=1.26 min, (ES+) (M+H$^+$) 224.2.

[Intermediate 78]—Methyl (2R)-1-phenylpiperazine-2-carboxylate

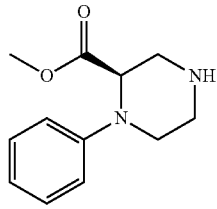 [SMILES: COC(=O)[C@H]1CNCCN1c1ccccc1]

1-tert-Butyl 3-methyl (3R)-4-phenylpiperazine-1,3-dicarboxylate [Intermediate 77] (1.13 g, 3.51 mmol) was suspended in a solution of 20% TFA in DCM (5 ml) and stirred at ambient temperature for 2 hours. TFA (1 ml) was added and the reaction mixture was stirred for 3 hours. Sat aq. NaHCO$_3$ (20 ml) was added and the reaction mixture was stirred for 5 minutes, then 2M. aq. NaOH (5 ml) was added. The organic layer was separated and the aqueous phase was extracted with DCM (2×10 ml). The organics were combined and concentrated in vacuo to afford the title compound as a brown oil (749 mg, 97%). $^1$H NMR (250 MHz, Chloroform-d) δ 7.34-7.23 (m, 2H), 6.97-6.80 (m, 3H), 4.49-4.39 (m, 1H), 3.70 (s, 3H), 3.60-2.83 (m, 6H), 2.34 (s, 1H). LCMS Method 3—Tr=1.47 min, (ES+) (M+H$^+$) 221.2.

[Intermediate 79]—[(2R)-1-Phenylpiperazin-2-yl]methanol

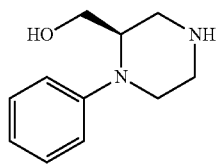 [SMILES: OC[C@H]1CNCCN1c1ccccc1]

Methyl (2R)-1-phenylpiperazine-2-carboxylate [Intermediate 78] (749 mg, 3.4 mmol) was suspended in anhydrous THF (10 ml) and stirred at 0° C. 2.4M LiAlH$_4$ in THF (4.25 ml) was added dropwise and the mixture was then stirred and allowed to warm to ambient temperature over 2 hours. The reaction was stirred for 1.5 hours then cooled to 0° C. and 2.4M LiAlH$_4$ in THF (1.5 ml) was added dropwise. The mixture was stirred for 1 hour at ambient temperature. The reaction was cooled to 0° C. and water (5.75 ml) was added in a dropwise manner over 10 min. 15% aq. NaOH (5.75 ml) was added, followed by water (17.25 ml). The mixture was then filtered through celite (washing with EtOAc) and the filtrate was concentrated in vacuo. The resultant residue was purified via flash column chromatography using gradients of 0-100% MeOH in DCM. The product containing fractions were combined and concentrated in vacuo to afford the title compound as a white solid (235 mg, 34%). $^1$H NMR (250 MHz, Chloroform-d) δ 7.34-7.26 (m, 2H), 7.26-7.18 (m, 1H), 7.01-6.77 (m, 3H), 4.33-4.21 (m, 2H), 4.05-3.70 (m, 3H), 3.46-2.82 (m, 6H). LCMS Method 3—Tr=1.35 min, (ES+) (M+H$^+$) 193.2.

[Intermediate 80]—tert-Butyl (3S)-4-(6-chloropyridazin-3-yl)-3-(hydroxymethyl)piperazine-1-carboxylate

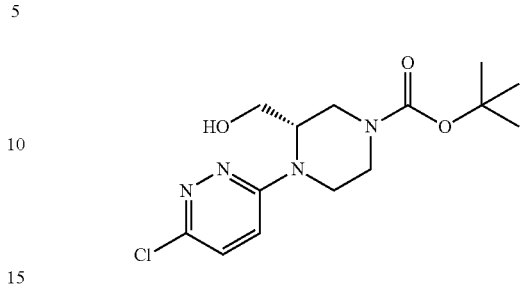

tert-Butyl (3S)-3-(hydroxymethyl)piperazine-1-carboxylate (4 g, 18.5 mmol), 3,6-dichloropyridazine (2.75 g, 18.5 mmol) and Cs$_2$CO$_3$ (6.63 g, 20.3 mmol) were suspended in toluene (10 ml). The reaction mixture was stirred at 110° C. for 16 hours. The reaction mixture was concentrated in vacuo and the resultant residue was partitioned between DCM (50 ml) and water (50 ml). The organic layer was separated and dried over sodium sulfate, filtered and concentrated in vacuo. The residue obtained was purified via flash column chromatography using gradients of 0 to 100% EtOAc in heptane, followed by 0 to 100% MeOH in EtOAc. The product containing fractions were combined and concentrated in vacuo, and the solid was washed with diethyl ether, then collected to afford the title compound as a white solid (1.69 g, 27%). $^1$H NMR (500 MHz, Chloroform-d) δ 7.41 (d, J=9.2 Hz, 1H), 7.01 (d, J=9.2 Hz, 1H), 4.47 (d, J=37.8 Hz, 2H), 3.96 (s, 1H), 3.19-3.12 (m, 1H), 3.04 (d, J=11.4 Hz, 1H), 3.00-2.88 (m, 1H), 2.82 (td, J=11.4, 3.1 Hz, 2H), 1.49 (s, 10H). LCMS Method 5—Tr=1.48 min (ES+) (M+H$^+$) 329.1.

[Intermediate 81]—tert-Butyl (3S)-3-(hydroxymethyl)-4-(pyridazin-3-yl)piperazine-1-carboxylate

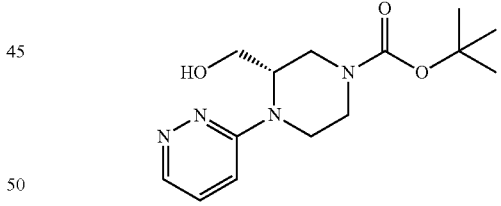

tert-Butyl (3S)-4-(6-chloropyridazin-3-yl)-3-(hydroxymethyl)piperazine-1-carboxylate [Intermediate 80] (1.69 g, 5.12 mmol) and 10% Pd/C (0.06 g, 0.56 mmol) were suspended in de-gassed ethanol (25 ml), and the mixture purged three times with nitrogen. The mixture was sealed under a hydrogen atmosphere and stirred at ambient temperature for 18 hours. The reaction mixture was filtered through celite, washing with EtOAc. The filtrate was concentrated in vacuo and the resultant oil was purified via flash column chromatography using gradients of 0-100% MeOH in DCM. The product containing fractions were combined and concentrated in vacuo to afford the title compound as a brown solid (1.4 g, 93%). $^1$H NMR (250 MHz, Chloroform-d) δ 8.84 (d, J=4.0 Hz, 1H), 7.40 (dd, J=8.9, 4.4 Hz, 1H), 7.20 (d, J=8.8 Hz, 1H), 4.87-4.69 (m, 2H), 4.19-3.94 (m, 3H), 3.61-3.49 (m, 1H), 3.44-3.21 (m, 3H), 3.03-2.86 (m, 1H), 1.46 (s, 9H). LCMS Method 3—Tr=1.54 min, (ES+) (M+H⁺) 295.2.

[Intermediate 82]—[(2S)-1-(Pyridazin-3-yl)piperazin-2-yl]methanol

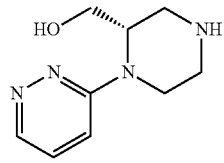

tert-Butyl (3 S)-3-(hydroxymethyl)-4-(pyridazin-3-yl)piperazine-1-carboxylate [Intermediate 81] (1.4 g, 4.76 mmol) was suspended in 4M HCl in Dioxane (5 ml) and stirred at ambient temperature for 1 hour. The reaction mixture was concentrated in vacuo to give a gray solid. The solid was loaded onto a Biotage SCX-2 column and washed with (1:1) DCM/MeOH (30 ml). The column was then eluted with 7N NH₃ in MeOH (50 ml) and the eluate collected and concentrated in vacuo to afford the title compound as a yellow solid (950 mg, 82%) 1H NMR (500 MHz, DMSO-d6) δ 8.91 (dd, J=4.5, 1.2 Hz, 1H), 7.65 (dd, J=9.0, 4.5 Hz, 1H), 7.27-7.20 (m, 2H), 4.44 (d, J=5.6 Hz, 2H), 3.30-3.19 (m, 3H), 3.16-3.10 (m, 1H), 3.08-3.02 (m, 1H), 2.98-2.89 (m, 1H), 2.87-2.80 (m, 1H), 2.76 (t, J=11.7 Hz, 1H) LCMS Method 3—Tr=1.03 min, (ES+) (M+H⁺) 195.2

[Intermediate 83]—1-tert-Butyl 3-methyl 4-(4-fluorophenyl)piperazine-1,3-dicarboxylate

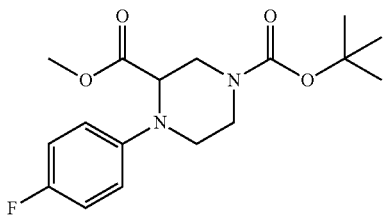 [SMILES: COC(=O)C1CN(C(=O)OC(C)(C)C)CCN1c1ccc(F)cc1]

1-tert-Butyl 3-methyl piperazine-1,3-dicarboxylate (500 mg, 2.05 mmol), (4-fluorophenyl)boronic acid (575 mg, 4.11 mmol), copper(II) acetate (372 mg, 2.05 mmol) and pyridine (0.33 ml, 4.09 mmol) were suspended in anhydrous DCM (10 ml) with 4 Å molecular sieves (500 mg). The mixture was stirred for 16 hours at ambient temperature, then for 5 hours at 35° C. Air was bubbled through the mixture for 10 min, then it was stirred for 18 hours at ambient temperature. Air was bubbled through the mixture for 10 min, then it was stirred at 35° C. for 6 hours and at ambient temperature for 72 hours. Additional (4-fluorophenyl)boronic acid (286 mg, 2.05 mmol) was added and the reaction was stirred for 4 hours at 35° C. The reaction was cooled to ambient temperature and filtered through celite. The filtrate was partitioned with sat. aq. NaHCO₃ (20 ml). The organic layer was separated and the aqueous extracted with DCM (2×20 ml). The organics were combined and concentrated in vacuo to give a green oil. The oil was purified via flash column chromatography using a gradient of 0-50% EtOAc in heptane. The product containing fractions were combined and concentrated in vacuo to afford the title compound as a yellow oil (213 mg, 26%). ¹H NMR (250 MHz, Chloroform-d) δ 7.01-6.90 (m, 2H), 6.87-6.78 (m, 2H), 4.47 (d, J=13.4 Hz, 1H), 4.32-4.22 (m, 1H), 4.09 (s, 1H), 3.63 (s, 3H), 3.59-3.46 (m, 1H), 3.37 (dd, J=13.3, 4.2 Hz, 1H), 3.28-3.00 (m, 2H), 1.46 (s, 9H). LCMS Method 3—Tr=1.90 min, (ES+) (M+H⁺) 339.2.

[Intermediate 84]—4-[(tert-Butoxy)carbonyl]-1-(4-fluorophenyl)piperazine-2-carboxylic Acid

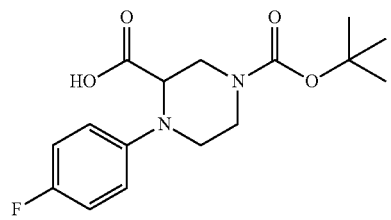 [SMILES: CC(C)(C)OC(=O)N1CCN(c2ccc(F)cc2)C(C(=O)O)C1]

1-tert-Butyl 3-methyl 4-(4-fluorophenyl)piperazine-1,3-dicarboxylate [Intermediate 83] (86%, 332 mg, 0.84 mmol) was taken up in (4:1) MeOH/water (5 ml) and 1M aq. LiOH (1.72 ml) was added. The reaction mixture was stirred at ambient temperature for 16 hours. 1M. aq. LiOH (1 ml) was added and the reaction was stirred for 2 hours. 1M. aq. LiOH (1 ml) was added and the reaction was stirred for 3 hours. The MeOH was removed in vacuo and 1M. aq. HCl (4.5 ml) was added. The aqueous mixture was extracted with DCM (3×10 ml). The organics were combined, dried over Mg₂SO₄, filtered, and concentrated in vacuo to afford the title compound as a yellow solid (255 mg, 88%). +H NMR (250 MHz, Chloroform-d) δ 7.00-6.90 (m, 2H), 6.86-6.76 (m, 2H), 4.47 (d, J=13.5 Hz, 1H), 4.27 (s, 1H), 4.18-3.97 (m, 1H), 3.51 (td, J=11.4, 3.6 Hz, 1H), 3.37 (dd, J=13.4, 4.3 Hz, 1H), 3.28-2.99 (m, 2H), 1.38 (s, 9H). LCMS Method 3—Tr=1.24 min, (ES+) (M+H⁺) 325.2.

[Intermediate 85]—tert-Butyl 3-carbamoyl-4-(4-fluorophenyl)piperazine-1-carboxylate

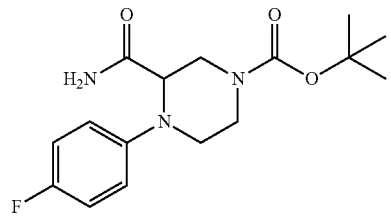 [SMILES: CC(C)(C)OC(=O)N1CCN(c2ccc(F)cc2)C(C(N)=O)C1]

4-[(tert-Butoxy)carbonyl]-1-(4-fluorophenyl)piperazine-2-carboxylic acid [Intermediate 84] (94%, 255 mg, 0.74 mmol), HATU (335 mg, 0.88 mmol) and DiPEA (300 µl, 1.72 mmol) were suspended in 1,4-dioxane (5 ml) and DMF (1 ml). The mixture was stirred at 40° C. for 1 hour, ammonium carbonate (90 mg, 0.94 mmol) was then added. The reaction mixture was stirred for 2 hours at 40° C. The reaction mixture was concentrated in vacuo. The resultant residue was partitioned between water (10 ml) and DCM (10 ml). The organic layer was separated and the aqueous extracted with DCM (10 ml). The organics were combined, concentrated in vacuo and purified by preparative HPLC [UV-Directed High pH prep method]. The fractions containing product were combined and concentrated in vacuo to afford the title compound as a white solid (117 mg, 49%). $^1$H NMR (250 MHz, Chloroform-d) δ 7.08-6.81 (m, 4H), 6.33 (s, 1H), 5.53 (s, 1H), 3.96-3.65 (m, 4H), 3.59-3.33 (m, 2H), 3.26-3.10 (m, 1H), 1.47 (s, 9H). LCMS Method 3—Tr=1.63 min, (ES+) (M+H$^+$) 324.2.

[Intermediate 86]—1-(4-Fluorophenyl)piperazine-2-carboxamide

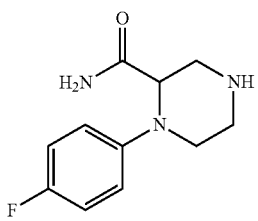

tert-Butyl 3-carbamoyl-4-(4-fluorophenyl)piperazine-1-carboxylate [Intermediate 85] (117 mg, 0.36 mmol) was suspended in 4M HCl in Dioxane (1.5 ml) and stirred at ambient temperature for 4 hours, then left standing for 16 hours. 4M HCl in Dioxane (1 ml) was added and the reaction was stirred for 3 hours. The mixture was concentrated in vacuo and the solid obtained was taken up in DCM (5 ml) and washed with 2M. aq. NaOH (5 ml). The organic layer was concentrated in vacuo to afford the title compound as a white solid (96 mg, 100%). $^1$H NMR (250 MHz, Chloroform-d) δ 7.07-6.86 (m, 4H), 6.34 (s, 1H), 5.43 (s, 1H), 3.97-3.87 (m, 1H), 3.38-3.15 (m, 3H), 3.14-2.93 (m, 3H). LCMS Method 3—Tr=1.28 min, (ES+) (M+H$^+$) 224.3.

[Intermediate 87]—tert-Butyl (3S)-4-(2-cyano-4-nitro-phenyl)-3-(hydroxymethyl)piperazine-1-carboxylate

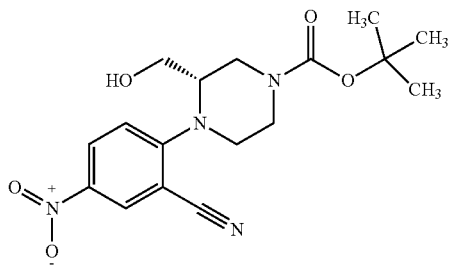

tert-butyl (3S)-3-(hydroxymethyl)piperazine-1-carboxylate (2.5 g, 11.56 mmol), 2-fluoro-5-nitro-benzonitrile (1.92 g, 11.6 mmol) and DiPEA (2.47 ml, 13.9 mmol) were dissolved in 1,4-dioxane (25 ml). The reaction was heated to 80° C. for 24 hours then increased to 90° C. for a further 18 hours. The reaction was concentrated in vacuo. The residue obtained was purified via flash column chromatography using gradients of 0 to 100% EtOAc in heptane, followed by 0 to 100% MeOH in EtOAc. The fractions containing product were combined and concentrated in vacuo to afford the title compound as a yellow gel (4.07 g, 67%).

LCMS Method 3—Tr=0.61 min (ES+) (M+H$^+$) 363.2

[Intermediate 88]—tert-Butyl (3S)-4-(4-amino-2-cyano-phenyl)-3-(hydroxymethyl)piperazine-1-carboxylate

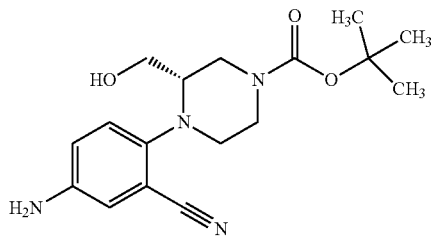 [SMILES: CC(C)(C)OC(=O)N1CCN(c2ccc(N)cc2C#N)[C@H](CO)C1]

Crude tert-butyl (3S)-4-(2-cyano-4-nitro-phenyl)-3-(hydroxymethyl)piperazine-1-carboxylate [Intermediate 87] (4.08 g, 11.2 mmol), ammonium chloride (3.61 g, 67.5 mmol) and Fe (3.14 g, 56.2 mmol) were suspended in (1:1) MeOH/water (75 ml) then the reaction was heated at 80° C. for 3 hours. The reaction mixture was cooled and filtered through celite. The filtrate was concentrated in vacuo to remove the bulk of the organics. The resultant residue was extracted with DCM (30 ml). The organics were dried over Na$_2$SO$_4$, filtered and concentrated in vacuo to afford the title compound as a brown solid (3.55 g, 100%). LCMS Method 1—Tr=0.98 min (ES+) (M+H$^+$) 333.05.

[Intermediate 89]—tert-Butyl (3S)-4-(4-amino-2-cyano-phenyl)-3-(hydroxymethyl)piperazine-1-carboxylate

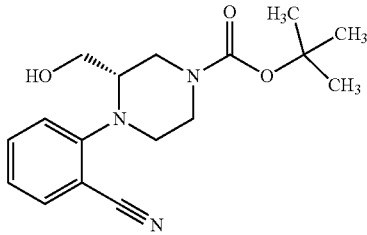 [SMILES: CC(C)(C)OC(=O)N1CCN(c2ccccc2C#N)[C@H](CO)C1]

tert-Butyl (3 S)-4-(4-amino-2-cyano-phenyl)-3-(hydroxymethyl)piperazine-1-carboxylate [Intermediate 88] (3.74 g, 11.2 mmol) was treated with pre-cooled (0° C.) 50% aq. hypophosphorous acid (50 ml). The reaction was stirred for 10 mins at 0° C. and NaNO$_2$ (1.94 g, 28.11 mmol) was added and stirred for 45 minutes at 0° C. The reaction had given rise to a sticky residue which retarded stirring. 1,4-Dioxane (50 ml) was chilled then added to the reaction and was then stirred at 0° C. for 2 hours. NaHCO$_3$ (35 g, 416.6 mmol) was suspended in water (100 ml) then the reaction was slowly added to the suspension. TBME (50 ml) was added and the biphasic solution was separated and the organics were dried over Na$_2$SO$_4$, filtered and concentrated in vacuo. The residue obtained was purified via flash column chromatography using gradients of 0 to 100% EtOAc in heptane, followed by 0 to 100% MeOH in EtOAc. The fractions containing product were combined and concentrated in vacuo to afford the title compound as a light orange oil (2.47 g, 72%). $^1$H NMR (500 MHz, DMSO-d6) δ 7.69

(dd, J=7.7, 1.6 Hz, 1H), 7.59 (ddd, J=8.9, 7.5, 1.6 Hz, 1H), 7.24 (d, J=8.3 Hz, 1H), 7.10 (t, J=7.5 Hz, 1H), 4.63 (s, 1H), 3.80 (s, 2H), 3.66 (dd, J=8.1, 4.3 Hz, 1H), 3.39 (d, J=11.4 Hz, 2H), 3.27-3.09 (m, 2H), 3.01 (dd, J=8.6, 3.9 Hz, 1H), 1.43 (s, 9H), 1.31-1.18 (m, 1H). LCMS Method 1—Tr=1.15 min (ES+) (M+H$^+$) 318.1.

[Intermediate 90]—2-[(2S)-2-(Hydroxymethyl)piperazin-1-yl]benzonitrile

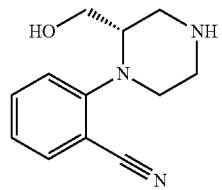 [SMILES: N#Cc1ccccc1N1CCNC[C@H]1CO]

tert-Butyl (3 S)-4-(2-cyanophenyl)-3-(hydroxymethyl) piperazine-1-carboxylate [Intermediate 89] (2.47 g, 7.77 mmol) was suspended in 20% TFA in DCM (25 ml). The reaction mixture was agitated for 18 hours. The reaction was concentrated in vacuo then the residue was taken up in (1:1) DCM/MeOH and loaded onto a 20 g SCX-2 column. The column was then washed with (1:1) DCM/MeOH (100 ml), then the product was eluted with 2.8M NH$_3$ in (1:1) DCM/MeOH [40 ml 7N NH$_3$ in MeOH, 10 ml MeOH, 50 ml DCM] which was subsequently concentrated in vacuo. The resultant residue obtained was purified via flash column chromatography using gradients of 0 to 100% EtOAc in heptane, followed by 0 to 100% MeOH in EtOAc. The fractions containing product were combined and concentrated in vacuo to afford the title compound as a pale yellow oil (930 mg, 55%). $^1$H NMR (500 MHz, DMSO-d6) δ 7.63 (dd, J=7.7, 1.6 Hz, 1H), 7.54 (ddd, J=8.8, 7.5, 1.7 Hz, 1H), 7.15 (d, J=8.3 Hz, 1H), 7.04-6.99 (m, 1H), 4.51 (s, 1H), 3.66 (q, J=8.2, 7.6 Hz, 1H), 3.62 (dd, J=8.1, 4.0 Hz, 1H), 3.23-3.15 (m, 1H), 2.97-2.91 (m, 2H), 2.88 (d, J=8.8 Hz, 2H), 2.75-2.68 (m, 1H), 2.52-2.50 (m, 1H), 2.25 (s, 1H). LCMS Method 3—Tr=1.37 min (ES+) (M+H$^+$) 218.2.

[Intermediate 91]—2,4,6-trimethyl-3-{[1-(pyrazin-2-yl)piperidin-4-yl]amino}benzoyl chloride Hydrochloride

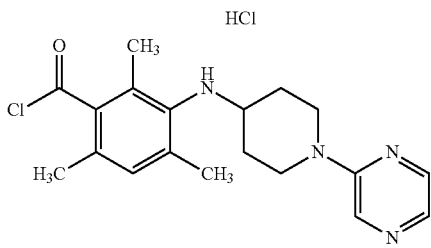 [SMILES: Cl ; Cc1cc(C)c(C(=O)Cl)c(C)c1NC1CCN(c2cnccn2)CC1]

2,4,6-Trimethyl-3-[(1-pyrazin-2-yl-4-piperidyl)amino] benzoic acid [Intermediate 101] (120 mg, 0.35 mmol) was suspended in toluene (2 ml) then SOCl$_2$ (103 μl, 1.41 mmol) was added and the sealed reaction was heated at 70° C. 1,4-dioxane (1.0 ml) was added and the reaction heated for 1.5 hours. SOCl$_2$ (103 μl, 1.41 mmol) was added and the reaction was heated at 70° C. for 4 hours. The reaction was then concentrated in vacuo to yield the title compound as a straw yellow solid (113 mg, 81%). $^1$H NMR (500 MHz, DMSO-d6) δ 8.36 (s, 1H), 8.11-8.08 (m, 1H), 7.83 (d, J=2.6 Hz, 1H), 7.27-7.14 (m, 1H), 7.06 (s, 1H), 4.41 (d, J=13.2 Hz, 2H), 2.90 (t, J=12.0 Hz, 2H), 2.38 (s, 2H), 2.33 (s, 2H), 2.27 (d, J=23.1 Hz, 1H), 2.21 (s, 3H), 2.13 (d, J=20.5 Hz, 1H), 1.97-1.87 (m, 2H), 1.75 (s, 2H).

[Intermediate 92]—3-{[1-(5-fluoropyridin-2-yl)piperidin-4-yl]amino}-2,4,6-trimethylbenzoyl chloride Hydrochloride

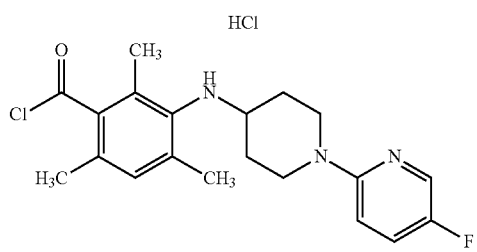 [SMILES: Cl ; Cc1cc(C)c(C(=O)Cl)c(C)c1NC1CCN(c2ccc(F)cn2)CC1]

3-[[1-(5-Fluoro-2-pyridyl)-4-piperidyl]amino]-2,4,6-trimethyl-benzoic acid [Intermediate 70] (100 mg, 0.27 mmol) was suspended in 1:1 toluene/1,4-dioxane (2.0 ml) then thionyl chloride (97 μl, 1.33 mmol) was added and the sealed reaction was heated at 70° C. for 18 hours. The reaction was concentrated in vacuo to yield the title compound as an off-white solid (103 mg, 98%). $^1$H NMR (500 MHz, DMSO-d6) δ 8.09 (d, J=3.1 Hz, 1H), 7.53 (td, J=9.2, 3.1 Hz, 1H), 7.08 (s, 1H), 6.93 (dd, J=9.4, 3.4 Hz, 1H), 4.27 (d, J=13.4 Hz, 2H), 2.82 (t, J=12.3 Hz, 2H), 2.38 (s, 3H), 2.33 (s, 3H), 2.21 (s, 3H), 1.95-1.84 (m, 2H), 1.75 (s, 2H).

[Intermediate 93]—3-{[1-(2-cyano-4-fluorophenyl) piperidin-4-yl]amino}-2,4,6-trimethylbenzoyl Chloride Hydrochloride

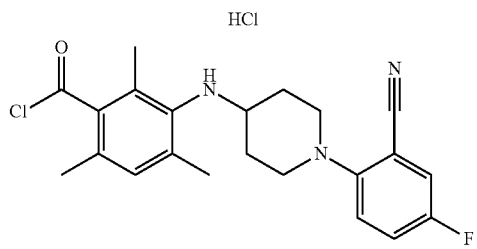 [SMILES: Cl ; Cc1cc(C)c(C(=O)Cl)c(C)c1NC1CCN(c2ccc(F)cc2C#N)CC1]

Prepared analogously to the method for [Intermediate 92] from 3-[[1-(2-Cyano-4-fluoro-phenyl)-4-piperidyl]amino]-2,4,6-trimethyl-benzoic acid hydrochloride [Intermediate 100] (103 mg, 0.27 mmol) to yield the title compound as an orange solid (149 mg, 85%). LCMS Method 1 [submitted in MeOH]—Tr=1.32 min (ES+) (M+H+) 396.15 (methyl ester analogue)

[Intermediate 94]—tert-Butyl 3-bromo-2,4,6-trimethylbenzoate

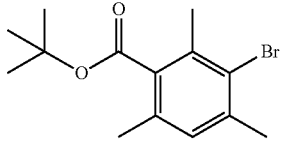 [SMILES: Cc1cc(C)c(C(=O)OC(C)(C)C)c(C)c1Br]

2,4-dibromo-1,3,5-trimethylbenzene (50 g, 180 mmol) was dissolved in anhydrous Et₂O (400 ml). The reaction mixture was cooled to −40° C. and 1.6M n-BuLi in hexane (130 ml, 208 mmol) was added dropwise over 45 minutes. The reaction mixture was stirred for 2 hour at −40° C. Di-tert-butyl dicarbonate (41 g, 188 mmol) was added to the reaction mixture at −40° C. and the reaction was stirred at −40° C. for 1 hour. The reaction mixture was quenched with 10% aq. citric acid (500 ml). The reaction mixture was warmed to ambient temperature and extracted with EtOAc (×2). The organics were combined and washed with brine, dried over MgSO₄, filtered and reduced in vacuo to yield the crude product as an off-white solid. The crude product was dissolved in heptane and was purified via flash column chromatography using a gradient of 0 to 50% DCM in heptane to yield the title compound as a white crystalline solid (15 g, 26%). ¹H NMR (250 MHz, Chloroform-d) δ 6.94 (s, 1H), 2.41 (d, J=5.7 Hz, 6H), 2.27 (s, 3H), 1.69-1.59 (m, 9H). LCMS Method 4—Tr=5.80 min (ES+) (M+H⁺) no mass ion seen.

[Intermediate 95]—tert-butyl 2,4,6-trimethyl-3-{[1-(pyrazin-2-yl)piperidin-4-yl]amino}benzoate

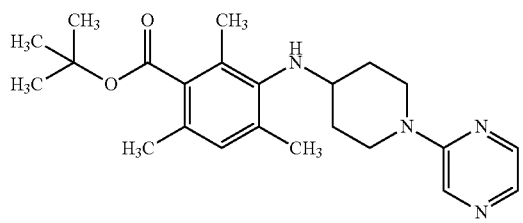 [SMILES: Cc1cc(C)c(C(=O)OC(C)(C)C)c(C)c1NC1CCN(c2cnccn2)CC1]

tert-Butyl 3-bromo-2,4,6-trimethyl-benzoate [Intermediate 94] (1.25 g, 4.18 mmol), 1-pyrazin-2-ylpiperidin-4-amine dihydrochloride (1.15 g, 4.6 mmol), Pd(dba)₂ (0.12 g, 0.21 mmol), (±)-BINAP (0.33 g, 0.52 mmol) and NaOtBu (1.69 g, 17.6 mmol) were suspended in nitrogen degassed toluene (20 ml) then the reaction was heated at 110° C. for 18 hours. The reaction mixture was partitioned between EtOAc (100 ml) and water (100 ml). The organics were separated, washed water, dried over Na₂SO₄, filtered and concentrated in vacuo. The resultant residue was purified via flash column chromatography using gradients of 0 to 100% EtOAc in heptane, followed by 0 to 100% MeOH in EtOAc. The fractions containing product were combined and concentrated in vacuo to afford the title compound as a tan viscous oil (1.74 g, 100%). ¹H NMR (500 MHz, DMSO-d6) δ 8.31 (d, J=1.4 Hz, 1H), 8.05 (dd, J=2.5, 1.5 Hz, 1H), 7.78 (d, J=2.6 Hz, 1H), 6.82 (s, 1H), 4.32 (d, J=13.4 Hz, 2H), 3.66 (d, J=10.4 Hz, 1H), 2.99 (dq, J=7.8, 5.4, 3.7 Hz, 1H), 2.87 (t, J=11.8 Hz, 2H), 2.19 (s, 3H), 2.14 (s, 3H), 2.12 (s, 3H), 1.79 (d, J=10.2 Hz, 2H), 1.53 (s, 9H), 1.44 (qd, J=12.0, 11.6, 3.5 Hz, 2H). LCMS Method 1—Tr=1.26 min (ES+) (M+H⁺) 397.25.

[Intermediate 96]—tert-Butyl N-[1-(2-cyano-4-fluoro-phenyl)-4-piperidyl]carbamate

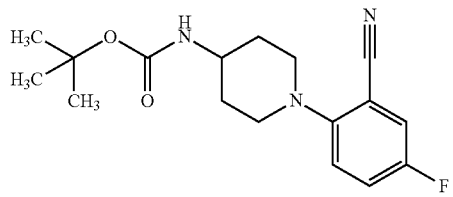 [SMILES: CC(C)(C)OC(=O)NC1CCN(c2ccc(F)cc2C#N)CC1]

tert-Butyl N-(4-piperidyl)carbamate (10 g, 49.9 mmol), 2,5-difluorobenzonitrile (7.29 g, 52.4 mmol) and K₂CO₃ (8.28 g, 59.9 mmol) were suspended in DMF (100 ml) then the reaction was heated to 110° C. for 18 hours. The reaction was cooled then partitioned between water (200 ml) and (3:1) EtOAc/Hept (200 ml). The organics were separated, the aqueous layer extracted with (3:1) EtOAc/Hept (100 ml). The organics were combined, washed with brine (200 ml), dried over Na₂SO₄, filtered and concentrated in vacuo. The resultant residue was purified via flash column chromatography using gradients of 0 to 100% EtOAc in heptane, followed by 0 to 100% MeOH in EtOAc. The fractions containing product were combined and concentrated in vacuo to afford the title compound as a white powdery solid (7.29 g, 44%). ¹H NMR (500 MHz, DMSO-d6) δ 7.69 (dd, J=8.4, 3.1 Hz, 1H), 7.48 (td, J=8.7, 3.1 Hz, 1H), 7.21 (dd, J=9.2, 4.7 Hz, 1H), 6.91 (d, J=7.8 Hz, 1H), 3.39 (s, 1H), 2.80 (t, J=10.8 Hz, 2H), 1.84 (d, J=10.6 Hz, 2H), 1.56 (qd, J=12.1, 3.9 Hz, 2H), 1.39 (s, 9H). LCMS Method 1—Tr=1.23 min (ES+) (M+H⁺) 320.0.

[Intermediate 97]—2-(4-Amino-1-piperidyl)-5-fluoro-benzonitrile Hydrochloride

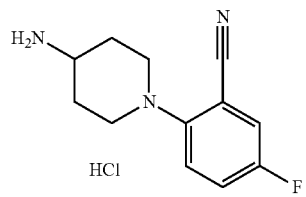 [SMILES: N#Cc1cc(F)ccc1N1CCC(N)CC1 ; Cl]

tert-Butyl N-[1-(2-cyano-4-fluoro-phenyl)-4-piperidyl]carbamate [Intermediate 96](7.29 g, 22.8 mmol) was taken up in 4M HCl in 1,4-dioxane (80 ml) and agitated for 30 mins. 1,4-Dioxane (80 ml) was added and the reaction mixture was agitated for 2 hours. The reaction was diluted with TBME (250 ml) and sonicated then filtered. The filter cake was washed with TBME (250 ml×2), MeCN (250 ml) and dried in vacuo to yield the title compound as a pale creme solid (5.30 g, 91%). ¹H NMR (500 MHz, DMSO-d6) δ 8.08 (s, 3H), 7.73 (dd, J=8.4, 3.1 Hz, 1H), 7.51 (td, J=8.7, 3.1 Hz, 1H), 7.22 (dd, J=9.1, 4.7 Hz, 1H), 3.41 (d, J=12.5 Hz, 2H), 3.24-3.12 (m, 1H), 2.84 (t, J=11.2 Hz, 2H), 2.04 (d, J=10.1 Hz, 2H), 1.72 (qd, J=12.1, 3.9 Hz, 2H). LCMS Method 3—Tr=1.68 min (ES+) (M+H⁺) 220.2.

[Intermediate 98]—tert-Butyl 3-[[1-(2-cyano-4-fluoro-phenyl)-4-piperidyl]amino]-2,4,6-trimethyl-benzoate

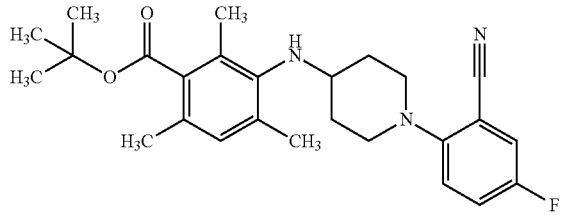 [SMILES: Cc1cc(C)c(C(=O)OC(C)(C)C)c(C)c1NC1CCN(c2ccc(F)cc2C#N)CC1]

Prepared analogously to [Intermediate 95] from tert-butyl 3-bromo-2,4,6-trimethyl-benzoate [Intermediate 94] (6.09 g, 20.3 mmol) and 2-(4-amino-1-piperidyl)-5-fluoro-benzonitrile hydrochloride [Intermediate 99] (5.2 g, 20.3 mmol) to yield the title compound as a straw viscous oil (8.25 g, 74%). $^1$H NMR (500 MHz, DMSO-d6) δ 7.68 (dd, J=8.4, 3.1 Hz, 1H), 7.47 (td, J=8.7, 3.1 Hz, 1H), 7.18 (dd, J=9.2, 4.7 Hz, 1H), 6.82 (s, 1H), 3.75 (d, J=10.5 Hz, 1H), 3.37 (d, J=12.2 Hz, 2H), 3.31 (s, 6H), 2.76 (t, J=11.1 Hz, 2H), 2.21 (d, J=9.3 Hz, 5H), 2.16 (s, 3H), 2.12 (s, 3H), 1.85 (d, J=10.4 Hz, 2H), 1.68 (qd, J=12.2, 3.8 Hz, 2H), 1.24 (qq, J=14.3, 6.6, 5.7 Hz, 3H), 0.91-0.75 (m, 4H). LCMS Method 1—Tr=1.47 min (ES+) (M+H$^+$) 438.55.

[Intermediate 99]—tert-Butyl 2,4,6-trimethyl-3-[(1-pyridazin-3-yl-4-piperidyl)amino]benzoate

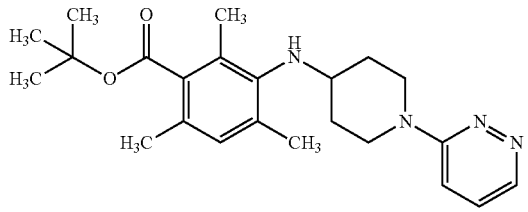 [SMILES: Cc1cc(C)c(C(=O)OC(C)(C)C)c(C)c1NC1CCN(c2cccnn2)CC1]

Prepared analogously to [Intermediate 95] from tert-butyl 3-bromo-2,4,6-trimethyl-benzoate [Intermediate 94] (5.0 g, 16.7 mmol) and 1-pyridazin-3-ylpiperidin-4-amine (3.28 g, 18.38 mmol) to yield the title compound as a brown oil (7.64 g, 83%). LCMS Method 1—Tr=0.98 min (ES+) (M+H$^+$) 397.55.

[Intermediate 100]—3-[[1-(2-Cyano-4-fluoro-phenyl)-4-piperidyl]amino]-2,4,6-trimethyl-benzoic Acid Hydrochloride

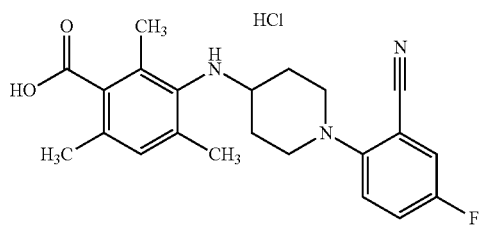 [SMILES: Cl ; Cc1cc(C)c(C(=O)O)c(C)c1NC1CCN(c2ccc(F)cc2C#N)CC1]

tert-Butyl 3-[[1-(2-cyano-4-fluoro-phenyl)-4-piperidyl]amino]-2,4,6-trimethyl-benzoate [Intermediate 98] (8.25 g, 18.9 mmol) was dissolved/suspended in 1,4-dioxane (40 ml). 4M HCl in 1,4-dioxane (160 ml) was added and left to stand with occasional agitation. The reaction mixture was concentrated in vacuo to yield the crude product as an oil. TBME (~150 ml) was gradually added, then the reaction was sonicated to give rise to an off-white suspension. The suspension was filtered, the filter cake was washed with TBME. The solid was dried in vacuo to yield the title compound as a tan solid (7.47 g, 92%). $^1$H NMR (500 MHz, DMSO-d6) δ 7.72 (dd, J=8.4, 3.1 Hz, 1H), 7.49 (td, J=8.7, 3.1 Hz, 1H), 7.19 (dd, J=9.2, 4.7 Hz, 1H), 7.05 (s, 1H), 3.57 (s, 1H), 3.21 (s, 2H), 2.81 (t, J=10.8 Hz, 2H), 2.42-2.30 (m, 6H), 2.21 (s, 3H), 1.98 (s, 4H). LCMS Method 3—Tr=1.29 min (ES+) (M+H$^+$) 382.1.

[Intermediate 101]—2,4,6-Trimethyl-3-[(1-pyrazin-2-yl-4-piperidyl)amino]benzoic Acid Dihydrochloride

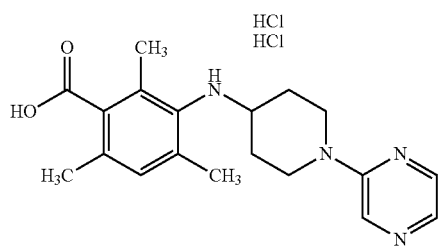 [SMILES: Cl ; Cl ; Cc1cc(C)c(C(=O)O)c(C)c1NC1CCN(c2cnccn2)CC1]

Prepared analogously to [Intermediate 100] from tert-butyl 2,4,6-trimethyl-3-{[1-(pyrazin-2-yl)piperidin-4-yl]amino}benzoate [Intermediate 95] (1.74 g, 4.39 mmol) to yield the title compound as a yellow powdery solid (1.87 g, 100%). $^1$H NMR (500 MHz, DMSO-d6) δ 8.37 (d, J=1.3 Hz, 1H), 8.10 (dd, J=2.5, 1.5 Hz, 1H), 7.83 (d, J=2.6 Hz, 1H), 7.10 (s, 1H), 4.42 (d, J=13.4 Hz, 2H), 3.72-3.65 (m, 1H), 2.90 (t, J=12.2 Hz, 2H), 2.41 (s, 3H), 2.36 (s, 3H), 2.22 (s, 3H), 1.95 (d, J=10.6 Hz, 2H), 1.78 (d, J=10.3 Hz, 2H). LCMS Method 3—Tr=1.19 min (ES+) (M+H$^+$) 341.2.

[Intermediate 102]—2,4,6-Trimethyl-3-{[1-(pyridazin-3-yl)piperidin-4-yl]amino}benzoic Acid Dihydrochloride

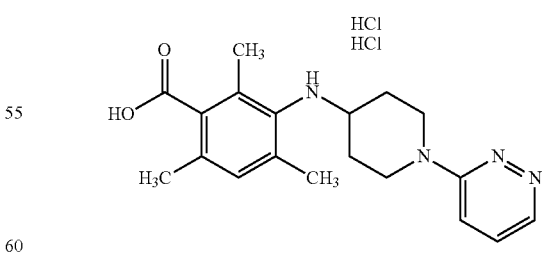

Prepared analogously to [Intermediate 100] from tert-butyl 2,4,6-trimethyl-3-[(1-pyridazin-3-yl-4-piperidyl)amino]benzoate [Intermediate 99] (72%, 7.63 g, 13.9 mmol) to yield the title compound as a pale yellow powdery solid (8.55 g, 100%). $^1$H NMR (500 MHz, DMSO-d6) δ 8.70 (d, J=4.2 Hz, 1H), 8.00 (d, J=9.5 Hz, 1H), 7.91 (dd, J=9.6, 4.5

Hz, 1H), 7.00 (s, 1H), 4.38 (d, J=13.3 Hz, 2H), 3.19-3.10 (m, 3H), 2.34 (d, J=21.2 Hz, 6H), 2.20 (s, 3H), 1.97 (d, J=10.8 Hz, 2H), 1.78 (s, 2H). LCMS Method 1—Tr=0.70 min (ES+) (M+H⁺) 341.15.

[Intermediate 103]—tert-Butyl N-[1-(2-cyano-6-fluorophenyl)piperidin-4-yl]carbamate

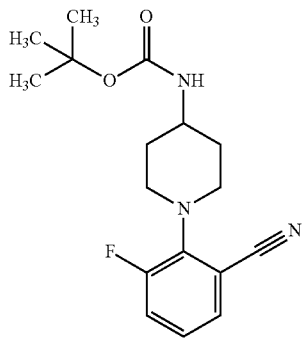 [SMILES: CC(C)(C)OC(=O)NC1CCN(c2c(F)cccc2C#N)CC1]

2,3-Difluorobenzonitrile (1.25 g, 8.99 mmol) and K₂CO₃ (1.49 g, 10.78 mmol) were suspended in DMF (10 ml) then tert-butyl N-(piperidin-4-yl)carbamate (1.8 g, 8.99 mmol) was added and the mixture was heated at 110° C. for 16 hours. The cooled reaction was diluted with water (40 ml) and extracted with DCM (3×30 ml) then the combined organics were washed with brine (50 ml), dried over Na₂SO₄, filtered and concentrated in vacuo. The residue was purified via flash column chromatography eluting with a gradient of 10% to 100% EtOAc in heptane to yield the title compound (2.12 g, 74%). ¹H NMR (500 MHz, Chloroform-d) δ 7.34 (d, J=7.7 Hz, 1H), 7.20 (ddd, J=12.2, 8.2, 1.4 Hz, 1H), 7.04-6.97 (m, 1H), 4.51 (s, 1H), 3.65 (s, 1H), 3.38 (d, J=12.2 Hz, 2H), 3.25 (t, J=11.8 Hz, 2H), 2.04 (d, J=10.2 Hz, 2H), 1.69-1.58 (m, 2H), 1.46 (s, 9H). LCMS Method 1—Tr=1.28 min (ES+) (M+H⁺) 320.1.

[Intermediate 104]—2-(4-Aminopiperidin-1-yl)-3-fluorobenzonitrile

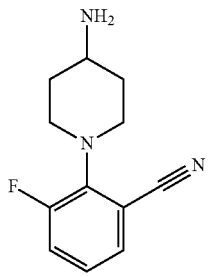 [SMILES: N#Cc1cccc(F)c1N1CCC(N)CC1]

tert-Butyl N-[1-(2-cyano-6-fluorophenyl)piperidin-4-yl] carbamate [Intermediate 103] (2.11 g, 6.61 mmol) was dissolved in MeOH (8 ml) and 4M HCl in 1,4-dioxane (8.26 ml) was added. The reaction mixture was stirred at ambient temperature for 16 hours. The reaction was concentrated in vacuo and the resultant residue was taken up in MeOH and loaded onto an SCX-2 cartridge (20 g) which was washed with MeOH. The product was eluted using 7N NH₃ in MeOH. The NH₃/MeOH eluate was concentrated in vacuo to yield the title compound (1.43 g, 99%). ¹H NMR (500 MHz, Chloroform-d) δ 7.26 (s, 1H), 7.18 (ddd, J=9.0, 7.9, 3.1 Hz, 1H), 6.99 (dd, J=9.1, 4.6 Hz, 1H), 3.50-3.37 (m, 2H), 2.94-2.75 (m, 3H), 2.04-1.88 (m, 2H), 1.69-1.56 (m, 2H). LCMS Method 3—Tr=3.16 min (ES+) (M+H⁺) 219.9.

[Intermediate 105]—2,4,6-Trimethyl-3-{[1-(pyridazin-3-yl)piperidin-4-yl]amino}benzoyl Chloride Hydrochloride

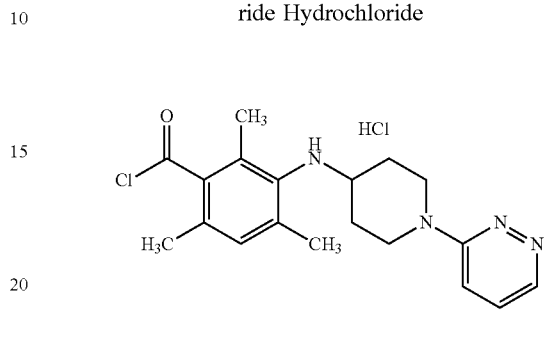

Prepared analogously to [Intermediate 92] 2,4,6-Trimethyl-3-{[1-(pyridazin-3-yl)piperidin-4-yl]amino}benzoic acid dihydrochloride [Intermediate 102] to yield the title compound as a light tan solid (505 mg, 96%). ¹H NMR (500 MHz, DMSO-d6) 8.74 (d, J=3.9 Hz, 1H), 8.06 (d, J=9.5 Hz, 1H), 7.97 (dd, J=9.6, 4.5 Hz, 1H), 7.07 (s, 1H), 4.42 (d, J=13.5 Hz, 3H), 3.62 (s, 1H), 3.16 (t, J=12.6 Hz, 2H), 2.44 (s, 3H), 2.38 (s, 3H), 2.22 (s, 3H), 2.03 (d, J=10.9 Hz, 2H), 1.90 (d, J=11.4 Hz, 2H), 1.24 (s, 1H). LCMS Method 1 [submitted in MeOH]—Tr=0.87 min (ES+) (M+H⁺) 355.2—mass ion of methyl ester.

[Intermediate 106]—Benzyl 4-(3-tert-butoxycarbonyl-2,4,6-trimethyl-anilino)piperidine-1-carboxylate

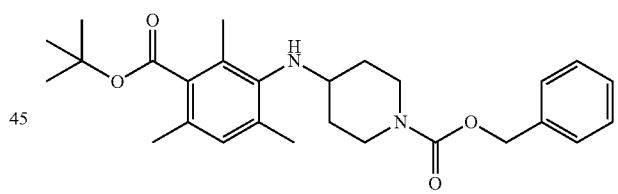

tert-Butyl 3-bromo-2,4,6-trimethyl-benzoate [Intermediate 94] (1 g, 3.34 mmol), benzyl 4-aminopiperidine-1-carboxylate (0.78 g, 3.34 mmol), (±)-BINAP (0.52 g, 0.84 mmol), NaOᵗBu (0.64 g, 6.68 mmol) and Pd₂(dba)₃ (0.31 g, 0.33 mmol) were suspended in toluene (10 ml). The reaction mixture was heated at 100° C. for 16 hours. The reaction was filtered through celite and concentrated in vacuo. The crude was purified via flash column chromatography using a gradient of 0% to 100% EtOAc in heptane followed by 0% to 100% MeOH in EtOAc. The product containing fractions were combined and concentrated in vacuo to give the title compound as a yellow oil (830 mg, 53%). ¹H NMR (500 MHz, Chloroform-d) δ 7.39-7.29 (m, 5H), 6.82 (s, 1H), 5.13 (s, 2H), 4.27-4.10 (m, 2H), 2.97 (tt, J=10.9, 3.8 Hz, 1H), 2.76 (s, 3H), 2.23 (s, 3H), 2.22 (s, 3H), 2.21 (s, 3H), 1.91 (s, 2H), 1.59 (s, 9H), 1.36-1.30 (m, 2H). LCMS Method 5—Tr 4.43 min (ES⁺) (M+H⁺) 453.

[Intermediate 107]—3-[(1-Benzyloxycarbonyl-4-piperidyl)amino]-2,4,6-trimethyl-benzoic Acid

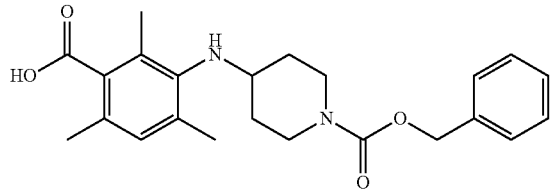 [SMILES: Cc1cc(C)c(C(=O)O)c(C)c1NC1CCN(C(=O)OCc2ccccc2)CC1]

Benzyl 4-(3-tert-butoxycarbonyl-2,4,6-trimethyl-anilino)piperidine-1-carboxylate [Intermediate 106] (860 mg, 1.9 mmol) was dissolved in 4M HCl in 1,4-dioxane (19 ml), the reaction mixture was stirred at ambient temperature for 16 hours. The precipitate was isolated via filtration. The filter cake was purified via reverse phase column chromatography [C18] using a gradient from 0% to 100% acetonitrile (with 1% formic acid modifier) in water (with 1% formic acid modifier). The product containing fractions were combined and concentrated in vacuo to give the title compound as a white solid (538 mg, 56%). $^1$H NMR (500 MHz, Chloroform-d) δ 7.42-7.28 (m, 5H), 6.87 (s, 1H), 5.13 (s, 2H), 4.19 (s, 2H), 3.01 (tt, J=11.1, 3.8 Hz, 1H), 2.76 (s, 2H), 2.35-2.26 (m, 6H), 2.23 (s, 3H), 1.98-1.84 (m, 2H), 1.41-1.23 (m, 2H). LCMS Method 5—Tr 2.87 min (ES+) (M+H+) 397.

[Intermediate 108]—Benzyl 4-[3-[(3S)-3-(hydroxymethyl)-4-phenyl-piperazine-1-carbonyl]-2,4,6-trimethyl-anilino]piperidine-1-carboxylate

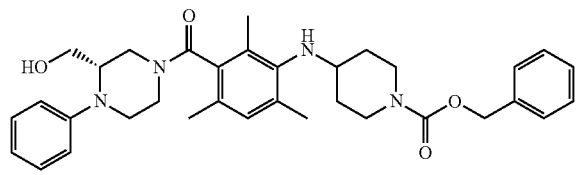 [SMILES: Cc1cc(C)c(C(=O)N2CCN(c3ccccc3)[C@H](CO)C2)c(C)c1NC1CCN(C(=O)OCc2ccccc2)CC1]

3-[(1-Benzyloxycarbonyl-4-piperidyl)amino]-2,4,6-trimethyl-benzoic Acid [Intermediate 107] (76%, 480 mg, 0.92 mmol), [(2S)-1-phenylpiperazin-2-yl]methanol [Intermediate 119] (230 mg, 1.2 mmol), HATU (385 mg, 1.01 mmol) and DiPEA (714 mg, 5.52 mmol) were suspended in NMP (5 ml). The reaction was heated at 50° C. for 16 hours. The reaction was concentrated in vacuo and the residue was purified via flash column chromatography using a gradient of 0% to 100% EtOAc in heptane. The product containing fractions were combined and concentrated in vacuo to give the title compound as a brown oil (230 mg, 42%). $^1$H NMR (500 MHz, Chloroform-d) δ 7.39-7.26 (m, 7H), 6.98-6.83 (m, 4H), 5.12 (d, J=2.4 Hz, 2H), 4.35-4.15 (m, 2H), 4.08-4.01 (m, 1H), 3.78-3.21 (m, 7H), 3.10-2.96 (m, 2H), 2.75 (s, 2H), 2.27-2.19 (m, 6H), 2.13 (s, 3H), 1.98-1.84 (m, 2H), 1.57 (s, 2H), 1.38-1.28 (m, 2H). LCMS Method 5—Tr 3.26, 3.41, 3.54, 3.61 min (ES$^+$) (M+H$^+$) 571.

[Intermediate 109]—[(3S)-3-(Hydroxymethyl)-4-phenyl-piperazin-1-yl]-[2,4,6-trimethyl-3-(4-piperidylamino)phenyl]methanone

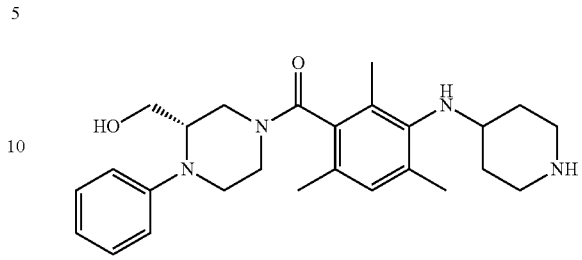

Benzyl 4-[3-[(3S)-3-(hydroxymethyl)-4-phenyl-piperazine-1-carbonyl]-2,4,6-trimethyl-anilino]piperidine-1-carboxylate [Intermediate 108] (50 mg, 0.09 mmol) was dissolved in nitrogen purged ethanol (2 ml). The reaction flask was purged three times with nitrogen before 5% Pd/C (18.7 mg, 0.01 mmol) was added. The reaction was purged with nitrogen three times before being sealed under a hydrogen atmosphere. The reaction was stirred at ambient temperature for 5 hours. The reaction mixture was filtered through celite and concentrated in vacuo to give a crude product as an oil. The oil was purified via preparative HPLC [UV-directed High pH prep method]. The product containing fractions were combined and concentrated in vacuo to give the title compound as a pale yellow oil (25 mg, 62%). $^1$H NMR (500 MHz, Chloroform-d) δ 7.31-7.23 (m, 2H), 6.98-6.82 (m, 4H), 4.80-3.99 (m, 2H), 3.78-3.19 (m, 7H), 3.12-2.90 (m, 4H), 2.62-2.48 (m, 2H), 2.29-2.18 (m, 6H), 2.16-2.11 (m, 3H), 1.96-1.86 (m, 2H), 1.35-1.22 (m, 2H). Purity by NMR>95%. LCMS Method 5—Tr 2.18 min (ES$^+$) (M+H$^+$) 437.

[Intermediate 110]—tert-Butyl 3-{[1-(2-cyanophenyl)piperidin-4-yl]amino}-2,4,6-trimethylbenzoate

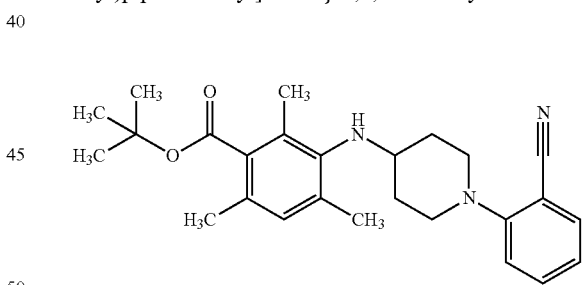

tert-Butyl 3-bromo-2,4,6-trimethylbenzoate [Intermediate 94] (80%, 200 mg, 0.53 mmol), 2-(4-aminopiperidin-1-yl)benzonitrile (121 mg, 0.6 mmol), NaO$^t$Bu (131 μl, 1.07 mmol), Pd$_2$(dba)$_3$ (49 mg, 0.05 mmol) and (±)-BINAP (67 mg, 0.11 mmol) were suspended in toluene (4 ml). The reaction mixture was degassed with N$_2$ (g) and heated at 110° C. for 16 hours. The reaction was allowed to cool to ambient temperature, filtered and concentrated in vacuo. The crude product was purified by flash column chromatography, eluting with 0 to 34% TBME in heptane, to yield the title compound as an orange solid (144 mg, 86%). $^1$H NMR (250 MHz, Chloroform-d) δ 7.55 (dd, J=7.9, 1.6 Hz, 1H), 7.50-7.40 (m, 1H), 7.05-6.93 (m, 2H), 6.84 (s. 1H), 3.57 (d, J=12.6 Hz, 2H), 3.13-2.68 (m, 4H), 2.34-2.15 (m, 9H), 2.06 (d, J=10.9 Hz, 2H), 1.80-1.64 (m, 2H), 1.60 (s, 9H). LCMS Method 3—Tr=2.14 min (ES+) (M+H$^+$) 420.2.

[Intermediate 111]—3-{[1-(2-Cyanophenyl)piperidin-4-yl]amino}-2,4,6-trimethylbenzoic Acid

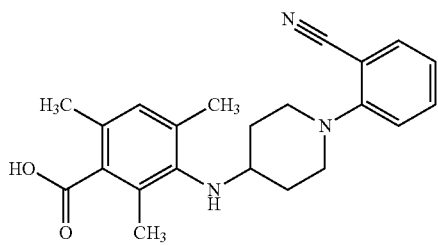 [SMILES: Cc1cc(C)c(C(=O)O)c(C)c1NC1CCN(c2ccccc2C#N)CC1]

To a stirred solution of tert-butyl 3-[[1-(2-cyanophenyl)-4-piperidyl]amino]-2,4,6-trimethyl-benzoate [Intermediate 110] (86%, 133 mg, 0.27 mmol) in MeOH (1 ml) was added 4M HCl in dioxane (0.4 ml). The reaction was stirred at ambient temperature overnight and then at 50° C. for 7 hours. The reaction mixture was cooled to ambient temperature and concentrated in vacuo. The crude product was dissolved in MeOH (1 ml) and loaded onto an SCX-2 cartridge (2 g). The cartridge was washed with MeOH (4×11 ml) and eluted with 2M NH$_3$ in MeOH (4×11 ml). The resulting fractions were concentrated in vacuo to yield the title compound as a brown solid (103 mg, 90%). $^1$H NMR (500 MHz, DMSO-d6) δ 7.67 (dd, J=7.7, 1.5 Hz, 1H), 7.60-7.54 (m, 1H), 7.14 (d, J=8.4 Hz, 1H), 7.05 (t, J=7.5 Hz, 1H), 6.76 (d, J=11.0 Hz, 1H), 3.48 (d, J=12.2 Hz, 2H), 2.94-2.82 (m, 1H), 2.78 (t, J=11.8 Hz, 2H), 2.20 (d, J=4.2 Hz, 3H), 2.15 (d, J=9.5 Hz, 3H), 2.12 (s, 3H), 1.86 (d, J=11.2 Hz, 2H), 1.67 (dt, J=20.4, 10.1 Hz, 2H). LCMS Method 1—Tr=1.07 min (ES+) (M+H$^+$) 364.1.

[Intermediate 112]—Methyl 2,4,6-trimethyl-3-{[1-(pyrimidin-2-yl)piperidin-4-yl]amino}benzoate

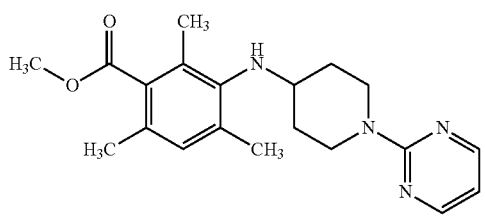 [SMILES: COC(=O)c1c(C)cc(C)c(NC2CCN(c3ncccn3)CC2)c1C]

Methyl 3-bromo-2,4,6-trimethyl-benzoate (1.13 g, 4.39 mmol), 1-(pyrimidin-2-yl)piperidin-4-amine (783 mg, 4.39 mmol), NaO$^t$Bu (1.08 ml, 8.79 mmol), Pd$_2$(dba)$_3$ (402 mg, 0.44 mmol) and (±)-BINAP (547 mg, 0.88 mmol) were suspended in toluene (20 ml). The reaction was degassed with N$_2$ (g) and then stirred at 100° C. for 18 hours. Pd$_2$(dba)$_3$ (402 mg, 0.44 mmol) and (±)-BINAP (547 mg, 0.88 mmol) were added to the reaction mixture and heated for 6 hours. The reaction was filtered through celite and the filtrate was concentrated in vacuo. The crude product was purified by flash column chromatography, eluting with 0 to 25% EtOAc in heptane. The product containing fractions were reduced in vacuo to yield the title compound as an orange solid (1.21 g, 74%). $^1$H NMR (250 MHz, Chloroform-d) δ 8.29 (d, J=4.7 Hz, 2H), 6.85 (s, 1H), 6.46 (t, J=4.7 Hz, 1H), 4.76 (d, J=13.5 Hz, 2H), 3.90 (s, 3H), 3.11 (t, J=10.9 Hz, 1H), 2.96-2.73 (m, 3H), 2.24 (s, 3H), 2.22 (s, 3H), 2.21 (s, 3H), 1.99 (d, J=12.6 Hz, 2H), 1.51-1.17 (m, 2H). LCMS Method 1—Tr=1.14 min (ES+) (M+H$^+$) 355.2

[Intermediate 113]—2,4,6-trimethyl-3-{[1-(pyrimidin-2-yl)piperidin-4-yl]amino}benzoic Acid

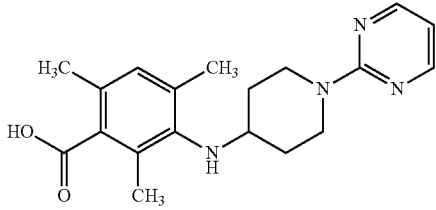 [SMILES: Cc1cc(C)c(C(=O)O)c(C)c1NC1CCN(c2ncccn2)CC1]

A flask was charged with methyl 2,4,6-trimethyl-3-[(1-pyrimidin-2-yl-4-piperidyl)amino]benzoate [Intermediate 112] (1.13 g, 3.19 mmol), powdered KOH (1.79 g, 31.9 mmol), N-methyl-N,N-dioctyloctan-1-aminium chloride (0.73 ml, 1.59 mmol) and water (0.17 ml). The reaction mixture was stirred for 5 minutes at ambient temperature. The reaction mixture was heated at 90° C. for 16 hours. The reaction was re-treated with powdered KOH (3.58 g, 63.8 mmol), N-methyl-N,N-dioctyloctan-1-aminium chloride (1.46 ml, 3.19 mmol) and water (0.17 ml). The reaction was then re-treated every 24 hours, for a period of 72 hours, with powdered KOH (3.58 g, 63.8 mmol), N-methyl-N,N-dioctyloctan-1-aminium chloride (1.46 ml, 3.19 mmol) and water (1.34 ml). Re-treatments took place at ambient temperature with stirring and then the reaction was heated at 90° C. After a final 24 hours heating at 90° C. the reaction was allowed to cool to ambient temperature. The reaction was diluted with water (50 ml) and washed with Et$_2$O (2×30 ml). The pH of the aqueous layer was modulated to pH 3 with 6M. aq. HCl. The aqueous layer was extracted with EtOAc (3×100 ml). The combined organics were dried over Na$_2$SO$_4$, filtered and concentrated in vacuo to yield the title compound as an orange solid (300 mg, 28%). $^1$H NMR (250 MHz, DMSO-d6) δ 8.33 (d, J=4.7 Hz, 2H), 6.83 (s, 1H), 6.57 (t, J=4.7 Hz, 1H), 4.63 (d, J=13.3 Hz, 2H), 3.01 (t, J=11.0 Hz, 1H), 2.85 (t, J=11.6 Hz, 2H), 2.20 (s, 3H), 2.17 (s, 3H), 2.14 (s, 3H), 1.78 (d, J=10.2 Hz, 2H), 1.39 (tt, J=11.9, 6.4 Hz, 2H). LCMS Method 1—Tr=0.87 min (ES+) (M+H$^+$) 341.15.

[Intermediate 114]—2-{4-[(3-{3-[(1,3-dioxo-2,3-dihydro-1H-isoindol-2-yl)methyl]piperazine-1-carbonyl}-2,4,6-trimethylphenyl)amino]piperidin-1-yl}benzonitrile

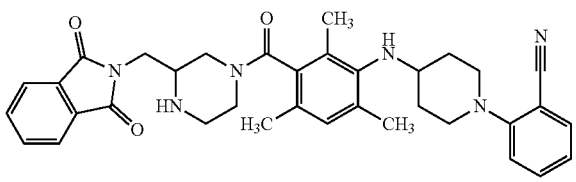 [SMILES: Cc1cc(C)c(C(=O)N2CCNC(CN3C(=O)c4ccccc4C3=O)C2)c(C)c1NC1CCN(c2ccccc2C#N)CC1]

To a stirred solution of 3-{[1-(2-cyanophenyl)piperidin-4-yl]amino}-2,4,6-trimethylbenzoic acid hydrochloride [Intermediate 111] (253 mg, 0.63 mmol) in dry DMF (2 ml) was added HATU (265 mg, 0.70 mmol) and DiPEA (221 µl, 1.27 mmol). The reaction mixture was stirred at ambient temperature for 35 minutes. In a separate flask, 3-{[1-(2-cyanophenyl)piperidin-4-yl]amino}-2,4,6-trimethylbenzoic acid hydrochloride (253 mg, 0.63 mmol) and DiPEA (221 μl, 1.27 mmol) were dissolved in dry DMF (2 ml) and stirred at ambient temperature for 35 minutes. After stirring each flask for 35 minutes, the two reaction mixtures were combined and stirred over the weekend. The reaction mixture was then concentrated in vacuo. The resultant residue was dissolved in DCM (10 ml) and washed with sat aq NaHCO$_3$ (15 ml). The aqueous phase was extracted with DCM (3×15 ml). The combined organics were dried over Na$_2$SO$_4$, filtered and concentrated in vacuo. The crude product was purified by flash column chromatography, eluting with 0 to 3% MeOH in DCM, to yield the title compound as an orange solid (320 mg, 73%). LCMS Method 6—Tr=3.51, 3.68, 3.74 min (ES+) (M+H$^+$) 591.4.

[Intermediate 115]—2-{4-[(3-{3-[(1,3-dioxo-2,3-dihydro-1H-isoindol-2-yl)methyl]-4-phenylpiperazine-1-carbonyl}-2,4,6-trimethylphenyl)amino]piperidin-1-yl}benzonitrile

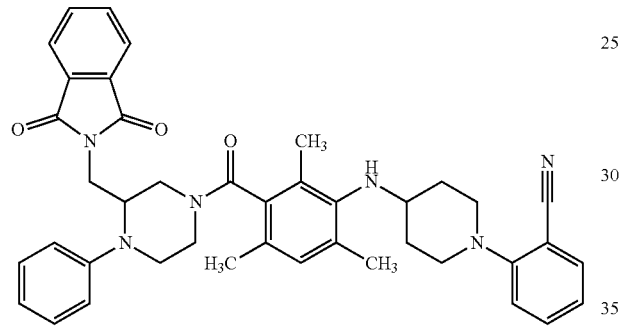

A pressure tube was charged with 2-{4-[(3-{3-[(1,3-dioxo-2,3-dihydro-1H-isoindol-2-yl)methyl]piperazine-1-carbonyl}-2,4,6-trimethylphenyl)amino]piperidin-1-yl}benzonitrile [Intermediate 114] (320 mg, 0.54 mmol), potassium fluoride (63 mg, 1.08 mmol), 2-(trimethylsilyl)phenyl trifluoromethanesulfonate (158 μl, 0.65 mmol) and dry MeCN (4 ml) under nitrogen. The reaction mixture was sealed and heated at 100° C. overnight. The reaction mixture was cooled to ambient temperature and concentrated in vacuo. The crude product was purified by flash column chromatography, eluting with 0% to 50% EtOAc in heptane. The product containing fractions were reduced in vacuo to yield the title compound as a yellow solid (160 mg, 39%). LCMS Method 1—Tr=1.39 min (ES+) (M+H+) 667.30.

[Intermediate 116]—2-[4-({3-[(3S)-3-(hydroxymethyl)-4-phenylpiperazine-1-carbonyl]-2,4,6-trimethylphenyl}amino)piperidin-1-yl]benzonitrile

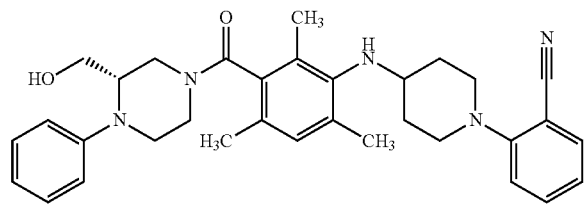 [SMILES: Cc1cc(C)c(C(=O)N2CCN(c3ccccc3)[C@H](CO)C2)c(C)c1NC1CCN(c2ccccc2C#N)CC1]

3-{[1-(2-cyanophenyl)piperidin-4-yl]amino}-2,4,6-trimethylbenzoic acid hydrochloride [Intermediate 111] (1.39 g, 3.48 mmol) and HATU (1.45 g, 3.82 mmol) were dissolved in dry DMF (15 ml). DiPEA (2.42 ml, 13.9 mmol) was added and the reaction mixture was stirred at ambient temperature for 20 minutes. A solution of [(2S)-1-phenylpiperazin-2-yl]methanol (668 mg, 3.48 mmol) in dry DMF (5 ml) was added and the reaction mixture was stirred at 40° C. overnight. The reaction mixture was concentrated in vacuo. The resultant residue was dissolved in DCM (50 ml) and washed with sat. aq. NaHCO$_3$ (50 ml). The aqueous layer was extracted with DCM (3×50 ml). The combined organics were dried over Na$_2$SO$_4$, filtered and concentrated in vacuo. The crude product was purified by flash column chromatography, eluting with 0 to 2% MeOH in DCM. The product containing fractions were reduced in vacuo to yield the title compound as a cream solid (865 mg, 45%). $^1$H NMR (500 MHz, Chloroform-d) δ 7.58-7.51 (m, 1H), 7.46 (dtd, J=7.5, 5.6, 2.7 Hz, 1H), 7.31-7.26 (m, 2H), 7.02-6.84 (m, 6H), 4.82-4.11 (m, 1H), 4.10-3.50 (m, 6H), 3.48-2.97 (m, 6H), 2.79-2.57 (m, 2H), 2.31-2.21 (m, 6H), 2.20-2.14 (m, 3H), 2.13-1.89 (m, 2H), 1.76-1.64 (m, 2H), 1.51-1.43 (m, 1H). LCMS Method 1—Tr=1.13, 1.16, 1.21 min (ES+) (M+H$^+$) 538.65.

[Intermediate 117]—2-[4-({3-[(3S)-3-[(1,3-dioxo-2,3-dihydro-1H-isoindol-2-yl)methyl]-4-phenylpiperazine-1-carbonyl]-2,4,6-trimethylphenyl}amino)piperidin-1-yl]benzonitrile

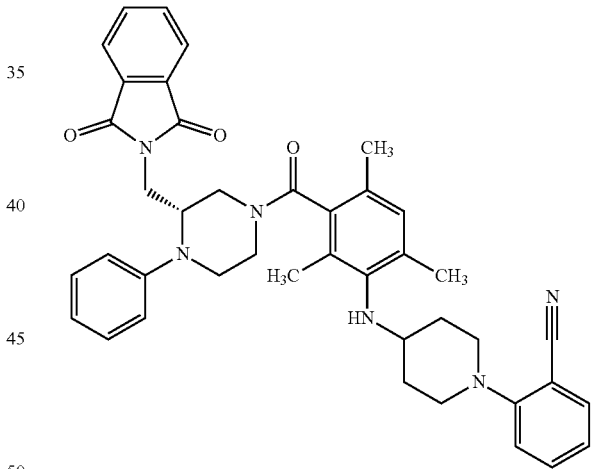

2-[4-({3-[(3S)-3-(hydroxymethyl)-4-phenylpiperazine-1-carbonyl]-2,4,6-trimethylphenyl}amino)piperidin-1-yl]benzonitrile [Intermediate 116] (765 mg, 1.42 mmol) was dissolved in dry THF (23 ml). The reaction mixture was cooled to 5° C. and triphenylphosphine (485 mg, 1.85 mmol) and 2,3-dihydro-1H-isoindole-1,3-dione (227 mg, 1.85 mmol) were added. Dipropan-2-yl diazene-1,2-dicarboxylate (363 μl, 1.85 mmol) was added dropwise to the reaction mixture at 5° C. The reaction was stirred at 5° C. for 2 hours and then allowed to warm to ambient temperature over 5 hours. The reaction was acidified with 1M. aq. HCl (5 ml) and extracted with EtOAc (3×20 ml). The combined organics were washed with sat. aq. NaHCO$_3$ (50 ml), dried over Na$_2$SO$_4$, filtered and concentrated in vacuo. The crude product was purified by flash column chromatography, eluting with 0 to 70% TBME in heptane. The product containing fractions were concentrated in vacuo to a volume of ~300 ml. The resulting suspension was sonicated and the precipitate collected by filtration to yield the title compound as a white solid (430 mg, 40%). LCMS Method 1—Tr=1.39 min (ES+) (M+H⁺) 667.30.

[Intermediate 118]—tert-Butyl (3S)-3-(hydroxymethyl)-4-phenylpiperazine-1-carboxylate

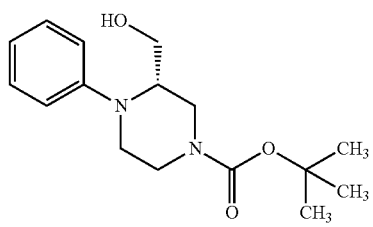 [SMILES: CC(C)(C)OC(=O)N1CCN(c2ccccc2)[C@H](CO)C1]

1-tert-Butyl 3-methyl (3S)-4-phenylpiperazine-1,3-dicarboxylate [Intermediate 117](13.7 g, 42.76 mmol) was dissolved in dry THF (250 ml). The reaction mixture was cooled to 0° C. and a solution of 2.4M LiAlH₄ in THF (35.6 ml, 85.5 mmol) was added dropwise. The reaction was stirred at 0° C. for 30 minutes and then allowed to warm to ambient temperature and stirred for 1 hour. The reaction mixture was cooled to 0° C. and quenched with water (3.2 ml). 15% aq. NaOH (3.2 ml) and then water (9.6 ml) were added and the reaction mixture was allowed to warm to ambient temperature overnight. The reaction mixture was filtered through celite, rinsing with EtOAc. The filtrate was concentrated in vacuo to yield the title compound as a white solid (11.6 g, 92%). ¹H NMR (500 MHz, Chloroform-d) δ 7.34-7.22 (m, 2H), 6.91 (d, J=7.9 Hz, 2H), 6.85 (t, J=7.2 Hz, 1H), 4.36-4.06 (m, 1H), 3.98 (d, J=10.8 Hz, 1H), 3.94-3.76 (m, 1H), 3.69-3.47 (m, 2H), 3.41-3.02 (m, 4H), 1.49 (s, 9H). LCMS Method 1—Tr=1.11 min (ES+) (M+H⁺) 293.05.

[Intermediate 119]—[(2S)-1-Phenylpiperazin-2-yl]methanol

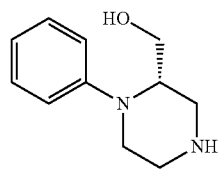 [SMILES: OC[C@@H]1CNCCN1c1ccccc1]

tert-Butyl (3S)-3-(hydroxymethyl)-4-phenylpiperazine-1-carboxylate [Intermediate 118] (11.6 g, 39.7 mmol) was dissolved in EtOH (110 ml). The reaction mixture was cooled to 0° C. and 4M HCl in dioxane (40 ml) was added dropwise. The reaction mixture was stirred at ambient temperature overnight. 4M HCl in dioxane (20 ml) was added and the reaction mixture was stirred for at ambient temperature for 4 hours. The reaction was concentrated in vacuo. The resultant residue was dissolved in (1:1) MeOH/DCM and loaded onto MP-TsOH (77 g, 240 mmol) resin. The resin solution was left to stand for 30 min, the resin was filtered, washed sequentially with DCM (50 ml), MeOH (50 ml), DCM (50 ml) and MeOH (50 ml). The product was eluted with 2M NH₃ in MeOH, the eluent was concentrated in vacuo. The resultant residue was purified by flash column chromatography (KP-NH) eluting with a gradient from 0% to 5% MeOH in DCM. The product containing fractions were concentrated in vacuo. The resultant residue was purified by flash column chromatography (KP-SIL) eluting with a gradient from 20% to 100% '2M NH₃ in MeOH' in DCM. The product containing fractions were concentrated in vacuo to afford the title compound as a white solid (4.7 g, 61%). With a chiral purity 78% ee. ¹H NMR (500 MHz, Chloroform-d) δ 7.29-7.24 (m, 2H), 6.92 (d, J=7.9 Hz, 2H), 6.84 (t, J=7.3 Hz, 1H), 3.95 (ddd, J=11.0, 4.4, 1.2 Hz, 1H), 3.86-3.74 (m, 2H), 3.45 (td, J=11.5, 3.7 Hz, 1H), 3.41-3.27 (m, 2H), 3.24-3.11 (m, 2H), 3.00 (td, J=11.3, 3.8 Hz, 1H). LCMS Method 1—Tr=0.38 min (ES+) (M+H⁺) 192.95.

[Intermediate 120]—tert-Butyl (3S)-3-{[(tert-butyldimethylsilyl)oxy]methyl}piperazine-1-carboxylate

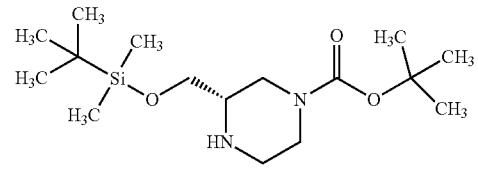 [SMILES: CC(C)(C)OC(=O)N1CCN[C@H](CO[Si](C)(C)C(C)(C)C)C1]

To a stirred solution of tert-butyl (3S)-3-(hydroxymethyl)piperazine-1-carboxylate (5.0 g, 23.1 mmol) and imidazole (2.36 g, 34.7 mmol) in DCM (25 ml) was added tert-butyl (chloro)dimethylsilane (3.59 g, 23.8 mmol). The reaction was stirred at ambient temperature for 72 hours. The reaction mixture was diluted with sat. aq. NaHCO₃ (50 ml) and the organic layer separated. The aqueous layer was extracted with DCM (2×30 ml), the combined organics were dried over Na₂SO₄, filtered and concentrated in vacuo. The crude product was purified by flash column chromatography, with a gradient from 10% to 100% EtOAc in heptane. The product contain fractions were combined and reduced in vacuo to yield the title compound as a yellow oil (7.0 g, 92% yield). ¹H NMR (250 MHz, Chloroform-d) δ 3.85 (d, J=11.9 Hz, 2H), 3.53 (dd, J=9.8, 4.3 Hz, 1H), 3.41 (dd, J=9.8, 7.0 Hz, 1H), 3.00-2.86 (m, 1H), 2.85-2.57 (m, 3H), 2.57-2.36 (m, 1H), 1.40 (s, 9H), 0.84 (s, 9H), 0.00 (s, 6H). LCMS Method 1 [ELS]—Tr=0.92 min (ES+) (M+H⁺) 331.25.

[Intermediate 121]—tert-butyl (3S)-3-{[(tert-butyldimethylsilyl)oxy]methyl}-4-(pyridin-2-yl)piperazine-1-carboxylate

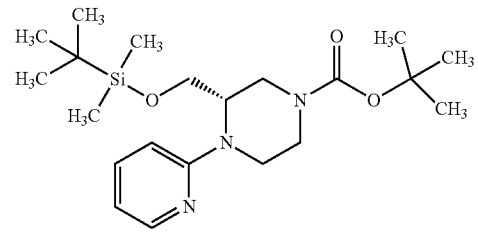 [SMILES: CC(C)(C)OC(=O)N1CCN(c2ccccn2)[C@H](CO[Si](C)(C)C(C)(C)C)C1]

A pressure tube was charged with tert-butyl (3S)-3-{[(tert-butyldimethylsilyl)oxy]methyl}piperazine-1-carboxylate [Intermediate 120] (1.0 g, 3.03 mmol), 2-bromopyridine (0.41 ml, 4.24 mmol), RuPhos Pd G3 (253 mg, 0.30 mmol), ʹBuONa (582 mg, 6.05 mmol), 1,4-dioxane (10 ml) and ʹBuOH (5 ml). The reaction was degassed with N₂. The tube was sealed and the reaction was stirred at 110° C. for 16 hours. The reaction was cooled to ambient temperature and water (60 ml) was added. The mixture was extracted with DCM (3×60 ml), the combined organics were dried over Na₂SO₄, filtered and concentrated in vacuo. The crude product was purified by flash column chromatography, eluting with a gradient of 0% to 7% EtOAc in heptane. The product containing fraction were combined and reduced in vacuo to yield the title compound as a yellow oil (840 mg, 68%). ¹H NMR (250 MHz, Chloroform-d) δ 8.25-8.05 (m, 1H), 7.46 (ddd, J=8.8, 7.2, 2.0 Hz, 1H), 6.72-6.48 (m, 2H), 4.37-4.15 (m, 2H), 4.14-3.81 (m, 2H), 3.77-3.47 (m, 2H), 3.32-2.82 (m, 3H), 1.48 (s, 9H), 0.85 (s, 9H), 0.02 (s, 6H). LCMS Method 1—Tr=1.24 min (ES+) (M+H⁺) 408.05.

[Intermediate 122]—[(2S)-1-(Pyridin-2-yl)piperazin-2-yl]methanol]

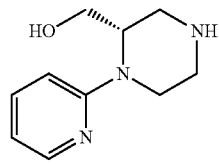 [SMILES: OC[C@@H]1CNCCN1c1ccccn1]

tert-Butyl (3S)-3-{[(tert-butyldimethylsilyl)oxy]methyl}-4-(pyridin-2-yl)piperazine-1-carboxylate [Intermediate 121] (840 mg, 2.06 mmol) was dissolved in MeOH (2 ml) and 5.15 ml) was added. The reaction was stirred for 16 hours at ambient temperature. The reaction was concentrated and the resultant residue was dissolved in the minimum volume of (1:1) MeOH/DCM and loaded onto an SCX-2 cartridge (10 g). The cartridge was washed sequentially with MeOH (30 ml), DCM, (30 ml), MeOH (30 ml), DCM, (30 ml) and MeOH (30 ml). The product was eluted with 7M NH₃ in MeOH (60 ml). The resulting fractions were concentrated in vacuo to yield the title compound as a colourless oil (424 mg, 100%). ¹H NMR (250 MHz, Chloroform-d) δ 8.19-8.03 (m, 1H), 7.48 (ddd, J=8.9, 7.1, 2.0 Hz, 1H), 6.71-6.54 (m, 2H), 4.52 (d, J=3.5 Hz, 1H), 4.05 (dd, J=11.0, 5.2 Hz, 1H), 4.00-3.91 (m, 1H), 3.91-3.78 (m, 1H), 3.56-3.38 (m, 1H), 3.38-3.29 (m, 1H), 3.17 (dt, J=11.5, 1.8 Hz, 1H), 3.07 (dd, J=12.3, 4.5 Hz, 1H), 2.93 (td, J=11.8, 3.9 Hz, 1H). LCMS Method 1 [ELS]—Tr=0.19 min (ES+) (M+H⁺) 194.30.

[Intermediate 123]—tert-Butyl (3S)-3-{[(tert-butyldimethylsilyl)oxy]methyl}-4-(5-fluoropyridin-2-yl)piperazine-1-carboxylate

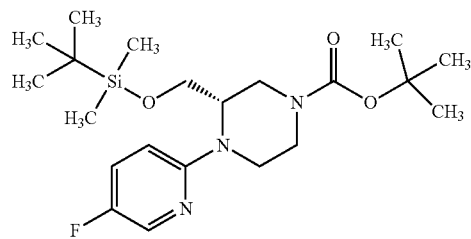 [SMILES: CC(C)(C)OC(=O)N1CCN(c2ccc(F)cn2)[C@H](CO[Si](C)(C)C(C)(C)C)C1]

A pressure tube was charged with tert-butyl (3S)-3-{[(tert-butyldimethylsilyl)oxy]methyl}piperazine-1-carboxylate [Intermediate 120] (0.90 g, 2.72 mmol), 2-bromo-5-fluoropyridine (0.39 ml, 3.81 mmol), RuPhos Pd G3 (228 mg, 0.27 mmol), ʹBuONa (523 mg, 5.45 mmol), dioxane (9 ml) and ʹBuOH (4.5 ml). The reaction was de-gassed with N₂ and the tube sealed. The reaction was heated at 110° C. for 16 hours. Water (60 ml) was added and the suspension was filtered. The filtrate was extracted with DCM (3×60 ml). The combined organic were dried over Na₂SO₄, filtered and concentrated in vacuo. The crude product was purified by flash column chromatography, eluting with a gradient of 0% to 7% EtOAc in heptane, to give the title compound as a yellow oil (0.91 g, 79%). ¹H NMR (500 MHz, Chloroform-d) δ 8.02 (d, J=3.0 Hz, 1H), 7.26-7.20 (m, 1H), 6.57 (d, J=7.9 Hz, 1H), 4.28-4.15 (m, 2H), 4.14-3.80 (m, 2H), 3.67 (t, J=9.2 Hz, 1H), 3.57 (s, 1H), 3.19-2.93 (m, 3H), 1.48 (s, 9H), 0.84 (s, 9H), 0.01 (s, 6H). LCMS Method 1—Tr=1.62 min (ES+) (M+H⁺) 426.2

[Intermediate 124]—[(2S)-1-(5-Fluoropyridin-2-yl)piperazin-2-yl]methanol

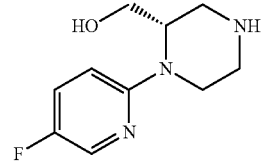 [SMILES: OC[C@@H]1CNCCN1c1ccc(F)cn1]

tert-Butyl (3S)-3-{[(tert-butyldimethylsilyl)oxy]methyl}-4-(5-fluoropyridin-2-yl)piperazine-1-carboxylate [Intermediate 123] (1.0 g, 2.37 mmol) was dissolved in MeOH (2 ml). 4M HCl in dioxane (5.93 ml) was added and the reaction mixture was stirred for 16 hours at ambient temperature. The reaction was concentrated in vacuo. The resultant residue was dissolved in the minimum volume of (1:1) MeOH/DCM and loaded onto an SCX-2 cartridge (10 g). The cartridge was washed sequentially with MeOH (30 ml), DCM, (30 ml), MeOH (30 ml), DCM, (30 ml) and MeOH (30 ml). The product was eluted with 7M NH₃ in MeOH (60 ml). The resulting fractions were concentrated in vacuo to yield the title compound as a colourless oil (416 mg, 83%). ¹H NMR (250 MHz, Chloroform-d) δ 8.01 (d, J=3.1 Hz, 1H), 7.36-7.15 (m, 1H), 6.58 (dd, J=9.3, 3.3 Hz, 1H), 4.39 (dd, J=4.2, 1.8 Hz, 1H), 4.06-3.88 (m, 2H), 3.74 (ddd, J=12.3, 3.8, 1.9 Hz, 1H), 3.44 (td, J=12.1, 3.8 Hz, 1H), 3.33 (dt, J=11.8, 1.7 Hz, 1H), 3.21-3.11 (m, 1H), 3.07 (ddd, J=11.8, 4.0, 0.9 Hz, 1H), 2.92 (td, J=11.7, 3.9 Hz, 1H). LCMS Method 1 [ELS]—Tr=0.26 min (ES+) (M+H⁺) 212.1.

[Intermediate 125]—2-(benzylamino)-N-(3,4-difluorophenyl)acetamide

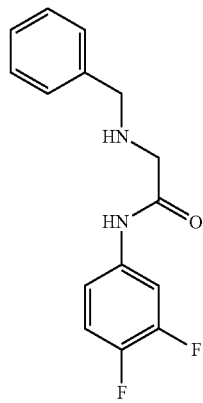 [SMILES: O=C(CNCc1ccccc1)Nc1ccc(F)c(F)c1]

To a stirred solution of 2-chloro-N-(3,4-difluorophenyl)acetamide (2.92 ml, 0.02 mol) in THF (42 ml) was added 1-phenylmethanamine (8.29 ml, 0.08 mol). The reaction was heated at 80° C. for 16 hours. The reaction was cooled to ambient temperature and filtered. The filtrate was concentrated in vacuo. The crude product was purified twice via reverse phase column chromatography [C18], using a gradient of 0% to 100% MeCN (with 0.1% $NH_3$ modifier) in water (with 0.1% $NH_3$ modifier), to give the title compound as a white solid (4.2 g, 82%). $^1$H NMR (500 MHz, Chloroform-d) δ 9.31 (s, 1H), 7.71-7.63 (m, 1H), 7.42-7.36 (m, 2H), 7.36-7.30 (m, 3H), 7.16-7.06 (m, 2H), 3.87 (s, 2H), 3.45 (s, 2H). LCMS Method 1—Tr=0.83 min (ES+) (M+H+) 277.1.

[Intermediate 126]—2-{Benzyl[(2R)-3-chloro-2-hydroxypropyl]amino}-N-(3,4-difluorophenyl)acetamide

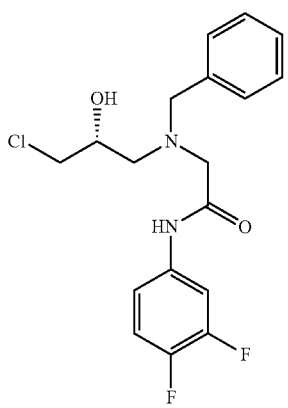 [SMILES: O=C(CN(Cc1ccccc1)C[C@@H](O)CCl)Nc1ccc(F)c(F)c1]

A flask was charged with 2-(benzylamino)-N-(3,4-difluorophenyl)acetamide [Intermediate 125] (3.9 g, 14.1 mmol), dry MeOH (62 ml), oven dried $MgSO_4$ (2.07 g, 17.2 mmol), dry DCM (21 ml) and (2R)-2-(chloromethyl)oxirane (2.77 ml, 0.04 mol). The reaction was stirred at 35° C. for 24 hours and stirred at ambient temperature over the weekend. The reaction was filtered through celite, rinsing with EtOAc. The filtrate was concentrated in vacuo to yield the title compound as a yellow oil (5.25 g, 96%). LCMS Method 1—Tr=1.05 min (ES+) (M+H+) 369.0, 371.1.

[Intermediate 127]—(6S)-4-Benzyl-1-(3,4-difluorophenyl)-6-(hydroxymethyl)piperazin-2-one

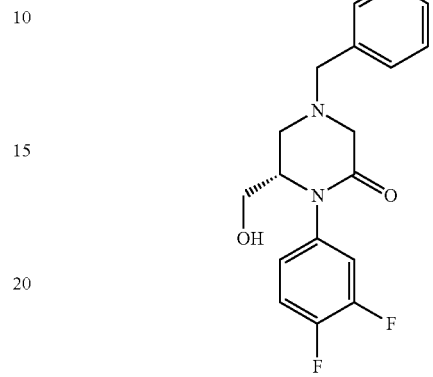

2-{benzyl[(2R)-3-chloro-2-hydroxypropyl]amino}-N-(3,4-difluorophenyl)acetamide [Intermediate 126] (5.2 g, 14.0 mmol) was dissolved in (1:1) MeOH/THF (155 ml). 1.25M aq. NaOH (77.6 ml, 97.0 mmol) was added dropwise and the reaction mixture stirred at ambient temperature for 1 hour. The reaction mixture was diluted with sat. aq. brine (130 ml) and extracted with EtOAc (3×150 ml). The combined organics were washed with sat. aq. brine (130 ml), dried over $Na_2SO_4$, filtered and concentrated in vacuo to yield the title compound as a colourless oil (4.54 g, 92%). $^1$H NMR (500 MHz, Chloroform-d) δ 7.40-7.36 (m, 2H), 7.35-7.29 (m, 3H), 7.24-7.13 (m, 2H), 7.06-7.01 (m, 1H), 4.50 (s, 1H), 3.72-3.56 (m, 6H), 3.27 (d, J=11.7 Hz, 1H), 3.02 (d, J=16.7 Hz, 1H), 2.94-2.84 (m, 1H). LCMS Method 1—Tr=0.88 min (ES+) (M+H+) 333.00.

[Intermediate 128]—(6S)-1-(3,4-Difluorophenyl)-6-(hydroxymethyl)piperazin-2-one

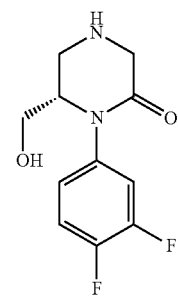

The H-Cube (Continuous Flow Hydrogenation Reactor) was loaded with a 20% $Pd(OH)_2$ cartridge. A solution of (6S)-4-benzyl-1-(3,4-difluorophenyl)-6-(hydroxymethyl)piperazin-2-one [Intermediate 127] (250 mg, 0.75 mmol) in MeOH (15 ml) was passed through the system twice at with a flow rate of 0.6 ml/min at 60° C. with pressure of 20 bar. The reaction mixture was concentrated in vacuo to yield the title compound as a colourless oil (123 mg, 65%). $^1$H NMR (500 MHz, Chloroform-d) δ 7.25-7.14 (m, 2H), 7.05 (ddt, J=8.4, 4.0, 2.2 Hz, 1H), 3.79 (dd, J=17.0, 1.4 Hz, 1H), 3.76 (dd, J=11.6, 1.4 Hz, 1H), 3.72-3.64 (m, 2H), 3.63 (dt, J=3.7, 1.8 Hz, 1H), 3.52 (dd, J=12.2, 1.6 Hz, 1H), 3.40 (ddd, J=12.2, 3.8, 2.1 Hz, 1H). LCMS Method 1 [ELS]—Tr=0.29 min (ES+) (M+H$^+$) 243.0.

[Intermediate 129]—3,5-Dibromo-2,4,6-trimethylpyridine

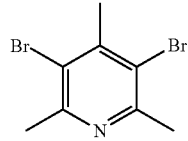

To a solution of 2,4,6-trimethylpyridine (13.1 ml, 99.0 mmol) in TFA (60 ml) was added conc. H$_2$SO$_4$ (79 ml, 1485 mmol) and NBS (88.1 g, 495 mmol). The resultant reaction was stirred at 50° C. for 25 hours, then additional NBS (17.6 g, 99.0 mmol) was added and the reaction stirred for a further 5 hours at 50° C. The mixture was poured onto crushed ice (1 dm$^3$) and the solution was basified to pH 8-9 with 50% aq. NaOH. The suspension was filtered and washed with water (200 ml), then the solid obtained was dried via vacuum oven overnight to afford the title compound as a white solid (22.1 g, 67%)

1H NMR (250 MHz, Chloroform-d) δ 2.61 (s, 6H), 2.60 (s, 3H)

LCMS Method 1—Tr=1.34 min, (ES+) (M+H$^+$) 277.9, 279.9

[Intermediate 130]—tert-Butyl 5-bromo-2,4,6-trimethylpyridine-3-carboxylate

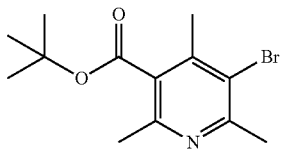 [SMILES: Cc1nc(C)c(C(=O)OC(C)(C)C)c(C)c1Br]

To a solution of 3,5-dibromo-2,4,6-trimethylpyridine [Intermediate 129] (84%, 4 g, 12.0 mmol) in Et$_2$O (100 ml) was slowly added 2.5M n-BuLi in hexane (6.7 ml) at −78° C. and the reaction was stirred for 1.5 hours at −78° C. Di-tert-butyl dicarbonate (3.68 g, 16.9 mmol) was then added to the reaction and the mixture was stirred at −78° C. for 1.5 hr. The reaction was quenched with 10% aq. citric acid solution (120 ml) and was extracted with EtOAc (120 ml). The organic layer was washed with brine, dried over Na$_2$SO$_4$, filtered and concentrated in vacuo to afford the title compound as a straw-coloured oil (3.88 g, 95%). $^1$H NMR (250 MHz, Chloroform-d) δ 2.65 (s, 3H), 2.46 (s, 3H), 2.38 (s, 3H), 1.60 (s, 9H). LCMS Method 1—Tr=1.34 min, (ES+) (M+H$^+$) 300.0, 302.0

[Intermediate 131]—tert-Butyl 5-{[1-(2-cyano-6-fluorophenyl)piperidin-4-yl]amino}-2,4,6-trimethylpyridine-3-carboxylate

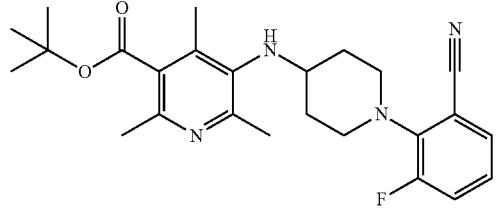 [SMILES: Cc1nc(C)c(C(=O)OC(C)(C)C)c(C)c1NC1CCN(c2c(F)cccc2C#N)CC1]

tert-Butyl 5-bromo-2,4,6-trimethylpyridine-3-carboxylate [Intermediate 130] (250 mg, 0.83 mmol), 3-fluoro-2-(piperazin-1-yl)benzonitrile [Intermediate 104] (171 mg, 0.83 mmol), NaO$^t$Bu (160 mg, 1.67 mmol), (±)-BINAP (104 mg, 0.17 mmol) and Pd$_2$(dba)$_3$ (76 mg, 0.08 mmol) were suspended in toluene (5 ml) and the mixture was de-gassed with nitrogen for 5 min. The mixture was then sealed under a nitrogen atmosphere and stirred at 110° C. for 16 hours. The reaction was cooled to ambient temperature and partitioned between water (15 ml) and EtOAc (15 ml). The aqueous layer was extracted with EtOAc (2×15 ml). The combined organics were washed with brine (25 ml), dried over Na$_2$SO$_4$ and concentrated in vacuo. The crude material was purified by flash column chromatography using a gradient of 20% to 100% EtOAc in heptane. The product containing fractions were combined and concentrated in vacuo to afford the title compound as a white solid (249 mg, 57%). $^1$H NMR (500 MHz, Chloroform-d) δ 7.38-7.31 (m, 1H), 7.21 (ddd, J=12.2, 8.2, 1.4 Hz, 1H), 7.06-6.99 (m, 1H), 3.39 (d, J=12.3 Hz, 2H), 3.17 (t, J=12.1 Hz, 2H), 3.05-2.93 (m, 1H), 2.50 (s, 3H), 2.46 (s, 3H), 2.25 (s, 3H), 2.01 (d, J=10.2 Hz, 2H), 1.75-1.56 (m, 11H). LCMS Method 1—Tr=1.16 min, (ES+) (M+H$^+$) 439.2.

[Intermediate 132]—5-{[1-(2-Cyano-6-fluorophenyl)piperidin-4-yl]amino}-2,4,6-trimethylpyridine-3-carboxylic Acid; bis TFA Salt

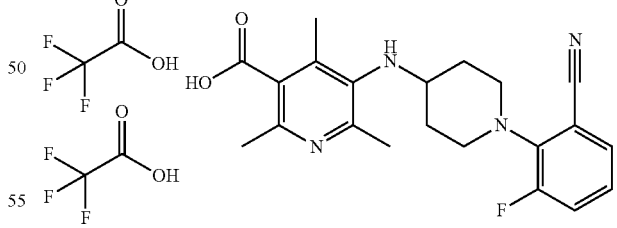

tert-Butyl 5-{[1-(2-cyano-6-fluorophenyl)piperidin-4-yl]amino}-2,4,6-trimethylpyridine-3-carboxylate [Intermediate 131] (249 mg, 0.57 mmol) was dissolved in DCM (0.5 ml) and TFA (0.5 ml, 6.53 mmol) was added. The mixture was stirred at ambient temperature for 16 hours, then the mixture was concentrated in vacuo and the product dried via vacuum oven to afford the title compound as a white solid (340 mg, 77%). $^1$H NMR (500 MHz, Chloroform-d) δ 7.37 (d, J=7.7 Hz, 1H), 7.28-7.20 (m, 1H), 7.12-7.04 (m, 1H), 3.39 (d, J=12.6 Hz, 2H), 3.29-3.11 (m, 3H), 2.71 (s, 3H), 2.66 (s, 3H), 2.50 (s, 3H), 2.01 (d, J=10.0 Hz, 2H), 1.85-1.66 (m, 2H). LCMS Method 1—Tr=0.93 min, (ES+) (M+H⁺) 383.2.

[Intermediate 133]—tert-Butyl 5-{[1-(2-cyano-4-fluorophenyl)piperidin-4-yl]amino}-2,4,6-trimethyl-pyridine-3-carboxylate

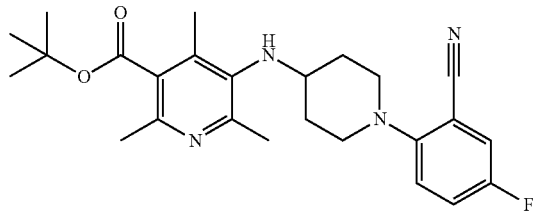 [SMILES: Cc1nc(C)c(C(=O)OC(C)(C)C)c(C)c1NC1CCN(c2ccc(F)cc2C#N)CC1]

Prepared analogously to the method for [Intermediate 131] using tert-butyl 5-bromo-2,4,6-trimethylpyridine-3-carboxylate [Intermediate 130] (250 mg, 0.83 mmol) and 5-fluoro-2-(piperazin-1-yl)benzonitrile [Intermediate 97] (171 mg, 0.83 mmol) to afford the title compound as a white solid (242 mg, 63%). ¹H NMR (500 MHz, Chloroform-d) δ 7.29-7.26 (m, 1H), 7.20 (ddd, J=9.0, 7.8, 3.0 Hz, 1H), 6.98 (dd, J=9.1, 4.6 Hz, 1H), 3.46 (d, J=12.4 Hz, 2H), 3.04-2.92 (m, 1H), 2.92-2.68 (m, 3H), 2.50 (s, 3H), 2.46 (s, 3H), 2.25 (s, 3H), 2.05 (d, J=12.3 Hz, 2H), 1.80-1.66 (m, 2H), 1.61 (s, 9H). LCMS Method 1—Tr=1.15 min, (ES+) (M+H+) 429.2.

[Intermediate 134]—5-{[1-(2-Cyano-4-fluorophenyl)piperidin-4-yl]amino}-2,4,6-trimethylpyridine-3-carboxylic Acid; bis-TFA Salt

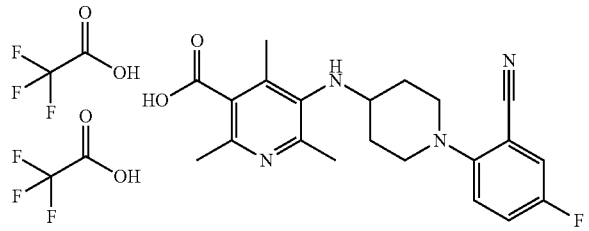

Prepared analogously to the method for [Intermediate 132] using tert-butyl 5-{[1-(2-cyano-4-fluorophenyl)piperidin-4-yl]amino}-2,4,6-trimethylpyridine-3-carboxylate [Intermediate 133] (242 mg, 0.55 mmol) to afford the title compound as a white solid (324 mg, 92%). ¹H NMR (500 MHz, Chloroform-d) δ 7.31 (dd, J=7.7, 3.0 Hz, 1H), 7.25 (ddd, J=8.9, 7.9, 3.0 Hz, 1H), 7.03 (dd, J=9.1, 4.5 Hz, 1H), 3.49 (d, J=12.3 Hz, 2H), 3.26-3.10 (m, 1H), 2.83 (t, J=11.2 Hz, 2H), 2.73 (s, 3H), 2.68 (s, 3H), 2.51 (s, 3H), 2.08 (d, J=10.1 Hz, 2H), 1.89-1.73 (m, 2H). LCMS Method 1—Tr=0.92 min, (ES+) (M+H+) 383.2.

[Intermediate 135]—tert-Butyl 2,4,6-trimethyl-5-{[1-(pyridin-2-yl)piperidin-4-yl]amino}pyridine-3-carboxylate

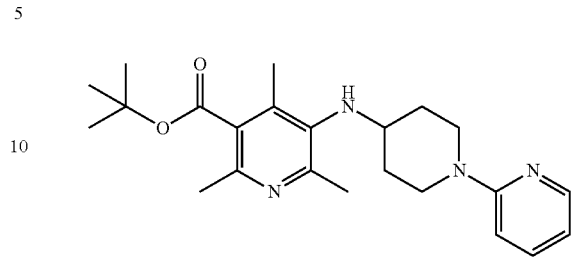

tert-Butyl 5-bromo-2,4,6-trimethylpyridine-3-carboxylate [Intermediate 130] (89%, 300 mg, 0.89 mmol), 1-(pyridin-2-yl)piperidin-4-amine (158 mg, 0.89 mmol), Pd₂(dba)₃ (81 mg, 0.09 mmol), (±)-BINAP (111 mg, 0.18 mmol) and NaOʳBu (171 mg, 1.78 mmol) were suspended in anhydrous toluene (5 ml) and stirred at 100° C. under nitrogen atmosphere for 20 hours. The reaction was filtered and the cake was washed through with DCM. The filtrate was concentrated in vacuo and the residue obtained was purified via reverse phase flash column chromatography [C18] using a gradient of 5% to 100% acetonitrile (+0.1% NH₃ modifier) in water (+0.1% NH₃ modifier). The product containing fractions were combined and concentrated in vacuo to afford the title compound as a straw coloured oil (183 mg, 48%). ¹H NMR (250 MHz, Chloroform-d) δ 8.24-8.13 (m, 1H), 7.52-7.43 (m, 1H), 6.67 (d, J=8.6 Hz, 1H), 6.64-6.57 (m, 1H), 4.39-4.25 (m, 2H), 3.17-3.00 (m, 1H), 2.91-2.77 (m, 2H), 2.49 (s, 3H), 2.47 (s, 3H), 2.25 (s, 3H), 2.06-1.95 (m, 2H), 1.62 (s, 9H), 1.55-1.37 (m, 2H). LCMS Method 1—Tr=0.81 min, (ES+) (M+H⁺) 182.8.

[Intermediate 136]—2,4,6-trimethyl-5-{[1-(pyridin-2-yl)piperidin-4-yl]amino}pyridine-3-carboxylic Acid; tris-TFA

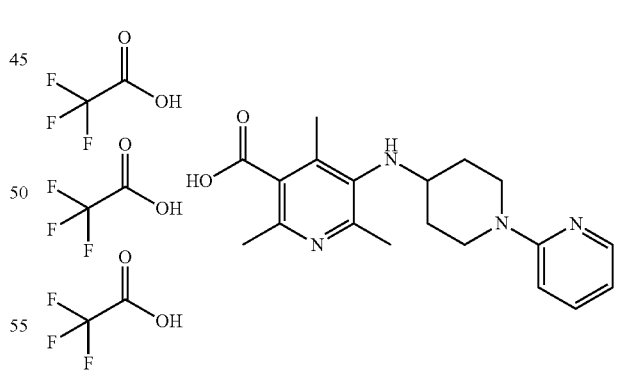

tert-Butyl 2,4,6-trimethyl-5-{[1-(pyridin-2-yl)piperidin-4-yl]amino}pyridine-3-carboxylate [Intermediate 135] (92%, 183 mg, 0.42 mmol) was suspended in TFA (1.63 ml, 21.2 mmol) and stirred at ambient temperature for 20 hours. The reaction mixture was concentrated in vacuo to afford the title compound as a yellow gum (320 mg, 88%). ¹H NMR (250 MHz, MeOH-d4) δ 8.10-8.00 (m, 1H), 8.00-7.93 (m, 1H), 7.49-7.40 (m, 1H), 7.04-6.94 (m, 1H), 4.33-4.16 (m, 2H), 3.52-3.42 (m, 1H), 3.41-3.27 (m, 2H), 2.74 (s, 3H), 2.68 (s, 3H), 2.56 (s, 3H), 2.20-2.06 (m, 2H), 1.87-1.68 (m, 2H). LCMS Method 1—Tr=0.21 min, (ES+) (M+H⁺) 341.2

[Intermediate 137]—tert-Butyl 5-{[1-(3-chloropyridin-2-yl)piperidin-4-yl]amino}-2,4,6-trimethylpyridine-3-carboxylate

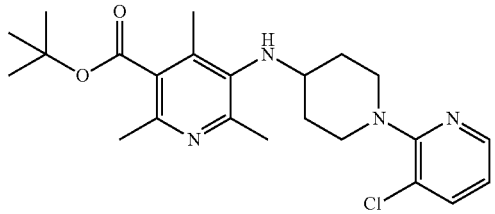 [SMILES: Cc1nc(C)c(C(=O)OC(C)(C)C)c(C)c1NC1CCN(c2ncccc2Cl)CC1]

Prepared analogously to the method for [Intermediate 135] using tert-butyl 5-bromo-2,4,6-trimethylpyridine-3-carboxylate [Intermediate 130] (89%, 170 mg, 0.50 mmol) and 1-(3-chloropyridin-2-yl)piperidin-4-amine hydrochloride (125 mg, 0.50 mmol) to afford the title compound as a straw-coloured oil (89 mg, 30%). ¹H NMR (250 MHz, Chloroform-d) δ 8.16 (dd, J=4.8, 1.6 Hz, 1H), 7.57 (dd, J=7.7, 1.7 Hz, 1H), 6.82 (dd, J=7.7, 4.8 Hz, 1H), 3.90-3.73 (m, 2H), 3.10-2.94 (m, 1H), 2.90-2.73 (m, 2H), 2.50 (s, 3H), 2.45 (s, 3H), 2.25 (s, 3H), 2.07-1.95 (m, 2H), 1.71-1.53 (m, 11H). LCMS Method 1—(2 min, low pH) Tr=1.06 min, (ES+) (M+H⁺) 431.2.

[Intermediate 138]—5-{[1-(3-Chloropyridin-2-yl)piperidin-4-yl]amino}-2,4,6-trimethylpyridine-3-carboxylic Acid; tris-TFA Salt

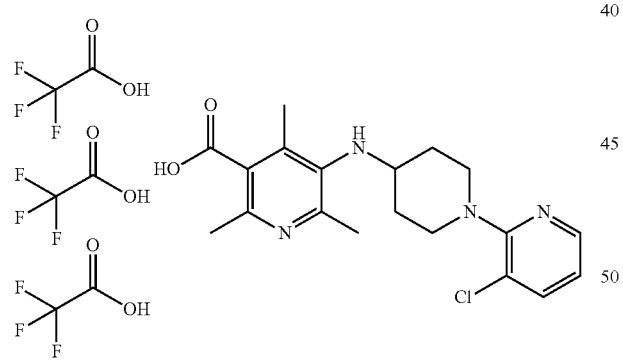

Prepared analogously to the method for [Intermediate 136] using tert-butyl 5-{[1-(3-chloropyridin-2-yl)piperidin-4-yl]amino}-2,4,6-trimethylpyridine-3-carboxylate [Intermediate 137] (68.4%, 183 mg, 0.29 mmol) to afford the title compound as a yellow gum (304 mg, 100%). ¹H NMR (250 MHz, MeOH-d4) δ 8.14 (dd, J=5.0, 1.6 Hz, 1H), 7.79 (dd, J=7.8, 1.6 Hz, 1H), 6.98 (dd, J=7.8, 5.0 Hz, 1H), 3.94-3.78 (m, 2H), 3.28-3.16 (m, 1H), 3.00-2.86 (m, 2H), 2.72 (s, 3H), 2.65 (s, 3H), 2.55 (s, 3H), 2.09-1.96 (m, 2H), 1.93-1.73 (m, 2H). LCMS Method 1—Tr=0.80 min, (ES+) (M+H⁺) 375.1

[Intermediate 139]—(2R or 2S)-1-phenylpiperazine-2-carboxamide

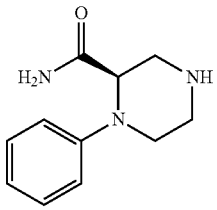 [SMILES: NC(=O)[C@H]1CNCCN1c1ccccc1]

The title compound was afforded from chiral separation of 1-Phenylpiperazine-2-carboxamide hydrochloride [Intermediate 50].

[Intermediate 140]—tert-butyl 2,4,6-trimethyl-3-{[1-(pyridin-2-yl)piperidin-4-yl]amino}benzoate

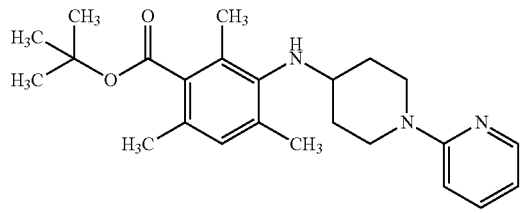 [SMILES: Cc1cc(C)c(C(=O)OC(C)(C)C)c(C)c1NC1CCN(c2ccccn2)CC1]

Prepared analogously to [Intermediate 95] from tert-butyl 3-bromo-2,4,6-trimethyl-benzoate [Intermediate 94] (500 mg, 1.67 mmol) and 1-(pyridin-2-yl)piperidin-4-amine (296 mg, 1.67 mmol) to yield the title compound as a brown oil (391 mg, 53%).
1H NMR (500 MHz, DMSO-d6) δ 8.11-8.05 (m, 1H), 7.49 (ddd, J=8.9, 7.1, 2.0 Hz, 1H), 6.81 (t, J=4.3 Hz, 2H), 6.57 (dd, J=7.0, 4.9 Hz, 1H), 4.27 (d, J=13.2 Hz, 2H), 3.64 (d, J=10.4 Hz, 1H), 3.01-2.88 (m, 1H), 2.77 (t, J=11.7 Hz, 2H), 2.19 (s, 3H), 2.14 (s, 3H), 2.12 (s, 3H), 1.76 (d, J=10.4 Hz, 2H), 1.53 (s, 9H), 1.42 (qd, J=12.4, 4.0 Hz, 2H) LCMS Method 1—Tr=1.05 min (ES+) (M+H⁺) 396.2

[Intermediate 141]—2,4,6-trimethyl-3-{[1-(pyridin-2-yl)piperidin-4-yl]amino}benzoic Acid

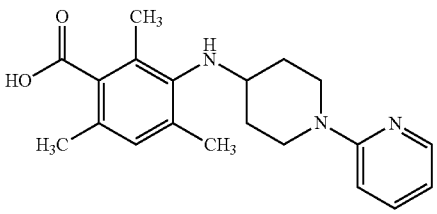 [SMILES: Cc1cc(C)c(C(=O)O)c(C)c1NC1CCN(c2ccccn2)CC1]

Prepared analogously to [Intermediate 100] from tert-butyl 2,4,6-trimethyl-3-{[1-(pyridin-2-yl)piperidin-4-yl]amino}benzoate [Intermediate 140] (90%, 391 mg, 0.89 mmol) to yield the title compound as a pale yellow powdery solid (299 mg, 94%).
H NMR (500 MHz, DMSO-d6) δ 8.12-8.06 (m, 1H), 7.49 (ddd, J=8.9, 7.1, 2.0 Hz, 1H), 6.82 (d, J=8.7 Hz, 1H), 6.74

(s, 1H), 6.58 (dd, J=7.0, 4.9 Hz, 1H), 4.27 (d, J=13.2 Hz, 2H), 2.99-2.90 (m, 1H), 2.77 (t, J=11.6 Hz, 2H), 2.17 (s, 3H), 2.14 (s, 3H), 2.10 (s, 3H), 1.78 (d, J=10.3 Hz, 2H), 1.41 (qd, J=12.4, 4.0 Hz, 2H) LCMS Method 1—Tr=0.69 min (ES+) (M+H$^+$) 340.1

[Intermediate 142]—1,3-Difluoro-2-methanesulfinylbenzene

To a stirred solution of 1,3-difluoro-2-(methylsulfanyl) benzene (25 g, 156 mmol) in THF (250 ml) at 0° C. was added a solution of m-CPBA (75%, 37.7 g, 164 mmol) in THF (250 ml) dropwise while maintaining the internal reaction temperature at <10° C. Then the reaction was stirred for 1 hour while allowing it to warm to room temperature. The reaction was stirred overnight at room temperature and then concentrated in vacuo. The residue was diluted with DCM (500 ml) and 2M aq. NaOH (500 ml). The phases were separated and the aqueous layer was extracted with (2×500 ml). The combined organic extracts were dried over Na$_2$SO$_4$, filtered and concentrated in vacuo to give the title compound as a yellow oil (5.5 g, 75%). 1H NMR (250 MHz, Chloroform-d) δ 7.48 (tt, J=8.3, 6.2 Hz, 1H), 7.01 (t, J=8.3 Hz, 2H), 3.11 (s, 3H).

LCMS Method 1—Tr=0.64 min (ES+) (M+H$^+$) 176.8

[Intermediate 143]—tert-Butyl N-[(2,6-difluorophenyl)(methyl)oxo-lambda6-sulfanylidene]carbamate

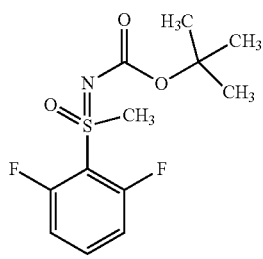 [SMILES: CC(C)(C)OC(=O)N=S(C)(=O)c1c(F)cccc1F]

To a stirred solution of 1,3-difluoro-2-methanesulfinylbenzene [Intermediate 142] (26.4 g, 150 mmol) in DCM (406 ml) was added tert-butyl carbamate (35.1 g, 300 mmol) in DCM (406 ml), magnesium (2+) ion oxidandiide (24.2 g, 599 mmol), rhodium (2+) acetate (1:2) (1.99 g, 4.49 mmol) and bis(acetyloxy)(phenyl)-lambda~3~-iodane (96.5 g, 300 mmol). The reaction was flushed with N$_2$ and the suspension was stirred at room temperature for 66 hours. Celite was added to the reaction. The reaction was filtered and the filtrate was concentrated in vacuo. The residue was mobilised in the minimum volume of DCM, filtered and the filtrate was concentrated (×2). The crude product was purified by flash column chromatography using a gradient of 0% to 100% EtOAc in heptane. The product containing fractions were combined and concentrated in vacuo to afford the title compound as a pale yellow oil (7.9 g, 16%).

1H NMR (250 MHz, Chloroform-d) δ 7.60 (tt, J=8.4, 5.9 Hz, 1H), 7.08 (t, J=8.7 Hz, 2H), 3.41 (s, 3H), 1.40 (s, 9H). LCMS Method 1—Tr=1.01 min (ES+) (M+H)+ 237.0

[Intermediate 144]—tert-Butyl 4-[2-({[(tert-butoxy)carbonyl]imino}(methyl)oxo-lambda6-sulfanyl)-3-fluorophenyl]piperazine-1-carboxylate

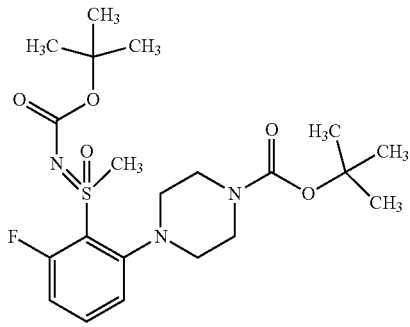 [SMILES: CC(C)(C)OC(=O)N=S(C)(=O)c1c(F)cccc1N1CCN(C(=O)OC(C)(C)C)CC1]

To a stirred solution of tert-butyl piperazine-1-carboxylate (1.24 g, 6.63 mmol) and tert-butyl N-[(2,6-difluorophenyl)(methyl)oxo-lambda6-sulfanylidene]carbamate [Intermediate 143] (84%, 2.00 g, 5.77 mmol) in PhMe (20 ml) was added Cs$_2$CO$_3$ (2.25 g, 6.92 mmol). The reaction was heated at 115° C. for 1 hour. The reaction was allowed to cool to room temperature and was diluted with water (20 ml). The layers were separated and the aqueous layer was extracted with DCM (2×20 ml). The combined organic extracts were dried over Na$_2$SO$_4$, filtered and concentrated in vacuo. The crude product was purified via reverse phase column chromatography [C18], using a gradient of 0 to 100% MeCN (with 0.1% ammonia modifier) in water (with 0.1% ammonia modifier), to give the title compound as a white solid (1.71 g, 65%). 1H NMR (250 MHz, Chloroform-d) δ 7.55 (td, J=8.2, 5.8 Hz, 1H), 7.10 (d, J=8.2 Hz, 1H), 7.01 (ddd, J=11.0, 8.3, 1.0 Hz, 1H), 4.38-2.57 (m, 11H), 1.47 (s, 9H), 1.44 (s, 9H). LCMS Method 1—Tr=1.19 min (ES+) (M+H)+ 458.1

[Intermediate 145]—2-fluoro-6-(piperazin-1-yl)phenyl](imino)methyl-lambda6-sulfanone

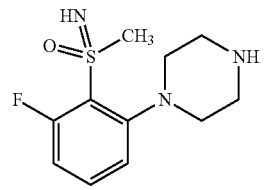 [SMILES: CS(=N)(=O)c1c(F)cccc1N1CCNCC1]

To a stirred solution of tert-butyl 4-[2-({[(tert-butoxy)carbonyl]imino}(methyl)oxo-lambda6-sulfanyl)-3-fluorophenyl]piperazine-1-carboxylate [Intermediate 144] (25.8 g, 56.4 mmol) in DCM (194 ml) was added TFA (64.7 ml, 846 mmol). The reaction was stirred at room temperature for 18 hours and was then concentrated in vacuo. The residue was dissolved in the minimum volume of (1:1) MeOH/DCM. A glass column was charged with MP-TsOH (109 g, 338 mmol) and the resin was washed with DCM (300 ml), MeOH (300 ml), DCM (300 ml) and MeOH (300 ml). The solution of crude product was loaded under gravity. When fully absorbed, the resin was left for 5 minutes and then the resin was washed with DCM (500 ml), MeOH (500 ml), DCM (500 ml) and MeOH (500 ml). The product was eluted with 3.5M $NH_3$ in MeOH (1.5 l). The resulting fractions were concentrated in vacuo to give the title compound as a beige solid (13.7 g, 93%).

1H NMR (500 MHz, Chloroform-d) δ 7.44 (td, J=8.2, 6.2 Hz, 1H), 7.17 (d, J=8.1 Hz, 1H), 6.99 (ddd, J=10.7, 8.4, 1.0 Hz, 1H), 5.52 (s, 1H), 3.42 (d, J=5.5 Hz, 3H), 3.34 (s, 1H), 3.20-2.94 (m, 6H), 2.78 (s, 1H).

LCMS Method 6—Tr=1.56 min (ES+) (M+H)+ 257.9

[Intermediate 146]—(R or S)-[2-fluoro-6-(piperazin-1-yl)phenyl](imino)methyl-lambda6-sulfanone

[Intermediate 147]—(S or R)-[2-fluoro-6-(piperazin-1-yl)phenyl](imino)methyl-lambda6-sulfanone

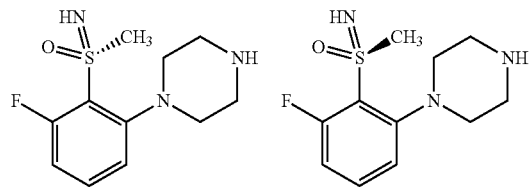

2-Fluoro-6-(piperazin-1-yl)phenyl](imino)methyl-lambda6-sulfanone (9.8 g, 38.08 mmol) was dissolved to 100 mg/ml in MeOH and was then purified by SFC on a Lux C4 column (21.2 mm×250 mm, 5 □m) eluting with 45:55 MeOH:$CO_2$ (containing 0.1% v/v $NH_3$). The product containing fractions were combined and concentrated in vacuo to afford the title compounds as white solids (4.77 g, 49%, with a chiral purity 99% ee and 4.86 g, 49%, with a chiral purity 98% ee respectively).

1H NMR (500 MHz, Chloroform-d) δ 7.44 (td, J=8.2, 6.2 Hz, 1H), 7.18 (d, J=8.1 Hz, 1H), 6.99 (ddd, J=10.7, 8.3, 1.0 Hz, 1H), 5.52 (s, 1H), 3.43 (d, J=5.5 Hz, 3H), 3.35 (s, 1H), 3.20-2.88 (m, 6H), 2.78 (s, 1H).

LCMS Method 6—Tr=1.59 min (ES+) (M+H)+ 258.0

$^1$H NMR (500 MHz, Chloroform-d) δ 7.44 (td, J=8.2, 6.2 Hz, 1H), 7.18 (d, J=8.1 Hz, 1H), 7.00 (ddd, J=10.7, 8.3, 1.0 Hz, 1H), 5.45 (s, 1H), 3.43 (d, J=5.5 Hz, 3H), 3.35 (s, 1H), 3.25-2.95 (m, 6H), 2.81 (s, 1H).

LCMS Method 6—Tr=1.59 min (ES+) (M+H)+ 258.0

The preparation of representative non-limiting examples of provided compounds are described below.

Example 1: 2-(4-(5-(1-(2-Cyanophenyl)-3,3-dimethylpiperidin-4-ylamino)-2,4-dimethylbenzoyl)piperazin-1-yl)benzenesulfonamide, I-52

I-52

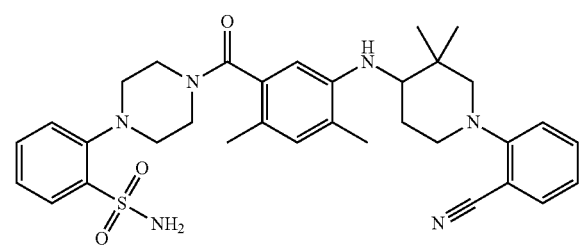

Synthetic Scheme:

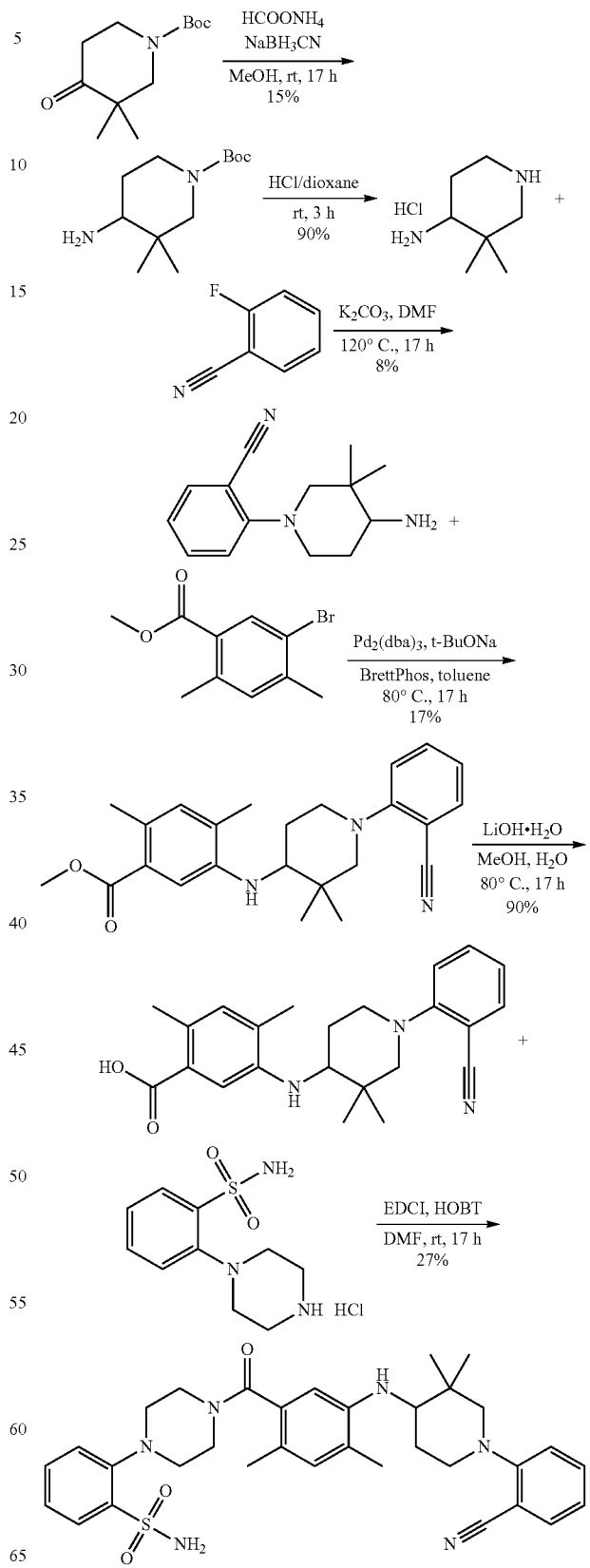

Procedures and Characterization:

The analysis method was following Method B and the separation method was following Method D.

Step 1: tert-Butyl 4-amino-3,3-dimethylpiperidine-1-carboxylate

Tert-Butyl 3,3-dimethyl-4-oxo-piperidine-1-carboxylate (2.50 g, 11.00 mmol) was dissolved in MeOH (50.00 mL) and ammonium formate (3.95 g, 62.69 mmol) and $NaBH_3CN$ (739.54 mg, 11.77 mmol) were added. The reaction mixture was stirred for 17 h at rt and then purified by reversed-phase column to give tert-butyl 4-amino-3,3-dimethyl-piperidine-1-carboxylate (400.00 mg, 1.65 mmol, 15%) as a white solid. ESI-MS (EI+, m/z): 173.3 [M−56]+.

Step 2: 3,3-Dimethylpiperidin-4-amine hydrochloride Salt

Tert-Butyl 4-amino-3,3-dimethyl-piperidine-1-carboxylate (2.00 g, 5.52 mmol) was dissolved in 4 M HCl/dioxane (25.00 mL). The mixture was stirred at rt for 3 h. The reaction mixture was concentrated to give 3,3-dimethylpiperidin-4-amine (1.00 g, 4.97 mmol, 90%, 2 HCl) as a yellow solid. ESI-MS (EI+, m/z): 129.1 [M+H]+.

Step 3: 2-(4-Amino-3,3-dimethylpiperidin-1-yl)benzonitrile 3,3-Dimethylpiperidin-4-amine (350.00 mg, 1.74 mmol, 2HCl) was dissolved in DMF (10.00 mL) then $K_2CO_3$ (1.44 g, 10.44 mmol) and 2-fluorobenzonitrile (210.74 mg, 1.74 mmol) were added. The mixture was stirred at 120° C. for 17 h. The mixture was cooled down to rt. Then water (150 mL) was added and extracted with EtOAc (3×50 mL). The combined organic layers were concentrated and the residue was purified by column chromatography (DCM/MeOH=30). 2-(4-amino-3, 3-dimethyl-1-piperidyl) benzonitrile (30.00 mg, 116.43 umol, 8%) was obtained as a yellow oil. ESI-MS (EI+, m/z): 230.2 [M+H]+.

Step 4: Methyl 5-(1-(2-cyanophenyl)-3,3-dimethylpiperidin-4-ylamino)-2,4-dimethylbenzoate 2-(4-amino-3,3-dimethyl-1-piperidyl)benzonitrile (100.00 mg, 436.07 umol), methyl 5-bromo-2,4-dimethylbenzoate (116.61 mg, 479.68 umol), tBuONa (83.81 mg, 872.14 umol), BrettPhos (46.81 mg, 87.21 umol), and $Pd_2(dba)_3$ (199.72 mg, 218.04 umol) were dissolved in toluene (5.00 mL) and the mixture was stirred at 85 C for 17 h. The mixture was purified by column chromatography (PE/EA=10/1) to afford methyl 5-[[1-(2-cyanophenyl)-3,3-dimethyl-4-piperidyl]amino]-2, 4-dimethyl-benzoate (30.00 mg, 76.63 umol, 17%) as a yellow oil. ESI-MS (EI+, m/z): 392.0 [M+H]+.

Step 5: 5-(1-(2-Cyanophenyl)-3, 3-dimethylpiperidin-4-ylamino)-2, 4-dimethylbenzoic Acid To a solution of methyl 5-[[1-(2-cyanophenyl)-3,3-dimethyl-4-piperidyl]amino]-2,4-dimethyl-benzoate (30.00 mg, 76.63 umol) in $H_2O$ (3.00 mL) and MeOH (5.00 mL) was added $LiOH.H_2O$ (32.15 mg, 766.30 umol). The mixture was stirred at 60° C. for 17 h. The mixture was concentrated and acidified with 1 N HCl and extracted with EtOAc. The organic layer was washed with brine, dried over $MgSO_4$, filtered and concentrated to give crude 5-[[1-(2-cyanophenyl)-3,3-dimethyl-4-piperidyl]amino]-2,4-dimethyl-benzoic acid (30.00 mg, 69.14 umol, 90%) as a yellow oil. ESI-MS (EI+, m/z): 378.3 [M+H]+.

Step 6: 2-(4-(5-(1-(2-Cyanophenyl)-3,3-dimethylpiperidin-4-ylamino)-2,4-dimethylbenzoyl) piperazin-1-yl) benzenesulfonamide Following the amide coupling HATU method 2-(4-(5-(1-(2-Cyanophenyl)-3,3-dimethylpiperidin-4-ylamino)-2,4-dimethylbenzoyl)piperazin-1-yl)benzenesulfonamide I-52 was obtained as a white solid. ESI-MS (EI+, m/z): 601.3 [M+H]+. $^1H$ NMR (500 MHz, MeOD-$d_4$) δ 8.04-7.93 (m, 1H), 7.70-7.52 (m, 4H), 7.37 (t, J=7.6 Hz, 1H), 7.21 (dd, J=8.2, 4.0 Hz, 1H), 7.09 (t, J=7.5 Hz, 1H), 6.97 (s, 1H), 6.61 (s, 1H), 4.01 (m, 1H), 3.53 (m, 3H), 3.38 (m, 1H), 3.29 (m, 1H), 3.22-3.09 (m, 2H), 3.00 (m, 3H), 2.82 (m, 1H), 2.20 (d, J=7.5 Hz, 6H), 2.00 (m, 1H), 1.90 (m, 1H), 1.32 (m, 1H), 1.26 (s, 3H), 1.06 (s, 3H).

Example 2: (R)-2-(4-(2, 4-Dimethyl-5-(3-methyl-4-(pyridin-2-yl) piperazine-1-carbonyl) phenylamino) piperidin-1-yl) benzonitrile, I-45

I-45

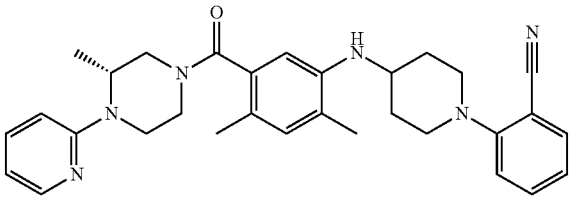

Synthetic Scheme:

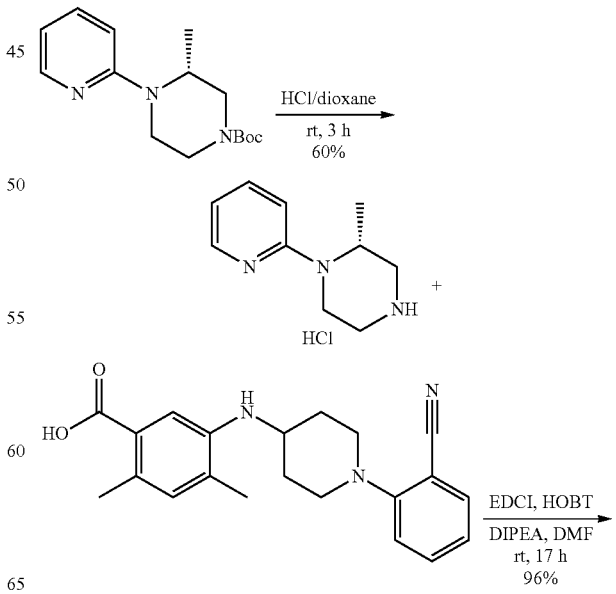

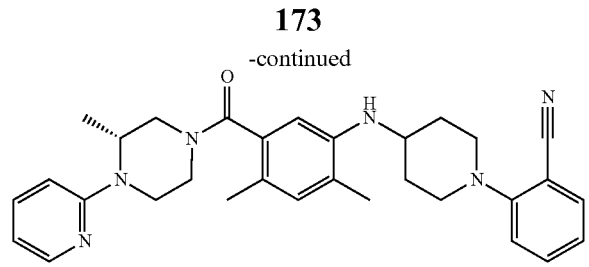

Procedures and Characterization:

The analysis method was following Method A and the separation method was following Method D.

Step 1: (R)-2-Methyl-1-(pyridin-2-yl)piperazine Hydrochloride Salt

Tert-Butyl (3R)-3-methyl-4-(2-pyridyl)piperazine-1-carboxylate (300.00 mg, 540.81 umol) was dissolved in HCl/dioxane (4 M, 10.00 mL). The mixture was stirred at rt for 3 h and concentrated to give crude (2R)-2-methyl-1-(2-pyridyl)piperazine (200.00 mg, 327.55 umol, 60%, HCl) as a yellow oil. ESI-MS (EI⁺, m/z): 178.3 [M+H]⁺.

Step 2: (R)-2-(4-(2,4-Dimethyl-5-(3-methyl-4-(pyridin-2-yl)piperazine-1-carbonyl)phenylamino)piperidin-1-yl)benzonitrile Followed the amide coupling EDCI/HOBT method to obtain (R)-2-(4-(2, 4-Dimethyl-5-(3-methyl-4-(pyridin-2-yl) piperazine-1-carbonyl) phenylamino)piperidin-1-yl)benzonitrile I-45 as a white solid. ESI-MS (EI⁺, m/z): 509.4 [M+H]+. ¹H NMR (500 MHz, CDCl₃) δ 8.19 (d, J=4.7 Hz, 1H), 7.51 (m, 3H), 6.98 (m, 3H), 6.75-6.33 (m, 3H), 4.47 (m, 2H), 4.02 (m, 1H), 3.66-2.92 (m, 10H), 2.20 (m, 8H), 1.73 (s, 2H), 1.30-0.99 (m, 3H).

Example 3: (R)-tert-Butyl 4-(5-(1-(2-cyanophenyl) piperidin-4-ylamino)-2, 4-dimethylbenzoyl)-2-(hydroxymethyl) piperazine-1-carboxylate, I-7

I-7

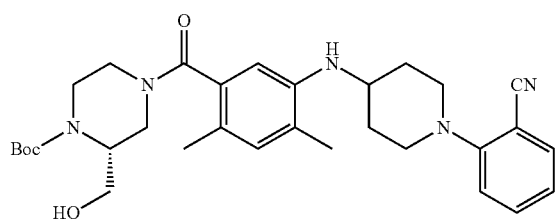

Synthetic Scheme:

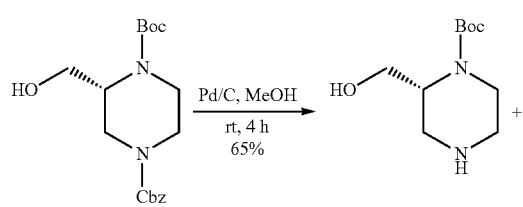

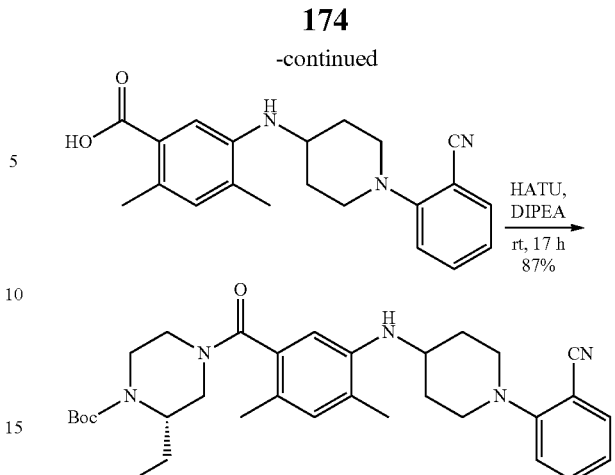

Procedures and Characterization:

The analysis method was following Method A and the separation method was following Method D.

Step 1: (R)-tert-Butyl-2-(hydroxyethyl)piperazine-1-carboxylate (R)-4-Benzyl 1-tert-butyl 2-(hydroxymethyl)piperazine-1,4-dicarboxylate (2.00 g, 4.85 mmol) was dissolved in MeOH (50.00 mL), Pd/C (480.00 mg, 3.95 mmol) was added and stirred at rt for 4 h under H₂. The reaction mixture was filtered and the filtrate was concentrated to give crude (R)-tert-butyl-2-(hydroxymethyl)piperazine-1-carboxylate (900.00 mg, 4.16 mmol, 85%) as a colorless oil. ESI-MS (EI⁺, m/z): 217.3 [M+H]⁺.

Step 2: (R)-tert-Butyl-4-(5-(1-(2-cyanophenyl)piperidin-4-ylamino)-2,4-dimethylbenzoyl)-2-(hydroxymethyl)piperazine-1-carboxylate Followed the amide coupling HATU method to obtain (R)-tert-Butyl-4-(5-(1-(2-cyanophenyl) piperidin-4-ylamino)-2, 4-dimethylbenzoyl)-2-(hydroxymethyl) piperazine-1-carboxylate I-7 as a red oil. ESI-MS (EI⁺, m/z): 548.3 [M+H]⁺. ¹H NMR (500 MHz, MeOD-d₄) δ 7.71-7.51 (m, 2H), 7.21 (d, J=8.5 Hz, 1H), 7.08 (t, J=7.6 Hz, 1H), 6.97 (m, 1H), 6.50 (m, 1H), 3.79 (m, 9H), 3.26-2.91 (m, 5H), 2.29-2.04 (m, 8H), 1.79 (m, 2H), 1.49 (s, 9H).

Example 4: (R)-2-(4-(5-(3-(Hydroxymethyl) piperazine-1-carbonyl)-2,4-dimethylphenylamino) piperidin-1-yl)benzonitrile, I-6

I-6

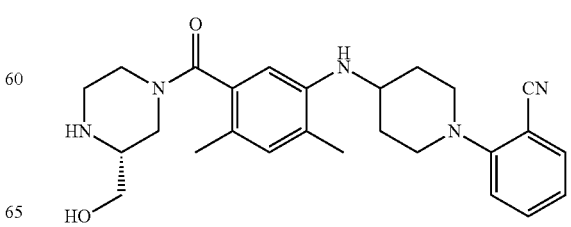

Synthetic Scheme:

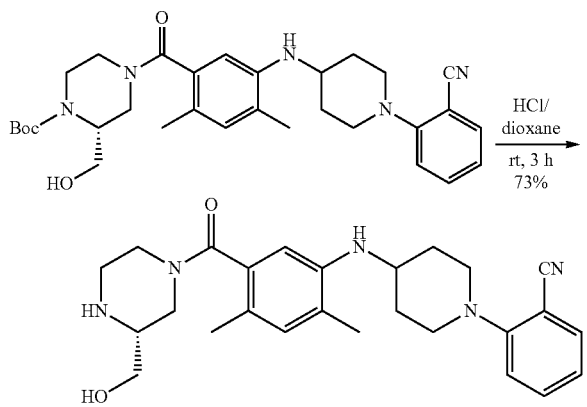

The analysis method was following Method B.

Step 1: (R)-2-(4-(5-(3-(Hydroxymethyl)piperazine-1-carbonyl)-2,4-dimethylphenylamino)piperidin-1-yl)benzonitrile tert-Butyl-(2R)-4-[5-[[1-(2-cyanophenyl)-4-piperidyl]amino]-2,4-dimethyl-benzoyl]-2-(hydroxymethyl)piperazine-1-carboxylate (500.00 mg, 912.93 umol) in 4 M HCl/dioxane (10.00 mL) was stirred at rt for 3 h. The solvent was concentrated and the residue was taken up in DCM. The mixture was washed with sat. NaHCO$_3$, the organic layer was dried over Na$_2$SO$_4$, filtered and concentrated to give 2-[4-[5-[(3R)-3-(hydroxymethyl)piperazine-1-carbonyl]-2,4-dimethyl-anilino]-1-piperidyl]benzonitrile I-6 (300.00 mg, 670.29 umol, 73%) as a yellow solid. ESI-MS (EI$^+$, m/z): 448.3 [M+H]+. $^1$H NMR (500 MHz, MeOD-d$_4$) δ 7.68-7.51 (m, 2H), 7.21 (d, J=8.3 Hz, 1H), 7.08 (t, J=7.6 Hz, 1H), 6.95 (m, 1H), 6.62-6.43 (m, 1H), 4.60 (m, 1H), 3.69-3.35 (m, 6H), 3.20-2.60 (m, 7H), 2.16 (m, 8H), 1.78 (m, 2H).

Example 5: 2-(4-(5-(1-(3-Methoxyphenyl) piperidin-4-ylamino)-2, 4-dimethylbenzoyl) piperazin-1-yl) benzenesulfonamide, I-5

I-5

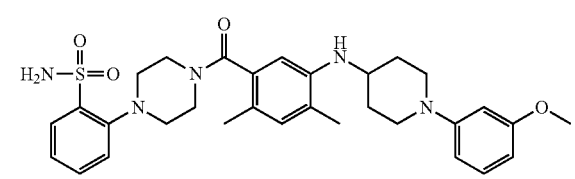

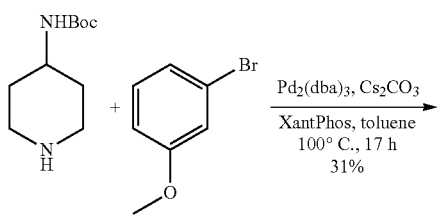

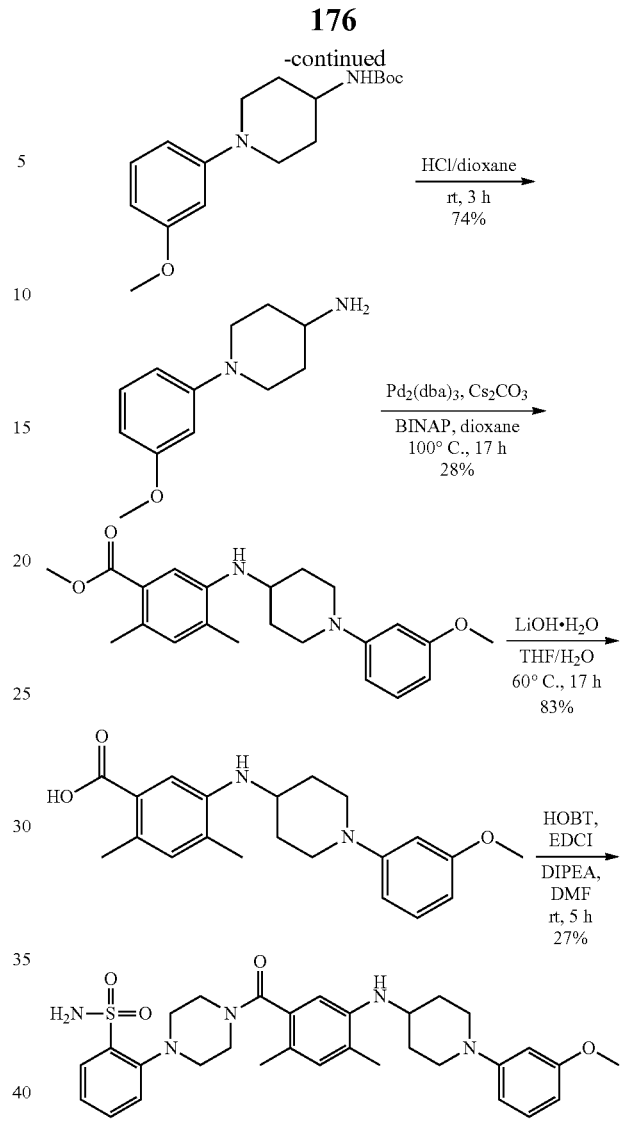

Procedures and Characterization:

The analysis method was following Method A and the separation method was following Method D.

Step 1: tert-Butyl 1-(3-methoxyphenyl)piperidin-4-ylcarbamate tert-Butyl N-(4-piperidyl) carbamate (1.00 g, 4.99 mmol), 1-bromo-3-methoxy-benzene (933.30 mg, 4.99 mmol), Cs$_2$CO$_3$ (3.25 g, 9.98 mmol) and Pd$_2$(dba)$_3$ (914.72 mg, 998.00 umol) were dissolved in toluene (30.00 mL) and the mixture was stirred at 100° C. for 17 h. The mixture was extracted and purified via preparative HPLC to give tert-butyl N-[1-(3-methoxyphenyl)-4-piperidyl] carbamate (600.00 mg, 1.57 mmol, 31%) as a yellow solid. ESI-MS (EI$^+$, m/z): 307.2 [M+H]+.

Step 2: 1-(3-Methoxyphenyl)piperidin-4-amine tert-Butyl N-[1-(3-methoxyphenyl)-4-piperidyl] carbamate (200.00 mg, 652.74 umol) in 4 M HCl/dioxane (652.74 umol, 10.00 mL) was stirred at rt for 3 h. The solvent was concentrated and the residue was taken up in DCM. The mixture was washed with sat. NaHCO$_3$, the organic layer was dried over Na$_2$SO$_4$, filtered and concentrated to give 1-(3-methoxyphenyl) piperidin-4-amine (100.00 mg, 484.78 umol, 74%) as a yellow oil. ESI-MS (EI⁺, m/z): 207.2 [M+H]⁺.

Step 3: Methyl 5-(1-(3-methoxyphenyl)piperidin-4-ylamino)-2,4-dimethylbenzoate A mixture of 1-(3-methoxyphenyl) piperidin-4-amine (100.00 mg, 484.78 umol), methyl 5-bromo-2,4-dimethylbenzoate (117.85 mg, 484.78 umol), BINAP (60.37 mg, 96.96 umol), Cs$_2$CO$_3$ (315.90 mg, 969.56 umol) and Pd$_2$(dba)$_3$ (88.81 mg, 96.96 umol) in dioxane (5.00 mL) was stirred at 100° C. for 17 h. The mixture was purified by column chromatography (PE/EA=5/1) to give methyl 5-[[1-(3-methoxyphenyl)-4-piperidyl]amino]-2,4-dimethyl-benzoate (50.00 mg, 135.70 umol, 28%) as a yellow oil. ESI-MS (EI⁺, m/z): 369.3 [M+H]⁺.

Step 4: 5-(1-(3-Methoxyphenyl)piperidin-4-ylamino)-2,4-dimethylbenzoic Acid

Methyl 5-[[1-(3-methoxyphenyl)-4-piperidyl]amino]-2,4-dimethyl-benzoate (50.00 mg, 135.70 umol) dissolved in THF (5.00 mL) and H$_2$O (3.00 mL) and LiOH.H$_2$O (20.00 mg, 476.64 umol) was added. The mixture was stirred at 60° C. for 17 h. The mixture was concentrated and acidified with 1 M HCl and extracted with EtOAc. The organic layer was washed with brine, dried over MgSO$_4$, filtered and concentrated to give crude 5-[[1-(3-methoxyphenyl)-4-piperidyl]amino]-2,4-dimethyl-benzoic acid (40.00 mg, 112.85 umol, 83%) as a yellow oil. ESI-MS (EI⁺, m/z): 355.2 [M+H]+.

Step 5: 2-(4-(5-(1-(3-Methoxyphenyl)piperidin-4-ylamino)-2,4-dimethylbenzoyl)piperazin-1-yl)benzenesulfonamide Followed the amide coupling general EDCI/HOBT method to obtain 2-(4-(5-(1-(3-Methoxyphenyl)piperidin-4-ylamino)-2,4-dimethylbenzoyl)piperazin-1-yl)benzenesulfonamide I-5 as a white solid. ESI-MS (EI⁺, m/z): 578.2 [M+H]⁺. ¹H NMR (500 MHz, DMSO-d$_6$) δ 7.87 (dd, J=7.9, 1.5 Hz, 1H), 7.66-7.51 (m, 2H), 7.43-7.29 (m, 1H), 7.09 (t, J=8.2 Hz, 1H), 6.97 (s, 2H), 6.86 (s, 1H), 6.54 (dd, J=8.3, 2.0 Hz, 1H), 6.45 (dd, J=6.6, 4.4 Hz, 2H), 6.33 (dd, J=8.1, 2.1 Hz, 1H), 4.44 (d, J=8.2 Hz, 1H), 4.04-3.60 (m, 7H), 3.42 (m, 3H), 3.08-2.69 (m, 6H), 2.13-2.01 (m, 6H), 1.96 (m, 2H), 1.55 (m, 2H).

Example 6: (S)-2-(4-(5-(3-(Hydroxymethyl)-4-(1-methyl-1H-tetrazol-5-yl) piperazine-1-carbonyl)-2,4-dimethylphenylamino) piperidin-1-yl) Benzonitrile, I-91

I-91

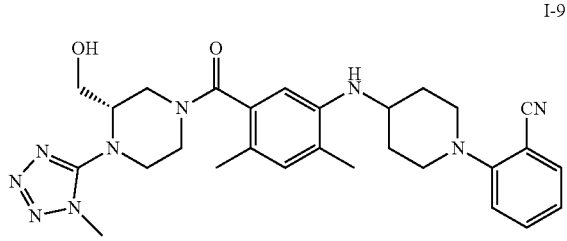

Synthetic Scheme:

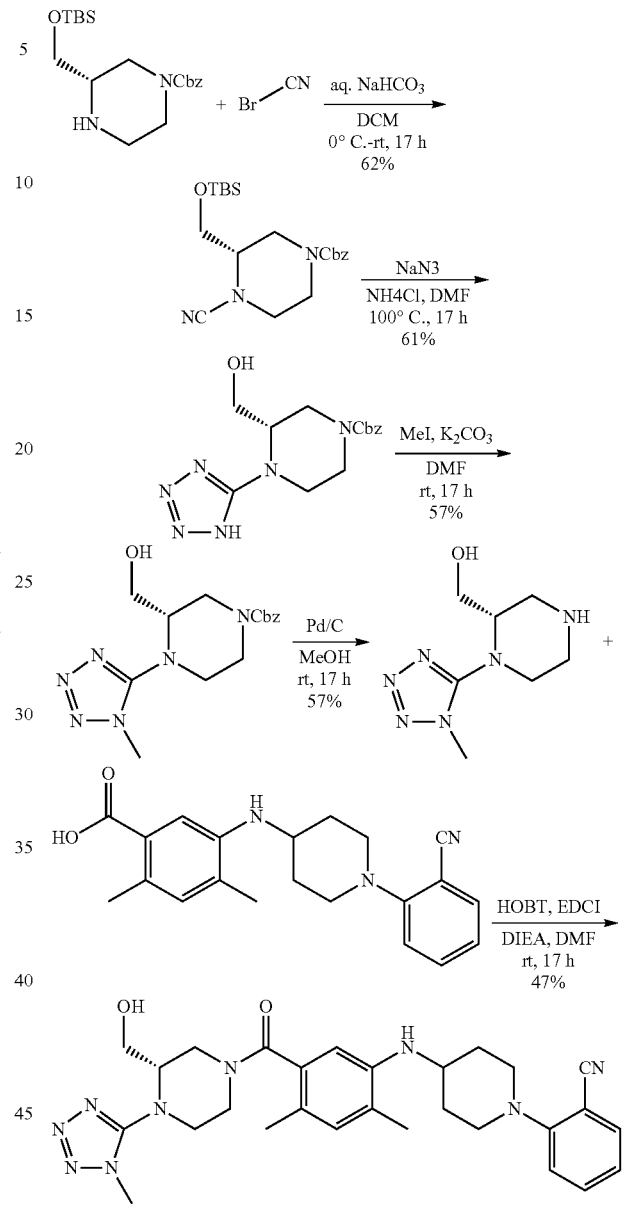

Procedures and Characterization:
The analysis method was following Method B and the separation method was following Method D.

Step 1: (S)-Benzyl 3-((tert-butyldimethylsilyloxy)methyl)-4-cyanopiperazine-1-carboxylate Benzyl (3S)-3-[[tert-butyl(dimethyl)silyl]oxymethyl]piperazine-1-carboxylate (120.00 mg, 329.17 umol) was dissolved in DCM (15.00 mL) and NaHCO$_3$ (110.62 mg, 1.32 mmol, 151.53 uL) was added at 0° C., carbononitridic bromide (69.73 mg, 658.34 umol) was added and stirred at 0° C. for 1 h. The mixture was stirred at rt for 16 h. LCMS showed desired product. The mixture was extracted with DCM, and the organic layer was washed with aq. NaHCO$_3$, brine and dried over Na$_2$SO$_4$, filtered and the filtrate was concentrated to give crude benzyl (3S)-3-[[tert-butyl(dimethyl)silyl]oxymethyl]-4-cyano-piperazine-1-carboxylate (100.00 mg, 205.36 umol, 62%) as a yellow oil. ESI-MS (EI⁺, m/z): 390.3 [M+H]⁺.

Step 2: (S)-Benzyl 3-(hydroxymethyl)-4-(1H-tetrazol-5-yl)piperazine-1-carboxylate Benzyl (3S)-3-[[tert-butyl (dimethyl) silyl] oxymethyl]-4-cyano-piperazine-1-carboxylate (100.00 mg, 256.70 umol), NaN₃ (66.75 mg, 1.03 mmol), and NH₄Cl (68.65 mg, 1.28 mmol) were dissolved in DMF (10.00 mL) and the mixture was stirred at 100° C. for 17 h. The mixture was extracted with EtOAc and the organic layer was washed with brine and purified via preparative HPLC (acid) to give benzyl (3S)-3-(hydroxymethyl)-4-(1H-tetrazol-5-yl)piperazine-1-carboxylate (50.00 mg, 157.07 umol, 61%) as a white solid. ESI-MS (EI⁺, m/z): 319.2 [M+H]⁺.

Step 3: (S)-Benzyl 3-(hydroxymethyl)-4-(1-methyl-1H-tetrazol-5-yl)piperazine-1-carboxylate Benzyl (3S)-3-(hydroxymethyl)-4-(1H-tetrazol-5-yl) piperazine-1-carboxylate (50.00 mg, 157.07 umol), MeI (66.88 mg, 471.21 umol) and K₂CO₃ (65.13 mg, 471.21 umol) were dissolved in DMF (5.00 mL) and the mixture was stirred at rt for 17 h. Silica gel purification gave benzyl (3S)-3-(hydroxymethyl)-4-(1-methyltetrazol-5-yl)piperazine-1-carboxylate (30.00 mg, 90.26 umol, 57%) as a yellow oil. ESI-MS (EI⁺, m/z): 333.7 [M+H]⁺.

Step 4: (S)-(1-(1-Methyl-1H-tetrazol-5-yl)piperazin-2-yl)methanol

Benzyl (3S)-3-(hydroxymethyl)-4-(1-methyltetrazol-5-yl)piperazine-1-carboxylate (30.00 mg, 90.26 umol) and Pd/C (20.00 mg) were dissolved in MeOH (10.00 mL). The mixture was stirred at rt for 17 h under H₂. The reaction mixture was filtered and the filtrate was concentrated to give [(2S)-1-(1-methyltetrazol-5-yl)piperazin-2-yl]methanol (10.00 mg, 50.45 umol, 55%) as a white solid. ESI-MS (EI⁺, m/z): 199.2 [M+H]⁺.

Step 5: (S)-2-(4-(5-(3-(Hydroxymethyl)-4-(1-methyl-1H-tetrazol-5-yl)piperazine-1-carbonyl)-2,4-dimethylphenylamino)piperidin-1-yl)benzonitrile Followed the amide coupling general EDCI/HOBT method to obtain (S)-2-(4-(5-(3-(Hydroxymethyl)-4-(1-methyl-1H-tetrazol-5-yl)piperazine-1-carbonyl)-2,4-dimethylphenylamino)piperidin-1-yl)benzonitrile I-91 as a white solid. ESI-MS (EI⁺, m/z): 530.3 [M+H]⁺. ¹H NMR (400 MHz, CDCl₃) δ 7.72-7.39 (m, 2H), 7.10-6.88 (m, 3H), 6.48 (m, 1H), 4.82 (m, 1H), 4.36 (m, 1H), 4.17 (s, 3H), 3.85-3.07 (m, 12H), 2.98 (m, 2H), 2.17 (m, 8H), 1.68 (m, 2H).

Example 7: (R)-2-(4-(2,4-Dimethyl-5-(4-(3-(S-methylsulfonimidoyl)pyridin-2-yl)piperazine-1-carbonyl)phenylamino)piperidin-1-yl)benzonitrile, I-94

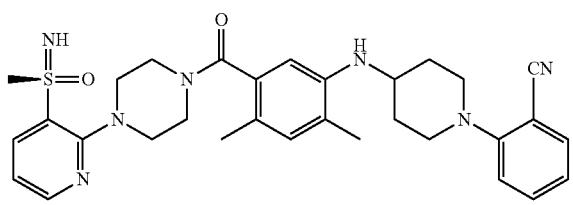

I-94

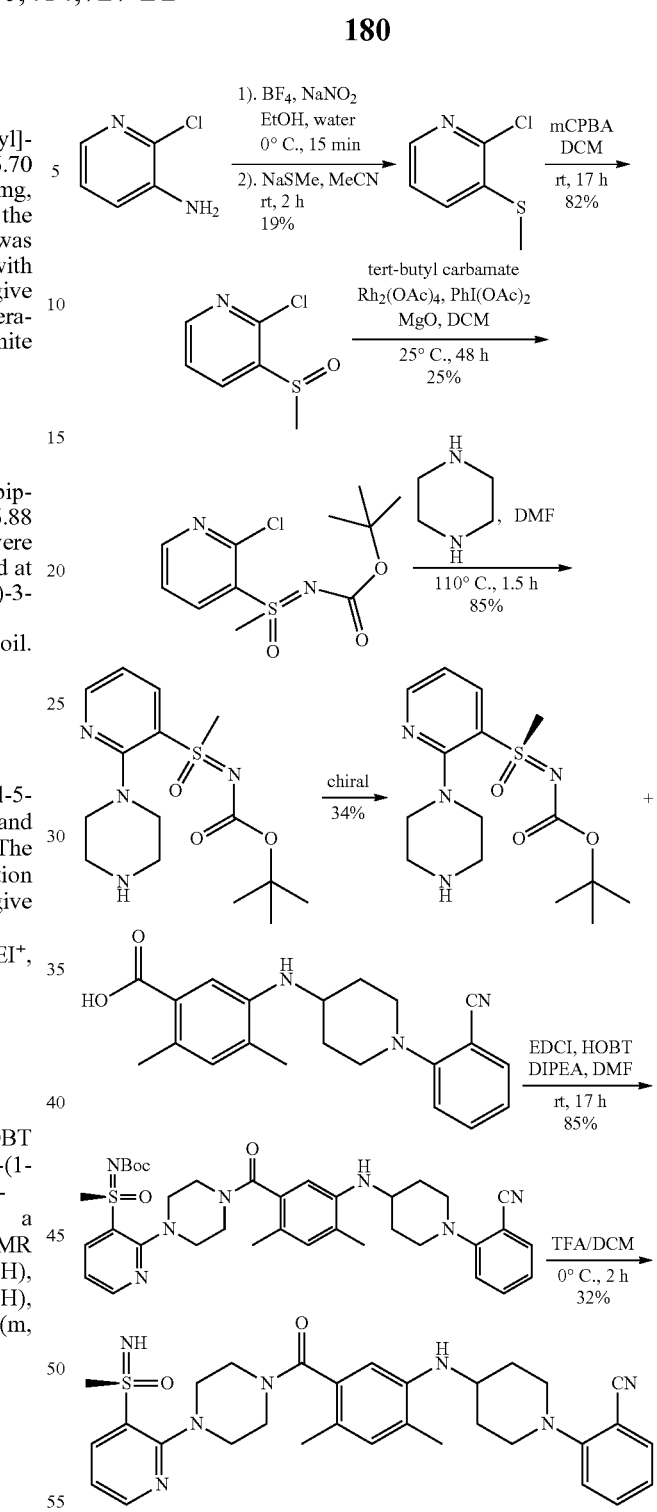

Procedures and Characterization:
The analysis method was following Method B and the separation method was following Method D.

Step 1: 2-Chloro-3-(methylthio)pyridine

A solution of 2-chloropyridin-3-amine (24.40 g, 189.79 mmol) in tetrafluoroboric acid (80.00 mL) and ethanol (95 percent, 75 mL) was cooled to 5° C. A solution of sodium nitrite (13.75 g, 199.28 mmol) in water (39.99 mL) was added in one portion. Diethyl ether (200 mL) was added and the resulting precipitate removed by filtration then dissolved in acetonitrile (400 mL) and cooled down to 0° C. Sodium thiomethoxide (26.60 g, 75.92 mmol, 20% purity) was added portionwise and the reaction stirred at rt for 2 h. The reaction mixture was filtered and the filtrate concentrated then passed through a plug of silica, eluting with 10 percent ethyl acetate/PE, to give 2-chloro-3-methylsulfanyl-pyridine (6.00 g, 19% yield) as a pale white solid. MS (EI+, m/z): 160.2 [M+H]+.

Step 2: 2-Chloro-3-(methylsulfinyl)pyridine

To a suspension of 2-chloro-3-methylsulfanyl-pyridine (13.20 g, 82.69 mmol) in THF (100 mL) at 0° C. was added dropwise a solution of m-CPBA (15.70 g, 90.96 mmol) in THF (40 mL) at a rate such that the temperature of the reaction mixture did not exceed 10° C. over the course of the addition. The reaction mixture was then allowed to warm to rt followed by stirring at rt overnight. The solvent was removed, the residue was extracted with DCM (250 mL×2) and 2 N NaOH (100 mL), washed with 2 N NaOH (800 mL×2), brine (80 mL), and concentrated to give a residue which was purified by flash column (from 0% to 20% and then to 50% of EtOAc in PE) to afford 2-chloro-3-methylsulfinyl-pyridine (20.8 g, 82%) as a pale white solid. ESI-MS (EI+, m/z): 175.2 [M+H]+.

Step 3: 2-Chloro-3-(N-tert-butoxycarbonyl-S-methylsulfonimidoyl)pyridine

To a suspension of tert-butyl carbamate (6.67 g, 56.94 mmol), 2-chloro-3-methylsulfinyl-pyridine (5.00 g, 28.47 mmol), MgO (4.70 g, 113.88 mmol) and Rh$_2$(OAc)$_4$ (503.35 mg, 1.14 mmol) in DCM (20.00 mL) was added portionwise PhI(OAc)$_2$ (18.33 g, 56.94 mmol) and the reaction mixture stirred at 25° C. for 17 h. The reaction mixture was filtered, washed with DCM (50 mL×2), and concentrated to give a residue which was purified via preparative HPLC (TFA, eluting from 10% to 20% of MeCN in water) to afford 2-chloro-3-(N-tert-butoxycarbonyl-S-methylsulfonimidoyl) pyridine (4.2 g, 25%) as a pale white solid. ESI-MS (EI+, m/z): 234.9 [M−55]+.

Step 4: 1-(3-(N-tert-Butoxycarbonyl-S-methylsulfonimidoyl)pyridin-2-yl)piperazine A mixture of 2-chloro-3-(N-tert-butoxycarbonyl-S-methylsulfonimidoyl)pyridine (300.00 mg, 1.03 mmol) and piperazine (354.90 mg, 4.12 mmol) in DMF (3.00 mL) was stirred at 110° C. for 1.5 h. The reaction mixture was filtered and the filtrate was purified via preparative HPLC (TFA, 5% to 10% of MeCN in water) to afford 1-(3-(N-tert-butoxycarbonyl-S-methylsulfonimidoyl)pyridin-2-yl)piperazine (300.00 mg, 85% yield) as a brown solid. ESI-MS (EI+, m/z): 341.0 [M+H]+. Chiral separation gave (R)-2-piperazine-3-(N-tert-butoxycarbonyl-methylsulfonimidoyl) pyridine (170 mg, 34%) as a colorless oil and (S)-2-piperazine-3-(N-tert-butoxycarbonyl-methylsulfonimidoyl) pyridine (180 mg, 36%) as a colorless oil.

Step 5: (R)-2-(4-(2,4-Dimethyl-5-(4-(3-(N-tert-butoxycarbonyl-S-methylsulfonimidoyl)pyridin-2-yl) piperazine-1-carbonyl)phenylamino)piperidin-1-yl) benzonitrile To a solution of (R)-2-piperazine-3-(N-tert-butoxycarbonyl-methylsulfonimidoyl)pyridine (160.00 mg, 469.98 umol) and 5-[[1-(2-cyanophenyl)-4-piperidyl]amino]-2,4-dimethyl-benzoic acid (197.07 mg, 563.98 umol) in DMF (1.50 mL) was added EDCI (180.19 mg, 939.96 umol) and HOBT (95.26 mg, 704.97 umol). The mixture was stirred at rt for 17 h. The reaction mixture was extracted with EtOAc (10 mL×3) and water (5 mL), dried and concentrated to afford (R)-2-(4-(2,4-dimethyl-5-(4-(3-(N-tert-butoxycarbonyl-S-methylsulfonimidoyl)pyridin-2-yl)piperazine-1-carbonyl)phenylamino)piperidin-1-yl)benzonitrile (300.00 mg, 85% yield) as a brown oil which used directly in the next step. ESI-MS (EI+, m/z): 671.9 [M+H]+.

Step 6: (R)-2-(4-(2,4-Dimethyl-5-(4-(3-(S-methylsulfonimidoyl)pyridin-2-yl)piperazine-1-carbonyl) phenylamino)piperidin-1-yl)benzonitrile A mixture of (R)-2-(4-(2,4-dimethyl-5-(4-(3-(N-tert-butoxycarbonyl-S-methylsulfonimidoyl)pyridin-2-yl)piperazine-1-carbonyl)phenylamino)piperidin-1-yl)benzonitrile (160.00 mg, 238.15 umol) in TFA (1.00 mL) and DCM (1.00 mL) was stirred at 0° C. for 2 h. The solvent was removed in vacuo at rt to give a residue, DIPEA was added to adjust the pH to 8, the crude material was then filtered and purified via preparative HPLC (NH$_4$HCO$_3$) to afford 2-[4-[2,4-dimethyl-5-[4-[3-(methylsulfonimidoyl)-2-pyridyl]piperazine-1-carbonyl]anilino]-1-piperidyl]benzonitrile I-94 (43.80 mg, 32% yield) as a white solid. The stereochemistry was arbitrarily assigned. ESI-MS (EI+, m/z): 572.3 [M+H]+; $^1$H NMR (400 MHz, MeOD-d$_4$) δ 8.59 (dd, J=4.8, 1.8 Hz, 1H), 8.43 (dd, J=7.9, 1.8 Hz, 1H), 7.68-7.51 (m, 2H), 7.41 (dd, J=7.9, 4.8 Hz, 1H), 7.22 (d, J=8.3 Hz, 1H), 7.08 (t, J=7.4 Hz, 1H), 6.98 (s, 1H), 6.57 (s, 1H), 4.00 (s, 2H), 3.55 (d, J=22.4 Hz, 5H), 3.43 (s, 3H), 3.22 (s, 5H), 3.05 (t, J=10.6 Hz, 3H), 2.19 (d, J=10.5 Hz, 8H), 1.77 (s, 2H).

Example 8: (S)-2-(4-(2,4-Dimethyl-5-(4-(3-(S-methylsulfonimidoyl)pyridin-2-yl)piperazine-1-carbonyl) phenylamino)piperidin-1-yl)benzonitrile, I-93

I-93

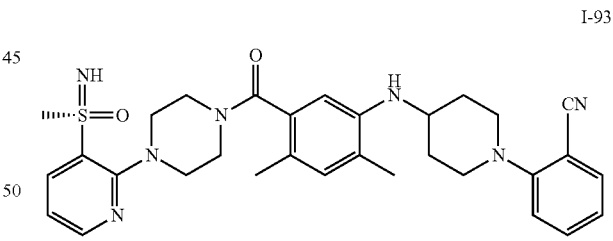

Synthetic Scheme:

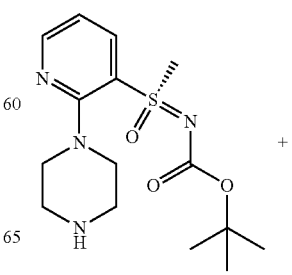

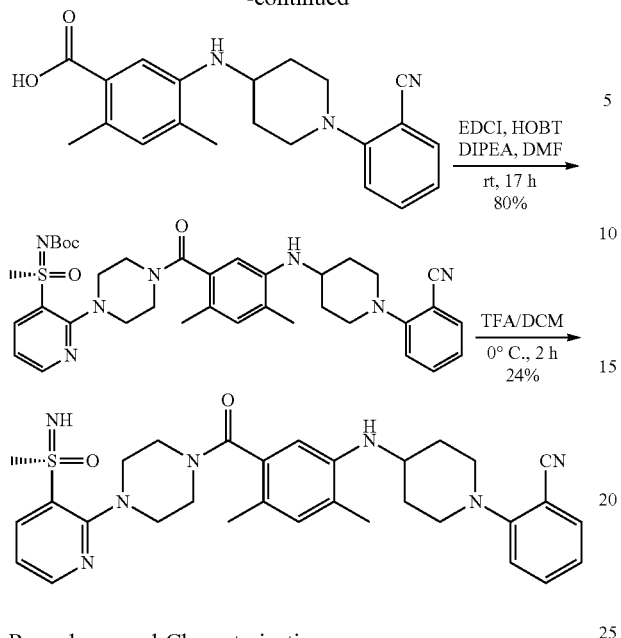

Procedures and Characterization:

The procedure for (S)-1-(3-(N-tert-butoxycarbonyl-S-methylsulfonimidoyl) pyridin-2-yl) piperazine was same as for example 7.

The analysis method was following Method B and the separation method was following Method D.

Step 5: (S)-2-(4-(2, 4-Dimethyl-5-(4-(3-(N-tert-butoxycarbonyl-S-methylsulfonimidoyl) pyridin-2-yl) piperazine-1-carbonyl) phenylamino) piperidin-1-yl) benzonitrile To a solution of (S)-1-(3-(N-tert-butoxycarbonyl-S-methylsulfonimidoyl)pyridin-2-yl)piperazine (170.00 mg, 499.35 umol) and 5-[[1-(2-cyanophenyl)-4-piperidyl]amino]-2,4-dimethyl-benzoic acid (209.39 mg, 599.22 umol) in DMF (1.50 mL) was added EDCI (191.45 mg, 998.70 umol) and HOBT (101.21 mg, 749.03 umol). The mixture was stirred at rt for 17 h. Then the reaction mixture was extracted with EtOAc (10 mL×3) and water (5 mL), dried and concentrated to afford (S)-2-(4-(2,4-dimethyl-5-(4-(3-(N-tert-butoxycarbonyl-S-methylsulfonimidoyl)pyridin-2-yl)piperazine-1-carbonyl)phenylamino)piperidin-1-yl)benzonitrile (300.00 mg, 80% yield, 90% purity) as a brown oil. MS (EI+, m/z): 671.9 [M+H]+.

Step 6: (S)-2-(4-(2, 4-Dimethyl-5-(4-(3-(S-methyl-sulfonimidoyl) pyridin-2-yl) piperazine-1-carbonyl) phenylamino) piperidin-1-yl) Benzonitrile A mixture of (S)-2-(4-(2,4-dimethyl-5-(4-(3-(N-tert-butoxycarbonyl-S-methylsulfonimidoyl)pyridin-2-yl)piperazine-1-carbonyl)phenylamino)piperidin-1-yl)benzonitrile (170.00 mg, 253.03 umol) in TFA (1.00 mL) and DCM (1.00 mL) was stirred at 0° C. for 2 h. The solvent was removed in vacuum at rt to give a residue, DIPEA was added to adjust the pH to 8. The residue was filtered and purified via preparative HPLC (NH$_4$HCO$_3$) to afford 2-[4-[2,4-dimethyl-5-[4-[3-(methylsulfonimidoyl)-2-pyridyl]piperazine-1-carbonyl]anilino]-1-piperidyl]benzonitrile I-93, (35.10 mg, 24% yield) as a white solid. The stereochemistry was arbitrarily assigned. ESI-MS (EI+, m/z): 572.3 [M+H]+; $^1$H NMR (400 MHz, CD$_3$OD-d$_4$) δ 8.59 (dd, J=4.8, 1.8 Hz, 1H), 8.43 (dd, J=7.9, 1.8 Hz, 1H), 7.70-7.47 (m, 2H), 7.41 (dd, J=7.9, 4.8 Hz, 1H), 7.21 (d, J=8.3 Hz, 1H), 7.08 (t, J=7.5 Hz, 1H), 6.98 (s, 1H), 6.57 (s, 1H), 4.00 (s, 2H), 3.55 (d, J=21.4 Hz, 5H), 3.43 (s, 3H), 3.21 (d, J=5.1 Hz, 3H), 3.04 (t, J=10.9 Hz, 2H), 2.19 (d, J=10.5 Hz, 8H), 1.78 (s, 2H).

Example 9: 2-(4-(5-(1-(2-Cyano-6-fluorophenyl) piperidin-4-ylamino)-2,4-dimethylbenzoyl)piperazin-1-yl)-6-fluorobenzenesulfonamide, I-92

I-92

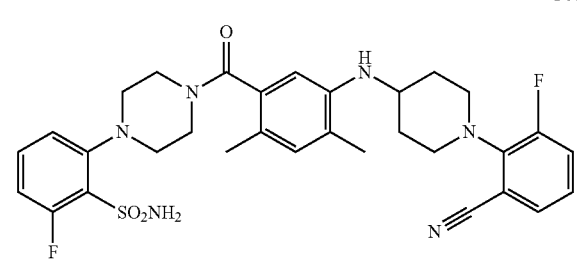

Synthetic Scheme:

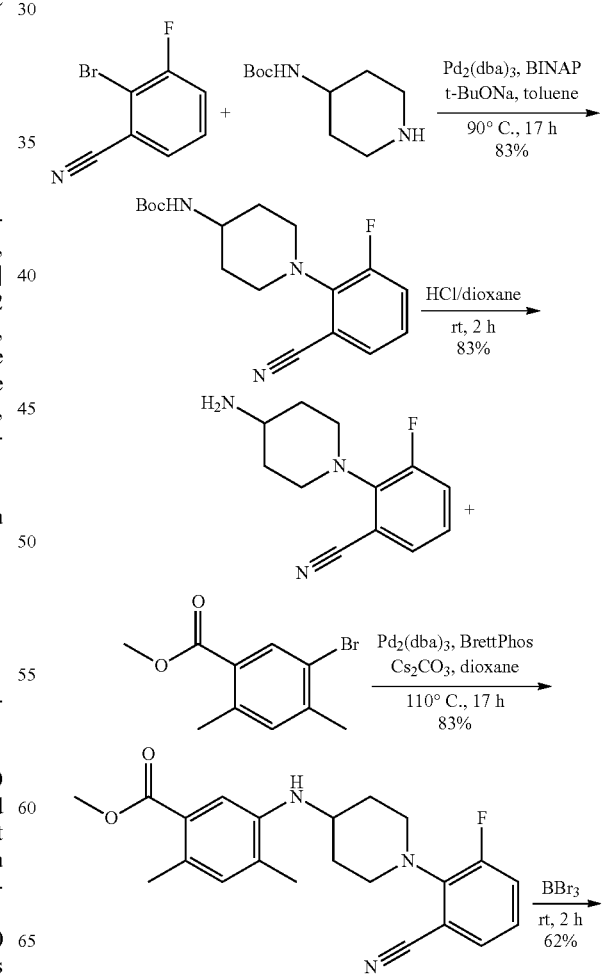

-continued

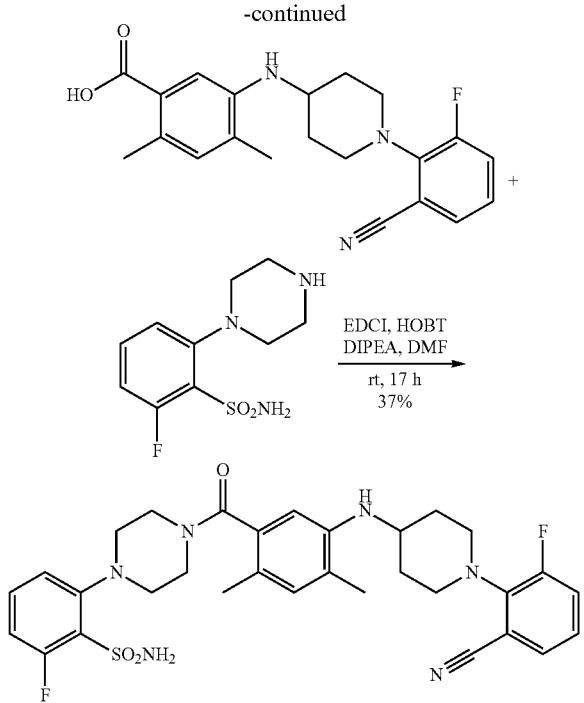

Procedures and Characterization:
The analysis method was following Method B and the separation method was following Method D.

Step 1: tert-Butyl 1-(2-cyano-6-fluorophenyl)piperidin-4-ylcarbamate

A mixture of 2-bromo-3-fluoro-benzonitrile (3.00 g, 15.00 mmol), tert-butyl N-(4-piperidyl)carbamate (3.61 g, 18.00 mmol), Pd$_2$(dba)$_3$ (1.37 g, 1.50 mmol), BINAP (932.95 mg, 1.50 mmol) and tBuONa (2.16 g, 22.50 mmol) in toluene (50.00 mL) was charged with N$_2$ for three times, then stirred at 90° C. for 17 h. The reaction mixture was cooled down to rt and concentrated to give a residue which was purified by a flash column (10% to 22% of EtOAc in PE) to afford tert-butyl N-[1-(2-cyano-6-fluoro-phenyl)-4-piperidyl] carbamate (4.00 g, 83% yield) as a yellow solid. MS (EI$^+$, m/z): 320.1 [M+H]$^+$.

Step 2: 2-(4-Aminopiperidin-1-yl)-3-fluorobenzonitrile

A mixture of tert-butyl N-[1-(2-cyano-6-fluoro-phenyl)-4-piperidyl] carbamate (3.00 g, 9.39 mmol) in HCl/dioxane (4 M, 15.00 mL) was stirred at rt for 2 h. The reaction mixture was filtered, washed with Et$_2$O (5 mL) and dried to afford 2-(4-amino-1-piperidyl)-3-fluoro-benzonitrile (2.00 g, 83% yield, HCl salt) as a pale white solid. ESI-MS (EI$^+$, m/z): 220.2 [M+H]$^+$.

Step 3: Methyl 5-(1-(2-cyano-6-fluorophenyl)piperidin-4-ylamino)-2,4-dimethylbenzoate A mixture of 2-(4-amino-1-piperidyl)-3-fluoro-benzonitrile (1.50 g, 6.84 mmol), methyl 5-bromo-2,4-dimethyl-benzoate (1.39 g, 5.70 mmol), tris(dibenzylideneacetone)dipalladium(0) (522.05 mg, 570.00 umol), dicyclohexyl-[3,6-dimethoxy-2-(2,4,6-triisopropylphenyl)phenyl]phosphane (612.02 mg, 1.14 mmol), cesium carbonate (5.57 g, 17.10 mmol) and dioxane (20.00 mL) was stirred at 110° C. for 17 h. The reaction mixture was cooled down to rt, filtered, and concentrated to give a residue which was purified by a flash column (5% to 10% of EtOAc in PE) to afford methyl 5-[[1-(2-cyano-6-fluoro-phenyl)-4-piperidyl]amino]-2,4-dimethyl-benzoate (1.80 g, 83% yield) as a red solid. ESI-MS (EI$^+$, m/z): 382.2 [M+H].

Step 4: 5-(1-(2-Cyano-6-fluorophenyl)piperidin-4-ylamino)-2,4-dimethylbenzoic Acid To a solid of methyl 5-[[1-(2-cyano-6-fluoro-phenyl)-4-piperidyl]amino]-2,4-dimethyl-benzoate (500.00 mg, 1.31 mmol) was added BBr$_3$ (1 M, 5.00 mL) at rt, then stirred at rt for 2 h. The reaction mixture was poured into 50 mL of DCM, washed with sat. NaHCO$_3$(15 mL), the aqueous layer was extracted with DCM/MeOH (v/v=10:1, 25 mL×2), dried, and concentrated to give a residue which was purified by a flash column (20% to 30% of EA in PE) to afford 5-[[1-(2-cyano-6-fluoro-phenyl)-4-piperidyl]amino]-2,4-dimethyl-benzoic acid (300.00 mg, 62% yield) as a pale white solid. MS (EI$^+$, m/z): 368.2 [M+H]$^+$.

Step 5: 2-(4-(5-(1-(2-Cyano-6-fluorophenyl) piperidin-4-ylamino)-2,4-dimethylbenzoyl)piperazin-1-yl)-6-fluorobenzenesulfonamide Followed the amide coupling general EDCI/HOBT method to obtain 2-(4-(5-(1-(2-Cyano-6-fluorophenyl)piperidin-4-ylamino)-2,4-dimethylbenzoyl)piperazin-1-yl)-6-fluorobenzenesulfonamide I-92 as a white solid. ESI-MS (EI$^+$, m/z): 609.3 [M+H]$^+$; $^1$H NMR (500 MHz, CD$_3$OD) δ 7.58 (td, J=8.2, 6.0 Hz, 1H), 7.47 (d, J=7.7 Hz, 1H), 7.38 (dd, J=12.2, 8.2 Hz, 1H), 7.29 (d, J=8.2 Hz, 1H), 7.16 (td, J=8.0, 4.6 Hz, 1H), 7.15-7.02 (m, 1H), 6.97 (s, 1H), 6.58 (s, 1H), 3.68-3.41 (m, 5H), 3.43-3.35 (m, 2H), 3.06 (dd, J=99.3, 41.0 Hz, 4H), 2.28-2.10 (m, 7H), 1.88-1.62 (m, 2H).

Example 10: 2-[4-[2,4-Dimethyl-5-[(3S)-3-methyl-4-(2-pyridyl)piperazine-1-carbonyl]anilino]-1-piperidyl]benzonitrile, I-34

I-34

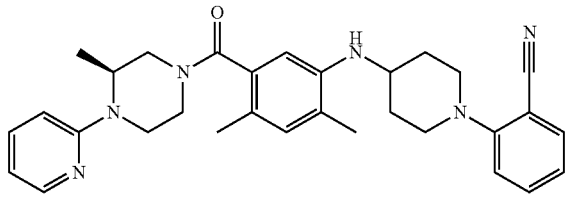 [SMILES: Cc1cc(C)c(C(=O)N2CCN(c3ccccc3)C(C)(C)C2)cc1NC1CCN(c2ccccc2C#N)CC1]

Synthetic Scheme:

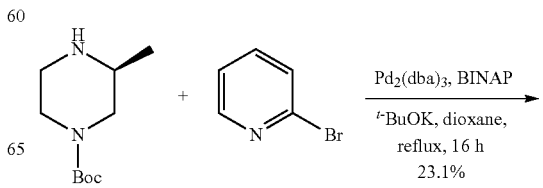

187

-continued

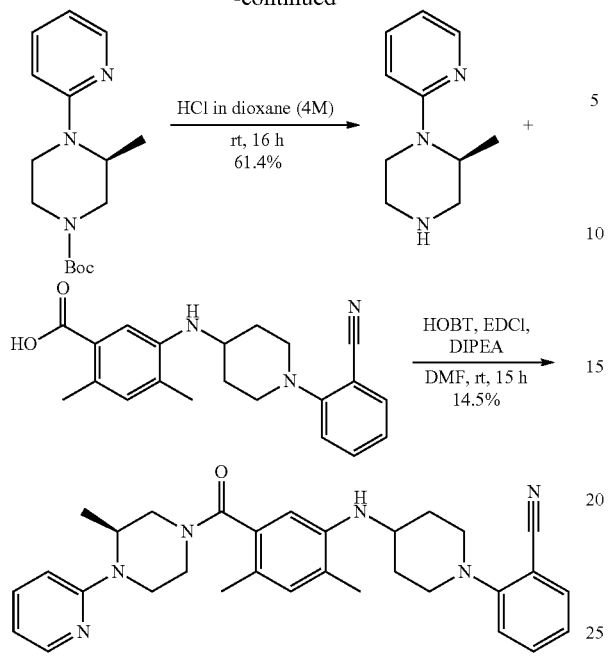

Procedures and Characterization:
The analysis method was following Method B and the separation method was following Method D.

Step 1: (S)-tert-Butyl-3-methyl-4-(pyridin-2-yl) piperazine-1-carboxylate

A mixture of (S)-tert-butyl-3-methylpiperazine-1-carboxylate (2.0 g, 10.0 mmol), 2-bromopyridine (1.9 g, 12.0 mmol), potassium tert-butylate (1.57 g, 14.0 mmol), 2,2'-(bisphenylphosphino)-1,1'-binaphthalene (311 mg, 0.5 mmol) and tris(dibenzylideneacetone)dipalladium (915 mg, 1.0 mmol) in dioxane (10 mL) was stirred at 110° C. for 16 h under $N_2$. Then the reaction mixture was filtered, concentrated, poured into water (100 mL) and extracted with EtOAc (100 mL×2). The combined organic layers were dried over $Na_2SO_4$, filtered and concentrated. Further purification was on column chromatography eluting with PE/EA from 100/1 to 10/1 to obtain (S)-tert-butyl-3-methyl-4-(pyridin-2-yl) piperazine-1-carboxylate (1.25 g, 23%) as light-yellow oil. ESI-MS (EI+, m/z): 278.3 [M+H]+

Step 2: (S)-2-Methyl-1-(pyridin-2-yl)piperazine

A mixture of (S)-tert-butyl-3-methyl-4-(pyridin-2-yl)piperazine-1-carboxylate (299 mg, 1.08 mmol) and HCl in dioxane (4 M) (10.8 mmol, 2.7 mL) was stirred at rt for 16 h. The mixture was concentrated, washed with EtOAc (50 mL×3), the pH adjusted to 6-7, then extracted with EtOAc (50 mL×3), dried and concentrated to obtain(S)-2-methyl-1-(pyridin-2-yl) piperazine (120 mg, 61.4%) as a light-yellow oil. ESI-MS (EI+, m/z): 178.2 [M+H]+. 1H NMR (500 MHz, DMSO-$d_6$) δ 8.08 (dd, J=4.8, 1.5 Hz, 1H), 7.48 (m, 1H), 6.71 (t, J=11.2 Hz, 1H), 6.59-6.51 (m, 1H), 4.40-4.26 (m, 1H), 3.92-3.81 (m, 1H), 2.98-2.90 (m, 1H), 2.80 (m, 3H), 2.65-2.56 (m, 1H), 1.08 (d, J=6.6 Hz, 3H).

Step 3: 2-[4-[2,4-Dimethyl-5-[(3S)-3-methyl-4-(2-pyridyl)piperazine-1-carbonyl]anilino]-1-piperidyl]benzonitrile Followed the amide coupling general EDCI/HOBT method to obtain 2-[4-[2, 4-dimethyl-5-[(3S)-3-methyl-4-(2-pyridyl)piperazine-1-carbonyl]anilino]—1-piperidyl] benzonitrile 1-34 as a white solid. ESI-MS (EI+, m/z): 509.3 [M+H]+. 1H NMR (400 MHz, DMSO-$d_6$) δ 8.11 (d, J=3.2 Hz, 1H), 7.68 (d, J=7.0 Hz, 1H), 7.55 (dt, J=14.4, 7.2 Hz, 2H), 7.16 (d, J=8.2 Hz, 1H), 7.06 (t, J=7.5 Hz, 1H), 6.89 (s, 1H), 6.76 (d, J=8.6 Hz, 1H), 6.66-6.59 (m, 1H), 6.42 (s, 1H), 4.55 (dd, J=51.4, 43.8 Hz, 2H), 4.03 (dd, J=55.5, 13.1 Hz, 1H), 3.54-3.39 (m, 3H), 2.98 (t, J=29.4 Hz, 6H), 2.12-1.63 (m, 11H), 1.08-0.86 (m, 3H).

Example 11: 2-(4-(5-(3,3-Dimethyl-4-phenylpiperazine-1-carbonyl)-2,4-dimethylphenylamino)piperidin-1-yl)benzonitrile, I-119

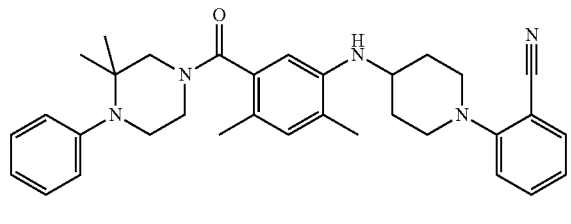

I-119

Synthetic Scheme:

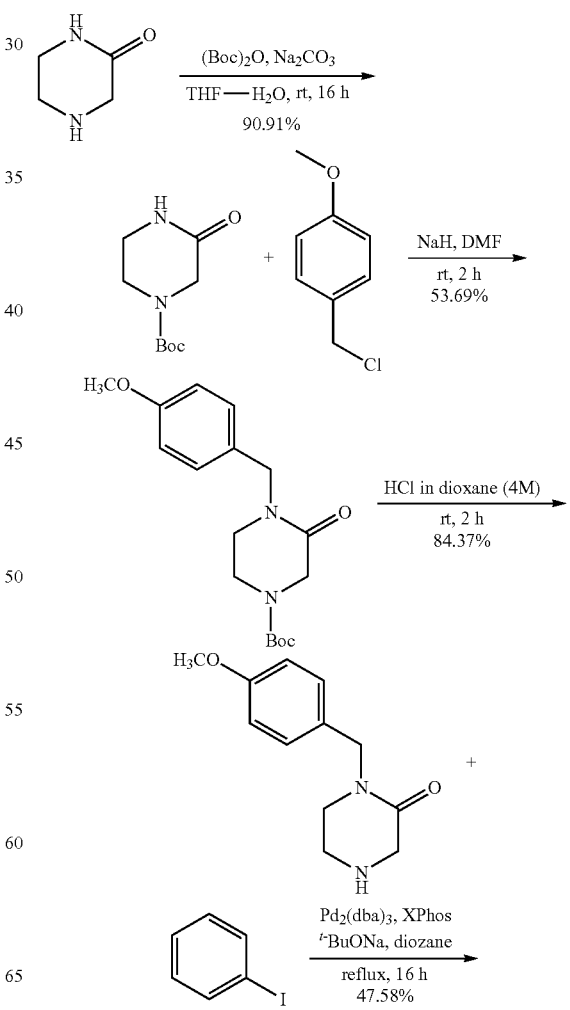

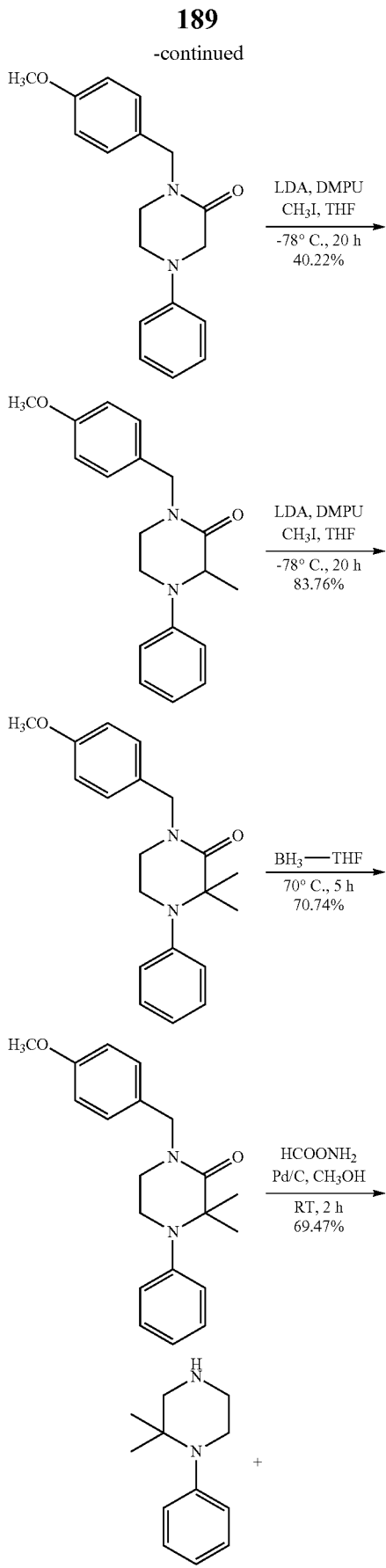

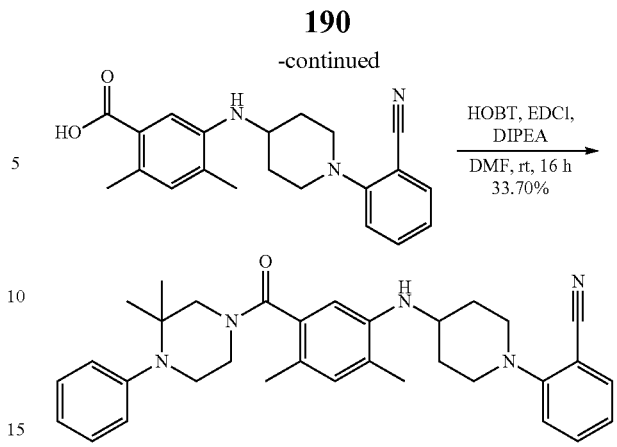

Procedures and Characterization:
The analysis method was following Method B and the separation method was following Method D.

Step 1: tert-Butyl-3-oxopiperazine-1-carboxylate

To a solution of piperazin-2-one (22.00 g, 219.7 mmol) in THF (300 mL) was added a mixture of $NaHCO_3$ (29.53 g, 307.6 mmol) in $H_2O$ (100 mL), $(Boc)_2O$ (43.16 g, 197.8 mmol), then the reaction solution was stirred at rt for 16 h. The mixture was concentrated, poured into water (100 mL) and extracted with EtOAc (100 mL×2). The combined organic layers were dried over $Na_2SO_4$, filtered and concentrated to obtain tert-butyl-3-oxopiperazine-1-carboxylate (40.00 g, 90.91%) as white solid. ESI-MS ($EI^+$, m/z): 145.2[M+H−56]+. $^1H$ NMR (500 MHz, $CDCl_3$) δ 4.08 (s, 2H), 3.62 (t, J=5.2 Hz, 2H), 3.37 (s, 2H), 1.47 (s, 9H).

Step 2: tert-Butyl-4-[(4-methoxyphenyl)methyl]-3-oxo-piperazine-1-carboxylate

To a solution of tert-butyl 3-oxopiperazine-1-carboxylate (20.02 g, 100 mmol) in DMF (50.00 mL) was added NaH (3.96 g, 165.00 mmol) at rt and the reaction mixture stirred for 30 min. Then 1-(chloromethyl)-4-methoxy-benzene (17.23 g, 110.00 mmol) was dropped in the mixture and stirred at rt for another 2 h. The reaction mixture was quenched with HCl (0.2 M, 30 mL), extracted with DCM (100 mL×3), dried and concentrated. Further purification was carried out by column chromatography eluting with PE/EtOAc=10/1 to obtain tert-butyl-4-[(4-methoxyphenyl)methyl]-3-oxo-piperazine-1-carboxylate (17.20 g, 53.69%) as white solid. ESI-MS ($EI^+$, m/z): 265.2 [M+H−56]+. $^1H$ NMR (400 MHz, $CDCl_3$) δ 7.20 (d, J=8.6 Hz, 2H), 6.90-6.82 (m, 2H), 4.55 (s, 2H), 4.12 (d, J=17.7 Hz, 2H), 3.80 (s, 3H), 3.61-3.52 (m, 2H), 3.29-3.19 (m, 2H), 1.47 (s, 9H).

Step 3: (S)-(4-((4-(3-chloropyridin-2-yl)piperazin-1-yl)methyl)-1,5-dimethyl-1H-pyrrol-2-yl)(4-(4-fluorophenyl)-2-methylpiperazin-1-yl)methanone tert-Butyl-4-[(4-methoxyphenyl)methyl]-3-oxo-piperazine-1-carboxylate (10.00 g, 31.21 mmol) was dissolved in HCl in dioxane (4 M) (16.00 mL, 62.42 mmol) and the mixture was stirred at rt for 2 h. Then the mixture was quenched with water (100 mL) and adjusted the pH to 6-7, extracted with EtOAc (100 mL×3), dried and concentrated to obtain 1-[(4-methoxyphenyl)methyl]piperazin-2-one (5.80 g, 84.37%) as white solid. ESI-MS ($EI^+$, m/z): 221.2 [M+H]+. $^1H$ NMR (500 MHz, $CDCl_3$) δ 7.20 (d, J=8.4 Hz, 2H), 6.86 (d, J=8.5 Hz, 2H), 4.54 (s, 2H), 3.80 (d, J=3.6 Hz, 3H), 3.58 (s, 2H), 3.21 (t, J=5.2 Hz, 2H), 3.09-2.98 (m, 2H).

Step 4: 1-[(4-Methoxyphenyl) methyl]-4-phenyl-piperazin-2-one

To a mixture of 1-[(4-methoxyphenyl) methyl] piperazin-2-one (3.00 g, 13.62 mmol), iodobenzene (2.78 g, 13.62 mmol), XPhos (324 mg, 680 umol), tBuONa (1.83 g, 19.07 mmol) in dioxane (3.00 mL) was added $Pd_2(dba)_3$ (623 mg, 680 umol), then stirred at 100° C. for 16 h. The mixture was filtered, concentrated and washed with water (100 mL), extracted with EtOAc (100 mL×3), dried and concentrated. Further purification was carried out by column chromatography eluting with PE/EA from 20/1 to 5/1 to obtain 1-[(4-methoxyphenyl)methyl]-4-phenyl-piperazin-2-one (2.32 g, 57.48%) as yellow solid. ESI-MS (EI+, m/z): 297.3 [M+H]+. $^1$H NMR (400 MHz, $CDCl_3$) δ 7.33-7.19 (m, 4H), 6.89 (m, 5H), 4.61 (s, 2H), 3.95 (s, 2H), 3.80 (s, 3H), 3.39 (m, 4H).

Step 5: 1-[(4-Methoxyphenyl)methyl]-3-methyl-4-phenyl-piperazin-2-one

To a mixture of diisopropylamine (2.52 g, 24.95 mmol) in THF (20.00 mL) was added n-BuLi (50.00 mmol, 10.00 mL) at −78° C. The reaction mixture was stirred at rt for 20 min. DMPU (1.28 g, 49.90 mmol) was added and stirred at −78° C. for another 1 h. A solution of 1-[(4-methoxyphenyl)methyl]-4-phenyl-piperazin-2-one (1.48 g, 4.99 mmol) in THF (20.00 mL) was added and stirred at −78° C. for 2 h. Then iodomethane (3.54 g, 24.95 mmol) was added and stirred at −78° C. overnight. The reaction mixture was quenched with $NH_4Cl$ (aq.), extracted with DCM (100 mL×3), dried and concentrated. Further purification was carried by a flash column eluting with PE/EA from 6/1 to 3/1 to afford 1-[(4-methoxyphenyl)methyl]-3-methyl-4-phenyl-piperazin-2-one (623 mg, 40.22%) as a yellow gum. ESI-MS (EI+, m/z): 311.0 [M+H]+. $^1$H NMR (500 MHz, $CDCl_3$) δ 7.30-7.16 (m, 4H), 6.91-6.76 (m, 5H), 5.26 (s, 1H), 4.68 (d, J=14.5 Hz, 1H), 4.53-4.37 (m, 2H), 3.78 (s, 3H), 3.50-3.17 (m, 4H), 1.41 (d, J=6.9 Hz, 3H).

Step 6: 1-[(4-Methoxyphenyl)methyl]-3,3-dimethyl-4-phenyl-piperazin-2-one

To a mixture of diisopropylamine (1.86 g, 18.40 mmol) in THF (20.00 mL) was added n-BuLi (18.40 mmol, 8.00 mL) at −78° C. Then the reaction mixture was stirred at rt for 0.51 h. DMPU (1.28 g, 18.36 mmol) was added and stirred at −78° C. for another 1 h. A solution of 1-[(4-methoxyphenyl)methyl]-3-methyl-4-phenyl-piperazin-2-one (570 mg, 1.84 mmol) in THF (20.00 mL) was added and stirred at −78° C. for 1 h. Then iodomethane (1.30 g, 9.18 mmol) was added in and stirred at rt overnight. The reaction mixture was quenched with $NH_4Cl$ (aq), extracted with DCM (100 mL×3), dried and concentrated. Further purification was carried out by flash column eluting with PE/EA from 10/1 to 5/1 to afford 1-[(4-methoxyphenyl)methyl]-3,3-dimethyl-4-phenyl-piperazin-2-one (500 mg, 83.76%) as a colorless gum. ESI-MS (EI+, m/z): 325.0 [M+H]+. $^1$H NMR (500 MHz, $CDCl_3$) δ 7.31-7.18 (m, 4H), 7.16-7.06 (m, 3H), 6.90-6.84 (m, 2H), 4.56 (s, 2H), 3.79 (s, 3H), 3.34-3.22 (m, 4H), 1.37 (s, 6H).

Step 7: 4-[(4-Methoxyphenyl)methyl]-2,2-dimethyl-1-phenyl-piperazine

To a solution of 1-[(4-methoxyphenyl)methyl]-3,3-dimethyl-4-phenyl-piperazin-2-one (480 mg, 1.48 mmol) in THF (3.00 mL) was added $BH_3$-THF (3.00 mL, 2.37 mmol) at rt and stirred at 70° C. for 5 h, then the reaction mixture was quenched with MeOH (3.00 mL). HCl (1.00 mL) was added and stirred at 70° C. for another 1 h. The reaction solution was concentrated, washed with water (30 mL×3), extracted with EtOAc (30 mL×3), dried and concentrated. Further purification was carried out by flash column eluting with PE/EA from 10/1 to 5/1 to afford 4-[(4-methoxyphenyl)methyl]-2,2-dimethyl-1-phenyl-piperazine (325 mg, 70.74%) as a white solid. ESI-MS (EI+, m/z): 311.0 [M+H]+. $^1$H NMR (500 MHz, $CDCl_3$) δ 7.24-7.12 (m, 4H), 7.09-6.96 (m, 3H), 6.79 (d, J=8.6 Hz, 2H), 3.73 (d, J=10.6 Hz, 3H), 3.44-3.31 (m, 2H), 3.23-3.00 (m, 2H), 2.59-2.38 (m, 2H), 2.30-2.13 (m, 2H), 0.97 (s, 6H).

Step 8: 2,2-Dimethyl-1-phenyl-piperazine

To a mixture of 4-[(4-methoxyphenyl)methyl]-2,2-dimethyl-1-phenyl-piperazine (310 mg, 998 umol), ammonium formate (629 mg, 10 mmol) in MeOH (20.00 mL) was added 10% Pd-C (100 mg, 998 umol), the reaction solution was stirred at 25° C. for 2 h. Then the mixture was filtered and concentrated, further purification was carried out via silica gel chromatography eluting with DCM/MeOH from 20/1 to 5/1 to afford 2, 2-dimethyl-1-phenyl-piperazine (132 mg, 69.47%) as a colorless gum. ESI-MS (EI+, m/z): 191.1 [M+H]+. $^1$H NMR (500 MHz, $CDCl_3$) δ 7.27-7.26 (m, 2H), 7.16-7.07 (m, 3H), 3.08 (m, 2H), 3.04-2.98 (m, 2H), 2.79 (s, 2H), 1.05 (s, 6H).

Step 9: 2-[4-[5-(3,3-Dimethyl-4-phenyl-piperazine-1-carbonyl)-2,4-dimethyl-anilino]-1-piperidyl]benzonitrile Followed the amide coupling general EDCI/HOBT method to obtain 2-(4-(5-(3,3-Dimethyl-4-phenylpiperazine-1-carbonyl)-2,4-dimethylphenylamino)piperidin-1-yl)benzonitrile 1-119 as a white solid. ESI-MS (EI+, m/z): 522.2 [M+H]+. $^1$H NMR (500 MHz, DMSO-$d_6$) δ 7.69 (d, J=7.5 Hz, 1H), 7.59 (dd, J=11.9, 7.2 Hz, 1H), 7.27 (t, J=7.7 Hz, 2H), 7.19 (d, J=8.3 Hz, 1H), 7.14-7.03 (m, 4H), 6.88 (d, J=17.0 Hz, 1H), 6.44 (s, 1H), 4.55 (t, J=9.6 Hz, 1H), 4.03-3.37 (m, 5H), 3.27-2.93 (m, 6H), 2.09 (dd, J=21.9, 16.2 Hz, 8H), 1.77-1.64 (m, 2H), 1.23-0.84 (m, 6H).

Example 12: 2-[4-[5-[3,3-Dimethyl-4-(2-pyridyl)piperazine-1-carbonyl]-2,4-dimethyl-anilino]-1-piperidyl]benzonitrile, I-118

I-118

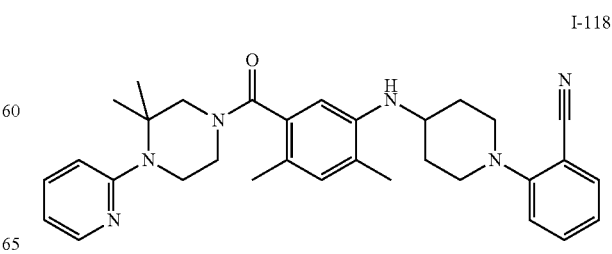

Synthetic Scheme:

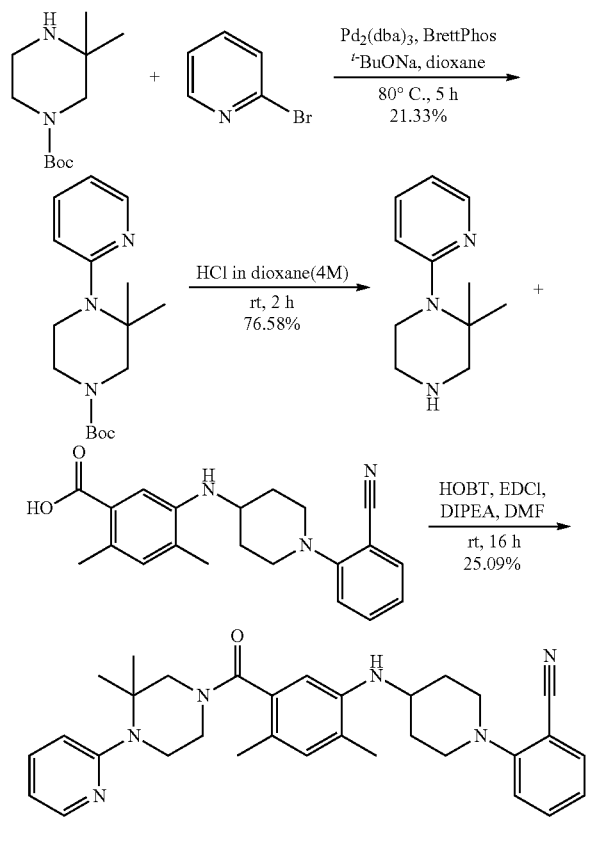

Procedures and Characterization:
The analysis method was following Method B and the separation method was following Method D.

Step 1: tert-Butyl-3,3-dimethyl-4-(2-pyridyl)piperazine-1-carboxylate

To a solution of tert-butyl-3,3-dimethylpiperazine-1-carboxylate (2.14 g, 9.99 mmol) and 2-bromopyridine (1.58 g, 9.99 mmol) in dioxane (20.00 mL) was added Pd$_2$(dba)$_3$ (548 mg, 599 umol), BrettPhos (745 mg, 1.20 mmol), tBuONa (2.04 g, 29.96 mmol). The resulting mixture was stirred at 80° C. for 5 h. The mixture was filtered and concentrated, further purification was via silica gel chromatography eluting with PE/EA from 10/1 to 5/1 to obtain tert-butyl 3,3-dimethyl-4-(2-pyridyl)piperazine-1-carboxylate (621 mg, 21.33%) as a yellow solid. ESI-MS (EI$^+$, m/z): 292.3 [M+H]$^+$.

Step 2: 2,2-Dimethyl-1-(2-pyridyl)piperazine

A mixture of tert-butyl-3,3-dimethyl-4-(2-pyridyl)piperazine-1-carboxylate (621 mg, 2.13 mmol) and HCl in dioxane (4 M, 3.00 mL, 12.00 mmol) was stirred at rt for 2 h. The reaction mixture was concentrated, diluted with water (50 mL×3), extracted with EtOAc (50 mL×3), washed with brine (50 mL×3), dried and concentrated. Further purification was carried out by a flash-column eluting with DCM/MeOH from 20/1 to 5/1 to obtain 2,2-dimethyl-1-(2-pyridyl)piperazine (312 mg, 76.58%) as a yellow gum. ESI-MS (EI$^+$, m/z): 192.3 [M+H]$^+$. $^1$H NMR (500 MHz, CDCl$_3$) δ 8.30 (d, J=7.3 Hz, 1H), 7.50 (m, 1H), 6.92 (t, J=7.6 Hz, 1H), 6.84 (m, 1H), 3.33-3.26 (m, 2H), 3.08-2.98 (m, 2H), 2.77 (s, 2H), 1.29 (s, 6H).

Step 3: 2-[4-[5-[3,3-Dimethyl-4-(2-pyridyl)piperazine-1-carbonyl]-2,4-dimethyl-anilino]-1-piperidyl]benzonitrile Followed the amide coupling general EDCI/HOBT method to obtain 2-[4-[5-[3,3-dimethyl-4-(2-pyridyl)piperazine-1-carbonyl]-2,4-dimethyl-anilino]-1-piperidyl]benzonitrile, I-118, as a white solid. ESI-MS (EI$^+$, m/z): 523.3 [M+H]$^+$. $^1$H NMR (500 MHz, DMSO-d$_6$) δ 8.16 (dd, J=3.3 Hz, 1H), 7.68 (d, J=7.6 Hz, 1H), 7.56 (dt, J=7.7 Hz, 2H), 7.17 (dd, J=8.2 Hz, 1H), 7.06 (t, J=7.5 Hz, 1H), 6.93-6.84 (m, 2H), 6.83-6.69 (m, 1H), 6.43 (d, J=12.6 Hz, 1H), 4.55 (d, J=8.4 Hz, 1H), 3.87-3.37 (m, 7H), 3.28 (d, J=14.6 Hz, 2H), 2.95 (t, J=10.9 Hz, 2H), 2.07 (dd, J=11.1 Hz, 8H), 1.76-1.64 (m, 2H), 1.32 (m, 6H).

Example 13: 2-(4-(2,4-Dimethyl-5-(4-(2-oxoindolin-7-yl)piperazine-1-carbonyl)phenylamino)piperidin-1-yl)benzonitrile, I-61

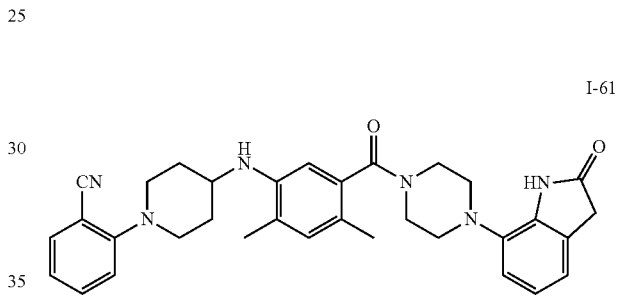

I-61

Synthetic Scheme:

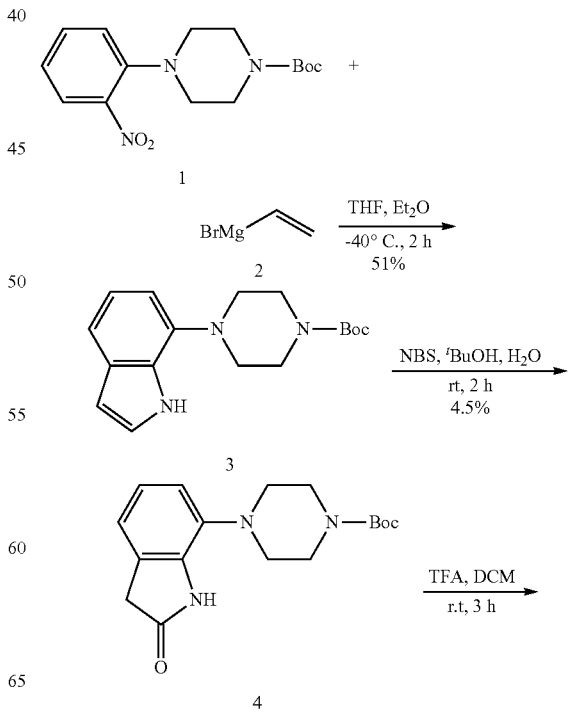

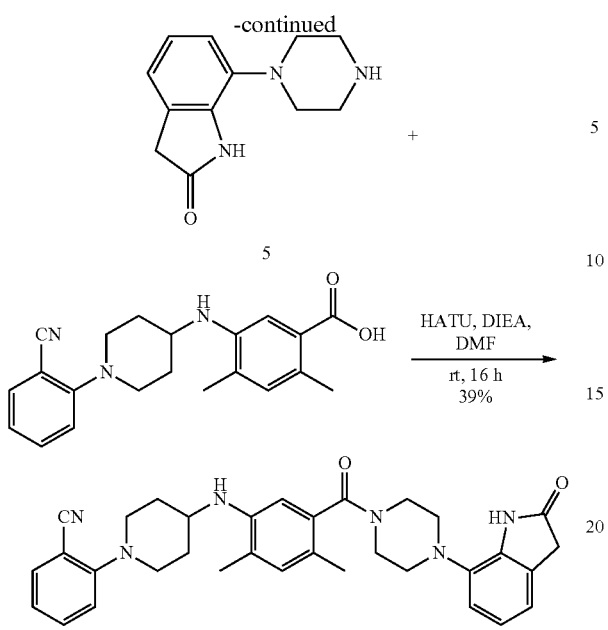

Procedures and Preparation:

The analysis method was following Method B and the separation method was following Method D.

Step 1: tert-Butyl 4-(1H-indol-7-yl)piperazine-1-carboxylate

Vinylmagnesium bromide (1 M in THF, 13 mL) and Et$_2$O (32.5 mL, 2.5 ml mmol$^{-1}$) were mixed in an oven dried flask and cooled to −40° C. under N$_2$ with stirring. tert-Butyl 4-(2-nitrophenyl)piperazine-1-carboxylate (1 g, 3.25 mmol) was dissolved in THF (8 mL) and added dropwise to the Grignard mixture. The solution was stirred at −40° C. for 4 hrs, and then quenched with sat. aq. NH$_4$Cl. The aqueous layer was separated and extracted using EtOAc, the organic layer was dried over MgSO$_4$ and concentrated in vacuo. The crude material was purified by silica column chromatography (silica, PE/EA=2/1) to yield the title compound tert-butyl 4-(1H-indol-7-yl)piperazine-1-carboxylate (500 mg, 1.66 mmol, 51%) as yellow solid. ESI-MS (EI$^+$, m/z): 302.3 [M+H]$^+$.

Step 2: tert-Butyl 4-(2-oxoindolin-7-yl)piperazine-1-carboxylate

To a 50 mL vial was added tert-butyl 4-(1H-indol-7-yl)piperazine-1-carboxylate (410 mg, 1.36 mmol) in t-butanol (12 mL) and water (5.5 mL). The solution was stirred at rt and then NBS (242 mg, 1.36 mmol) was added, the reaction was allowed to stir at rt for 3 hrs. The reaction mixture was diluted with ethyl acetate and washed with water. The organic layer was separated, washed with brine and dried over Na$_2$SO$_4$. The solvent was evaporated in vacuo and the resulting crude oil was purified via preparative HPLC to afford the desired product tert-butyl 4-(2-oxoindolin-7-yl)piperazine-1-carboxylate (19.4 mg, 0.061 mmol, 4.5%) as white solid. ESI-MS (EI$^+$, m/z): 318.2 [M+H]$^+$.

Step 3: 7-(Piperazin-1-yl)indolin-2-one

The mixture of tert-butyl 4-(2-oxoindolin-7-yl)piperazine-1-carboxylate (21 mg, 0.066 mmol) in TFA (0.5 mL) and DCM (2 mL) was stirred at rt for 2 hrs. The reaction mixture was concentrated to give crude product 7-(piperazin-1-yl)indolin-2-one as yellow solid that directly used for the next step. ESI-MS (EI$^+$, m/z): 218.3 [M+H]$^+$.

Following the amide coupling general EDCI/HOBT method to obtain 2-(4-(2, 4-Dimethyl-5-(4-(2-oxoindolin-7-yl) piperazine-1-carbonyl) phenylamino) piperidin-1-yl) benzonitrile I-61 as a white solid.

$^1$H NMR (500 MHz, CDCl3) δ 8.68 (s, 1H), 7.57 (dd, J=7.5, 1.5 Hz, 1H), 7.53-7.45 (m, 1H), 7.07-6.97 (m, 4H), 6.96-6.90 (m, 2H), 6.51 (s, 1H), 4.02 (s, 2H), 3.72-3.32 (m, 8H), 3.08-2.90 (m, 4H), 2.84 (s, 2H), 2.30-2.18 (m, 5H), 2.13 (s, 3H), 1.84-1.60 (m, 2H). ESI-MS (EI$^+$, m/z): 549.3 [M+H]$^+$.

Example 14: 2-(4-(5-(4-(1H-Pyrazolo[4,3-c]pyridin-7-yl)piperazine-1-carbonyl)-2,4-dimethylphenylamino)piperidin-1-yl)benzonitrile, I-44

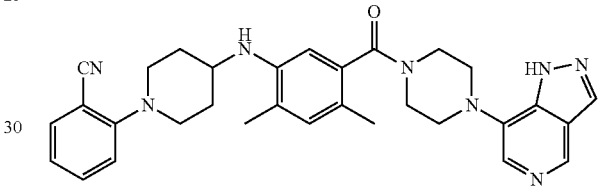

Synthetic Scheme:

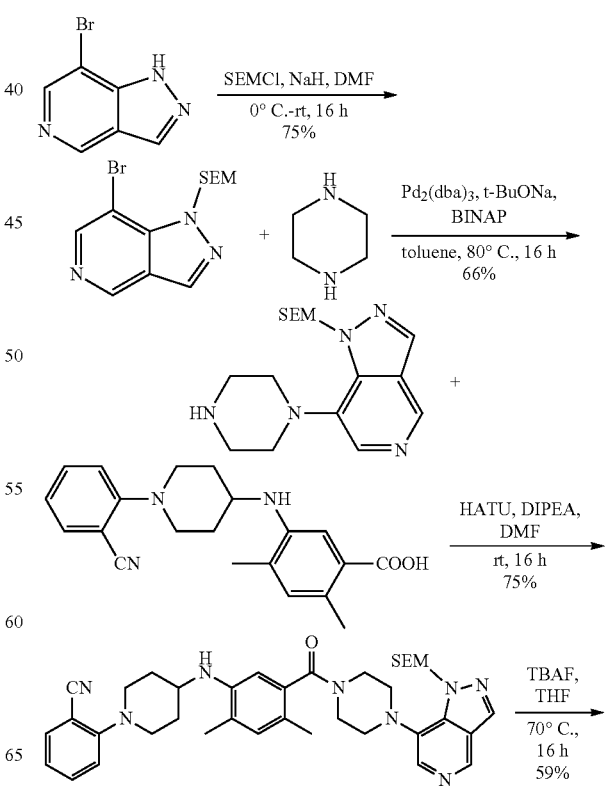

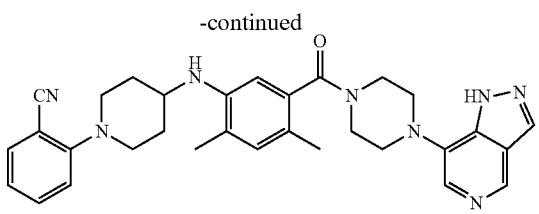

Procedures and Characterization:

The analysis method was following Method B and the separation method was following Method D.

Step 1: 7-Bromo-1-((2-(trimethylsilyl)ethoxy) methyl)-1H-pyrazolo[4,3-c]pyridine To a solution of 7-bromo-1H-pyrazolo[4,3-c]pyridine (500.00 mg, 2.52 mmol) in DMF (20.00 mL) was added NaH (100.80 mg, 2.52 mmol, 60% purity) slowly at 0° C. The mixture was stirred at 0° C. for 2 h. The reaction mixture was quenched with saturated aqueous $NH_4Cl$ solution (10 mL). Then the mixture was diluted with EtOAc and washed with water and brine. The organic phase was dried and concentrated. The residue was purified by column chromatography (PE: EA=3:1) to give (620 mg, 827 umol, 66% yield) as a yellow liquid. ESI-MS (EI$^+$, m/z): 328.0 [M+H]$^+$.

Step 2: 7-(Piperazin-1-yl)-1-((2-(trimethylsilyl) ethoxy)methyl)-1H-pyrazolo[4,3-c]pyridine 7-Bromo-1-((2-(trimethylsilyl)ethoxy)methyl)-1H-pyrazolo[4,3-c]pyridine (328.00 mg, 999.15 umol), piperazine (172.13 mg, 2.00 mmol), $Pd_2(dba)_3$ (91.49 mg, 99.92 umol), BINAP (62.21 mg, 99.92 umol) and tBuONa (192.04 mg, 2.00 mmol) were dissolved in toluene (5.00 mL). The mixture was stirred under $N_2$ at 80° C. for 16 h. The mixture was purified via preparative HPLC to afford 7-(piperazin-1-yl)-1-((2-(trimethylsilyl) ethoxy)methyl)-1H-pyrazolo[4,3-c]pyridine (220 mg, 660 umol, 66% yield) as a yellow oil. ESI-MS (EI$^+$, m/z): 333.9 [M+H]$^+$.

Step 3: 2-(4-(2,4-Dimethyl-5-(4-(1-((2-(trimethylsilyl)ethoxy)methyl)-1H-pyrazolo[4,3-c]pyridin-7-yl) piperazine-1-carbonyl)phenylamino)piperidin-1-yl) benzonitrile Followed the amide coupling HATU method to obtain the crude and purified by SGC (PE:EA=1:1) to obtain the product (80 mg, 106 umol, 75% yield) as a yellow solid. ESI-MS (EI$^+$, m/z): 665.3 [M+H]$^+$.

Step 4: 2-(4-(5-(4-(1H-Pyrazolo[4,3-c]pyridin-7-yl) piperazine-1-carbonyl)-2,4-dimethylphenylamino) piperidin-1-yl)benzonitrile A solution of 2-(4-(2,4-dimethyl-5-(4-(1-((2-(trimethylsilyl)ethoxy)methyl)-1H-pyrazolo[4,3-c]pyridin-7-yl)piperazine-1-carbonyl)phenylamino)piperidin-1-yl)benzonitrile (70.00 mg, 105.28 umol) in TBAF (1 M, 3.00 mL) was stirred at 70° C. for 16 h. The mixture was purified via preparative HPLC to afford 2-(4-(5-(4-(1H-pyrazolo[4,3-c] pyridin-7-yl)piperazine-1-carbonyl)-2,4-dimethylphenylamino)piperidin-1-yl)benzonitrile I-44 (33.2 mg, 62 umol, 59% yield) as a white solid. $^1$H NMR (500 MHz, CDCl$_3$) δ 8.86 (s, 1H), 8.21 (s, 1H), 8.00 (s, 1H), 7.56 (d, J=7.5 Hz, 1H), 7.48 (t, J=8.0 Hz, 1H), 7.06-6.97 (m, 2H), 6.92 (s, 1H), 6.49 (s, 1H), 4.04 (d, J=16.0 Hz, 2H), 3.61 (d, J=10.0 Hz, 1H), 3.54-3.39 (m, 4H), 3.32 (s, 2H), 3.13 (s, 2H), 3.03-2.87 (m, 2H), 2.26-2.16 (m, 5H), 2.12 (s, 3H), 1.72-1.58 (m, 2H). LCMS Method (10 mM Ammonium hydrogen carbonate) Tr=2.10 min ESI-MS (EI$^+$, m/z): 535.3 [M+H]$^+$.

Example 15: 2-((1-(2-Cyanophenyl)piperidin-4-yl) (2,4-dimethyl-5-(4-(2-sulfamoylphenyl)piperazine-1-carbonyl)phenyl)amino)acetamide, I-27

I-27

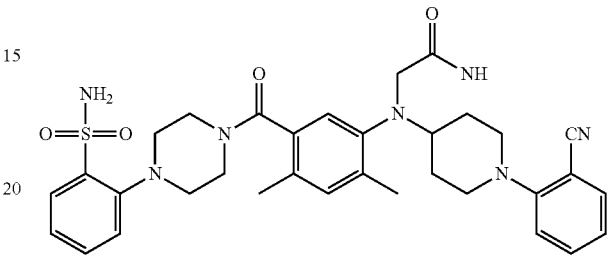

Synthetic Scheme:

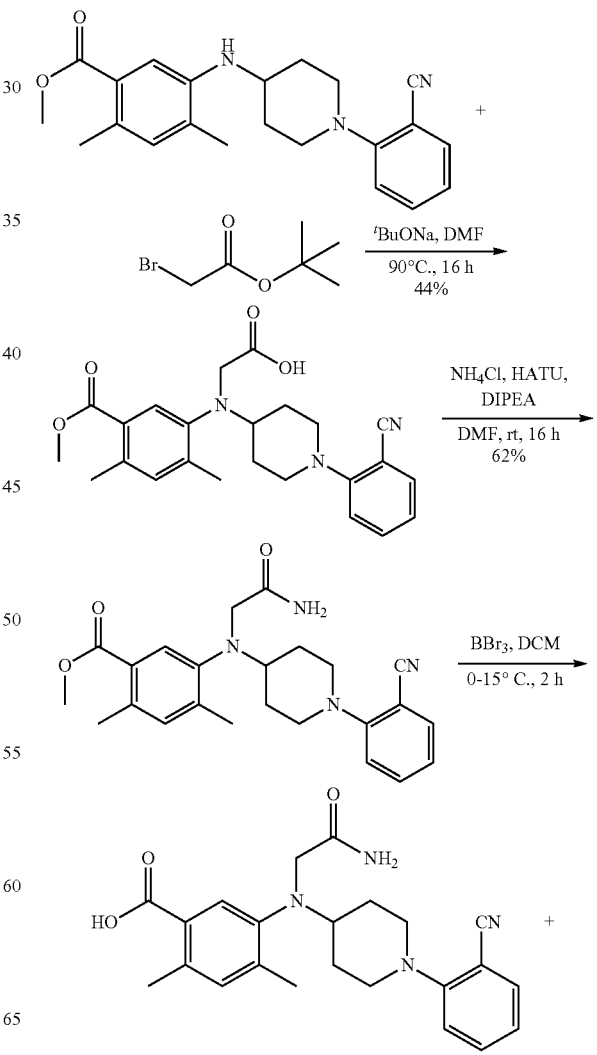

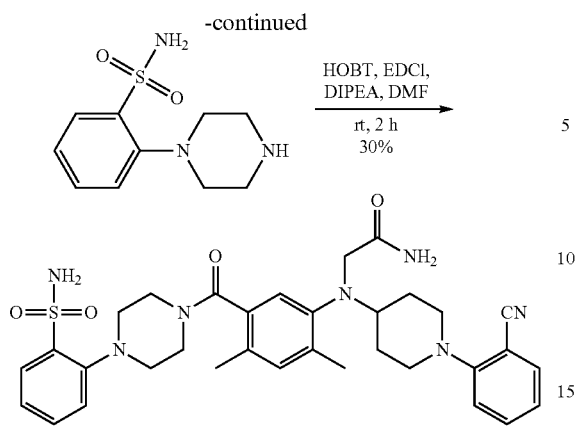

Procedures and Characterization:

The analysis method was following Method B and the separation method was following Method D.

Step 1: 2-((1-(2-Cyanophenyl) piperidin-4-yl)(5-(methoxycarbonyl)-2,4-dimethylphenyl)amino)acetic Acid To a solution of methyl 5-(1-(2-cyanophenyl)piperidin-4-ylamino)-2,4-dimethylbenzoate (1.17 g, 3.22 mmol) in DMF (10.00 mL) at 15° C. was added tBuONa (928.33 mg, 9.66 mmol) followed by tert-butyl 2-bromoacetate (3.14 g, 16.10 mmol). Then the mixture was stirred at 90° C. for 16 h. The mixture was purified by chromatography (silica, ethyl acetate/petroleum ether=1/1) to afford 2-((1-(2-cyanophenyl)piperidin-4-yl)(5-(methoxycarbonyl)-2,4-dimethylphenyl)amino)acetic acid (600 mg, 1.42 mmol, 44% yield) as a brown solid. ESI-MS (EI+, m/z): 422.3 [M+H]+.

Step 2: Methyl 5-((2-amino-2-oxoethyl) (1-(2-cyanophenyl) piperidin-4-yl) amino)-2, 4-dimethylbenzoate 2-((1-(2-cyanophenyl)piperidin-4-yl)(5-(methoxycarbonyl)-2,4-dimethylphenyl)amino)acetic acid (421.00 mg, 998.84 umol), HATU (489.88 mg, 1.30 mmol), DIPEA (645.45 mg, 4.99 mmol, 872.23 uL) and NH₄Cl (106.86 mg, 2.00 mmol) were dissolved in DMF (6.00 mL). The mixture was stirred at 15° C. for 3 h. The reaction mixture was purified via preparative HPLC to afford methyl 5-((2-amino-2-oxoethyl)(1-(2-cyanophenyl)piperidin-4-yl)amino)-2,4-dimethylbenzoate (260 mg, 618 umol, 62% yield) as a white solid. ESI-MS (EI+, m/z): 421.3 [M+H]+.

Step 3: 5-((2-Amino-2-oxoethyl) (1-(2-cyanophenyl) piperidin-4-yl) amino)-2, 4-dimethylbenzoic Acid To a solution of methyl 5-((2-amino-2-oxoethyl)(1-(2-cyanophenyl)piperidin-4-yl)amino)-2,4-dimethylbenzoate (100.00 mg, 237.81 umol) in DCM (2.00 mL) at 0° C. was added BBr₃ (237.81 umol, 2.00 mL, 17% purity). Then the mixture was stirred at 0-15° C. for 2 h. The mixture was quenched with MeOH (2 mL) at 0° C., and then concentrated in vacuo. The residue was directly used for the next step. ESI-MS (EI+, m/z): 407.3 [M+H]+.

Step 4: 2-((1-(2-Cyanophenyl)piperidin-4-yl)(2,4-dimethyl-5-(4-(2-sulfamoylphenyl)piperazine-1-carbonyl)phenyl)amino)acetamide Followed the amide coupling EDCI/HOBT method to obtain 2-((1-(2-cyanophenyl)piperidin-4-yl)(2,4-dimethyl-5-(4-(2-sulfamoylphenyl)piperazine-1-carbonyl)phenyl)amino)acetamide I-27 as a white solid. ¹H NMR (500 MHz, CDCl₃) δ 8.02 (dd, J=8.0, 1.0 Hz, 1H), 7.62-7.57 (m, 1H), 7.53 (dd, J=8.0, 1.0 Hz, 1H), 7.48-7.38 (m, 2H), 7.34 (t, J=7.5 Hz, 1H), 7.13 (s, 1H), 7.03-6.92 (m, 3H), 6.66 (s, 1H), 5.61 (s, 2H), 5.52 (s, 1H), 3.82-3.68 (m, 2H), 3.59 (d, J=12.0 Hz, 2H), 3.46 (s, 1H), 3.40 (s, 1H), 3.29-2.86 (m, 5H), 2.82-2.63 (m, 2H), 2.38 (s, 3H), 2.30 (s, 3H), 1.99-1.76 (m, 4H).

ESI-MS (EI+, m/z): 630.3 [M+H]+.

Example 16: (R)-2-(4-(5-(4-(5-Fluoropyridin-2-yl)-3-(hydroxymethyl)piperazine-1-carbonyl)-2,4-dimethylphenylamino)piperidin-1-yl)benzonitrile, I-116

I-116

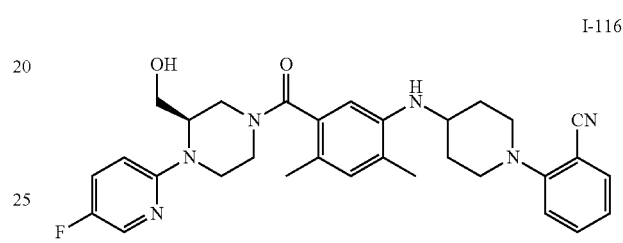

Synthetic Scheme:

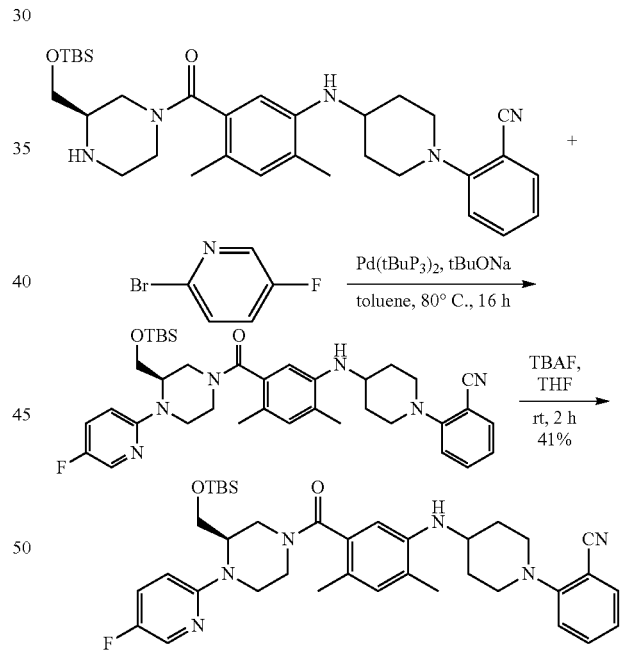

Procedures and Characterization:

The analysis method was following Method B and the separation method was following Method D.

Step 1: (R)-2-(4-(5-(3-((tert-Butyldimethylsilyloxy)methyl)-4-(5-fluoropyridin-2-yl)piperazine-1-carbonyl)-2,4-dimethylphenylamino)piperidin-1-yl)benzonitrile (R)-2-(4-(5-(3-((tert-butyldimethylsilyloxy)methyl)piperazine-1-carbonyl)-2,4-dimethylphenylamino)piperidin-1-yl)benzonitrile (200.00 mg, 355.98 umol), 2-bromo-5-fluoropyridine (125.30 mg, 711.96 umol), tBuONa (68.42 mg, 711.96 umol) and bis(tri-tert-butylphosphine)palladium (36.38 mg, 71.20 umol) were dissolved in toluene (5.00 mL). The mixture was stirred under N₂ at 80° C. for 16 h. The mixture was concentrated in vacuo. The residue was dissolved in EtOAc (100 mL) and washed with H₂O (100 mL×2). The layers were separated, The EtOAc extracts were dried (Na₂SO₄), filtered and concentrated under vacuum to afford the crude product (R)-2-(4-(5-(3-((tert-butyldimethylsilyloxy)methyl)-4-(5-fluoropyridin-2-yl)piperazine-1-carbonyl)-2,4-dimethylphenylamino)piperidin-1-yl)benzonitrile (200 mg, crude) as a yellow oil which was used for the next step without further purification. ESI-MS (EI+, m/z): 657.3 [M+H]⁺.

Step 2: (R)-2-(4-(5-(4-(5-fluoropyridin-2-yl)-3-(hydroxymethyl)piperazine-1-carbonyl)-2,4-dimethylphenylamino)piperidin-1-yl)benzonitrile (R)-2-(4-(5-(3-((tert-butyldimethylsilyloxy)methyl)-4-(5-fluoropyridin-2-yl)piperazine-1-carbonyl)-2,4-dimethylphenylamino)piperidin-1-yl)benzonitrile (200.00 mg, 304.46 umol) and TBAF (1 M, 2.00 mL) were dissolved in THF (2.00 mL). The mixture was stirred at 20° C. for 2 h. The mixture was purified via preparative HPLC to afford (R)-2-(4-(5-(4-(5-fluoropyridin-2-yl)-3-(hydroxymethyl)piperazine-1-carbonyl)-2,4-dimethylphenylamino)piperidin-1-yl)benzonitrile I-116 (67 mg, 123 umol, 41% yield) as a white solid. ¹H NMR (400 MHz, CDCl₃) δ 8.06-7.94 (m, 1H), 7.56 (d, J=7.6 Hz, 1H), 7.48 (t, J=7.8 Hz, 1H), 7.35-7.22 (m, 1H), 7.09-6.88 (m, 3H), 6.69-6.58 (m, 1H), 6.56-6.32 (m, 1H), 4.90-4.22 (m, 2H), 3.86 (d, J=11.6 Hz, 1H), 3.81-3.37 (m, 9H), 3.37-3.14 (m, 2H), 3.09-2.87 (m, 3H), 2.34-2.05 (m, 8H).

ESI-MS (EI⁺, m/z): 543.3 [M+H]⁺.

Example 17: (R)-2-(4-(5-(4-(3-Fluoropyridin-2-yl)-3-(hydroxymethyl)piperazine-1-carbonyl)-2,4-dimethylphenylamino)piperidin-1-yl)benzonitrile, I-115

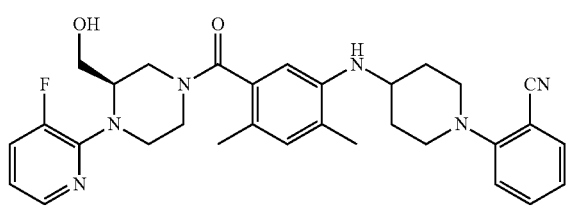

I-115

Procedures and Characterization:

The analysis method was following Method B and the separation method was following Method D.

The procedure was the same as example 16.

¹H NMR (400 MHz, CDCl₃) δ 7.98-7.88 (m, 1H), 7.56 (d, J=7.6 Hz, 1H), 7.48 (t, J=8.0 Hz, 1H), 7.34-7.20 (m, 1H), 7.11-6.86 (m, 3H), 6.86-6.75 (m, 1H), 6.60-6.31 (m, 1H), 4.80-4.50 (m, 1H), 4.48-3.84 (m, 4H), 3.76-3.21 (m, 9H), 3.08-2.86 (m, 2H), 2.34-2.05 (m, 8H).

ESI-MS (EI⁺, m/z): 543.3 [M+H]⁺.

Example 18: (R)-2-(4-(5-(4-(4-Fluoropyridin-2-yl)-3-(hydroxymethyl)piperazine-1-carbonyl)-2,4-dimethylphenylamino)piperidin-1-yl)benzonitrile, I-99

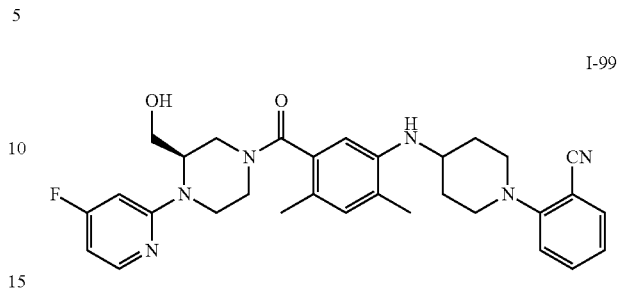

I-99

Procedures and Characterization:

The analysis method was following Method B and the separation method was following Method D.

The procedure was same as example 16.

¹H NMR (400 MHz, CDCl₃) δ 8.14-8.00 (m, 1H), 7.56 (d, J=7.6 Hz, 1H), 7.48 (t, J=7.6 Hz, 1H), 7.08-6.87 (m, 3H), 6.60-6.23 (m, 3H), 4.92-4.18 (m, 2H), 3.97-3.84 (m, 1H), 3.82-3.37 (m, 9H), 3.35-2.88 (m, 4H), 2.31-2.07 (m, 8H).

ESI-MS (EI⁺, m/z): 543.3 [M+H]⁺.

Example 19: (S)-2-(4-(5-(4-(4-Fluoropyridin-2-yl)-3-(hydroxymethyl)piperazine-1-carbonyl)-2,4-dimethylphenylamino)piperidin-1-yl)benzonitrile, I-100

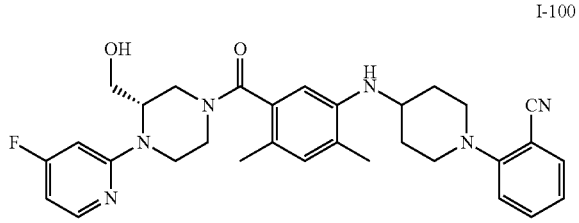 [SMILES: Cc1cc(C)c(C(=O)N2CCN(c3cc(F)ccn3)[C@H](CO)C2)cc1NC1CCN(c2ccccc2C#N)CC1]

I-100

Procedures and Characterization:

The analysis method was following Method B and the separation method was following Method D.

The procedure was same as example 16.

¹H NMR (500 MHz, CDCl₃) δ 8.14-8.00 (m, 1H), 7.56 (d, J=7.5 Hz, 1H), 7.48 (t, J=7.5 Hz, 1H), 7.08-6.87 (m, 3H), 6.58-6.23 (m, 3H), 4.90-4.22 (m, 2H), 3.97-3.84 (m, 1H), 3.82-3.37 (m, 9H), 3.35-2.88 (m, 4H), 2.31-2.07 (m, 8H).

ESI-MS (EI⁺, m/z): 543.3 [M+H]⁺.

Example 20: (R)-2-(4-(5-(3-(Hydroxymethyl)-4-isopropylpiperazine-1-carbonyl)-2,4-dimethylphenylamino)piperidin-1-yl)benzonitrile, I-114

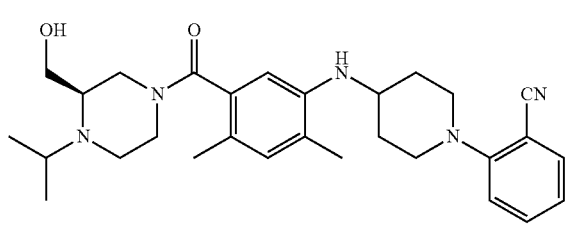

I-114

Synthetic Scheme:

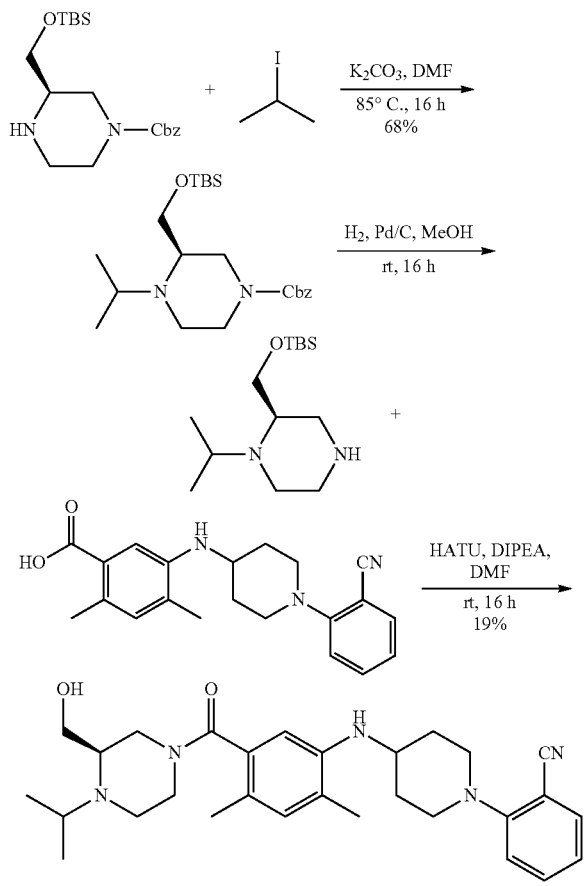

Procedures and Characterization:
The analysis method was following Method B and the separation method was following Method D.

Step 1: (R)-Benzyl 3-(hydroxymethyl)-4-isopropylpiperazine-1-carboxylate (R)-Benzyl 3-((tert-butyldimethylsilyloxy)methyl)piperazine-1-carboxylate (365.00 mg, 1.00 mmol), 2-iodopropane (1.70 g, 10.00 mmol) and K$_2$CO$_3$ (414.63 mg, 3.00 mmol) were dissolved in DMF (4.00 mL). The mixture was stirred at 85° C. for 16 h. The mixture was purified via preparative HPLC to afford (R)-benzyl 3-(hydroxymethyl)-4-isopropylpiperazine-1-carboxylate (200 mg, 684 umol, 68% yield) as a colorless oil. ESI-MS (EI$^+$, m/z): 293.3 [M+H]$^+$.

Step 2: (R)-(1-Isopropylpiperazin-2-yl)methanol (R)-Benzyl 3-(hydroxymethyl)-4-isopropylpiperazine-1-carboxylate (200.00 mg, 684.06 umol) and Pd/C (16.62 mg, 136.81 umol) were dissolved in MeOH (10.00 mL). The mixture was stirred under H$_2$ at 20° C. for 16 h. The mixture was filtered and concentrated to afford a colorless oil that was used directly in the next step.

Step 3: (R)-2-(4-(5-(3-(Hydroxymethyl)-4-isopropylpiperazine-1-carbonyl)-2,4-dimethylphenylamino) piperidin-1-yl)benzonitrile Followed the amide coupling HATU method to obtain (R)-2-(4-(5-(3-(hydroxymethyl)-4-isopropylpiperazine-1-carbonyl)-2,4-dimethylphenylamino)piperidin-1-yl)benzonitrile I-114 as a white solid. $^1$H NMR (400 MHz, CDCl$_3$) δ 7.56 (d, J=7.6 Hz, 1H), 7.49 (t, J=7.6 Hz, 1H), 7.06-6.97 (m, 2H), 6.90 (d, J=2.8 Hz, 1H), 6.45 (d, J=7.6 Hz, 1H), 4.52-3.92 (m, 1H), 3.91-3.10 (m, 10H), 3.04-2.35 (m, 6H), 2.28-2.05 (m, 9H), 1.14 (q, J=6.5 Hz, 3H), 1.03-0.92 (m, 3H).
ESI-MS (EI$^+$, m/z): 490.3 [M+H]$^+$.

Example 21: (S)-2-(4-(5-(3-(Hydroxymethyl)-4-isopropylpiperazine-1-carbonyl)-2,4-dimethylphenylamino)piperidin-1-yl)benzonitrile, I-95

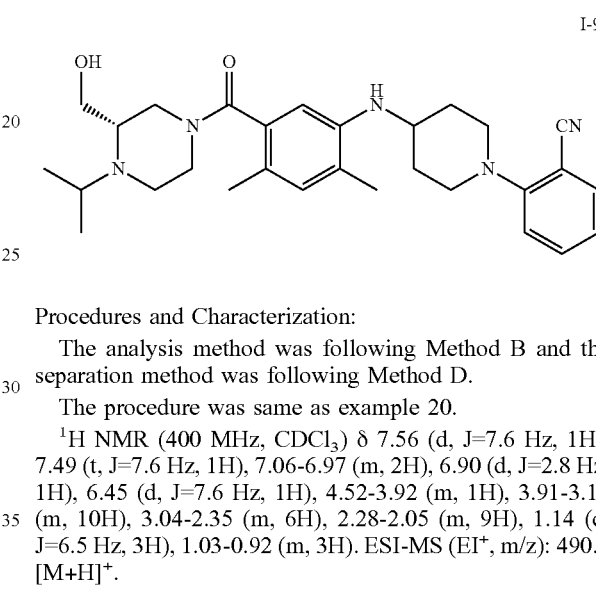

I-95

Procedures and Characterization:
The analysis method was following Method B and the separation method was following Method D.

The procedure was same as example 20.
$^1$H NMR (400 MHz, CDCl$_3$) δ 7.56 (d, J=7.6 Hz, 1H), 7.49 (t, J=7.6 Hz, 1H), 7.06-6.97 (m, 2H), 6.90 (d, J=2.8 Hz, 1H), 6.45 (d, J=7.6 Hz, 1H), 4.52-3.92 (m, 1H), 3.91-3.10 (m, 10H), 3.04-2.35 (m, 6H), 2.28-2.05 (m, 9H), 1.14 (q, J=6.5 Hz, 3H), 1.03-0.92 (m, 3H). ESI-MS (EI$^+$, m/z): 490.3 [M+H]$^+$.

Example 22: (S)-2-(4-(5-(3-(Hydroxymethyl)-4-(2,2,2-trifluoroethyl)piperazine-1-carbonyl)-2,4-dimethylphenylamino)piperidin-1-yl)benzonitrile, I-98

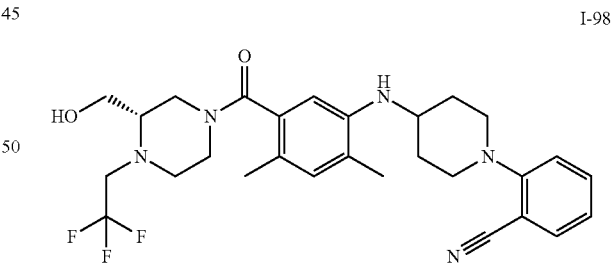

I-98

Synthetic Scheme:

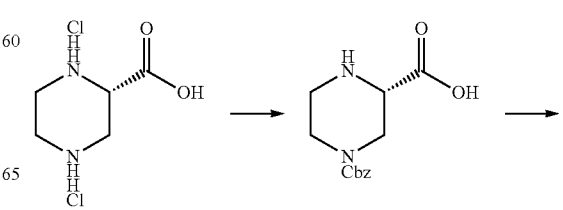

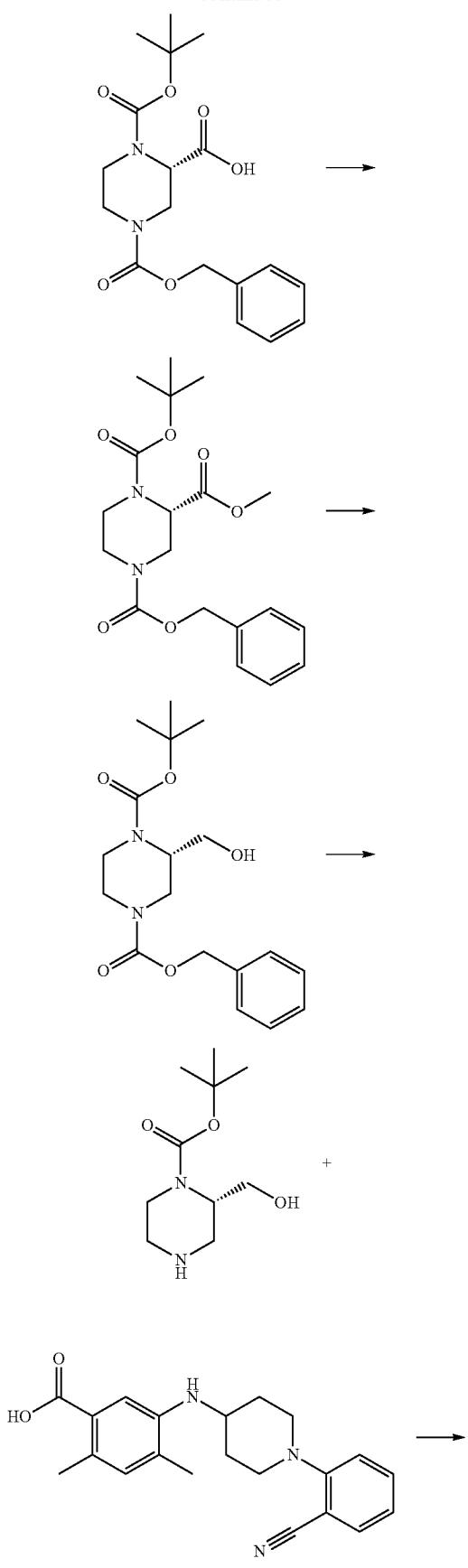
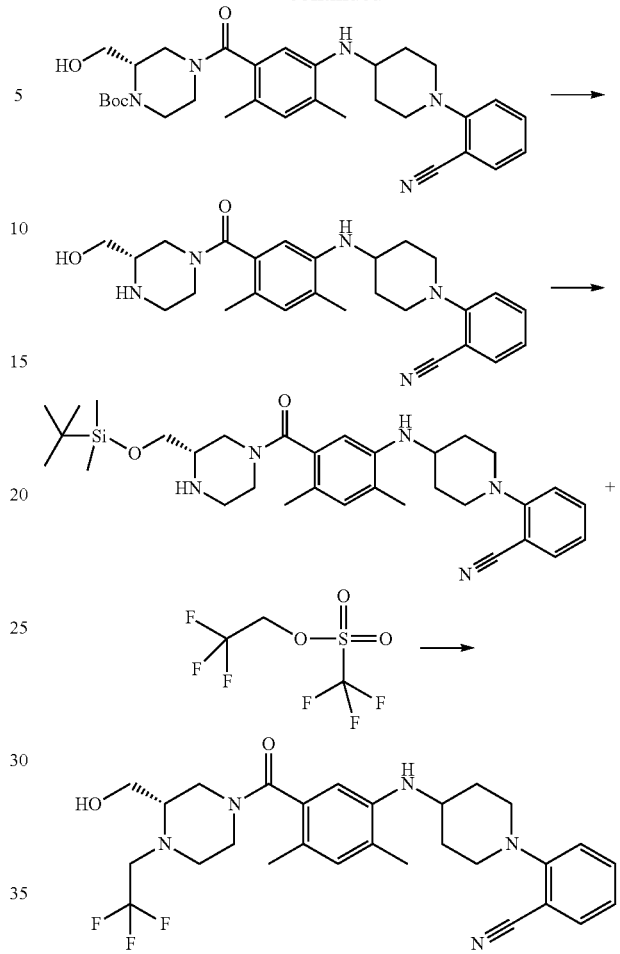

Procedures and Characterization:

The analysis method was following Method B and the separation method was following Method D.

Step 1:
(S)-4-(Benzyloxycarbonyl)piperazine-2-carboxylic Acid

To solution of (2S)-piperazine-2-carboxylic acid (10.00 g, 76.84 mmol) and NaOH (9.22 g, 230.52 mmol) in $H_2O$ (50.00 mL) was added a solution of cupric sulfate pentahydrate (9.61 g, 38.42 mmol) in water (10 ml) at 30° C. After cooling to 0° C., $NaHCO_3$ (7.75 g, 92.21 mmol) was added followed by the dropwise addition of benzyl chloroformate (13.11 g, 76.84 mmol). The reaction mixture was stirred at 0° C. for 3 h and then at rt overnight. The N-Cbz-Lys-Cu2+-complex precipitate was collected and washed with water (20 mL) and acetone (10 mL), then dried. To a boiling suspension of EDTA (24.70 g, 84.52 mmol) in water (80 mL), the powdered N-Cbz-Lys-Cu2+ complex was added portionwise, while the pH was maintained at 7.0 by addition of conc. HCl (5 mL). The white precipitate was collected, washed with water and methanol and dried. The product was recrystallized from ethanol-water to afford (2S)-4-benzyloxycarbonylpiperazine-2-carboxylic acid (12.00 g, 45.41 mmol) as a white solid. MS (EI$^+$, m/z): 265.0 [M+H]$^+$.

Step 2: (S)-4-(Benzyloxycarbonyl)-1-(tert-butoxycarbonyl)piperazine-2-carboxylic Acid (2S)-4-Benzyloxycarbonylpiperazine-2-carboxylic acid (12.00 g, 45.41 mmol) and tert-butoxycarbonyl tert-butyl carbonate (19.82 g, 90.82 mmol) were dissolved in THF (50.00 mL), followed by addition of NaHCO$_3$ (15.26 g, 181.64 mmol) in H$_2$O (50.00 mL). The solution was stirred at 20° C. for 10 h. The reaction mixture was extracted with ether (100 mL). The layers were separated, and to the aqueous phase was added 1 N HCl (182 mL) to adjust the pH to 3. The aqueous layer was extracted with DCM (100 mL×3). The combined DCM extracts were dried (Na$_2$SO$_4$), filtered and concentrated under vacuum. The residue was purified by recrystallization to afford (S)-4-(benzyloxycarbonyl)-1-(tert-butoxycarbonyl)piperazine-2-carboxylic acid (15.00 g, 41.16 mmol) as a white solid. MS (EI$^+$, m/z): 309.0 [M+H]+.

Step 3: (S)-4-Benzyl 1-tert-butyl 2-methylpiperazine-1,2,4-tricarboxylate (S)-4-(Benzyloxycarbonyl)-1-(tert-butoxycarbonyl)piperazine-2-carboxylic acid (6.60 g, 19.92 mmol) was dissolved in DMF (30.00 mL), followed by the addition of MeI (2.83 g, 19.92 mmol) and K$_2$CO$_3$ (5.51 g, 39.83 mmol). The solution was stirred at rt for 2 h. The mixture was diluted by H$_2$O (100 ml) and extracted with EtOAc (100 ml×3). The combined organic phase was washed with brine, dried (Na$_2$SO$_4$), filtered, and concentrated. The residue was purified by chromatography (silica, ethyl acetate/petroleum ether=1/10 as eluent) to give the desire product (S)-4-benzyl 1-tert-butyl 2-methylpiperazine-1,2,4-tricarboxylate (4.50 g, 13.03 mmol) as a yellow oil. MS (EI$^+$, m/z): 279.2 [M+H]$^+$.

Step 4: (S)-4-Benzyl 1-tert-butyl 2-(hydroxymethyl)piperazine-1,4-dicarboxylate (S)-4-Benzyl 1-tert-butyl 2-methylpiperazine-1,2,4-tricarboxylate (2.90 g, 7.66 mmol) was dissolved in THF (30.00 mL) in an ice bath, followed by the addition of LiBH$_4$ in THF (1.31 g, 60.00 mmol). The solution was stirred at rt for 14 h. The reaction mixture was quenched by aq. NH$_4$Cl (20 mL). The layers were separated. The aqueous layer was extracted with EtOAc (50 mL). The combined EtOAc extracts were dried (Na$_2$SO$_4$), filtered and concentrated under vacuum. The residue was purified by chromatography (silica, ethyl acetate/petroleum ether=1/5) to afford (S)-4-benzyl 1-tert-butyl 2-(hydroxymethyl)piperazine-1,4-dicarboxylate (2.10 g, 5.99 mmol) as a white oil. MS (EI$^+$, m/z): 251.2 [M+H]$^+$.

Step 5: (S)-2-(4-(5-(3-(Hydroxymethyl)-4-(2,2,2-trifluoroethyl)piperazine-1-carbonyl)-2,4-dimethylphenylamino)piperidin-1-yl)benzonitrile (S)-2-(4-(5-(3-((tert-Butyldimethylsilyloxy)methyl)piperazine-1-carbonyl)-2,4-dimethylphenylamino)piperidin-1-yl)benzonitrile (561 mg, 0.10 mmol) was dissolved in DMF (30.00 mL), followed by the addition of 2,2,2-trifluoroethyl trifluoromethanesulfonate (696 mg, 0.30 mmol) and K$_2$CO$_3$ (41.4 mg, 0.30 mmol). The mixture was heated to 120° C. for 14 h. The reaction mixture was filtered and purified via preparative HPLC to afford (S)-2-(4-(5-(3-(hydroxymethyl)-4-(2,2,2-trifluoroethyl)piperazine-1-carbonyl)-2,4-dimethylphenylamino)piperidin-1-yl)benzonitrile I-98 as a white solid. MS (EI$^+$, m/z): 530.3 [M+H]$^+$. $^1$H NMR (500 MHz, DMSO-d$_6$) δ 7.69 (dd, J=7.6, 1.5 Hz, 1H), 7.64-7.52 (m, 1H), 7.18 (d, J=8.3 Hz, 1H), 7.07 (t, J=7.6 Hz, 1H), 6.85 (d, J=5.5 Hz, 1H), 6.37 (s, 1H), 4.74 (d, J=91.9 Hz, 1H), 4.59-4.44 (m, 1H), 3.97 (d, J=79.0 Hz, 1H), 3.70-3.39 (m, 6H), 2.96 (t, J=11.1 Hz, 3H), 2.71 (d, J=73.7 Hz, 2H), 2.08 (s, 3H), 2.03 (s, 5H), 1.69 (d, J=10.0 Hz, 2H).

Example 23: (R)-2-(4-(5-(3-(Hydroxymethyl)-4-(2,2,2-trifluoroethyl)piperazine-1-carbonyl)-2,4-dimethylphenylamino)piperidin-1-yl)benzonitrile, I-96

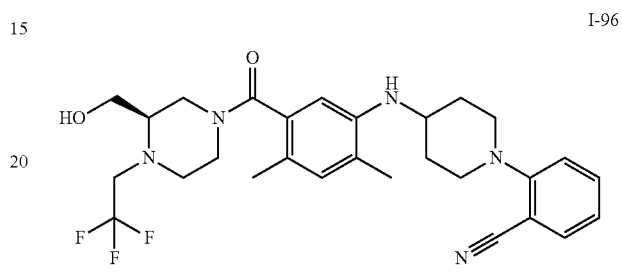

I-96

Procedures and Characterization:

The analysis method was following Method B and the separation method was following Method D.

The procedure is the same as that used for example 22.

MS (EI$^+$, m/z): 530.3 [M+H]$^+$. $^1$H NMR (500 MHz, DMSO-d$_6$) δ 7.69 (dd, J=7.7, 1.4 Hz, 1H), 7.59 (dd, J=11.5, 4.3 Hz, 1H), 7.18 (d, J=8.3 Hz, 1H), 7.07 (t, J=7.5 Hz, 1H), 6.85 (d, J=5.6 Hz, 1H), 6.37 (s, 1H), 4.74 (d, J=90.3 Hz, 1H), 4.61-4.42 (m, 1H), 3.97 (d, J=77.9 Hz, 1H), 3.72-3.40 (m, 6H), 3.15 (d, J=39.4 Hz, 3H), 2.96 (t, J=11.3 Hz, 3H), 2.71 (d, J=74.3 Hz, 2H), 2.08 (s, 3H), 2.03 (s, 5H), 1.68 (d, J=9.2 Hz, 2H).

Example 24: 2-(4-(5-(1-(2-Cyanophenyl)piperidin-4-ylamino)-2,4-dimethylbenzoyl)piperazin-1-yl)-4,5-difluorobenzenesulfonamide, I-104

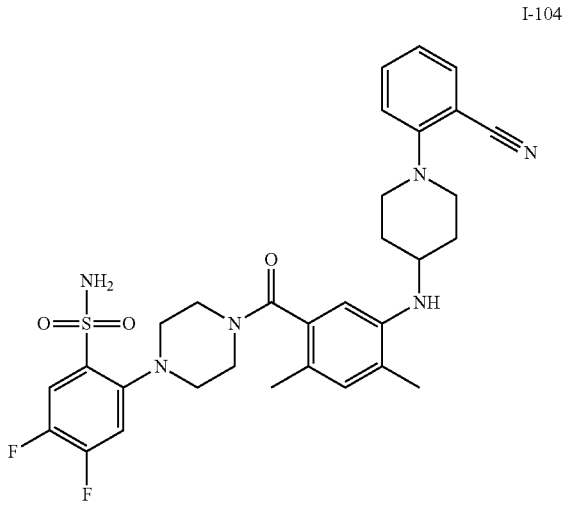 [SMILES: Cc1cc(C)c(C(=O)N2CCN(c3cc(F)c(F)cc3S(N)(=O)=O)CC2)cc1NC1CCN(c2ccccc2C#N)CC1]

I-104

Synthetic Scheme:

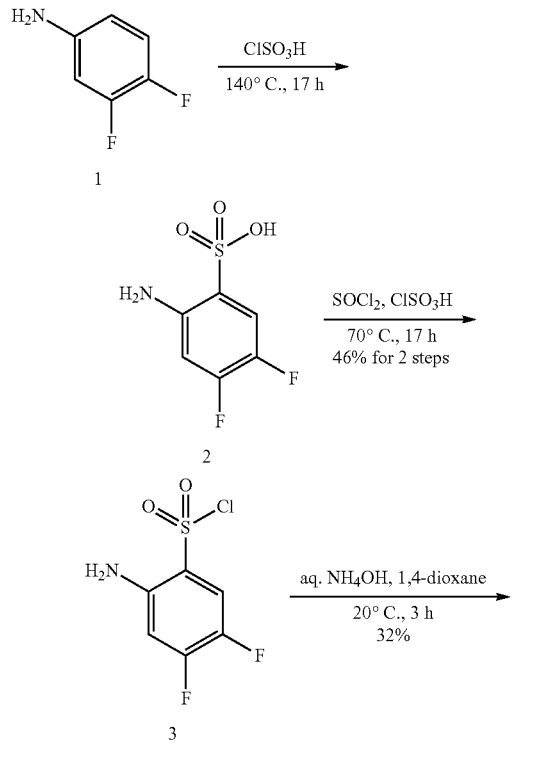

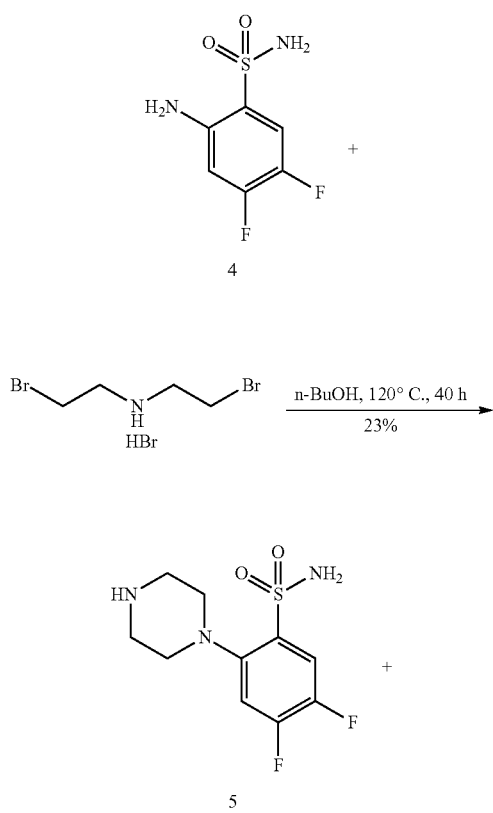

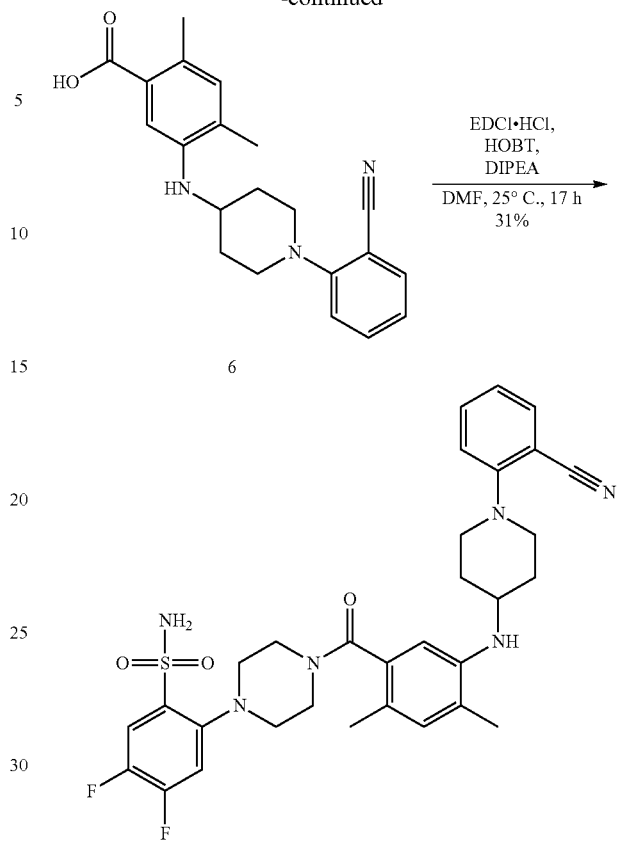

Procedures and Characterization:

The analysis method was following Method B and the separation method was following Method D.

Step 1: 2-Amino-4,5-difluorobenzenesulfonic Acid

A mixture of 3,4-difluoroaniline (20.00 g, 154.91 mmol) and chlorosulfonic acid (60.00 mL) was stirred at 140° C. for 17 h. The reaction mixture was used for the next step directly. MS (EI$^+$, m/z): 209.9 [M+H]$^+$.

Step 2: 2-Amino-4,5-difluorobenzene-1-sulfonyl Chloride

To the mixture of step 1 was added thionyl chloride (60.00 mL) and the resulting mixture was stirred at 70° C. for 17 h. The reaction mixture was poured into water (400 mL) slowly. The aqueous layer was extracted with Et$_2$O (400 mL×2). The combined organic layers were dried (Na$_2$SO$_4$), filtered and concentrated under vacuum to obtain 2-amino-4,5-difluoro-benzenesulfonyl chloride (33.00 g, 72.49 mmol, 47% yield, 50% purity) as a dark oil. MS (EI$^+$, m/z): 227.9 [M+H]+.

Step 3: 2-Amino-4,5-difluorobenzenesulfonamide

To a mixture of 2-amino-4,5-difluoro-benzenesulfonyl chloride (33.00 g, 72.49 mmol) and 1,4-dioxane (400 mL) was added aqueous ammonium hydroxide solution (300.02 mL) at 20° C. The resulting mixture was stirred at 20° C. for 3 h. 1,4-Dioxane was removed by evaporation. The aqueous layer was extracted with EtOAc (400 mL×2). The combined organic layers were dried (Na$_2$SO$_4$), filtered and concentrated under vacuum. The residue was purified by chromatography (silica, ethyl acetate/petroleum ether=1/1) to afford 2-amino-4,5-difluoro-benzenesulfonamide (5.50 g, 23.78 mmol, 33% yield, 90% purity) as a black solid. MS (EI+, m/z): 208.9 [M+H]+. 1H NMR (500 MHz, DMSO-d6) δ 7.49 (dd, J=10.8, 9.0 Hz, 1H), 7.40 (s, 2H), 6.77 (dd, J=13.0, 6.9 Hz, 1H), 5.97 (s, 2H). The sulfonyl amide position was confirmed by COSY and NOESY spectrum.

Step 4: 4,5-Difluoro-2-(piperazin-1-yl)benzenesulfonamide

A mixture of 2-amino-4,5-difluoro-benzenesulfonamide (1.04 g, 5.00 mmol), 2-bromo-N-(2-bromoethyl)ethanamine hydrobromide (15.59 g, 50.00 mmol) and n-butyl alcohol (50.00 mL) was stirred at 120° C. for 40 h. The reaction mixture was filtered and the filtrate was concentrated in vacuo. The residue was purified via preparative HPLC to afford 4,5-difluoro-2-piperazin-1-yl-benzenesulfonamide (400.00 mg, 1.15 mmol, 23% yield, 80% purity) as a white solid. MS (EI+, m/z): 278.1 [M+H]+.

Step 5: 2-(4-(5-(1-(2-Cyanophenyl)piperidin-4-ylamino)-2,4-dimethylbenzoyl)piperazin-1-yl)-4,5-difluorobenzenesulfonamide Followed the amide coupling EDCI/HOBT method to afford 2-[4-[5-[[1-(2-cyanophenyl)-4-piperidyl]amino]-2,4-dimethyl-benzoyl]piperazin-1-yl]-4,5-difluoro-benzenesulfonamide I-104 as a white solid. MS (EI+, m/z): 609.3 [M+H]+. 1H NMR (500 MHz, DMSO-d6) δ 7.85-7.77 (m, 2H), 7.70-7.68 (m, 1H), 7.61-7.57 (m, 1H), 7.17-7.16 (m, 3H), 7.09-7.06 (m, 1H), 6.87 (s, 1H), 6.44 (s, 1H), 4.56-4.54 (m, 1H), 3.84 (br, 2H), 3.52-3.49 (m, 3H), 3.39-3.37 (m, 2H), 2.99-2.92 (m, 4H), 2.83-2.78 (m, 2H), 2.09 (s, 6H), 2.05-2.03 (m, 2H), 1.71 (br, 2H).

Example 25: Synthesis of 2-(4-(6-(1-(2-cyanophenyl)piperidin-4-ylamino)-3,5-dimethylpicolinoyl)piperazin-1-yl)-5-fluorobenzenesulfonamide, I-103

I-103

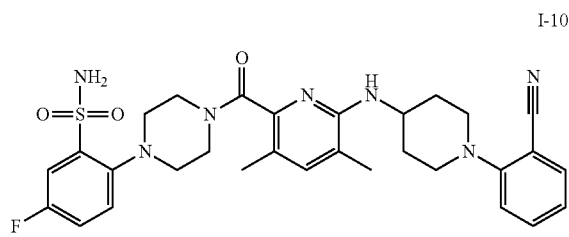

Synthetic Scheme:

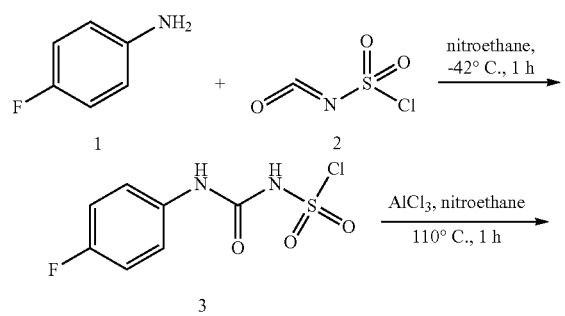

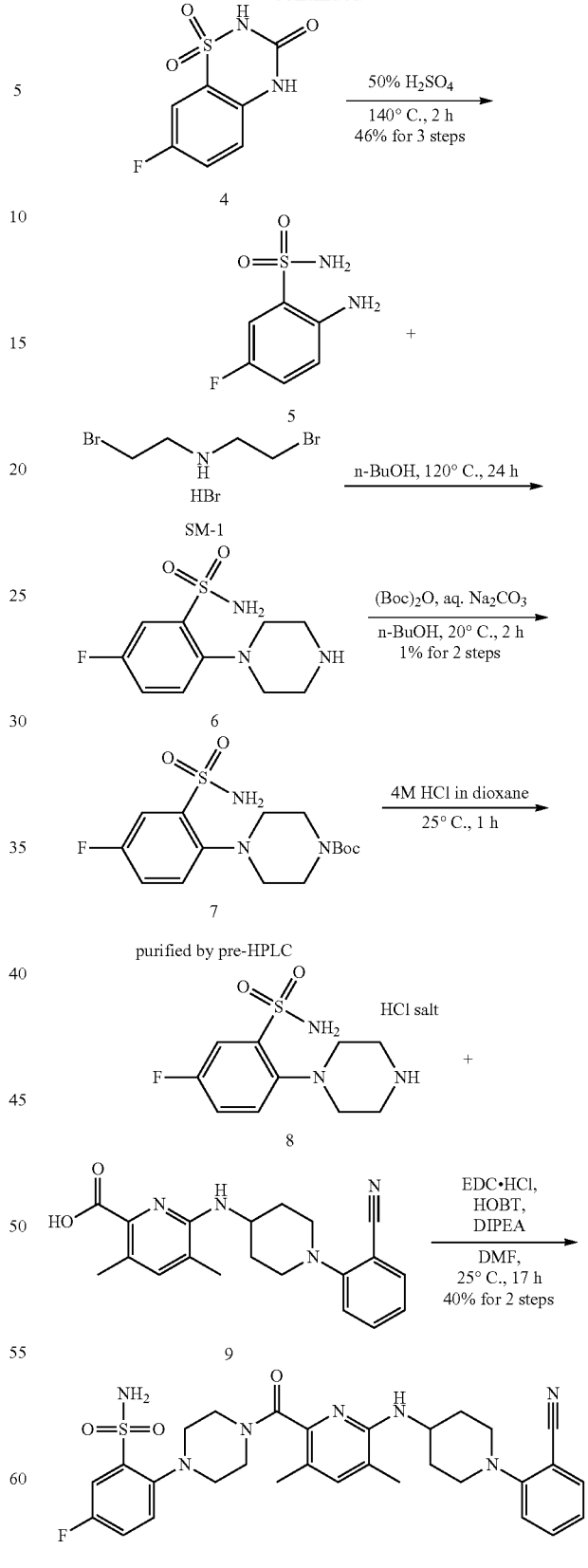

Procedures and Characterization:
The analysis method was following Method B and the separation method was following Method D.

Step 1: 4-Fluorophenylcarbamoylsulfamoyl Chloride

To a solution of N-(oxomethylene) sulfamoyl chloride (5.67 g, 40.05 mmol) in nitroethane (80.00 mL) was added 4-fluoroaniline (4.45 g, 40.05 mmol) at −42° C. The resulting mixture was stirred at −42° C. for 1 h. The reaction mixture was used for the next step directly. MS (EI+, m/z): 155.1 [M-SO$_2$Cl+H]+.

Step 2: 7-Fluoro-3-oxo-3,4-dihydro-2H-1,2,4-benzothiadiazine-1, 1-dioxide

A mixture of N-[(4-fluorophenyl) carbamoyl] sulfamoyl chloride (10.11 g, 40.00 mmol), AiCl$_3$ (6.13 g, 46.00 mmol) and nitroethane (80.00 mL) was stirred at 110° C. for 1 h. The reaction mixture was poured into water (200 mL). The aqueous layer was extracted with EtOAc (150 mL×2). The combined organic layers were dried (Na$_2$SO$_4$), filtered and concentrated under reduced pressure to obtain 7-fluoro-3-oxo-3,4-dihydro-2H-1,2,4-benzothiadiazine-1,1-dioxide (7.50 g, 22.20 mmol, 56% yield, 64% purity) as a yellow solid. MS (EI+, m/z): 216.9 [M+H]+.

Step 3: 2-Amino-5-fluorobenzenesulfonamide

Conc. sulfuric acid (75.00 mL) was added slowly to a mixture of 7-fluoro-3-oxo-3,4-dihydro-2H-1,2,4-benzothiadiazine-1,1-dioxide (7.50 g, 22.20 mmol) in water (75.00 mL). The resulting mixture was stirred at 140° C. for 2 h. The reaction mixture was diluted with water (200 mL). The aqueous layer was neutralized with 40% aqueous NaOH solution (about 100 mL) and extracted with EtOAc (500 mL×2). The combined organic layers were dried (Na$_2$SO$_4$), filtered and concentrated under reduced pressure. The residue was purified by chromatography (silica, ethyl acetate/petroleum ether=1/1) to afford 2-amino-5-fluoro-benzenesulfonamide (3.70 g, 18.48 mmol, 83% yield, 95% purity) as a brown solid. MS (EI+, m/z): 191.0 [M+H]+.

Step 4: 5-Fluoro-2-(piperazin-1-yl)benzenesulfonamide

A mixture of 2-amino-5-fluoro-benzenesulfonamide (950.00 mg, 4.99 mmol), 2-bromo-N-(2-bromoethyl) ethanamine hydrobromide (7.78 g, 24.95 mmol) and n-butyl alcohol (50.00 mL) was stirred at 120° C. for 24 h. The reaction mixture was allowed to cool to rt. Filtered and the filtrate was used for the next step directly. MS (EI+, m/z): 260.2 [M+H]+.

Step 5: tert-Butyl 4-(4-fluoro-2-sulfamoylphenyl)piperazine-1-carboxylate

A mixture of 5-fluoro-2-piperazin-1-yl-benzenesulfonamide (12.71 g, 49.00 mmol), Boc$_2$O (53.47 g, 245.00 mmol), sodium carbonate (31.16 g, 294.00 mmol), and n-butyl alcohol (49.02 mL) in water (149.99 mL) was stirred at 20° C. for 17 h. n-BuOH was removed by evaporation. The aqueous layer was extracted with EtOAc (50 mL×2). The combined EtOAc extracts were dried (Na$_2$SO$_4$), filtered and concentrated under reduced pressure. The residue was purified by chromatography (silica, ethyl acetate/petroleum ether=1/5) to afford 3.5 g crude product. The crude product was purified via preparative HPLC to afford 350 mg crude product. This crude product was purified by Prep-TLC to afford tert-butyl 4-(4-fluoro-2-sulfamoyl-phenyl)piperazine-1-carboxylate (170.00 mg, 132.16 umol, 1% yield, 95% purity) as a white solid. MS (EI+, m/z): 360.1 [M+H]+.

Step 6: 5-Fluoro-2-(piperazin-1-yl)benzenesulfonamide Hydrochloride

A mixture of tert-butyl 4-(4-fluoro-2-sulfamoyl-phenyl)piperazine-1-carboxylate (120.00 mg, 333.87 umol) and 4 M HCl in dioxane (4.17 mL) was stirred at 25° C. for 1 h. The reaction mixture was concentrated under reduced pressure to give 5-fluoro-2-piperazin-1-yl-benzenesulfonamide hydrochloride (95.00 mg, 317.99 umol, 95% yield, and 99% purity) as a white solid. MS (EI+, m/z): 260.2 [M+H]+.

Step 7: 5-Fluoro-2-(piperazin-1-yl)benzenesulfonamide Hydrochloride

Following the amide coupling EDCI/HOBT method to afford 2-[4-[6-[[1-(2-cyanophenyl)-4-piperidyl] amino]-3,5-dimethyl-pyridine-2-carbonyl]piperazin-1-yl]-5-fluoro-benzenesulfonamide I-103 as a white solid. MS (EI+, m/z): 592.3 [M+H]+. $^1$H NMR (500 MHz, DMSO-d$_6$) δ 7.70-7.68 (m, 1H), 7.67-7.53 (m, 3H), 7.47-7.43 (m, 1H), 7.17-7.13 (m, 4H), 7.09-7.06 (m, 1H), 5.64-5.63 (m, 1H), 4.04 (br, 1H), 3.85 (br, 2H), 3.51-3.49 (m, 2H), 3.40-3.38 (m, 2H), 2.95-2.89 (m, 4H), 2.83 (br, 2H), 2.07 (s, 3H), 2.06 (s, 3H), 2.01-1.99 (m, 2H), 1.79-1.71 (m, 2H).

Example 26: Synthesis of 2-(4-(5-(1-(2-cyanophenyl)piperidin-4-ylamino)-4-fluoro-2-methylbenzoyl)piperazin-1-yl)benzenesulfonamide, I-90

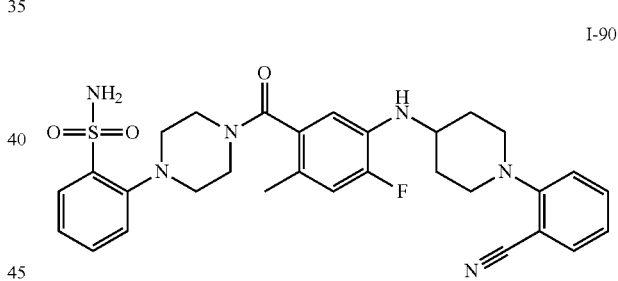

I-90

Synthetic Scheme:

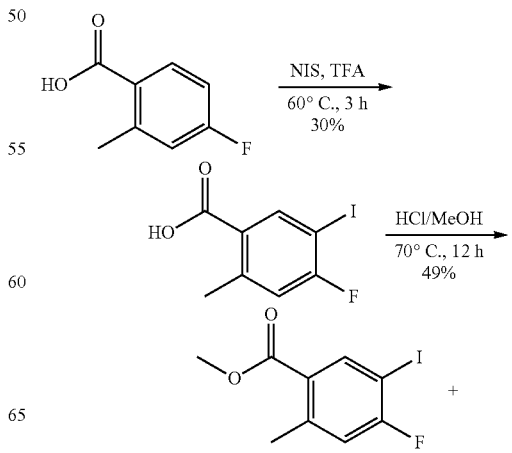

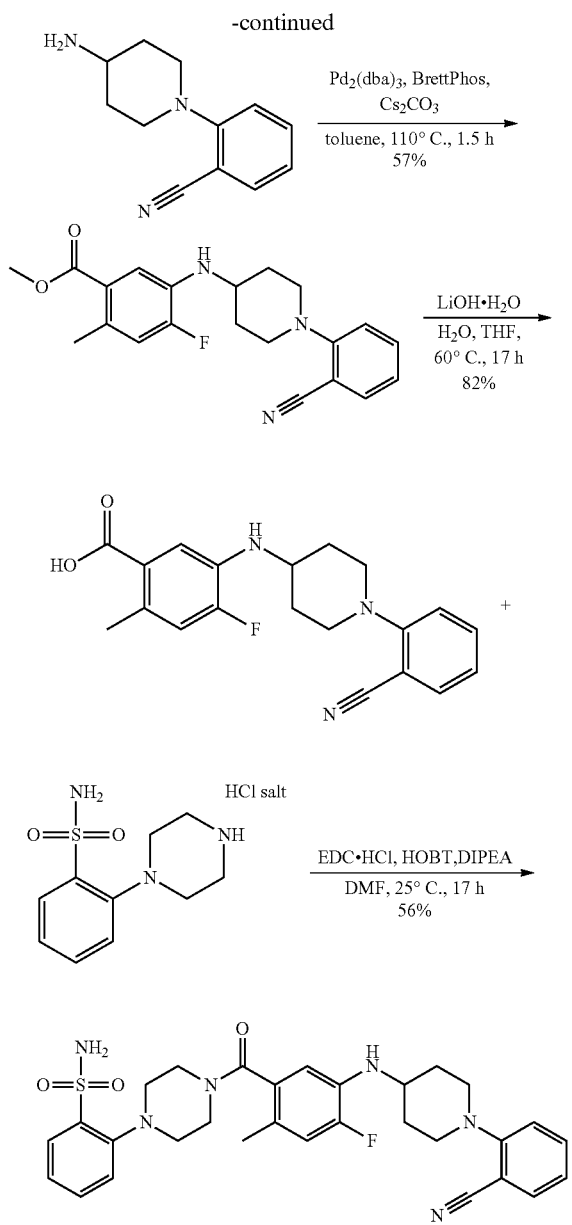

Procedures and Characterization:
The analysis method was following Method B and the separation method was following Method D.

Step 1: 4-Fluoro-5-iodo-2-methylbenzoic Acid

4-Fluoro-2-methyl-benzoic acid (11.00 g, 71.36 mmol) was dissolved in TFA, and the reaction mixture was stirred at 5° C. upon which the NIS (16.86 g, 74.93 mmol) was added in portions. Then the temperature was warmed to 60° C. for 3 h. The reaction mixture was poured into ice water and a precipitate appeared. After filtration of the mixture, the precipitate was triturated with n-hexane to give 4-fluoro-5-iodo-2-methylbenzoic acid (6.00 g, 21.43 mmol, 30% yield) as a pink solid. MS (EI⁻, m/z): 278.9 [M−H]—.

Step 2: Methyl 4-fluoro-5-iodo-2-methylbenzoate

4-Fluoro-5-iodo-2-methyl-benzoic acid (6.00 g, 21.43 mmol) was dissolved in a solution of 3 M HCl in MeOH (50.00 mL) and the reaction mixture was stirred at 70° C. for 12 h. The reaction mixture was concentrated under reduced pressure to give methyl 4-fluoro-5-iodo-2-methylbenzoate (3.10 g, 10.54 mmol, 49% yield) as a yellow solid which was used for the next step without further purification. MS (EI⁺, m/z): 295.0 [M+H]⁺.

Step 3: Methyl 5-(1-(2-cyanophenyl)piperidin-4-ylamino)-4-fluoro-2-methylbenzoate A mixture of methyl 4-fluoro-5-iodo-2-methyl-benzoate (1.00 g, 3.40 mmol), 2-(4-amino-1-piperidyl)benzonitrile (1.03 g, 5.10 mmol), Pd₂(dba)₃ (311.34 mg, 340.00 umol), BrettPhos (365.00 mg, 680.00 umol), and Cs₂CO₃ (2.22 g, 6.80 mmol) in toluene (17.00 mL) was stirred at 110° C. for 1.5 h under a nitrogen atmosphere. The resulting mixture was partitioned between EtOAc (150 mL) and water (100 mL). The layers were separated. The aqueous layer was extracted with EtOAc (150 mL). The combined EtOAc extracts were dried (Na₂SO₄), filtered and concentrated under reduced pressure. The residue was purified by chromatography (silica, ethyl acetate/petroleum ether=1/10) to afford methyl 5-[[1-(2-cyanophenyl)-4-piperidyl]amino]-4-fluoro-2-methyl-benzoate (800.00 mg, 1.96 mmol, 58% yield, 90% purity) as a yellow oil. MS (EI⁺, m/z): 368.0 [M+H]⁺.

Step 4: 5-(1-(2-Cyanophenyl) piperidin-4-ylamino)-4-fluoro-2-methylbenzoic Acid

A mixture of methyl 5-[[1-(2-cyanophenyl)-4-piperidyl]amino]-4-fluoro-2-methyl-benzoate (760.00 mg, 2.07 mmol), lithium hydroxide monohydrate (1.74 g, 41.40 mmol) in THF (21.00 mL) and water (21.00 mL) was stirred at 60° C. for 18 h. THF was removed by evaporation. Water (30 mL) was added. The aqueous layer was extracted with DCM (50 mL). The DCM layer was discarded. The obtained aqueous layer was acidified with 1 N HCl to pH 5 and extracted with 2-methyltetrahydrofuran (50 mL×2). The combined 2-methyltetrahydrofuran layers were dried (Na₂SO₄), filtered and concentrated under reduced pressure to give 5-[[1-(2-cyanophenyl)-4-piperidyl]amino]-4-fluoro-2-methyl-benzoic acid (670.00 mg, 1.71 mmol, 82% yield, 90% purity) as a yellow solid. MS (EI⁺, m/z): 354.0 [M+H]⁺.

Step 5: 2-(4-(5-(1-(2-Cyanophenyl) piperidin-4-ylamino)-4-fluoro-2-methylbenzoyl)piperazin-1-yl)benzenesulfonamide Followed the amide coupling EDCI/HOBT method to afford 2-[4-[5-[[1-(2-cyanophenyl)-4-piperidyl]amino]-4-fluoro-2-methyl-benzoyl]piperazin-1-yl]benzenesulfonamide I-90 as a light-yellow solid. MS (EI⁺, m/z): 577.3 [M+H]+. ¹H NMR (400 MHz, DMSO-d6) δ 7.88-7.86 (m, 1H), 7.70-7.68 (m, 1H), 7.64-7.55 (m, 3H), 7.37-7.33 (m, 1H), 7.18-7.16 (m, 1H), 7.09-7.05 (m, 1H), 6.98-6.95 (m, 3H), 6.66-6.64 (m, 1H), 5.28-5.26 (m, 1H), 3.94-3.73 (m, 2H), 3.56-3.45 (m, 3H), 3.41-3.36 (m, 2H), 3.10-2.76 (m, 7H), 2.12 (s, 3H), 2.02-2.00 (m, 2H), 1.72-1.67 (m, 2H).

Example 27: 2-(4-(3,5-Dimethyl-6-(4-(2-(S-methyl-sulfonimidoyl)phenyl)piperazine-1-carbonyl)pyridin-2-ylamino)piperidin-1-yl)benzonitrile, I-126

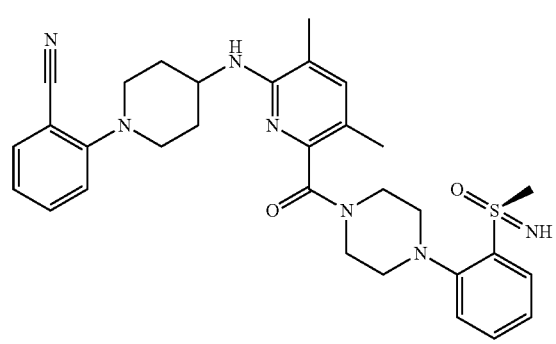

I-126

Synthetic Scheme:

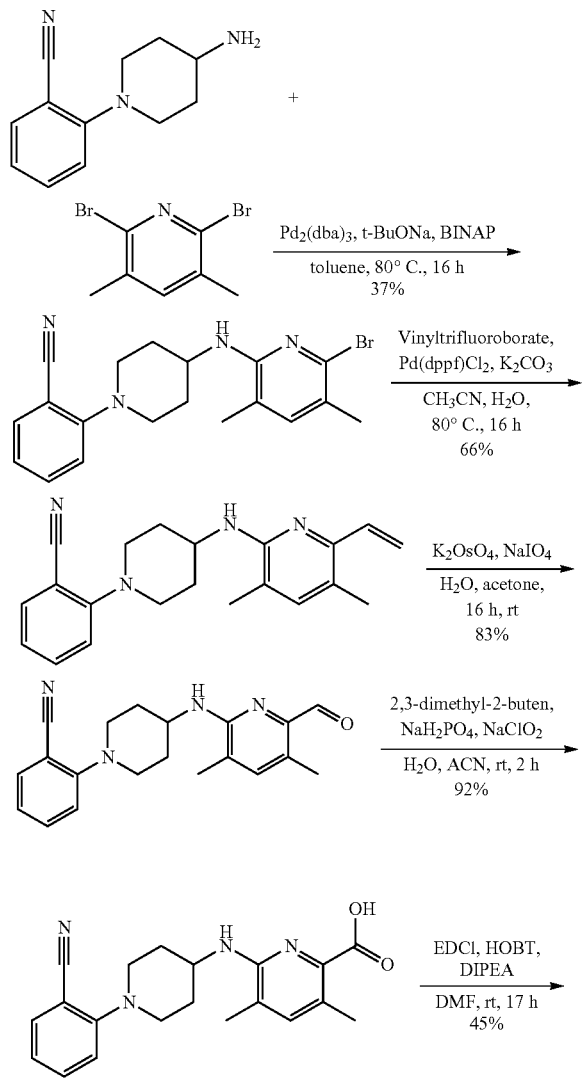

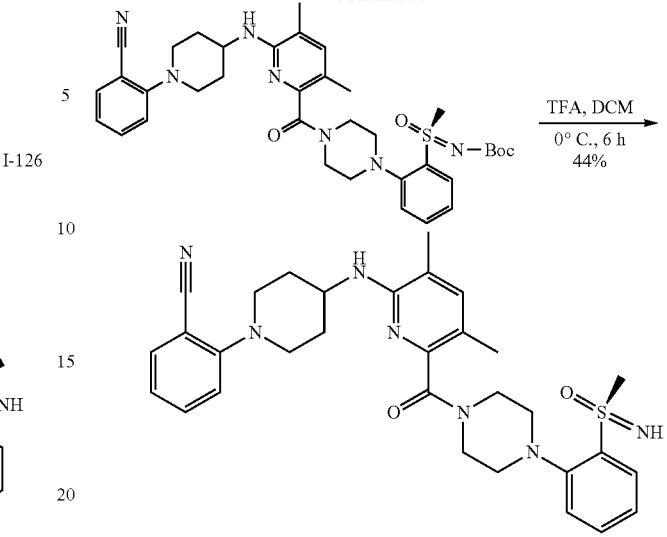

Procedures and Characterization:

The analysis method was following Method B and the separation method was following Method D.

Step 1: 2-(4-(6-Bromo-3,5-dimethylpyridin-2-ylamino)piperidin-1-yl)benzonitrile A mixture of 2-(4-amino-1-piperidyl)benzonitrile (3.00 g, 14.91 mmol), 2,6-dibromo-3,5-dimethyl-pyridine (4.74 g, 17.89 mmol), tBuONa (2.15 g, 22.36 mmol), Pd$_2$(dba)$_3$ (136.53 mg, 149.05 umol) and BINAP (278.43 mg, 447.16 umol) in toluene (50.00 mL) was stirred at 80° C. for 17 h. The mixture was filtered and purified by silica gel chromatography to afford 2-(4-(6-bromo-3,5-dimethylpyridin-2-ylamino)piperidin-1-yl)benzonitrile (2.10 g, 5.45 mmol, 36.55% yield) as product. ESI-MS (EI$^+$, m/z): 385.1 [M+H]$^+$.

Step 2: 2-(4-(3,5-Dimethyl-6-vinylpyridin-2-ylamino)piperidin-1-yl)benzonitrile A mixture of 2-(4-(6-bromo-3,5-dimethylpyridin-2-ylamino)piperidin-1-yl)benzonitrile (2.10 g, 5.45 mmol), potassium vinyltrifluoroborate (1.10 g, 8.18 mmol), K$_2$CO$_3$ (1.51 g, 10.90 mmol) and Pd(dppf)Cl$_2$ (199.40 mg, 272.50 umol) in H$_2$O (5.00 mL) and CH$_3$CN (20 mL) was stirred at 80° C. for 17 h. The mixture was washed with water and extracted with EtOAc (100 mL). The organic layer was purified by SGC to obtain 2-(4-(3,5-dimethyl-6-vinylpyridin-2-ylamino)piperidin-1-yl)benzonitrile (1.20 g, 3.61 mmol, 66.23% yield). ESI-MS (EI$^+$, m/z): 333.3 [M+H]$^+$.

Step 3: 2-(4-(6-Formyl-3,5-dimethylpyridin-2-ylamino)piperidin-1-yl)benzonitrile A mixture of 2-(4-(3,5-dimethyl-6-vinylpyridin-2-ylamino)piperidin-1-yl)benzonitrile (1.20 g, 3.61 mmol), K$_2$OsO$_4$ (66.42 mg, 180.50 umol) and NMO (845.82 mg, 7.22 mmol) in H$_2$O (20.00 mL) and acetone (40.00 mL) was stirred at 20° C. for 16 h. The mixture was extracted with EtOAc and purified by SGC to obtain 2-(4-(6-formyl-3,5-dimethylpyridin-2-ylamino)piperidin-1-yl)benzonitrile (1.00 g, 2.99 mmol, 82.83% yield) as product. ESI-MS (EI$^+$, m/z): 335.3 [M+H]$^+$.

Step 4: 6-[[1-(2-Cyanophenyl)-4-piperidyl]amino]-3,5-dimethyl-pyridine-2-carboxylic Acid A mixture of 2-[4-[(6-formyl-3,5-dimethyl-2-pyridyl)amino]-1-piperidyl]benzonitrile (350.00 mg, 1.05 mmol), 2-methyl-2-butene (147.27 mg, 2.10 mmol), NaH$_2$PO$_4$ (252.00 mg, 2.10 mmol) and NaClO$_2$ (189.92 mg, 2.10 mmol) in H$_2$O (2.00 mL) and CH$_3$CN (25.00 mL) was stirred at 20° C. for 16 h. The mixture was extracted with EtOAc and purified via preparative HPLC to afford 6-[[1-(2-cyanophenyl)-4-piperidyl]amino]-3,5-dimethyl-pyridine-2-carboxylic acid (340.00 mg, 970.29 umol, 92.41% yield) as product. ESI-MS (EI$^+$, m/z): 351.3 [M+H]$^+$.

Step 5: tert-Butyl N-[[2-[4-[6-[[1-(2-cyanophenyl)-4-piperidyl]amino]-3,5-dimethyl-pyridine-2-carbonyl]piperazin-1-yl]phenyl]-methyl-oxo-{6}-sulfanylidene]carbamate A mixture of tert-butyl N-[methyl-oxo-(2-piperazin-1-ylphenyl)-{6}-sulfanylidene]carbamate (100.00 mg, 294.59 umol), 6-[[1-(2-cyanophenyl)-4-piperidyl]amino]-3,5-dimethyl-pyridine-2-carboxylic acid (103.23 mg, 294.59 umol), EDCI (84.71 mg, 441.89 umol), HOBT (59.71 mg, 441.89 umol) and DIPEA (114.22 mg, 883.78 umol, 154.35 uL) in DMF (5 mL) was stirred at 20° C. for 16 h. The mixture was purified via preparative HPLC to afford tert-butyl N-[[2-[4-[6-[[1-(2-cyanophenyl)-4-piperidyl]amino]-3,5-dimethyl-pyridine-2-carbonyl]piperazin-1-yl]phenyl]-methyl-oxo-{6}-sulfanylidene]carbamate (90.00 mg, 133.96 umol, 45.47% yield) as product. ESI-MS (EI$^+$, m/z): 672.3 [M+H]$^+$.

Step 6: 2-(4-(3,5-Dimethyl-6-(4-(2-(S-methylsulfonimidoyl)phenyl)piperazine-1-carbonyl)pyridin-2-ylamino)piperidin-1-yl)benzonitrile A mixture of tert-butyl N-[[2-[4-[6-[[1-(2-cyanophenyl)-4-piperidyl]amino]-3,5-dimethyl-pyridine-2-carbonyl]piperazin-1-yl]phenyl]-methyl-oxo-{6}-sulfanylidene]carbamate (80.00 mg, 119.07 umol) in TFA (2.00 mL) and DCM (6.00 mL) was stirred at 0° C. for 6 h. The mixture was purified via preparative HPLC to afford 2-(4-(3,5-dimethyl-6-(4-(2-(S-methylsulfonimidoyl)phenyl)piperazine-1-carbonyl)pyridin-2-ylamino)piperidin-1-yl)benzonitrile I-126 (30.00 mg, 52.47 umol, 44.07% yield) as product. The stereochemistry was arbitrarily assigned. ESI-MS (EI$^+$, m/z): 572.3 [M+H]$^+$. $^1$H NMR (500 MHz, CDCl$_3$) δ 8.05 (dd, J=7.9, 1.5 Hz, 1H), 7.60-7.53 (m, 2H), 7.48 (dd, J=12.4, 5.0 Hz, 1H), 7.40-7.32 (m, 2H), 7.11 (s, 1H), 7.01 (dd, J=14.2, 7.7 Hz, 2H), 4.24-4.12 (m, 1H), 3.98 (d, J=7.6 Hz, 1H), 3.56 (d, J=12.2 Hz, 2H), 3.49 (s, 2H), 3.43 (s, 3H), 3.16 (s, 2H), 2.99 (dd, J=20.3, 8.5 Hz, 5H), 2.23 (d, J=10.8 Hz, 2H), 2.19 (s, 3H), 2.07 (s, 3H), 1.72 (qd, J=11.8, 3.9 Hz, 2H).

Example 28: 2-(4-(6-(1-(2-Cyanophenyl)piperidin-4-ylamino)-3,5-dimethylpicolinoyl)piperazin-1-yl)benzenesulfonamide, I-66

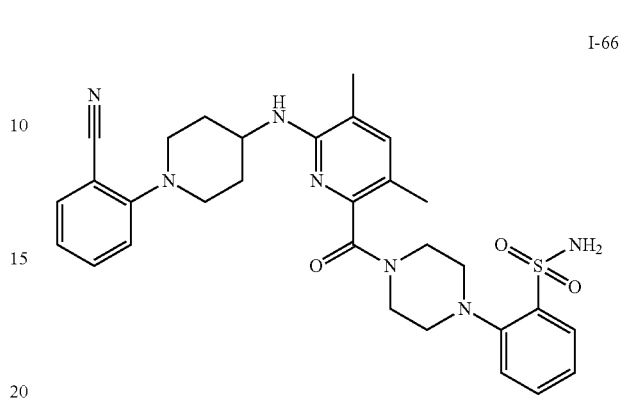

I-66

Synthetic Scheme:

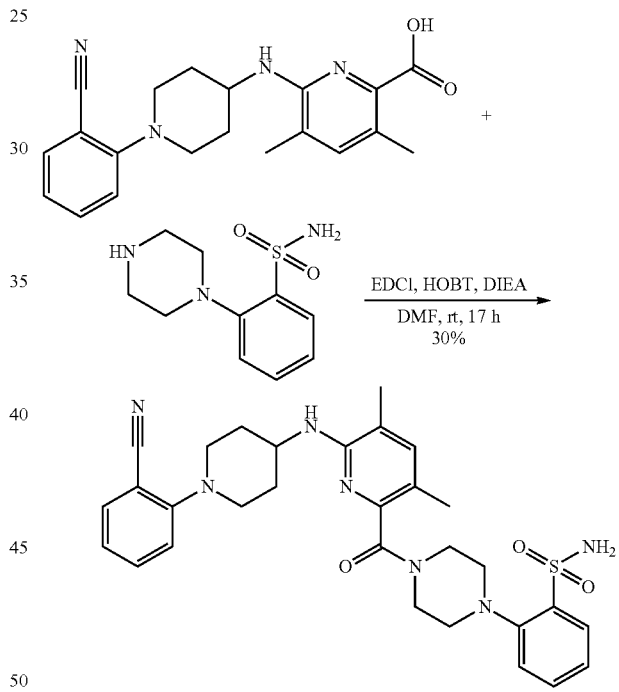

Procedures and Characterization:
The procedure was similar to that of example 27.
The analysis method was following Method B and the separation method was following Method D.

2-(4-(6-(1-(2-Cyanophenyl)piperidin-4-ylamino)-3,5-dimethylpicolinoyl)piperazin-1-yl)benzenesulfonamide ESI-MS (EI$^+$, m/z): 574.3 [M+H]$^+$. $^1$H NMR (500 MHz, CDCl$_3$) δ 8.04 (dd, J=7.9, 1.5 Hz, 1H), 7.69-7.53 (m, 2H), 7.52-7.45 (m, 1H), 7.39 (d, J=8.0 Hz, 1H), 7.35 (t, J=7.6 Hz, 1H), 7.11 (s, 1H), 7.08-6.94 (m, 2H), 5.56 (s, 2H), 4.25-4.08 (m, 1H), 4.00 (d, J=7.7 Hz, 1H), 3.54 (t, J=13.6 Hz, 4H), 3.18 (s, 2H), 2.99 (dd, J=19.5, 8.9 Hz, 3H), 2.23 (s, 2H), 2.19 (s, 3H), 2.07 (s, 3H), 1.73 (qd, J=11.6, 3.7 Hz, 2H).

Example 29: (S)-2-(4-(6-(1-(2-Cyanophenyl)piperidin-4-ylamino)-3,5-dimethylpicolinoyl)-3-methylpiperazin-1-yl)benzenesulfonamide, I-26

I-26

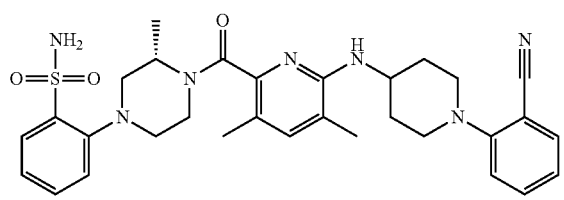

Synthetic Scheme:

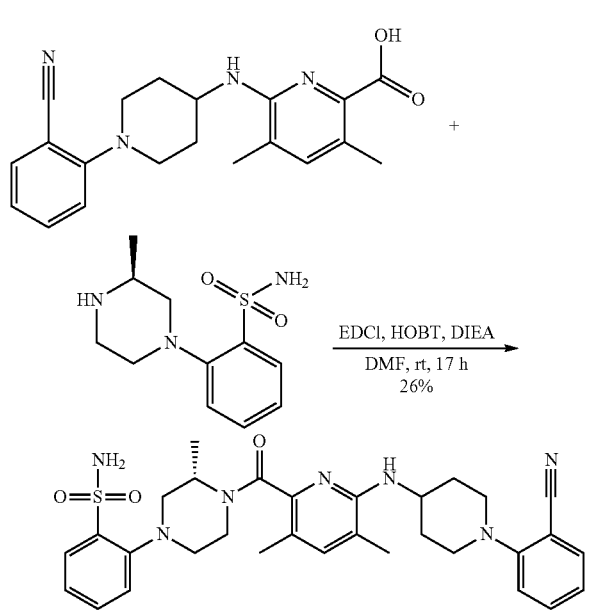

Procedures and Characterization:

The procedure was same as the procedure of example 27.

The analysis method was following Method B and the separation method was following Method D.

(S)-2-(4-(6-(1-(2-Cyanophenyl)piperidin-4-ylamino)-3,5-dimethylpicolinoyl)-3-methylpiperazin-1-yl)benzenesulfonamide ESI-MS (EI+, m/z): 588.3 [M+H]+. $^1$H NMR (500 MHz, CDCl$_3$) δ 8.03 (dd, J=7.9, 1.3 Hz, 1H), 7.62-7.53 (m, 2H), 7.48 (dd, J=10.7, 4.9 Hz, 1H), 7.41 (d, J=8.0 Hz, 1H), 7.33 (td, J=7.7, 2.6 Hz, 1H), 7.11 (d, J=13.1 Hz, 1H), 7.06-6.96 (m, 2H), 5.63 (s, 2H), 5.23-4.70 (m, 1H), 4.26-4.09 (m, 1H), 4.01 (t, J=7.5 Hz, 1H), 3.93 (s, 0.5H), 3.63-3.49 (m, 2.5H), 3.46 (d, J=13.6 Hz, 0.5H), 3.30 (dt, J=11.6, 7.3 Hz, 2H), 3.16-3.07 (m, 1H), 3.06-2.87 (m, 3H), 2.69 (td, J=11.4, 2.9 Hz, 0.5H), 2.25-2.13 (m, 5H), 2.07 (d, J=6.1 Hz, 3H), 1.82-1.63 (m, 2H), 1.58-1.46 (m, 3H).

Example 30: 2-(4-(6-(1-(2-Cyanophenyl)piperidin-4-ylamino)-3,5-dimethylpicolinoyl)piperazin-1-yl)-6-fluorobenzenesulfonamide, I-16

I-16

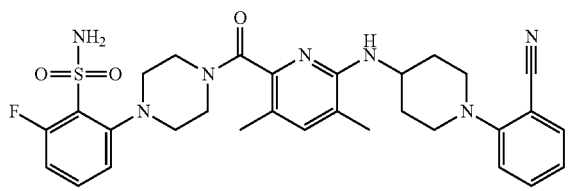

Synthetic Scheme:

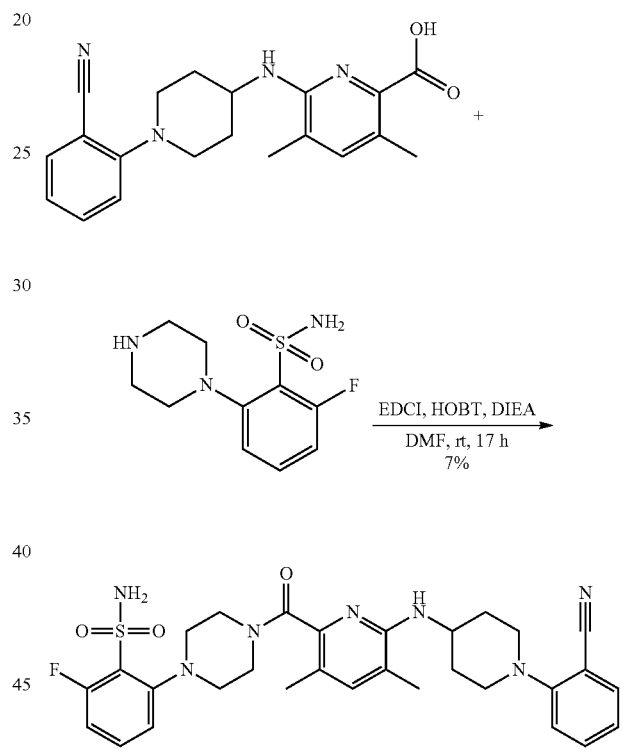

Procedures and Characterization:

The procedure was same as example the procedure of example 27.

The analysis method was following Method B and the separation method was following Method D.

2-(4-(6-(1-(2-Cyanophenyl)piperidin-4-ylamino)-3,5-dimethylpicolinoyl)piperazin-1-yl)-6-fluorobenzenesulfonamide ESI-MS (EI+, m/z): 592.3 [M+H]+. $^1$H NMR (400 MHz, CDCl$_3$) δ 7.56 (dd, J=7.6, 1.5 Hz, 1H), 7.53-7.45 (m, 2H), 7.12 (d, J=7.8 Hz, 2H), 7.08-6.94 (m, 3H), 5.85 (s, 2H), 4.22-4.07 (m, 1H), 4.00 (d, J=7.5 Hz, 1H), 3.56 (m, 5H), 3.18 (s, 2H), 2.99 (t, J=11.4 Hz, 4H), 2.20 (m, 5H), 2.07 (s, 3H), 1.79-1.66 (m, 2H).

Example 31: 2-(4-(6-(1-(2-Cyanophenyl)piperidin-4-ylamino)-3,5-dimethylpicolinoyl)piperazin-1-yl)pyridine-3-sulfonamide, I-25

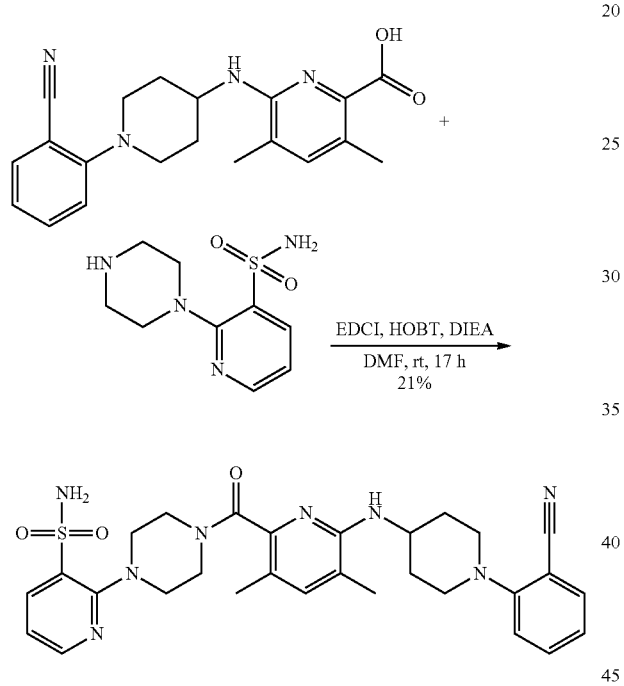

Synthetic Scheme:

Procedures and Characterization:

The procedure was same as example the procedure of example 27.

The analysis method was following Method B and the separation method was following Method D.

2-(4-(6-(1-(2-Cyanophenyl)piperidin-4-ylamino)-3,5-dimethylpicolinoyl)piperazin-1-yl)pyridine-3-sulfonamide ESI-MS (EI$^+$, m/z): 575.3 [M+H]$^+$. $^1$H NMR (500 MHz, CDCl$_3$) δ 8.53 (d, J=3.8 Hz, 1H), 8.30 (d, J=7.5 Hz, 1H), 7.55 (d, J=7.6 Hz, 1H), 7.48 (t, J=7.7 Hz, 1H), 7.25 (d, J=5.0 Hz, 1H), 7.10 (s, 1H), 7.04 (d, J=8.3 Hz, 1H), 6.99 (t, J=7.5 Hz, 1H), 5.61 (s, 2H), 4.16 (d, J=6.7 Hz, 1H), 4.01 (d, J=7.1 Hz, 3H), 3.56 (d, J=11.8 Hz, 2H), 3.51 (s, 2H), 3.35 (s, 2H), 3.21 (s, 2H), 3.02 (t, J=11.3 Hz, 2H), 2.22 (d, J=11.3 Hz, 2H), 2.18 (s, 3H), 2.07 (s, 3H), 1.74 (dd, J=22.1, 11.0 Hz, 2H).

Example 32: 2-(4-(5-(1-(2-Cyanophenyl)azetidin-3-ylamino)-2,4-dimethylbenzoyl) piperazin-1-yl)benzenesulfonamide, I-130

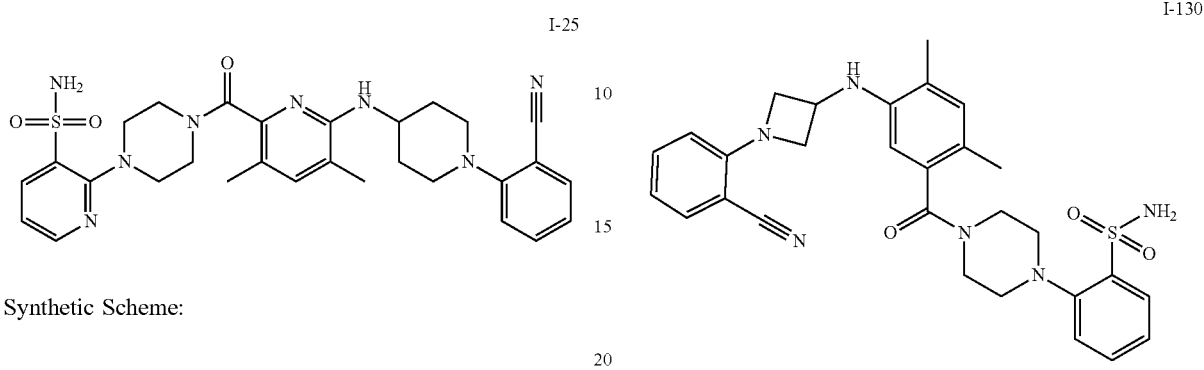

Synthetic Scheme:

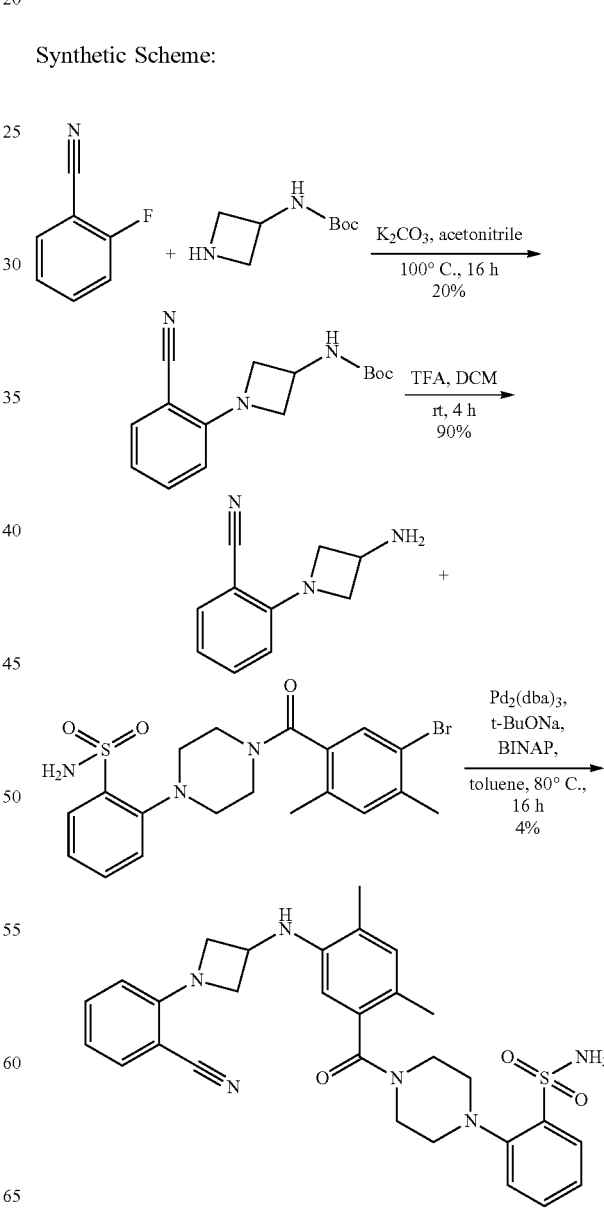

Procedures and Characterization:
The analysis method was following Method B and the separation method was following Method D.

Step 1: tert-Butyl N-[1-(2-cyanophenyl)azetidin-3-yl]carbamate

A mixture of 2-fluorobenzonitrile (1.50 g, 12.39 mmol), tert-butyl N-(azetidin-3-yl)carbamate (2.35 g, 13.63 mmol) and K$_2$CO$_3$ (3.44 g, 24.78 mmol) in CH$_3$CN (50.00 mL) was stirred at 100° C. for 16 h. The mixture was purified by SGC (EtOAc:PE=1:5) to afford tert-butyl N-[1-(2-cyanophenyl)azetidin-3-yl]carbamate (680.00 mg, 2.49 mmol, 20.08% yield) as product. ESI-MS (EI$^+$, m/z): 274.1 [M+H]$^+$.

Step 2: 2-(3-Aminoazetidin-1-yl)benzonitrile

A mixture of tert-butyl N-[1-(2-cyanophenyl)azetidin-3-yl]carbamate (700.00 mg, 2.56 mmol) in TFA (5.00 mL) and DCM (5.00 mL) was stirred at 20° C. for 4 h. The mixture was concentrated to afford 2-(3-aminoazetidin-1-yl)benzonitrile (440.00 mg, 2.54 mmol, 99.23% yield) as product. ESI-MS (EI$^+$, m/z): 174.1 [M+H]$^+$.

Step 3: 2-(4-(5-(1-(2-Cyanophenyl)azetidin-3-ylamino)-2,4-dimethylbenzoyl)piperazin-1-yl)benzenesulfonamide A mixture of 2-(3-aminoazetidin-1-yl)benzonitrile (100.00 mg, 577.33 umol), 2-[4-(5-bromo-2,4-dimethyl-benzoyl)piperazin-1-yl]benzenesulfonamide (313.40 mg, 692.80 umol), tBuONa (83.14 mg, 866.00 umol), Pd$_2$(dba)$_3$ (5.29 mg, 5.77 umol) and BINAP (10.78 mg, 17.32 umol) in toluene (5.00 mL) was stirred at 80° C. for 17 h. The mixture was filtered and purified via preparative HPLC to afford 2-[4-[5-[[1-(2-cyanophenyl)azetidin-3-yl]amino]-2,4-dimethyl-benzoyl]piperazin-1-yl]benzenesulfonamide I-130 (10.00 mg, 18.36 umol, 3.18% yield) as product. ESI-MS (EI$^+$, m/z): 545.2 [M+H]$^+$. $^1$H NMR (500 MHz, CDCl$_3$) δ 8.04 (d, J=7.8 Hz, 1H), 7.61 (t, J=7.0 Hz, 1H), 7.45-7.32 (m, 4H), 6.96 (s, 1H), 6.74 (t, J=7.4 Hz, 1H), 6.46 (d, J=8.1 Hz, 1H), 6.23 (s, 1H), 5.52 (s, 2H), 4.71 (s, 1H), 4.56 (s, 1H), 4.38 (s, 1H), 4.06 (s, 1H), 3.92 (s, 1H), 3.87 (d, J=6.2 Hz, 1H), 3.49 (s, 2H), 3.18 (s, 4H), 2.23 (s, 3H), 2.16 (s, 3H).

Example 33: 2-(4-(5-(3-(2-Cyanophenyl)-3-azabicyclo[3.1.0]hexan-6-ylamino)-2,4-dimethylbenzoyl)piperazin-1-yl)benzenesulfonamide, I-132

I-132

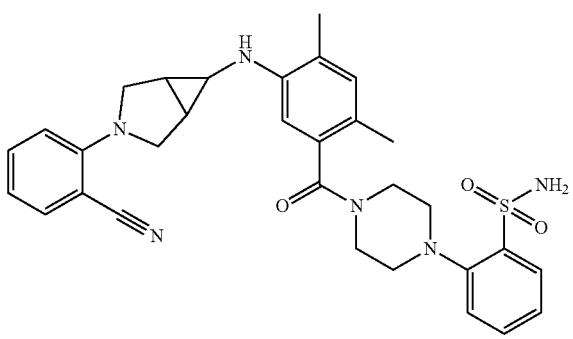

Synthetic Scheme:

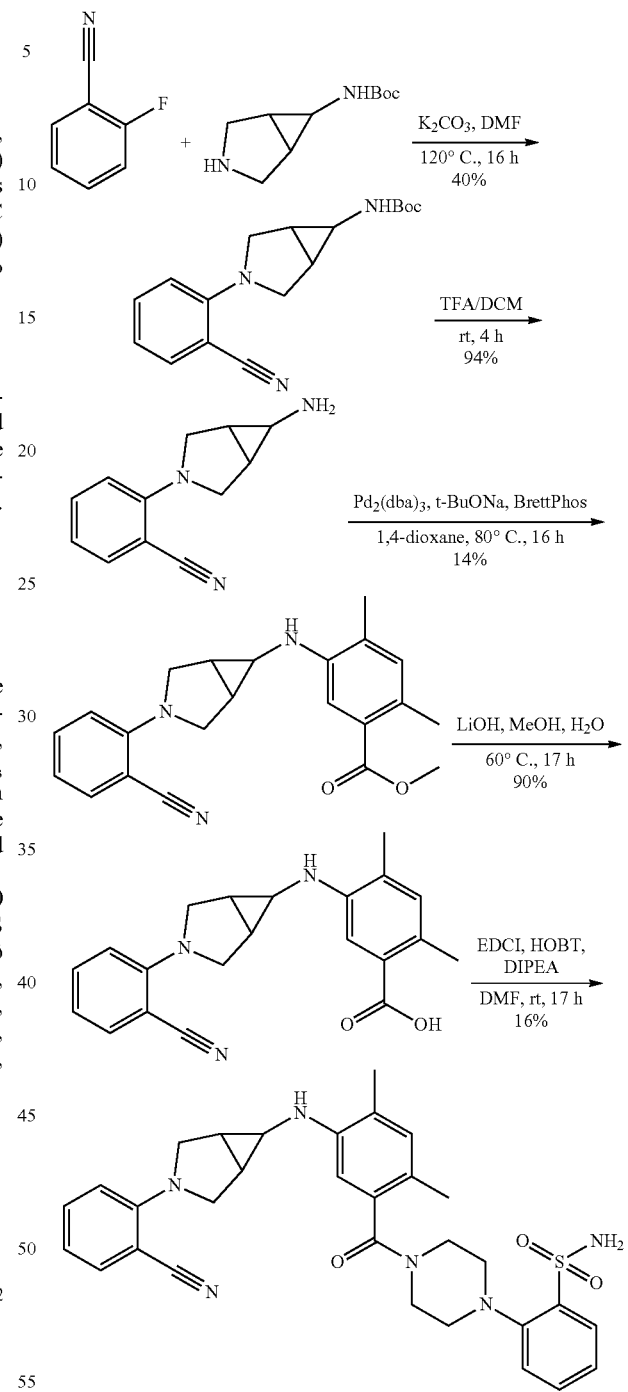

Procedures and Characterization:
The analysis method was following Method B and the separation method was following Method D.

Step 1: 2-(6-Amino-3-azabicyclo[3.1.0]hexan-3-yl)benzonitrile

A mixture of tert-butyl N-[3-(2-cyanophenyl)-3-azabicyclo[3.1.0]hexan-6-yl]carbamate (400.00 mg, 1.34 mmol) in TFA (10.00 mL) and DCM (10.00 mL) was stirred at 20° C. for 4 h. The mixture was concentrated to afford 2-(6-amino- 3-azabicyclo[3.1.0]hexan-3-yl)benzonitrile (250.00 mg, 1.25 mmol, 93.63% yield) as product. ESI-MS (EI+, m/z): 200.1 [M+H]+.

Step 2: Methyl 5-(3-(2-cyanophenyl)-3-azabicyclo [3.1.0]hexan-6-ylamino)-2,4-dimethylbenzoate A mixture of 2-(6-amino-3-azabicyclo[3.1.0]hexan-3-yl) benzonitrile (20.00 mg, 100.38 umol), methyl 5-bromo-2, 4-dimethyl-benzoate (24.40 mg, 100.38 umol), tBuONa (14.45 mg, 150.56 umol), Pd$_2$(dba)$_3$ (1.84 mg, 2.01 umol) and BrettPhos (2.16 mg, 4.02 umol) in toluene (5.00 mL) was stirred at 80° C. for 17 h. The mixture was filtered and purified by SGC to get methyl 5-[[3-(2-cyanophenyl)-3-azabicyclo[3.1.0]hexan-6-yl]amino]-2,4-dimethyl-benzoate (5.00 mg, 13.83 umol, 13.78% yield) as product. ESI-MS (EI+, m/z): 362.2 [M+H]+.

Step 3: 5-[[3-(2-Cyanophenyl)-3-azabicyclo[3.1.0] hexan-6-yl]amino]-2,4-dimethyl-benzoic Acid A mixture of methyl 5-[[3-(2-cyanophenyl)-3-azabicyclo [3.1.0]hexan-6-yl]amino]-2,4-dimethyl-benzoate (40.00 mg, 110.67 umol) and LiOH (21.20 mg, 885.36 umol) in MeOH (5.00 mL) and H$_2$O (499.95 uL) was stirred at 60° C. for 17 h. The mixture was extracted with EtOAc after adjusting the pH to 4. The organic layers were concentrated to afford 5-[[3-(2-cyanophenyl)-3-azabicyclo[3.1.0]hexan-6-yl]amino]-2,4-dimethyl-benzoic acid (36.00 mg, 103.62 umol, 93.63% yield) as product. ESI-MS (EI+, m/z): 348.3 [M+H]+.

Step 4: 2-(4-(5-(3-(2-Cyanophenyl)-3-azabicyclo [3.1.0]hexan-6-ylamino)-2,4-dimethylbenzoyl)piperazin-1-yl)benzenesulfonamide Followed the amide coupling EDCI/HOBT method to afford 2-[4-[5-[[3-(2-cyanophenyl)-3-azabicyclo[3.1.0] hexan-6-yl]amino]-2,4-dimethyl-benzoyl]piperazin-1-yl] benzenesulfonamide, I-132. ESI-MS (EI+, m/z): 571.3 [M+H]+. $^1$H NMR (500 MHz, CDCl$_3$) δ 8.02 (d, J=7.8 Hz, 1H), 7.58 (t, J=7.6 Hz, 1H), 7.48 (d, J=7.8 Hz, 2H), 7.38 (t, J=7.9 Hz, 1H), 7.33 (t, J=7.6 Hz, 1H), 6.92 (s, 1H), 6.75 (t, J=7.5 Hz, 1H), 6.71-6.64 (m, 2H), 5.55 (s, 2H), 4.13 (s, 2H), 3.96 (s, 1H), 3.77-3.47 (m, 4H), 3.06 (m, 5H), 2.38 (s, 1H), 2.23 (s, 3H), 2.09 (s, 3H), 1.91 (s, 2H).

Example 34: 2-(4-(5-(1-(2-Cyanophenyl)piperidin-4-ylamino)-4-methoxy-2-methylbenzoyl)piperazin-1-yl)benzenesulfonamide, I-127

I-127

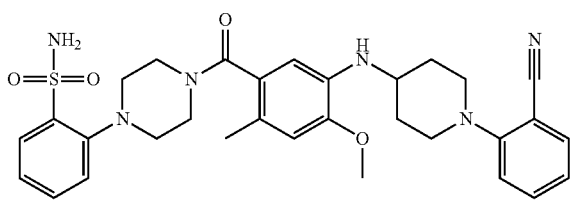

Synthetic Scheme:

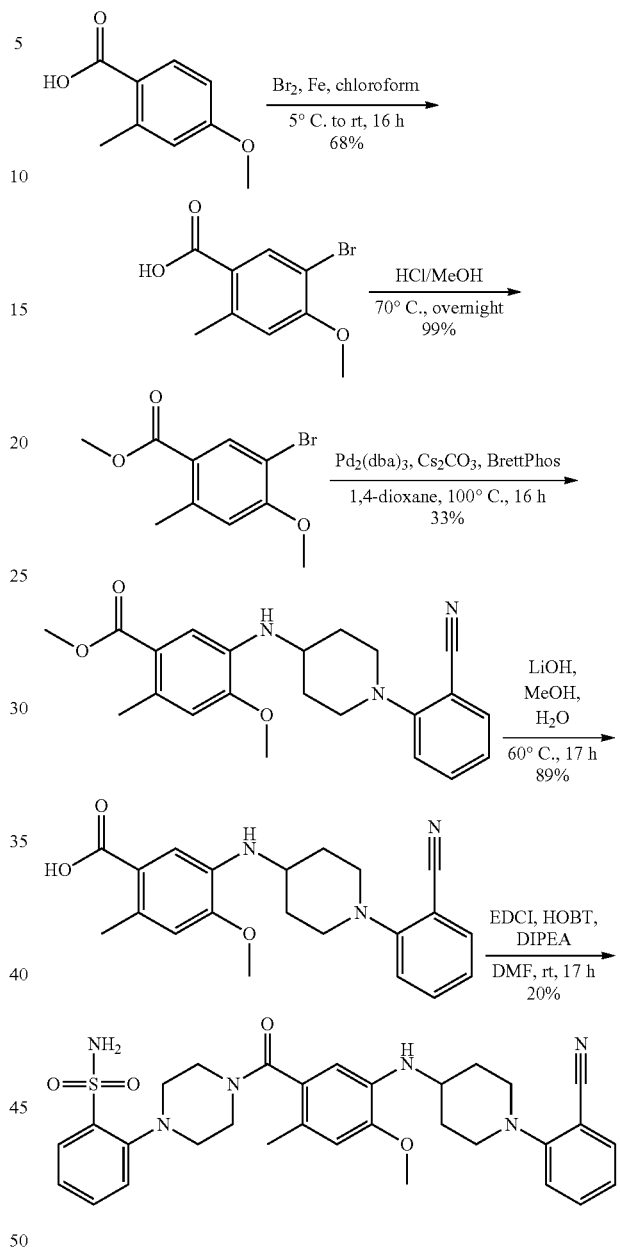

Procedures and Characterization:

The analysis method was following Method B and the separation method was following Method D.

Step 1: 5-Bromo-4-methoxy-2-methyl-benzoic Acid

To a solution of 4-methoxy-2-methyl-benzoic acid (1.00 g, 6.02 mmol) and Fe (672.20 mg, 12.04 mmol) in chloroform (20 mL) was added bromine (1.06 g, 6.62 mmol) at 5° C., and the mixture was stirred at rt for 16 h. Then the pH was adjusted to 3~4 and the mixture was extracted with EtOAc. The organic layers were concentrated to afford 5-bromo-4-methoxy-2-methyl-benzoic acid (1.00 g, 4.08 mmol, 67.78% yield) as product. ESI-MS (EI+, m/z): 245 [M+H]+.

Step 2: Methyl 5-bromo-4-methoxy-2-methyl-benzoate

A mixture of 5-bromo-4-methoxy-2-methyl-benzoic acid (950.00 mg, 3.88 mmol) in HCl/MeOH (10.00 mL) was stirred at 70° C. for 16 h. The mixture was concentrated to afford methyl 5-bromo-4-methoxy-2-methyl-benzoate (1.00 g, 3.86 mmol, 99.47% yield) as product. ESI-MS (EI+, m/z): 259 [M+H]+.

Step 3: Methyl 5-[[1-(2-cyanophenyl)-4-piperidyl]amino]-4-methoxy-2-methyl-benzoate A mixture of 2-(4-amino-1-piperidyl)benzonitrile (1.10 g, 5.47 mmol), methyl 5-bromo-4-methoxy-2-methyl-benzoate (944.04 mg, 3.65 mmol), tBuONa (700.29 mg, 7.29 mmol), Pd$_2$(dba)$_3$ (66.75 mg, 72.93 umol) and BrettPhos (78.26 mg, 145.87 umol) in 1,4-dioxane (70.00 mL) was stirred at 90° C. for 17 h. The mixture was purified by SGC (EtOAc:PE=1:10) to afford methyl 5-[[1-(2-cyanophenyl)-4-piperidyl]amino]-4-methoxy-2-methyl-benzoate (450.00 mg, 1.19 mmol, 32.52% yield) as product. ESI-MS (EI+, m/z): 380.2 [M+H]+.

Step 4: 5-[[1-(2-Cyanophenyl)-4-piperidyl]amino]-4-methoxy-2-methyl-benzoic Acid A mixture of methyl 5-[[1-(2-cyanophenyl)-4-piperidyl]amino]-4-methoxy-2-methyl-benzoate (410.00 mg, 1.08 mmol) and LiOH (207.03 mg, 8.64 mmol) in MeOH (5.00 mL) and H$_2$O (0.5 mL) was stirred at 60° C. for 17 h. The mixture was extracted with EtOAc after adjusting the pH value to 4. The organic layers were concentrated to afford 5-[[1-(2-cyanophenyl)-4-piperidyl]amino]-4-methoxy-2-methyl-benzoic acid (350.00 mg, 957.80 umol, 88.69% yield) as product. ESI-MS (EI+, m/z): 366.0 [M+H]+.

Step 5: 2-[4-[5-[[1-(2-Cyanophenyl)-4-piperidyl]amino]-4-methoxy-2-methyl-benzoyl]piperazin-1-yl]benzenesulfonamide Followed the amide coupling EDCI/HOBT method to afford 2-[4-[5-[[1-(2-cyanophenyl)-4-piperidyl]amino]-4-methoxy-2-methyl-benzoyl]piperazin-1-yl]benzenesulfonamide, I-127. ESI-MS (EI+, m/z): 589.3 [M+H]+. $^1$H NMR (500 MHz, CDCl$_3$) δ 8.04 (dd, J=7.9, 1.5 Hz, 1H), 7.60 (td, J=7.9, 1.6 Hz, 1H), 7.56 (dd, J=7.7, 1.5 Hz, 1H), 7.51-7.45 (m, 1H), 7.40-7.32 (m, 2H), 7.07-6.96 (m, 2H), 6.60 (s, 1H), 6.48 (s, 1H), 5.53 (s, 2H), 4.16 (d, J=7.3 Hz, 1H), 3.85 (s, 3H), 3.60 (s, 1H), 3.48 (d, J=32.2 Hz, 4H), 3.17 (s, 2H), 2.99 (s, 3H), 2.23 (m, 5H), 1.73 (d, J=40.3 Hz, 2H).

Example 35: 2-(4-(5-(1-(2-Cyanophenyl)piperidin-4-ylamino)-2-methoxy-4-methylbenzoyl)piperazin-1-yl)benzenesulfonamide, I-105

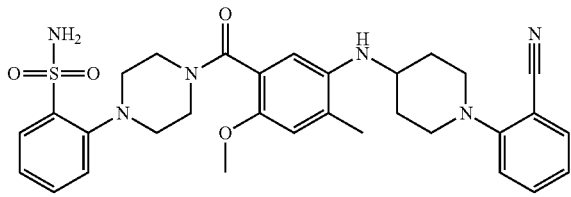

I-105

Synthetic Scheme:

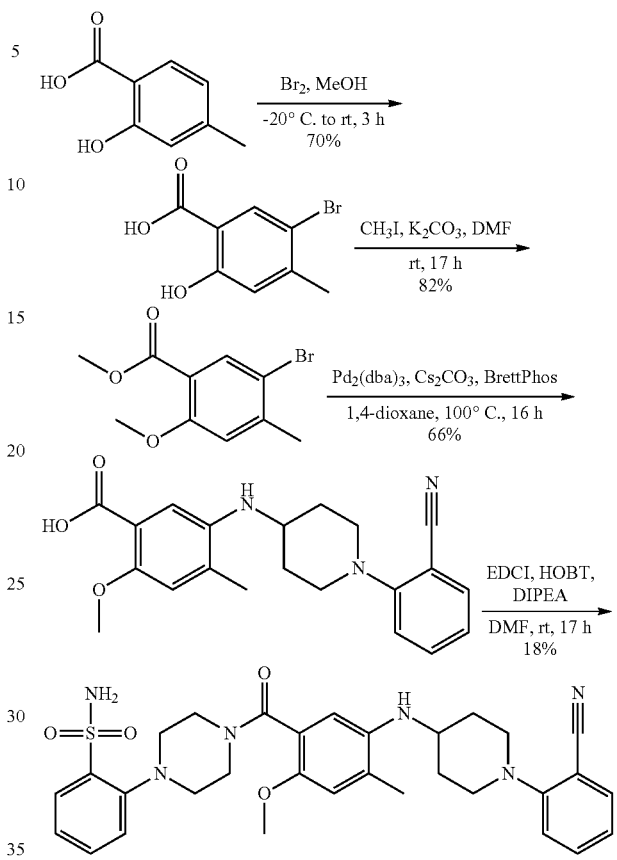

Procedures and Characterization:
The analysis method was following Method B and the separation method was following Method D.

Step 1: 5-[[1-(2-Cyanophenyl)-4-piperidyl]amino]-2-methoxy-4-methyl-benzoi

A mixture of 2-(4-amino-1-piperidyl)benzonitrile (1.10 g, 5.47 mmol), methyl 5-bromo-2-methoxy-4-methyl-benzoate (944.84 mg, 3.65 mmol), Cs$_2$CO$_3$ (700.29 mg, 7.29 mmol), Pd$_2$(dba)$_3$ (66.75 mg, 72.93 umol) and BrettPhos (78.26 mg, 145.87 umol) in 1,4-dioxane (20.00 mL) was stirred at 90° C. for 17 h. The mixture was purified by SGC (EtOAc:PE=1:10) to afford 5-[[1-(2-cyanophenyl)-4-piperidyl]amino]-2-methoxy-4-methyl-benzoic acid (880.00 mg, 2.41 mmol, 66.04% yield) as product. ESI-MS (EI+, m/z): 366.0 [M+H]+.

Step 2: 2-[4-[5-[[1-(2-Cyanophenyl)-4-piperidyl]amino]-2-methoxy-4-methyl-benzoyl]piperazin-1-yl]benzenesulfonamide Followed the amide coupling EDCI/HOBT method to afford 2-[4-[5-[[1-(2-cyanophenyl)-4-piperidyl]amino]-2-methoxy-4-methyl-benzoyl]piperazin-1-yl]benzenesulfonamide, I-105. ESI-MS (EI+, m/z): 589.3 [M+H]+. $^1$H NMR (500 MHz, CDCl$_3$) δ 8.03 (dd, J=7.9, 1.5 Hz, 1H), 7.60 (td, J=7.9, 1.5 Hz, 1H), 7.57 (dd, J=7.7, 1.5 Hz, 1H), 7.52-7.46 (m, 1H), 7.39 (d, J=7.9 Hz, 1H), 7.35 (t, J=7.6 Hz, 1H), 7.06-6.97 (m, 2H), 6.71 (s, 1H), 6.62 (s, 1H), 5.58 (s, 2H), 3.79 (s, 3H), 3.65-3.41 (m, 5H), 3.16 (m, 3H), 2.97 (dd, J=23.1, 11.9 Hz, 4H), 2.23 (t, 2H), 2.17 (s, 3H), 1.81-1.64 (m, 2H).

Example 36: 2-(4-(5-(1-(2-Cyanophenyl)-3-methyl-piperidin-4-ylamino)-2,4-dimethylbenzoyl)piperazin-1-yl)benzenesulfonamide, I-43

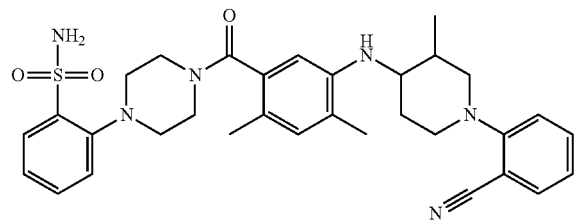

I-43

Synthetic Scheme:

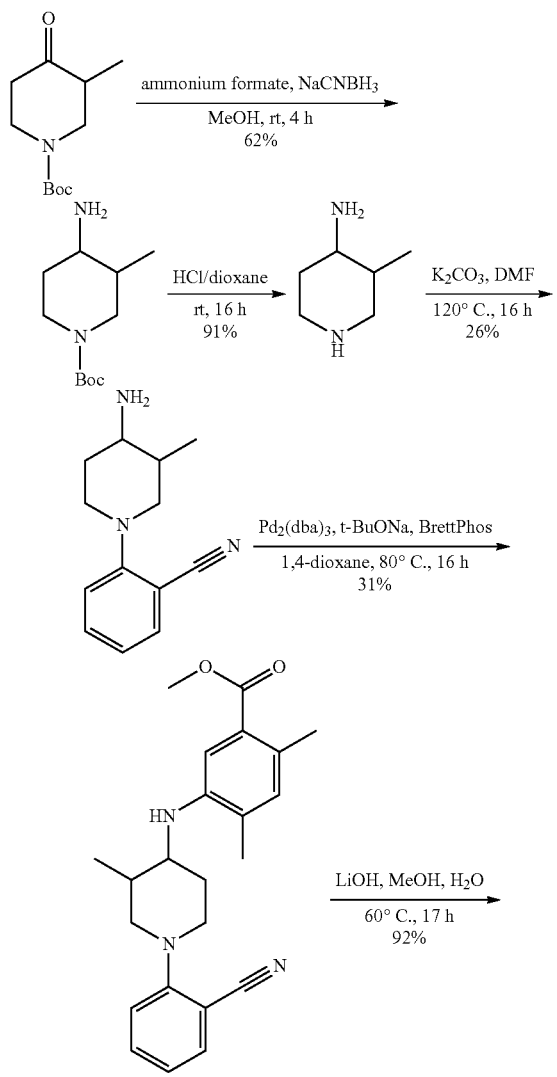

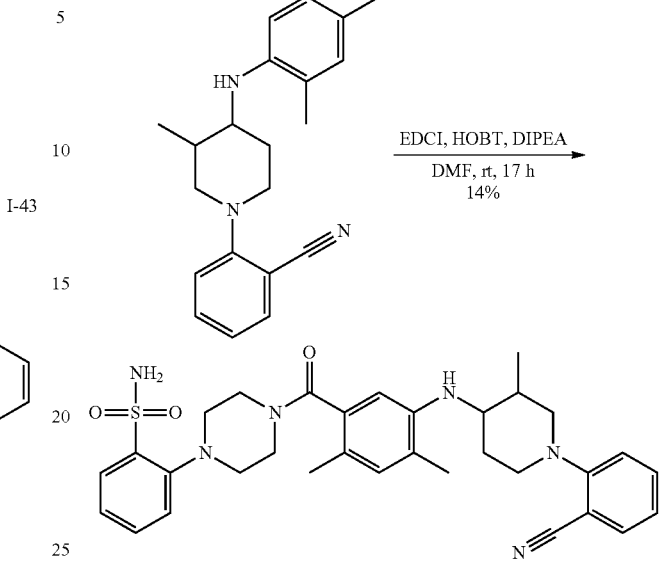

Procedures and Characterization:
The analysis method was following Method B and the separation method was following Method D.

Step 1: tert-Butyl 4-amino-3-methyl-piperidine-1-carboxylate

To a solution of tert-butyl 3-methyl-4-oxo-piperidine-1-carboxylate (5.00 g, 23.44 mmol), ammonium formate (8.87 g, 140.67 mmol), molecular sieves (1.00 g) and NaCNBH$_3$ (1.77 g, 28.13 mmol) in MeOH (50.00 mL) was added NaCNBH$_3$ (1.77 g, 28.13 mmol) at 20° C., after 16 h. The mixture was purified by SGC to afford tert-butyl 4-amino-3-methyl-piperidine-1-carboxylate (3.10 g, 14.47 mmol, 61.71% yield) as product. ESI-MS (EI$^+$, m/z): 159.3 [M+H]$^+$.

Step 2: 3-Methylpiperidin-4-amine

A mixture of tert-butyl 4-amino-3-methyl-piperidine-1-carboxylate (6.40 g, 29.86 mmol) in HCl (4N in dioxane) (100.00 mL) was stirred at 20° C. for 3 h. The mixture was concentrated to get 3-methylpiperidin-4-amine (3.10 g, 27.15 mmol, 90.92% yield) as product. ESI-MS (EI$^+$, m/z): 115.3 [M+H]$^+$.

Step 3: 2-(4-Amino-3-methyl-1-piperidyl)benzonitrile

A mixture of 2-fluorobenzonitrile (3.20 g, 26.42 mmol), 3-methylpiperidin-4-amine (3.02 g, 26.42 mmol) and K$_2$CO$_3$ (11.02 g, 79.27 mmol) in DMF (50.00 mL) was stirred at 120° C. for 16 h. The mixture was purified by SGC to afford 2-(4-amino-3-methyl-1-piperidyl)benzonitrile (1.50 g, 6.97 mmol, 26.37% yield) as product. ESI-MS (EI$^+$, m/z): 216.1 [M+H]$^+$.

Step 4: Methyl 5-[[1-(2-cyanophenyl)-3-methyl-4-piperidyl]amino]-2,4-dimethyl-benzoate A mixture of 2-(4-amino-3-methyl-1-piperidyl)benzonitrile (410.00 mg, 1.90 mmol), methyl 5-bromo-2,4-dimethyl-benzoate (461.89 mg, 1.90 mmol), tBuONa (273.60 mg, 2.85 mmol), Pd₂(dba)₃ (34.81 mg, 38.00 umol) and BrettPhos (40.81 mg, 76.00 umol) in toluene (15.00 mL) was stirred at 80° C. for 17 h. The mixture was filtered and purified by SGC to afford methyl 5-[[1-(2-cyanophenyl)-3-methyl-4-piperidyl]amino]-2,4-dimethyl-benzoate (220.00 mg, 582.81 umol, 30.67% yield) as product. ESI-MS (EI⁺, m/z): 378.3 [M+H]⁺.

Step 5: 5-[[1-(2-Cyanophenyl)-3-methyl-4-piperidyl]amino]-2,4-dimethyl-benzoic Acid A mixture of methyl 5-[[1-(2-cyanophenyl)-3-methyl-4-piperidyl]amino]-2,4-dimethyl-benzoate (170.00 mg, 450.35 umol) and LiOH (86.29 mg, 3.60 mmol) in MeOH (20.00 mL) and H₂O (2.00 mL) was stirred at 60° C. for 17 h. The mixture was extracted with EtOAc after adjusting the pH value to 4. The organic layers were concentrated to afford 5-[[1-(2-cyanophenyl)-3-methyl-4-piperidyl]amino]-2,4-dimethyl-benzoic acid (150.00 mg, 412.71 umol, 91.64% yield) as product. ESI-MS (EI⁺, m/z): 364.3 [M+H]⁺.

Step 6: 2-[4-[5-[[1-(2-Cyanophenyl)-3-methyl-4-piperidyl]amino]-2,4-dimethyl-benzoyl]piperazin-1-yl]benzenesulfonamide Following the amide coupling EDCI/HOBT method to afford 2-[4-[5-[[1-(2-cyanophenyl)-3-methyl-4-piperidyl]amino]-2,4-dimethyl-benzoyl]piperazin-1-yl]benzenesulfonamide, I-43. ESI-MS (EI⁺, m/z): 587.3 [M+H]⁺. ¹H NMR (500 MHz, CDCl₃) δ 8.03 (dd, J=7.9, 1.3 Hz, 1H), 7.60 (t, J=7.7 Hz, 1H), 7.56 (d, J=7.6 Hz, 1H), 7.49 (t, J=7.9 Hz, 1H), 7.40-7.31 (m, 2H), 7.08-6.97 (m, 2H), 6.92 (d, J=4.1 Hz, 1H), 6.46 (d, J=6.7 Hz, 1H), 5.54 (s, 2H), 3.59 (m, 4H), 3.05 (m, 7H), 2.74-2.27 (m, 2H), 2.20 (s, 3H), 2.14 (d, J=10.7 Hz, 3H), 2.07-1.89 (m, 2H), 1.17-1.03 (m, 3H).

Example 37: 2-(4-(5-(1-(2-Chlorophenyl)piperidin-4-ylamino)-2,4-dimethylbenzoyl)piperazin-1-yl)benzonitrile, I-37

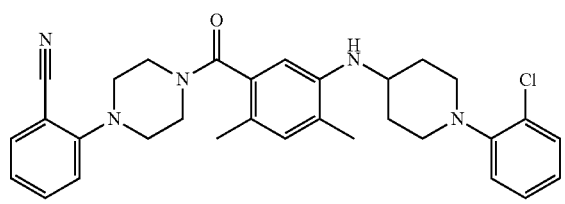

Synthetic Scheme:

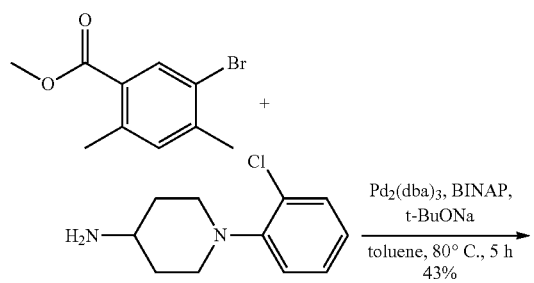

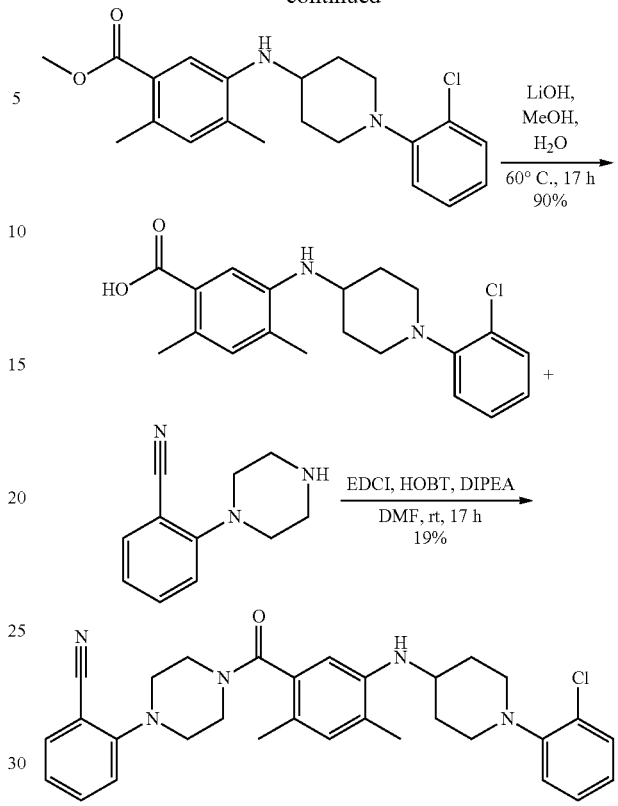

Procedures and Characterization:
The procedure was same as the procedure of example 5.
The analysis method was following Method B and the separation method was following Method D.

2-(4-(5-(1-(2-Chlorophenyl)piperidin-4-ylamino)-2,4-dimethylbenzoyl)piperazin-1-yl)benzonitrile ESI-MS (EI⁺, m/z): 528.3 [M+H]⁺. ¹H NMR (500 MHz, CDCl₃) δ 7.59 (dd, J=7.6, 1.3 Hz, 1H), 7.53-7.48 (m, 1H), 7.36 (dd, J=7.9, 1.3 Hz, 1H), 7.24-7.20 (m, 1H), 7.10-7.04 (m, 2H), 7.01 (d, J=8.3 Hz, 1H), 6.99-6.95 (m, 1H), 6.92 (s, 1H), 6.49 (s, 1H), 4.04 (d, J=17.5 Hz, 2H), 3.52 (t, J=4.8 Hz, 2H), 3.39 (dd, J=44.5, 19.5 Hz, 4H), 3.31-3.22 (m, 2H), 3.10 (s, 2H), 2.82 (dd, J=24.3, 12.3 Hz, 2H), 2.22 (m, 5H), 2.13 (s, 3H), 1.69 (dd, J=45.7, 9.9 Hz, 2H).

Example 38: (5-(1-(2-Chlorophenyl)piperidin-4-ylamino)-2,4-dimethylphenyl)(4-(5-fluoropyridin-2-yl)piperazin-1-yl)methanone, I-36

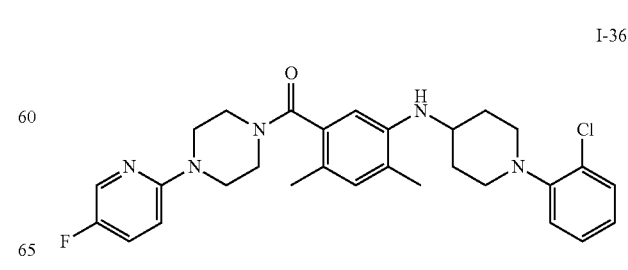

Synthetic Scheme:

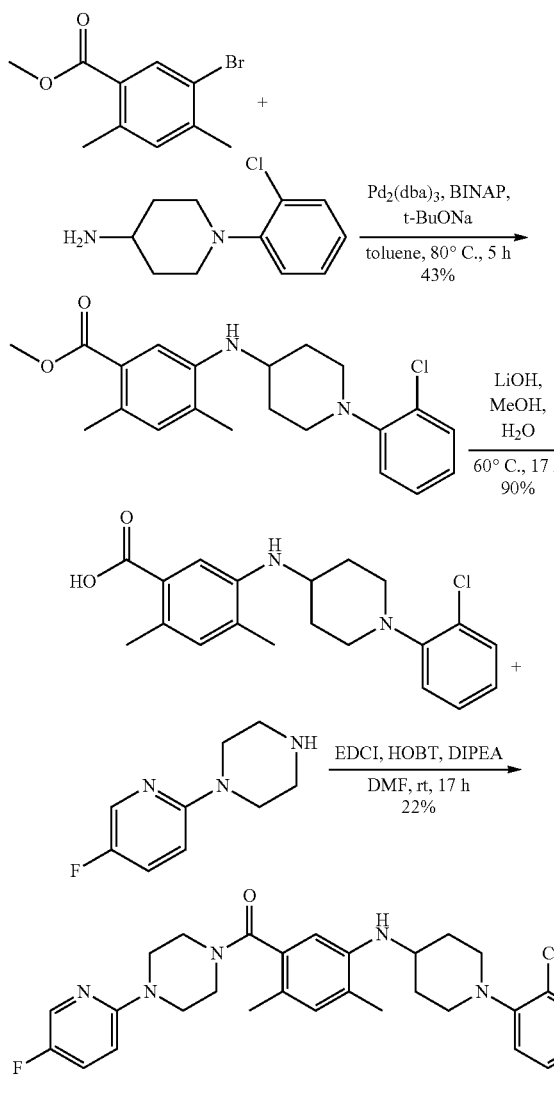

Procedures and Characterization:

The procedure was same as the procedure of example 5.

The analysis method was following Method B and the separation method was following Method D.

(5-(1-(2-Chlorophenyl)piperidin-4-ylamino)-2,4-dimethylphenyl)(4-(5-fluoropyridin-2-yl)piperazin-1-yl)methanone ESI-MS (EI+, m/z): 522.0 [M+H]+. $^1$H NMR (500 MHz, CDCl$_3$) δ 8.06 (d, J=3.0 Hz, 1H), 7.36 (dd, J=7.9, 1.3 Hz, 1H), 7.29 (dd, J=8.5, 2.3 Hz, 1H), 7.21 (dd, J=11.4, 3.9 Hz, 1H), 7.05 (d, J=8.0 Hz, 1H), 6.97 (dd, J=10.8, 4.4 Hz, 1H), 6.93 (s, 1H), 6.63 (dd, J=9.2, 3.2 Hz, 1H), 6.49 (s, 1H), 3.94 (d, J=4.1 Hz, 2H), 3.55 (t, J=5.1 Hz, 2H), 3.41 (s, 8H), 2.81 (d, J=9.9 Hz, 2H), 2.29-2.16 (m, 5H), 2.14 (s, 3H), 1.69 (d, J=36.6 Hz, 2H).

Example 39: 3-(4-(5-(1-(2-Chlorophenyl)piperidin-4-ylamino)-2,4-dimethylbenzoyl)piperazin-1-yl)benzenesulfonamide, I-4

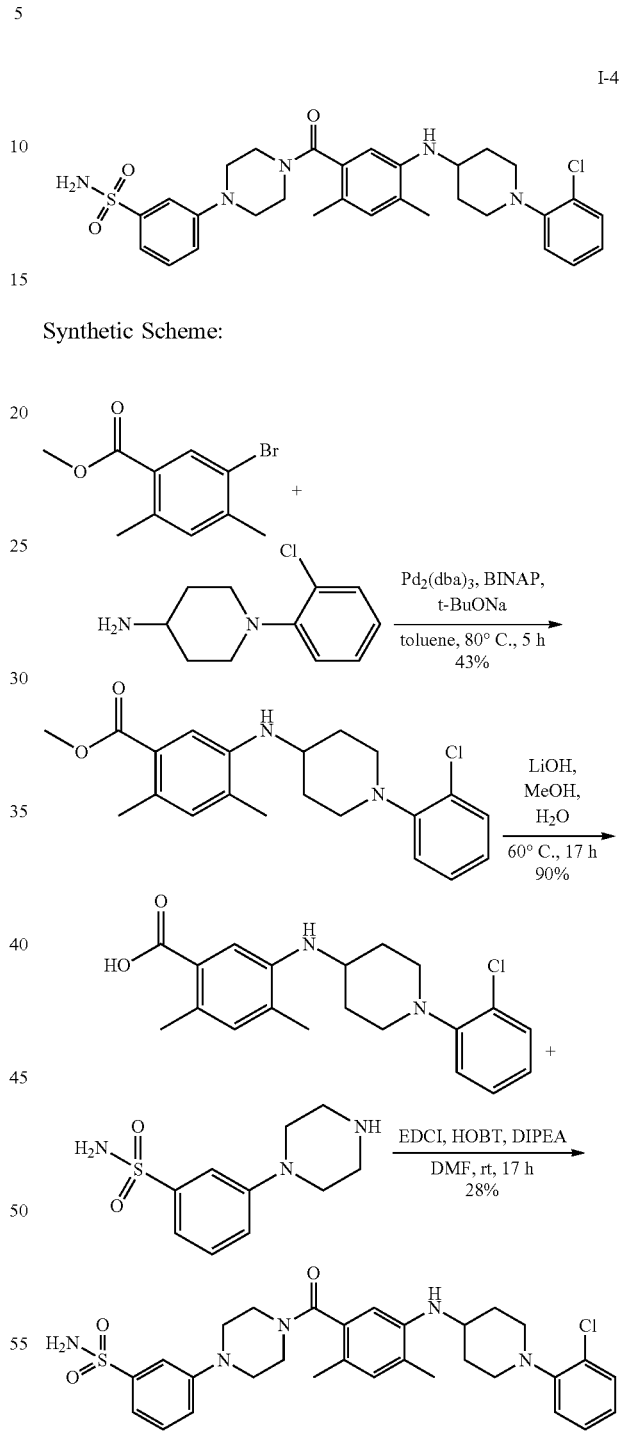

Synthetic Scheme:

Procedures and Characterization:

The procedure was same as the procedure of example 5.

The analysis method was following Method B and the separation method was following Method D.

3-(4-(5-(1-(2-Chlorophenyl)piperidin-4-ylamino)-2,4-dimethylbenzoyl)piperazin-1-yl)benzenesulfonamide ESI-MS (EI+, m/z): 582.3 [M+H]+. 1H NMR (500 MHz, CDCl3) δ 7.43 (s, 1H), 7.40 (dd, J=3.7, 2.3 Hz, 2H), 7.36 (dd, J=7.9, 1.4 Hz, 1H), 7.23-7.19 (m, 1H), 7.10-7.07 (m, 1H), 7.05 (dd, J=8.0, 1.3 Hz, 1H), 6.96 (td, J=7.8, 1.4 Hz, 1H), 6.92 (s, 1H), 6.49 (s, 1H), 4.86 (s, 2H), 3.97 (d, J=3.2 Hz, 2H), 3.41 (dd, J=32.9, 23.4 Hz, 8H), 3.14 (s, 2H), 2.81 (d, J=11.3 Hz, 2H), 2.22 (m, J=39.5 Hz, 5H), 2.14 (s, 3H), 1.68 (d, J=50.2 Hz, 2H).

Example 40: N-(1-(2-Cyanophenyl)piperidin-4-yl)-5-(1-(2-cyanophenyl)piperidin-4-ylamino)-2,4-dimethylbenzamide, I-97

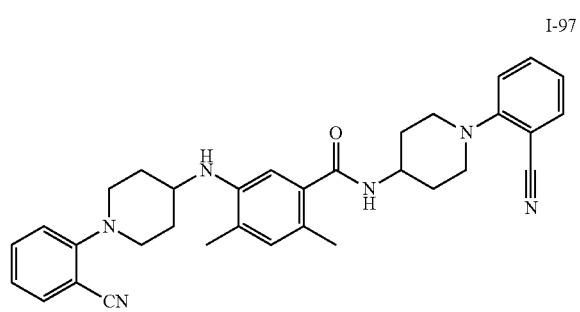 [SMILES: Cc1cc(C)c(C(=O)NC2CCN(c3ccccc3C#N)CC2)cc1NC1CCN(c2ccccc2C#N)CC1]

I-97

Synthetic Scheme:

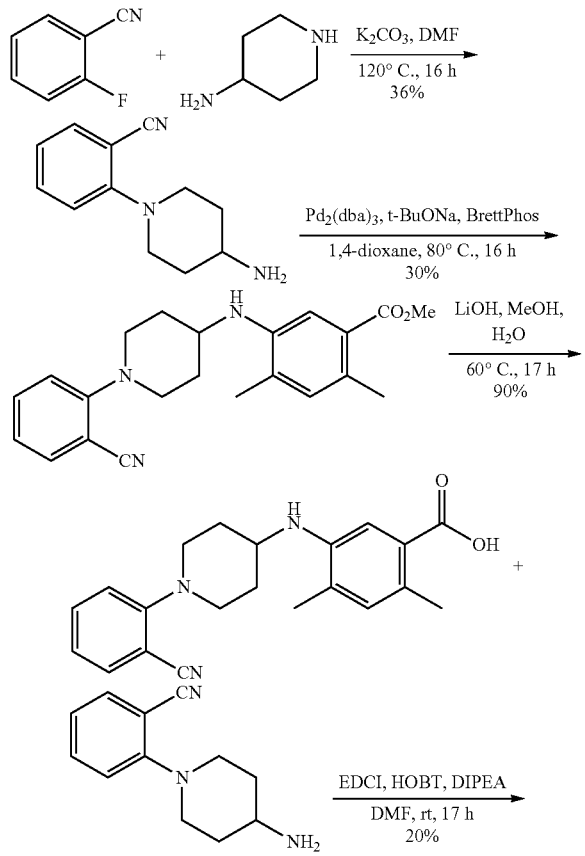

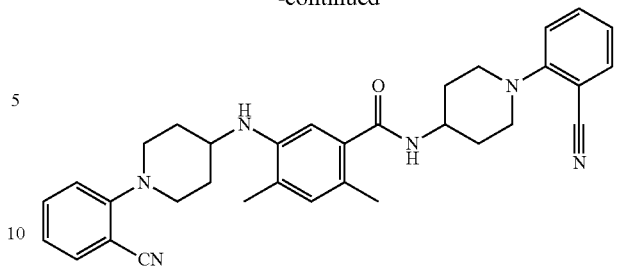

Procedures and Characterization:

The procedure was same as the procedure of example 5. The analysis method was following Method B and the separation method was following Method D.

N-(1-(2-Cyanophenyl)piperidin-4-yl)-5-(1-(2-cyanophenyl)piperidin-4-ylamino)-2,4-dimethylbenzamide ESI-MS (EI+, m/z): 533.3 [M+H]+. 1H NMR (500 MHz, CDCl3) δ 7.57 (dd, J=7.6, 1.4 Hz, 2H), 7.52-7.41 (m, 2H), 7.07-6.98 (m, 4H), 6.92 (s, 1H), 6.69 (s, 1H), 5.67 (d, J=8.1 Hz, 1H), 4.24-4.11 (m, 1H), 3.63-3.49 (m, 5H), 3.38 (d, J=8.2 Hz, 1H), 2.99 (q, J=10.6 Hz, 4H), 2.32 (d, J=6.5 Hz, 3H), 2.24 (t, J=10.5 Hz, 4H), 2.13 (s, 3H), 1.85-1.68 (m, 4H).

Example 41: (R)-2-(4-(3,5-Dimethyl-6-(4-(2-(S-methylsulfonimidoyl)phenyl)piperazine-1-carbonyl)pyridin-2-ylamino)piperidin-1-yl)benzonitrile, I-110

I-110

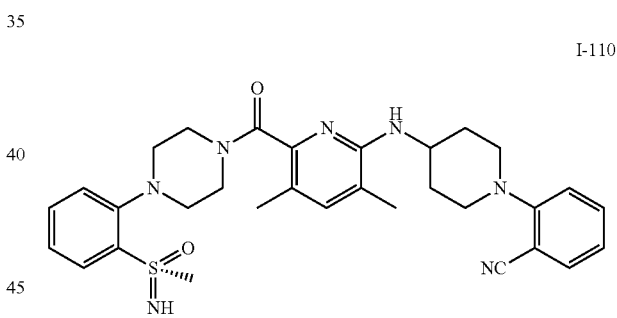

Synthetic Scheme:

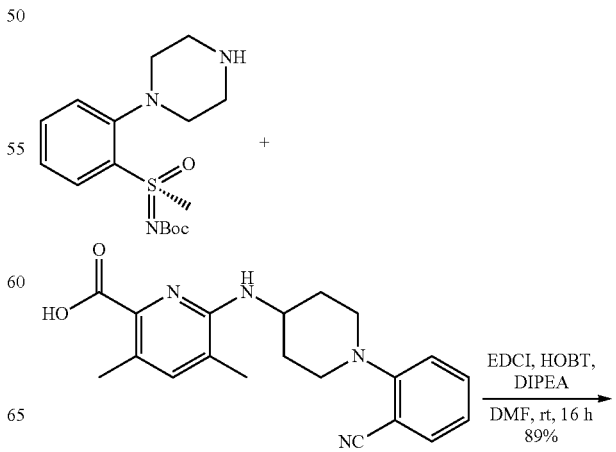

-continued

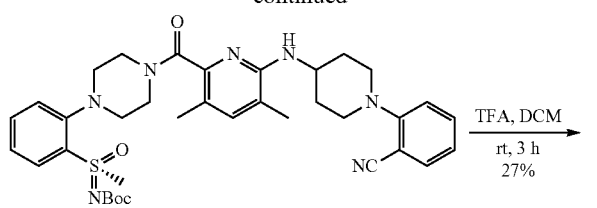

TFA, DCM
rt, 3 h
27%

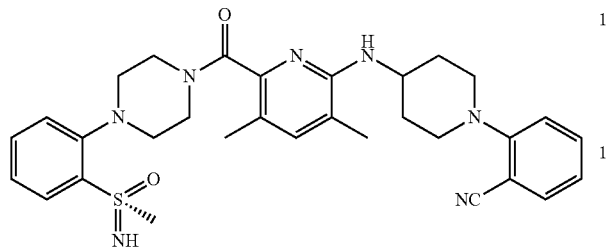

Procedures and Characterization:

The analysis method was following Method B and the separation method was following Method D.

Step 1: (R)-2-(4-(3,5-Dimethyl-6-(4-(2-(S-methyl-sulfonimidoyl)N-Boc-phenyl) piperazine-1-carbonyl)pyridin-2-ylamino)piperidin-1-yl)benzonitrile To a solution of (R)-1-(2-(S-methylsulfonimidoyl)N-Boc-phenyl)piperazine (170.00 mg, 500.81 umol) and 6-(1-(2-cyanophenyl)piperidin-4-ylamino)-3,5-dimethylpicolinic acid (228.14 mg, 651.05 umol) in DMF (5.00 mL) was added EDCI (144.01 mg, 751.21 umol), HOBT (101.50 mg, 751.21 umol) and DIPEA (194.17 mg, 1.50 mmol, 262.39 uL). The reaction mixture was stirred at rt for 16 h, then diluted with H₂O (200 mL) and extracted with EtOAc (60 mL×3), The combined organic layer was washed with brine, dried (Na₂SO₄), filtered and concentrated to afford (R)-2-(4-(3,5-dimethyl-6-(4-(2-(S-methylsulfonimidoyl)N-Boc-phenyl)piperazine-1-carbonyl)pyridin-2-ylamino)piperidin-1-yl)benzonitrile (300 mg, 0.446 mmol, 89% yield) as product. ESI-MS (EI⁺, m/z): 672.0 [M+H]⁺.

Step 2: (R)-2-(4-(3,5-Dimethyl-6-(4-(2-(S-methyl-sulfonimidoyl)phenyl)piperazine-1-carbonyl)pyridin-2-ylamino)piperidin-1-yl)benzonitrile To a solution of (R)-2-(4-(3,5-dimethyl-6-(4-(2-(S-methylsulfonimidoyl)N-Boc-phenyl)piperazine-1-carbonyl)pyridin-2-ylamino)piperidin-1-yl)benzonitrile (300 mg, 0.446 mmol) in DCM (6.00 mL) was added TFA (2.00 mL) at rt. The reaction mixture was stirred at rt for 3 h, then concentrated and purified via preparative HPLC to afford (R)-2-(4-(3,5-dimethyl-6-(4-(2-(S-methylsulfonimidoyl)phenyl) piperazine-1-carbonyl)pyridin-2-ylamino)piperidin-1-yl) benzonitrile I-110 (70.00 mg, 122.44 umol, 27.45% yield) as a white solid. ESI-MS (EI⁺, m/z): 572.0 [M+H]⁺. ¹H NMR (400 MHz, CDCl₃) δ 8.05 (d, J=7.9 Hz, 1H), 7.57 (t, J=7.9 Hz, 2H), 7.49 (t, J=7.9 Hz, 1H), 7.36 (dd, J=15.1, 7.6 Hz, 2H), 7.11 (s, 1H), 7.06-6.95 (m, 2H), 4.17 (s, 1H), 3.99 (d, J=7.6 Hz, 1H), 3.60-3.41 (m, 7H), 3.16 (s, 2H), 3.00 (t, J=11.3 Hz, 4H), 2.22 (d, J=18.7 Hz, 5H), 2.07 (s, 3H), 1.72 (dd, J=19.7, 10.8 Hz, 4H).

Example 42: (R)-2-(4-(5-(1-(2-Cyanophenyl)piperidin-4-ylamino)-2,4-dimethylbenzoyl)-2-methylpiperazin-1-yl)pyridine-3-sulfonamide, I-122

I-122

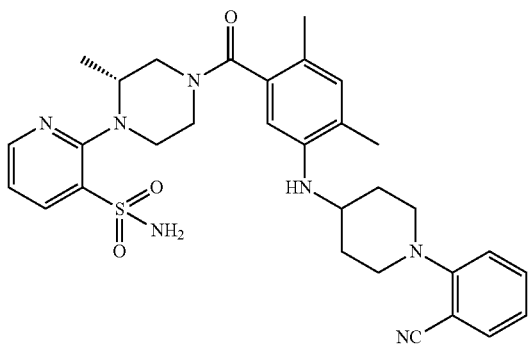

Synthetic Scheme:

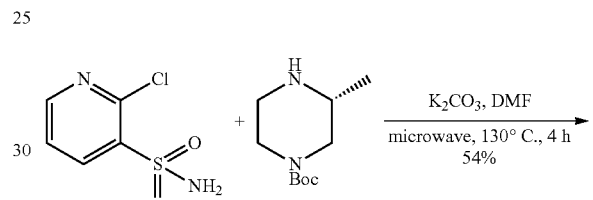

K₂CO₃, DMF
microwave, 130° C., 4 h
54%

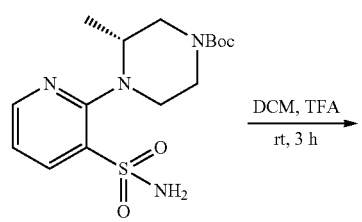

DCM, TFA
rt, 3 h

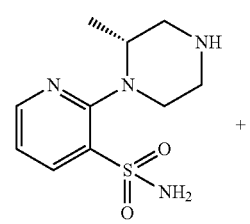

+

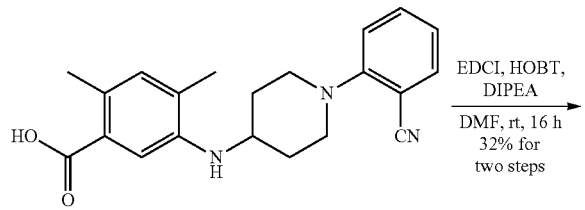

EDCI, HOBT, DIPEA
DMF, rt, 16 h
32% for two steps

-continued

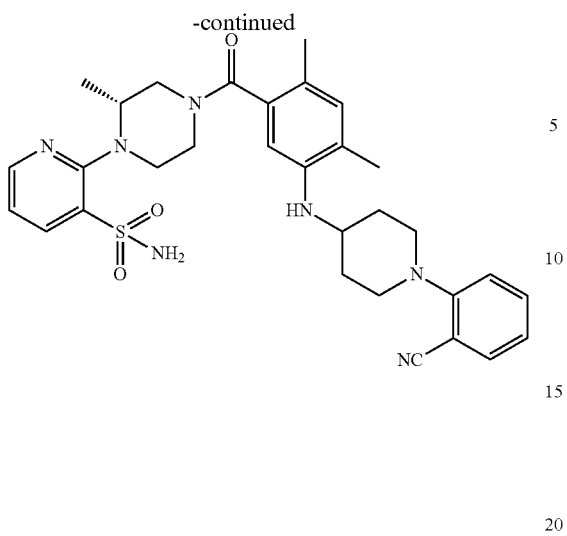

Procedures and Characterization:

The analysis method was following Method B and the separation method was following Method D.

Step 1: (R)-tert-Butyl 3-methyl-4-(3-sulfamoylpyridin-2-yl)piperazine-1-carboxylate To a solution of 2-chloropyridine-3-sulfonamide (600.00 mg, 3.115 mmol) and (R)-tert-butyl 3-methylpiperazine-1-carboxylate (1.871 g, 9.34 mmol) in DMF (10.00 mL) was added $K_2CO_3$ (1.293 g, 9.36 mmol) at rt. The reaction mixture was stirred at 130° C. under microwave for 4 h, then cooled to rt and purified via preparative HPLC to afford (R)-tert-butyl 3-methyl-4-(3-sulfamoylpyridin-2-yl)piperazine-1-carboxylate (600 mg, 1.68 mmol, 54% yield) as product. ESI-MS (EI+, m/z): 357.0 [M+H]+.

Step 2: (R)-2-(2-Methylpiperazin-1-yl)pyridine-3-sulfonamide

A mixture of tert-butyl (R)-tert-butyl 3-methyl-4-(3-sulfamoylpyridin-2-yl)piperazine-1-carboxylate (120.00 mg, 336.66 umol) in DCM (9.00 mL) and TFA (3.00 mL) was stirred at rt for 3 h, then concentrated to afford 2-[(2R)-2-methylpiperazin-1-yl]pyridine-3-sulfonamide (120.00 mg, 468.16 umol) as product. ESI-MS (EI+, m/z): 257.0 [M+H]+.

Step 3: (R)-2-(4-(5-(1-(2-Cyanophenyl)piperidin-4-ylamino)-2,4-dimethylbenzoyl)-2-methylpiperazin-1-yl)pyridine-3-sulfonamide Followed the amide coupling EDCI/HOBT method to afford (R)-2-(4-(5-(1-(2-cyanophenyl)piperidin-4-ylamino)-2,4-dimethylbenzoyl)-2-methylpiperazin-1-yl)pyridine-3-sulfonamide I-122 as product. ESI-MS (EI+, m/z): 588.0 [M+H]+. $^1$H NMR (500 MHz, DMSO-$d_6$) δ 8.44 (s, 1H), 8.22 (d, J=7.7 Hz, 1H), 7.69 (d, J=7.5 Hz, 1H), 7.59 (t, J=7.5 Hz, 1H), 7.42 (s, 2H), 7.19 (d, J=8.1 Hz, 2H), 7.07 (t, J=7.5 Hz, 1H), 6.88 (d, J=7.2 Hz, 1H), 6.40 (t, J=28.6 Hz, 1H), 4.90-4.27 (m, 2H), 3.97-3.44 (m, 6H), 3.29-2.73 (m, 5H), 2.24-1.89 (m, 8H), 1.82-1.57 (m, 2H), 1.35-1.15 (m, 3H).

Example 43: (R)-2-(4-(5-(1-(2-Cyanophenyl)piperidin-4-ylamino)-2,4-dimethylbenzoyl)-2-methylpiperazin-1-yl)-N-methylnicotinamide, I-123

I-123

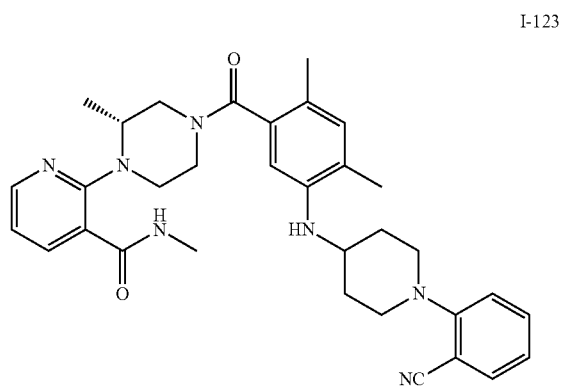 [SMILES: CNC(=O)c1cccnc1N1CCN(C(=O)c2cc(NC3CCN(c4ccccc4C#N)CC3)c(C)cc2C)C[C@H]1C]

Synthetic Scheme:

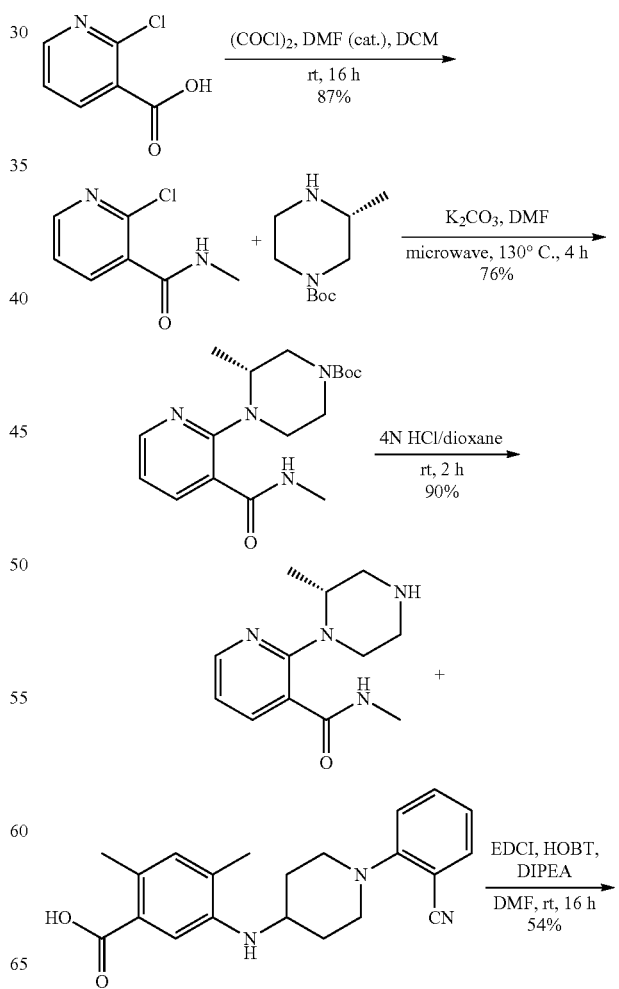

-continued

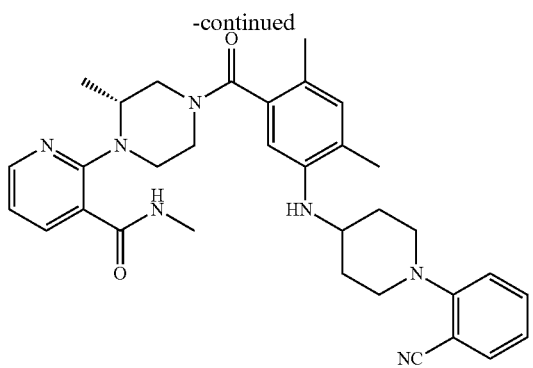

Procedures and Characterization:
The analysis method was following Method B and the separation method was following Method D.

Step 1: 2-Chloro-N-methylnicotinamide

To a solution of 2-chloropyridine-3-carboxylic acid (4.00 g, 25.39 mmol) in DCM (80.00 mL) was added DMF (92.79 mg, 1.27 mmol) and then oxalyl dichloride (6.45 g, 50.78 mmol). The reaction mixture was stirred at rt for 2 h, then concentrated to dryness, the residue was dissolved in 1, 4-dioxane (80.00 mL) and added this solution to methanamine (7.89 g, 253.90 mmol) and stirred at rt for 3 h. Then the mixture was diluted with H$_2$O (200 mL) and extracted with EtOAc (100 mL×3). The combined organic layer was washed with brine, dried (Na$_2$SO$_4$), filtered, concentrated and purified by chromatography (silica, ethyl acetate/petroleum ether=1/3) to afford 2-chloro-N-methyl-pyridine-3-carboxamide (3.80 g, 22.27 mmol, 87.71% yield) as product. ESI-MS (EI$^+$, m/z): 171.6 [M+H]$^+$.

Step 2: (R)-tert-Butyl 3-methyl-4-(3-(methylcarbamoyl)pyridin-2-yl)piperazine-1-carboxylate At rt, to a solution of 2-chloro-N-methyl-pyridine-3-carboxamide (300.00 mg, 1.76 mmol) in DMF (8.00 mL) was added (R)-tert-butyl 3-methylpiperazine-1-carboxylate (1.06 g, 5.28 mmol) and K$_2$CO$_3$ (729.75 mg, 5.28 mmol). The reaction mixture was stirred at 130° C. for 4 h under microwave. Then cooled to rt and diluted with H$_2$O (100 mL), extracted with EtOAc (60 mL×3), the combined organic layer was washed with brine, dried (Na$_2$SO$_4$), filtered, concentrated and purified by chromatography (silica, ethyl acetate/petroleum ether=1/5) to afford (R)-tert-butyl 3-methyl-4-(3-(methylcarbamoyl)pyridin-2-yl)piperazine-1-carboxylate (450.00 mg, 1.35 mmol, 76.70% yield) as solid. ESI-MS (EI$^+$, m/z): 335.0 [M+H]$^+$.

Step 3: (R)-2-(2-Methylpiperazin-1-yl)pyridine-3-sulfonamide

A mixture of (R)-tert-butyl 3-methyl-4-(3-(methylcarbamoyl)pyridin-2-yl)piperazine-1-carboxylate (250.00 mg, 747.59 umol) in 4 N HCl/1,4-dioxane (10.00 mL) was stirred at rt for 2 h, then concentrated to afford (R)—N-methyl-2-(2-methylpiperazin-1-yl)nicotinamide (182.00 mg, 0.67 mmol, 90% yield) as product. ESI-MS (EI$^+$, m/z): 235.3 [M+H]$^+$.

Step 4: (R)-2-(4-(5-(1-(2-Cyanophenyl)piperidin-4-ylamino)-2,4-dimethylbenzoyl)-2-methylpiperazin-1-yl)-N-methylnicotinamide Followed the amide coupling EDCI/HOBT method to afford (R)-2-(4-(5-(1-(2-cyanophenyl)piperidin-4-ylamino)-2,4-dimethylbenzoyl)-2-methylpiperazin-1-yl)-N-methylnicotinamide I-123 (200.00 mg, 353.54 umol, 54.50% yield) as a white solid. ESI-MS (EI$^+$, m/z): 566.0 [M+H. $^1$H NMR (400 MHz, DMSO-d$_6$) δ 8.35 (d, J=4.6 Hz, 1H), 8.22 (d, J=2.7 Hz, 1H), 7.75-7.50 (m, 3H), 7.18 (d, J=8.3 Hz, 1H), 7.07 (t, J=7.5 Hz, 1H), 6.87 (s, 2H), 6.42 (s, 1H), 4.87-4.26 (m, 2H), 3.88-3.47 (m, 5H), 3.13 (s, 2H), 2.97 (t, J=10.5 Hz, 3H), 2.74 (d, J=4.3 Hz, 3H), 2.12-2.00 (m, 8H), 1.69 (s, 2H), 1.32-1.05 (m, 4H).

Example 44: 2-(4-(5-((1-(2-Cyanophenyl)piperidin-4-yl)(2-hydroxyethyl)amino)-2,4-dimethylbenzoyl)piperazin-1-yl)benzenesulfonamide, I-1

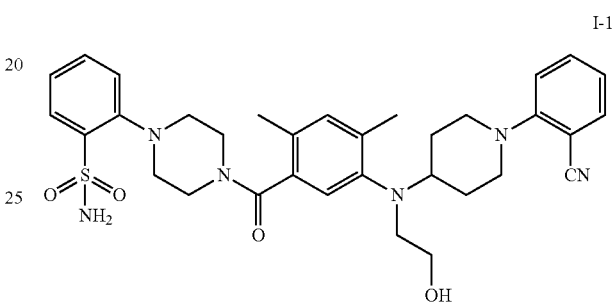

Synthetic Scheme:

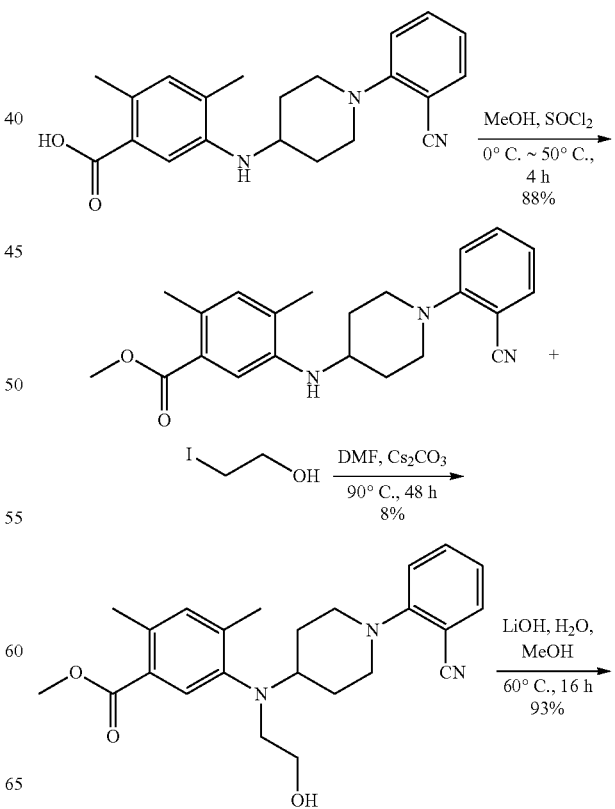

245

-continued

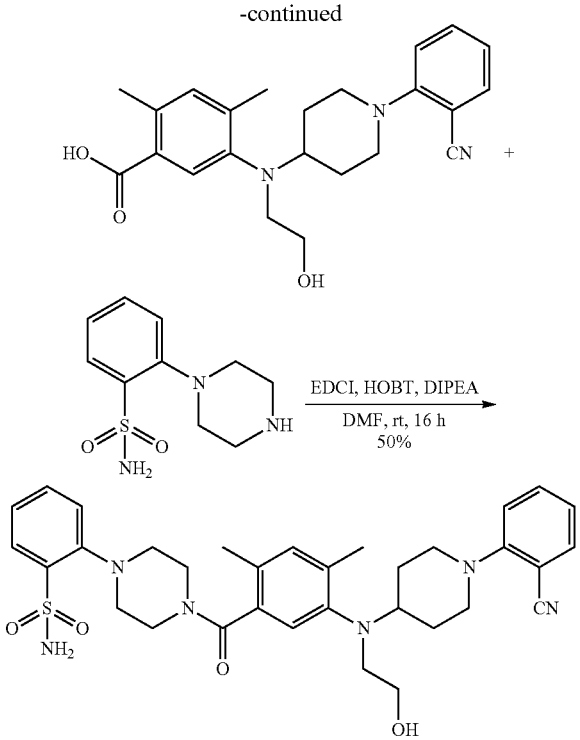

Procedures and Characterization:

The analysis method was following Method B and the separation method was following Method D.

Step 1: Methyl 5-(1-(2-cyanophenyl) piperidin-4-ylamino)-2,4-dimethylbenzoate

At 0° C., to MeOH (80.00 mL) was added dropwise $SOCl_2$ (3.40 g, 28.60 mmol). After addition, the mixture was stirred at 0° C. for 20 min, then 5-(1-(2-cyanophenyl) piperidin-4-ylamino)-2,4-dimethylbenzoic acid (2.50 g, 7.15 mmol) was added to this mixture. The reaction mixture was stirred at 60° C. for 4 h, then cooled to rt and concentrated. The residue was dissolved in EtOAc (200 mL) and washed with aqueous $NaHCO_3$ (100 mL) and brine. The organic layer was washed with brine, dried over $Na_2SO_4$, filtered, concentrated and purified by chromatography (silica, ethyl acetate/petroleum ether=1/5) to afford methyl 5-(1-(2-cyanophenyl)piperidin-4-ylamino)-2,4-dimethylbenzoate (2.30 g, 6.33 mmol, 88.51% yield) as a yellow solid. ESI-MS (EI$^+$, m/z): 364.2 [M+H]$^+$.

Step 2: Methyl 5-((1-(2-cyanophenyl)piperidin-4-yl)(2-hydroxyethyl)amino)-2,4-dimethylbenzoate To a solution of methyl 5-[[1-(2-cyanophenyl)-4-piperidyl]amino]-2,4-dimethyl-benzoate (1.00 g, 2.75 mmol) in DMF (20.00 mL) was added 2-iodoethanol (23.64 g, 137.50 mmol) and $Cs_2CO_3$ (2.69 g, 8.25 mmol). The reaction mixture was stirred at 90° C. for 48 h. Then the mixture was cooled to rt and purified via preparative HPLC to afford methyl 5-[[1-(2-cyanophenyl)-4-piperidyl]-(2-hydroxyethyl)amino]-2,4-dimethyl-benzoate (100.00 mg, 245.40 umol, 8.92% yield) as product. ESI-MS (EI$^+$, m/z): 408.5 [M+H]$^+$.

Step 3: 5-((1-(2-Cyanophenyl)piperidin-4-yl)(2-hydroxyethyl)amino)-2,4-dimethylbenzoic Acid To a solution of methyl 5-((1-(2-cyanophenyl)piperidin-4-yl)(2-hydroxyethyl)amino)-2,4-dimethylbenzoate (100.00 mg, 245.4 umol) in MeOH (8.00 mL) and $H_2O$ (799.91 uL) was added LiOH (37.61 mg, 1.57 mmol). The reaction mixture was stirred at 60° C. for 16 h, cooled to rt, diluted with $H_2O$ (100 mL) and the pH adjusted to 4 to 5 with 2 N HCl and then extracted with EtOAc (60 mL×3). The combined organic layer was washed with brine, dried ($Na_2SO_4$), filtered and concentrated to afford 5-((1-(2-cyanophenyl)piperidin-4-yl)(2-hydroxyethyl)amino)-2,4-dimethylbenzoic acid (90.00 mg, 0.228 mmol, 93% yield) as product. ESI-MS (EI$^+$, m/z): 394.0 [M+H]$^+$.

Step 4: 2-(4-(5-((1-(2-Cyanophenyl)piperidin-4-yl)(2-hydroxyethyl)amino)-2,4-dimethylbenzoyl)piperazin-1-yl)benzenesulfonamide Followed the amide coupling EDCI/HOBT method to afford 2-(4-(5-((1-(2-cyanophenyl)piperidin-4-yl)(2-hydroxyethyl)amino)-2,4-dimethylbenzoyl)piperazin-1-yl)benzenesulfonamide I-1 as a white solid. ESI-MS (EI$^+$, m/z): 617.2 [M+H]$^+$. $^1$H NMR (500 MHz, DMSO-$d_6$) δ 7.87 (d, J=7.5 Hz, 1H), 7.70-7.60 (m, 2H), 7.59-7.52 (m, 2H), 7.35 (t, J=7.4 Hz, 1H), 7.12 (d, J=4.8 Hz, 2H), 7.09-7.01 (m, 2H), 6.97 (s, 2H), 4.35 (dd, J=22.1, 16.9 Hz, 1H), 3.87 (s, 2H), 3.49 (d, J=11.5 Hz, 2H), 3.27 (d, J=5.6 Hz, 4H), 3.15-2.74 (m, 9H), 2.23 (d, J=27.5 Hz, 6H), 1.86 (d, J=11.2 Hz, 2H), 1.74-1.58 (m, 2H).

Example 45: 2-(4-(5-((1-(2-Cyanophenyl)-3-methylpiperidin-4-yl)(ethyl)amino)-2,4-dimethylbenzoyl)piperazin-1-yl)benzenesulfonamide, I-10

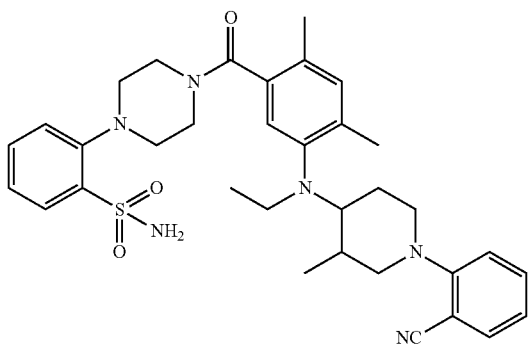

I-10

Synthetic Scheme:

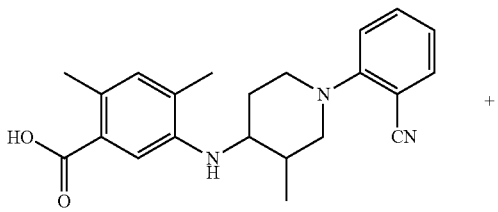

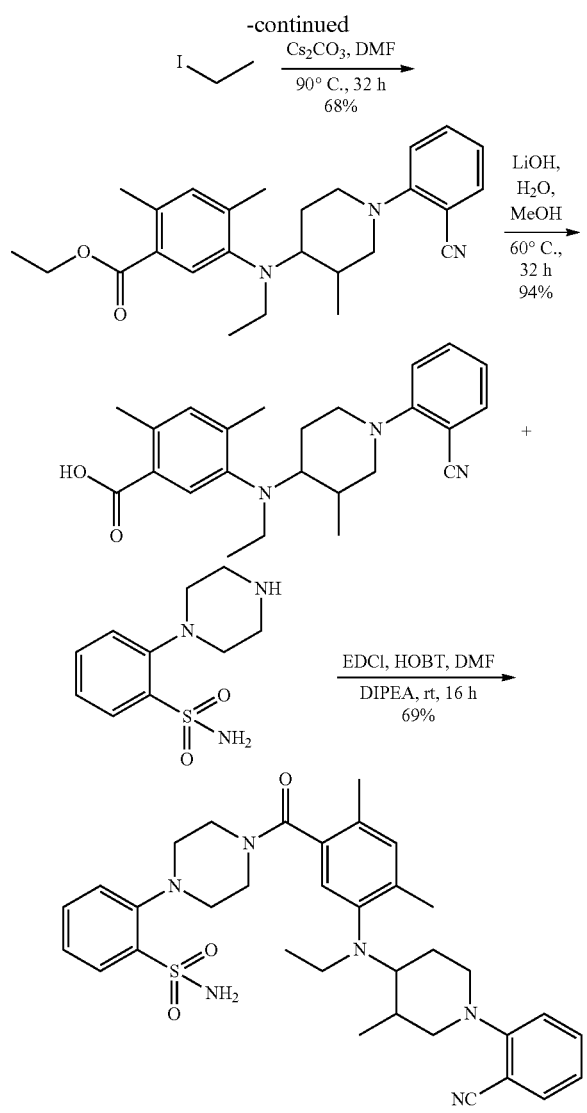

Procedures and Characterization:

The analysis method was following Method B and the separation method was following Method D.

Step 1: Ethyl 5-((1-(2-cyanophenyl)-3-methylpiperidin-4-yl)(ethyl)amino)-2,4-dimethylbenzoate To a solution of 5-[[1-(2-cyanophenyl)-3-methyl-4-piperidyl]amino]-2,4-dimethyl-benzoic acid (102.00 mg, 487.74 umol) in DMF (15.00 mL) was added iodomethane (2.19 g, 3.736 mmol) and Cs$_2$CO$_3$ (274.31 mg, 467.94 umol). The reaction mixture was stirred at 90° C. for 16 h, then cooled to rt and diluted with H$_2$O (200 mL) and extracted with EtOAc (60 mL×3). The combined organic layer was washed with brine, dried over Na$_2$SO$_4$, filtered, concentrated and purified by chromatography (silica, ethyl acetate/petroleum ether=1/10) to afford ethyl 5-((1-(2-cyanophenyl)-3-methylpiperidin-4-yl)(ethyl)amino)-2,4-dimethylbenzoate (137 mg, 0.326 mmol, 68.2% yield) as product. ESI-MS (EI$^+$, m/z): 420.2 [M+H]$^+$.

Step 2: 5-((1-(2-Cyanophenyl)-3-methylpiperidin-4-yl)(ethyl)amino)-2,4-dimethylbenzoic Acid To a solution of ethyl 5-((1-(2-cyanophenyl)-3-methylpiperidin-4-yl)(ethyl)amino)-2,4-dimethylbenzoate (137 mg, 0.326 mmol) in MeOH (12.00 mL) and H$_2$O (1.50 mL) was added LiOH (109 mg, 2.61 mmol). The reaction mixture was stirred at 60° C. for 16 h, then cooled to rt and diluted with H$_2$O (100 mL), the pH was adjusted to 4 to 5 with 2 N HCl, then the mixture was extracted with EtOAc (60 mL×3). The organic layer was washed with brine, dried over Na$_2$SO$_4$, filtered and concentrated to afford 5-((1-(2-cyanophenyl)-3-methylpiperidin-4-yl)(ethyl)amino)-2,4-dimethylbenzoic acid (120.00 mg, 0.306 mmol, 94% yield) as product. ESI-MS (EI$^+$, m/z): 392.2 [M+H]$^+$.

Step 3: 2-(4-(5-((1-(2-Cyanophenyl)-3-methylpiperidin-4-yl)(ethyl)amino)-2,4-dimethylbenzoyl)piperazin-1-yl)benzenesulfonamide Followed the amide coupling EDCI/HOBT method to afford 2-(4-(5-((1-(2-cyanophenyl)-3-methylpiperidin-4-yl)(ethyl)amino)-2,4-dimethylbenzoyl)piperazin-1-yl)benzenesulfonamide I-10 as a white solid. ESI-MS (EI$^+$, m/z): 615.8 [M+H]$^+$. $^1$H NMR (400 MHz, DMSO-d6) δ 7.87 (d, J=7.0 Hz, 1H), 7.69-7.44 (m, 4H), 7.35 (t, J=7.4 Hz, 1H), 7.19-6.83 (m, 6H), 4.14-3.70 (m, 2H), 3.19 (s, 3H), 3.11-2.55 (m, 8H), 2.24 (dd, J=30.0, 7.0 Hz, 7H), 2.01-1.23 (m, 3H), 1.09 (d, J=6.5 Hz, 3H), 0.94-0.75 (m, 3H).

Example 46: 2-(4-(5-(Allyl(1-(2-cyanophenyl)piperidin-4-yl)amino)-2,4-dimethylbenzoyl)piperazin-1-yl)benzenesulfonamide, I-46

I-46

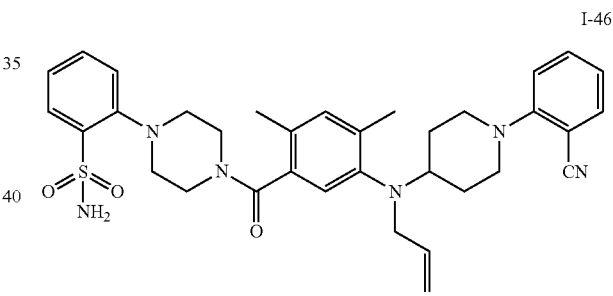

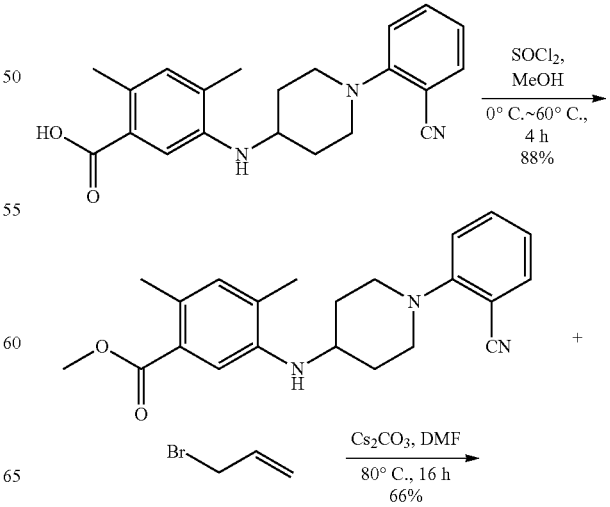

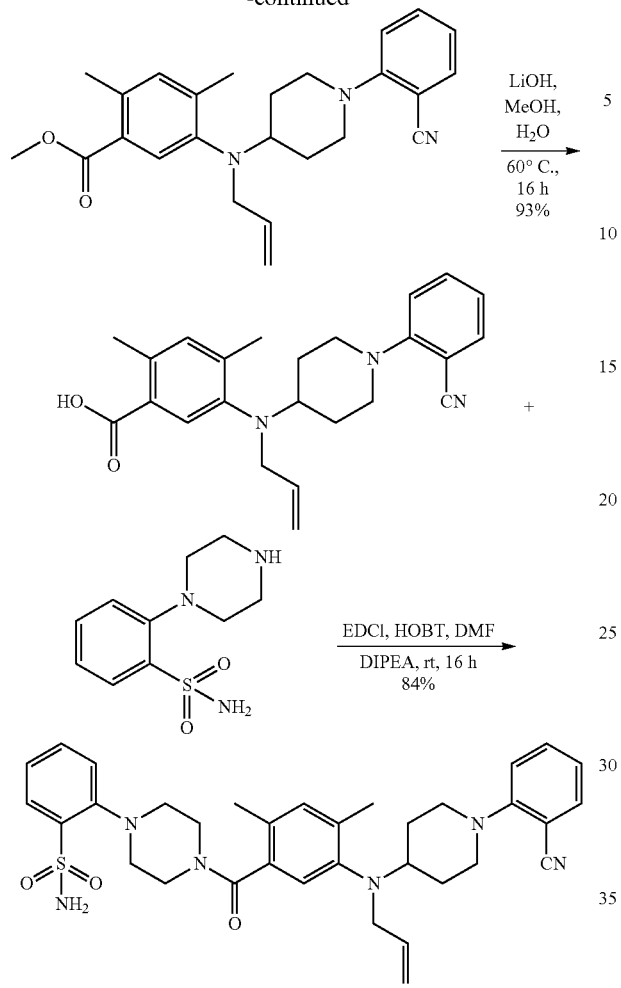

Procedures and Characterization:

The analysis method was following Method B and the product was obtained by purified by SGC.

Step 1: Methyl 5-(1-(2-cyanophenyl)piperidin-4-ylamino)-2,4-dimethylbenzoate

At 0 OC, to MeOH (80.00 mL) was added dropwise SOCl$_2$ (3.40 g, 28.60 mmol, 2.07 mL). The mixture was stirred at 0° C. for 20 min, then 5-(1-(2-cyanophenyl)piperidin-4-ylamino)-2,4-dimethylbenzoic acid (2.50 g, 7.15 mmol) was added. The reaction mixture was stirred at 60° C. for 4 h, then cooled to rt and concentrated. The residue was dissolved in EtOAc (150 mL) and washed with aqueous NaHCO$_3$ (200 mL), brine (200 mL). The organic layer was washed with brine, dried over Na$_2$SO$_4$, filtered, concentrated and purified by chromatography (silica, ethyl acetate/petroleum ether=1/5) to afford methyl 5-(1-(2-cyanophenyl)piperidin-4-ylamino)-2,4-dimethylbenzoate (2.30 g, 6.33 mmol, 88.51% yield) as a yellow solid. ESI-MS (EI$^+$, m/z): 364.2 [M+H]$^+$.

Step 2: Methyl 5-(allyl (1-(2-cyanophenyl) piperidin-4-yl) amino)-2, 4-dimethylbenzoate A mixture of methyl 5-(1-(2-cyanophenyl)piperidin-4-ylamino)-2,4-dimethylbenzoate (1.50 g, 4.13 mmol), 3-bromoprop-1-ene (9.99 g, 82.60 mmol) and cesium carbonate (1.35 g, 4.13 mmol) in N,N-dimethylacetamide (30.00 mL) was stirred at 80° C. for 16 h, then the mixture was cooled to rt and diluted with H$_2$O (200 mL) and extracted with EtOAc (80 mL×3). The combined organic layer was washed with brine, dried over Na$_2$SO$_4$, filtered, concentrated and purified by chromatography (silica, ethyl acetate/petroleum ether=1/20) to afford methyl 5-(allyl (1-(2-cyanophenyl) piperidin-4-yl) amino)-2,4-dimethylbenzoate (1.10 g, 2.73 mmol, 66.10% yield) as a solid. ESI-MS (EI$^+$, m/z): 404.2 [M+H]$^+$.

Step 3: 5-(Allyl(1-(2-cyanophenyl)piperidin-4-yl) amino)-2,4-dimethylbenzoic Acid To a solution of methyl 5-(allyl(1-(2-cyanophenyl)piperidin-4-yl)amino)-2,4-dimethylbenzoate (1.00 g, 2.48 mmol) in MeOH (100.00 mL) and H$_2$O (10.00 mL) was added LiOH (59.39 mg, 2.48 mmol). The reaction mixture was stirred at 60° C. for 16 h, then cooled to rt and diluted with H$_2$O. The pH was adjusted to 3-4 with 2 N HCl aqueous solution. The mixture was extracted with EtOAc (80 mL×3), washed with brine, dried over Na$_2$SO$_4$, filtered and concentrated to afford 5-(allyl(1-(2-cyanophenyl)piperidin-4-yl) amino)-2,4-dimethylbenzoic acid (900 mg, 2.31 mmol, 93% yield) as product. ESI-MS (EI$^+$, m/z): 390.2 [M+H]$^+$.

Step 4: 2-(4-(5-(Allyl(1-(2-cyanophenyl)piperidin-4-yl)amino)-2,4-dimethylbenzoyl)piperazin-1-yl)benzenesulfonamide Followed the amide coupling EDCI/HOBT method to afford 2-(4-(5-(allyl(1-(2-cyanophenyl)piperidin-4-yl)amino)-2,4-dimethylbenzoyl)piperazin-1-yl)benzenesulfonamide I-46 as a white solid. ESI-MS (EI$^+$, m/z): 613.0 [M+H]$^+$. $^1$H NMR (500 MHz, DMSO-d6) δ 7.91-7.83 (m, 1H), 7.69-7.59 (m, 2H), 7.59-7.53 (m, 2H), 7.35 (t, J=7.4 Hz, 1H), 7.16-7.08 (m, 2H), 7.05 (t, J=7.5 Hz, 1H), 6.98 (d, J=9.0 Hz, 3H), 5.66 (dq, J=10.5, 6.0 Hz, 1H), 5.04 (d, J=16.9 Hz, 1H), 4.92 (d, J=10.5 Hz, 1H), 4.06-3.60 (m, 4H), 3.49 (d, J=10.2 Hz, 2H), 3.33 (s, 2H), 2.92 (d, J=50.2 Hz, 4H), 2.79 (s, 3H), 2.27 (s, 3H), 2.18 (s, 3H), 1.86 (s, 2H), 1.70 (s, 2H).

Example 47: 2-(4-(5-((1-(2-Cyanophenyl)piperidin-4-yl)(propyl)amino)-2,4-dimethylbenzoyl)piperazin-1-yl)benzenesulfonamide, I-23

I-23

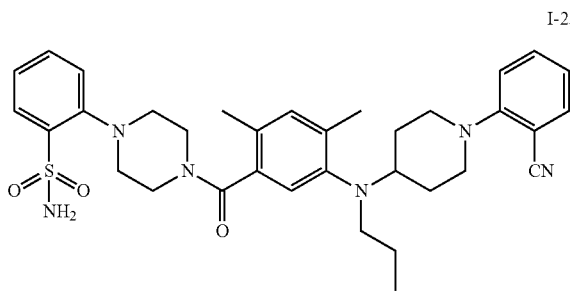

Synthetic Scheme:

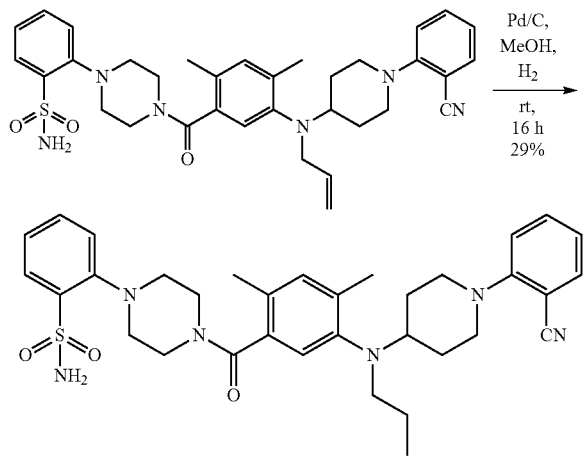

Procedures and Characterization:

The procedure was similar to that of example 46.

The analysis method was following Method B and the separation method was following Method D.

Step 1: 2-(4-(5-((1-(2-Cyanophenyl)piperidin-4-yl)(propyl)amino)-2,4-dimethylbenzoyl) piperazin-1-yl)benzenesulfonamide To a solution of 2-(4-(5-(allyl(1-(2-cyanophenyl)piperidin-4-yl)amino)-2,4-dimethylbenzoyl)piperazin-1-yl)benzenesulfonamide (210.00 mg, 342.70 umol) in methanol (15.00 mL) was added Pd/C (199.80 mg, 1.64 mmol). The mixture was hydrogenated for 16 h, then filtered, concentrated and the residue was purified via preparative HPLC to afford 2-(4-(5-((1-(2-cyanophenyl)piperidin-4-yl)(propyl)amino)-2,4-dimethylbenzoyl)piperazin-1-yl)benzenesulfonamide I-23 (63.00 mg, 102.47 umol, 29.90% yield) as product. ESI-MS (EI⁺, m/z): 615.0 [M+H]⁺. ¹H NMR (500 MHz, DMSO-$d_6$) δ 7.88 (d, J=7.8 Hz, 1H), 7.59 (ddd, J=21.3, 16.7, 7.5 Hz, 4H), 7.35 (t, J=7.4 Hz, 1H), 7.11 (d, J=8.3 Hz, 2H), 7.08-6.92 (m, 4H), 3.87 (s, 2H), 3.50 (d, J=11.2 Hz, 2H), 3.38 (s, 2H), 3.09-2.72 (m, 9H), 2.23 (d, J=33.1 Hz, 6H), 1.82 (s, 2H), 1.73 (s, 2H), 1.22 (dd, J=14.1, 6.9 Hz, 2H), 0.78 (t, J=7.3 Hz, 3H).

Example 48: 2-(4-(5-((1-(2-Cyanophenyl)piperidin-4-yl)(ethyl)amino)-2,4-dimethylbenzoyl) piperazin-1-yl)benzenesulfonamide, I-51

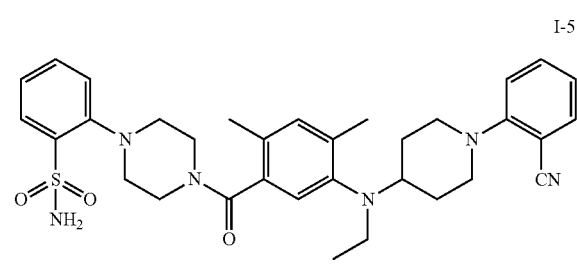

I-51

Synthetic Scheme:

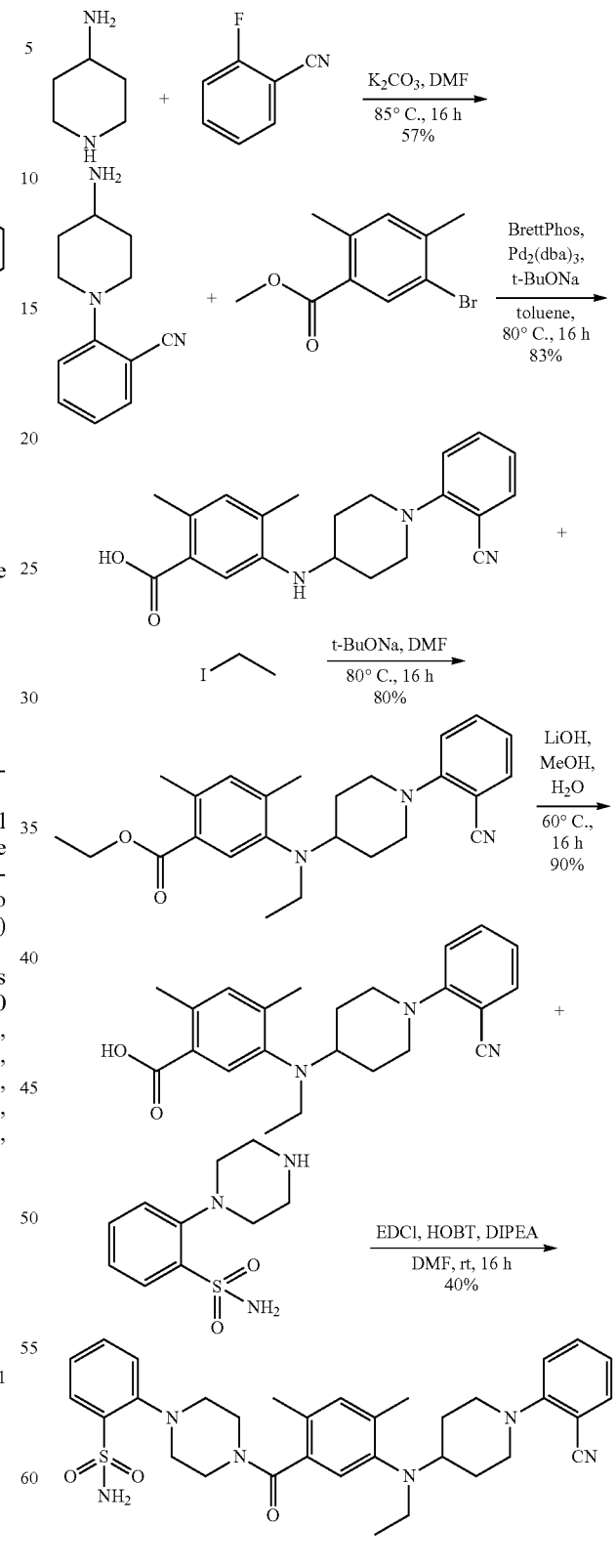

Procedures and Characterization:

The analysis method was following Method B and the crude was purified by SGC to obtain the target.

Step 1: 2-(4-Aminopiperidin-1-yl)benzonitrile

To a solution of 2-fluorobenzonitrile (10.00 g, 82.57 mmol), piperidin-4-amine (10.75 g, 107.34 mmol) in DMF (100.00 mL) was added $K_2CO_3$ (28.49 g, 206.43 mmol). The reaction mixture was stirred at 85° C. for 16 h. then cooled to r.t and diluted with $H_2O$ (400 mL) and extracted with EtOAc (100 mL×3). The combined organic layer was washed with brine, dried over $Na_2SO_4$, filtered and concentrated to afford the crude product, which was purified by chromatography (silica, dichloromethane/methanol: 1/10) to afford 2-(4-amino-1-piperidyl)benzonitrile (9.60 g, 47.70 mmol, 57.77% yield) as product. ESI-MS ($EI^+$, m/z): 202.0 $[M+H]^+$.

Step 2: 5-(1-(2-Cyanophenyl) piperidin-4-ylamino)-2, 4-dimethylbenzoic Acid

To a solution of methyl 5-bromo-2,4-dimethyl-benzoate (920.00 mg, 3.78 mmol), 2-(4-amino-1-piperidyl)benzonitrile (989.04 mg, 4.91 mmol) in toluene (20.00 mL) was added BrettPhos (284.05 mg, 529.20 umol), $Pd_2(dba)_3$ (242.30 mg, 264.60 umol) and sodium tert-butoxide (1.09 g, 11.34 mmol) under nitrogen. The reaction mixture was stirred at 80° C. for 16 h. then cooled to rt and diluted with $H_2O$ (100 mL). The pH was adjusted to 4 to 5 with 1 N HCl and then extracted with EtOAc (80 mL×3). The combined organic layer was washed with brine, dried over $Na_2SO_4$, filtered and concentrated to obtain the crude product, which was purified by chromatography (silica, ethyl acetate/petroleum ether=1/3) to afford the desired product 5-[[1-(2-cyanophenyl)-4-piperidyl]amino]-2,4-dimethyl-benzoic acid (1.10 g, 3.15 mmol, 83.33% yield) as a solid. ESI-MS ($EI^+$, m/z): 350.2 $[M+H]^+$.

Step 3: Ethyl 5-((1-(2-cyanophenyl)piperidin-4-yl)(ethyl)amino)-2,4-dimethylbenzoate At rt, to a solution of 5-[[1-(2-cyanophenyl)-4-piperidyl]amino]-2,4-dimethyl-benzoic acid (400.00 mg, 1.14 mmol) in N,N-dimethylacetamide (30.00 mL) was added sodium tert-butoxide (328.66 mg, 3.42 mmol) and iodoethane (3.56 g, 22.80 mmol). Then reaction mixture was stirred at 80° C. for 16 h, cooled to rt and diluted with $H_2O$ (200 mL) and extracted with EtOAc (80 mL×3). The combined organic layer was washed with brine, dried over $Na_2SO_4$, filtered, concentrated and purified by chromatography (silica, ethyl acetate/petroleum ether=1/10) to afford ethyl 5-((1-(2-cyanophenyl)piperidin-4-yl)(ethyl)amino)-2,4-dimethylbenzoate (370.00 mg, 912.39 umol, 80.03% yield) as product. ESI-MS ($EI^+$, m/z): 406.2 $[M+H]^+$.

Step 4: 5-((1-(2-Cyanophenyl)piperidin-4-yl)(ethyl)amino)-2,4-dimethylbenzoic Acid At rt, a solution of ethyl 5-[[1-(2-cyanophenyl)-4-piperidyl]-ethyl-amino]-2,4-dimethyl-benzoate (300.00 mg, 739.77 umol) in MeOH (30.00 mL) and $H_2O$ (3.00 mL) was added LiOH (141.74 mg, 5.92 mmol). The reaction mixture was stirred at 60° C. for 16 h, cooled to rt and diluted with $H_2O$ (200 mL). The pH was adjusted to 3 to 4 with 1 N HCl and extracted with EtOAc (80 mL×3). The combined organic layer was washed with brine, dried over $Na_2SO_4$, filtered and concentrated to afford 5-((1-(2-cyanophenyl)piperidin-4-yl)(ethyl)amino)-2,4-dimethylbenzoic acid (251 mg, 0.665 mmol, 90% yield) as product. ESI-MS ($EI^+$, m/z): 378.2 $[M+H]^+$.

Step 5: 2-(4-(5-((1-(2-Cyanophenyl)piperidin-4-yl)(ethyl)amino)-2,4-dimethylbenzoyl)piperazin-1-yl)benzenesulfonamide Followed the amide coupling EDCI/HOBT method to afford 2-[4-[5-[[1-(2-cyanophenyl)-4-piperidyl]-ethyl-amino]-2,4-dimethyl-benzoyl]piperazin-1-yl]benzenesulfonamide I-51 as a white solid. ESI-MS ($EI^+$, m/z): 601.0 $[M+H]^+$. $^1$H NMR (500 MHz, DMSO-$d_6$) δ 7.87 (d, J=7.3 Hz, 1H), 7.72-7.48 (m, 4H), 7.35 (t, J=7.5 Hz, 1H), 7.12 (d, J=11.0 Hz, 2H), 7.08-6.90 (m, 4H), 3.87 (s, 2H), 3.48 (d, J=10.9 Hz, 2H), 3.36 (d, J=10.5 Hz, 2H), 3.17-2.68 (m, 9H), 2.23 (d, J=28.6 Hz, 6H), 1.84 (d, J=11.0 Hz, 2H), 1.67 (d, J=10.1 Hz, 2H), 0.82 (t, J=6.8 Hz, 3H).

Example 49: (R)-2-(4-(2,4-Dimethyl-5-(3-methyl-4-phenylpiperazine-1-carbonyl)phenylamino)piperidin-1-yl)benzonitrile, I-47

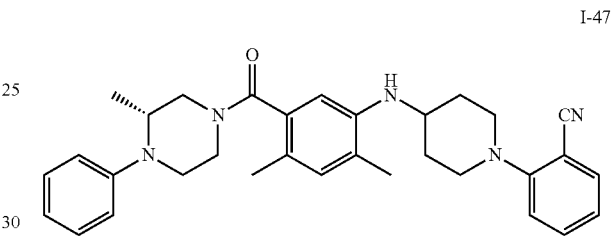

I-47

Synthetic Scheme:

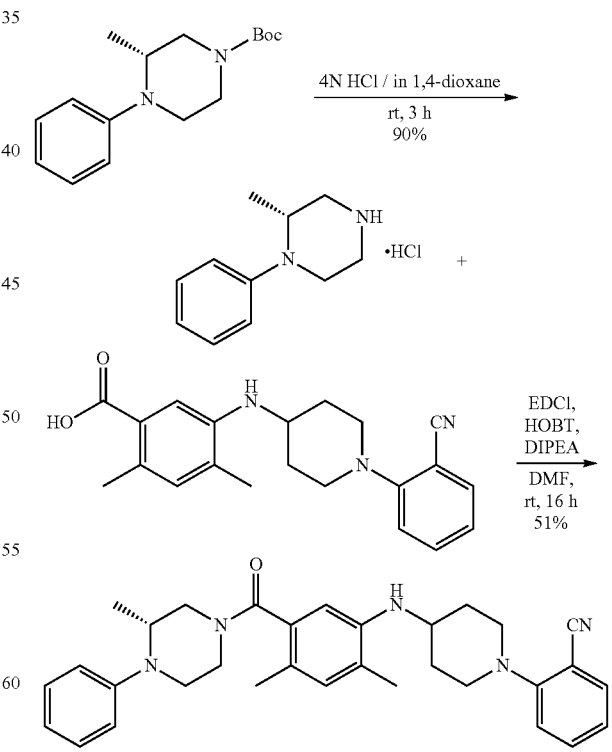

Procedures and Characterization:
The analysis method was following Method B and the separation method was following Method D.

Step 1: (R)-2-Methyl-1-phenylpiperazine Hydrochloride

A mixture of tert-butyl (R)-tert-butyl 3-methyl-4-phenylpiperazine-1-carboxylate (300.00 mg, 1.09 mmol) in 4 N HCl (1, 4-dioxane, 10 mL) was stirred at rt for 3 h and concentrated to afford (R)-2-methyl-1-phenylpiperazine hydrochloride (208 mg, 0.977 mmol, 90% yield) as product. ESI-MS (EI$^+$, m/z): 177.2 [M+H]$^+$.

Step 2: (R)-2-(4-(2,4-Dimethyl-5-(3-methyl-4-phenylpiperazine-1-carbonyl)phenylamino)piperidin-1-yl)benzonitrile Followed the amide coupling EDCI/HOBT method to afford (R)-2-(4-(2,4-dimethyl-5-(3-methyl-4-phenylpiperazine-1-carbonyl)phenylamino)piperidin-1-yl)benzonitrile I-47 as a white solid. ESI-MS (EI$^+$, m/z): 508.0 [M+H]$^+$. $^1$H NMR (500 MHz, DMSO-d$_6$) δ 7.68 (d, J=7.2 Hz, 1H), 7.57 (d, J=7.2 Hz, 1H), 7.26-7.13 (m, 3H), 7.06 (t, J=7.4 Hz, 1H), 6.90 (t, J=6.7 Hz, 3H), 6.77 (s, 1H), 6.43 (d, J=5.9 Hz, 1H), 4.64-3.85 (m, 3H), 3.58-3.40 (m, 4H), 3.30-2.71 (m, 6H), 2.15-1.96 (m, 8H), 1.71 (d, J=10.0 Hz, 2H), 0.89 (dd, J=73.1, 26.1 Hz, 3H).

Example 50: (S)-2-(4-(2,4-Dimethyl-5-(3-methyl-4-phenylpiperazine-1-carbonyl)phenylamino)piperidin-1-yl)benzonitrile, I-33

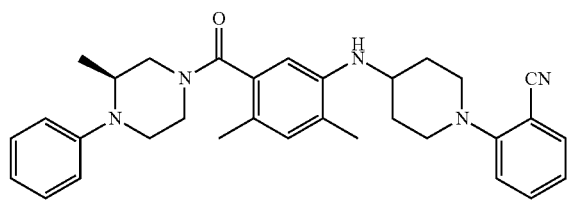

I-33

Synthetic Scheme:

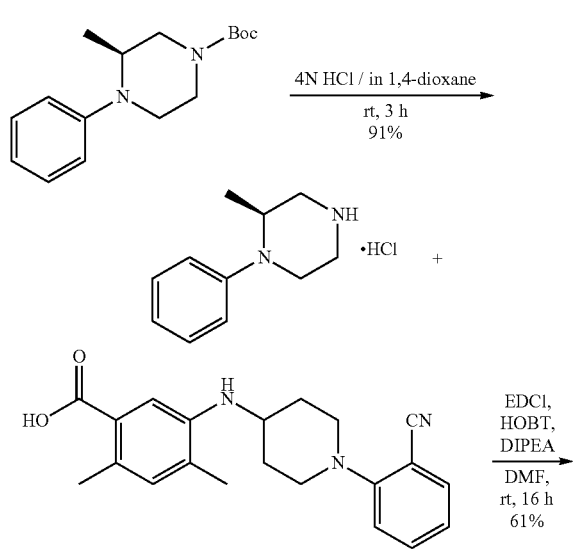

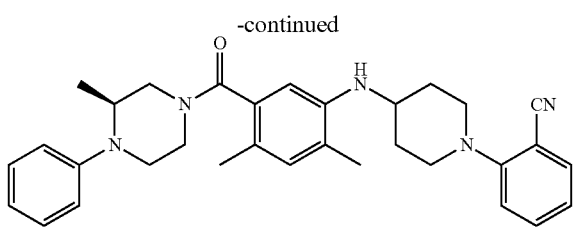

Procedures and Characterization:
The analysis method was following Method B and the separation method was following Method D.

Step 1: (S)-2-Methyl-1-phenylpiperazine Hydrochloride

A solution of (S)-tert-butyl 3-methyl-4-phenylpiperazine-1-carboxylate (300.00 mg, 1.09 mmol) in 4N HCl (in dioxane, 20 mL) was stirred for 3 h, then concentrated to obtain (S)-2-methyl-1-phenylpiperazine hydrochloride (210.00 mg, 0.986 mmol, 91% yield) as product. ESI-MS (EI$^+$, m/z): 177.2 [M+H]$^+$.

Step 2: (S)-2-(4-(2,4-Dimethyl-5-(3-methyl-4-phenylpiperazine-1-carbonyl)phenylamino)piperidin-1-yl)benzonitrile Followed the amide coupling EDCI/HOBT method to afford (S)-2-(4-(2,4-dimethyl-5-(3-methyl-4-phenylpiperazine-1-carbonyl)phenylamino)piperidin-1-yl)benzonitrile I-33 as a white solid. ESI-MS (EI$^+$, m/z): 508.0 [M+H]$^+$. $^1$H NMR (400 MHz, DMSO) δ 7.63 (dd, J=43.8, 7.2 Hz, 2H), 7.37-7.12 (m, 3H), 7.06 (t, J=7.5 Hz, 1H), 6.90 (s, 3H), 6.78 (d, J=6.8 Hz, 1H), 6.43 (s, 1H), 4.59-3.89 (m, 3H), 3.44 (dd, J=32.8, 17.3 Hz, 5H), 3.24-2.79 (m, 5H), 2.25-1.86 (m, 8H), 1.71 (s, 2H), 0.90 (dd, J=57.1, 19.8 Hz, 3H).

Example 51: 2-(4-(5-(1-(3-Cyanophenyl)piperidin-4-ylamino)-2,4-dimethylbenzoyl)piperazin-1-yl)benzonitrile Trifluoroacetate, I-18

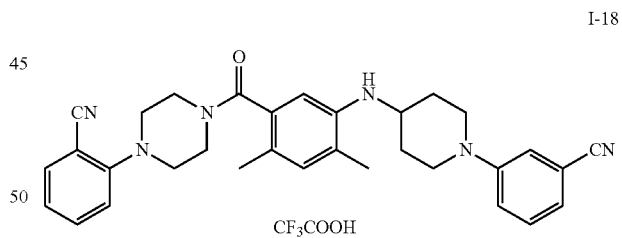

I-18

CF$_3$COOH

Synthetic Scheme:

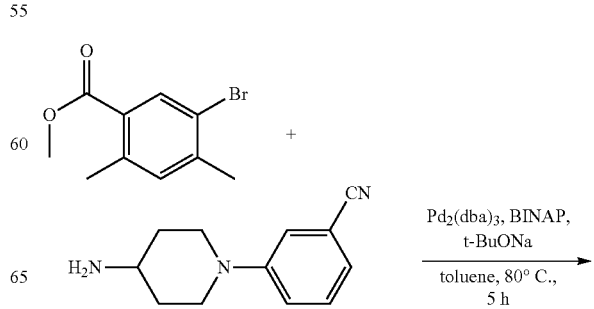

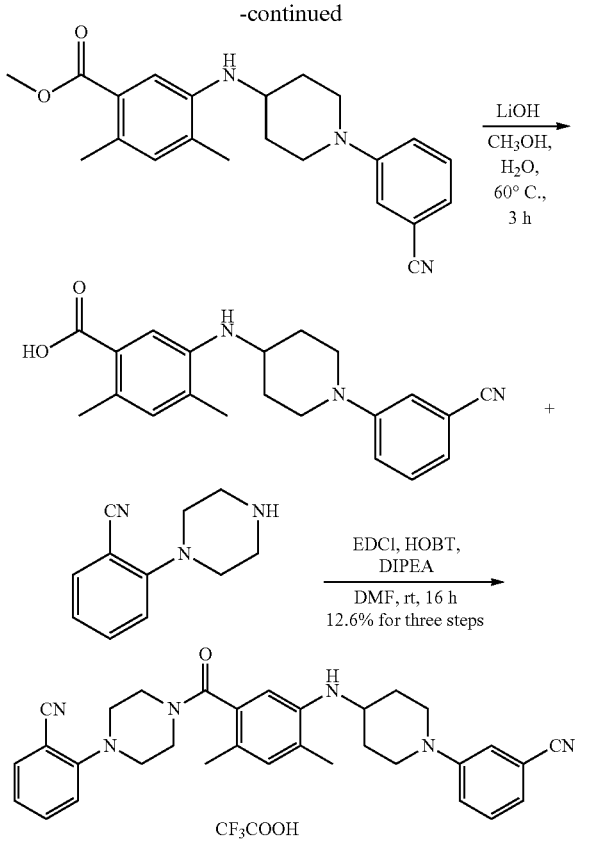

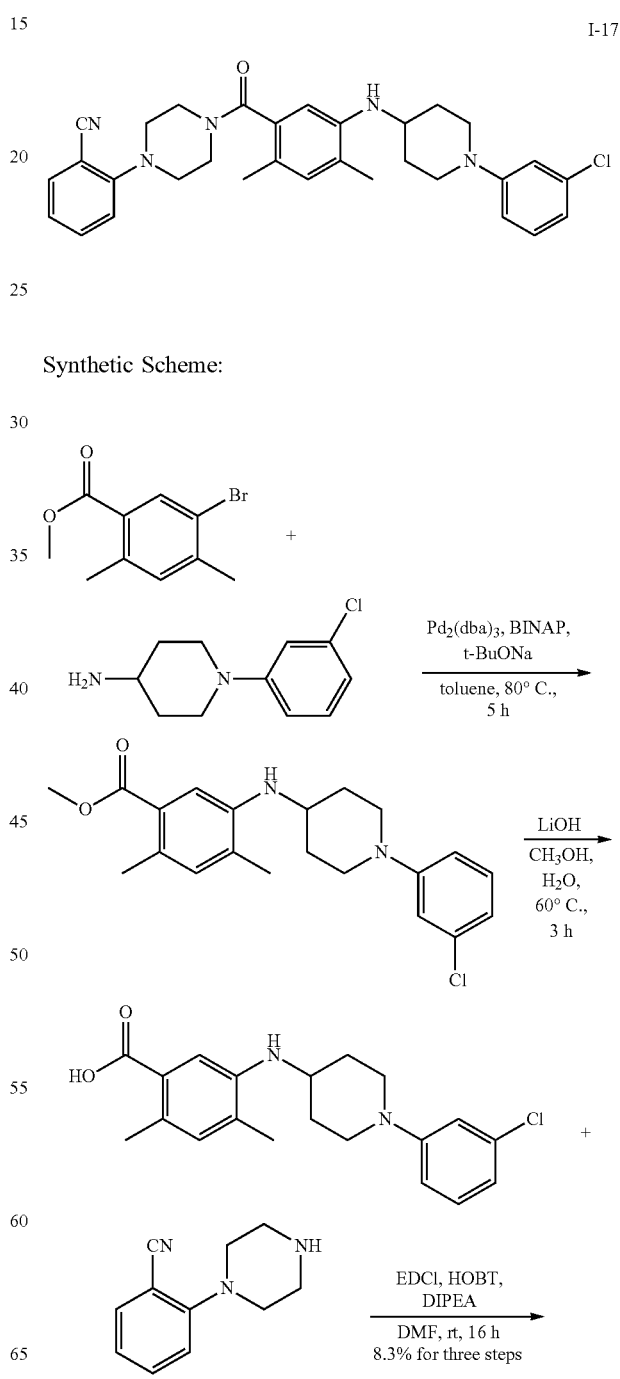

Procedures and Characterization:

The analysis method was following Method A and the separation method was following Method C.

Step 1: Methyl 5-(1-(3-cyanophenyl)piperidin-4-ylamino)-2,4-dimethylbenzoate

The procedure for methyl 5-(1-(3-cyanophenyl)piperidin-4-ylamino)-2,4-dimethylbenzoate was the same as example 32. ESI-MS (EI+, m/z): 364.1 [M+H]$^+$.

Step 2: 5-(1-(3-Cyanophenyl)piperidin-4-ylamino)-2,4-dimethylbenzoic Acid

To a solution of methyl 5-(1-(3-cyanophenyl)piperidin-4-ylamino)-2,4-dimethylbenzoate (110 mg, crude) in MeOH (20 mL) and water (10 mL) was added LiOH (27 mg, 1.13 mmol). The mixture was stirred at 60° C. for 3 h. Then the solvent was remove and the residue was dissolved in water, the resulting mixture was adjusted to pH 3 with 1M HCl, extracted with EtOAc (100 mL×2), then the organic phase was washed with brine (50 mL), dried and concentrated to give 5-(1-(3-cyanophenyl) piperidin-4-ylamino)-2, 4-dimethylbenzoic acid (120 mg, crude) as a yellow oil. ESI-MS (EI+, m/z): 350.2 [M+H]$^+$.

Step 3: 2-(4-(5-(1-(3-Cyanophenyl)piperidin-4-ylamino)-2,4-dimethylbenzoyl)piperazin-1-yl)benzonitrile Trifluoroacetate Using EDCI/HOBT Generic Method B 2-(4-(5-(1-(3-cyanophenyl)piperidin-4-ylamino)-2,4-dimethylbenzoyl)piperazin-1-yl)benzonitrile trifluoroacetate I-18 was obtained. ESI-MS (EI+, m/z): 519.0 [M+H]$^+$. $^1$H NMR (400 MHz, CD$_3$OD-d$_4$) δ: 7.59-7.68 (m, 2H), 7.38-7.42 (m, 1H), 7.30-7.32 (m, 2H), 7.13-7.23 (m, 4H), 6.93 (s, 1H), 3.87-4.04 (m, 4H), 3.63-3.67 (m, 1H), 3.51-3.53 (t, J=4.8 Hz, 2H), 3.14-3.24 (m, 4H), 2.92-2.98 (m, 2H), 2.35 (s, 3H), 2.29 (s, 3H), 2.15 (d, J=11.6 Hz, 2H), 1.77 (s, 2H).

Example 52: 2-(4-(5-(1-(3-Chlorophenyl)piperidin-4-ylamino)-2,4-dimethylbenzoyl)piperazin-1-yl)benzonitrile, I-17

I-17

Synthetic Scheme:

-continued

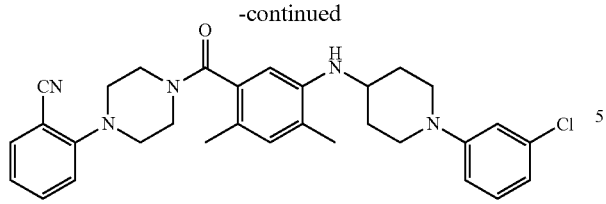

Procedures and Characterization:

The analysis method was following Method B and the separation method was following Method D.

The procedure for 2-(4-(5-(1-(3-chlorophenyl)piperidin-4-ylamino)-2,4-dimethylbenzoyl)piperazin-1-yl)benzonitrile was similar to example 51. ESI-MS (EI+, m/z): 527.9 [M+H]+. 1H NMR (400 MHz, CDCl3) δ: 7.49-7.59 (m, 2H), 7.13-7.17 (t, J=8.0 Hz, 1H), 7.00-7.08 (m, 2H), 6.90 (d, J=8.0 Hz, 2H), 6.78-6.82 (m, 2H), 6.47 (s, 1H), 4.01-4.05 (m, 2H), 3.60-3.67 (t, J=14.0 Hz, 2H), 3.22-3.51 (m, 6H), 3.10 (s, 2H), 2.89-2.98 (m, 2H), 2.19 (s, 3H), 2.11 (s, 3H), 1.50-1.74 (m, 3H).

Example 53: 2-(4-(5-(4-(2-Cyanophenyl)piperazine-1-carbonyl)-2,6-dimethylpyridin-3-ylamino)piperidin-1-yl)benzonitrile, I-13

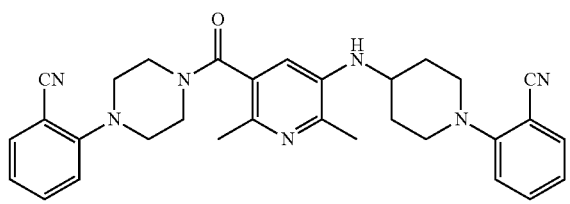

I-13

Synthetic Scheme:

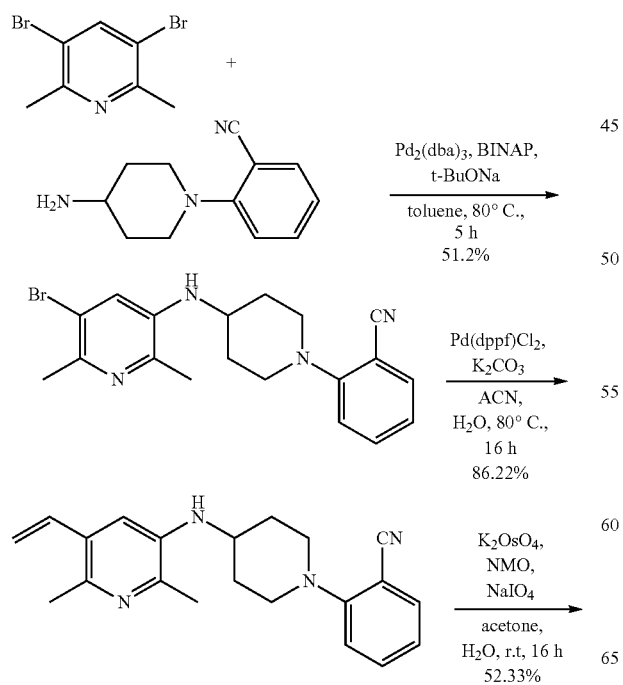

-continued

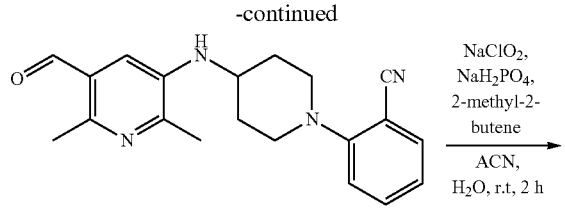

Procedures and Characterization:

The analysis method was following Method B and the separation method was following Method D.

The procedure for 2-(4-(5-(4-(2-cyanophenyl)piperazine-1-carbonyl)-2,6-dimethylpyridin-3-ylamino)piperidin-1-yl)benzonitrile was similar to example 51. ESI-MS (EI+, m/z): 520.0 [M+H]+. 1H NMR (500 MHz, CD3OD-d4) δ: 7.65-7.66 (m, 1H), 7.55-7.62 (m, 3H), 7.19-7.22 (t, J=8.0 Hz, 2H), 7.13-7.16 (t, J=7.5 Hz, 1H), 7.06-7.09 (t, J=8.0 Hz, 1H), 6.98 (s, 1H), 3.98-4.05 (m, 2H), 3.53-3.60 (m, 6H), 3.15-3.24 (m, 3H), 3.01-3.05 (t, J=11.5 Hz, 2H), 2.42 (s, 3H), 2.38 (s, 3H), 2.18 (d, J=10.5 Hz, 2H), 1.31-1.33 (m, 2H).

Example 54: 2-(4-(5-(1-(2-Cyanophenyl)piperidin-4-ylamino)-2,6-dimethylnicotinoyl)piperazin-1-yl)benzenesulfonamide, I-12

I-12

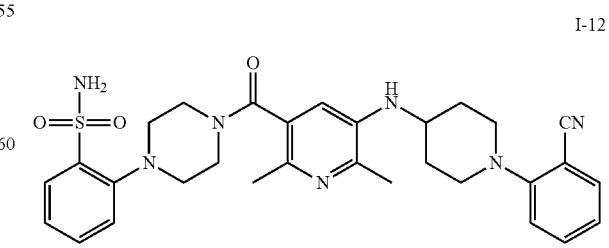

Synthetic Scheme:

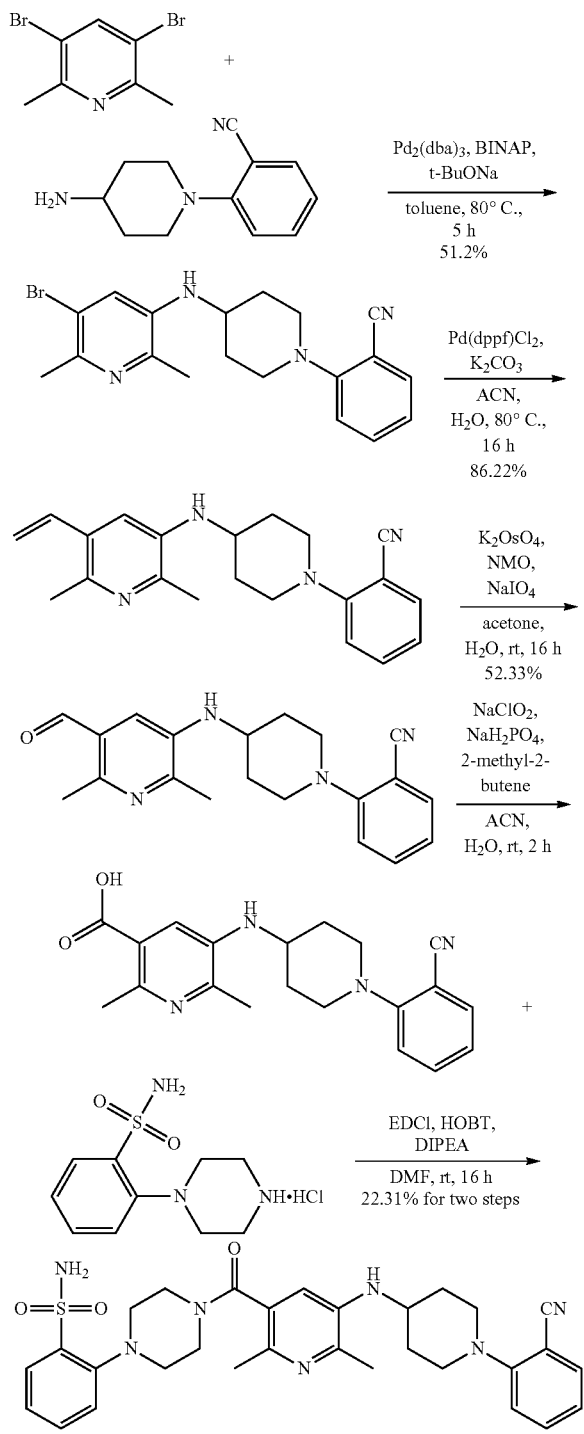

Procedures and Characterization:
The analysis method was following Method B and the separation method was following Method D.
The procedure for 2-(4-(5-(1-(2-cyanophenyl)piperidin-4-ylamino)-2,6-dimethylnicotinoyl)piperazin-1-yl)benzenesulfonamide was similar to example 51.
ESI-MS (EI+, m/z): 573.9 [M+H]+. 1H NMR (500 MHz, CDCl3) δ: 8.02-8.04 (dd, J1=7.5 Hz, J2=1.0 Hz, 1H), 7.56-7.62 (m, 2H), 7.47-7.51 (m, 1H), 7.34-7.39 (m, 2H), 7.00-7.05 (m, 2H), 6.73 (s, 1H), 5.52 (s, 2H), 3.45-3.61 (m, 6H), 2.99-3.18 (m, 6H), 2.42 (s, 3H), 2.39 (s, 3H), 2.22 (d, J=7.5 Hz, 2H), 1.72-1.80 (m, 2H).

Example 55: (S)-tert-butyl 4-(5-(1-(2-cyanophenyl)piperidin-4-ylamino)-2,4-dimethylbenzoyl)-2-(hydroxymethyl)piperazine-1-carboxylate, I-9

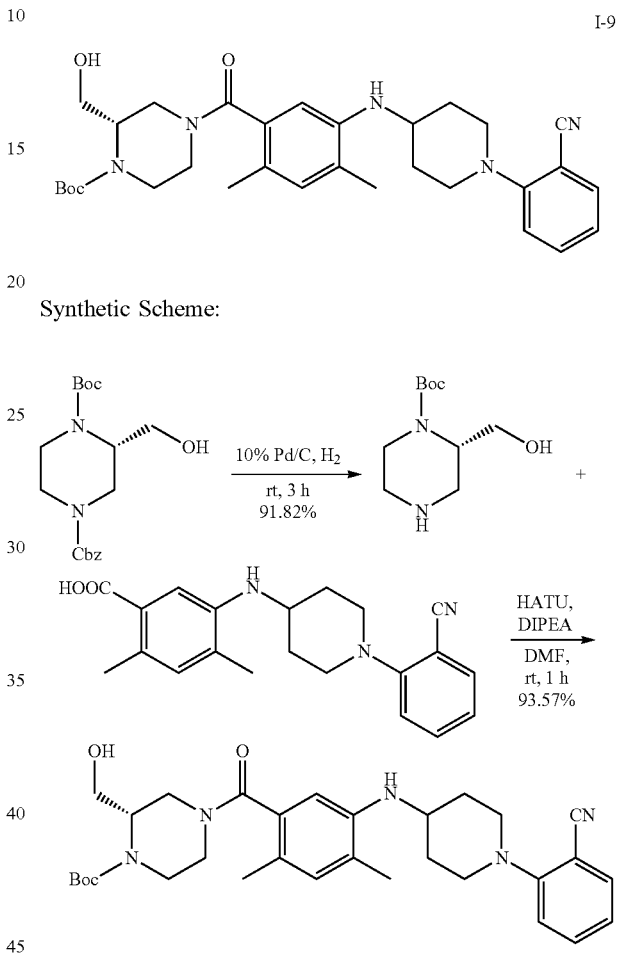

Synthetic Scheme:

Procedures and Characterization:
The analysis method was following Method B and the separation method was following Method D.

Step 1: (S)-tert-butyl 2-(hydroxymethyl)piperazine-1-carboxylate

To a solution of (S)-4-benzyl 1-tert-butyl 2-(hydroxymethyl)piperazine-1,4-dicarboxylate (1.5 g, 4.28 mmol) in MeOH (20 mL) was added 10% Pd/C (150 mg). The mixture was stirred at rt for 3 h under H2. Then the solid was remove by filtration and the filter was concentrated to give (S)-tert-butyl 2-(hydroxymethyl)piperazine-1-carboxylate (850 mg, 3.93 mmol, 91.82%) as a white solid. ESI-MS (EI+, m/z): 217.3 [M+H]+.

Step 2: (S)-tert-butyl 4-(5-(1-(2-cyanophenyl)piperidin-4-ylamino)-2,4-dimethylbenzoyl)-2-(hydroxymethyl)piperazine-1-carboxylate The procedure for (S)-tert-butyl 4-(5-(1-(2-cyanophenyl)piperidin-4-ylamino)-2,4-dimethylbenzoyl)-2-(hydroxymethyl)piperazine-1-carboxylate was HATU generic method A. ESI-MS (EI+, m/z): 548.0 [M+H]+. 1H NMR (500 MHz, CD3OD-d4) δ: 7.55-7.62 (m, 2H), 7.20 (d, J=8.5 Hz, 1H), 7.06-7.09 (t, J=7.5 Hz, 1H), 6.96 (s, 1H), 6.49-6.58 (m, 2H), 3.47-4.32 (m, 9H), 2.97-3.21 (m, 5H), 2.10-2.22 (m, 8H), 1.77 (d, J=10.0 Hz, 2H), 1.48 (s, 9H).

Example 56: (S)-2-(4-(5-(3-(hydroxymethyl)piperazine-1-carbonyl)-2,4-dimethylphenylamino)piperidin-1-yl)benzonitrile, I-8

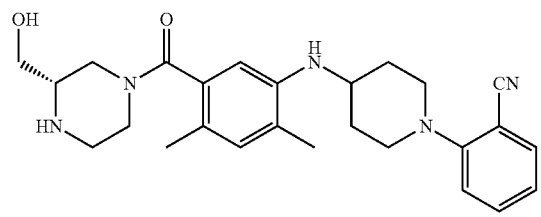

I-8

Synthetic Scheme:

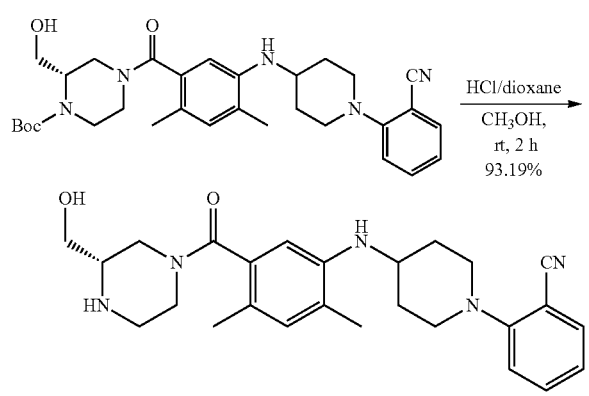

Procedures and Characterization:

The analysis method was following Method B and the separation method was following Method D.

To a solution of (S)-tert-butyl 4-(5-(1-(2-cyanophenyl)piperidin-4-ylamino)-2,4-dimethylbenzoyl)-2-(hydroxymethyl)piperazine-1-carboxylate (170 mg, 0.31 mmol) in MeOH (2 mL) was added HCl (4M in dioxane, 4 mL). The mixture was stirred at rt for 2 h. Then the mixture was concentrated and the residue was dissolved in water, then saturated NaHCO3 was added to above mixture until the pH of the mixture was 8. The reaction mixture was extracted with EtOAc (100 mL), and washed with water (50 mL) and brine (50 mL). The resulting organic phase was dried, filtered and concentrated. The residue was purified via preparative HPLC to give (S)-2-(4-(5-(3-(hydroxymethyl)piperazine-1-carbonyl)-2,4-dimethylphenylamino)piperidin-1-yl)benzonitrile I-8 (140 mg, 0.29 mmol, 93.19%) as a white solid.

ESI-MS (EI+, m/z): 448.3 [M+H]+. 1H-NMR (500 MHz, MeOD) δ: 7.55-7.62 (m, 2H), 7.20 (d, J=8.5 Hz, 1H), 7.06-7.09 (t, J=7.5 Hz, 1H), 6.95 (s, 1H), 6.48-6.55 (m, 1H), 4.57-4.61 (m, 1H), 3.41-3.62 (m, 6H), 2.69-3.14 (m, 7H), 2.11-2.19 (m, 8H), 1.73-1.77 (m, 2H).

Example 57: (S)-2-(4-(5-(4-(5-fluoropyridin-2-yl)-3-(hydroxymethyl)piperazine-1-carbonyl)-2,4-dimethylphenylamino)piperidin-1-yl)benzonitrile, I-117

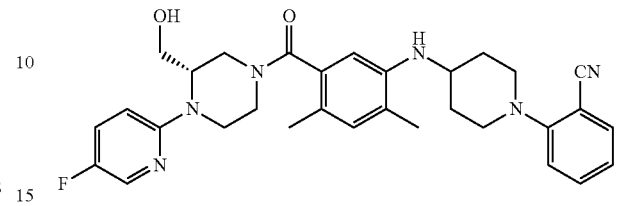

I-117

Synthetic Scheme:

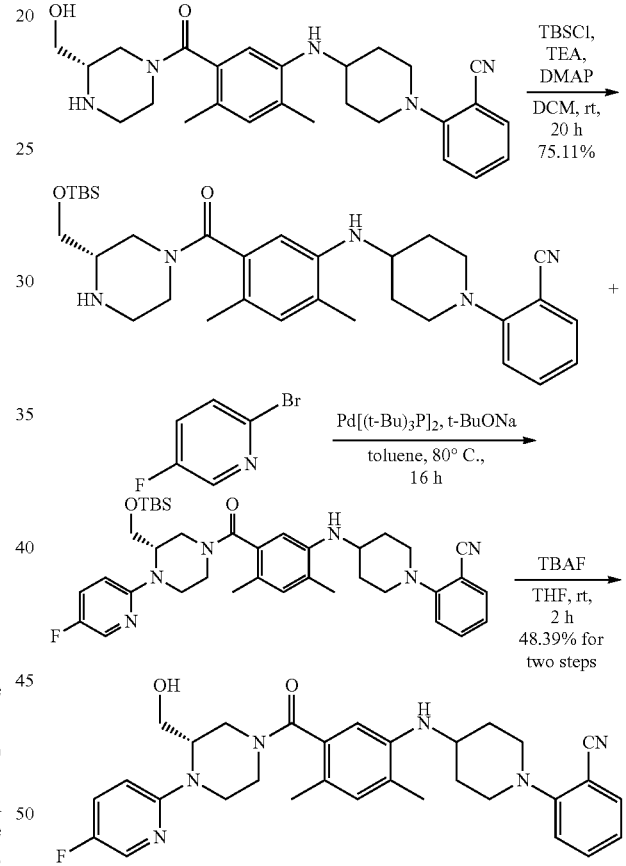

Procedures and Characterization:

The analysis method was following Method B and the separation method was following Method D.

Step 1: (S)-2-(4-(5-(3-((tert-butyldimethylsilyloxy)methyl)piperazine-1-carbonyl)-2,4-dimethylphenylamino)piperidin-1-yl)benzonitrile To a solution of (S)-2-(4-(5-(3-(hydroxymethyl)piperazine-1-carbonyl)-2,4-dimethylphenylamino)piperidin-1-yl)benzonitrile (3.5 g, 7.82 mmol) in DCM (100 mL) was added TEA (5.4 mL, 39.1 mmol) and DMAP (191 mg, 1.56 mmol). The mixture was cooled to 0° C., and TBSCl (4.71 g, 31.28 mmol) was added. The resulting mixture was warmed to rt, and stirred for 20 h. Then the reaction mixture was quenched with saturated aqueous NH₄Cl solution (30 mL) and washed with water (50 mL×2) and brine (50 mL). The organic phase was dried over Na₂SO₄, filtered and concentrated. The residue was purified by column chromatography on silica gel to give (S)-2-(4-(5-(3-((tert-butyldimethylsilyloxy)methyl)piperazine-1-carbonyl)-2,4-dimethylphenylamino)piperidin-1-yl)benzonitrile (3.3 g, 5.87 mmol, 75.11%) as a pale yellow solid. ESI-MS (EI+, m/z): 562.3 [M+H]⁺.

Step 2: (S)-2-(4-(5-(3-((tert-butyldimethylsilyloxy)methyl)-4-(5-fluoropyridin-2-yl)piperazine-1-carbonyl)-2,4-dimethylphenylamino)piperidin-1-yl)benzonitrile To a solution of (S)-2-(4-(5-(3-((tert-butyldimethylsilyloxy)methyl)piperazine-1-carbonyl)-2,4-dimethylphenylamino)piperidin-1-yl)benzonitrile (200 mg, 0.35 mmol) and 2-bromo-5-fluoropyridine (188 mg, 1.07 mmol) in toluene (10 mL) was added Pd[(t-Bu)₃P]₂ (18.19 mg, 0.035 mmol) and tBuONa (68.42 mg, 0.71 mmol). The mixture was stirred at 80° C. for 16 h under nitrogen. The resulting reaction mixture was concentrated in vacuum and the residue was purified by column chromatography on silica gel to give (S)-2-(4-(5-(3-((tert-butyldimethylsilyloxy)methyl)-4-(5-fluoropyridin-2-yl)piperazine-1-carbonyl)-2,4-dimethylphenylamino)piperidin-1-yl)benzonitrile (300 mg, crude) as a yellow oil which was used for the next step directly. ESI-MS (EI+, m/z): 657.2 [M+H]⁺.

Step 3: (S)-2-(4-(5-(4-(5-fluoropyridin-2-yl)-3-(hydroxymethyl)piperazine-1-carbonyl)-2,4-dimethylphenylamino)piperidin-1-yl)benzonitrile To a solution of (S)-2-(4-(5-(3-((tert-butyldimethylsilyloxy)methyl)-4-(5-fluoropyridin-2-yl)piperazine-1-carbonyl)-2,4-dimethylphenylamino)piperidin-1-yl)benzonitrile (300 mg, crude) in THF (5 mL) was added TBAF (1M in THF, 1.2 mL). The mixture was stirred at rt for 2 h. The resulting mixture was diluted with EtOAc (200 mL), and washed with water (50 mL×2) and brine (50 mL). The organic phase was dried over Na₂SO₄, filtered and concentrated. The residue was purified via preparative HPLC to give (S)-2-(4-(5-(4-(5-fluoropyridin-2-yl)-3-(hydroxymethyl)piperazine-1-carbonyl)-2,4-dimethylphenylamino)piperidin-1-yl)benzonitrile I-117 (93.4 mg, 0.17 mmol, 48.39% for two steps) as a white solid. ESI-MS (EI+, m/z): 543.3 [M+H]⁺. ¹H NMR (400 MHz, CDCl₃) δ: 7.98-8.01 (dd, J₁=2.8 Hz, J₂=8.0 Hz, 1H), 7.46-7.57 (m, 2H), 7.29-7.30 (m, 1H), 6.94-7.04 (m, 3H), 6.50-6.66 (m, 2H), 4.51-4.85 (m, 2H), 2.99-3.88 (m, 15H), 2.12-2.23 (m, 8H).

Example 58: (S)-2-(4-(5-(4-(3-fluoropyridin-2-yl)-3-(hydroxymethyl)piperazine-1-carbonyl)-2,4-dimethylphenylamino)piperidin-1-yl)benzonitrile, I-106

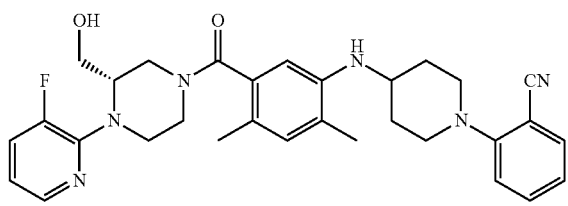

I-106

Synthetic Scheme:

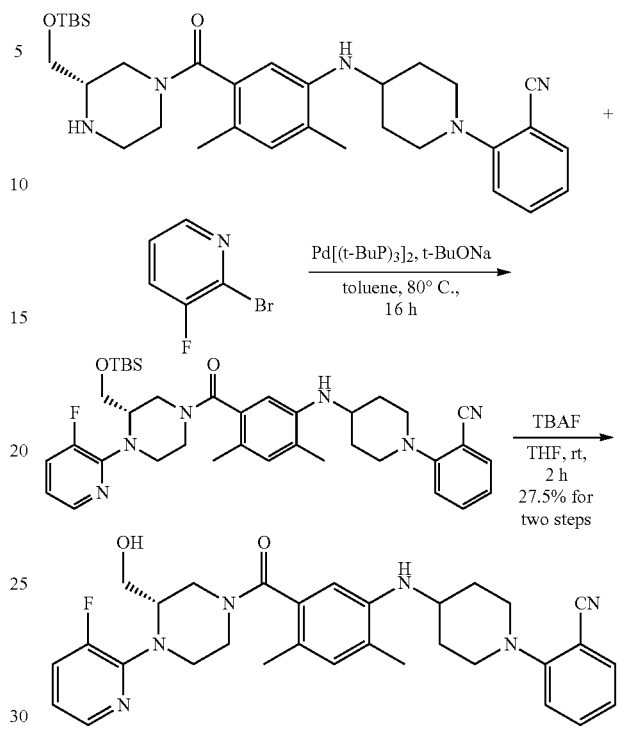

Procedures and Characterization:
The analysis method was following Method B and the separation method was following Method D.

The procedure for (S)-2-(4-(5-(4-(3-fluoropyridin-2-yl)-3-(hydroxymethyl)piperazine-1-carbonyl)-2,4-dimethylphenylamino)piperidin-1-yl)benzonitrile was similar to example 57. ESI-MS (EI+, m/z): 543.3 [M+H]⁺. ¹H-NMR (500 MHz, CDCl₃) δ: 7.91-7.94 (dd, J₁=4.5 Hz, J₂=12.5 Hz, 1H), 7.56 (d, J=8.0 Hz, 1H), 7.46-7.49 (m, 1H), 7.29-7.31 (m, 1H), 6.90-7.05 (m, 3H), 6.42-6.52 (m, 1H), 3.87-4.75 (m, 5H), 3.22-3.60 (m, 9H), 2.96-3.01 (m, 2H), 2.11-2.26 (m, 8H), 1.76-1.78 (m, 2H).

Example 59: 2-(4-(4-Cyano-5-(1-(2-cyanophenyl)piperidin-4-ylamino)-2-methylbenzoyl)piperazin-1-yl)benzenesulfonamide, I-86

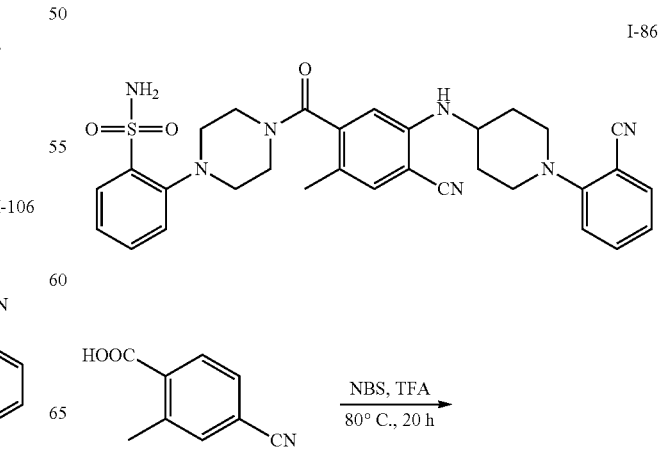

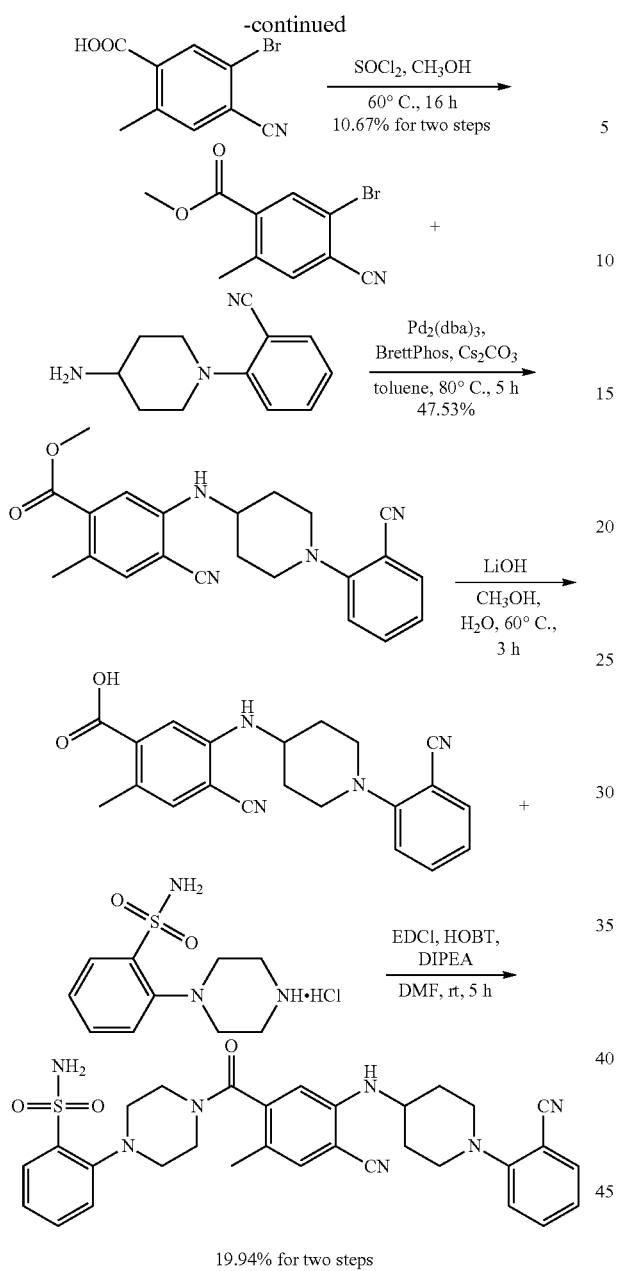

19.94% for two steps

Procedures and Characterization:
The analysis method was following Method B and the separation method was following Method D.

Step 1: 5-Bromo-4-cyano-2-methylbenzoic Acid

To a solution of 4-cyano-2-methylbenzoic acid (2 g, 12.42 mmol) in TFA (50 mL) was added NBS (4.42 g, 24.82 mmol). The mixture was stirred at 80° C. for 20 h. The resulting mixture was poured into water (300 mL) and stirred for 20 min at rt. The precipitate was collected by filtration and dried to give 5-bromo-4-cyano-2-methylbenzoic acid (1 g, crude) as a white solid which was used for next step directly. ESI-MS (EI+, m/z): 239.9 [M+H]+.

Step 2: Methyl 5-bromo-4-cyano-2-methylbenzoate

To a solution of 5-bromo-4-cyano-2-methylbenzoic acid (850 mg, crude) in MeOH (10 mL) was added SOCl$_2$ (0.33 mL, 4.6 mmol) at 0° C. Then the mixture was stirred at 60° C. for 16 h. The resulting mixture was cooled and concentrated. The residue was purified via preparative HPLC to give methyl 5-bromo-4-cyano-2-methylbenzoate (320 mg, 1.26 mmol, 10.67% for two steps) as a white solid.

Step 3: Methyl 4-cyano-5-(1-(2-cyanophenyl)piperidin-4-ylamino)-2-methylbenzoate To a solution of 5-bromo-4-cyano-2-methylbenzoate (300 mg, 1.18 mmol) and 2-(4-aminopiperidin-1-yl)benzonitrile (475 mg, 2.36 mmol) in toluene (15 mL) was added Pd$_2$(dba)$_3$ (108 mg, 0.12 mmol), BrettPhos (127 mg, 0.24 mmol) and Cs$_2$CO$_3$ (769 mg, 2.36 mmol). The mixture was stirred at 80° C. for 5 h under nitrogen. The resulting mixture was concentrated under vacuum and the residue was purified by column chromatography on silica gel to give methyl 4-cyano-5-(1-(2-cyanophenyl) piperidin-4-ylamino)-2-methylbenzoate (210 mg, 0.56 mmol, 47.53%) as a yellow oil. ESI-MS (EI+, m/z): 375.1 [M+H]+.

Step 4: 4-Cyano-5-(1-(2-cyanophenyl)piperidin-4-ylamino)-2-methylbenzoic Acid

The procedure for 4-cyano-5-(1-(2-cyanophenyl)piperidin-4-ylamino)-2-methylbenzoic acid was the same as example 52.

Step 5: 2-(4-(4-Cyano-5-(1-(2-cyanophenyl)piperidin-4-ylamino)-2-methylbenzoyl)piperazin-1-yl)benzenesulfonamide The procedure for 2-(4-(4-cyano-5-(1-(2-cyanophenyl) piperidin-4-ylamino)-2-methylbenzoyl)piperazin-1-yl)benzenesulfonamide was generic amide coupling method B. ESI-MS (EI+, m/z): 584.2 [M+H]+. $^1$H NMR (400 MHz, CDCl$_3$) δ: 8.02-8.04 (dd, J$_1$=1.2 Hz, J$_2$=7.6 Hz, 1H), 7.56-7.63 (m, 2H), 7.47-7.52 (m, 1H), 7.34-7.39 (m, 2H), 7.28 (s, 1H), 7.01-7.05 (m, 2H), 6.55 (s, 1H), 5.51 (s, 2H), 4.51 (d, J=7.6 Hz, 1H), 2.99-3.61 (m, 12H), 2.21 (s, 5H), 1.79-1.85 (m, 2H).

Example 60: 2-(4-(5-(1-(2-cyanophenyl)pyrrolidin-3-ylamino)-2,4-dimethylbenzoyl)piperazin-1-yl)benzenesulfonamide, I-131

I-131

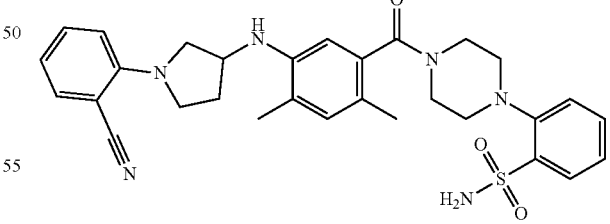

Synthetic Scheme:

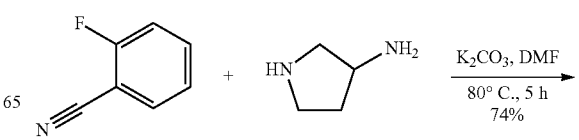

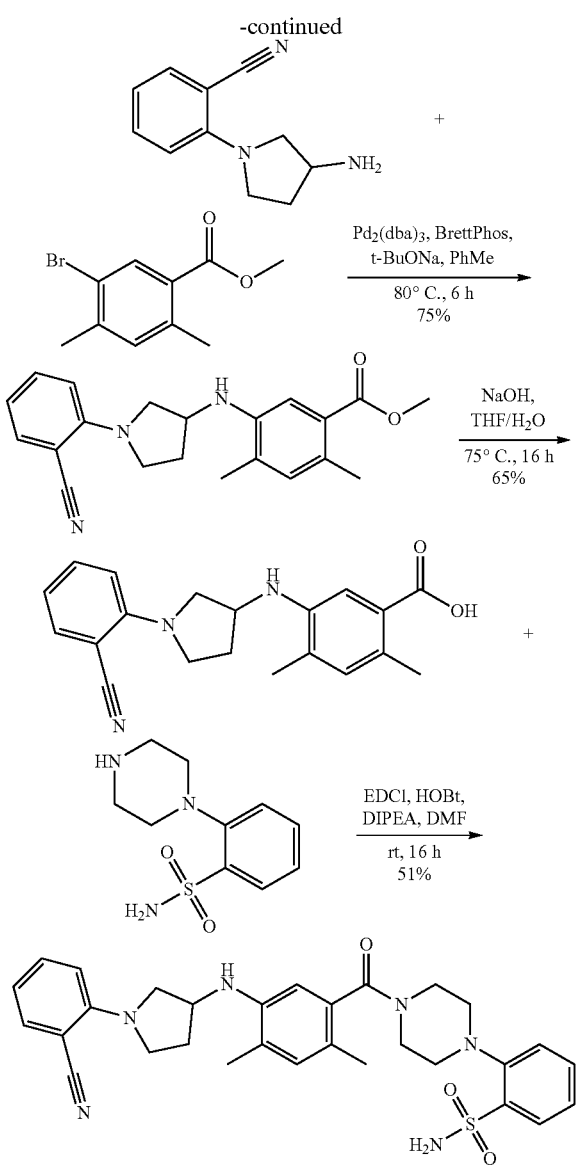

Procedures and Characterization:
The analysis method was following Method B and the separation method was following Method D.

Step 1: 2-(3-aminopyrrolidin-1-yl)benzonitrile

A mixture of 2-fluorobenzonitrile (2.00 g, 16.51 mmol), pyrrolidin-3-amine (2.13 g, 24.77 mmol) and $K_2CO_3$ (6.85 g, 49.53 mmol) in DMF (20.00 mL) was heated at 80° C. for 5 h. $H_2O$ (20 mL) and EtOAc (20 mL) was added, the organic phase was separated and the aqueous was further extracted with EtOAc (20 mL×2). The combined extracts were washed with brine (20 mL), dried over anhydrous $Na_2SO_4$, filtered and concentrated and the residue was purified by silica gel chromatography (DCM/MeOH=30/1-20/1) to afford 2-(3-aminopyrrolidin-1-yl)benzonitrile (2.5 g, 12.28 mmol, 74% yield) as a yellow oil. ESI-MS (EI+, m/z): 188.2 [M+H]+.

Step 2: methyl 5-(1-(2-cyanophenyl)pyrrolidin-3-ylamino)-2,4-dimethylbenzoate

A mixture of 2-(3-aminopyrrolidin-1-yl)benzonitrile (385.00 mg, 2.06 mmol), methyl 5-bromo-2,4-dimethyl-benzoate (500.79 mg, 2.06 mmol), $Pd_2(dba)_3$ (94.32 mg, 103.00 umol), BrettPhos (110.57 mg, 206.00 umol), and sodium tert-butoxide (395.93 mg, 4.12 mmol) in toluene (30.00 mL) was heated at 80° C. under $N_2$ atmosphere for 6 h. The reaction mixture was concentrated and purified via preparative HPLC to afford methyl 5-[[1-(2-cyanophenyl)pyrrolidin-3-yl]amino]-2,4-dimethyl-benzoate (540.00 mg, 1.55 mmol, 75% yield) as a slight oil. ESI-MS (EI+, m/z): 350.0 [M+H]+.

Step 3: 5-(1-(2-cyanophenyl)pyrrolidin-3-ylamino)-2,4-dimethylbenzoic Acid

A mixture of methyl 5-[[1-(2-cyanophenyl)pyrrolidin-3-yl]amino]-2,4-dimethyl-benzoate (540.00 mg, 1.55 mmol) and NaOH (620.00 mg, 15.50 mmol) in THF (10.00 mL) and $H_2O$ (4.00 mL) was heated at 80° C. for 24 h. The reaction mixture was cooled and acidified to pH=1~2 by added 1M HCl, EtOAc (20 mL) was added and the organic phase was separated, the aqueous was further extracted with EtOAc (20 mL×3). The combined extracts were washed with brine (20 mL), dried over anhydrous $Na_2SO_4$, filtered and concentrated. The residue was purified via preparative HPLC to afford 5-[[1-(2-cyanophenyl)pyrrolidin-3-yl]amino]-2,4-dimethyl-benzoic acid (340.00 mg, 1.01 mmol, 65% yield) as a white solid. ESI-MS (EI+, m/z): 336.0 [M+H]+.

Step 4: 2-(4-(5-(1-(2-cyanophenyl)pyrrolidin-3-ylamino)-2,4-dimethylbenzoyl)piperazin-1-yl)benzenesulfonamide Followed the amide coupling EDCI/HOBT method to afford 2-[4-[5-[[1-(2-cyanophenyl)pyrrolidin-3-yl]amino]-2,4-dimethyl-benzoyl]piperazin-1-yl]benzenesulfonamide I-131 as a white solid. ESI-MS (EI+, m/z): 559.3 [M+H]+. $^1$H NMR (500 MHz, CDCl$_3$) δ 8.04 (d, J=1.5 Hz, 1H), 8.03-8.01 (m, 1H), 7.61-7.33 (m, 4H), 6.93 (s, 1H), 6.72-6.65 (m, 2H), 6.47 (d, J=10.0 Hz, 1H), 5.55 (s, 2H), 4.21-4.12 (m, 2H), 3.91 (br, 1H), 3.81-3.18 (m, 6H), 3.02-2.96 (m, 3H), 2.39 (br, 1H), 2.21 (s, 3H), 2.11-2.04 (m, 4H).

Example 61: (R)-2-(4-(5-(3-(Hydroxymethyl)-4-o-tolylpiperazine-1-carbonyl)-2,4-dimethylphenylamino)piperidin-1-yl)benzonitrile, I-112

I-112

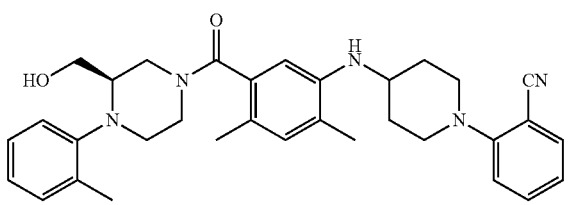

The procedure for (R)-2-(4-(5-(3-(Hydroxymethyl)-4-o-tolylpiperazine-1-carbonyl)-2,4-dimethylphenylamino)piperidin-1-yl)benzonitrile was similar to example 57.
ESI-MS (EI+, m/z): 538.3 [M+H]+. $^1$H NMR (500 MHz, CDCl$_3$) δ 7.57 (d, J=7.5 Hz, 1H), 7.49 (t, J=7.5 Hz, 1H), 7.25-7.11 (m, 2H), 7.10-6.97 (m, 4H), 6.93 (s, 1H), 6.56-6.48 (m, 1H), 4.51-4.16 (m, 1H), 3.91-2.91 (m, 13H), 2.85-2.66 (m, 1H), 2.35-2.16 (m, 9H), 2.13 (s, 3H).

Example 62: (S)-2-(4-(5-(3-(Hydroxymethyl)-4-o-tolylpiperazine-1-carbonyl)-2,4-dimethylphenylamino)piperidin-1-yl)benzonitrile, I-107

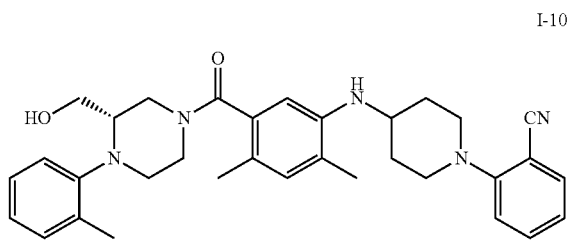

The procedure for (S)-2-(4-(5-(3-(Hydroxymethyl)-4-o-tolylpiperazine-1-carbonyl)-2,4-dimethylphenylamino)piperidin-1-yl)benzonitrile was similar to example 57. ESI-MS (EI$^+$, m/z): 538.0 [M+H]$^+$. $^1$H NMR (500 MHz, CDCl$_3$) δ 7.57 (d, J=7.5 Hz, 1H), 7.49 (t, J=7.5 Hz, 1H), 7.25-7.11 (m, 2H), 7.10-6.97 (m, 4H), 6.93 (s, 1H), 6.56-6.48 (m, 1H), 4.51-4.16 (m, 1H), 3.91-2.91 (m, 13H), 2.85-2.66 (m, 1H), 2.35-2.16 (m, 9H), 2.13 (s, 3H).

Example 63: (R)-2-(4-(5-(3-(Hydroxymethyl)-4-(6-methylpyridin-2-yl)piperazine-1-carbonyl)-2,4-dimethylphenylamino)piperidin-1-yl)benzonitrile, I-101

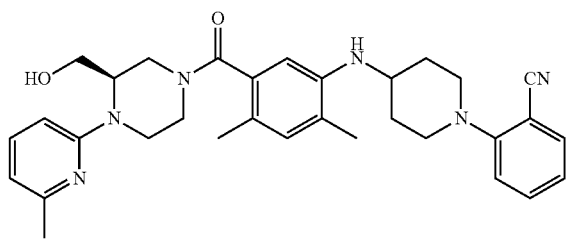

The procedure for (R)-2-(4-(5-(3-(Hydroxymethyl)-4-(6-methylpyridin-2-yl)piperazine-1-carbonyl)-2,4-dimethylphenylamino)piperidin-1-yl)benzonitrile was similar to example 57.

ESI-MS (EI$^+$, m/z): 539.0 [M+H]$^+$. $^1$H NMR (400 MHz, CDCl$_3$) δ 7.56 (d, J=7.6 Hz, 1H), 7.50-7.36 (m, 2H), 7.05-6.98 (m, 2H), 6.94 (s, 1H), 6.56-6.41 (m, 3H), 4.77-4.68 (m, 1H), 4.39 (br, 1H), 3.92-3.71 (m, 3H), 3.58-3.23 (m, 8H), 3.15-2.96 (m, 3H), 2.37 (s, 3H), 2.22-2.12 (m, 9H).

Example 64: (S)-2-(4-(5-(3-(Hydroxymethyl)-4-(6-methylpyridin-2-yl)piperazine-1-carbonyl)-2,4-dimethylphenylamino)piperidin-1-yl)benzonitrile, I-102

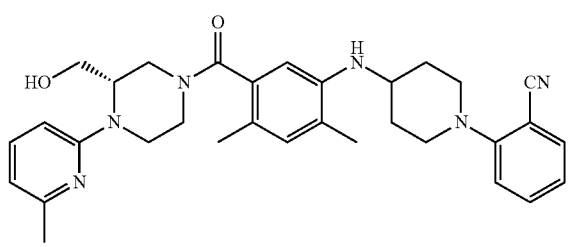

The procedure for (S)-2-(4-(5-(3-(Hydroxymethyl)-4-(6-methylpyridin-2-yl)piperazine-1-carbonyl)-2,4-dimethylphenylamino)piperidin-1-yl)benzonitrile was similar to example 57.

ESI-MS (EI$^+$, m/z): 539.3 [M+H]$^+$. 1 H NMR (400 MHz, CDCl$_3$) δ 7.56 (d, J=7.6 Hz, 1H), 7.50-7.36 (m, 2H), 7.05-6.98 (m, 2H), 6.94 (s, 1H), 6.56-6.41 (m, 3H), 4.77-4.68 (m, 1H), 4.39 (br, 1H), 3.92-3.71 (m, 3H), 3.58-3.23 (m, 8H), 3.15-2.96 (m, 3H), 2.37 (s, 3H), 2.22-2.12 (m, 9H).

Example 65: 2-(4-(3-(1-(2-Cyanophenyl)piperidin-4-ylamino)-2,4,6-trimethylbenzoyl)piperazin-1-yl)pyridine-3-sulfonamide, I-15

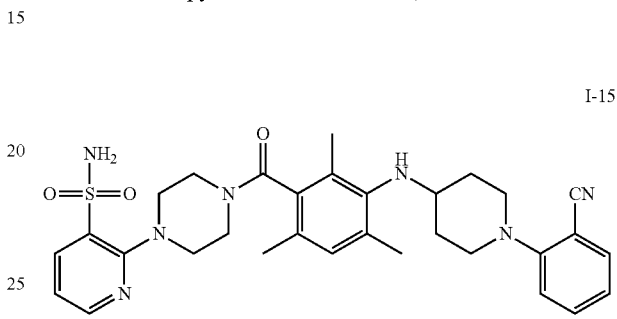

Synthetic Scheme:

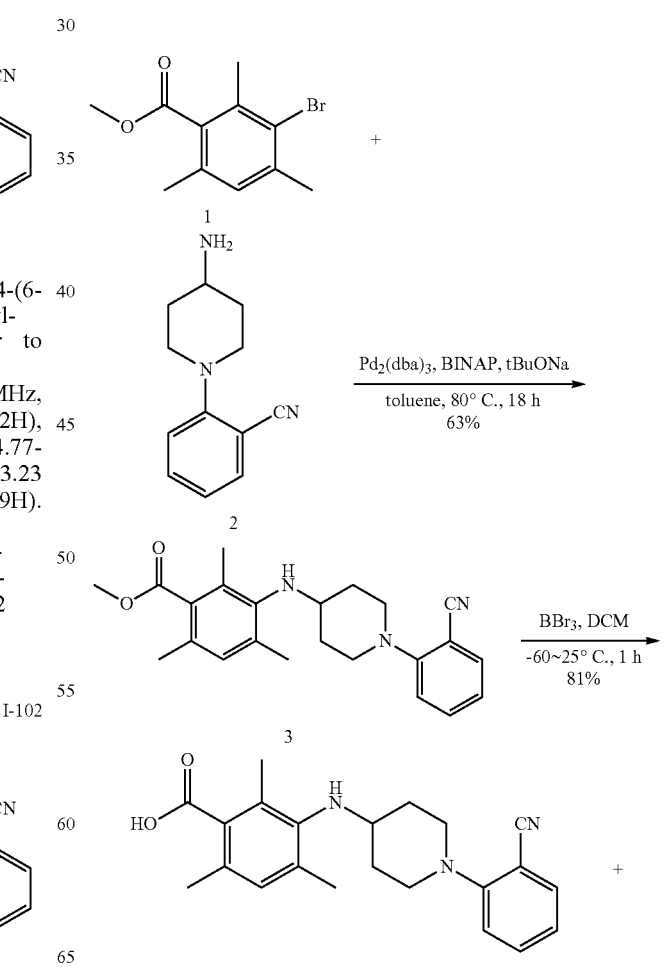

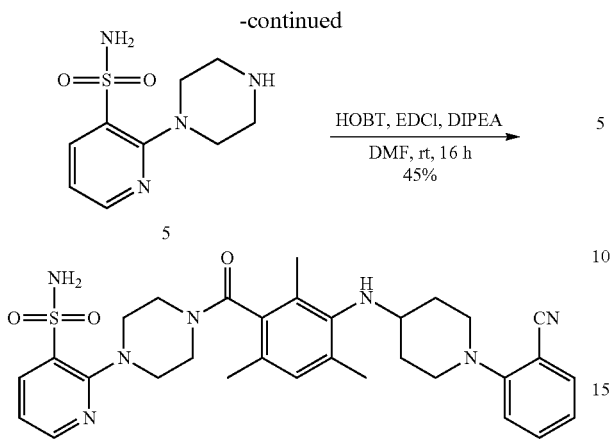

Procedures and Characterization:
The analysis method was following Method B and the separation method was following Method D.

Step 1: Methyl 3-(1-(2-cyanophenyl)piperidin-4-ylamino)-2,4,6-trimethylbenzoate

To a mixture of methyl 3-bromo-2,4,6-trimethyl-benzoate (2.00 g, 7.78 mmol) and 2-(4-amino-1-piperidyl)benzonitrile (1.88 g, 9.34 mmol) in toluene (50.00 mL) was added BINAP (484.44 mg, 778.00 umol) and sodium tert-butoxide (1.50 g, 15.56 mmol). The mixture was degassed for 3 mins, then Pd$_2$(dba)$_3$ (712.43 mg, 778.00 umol) was added, and the resulting mixture was degassed for 3 mins then kept stirring at 80° C. for 18 h under N$_2$. The mixture was filtered and the solvent removed. The residue was purified by CombiFlash® (UV254, silica gel, 40 g, EtOAc/PE from 20%-50%) to give the product methyl 3-[[1-(2-cyanophenyl)-4-piperidyl]amino]-2,4,6-trimethyl-benzoate (1.85 g, 4.90 mmol, 62.99% yield) as yellow solid. ESI-MS (EI$^+$, m/z): 378.3 [M+H]$^+$. $^1$H NMR (500 MHz, CDCl$_3$) δ 7.55 (dd, J=7.8, 1.4 Hz, 1H), 7.49-7.42 (m, 1H), 7.01-6.96 (m, 2H), 6.86 (s, 1H), 3.90 (s, 3H), 3.57 (d, J=12.3 Hz, 2H), 2.99 (s, 1H), 2.90 (s, 1H), 2.82-2.74 (m, 2H), 2.26 (s, 3H), 2.23 (s, 3H), 2.21 (s, 3H), 2.09-2.01 (m, 2H), 1.69 (qd, J=12.1, 3.6 Hz, 2H).

Step 2: 3-(1-(2-Cyanophenyl)piperidin-4-ylamino)-2,4,6-trimethylbenzoic Acid

A mixture of methyl 3-[[1-(2-cyanophenyl)-4-piperidyl]amino]-2,4,6-trimethyl-benzoate (650.00 mg, 1.72 mmol) in DCM (6.00 mL) was cooled to −60° C. and boron tribromide (1 M, 4.30 mL) was added. The resulting mixture was kept stirring at 30° C. for 1 h. The mixture was poured into ice-water, and the pH was adjusted to 4 with sat. Na$_2$CO$_3$ and extracted with DCM (40 mL×3). The organic layer was dried over Na$_2$SO$_4$ for 20 mins, filtrated and concentrated in vacuo to give the product 3-[[1-(2-cyanophenyl)-4-piperidyl]amino]-2,4,6-trimethyl-benzoic acid (510.00 mg, 1.40 mmol, 81.58% yield) as a yellow solid. ESI-MS (EI$^+$, m/z): 364.4 [M+H]$^+$.

Step 3: 2-(4-(3-(1-(2-Cyanophenyl)piperidin-4-ylamino)-2,4,6-trimethylbenzoyl)piperazin-1-yl) pyridine-3-sulfonamide Followed the amide coupling EDCI/HOBT method to afford 2-(4-(3-(1-(2-cyanophenyl)piperidin-4-ylamino)-2,4, 6-trimethylbenzoyl)piperazin-1-yl)pyridine-3-sulfonamide I-15 as white solid. ESI-MS (EI$^+$, m/z): 588.3 [M+H]$^+$. $^1$H NMR (400 MHz, MeOD-d$_4$) δ 8.53 (dd, J=4.8, 1.8 Hz, 1H), 8.34 (dd, J=7.8, 1.8 Hz, 1H), 7.61 (dd, J=7.7, 1.5 Hz, 1H), 7.54 (d, J=7.4 Hz, 1H), 7.32 (dd, J=7.8, 4.8 Hz, 1H), 7.16 (d, J=8.3 Hz, 1H), 7.07 (t, J=7.5 Hz, 1H), 6.97 (s, 1H), 4.09-3.99 (m, 2H), 3.58 (d, J=11.9 Hz, 2H), 3.49-3.42 (m, 2H), 3.40-3.34 (m, 2H), 3.19 (dd, J=10.9, 6.8 Hz, 2H), 3.11-3.00 (m, 1H), 2.84 (dd, J=20.3, 10.8 Hz, 2H), 2.33 (s, 3H), 2.27 (s, 3H), 2.22 (s, 3H), 2.02 (t, J=13.0 Hz, 2H), 1.84-1.70 (m, 2H).

Example 66: 2-(4-(3-(1-(2-Cyanophenyl)piperidin-4-ylamino)-2,4,6-trimethylbenzoyl)piperazin-1-yl)-6-fluorobenzenesulfonamide, I-14

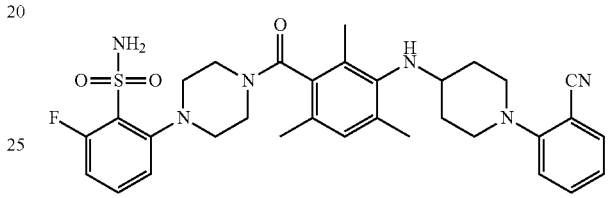

I-14

Procedures and Characterization:
The procedure was similar to example 65.
The analysis method was following Method B and the separation method was following Method D.

(S)-(4-((4-(3-chloropyridin-2-yl)piperazin-1-yl)methyl)-1,5-dimethyl-1H-pyrrol-2-yl)(4-(3,4-difluorophenyl)-2-methylpiperazin-1-yl)methanone ESI-MS (EI$^+$, m/z): 604.9 [M+H]$^+$. $^1$H NMR (500 MHz, MeOD-d$_4$) δ 7.63-7.51 (m, 3H), 7.27 (d, J=8.2 Hz, 1H), 7.16 (d, J=8.3 Hz, 1H), 7.11-7.03 (m, 2H), 6.96 (s, 1H), 3.58 (d, J=12.1 Hz, 2H), 3.46-3.39 (m, 2H), 3.12-3.02 (m, 2H), 2.85 (dd, J=22.8, 10.9 Hz, 2H), 2.33 (s, 3H), 2.27 (s, 3H), 2.22 (s, 3H), 2.06-1.95 (m, 2H), 1.84-1.71 (m, 2H).

Example 67: 3-(4-(3-(1-(2-Cyanophenyl)piperidin-4-ylamino)-2,4,6-trimethylbenzoyl) piperazin-1-yl) pyridine-2-sulfonamide, I-2

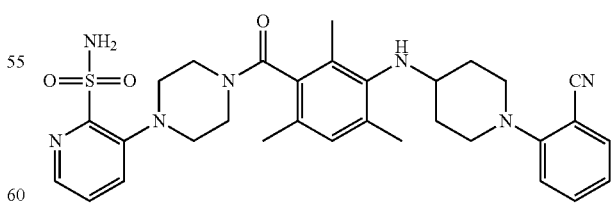

I-2

Procedures and Characterization:
The procedure was The procedure was similar to example 65.
The analysis method was following Method B and the separation method was following Method D.

275

3-(4-(3-(1-(2-cyanophenyl)piperidin-4-ylamino)-2,4,6-trimethylbenzoyl)piperazin-1-yl)pyridine-2-sulfonamide ESI-MS (EI+, m/z): 588.3 [M+H]+. $^1$H NMR (400 MHz, MeOD-d$_4$) δ 8.53 (dd, J=4.8, 1.8 Hz, 1H), 8.34 (dd, J=7.8, 1.8 Hz, 1H), 7.61 (dd, J=7.7, 1.5 Hz, 1H), 7.54 (d, J=7.4 Hz, 1H), 7.32 (dd, J=7.8, 4.8 Hz, 1H), 7.16 (d, J=8.3 Hz, 1H), 7.07 (t, J=7.5 Hz, 1H), 6.97 (s, 1H), 4.09-3.99 (m, 2H), 3.58 (d, J=11.9 Hz, 2H), 3.49-3.42 (m, 2H), 3.40-3.34 (m, 2H), 3.19 (dd, J=10.9, 6.8 Hz, 2H), 3.11-3.00 (m, 1H), 2.84 (dd, J=20.3, 10.8 Hz, 2H), 2.33 (s, 3H), 2.27 (s, 3H), 2.22 (s, 3H), 2.02 (t, J=13.0 Hz, 2H), 1.84-1.70 (m, 2H).

Example 68: 2-(4-(5-(1-(2-Methoxyphenyl)piperidin-4-ylamino)-2,4-dimethylbenzoyl)piperazin-1-yl)benzenesulfonamide, I-128

Synthetic Scheme;

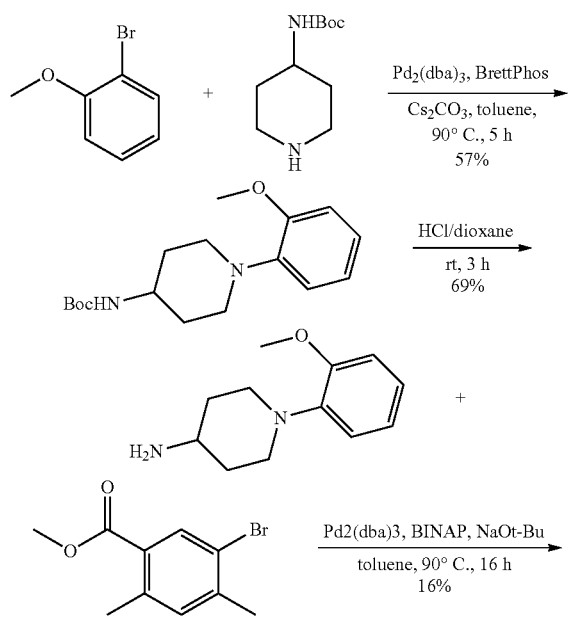

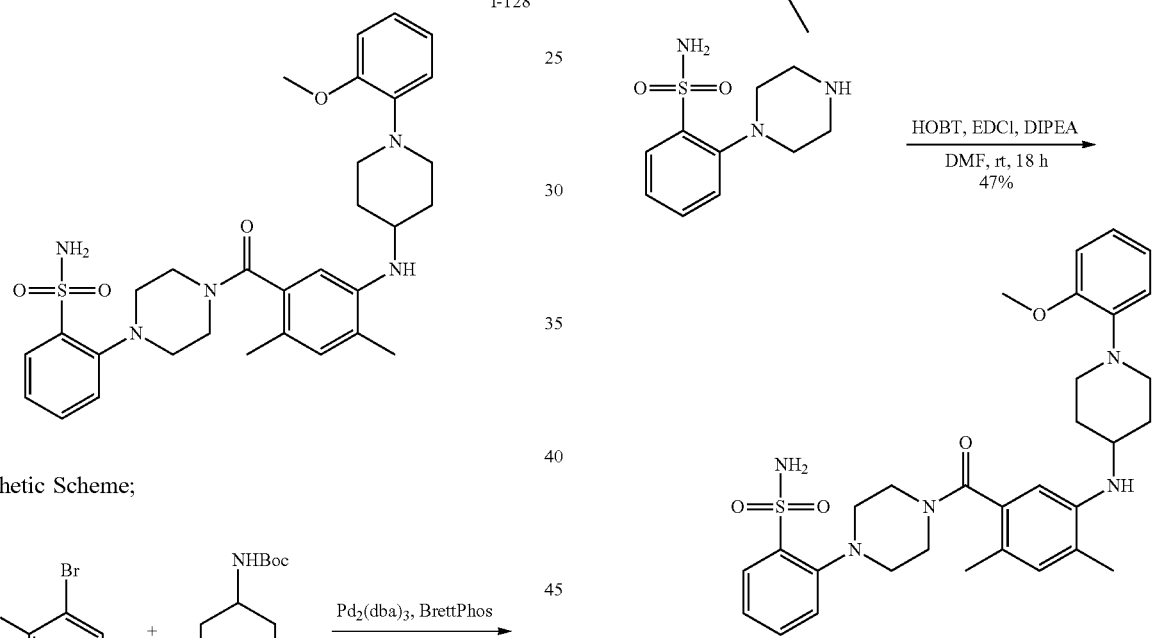

Procedures and Characterization:

The analysis method was following Method B and the separation method was following Method D.

Step 1: tert-Butyl (1-(2-methoxyphenyl)piperidin-4-yl)carbamate

A mixture of 1-bromo-2-methoxy-benzene (2.00 g, 10.69 mmol), tert-butyl N-(4-piperidyl) carbamate (2.36 g, 11.76 mmol), BrettPhos (573.81 mg, 1.07 mmol) and cesium carbonate (6.97 g, 21.38 mmol) in toluene (35.00 mL) was degassed for 3 mins. Then Pd$_2$ (dba)$_3$ (978.90 mg, 1.07 mmol) was added and the mixture degassed for 3 mins again. The mixture was kept stirring at 90° C. for 5 h. The mixture was diluted with DCM (60 mL), filtered and concentrated. The residue was purified by CombiFlash® (silica gel, 40 g, UV254, EA/PE from 0%-40%) to give the product tert-butyl N-[1-(2-methoxyphenyl)-4-piperidyl]carbamate (1.86 g, 6.07 mmol, 56.79% yield) as yellow solid. ESI-MS (EI⁺, m/z): 307.2 [M+H]+. ¹H NMR (500 MHz, MeOD-d₄) δ 7.01 (d, J=7.5 Hz, 2H), 6.97-6.93 (m, 1H), 6.92-6.88 (m, 1H), 3.87 (s, 3H), 3.52-3.42 (m, 1H), 3.38 (d, J=12.3 Hz, 2H), 2.67 (td, J=11.8, 2.0 Hz, 2H), 1.95 (d, J=11.8 Hz, 2H), 1.67 (qd, J=11.6, 3.7 Hz, 2H), 1.47 (s, 9H).

Step 2: 1-(2-Methoxyphenyl)piperidin-4-amine

A mixture of tert-butyl N-[1-(2-methoxyphenyl)-4-piperidyl]carbamate (1.86 g, 6.07 mmol) in HCl (4 M in 1,4-dioxane, 19.77 mL) was kept stirring at 23° C. for 3 h. The solvent was removed, the residue was adjusted to pH 10 with sat. Na₂CO₃ and extracted with a mixed solvent system MeOH/DCM (1:3) (30 mL×3). The organic layer was washed with H₂O (20 mL×2), dried over Na₂SO₄ for 20 mins, filtrated and concentrated under vacuum to give the product 1-(2-methoxyphenyl)piperidin-4-amine (860.00 mg, 4.17 mmol, 68.68% yield) as a yellow solid. ESI-MS (EI⁺, m/z): 207.3 [M+H]⁺.

Step 3: Methyl 5-(1-(2-methoxyphenyl)piperidin-4-ylamino)-2,4-dimethylbenzoate

A mixture of methyl 5-bromo-2,4-dimethyl-benzoate (785.66 mg, 3.23 mmol), 1-(2-methoxyphenyl)piperidin-4-amine (800.00 mg, 3.88 mmol) in toluene (25.00 mL) was added BINAP (201.24 mg, 323.19 umol) and sodium tert-butoxide (621.16 mg, 6.46 mmol). The mixture was degassed for 3 mins, then, Pd₂(dba)₃ (295.95 mg, 323.19 umol) was added. The resulting mixture was degassed for 3 mins. After that, the mixture was kept stirring at 90° C. for 18 h under N₂. The mixture was diluted with EtOAc (60 mL), filtrated and concentrated in vacuo, the residue was purified by CombiFlash® (UV254, silica gel, 40 g, EA/PE from 0% to 40% to give the desired product methyl 5-[[1-(2-methoxyphenyl)-4-piperidyl]amino]-2,4-dimethyl-benzoate (189.00 mg, 512.93 umol, 15.87% yield) as a yellow solid. ESI-MS (EI⁺, m/z): 369.3 [M+H]⁺. ¹H NMR (500 MHz, MeOD-d₄) δ 7.24 (s, 1H), 7.08-7.01 (m, 2H), 6.99-6.95 (m, 2H), 6.93 (td, J=7.6, 1.5 Hz, 1H), 3.89 (s, 3H), 3.87 (s, 3H), 3.52-3.40 (m, 3H), 2.78 (td, J=11.8, 2.1 Hz, 2H), 2.43 (s, 3H), 2.19 (s, 3H), 2.16 (d, J=12.6 Hz, 2H), 1.73 (td, J=14.3, 3.6 Hz, 2H).

Step 4: 5-(1-(2-Methoxyphenyl)piperidin-4-ylamino)-2,4-dimethylbenzoic Acid

A mixture of methyl 5-[[1-(2-methoxyphenyl)-4-piperidyl]amino]-2,4-dimethyl-benzoate (170.00 mg, 461.37 umol) and LiOH.H₂O (193.77 mg, 4.61 mmol) in water (2.00 mL) and MeOH (7.00 mL) was kept stirring at 60° C. for 4 h. Methanol was removed, the pH adjusted to 4 with 4 N HCl aqueous solution, extracted with DCM (25 mL×3) and washed with water (10 mL×2). The organic layer was dried over Na₂SO₄ for 20 min, filtered and concentrated under reduced pressure to give the desired product 5-[[1-(2-methoxyphenyl)-4-piperidyl]amino]-2,4-dimethyl-benzoic acid (140.00 mg, 394.99 umol, 85.61% yield) as white solid. ESI-MS (EI⁺, m/z): 355.1 [M+H]⁺.

Step 5: 2-(4-(5-(1-(2-Methoxyphenyl)piperidin-4-ylamino)-2,4-dimethylbenzoyl)piperazin-1-yl)benzenesulfonamide Followed the amide coupling EDCI/HOBT method to give the desire product 2-[4-[5-[[1-(2-methoxyphenyl)-4-piperidyl]amino]-2,4-dimethyl-benzoyl]piperazin-1-yl]benzenesulfonamide I-128 (93.00 mg, 160.97 umol, 47.55% yield) as white solid. ESI-MS (EI⁺, m/z): 578.3 [M+H]⁺. ¹H NMR (500 MHz, DMSO-d₆) δ 10.75-7.83 (m, 1H), 7.63-7.58 (m, 1H), 7.56 (d, J=7.1 Hz, 1H), 7.37-7.31 (m, 1H), 6.96 (s, 2H), 6.95-6.90 (m, 3H), 6.89-6.85 (m, 2H), 6.42 (s, 1H), 4.42 (d, J=8.4 Hz, 1H), 3.84 (s, 2H), 3.77 (s, 3H), 3.42-3.39 (m, 5H) 3.02-2.71 (m, 6H), 2.09 (d, J=1.9 Hz, 6H), 1.99 (d, J=11.0 Hz, 2H), 1.65 (dd, J=20.2, 10.4 Hz, 2H).

Example 69: 2-(4-(2,4-Dimethyl-5-(1-m-tolylpiperidin-4-ylamino)benzoyl)piperazin-1-yl)benzenesulfonamide, I-129

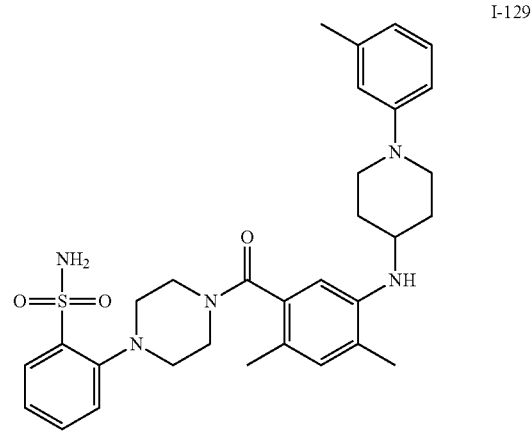 [SMILES: Cc1cccc(N2CCC(Nc3cc(C(=O)N4CCN(c5ccccc5S(N)(=O)=O)CC4)c(C)cc3C)CC2)c1]

I-129

The procedure was similar to example 68.
The analysis method was following Method B and the separation method was following Method D.

2-(4-(2,4-dimethyl-5-(1-m-tolylpiperidin-4-ylamino)benzoyl)piperazin-1-yl)benzenesulfonamide ESI-MS (EI⁺, m/z): 562.3 [M+H]⁺. ¹H NMR (500 MHz, DMSO-d₆) δ 7.87 (dd, J=7.9, 1.5 Hz, 1H), 7.60 (dd, J=11.3, 4.0 Hz, 1H), 7.56 (d, J=7.1 Hz, 1H), 7.35 (t, J=7.5 Hz, 1H), 7.07 (t, J=7.8 Hz, 1H), 6.97 (s, 2H), 6.86 (s, 1H), 6.74 (dd, J=13.2, 5.0 Hz, 2H), 6.56 (d, J=7.5 Hz, 1H), 6.43 (s, 1H), 4.43 (d, J=8.3 Hz, 1H), 3.84 (dd, J=17.4, 9.6 Hz, 2H), 3.73-3.62 (m, 2H), 3.51-3.42 (m, 1H), 3.38 (dt, J=8.7, 4.5 Hz, 2H), 3.08-2.91 (m, 2H), 2.91-2.76 (m, 4H), 2.24 (s, 3H), 2.09 (s, 3H), 2.07 (s, 3H), 1.96 (dd, J=13.0, 2.0 Hz, 2H), 1.61-1.49 (m, 2H).

Example 70: 2-(4-(2,4-Dimethyl-5-(1-o-tolylpiperidin-4-ylamino)benzoyl)piperazin-1-yl)benzenesulfonamide, I-108

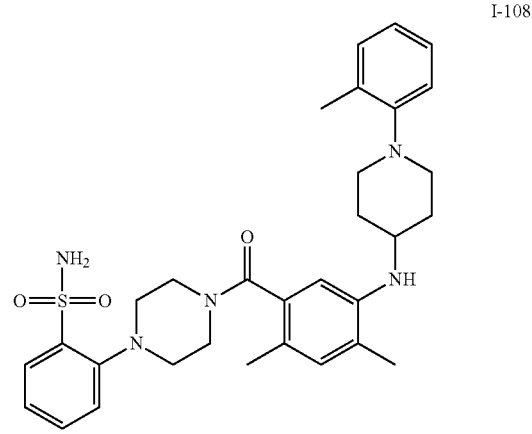 [SMILES: Cc1cc(C)c(C(=O)N2CCN(c3ccccc3S(N)(=O)=O)CC2)cc1NC1CCN(c2ccccc2C)CC1]

I-108

The procedure was similar to
The analysis method was following Method B example 68. and the separation method was following Method D.

2-(4-(2,4-dimethyl-5-(1-o-tolylpiperidin-4-ylamino)benzoyl)piperazin-1-yl)benzenesulfonamide ESI-MS (EI+, m/z): 562.3 [M+H]+. ¹H NMR (400 MHz, DMSO-$d_6$) δ 7.87 (d, J=6.6 Hz, 1H), 7.65-7.53 (m, 2H), 7.34 (t, J=7.2 Hz, 1H), 7.15 (t, J=7.0 Hz, 2H), 7.04 (d, J=7.6 Hz, 1H), 6.95 (dd, J=14.3, 6.4 Hz, 3H), 6.87 (s, 1H), 6.43 (s, 1H), 4.47 (d, J=7.9 Hz, 1H), 3.84 (s, 2H), 3.39 (s, 2H), 3.16-2.61 (m, 9H), 2.25 (s, 3H), 2.09 (s, 6H), 2.06-1.96 (m, 2H), 1.74-1.58 (m, 2H).

Example 71: 2-(4-(5-(1-(2-Cyanophenyl)piperidin-4-ylamino)-2-fluoro-4-methylbenzoyl)piperazin-1-yl)benzenesulfonamide, I-113

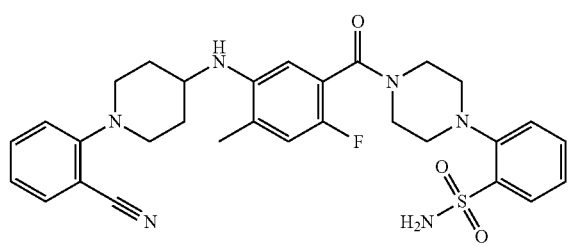

I-113

Synthetic Scheme:

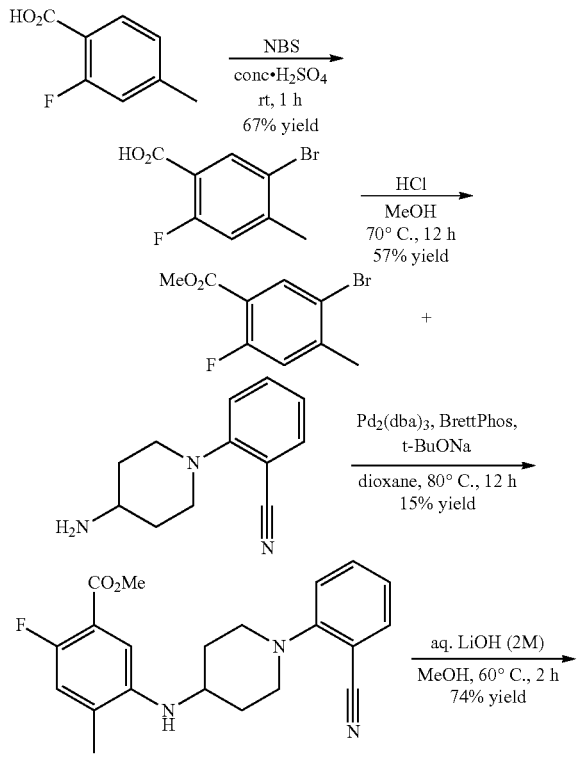

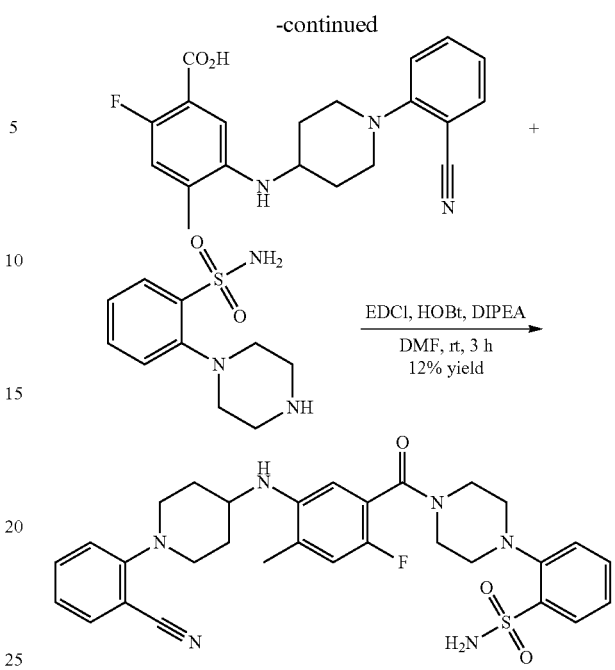

Procedures and Characterization:

The analysis method was following Method A and the separation method was following Method C.

Step 1: 5-Bromo-2-fluoro-4-methylbenzoic Acid

To a solution of 2-fluoro-4-methylbenzoic acid (5.00 g, 32.44 mmol) in conc. $H_2SO_4$ (20.00 mL) was added NBS (6.06 g, 34.06 mmol). The resulting mixture was poured into ice-water (100 mL) after stirring for 1 h, the product precipitated as a white solid. The solid was collected by filtration and was dissolved in dichloromethane (50 mL) and dried over anhydrous sodium sulfate. The solvent was removed under reduced pressure to afford 5-bromo-2-fluoro-4-methyl-benzoic acid (5.10 g, 21.89 mmol, 67% yield). ESI-MS (EI+, m/z): 233.0 [M+H]+.

Step 2: Methyl 5-bromo-2-fluoro-4-methylbenzoate 5-bromo-2-fluoro-4-methylbenzoic acid (5.10 g, 21.43 mmol) was dissolved in HCl-MeOH (3 M, 50.00 mL) and the solution was stirred at 70° C. for 12 h. The solvent was removed and the product was attained without further purification. ESI-MS (EI+, m/z): 246.9 [M+H]+.

Step 3: Methyl 5-(1-(2-cyanophenyl)piperidin-4-ylamino)-2-fluoro-4-methylbenzoate A mixture of methyl 5-bromo-2-fluoro-4-methylbenzoate (1.00 g, 4.05 mmol), $Pd_2(dba)_3$ (185.49 mg, 202.50 umol), BrettPhos (128.99 mg, 202.50 umol), tBuONa (777.60 mg, 8.10 mmol) and 2-(4-amino-1-piperidyl)benzonitrile (1.63 g, 8.10 mmol) in dioxane (30.00 mL) was heated at 80° C. under $N_2$ for 17 h. After cooling to rt, the reaction mixture was diluted with 30 mL water and extracted with ethyl acetate. The organic layer was collected and concentrated. Then desired product, methyl 5-(1-(2-cyanophenyl) piperidin-4-ylamino)-2-fluoro-4-methylbenzoate (230.00 mg, 625.99 umol, 15.46% yield), was obtained as a yellow oil after purification by column chromatography. ESI-MS (EI+, m/z): 368.0 [M+H]+.

Step 4: 5-(1-(2-Cyanophenyl)piperidin-4-ylamino)-2-fluoro-4-methylbenzoic Acid

Methyl 5-(1-(2-cyanophenyl)piperidin-4-ylamino)-2-fluoro-4-methylbenzoate (230.00 mg, 625.99 umol) was dissolved in a mixture of aqueous LiOH (2 M, 20.00 mL) and MeOH (30.00 mL). The solution was heated to 60° C. for 2 h. Then LC-MS analysis showed the reaction proceeded smoothly. The solvent was cooled to rt and the pH value was adjusted to 7. Then the solvent was extracted with EtOAc and concentrated to yield the product without further purification. ESI-MS (EI+, m/z): 354.2 [M+H]+.

Step 5: 2-(4-(5-(1-(2-Cyanophenyl)piperidin-4-ylamino)-2-fluoro-4-methylbenzoyl)piperazin-1-yl)benzenesulfonamide Followed the amide coupling EDCI/HOBT method to afford 2-(4-(5-(1-(2-cyanophenyl)piperidin-4-ylamino)-2-fluoro-4-methylbenzoyl)piperazin-1-yl)benzenesulfonamide I-113 as a white solid. MS (EI+, m/z): 576.8 [M+H]+. 1H NMR (500 MHz, CDCl3) δ 8.03 (dd, J=7.9, 1.3 Hz, 1H), 7.64-7.55 (m, 2H), 7.50 (t, J=7.9 Hz, 1H), 7.43-7.33 (m, 2H), 7.03 (t, J=8.1 Hz, 2H), 6.90 (d, J=9.6 Hz, 1H), 6.81 (s, 1H), 3.67-3.45 (m, 5H), 3.20-3.17 (m, 9H), 2.96 (t, J=11.3 Hz, 3H), 2.22 (s, 4H).

Example 72: 2-(4-(3-(1-(2-cyanophenyl)piperidin-4-ylamino)-2,6-dimethylbenzoyl) piperazin-1-yl)-6-fluorobenzenesulfonamide, I-87

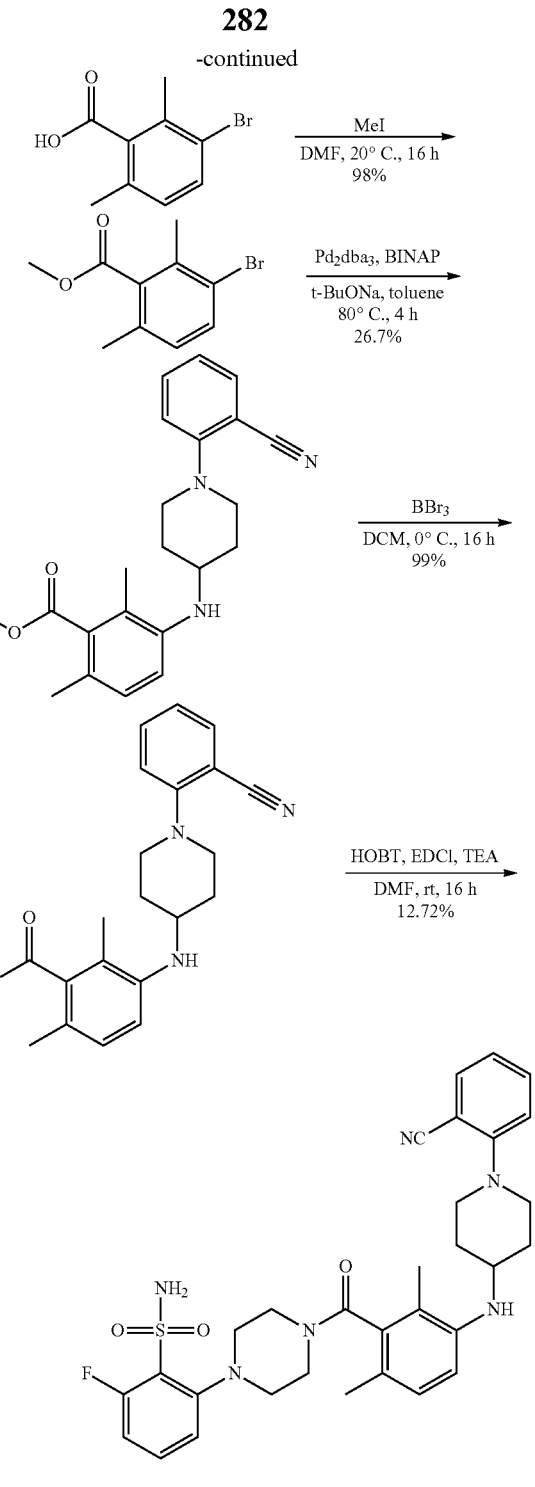

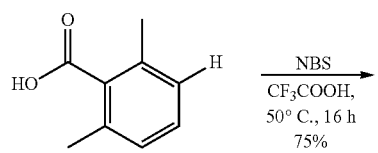

Synthetic Scheme:

Procedures and Characterization:
The analysis method was following Method B and the separation method was following Method D.

Step 1: 3-Bromo-2,6-dimethylbenzoic Acid

To a solution of 2,6-dimethylbenzoic acid (2.00 g, 13.32 mmol) in trifluoroacetic acid (20.00 mL) was added NBS (2.37 g, 13.32 mmol), and then heated to 50° C. for 16 h. The reaction was monitored by LCMS and poured into ice water (50 g) when the reaction was complete to a form a solid precipitate which was filtered and dried to obtain 3-bromo- 2,6-dimethyl-benzoic acid (2.30 g, 10.04 mmol, 75.38%). MS (EI+, m/z): 228.98 [M+H]+. $^1$H NMR (500 MHz, MeOD) δ 7.50 (d, J=8.2 Hz, 1H), 7.01 (d, J=8.2 Hz, 1H), 2.40 (s, 3H), 2.30 (s, 3H).

Step 2: Methyl 3-bromo-2,6-dimethylbenzoate

To a solution of 3-bromo-2,6-dimethyl-benzoic acid (2.20 g, 9.60 mmol) in DMF (30.00 mL) was added iodomethane (2.04 g, 14.41 mmol, 896.84 uL), K$_2$CO$_3$ (2.65 g, 19.21 mmol), and then stirred at rt for 16 h. The reaction was monitored by LCMS, when the reaction was done, ethyl acetate (100 mL) and water (100 mL) was added, the organic layer separated, and washed with water (100 mL×3) and brine (80 mL), dried and concentrated to afford methyl 3-bromo-2,6-dimethyl-benzoate (2.30 g, 9.46 mmol, 98.55%). MS (EI+, m/z): 242.99 [M+H]+.

Step 3: Methyl 3-(1-(2-cyanophenyl)piperidin-4-ylamino)-2,6-dimethylbenzoate

To a solution of methyl 3-bromo-2,6-dimethyl-benzoate (2.30 g, 9.46 mmol) in toluene (30.00 mL) was added 2-(4-amino-1-piperidyl)benzonitrile (1.90 g, 9.46 mmol), BINAP (589.12 mg, 946.00 umol), Pd$_2$(dba)$_3$ (433.19 mg, 473.00 umol) and tBuONa (2.73 g, 28.38 mmol), and the reaction mixture heated to 80° C. for 16 h. The reaction was monitored by LCMS, when the reaction was done, ethyl acetate (100 mL) and water (80 mL) were added, the organic layer separated and washed with water (50 mL×2) and brine (50 mL), dried and concentrated to afford the crude, which was purified by SGC (EtOAc/PE=1%-20%) to afford methyl 3-[[1-(2-cyanophenyl)-4-piperidyl]amino]-2,6-dimethyl-benzoate (3.00 g, 8.25 mmol, 87.25%). MS (EI+, m/z): 364.19 [M+H]+.

Step 4: 3-(1-(2-Cyanophenyl)piperidin-4-ylamino)-2,6-dimethylbenzoic Acid

To a solution of methyl 3-[[1-(2-cyanophenyl)-4-piperidyl]amino]-2,6-dimethyl-benzoate (100.00 mg, 275.14 umol) in DCM was added BBr$_3$ (4.05 g, 2.75 mmol, 4.05 mL, 17% purity) at 0° C., and then warmed slowly to rt for 16 h. The reaction was monitored by LCMS, when no starting material was observed, the reaction was quenched by the addition of ice (20 g). Dichloromethane (50 mL) and water (20 mL) was added, the organic layer was separated, dried and concentrated to afford 3-[[1-(2-cyanophenyl)-4-piperidyl]amino]-2,6-dimethyl-benzoic acid (96.00 mg, 274.73 umol, 99.85%), which was used in the next step directly. MS (EI+, m/z): 350.18 [M+H]+.

Step 5: 2-(4-(3-(1-(2-Cyanophenyl)piperidin-4-ylamino)-2,6-dimethylbenzoyl)piperazin-1-yl)-6-fluorobenzenesulfonamide Followed the amide coupling EDCI/HOBT method to afford 2-[4-[3-[[1-(2-cyanophenyl)-4-piperidyl]amino]-2,6-dimethyl-benzoyl]piperazin-1-yl]-6-fluoro-benzenesulfonamide, I-87. MS (EI+, m/z): 591.25 [M+H]+. $^1$H NMR (400 MHz, DMSO-d$_6$) δ 7.69 (d, J=7.6 Hz, 1H), 7.63-7.51 (m, 2H), 7.42 (s, 2H), 7.27-7.05 (m, 4H), 6.95 (s, 1H), 6.69 (s, 1H), 3.52 (s, 4H), 3.27 (s, 2H), 2.93 (dd, J=28.5, 18.2 Hz, 6H), 2.15-1.90 (m, 8H), 1.74 (d, J=12.2 Hz, 2H).

Example 73: 2-(4-(3-(1-(2-cyanophenyl)piperidin-4-ylamino)-2,4-difluorobenzoyl)piperazin-1-yl)benzenesulfonamide, I-109

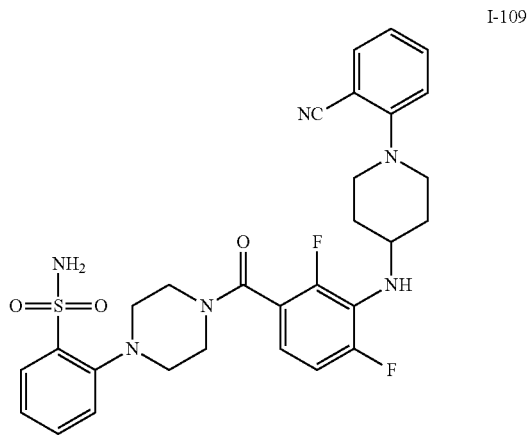 [SMILES: N#Cc1ccccc1N1CCC(Nc2c(F)ccc(C(=O)N3CCN(c4ccccc4S(N)(=O)=O)CC3)c2F)CC1]

Synthetic Scheme:

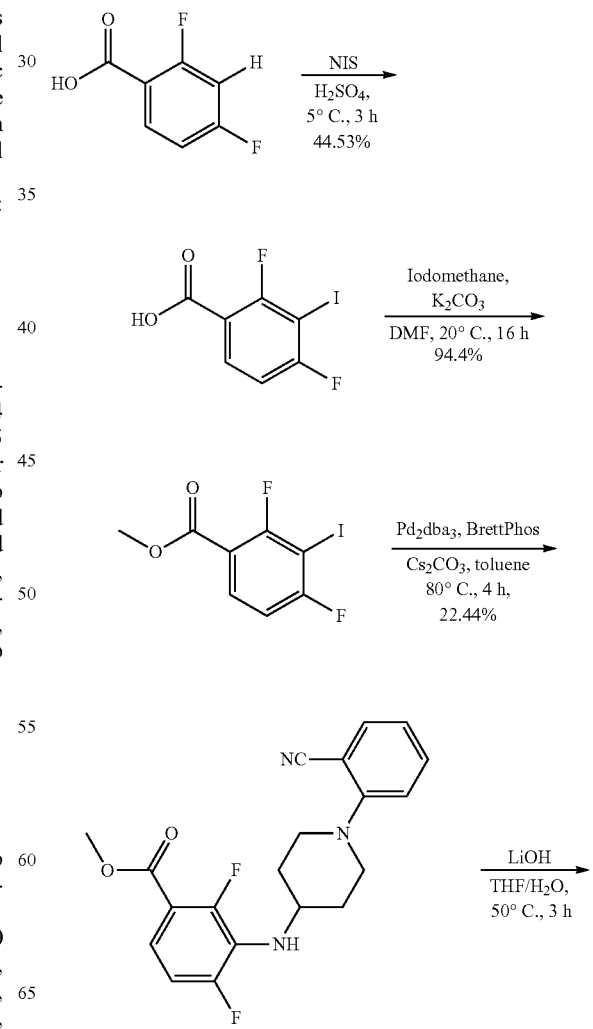

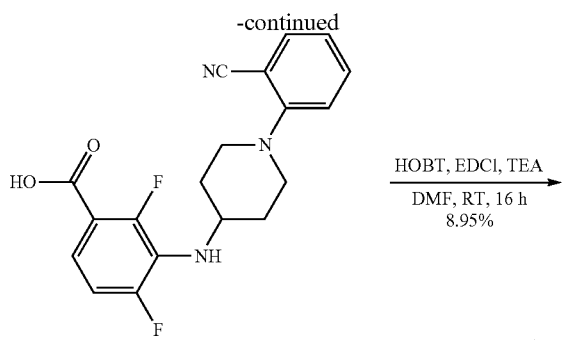

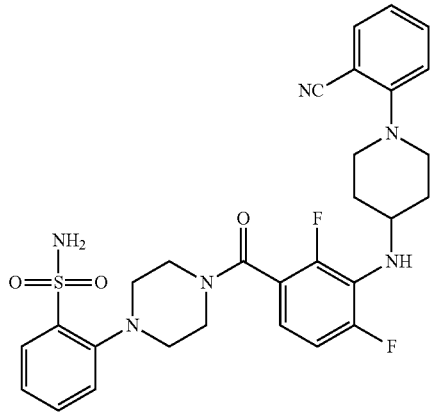

Procedures and Characterization:

The analysis method was following Method B and the separation method was following Method D.

Step 1: 2, 4-Difluoro-3-iodobenzoic Acid

To a solution of 2,4-difluorobenzoic acid (5.00 g, 31.63 mmol) in H$_2$SO$_4$ (30.00 mL) was added NIS (6.76 g, 30.04 mmol) at 5° C. for 3 h. The reaction mixture was monitored by LCMS, when the reaction was done, it was poured into ice-water (100 g), then filtered and recrystallized (50%, EtOH, water) to obtain 2,4-difluoro-5-iodo-benzoic acid (4.00 g, 14.08 mmol, 44.53%). MS (EI$^+$, m/z): 284.91 [M+H]$^+$.

Step 2: Methyl 2,4-difluoro-3-iodobenzoate

To a solution of 2,4-difluoro-3-iodobenzoic acid (2.00 g, 8.44 mmol) in DMF (50.00 mL) was added iodomethane (1.80 g, 12.66 mmol, 788.03 uL), K$_2$CO$_3$ (2.33 g, 16.88 mmol), and the reaction mixture was stirred at rt for 3 h. The reaction mixture was monitored by LCMS, when the reaction was complete, ethyl acetate (100 mL) and water (100 mL) were added, the organic layer was separated and washed with water (100 mL×3) and brine (80 mL), dried and concentrated to afford methyl 5-bromo-2,4-difluoro-benzoate (2.00 g, 7.97 mmol, 94.40%). MS (EI$^+$, m/z): 298.9 [M+H]$^+$.

Step 3: Methyl 3-(1-(2-cyanophenyl)piperidin-4-ylamino)-2,4-difluorobenzoate

To a solution of methyl 2,4-difluoro-3-iodo-benzoate (1.00 g, 3.36 mmol) in toluene (20.00 mL) was added 2-(4-amino-1-piperidyl)benzonitrile (675.36 mg, 3.36 mmol), tris(dibenzylideneacetone)dipalladium(0) (153.63 mg, 167.77 umol), BrettPhos (180.09 mg, 335.55 umol), and Cs$_2$CO$_3$ (2.19 g, 6.71 mmol). The reaction mixture was heated to 70° C. for 16 h. The reaction mixture was monitored by LCMS, when the reaction was done, ethyl acetate (100 mL) and water (100 mL) were added, the organic layer separated and washed with water (100 mL) and brine (80 mL), dried and concentrated to afford methyl 3-[[1-(2-cyanophenyl)-4-piperidyl]amino]-2,4-difluoro-benzoate (280.00 mg, 753.94 umol, 22.44%). MS (EI$^+$, m/z): 372 [M+H]$^+$.

Step 4: 3-(1-(2-Cyanophenyl)piperidin-4-ylamino)-2,4-difluorobenzoic Acid

To a solution of methyl 3-[[1-(2-cyanophenyl)-4-piperidyl]amino]-2,4-difluoro-benzoate (250.00 mg, 673.16 umol) in THF (5.00 mL) and water (2.50 mL) was added lithium hydroxide (161.22 mg, 6.73 mmol), and the reaction mixture was heated to 50° C. for 3 h. The reaction mixture was monitored by LCMS, when the reaction was done, the reaction mixture was extracted with EtOAc (50 mL), washed with water (30 mL×3) and brine (30 mL), dried, filtered and concentrated to afford 3-[[1-(2-cyanophenyl)-4-piperidyl]amino]-2,4-difluoro-benzoic acid (120.00 mg, 335.81 umol, 49.88%). MS (EI$^+$, m/z): 358.13 [M+H]$^+$.

Step 5: 2-(4-(3-(1-(2-Cyanophenyl)piperidin-4-ylamino)-2,4-difluorobenzoyl)piperazin-1-yl)benzenesulfonamide Followed the amide coupling EDCI/HOBT method to afford 2-[4-[3-[[1-(2-cyanophenyl)-4-piperidyl]amino]-2,4-difluoro-benzoyl]piperazin-1-yl]benzenesulfonamide, I-109. MS (EI$^+$, m/z): 581.21 [M+H]$^+$. $^1$H NMR (500 MHz, DMSO) δ 7.87 (dd, J=7.9, 1.5 Hz, 1H), 7.69 (dd, J=7.7, 1.6 Hz, 1H), 7.64-7.57 (m, 2H), 7.54 (d, J=7.3 Hz, 1H), 7.35 (t, J=7.6 Hz, 1H), 7.24-7.15 (m, 2H), 7.07 (t, J=7.7 Hz, 1H), 6.98 (s, 2H), 6.83-6.78 (m, 1H), 3.66-3.59 (m, 1H), 3.56-3.41 (m, 6H), 2.94 (dd, J=31.6, 20.5 Hz, 6H), 2.01 (d, J=11.0 Hz, 2H), 1.69 (d, J=9.7 Hz, 2H).

Example 74: 2-(4-(2,4-dichloro-5-(1-(2-cyanophenyl)piperidin-4-ylamino)benzoyl) piperazin-1-yl)benzenesulfonamide, I-125

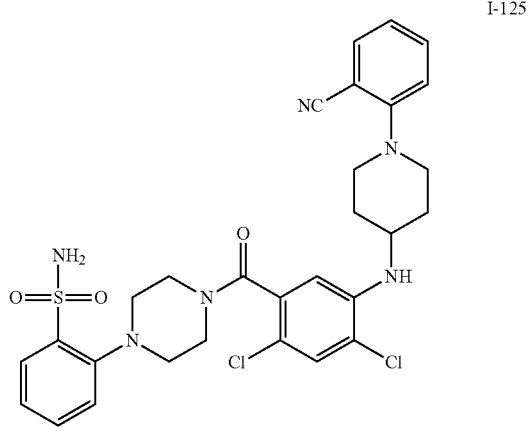 [SMILES: N#Cc1ccccc1N1CCC(Nc2cc(C(=O)N3CCN(c4ccccc4S(N)(=O)=O)CC3)c(Cl)cc2Cl)CC1]

I-125

Synthetic Scheme:

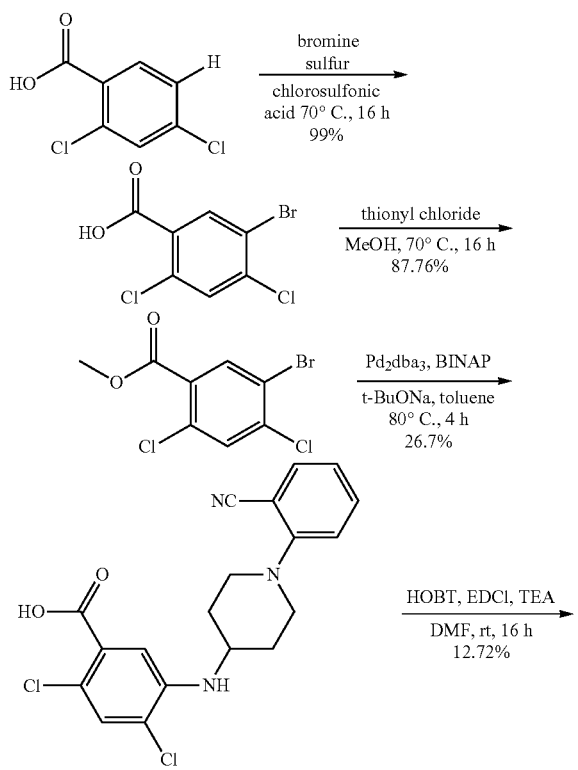

Procedures and Characterization:

The analysis method was following Method B and the separation method was following Method D.

Step 1: 5-Bromo-2,4-dichlorobenzoic Acid

To a solution of 2,4-dichlorobenzoic acid (10.00 g, 52.35 mmol) in chlorosulfonic acid (50.00 mL) was added bromine (4.18 g, 26.18 mmol, 1.34 mL) and sulfur (83.94 mg, 2.62 mmol). The reaction mixture was heated to 70° C. for 16 h. The reaction was monitored by LCMS, when the reaction was complete, it was cooled and poured on ice (50 g), filtered, dissolved in EtOAc (300 mL), washed with water (200 mL), dried and concentrated to get 5-bromo-2, 4-dichloro-benzoic acid (14.00 g, 51.87 mmol, 99.08%). MS (EI+, m/z): 190.96[M+H]+.

Step 2: Methyl 5-bromo-2,4-dichlorobenzoate

To a suspension of 5-bromo-2,4-dichloro-benzoic acid (13.00 g, 48.16 mmol) in MeOH (200.00 mL) was added thionyl chloride (11.46 g, 96.32 mmol, 6.99 mL), and then heated to 70° C. for 16 h. The reaction was monitored by LCMS, when it showed no started material remaining, the reaction mixture was directly concentrated to afford methyl 5-bromo-2,4-dichloro-benzoate (12.00 g, 42.26 mmol, 87.76%). MS (EI+, m/z): 282.88 [M+H]+.

Step 3: 2,4-Dichloro-5-(1-(2-cyanophenyl)piperidin-4-ylamino)benzoic Acid

To a solution of methyl 5-bromo-2,4-dichloro-benzoate (1.00 g, 3.52 mmol) in toluene (20.00 mL) was added 2-(4-amino-1-piperidyl)benzonitrile (708.47 mg, 3.52 mmol), tris(dibenzylideneacetone)dipalladium(0) (161.26 mg, 176.00 umol), BINAP (219.30 mg, 352.00 umol) and tBuONa (0.68 g, 0.7 mmol). The reaction mixture was heated to 80° C. for 16 h and monitored by LCMS. When the reaction was complete, ethyl acetate (100 mL) and water (100 mL) were added, and the pH was adjusted to 5-6 by aqueous hydrochloric acid (1N) at rt. The organic layer was separated and washed with water (100 mL) and brine (80 mL), dried and concentrated, purified by SGC (MeOH/DCM=1%-10%) to afford methyl 2,4-dichloro-5-[[1-(2-cyanophenyl)-4-piperidyl]amino]benzoate (190 mg, 469.96 umol, 13.35%) as a yellow solid. MS (EI+, m/z): 390.0 [M+H]+.

Step 4: 2-[4-[2,4-dichloro-5-[[1-(2-cyanophenyl)-4-piperidyl]amino]benzoyl]piperazin-1-yl]benzenesulfonamide Followed the amide coupling EDCI/HOBT method to afford 2-[4-[2,4-dichloro-5-[[1-(2-cyanophenyl)-4-piperidyl]amino]benzoyl]piperazin-1-yl]benzenesulfonamide I-125 as a white solid. MS (EI+, m/z): 613.15 [M+H]+.
$^1$H NMR (500 MHz, DMSO-d$_6$) δ 7.88 (dd, J=7.9, 1.5 Hz, 1H), 7.70 (dd, J=7.7, 1.6 Hz, 1H), 7.61 (dt, J=10.2, 4.9 Hz, 2H), 7.53 (d, J=7.9 Hz, 1H), 7.48 (s, 1H), 7.35 (t, J=7.6 Hz, 1H), 7.19 (t, J=6.7 Hz, 1H), 7.08 (dd, J=13.0, 5.9 Hz, 1H), 6.99 (d, J=5.9 Hz, 2H), 6.86 (s, 1H), 5.38 (s, 1H), 3.70-3.32 (m, 6H), 3.10-2.83 (m, 6H), 2.02 (d, J=12.2 Hz, 2H), 1.79 (s, 2H).

Example 75: 2-(4-(5-(1-(2-Cyanophenyl)piperidin-4-ylamino)-2-methylbenzoyl)piperazin-1-yl)benzenesulfonamide, I-22

I-22

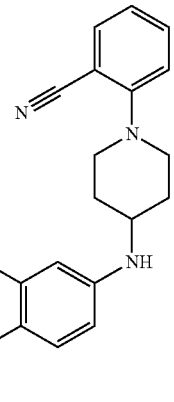

289

Synthetic Scheme:

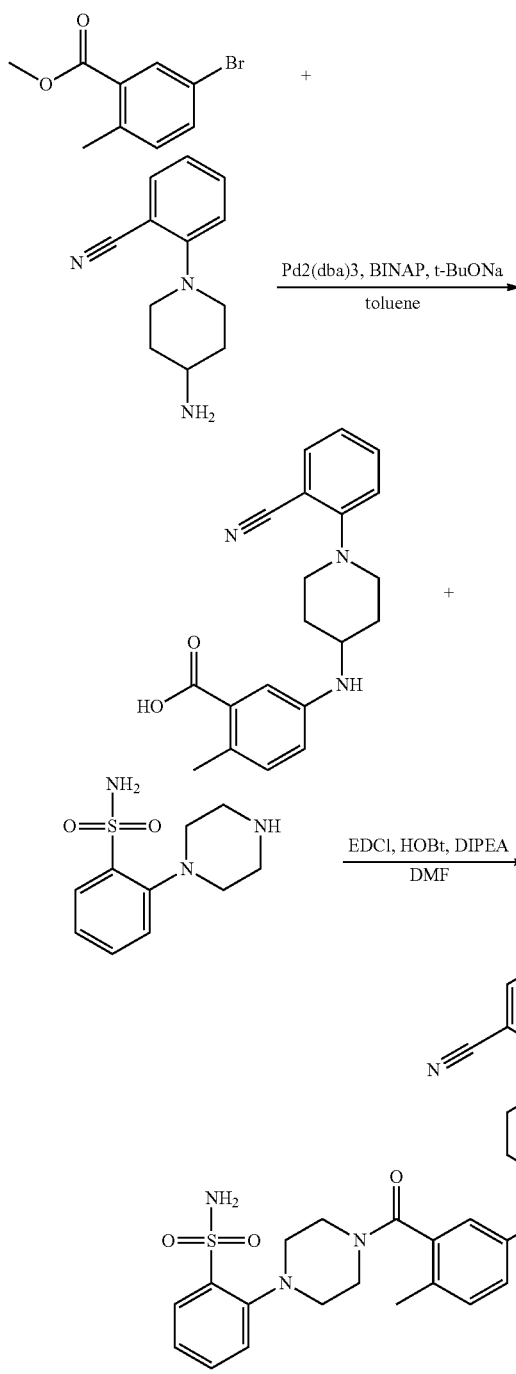

Procedures and Characterization:
The analysis method was following Method B and the separation method was following Method D.

Step 1: 5-(1-(2-Cyanophenyl)piperidin-4-ylamino)-2-methylbenzoic Acid

Pd$_2$(dba)$_3$ (183.09 mg, 200.00 umol), tBuONa (384.00 mg, 4.00 mmol) and BINAP (249.07 mg, 400.00 umol) were added to a mixture of methyl 5-bromo-2-methyl-benzoate (458.00 mg, 2.00 mmol) and 2-(4-amino-1-piperidyl)ben- zonitrile (402.42 mg, 2.00 mmol) in toluene (20.00 mL). The mixture was stirred at 90° C. for 1 h under nitrogen atmosphere. After being cooled, the mixture was concentrated to obtain a residue. The residue was purified via preparative HPLC to afford 5-(1-(2-cyanophenyl)piperidin-4-ylamino)-2-methylbenzoic acid (40 mg, 0.12 mmol, 6%) as a white solid. ESI-MS (EI$^+$, m/z): 350.2 [M+1]+.

Step 2: 2-(4-(5-(1-(2-Cyanophenyl) piperidin-4-ylamino)-2-methylbenzoyl)piperazin-1-yl)benzenesulfonamide Following the amide coupling EDCI/HOBT method to afford 2-(4-(5-(1-(2-cyanophenyl)piperidin-4-ylamino)-2-methylbenzoyl)piperazin-1-yl)benzenesulfonamide I-22 as a white solid. ESI-MS (EI$^+$, m/z): 559.3 [M+1]$^+$. $^1$H NMR (500 MHz, CDCl$_3$) δ 8.05-8.07 (d, J=7.9, 1.5 Hz, 1H), 7.61-7.65 (t, 1H), 7.58-7.59 (d, 1H), 7.49-7.52 (t, 1H), 7.36-7.41 (m, 2H), 7.01-7.06 (m, 3H), 6.59-6.61 (d, J=7.9 Hz, 1H), 6.50 (s, 1H), 5.56 (s, 2H), 3.44-3.59 (m, 6H), 3.19 (s, 2H), 2.97-3.03 (m, 3H), 2.20-2.25 (m, 5H), 1.70-1.73 (m, 2H), 1.28-1.31 (m, 2H).

Example 76: 3-(4-(5-(1-(2-Cyanophenyl)piperidin-4-ylamino)-2,4-dimethylbenzoyl) piperazin-1-yl) pyridine-2-sulfonamide, I-3

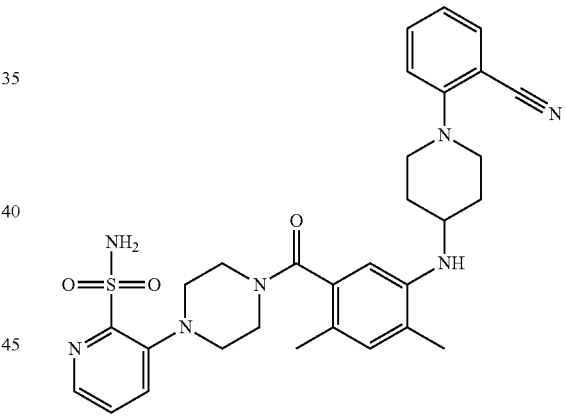

Synthetic Scheme:

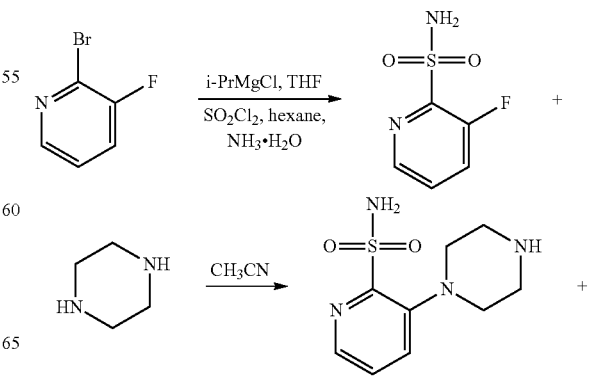

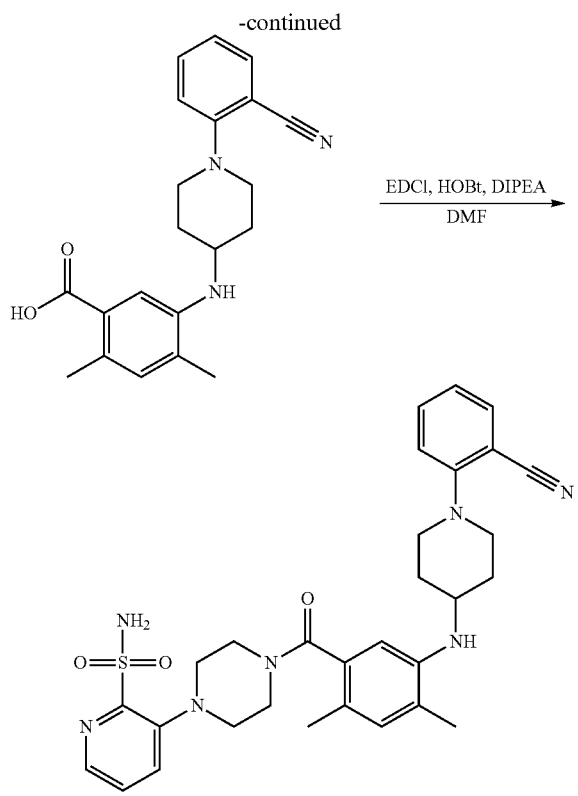

Procedures and Characterization:
The analysis method was following Method B and the separation method was following Method D.

Step 1: 3-Fluoropyridine-2-sulfonamide i-PrMgCl (29.84 mmol) was added dropwise to a solution of 2-bromo-3-fluoro-pyridine (3.50 g, 19.89 mmol) in THF (15.00 mL) and the mixture was stirred at 25° C. for 1.5 h. To a solution of $SO_2Cl_2$ (5.37 g, 39.78 mmol) in hexane (100.00 mL) was slowly added the above mixture at 0° C. After stirring for 10 min, the reaction mixture was distilled at reduced pressure and the residue was added to ammonia water (50.00 mL) at 0° C. The mixture was stirred at 25° C. for 1 h. The mixture was concentrated to obtain a residue. The residue was purified by chromatography on silica gel (DCM/MeOH=15:1) to obtain 3-fluoropyridine-2-sulfonamide (1 g, 5.68 mmol, 28%) as yellow solid. ESI-MS (EI⁺, m/z): 177.1[M+1]+.

Step 2: 3-(Piperazin-1-yl)pyridine-2-sulfonamide

3-Fluoropyridine-2-sulfonamide (900.00 mg, 5.11 mmol) and piperazine (440.06 mg, 5.11 mmol) were dissolved in acetonitrile (10.00 mL). The mixture was stirred at 110° C. for 1 h by microwave. The mixture was purified by chromatography on silica gel (DCM/MeOH=10:1) to obtain 3-(piperazin-1-yl) pyridine-2-sulfonamide (1 g, 4.13 mmol, 80%) as yellow oil. ESI-MS (EI⁺, m/z): 243.1 [M+1]+.

Step 3: 3-(4-(5-(1-(2-Cyanophenyl)piperidin-4-ylamino)-2,4-dimethylbenzoyl)piperazin-1-yl)pyridine-2-sulfonamide Followed the amide coupling EDCI/HOBt method to obtain 3-(4-(5-(1-(2-cyanophenyl)piperidin-4-ylamino)-2,4-dimethylbenzoyl)piperazin-1-yl)pyridine-2-sulfonamide I-3 as a white solid. ESI-MS (EI⁺, m/z): 574.3 [M+1]⁺. ¹H NMR (500 MHz, CDCl₃) δ 8.39-8.40 (d, J=4.5, 1.2 Hz, 1H), 7.69-7.71 (d, J=8.2, 1.2 Hz, 1H), 7.58-7.60 (d, J=7.7, 1.5 Hz, 1H), 7.49-7.54 (m, 2H), 7.02-7.08 (m, 2H), 6.94 (s, 1H), 6.50 (s, 1H), 5.28 (s, 2H), 4.11-4.13 (m, 1H), 3.98-4.00 (m, 2H), 3.17-3.25 (m, 2H), 2.97-3.05 (m, 4H), 2.24-2.229 (m, 2H), 2.22 (s, 3H), 2.14 (s, 3H), 1.67-1.82 (m, 2H).

Example 77: 2-(4-(6-(1-(2-Cyanophenyl)piperidin-4-ylamino)-3,5-dimethylpyridin-2-ylsulfonyl)piperazin-1-yl)benzenesulfonamide, I-1

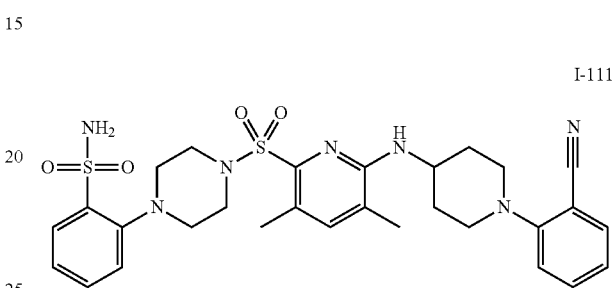

I-111

Synthetic Scheme:

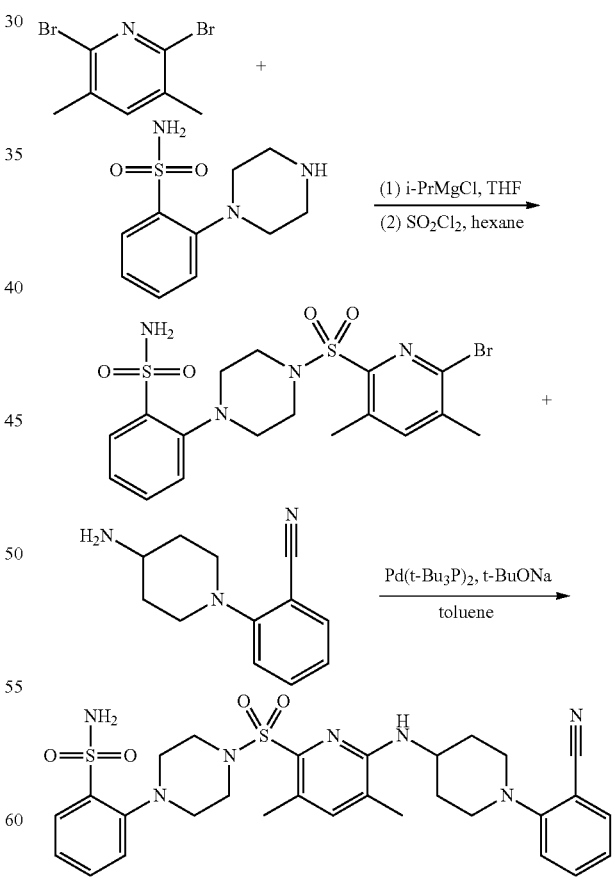

Procedures and Characterization:
The analysis method was following Method B and the separation method was following Method D.

Step 1: 2-(4-(6-Bromo-3,5-dimethylpyridin-2-ylsulfonyl)piperazin-1-yl)benzenesulfonamide i-PrMgCl (29.84 mmol) was added dropwise to a solution of 2-bromo-3-fluoro-pyridine (3.50 g, 19.89 mmol) in THF (15.00 mL) and the mixture was stirred at 25° C. for 1.5 h. To a solution of SO$_2$Cl$_2$ (5.37 g, 39.78 mmol) in hexane (100.00 mL) was slowly added the above mixture at 0° C. After stirring for 10 min, the reaction mixture was distilled at reduced pressure and the residue was added to ammonia water (50.00 mL) at 0° C. The mixture was stirred at 25° C. for 1 h. The mixture was concentrated to obtain a residue. The residue was purified by chromatography on silica gel (DCM/MeOH=15:1) to obtain 2-(4-(6-bromo-3,5-dimethyl-pyridin-2-ylsulfonyl) piperazin-1-yl) benzenesulfonamide (1.6 g, 3.27 mmol, 20%) as yellow solid. ESI-MS (EI$^+$, m/z): 489.0 [M+1]$^+$.

Step 2: 2-(4-(6-(1-(2-Cyanophenyl)piperidin-4-ylamino)-3,5-dimethylpyridin-2-ylsulfonyl)piperazin-1-yl)benzenesulfonamide tBuONa (236.16 mg, 2.46 mmol) and Pd(t-Bu$_3$P)$_2$ (62.85 mg, 123.00 umol) were added to a mixture of 2-[4-[(6-bromo-3,5-dimethyl-2-pyridyl)sulfonyl]piperazin-1-yl]benzenesulfonamide (600.00 mg, 1.23 mmol) and 2-(4-amino-1-piperidyl)benzonitrile (247.56 mg, 1.23 mmol) in toluene (30.00 mL). The mixture was stirred at 90° C. for 18 h. Then the mixture was concentrated to obtain a residue. The residue was purified via preparative HPLC to obtain 2-(4-(6-(1-(2-cyanophenyl)piperidin-4-ylamino)-3,5-dimethyl-pyridin-2-ylsulfonyl)piperazin-1-yl)benzenesulfonamide I-111 (25 mg, 0.04 mmol, 3%) as a white solid. ESI-MS (EI$^+$, m/z): 610.3[M+1]$^+$. $^1$H NMR (500 MHz, DMSO-d$_6$) δ 7.85-7.86 (d, J=7.3 Hz, 1H), 7.66-7.69 (d, J=7.5 Hz, 1H), 7.62-7.65 (m, 2H), 7.54-7.58 (t, 1H), 7.36-7.39 (t, 1H), 7.33 (s, 1H), 7.26-7.28 (d, J=8.3 Hz, 1H), 7.05-7.09 (t, 1H), 6.93 (s, 2H), 6.00-6.01 (d, J=7.7 Hz, 1H), 4.06-4.07 (m, 1H), 3.49-3.57 (m, 6H), 3.07-3.14 (m, 6H), 2.36 (s, 3H), 2.09-2.13 (m, 5H), 1.76-1.84 (m, 2H).

Example 78: (R)-2-(4-(5-(4-(3-Fluoro-2-(S-methylsulfonimidoyl)phenyl)piperazine-1-carbonyl)-2,4-dimethylphenylamino)piperidin-1-yl) Benzonitrile, I-89

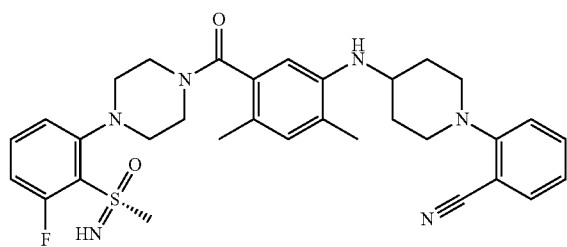

I-89

Synthetic Scheme:

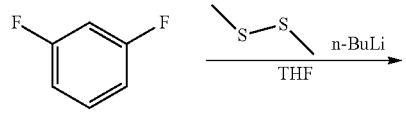

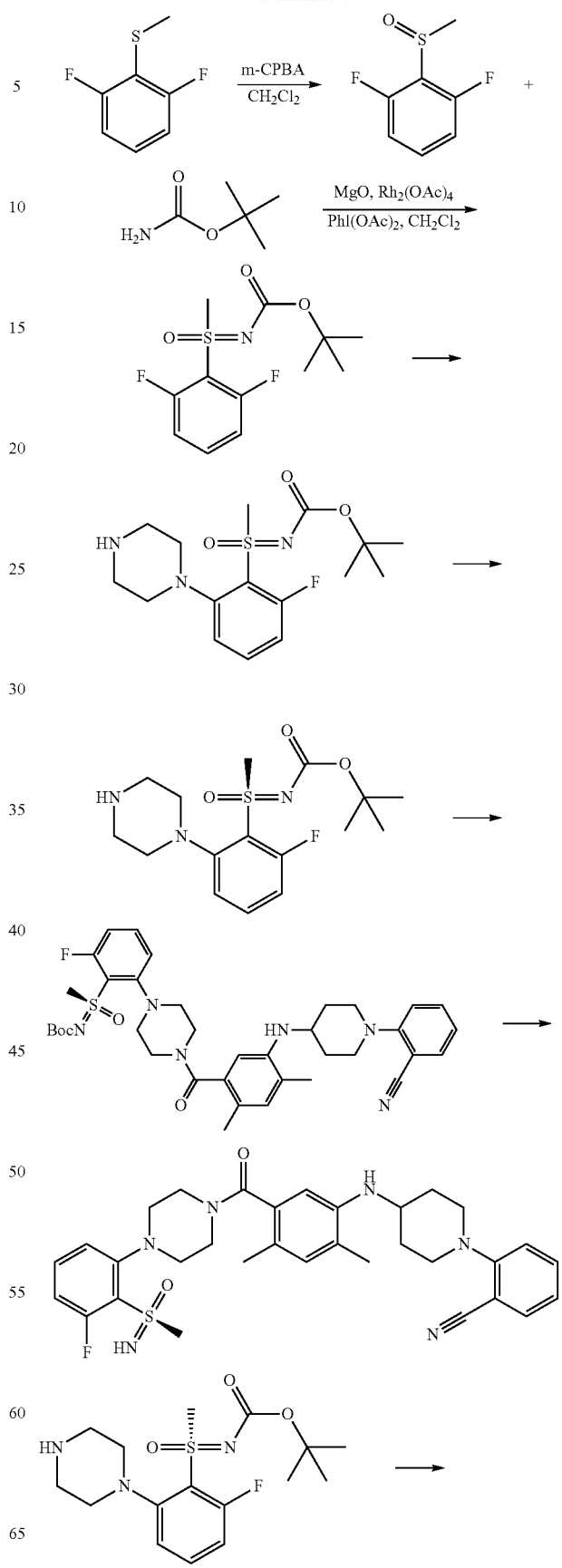

-continued

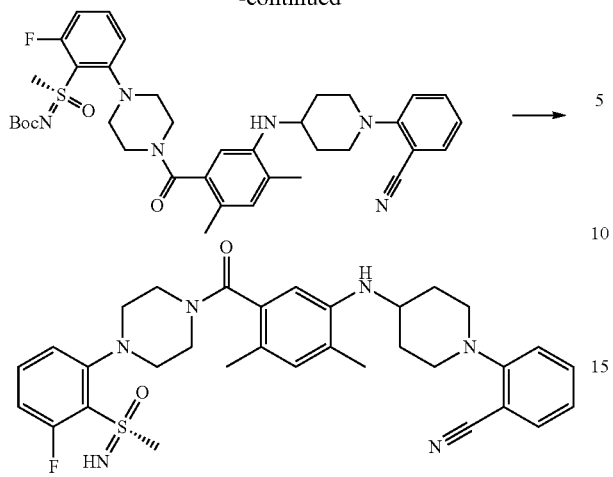

Procedures and Characterization:
The analysis method was following Method B and the separation method was following Method D.

Step 1: (2, 6-Difluorophenyl)(methyl)sulfane n-BuLi (92.03 mmol, 2 M in THF, 46 mL) was added slowly to a solution of 1,3-difluorobenzene (10.50 g, 92.03 mmol) in THF (300.00 mL). The mixture was stirred at −78° C. for 20 min. Then (methyldisulfanyl) methane (10.40 g, 110.44 mmol) was added to the mixture. The cooling bath was removed and the reaction mixture was warmed to 25° C. The reaction mixture was poured onto ice (200 mL) and extracted with EtOAc (300 mL). The organic layer was washed with brine and dried to obtain (2,6-difluorophenyl)(methyl)sulfane (12.6 g, 78.66 mmol, 85%) as a colorless oil.

Step 2: 1, 3-Difluoro-2-(methylsulfinyl)benzene

To a suspension of 1,3-difluoro-2-methylsulfanyl-benzene (11.00 g, 68.67 mmol) in DCM (250.00 mL) at 0° C. was added m-CPBA (12.99 g, 75.54 mmol) at a rate such that the temperature of the reaction mixture did not exceed 10° C. over the course of the addition. The reaction mixture was then allowed to warm to rt followed by stirring at rt overnight. The solution was washed with 2 N NaOH (80 mL) and brine (50 mL), then concentrated to give a residue. The residue was purified by flash column (0% to 20% and to 35% of EtOAc in PE) to afford 1,3-difluoro-2-(methylsulfinyl)benzene (10.7 g, 60.7 mmol, 88%) as a colorless oil. ESI-MS (EI$^+$, m/z): 177.0[M+1]$^+$.

Step 3: N-Boc-1,3-difluoro-2-(S-methylsulfonimidoyl)benzene

To a suspension of 1,3-difluoro-2-methylsulfinyl-benzene (11.00 g, 62.44 mmol), MgO (10.32 g, 249.76 mmol) and Rh$_2$(OAc)$_4$ (827.95 mg, 1.87 mmol) in DCM (200.00 mL) was added portion-wise PhI(OAc)$_2$ (40.21 g, 124.88 mmol) and the reaction mixture was stirred at 25° C. for 18 h. The mixture was filtered and concentrated to obtain a residue. The residue was dissolved in DMF, filtered and purified via preparative HPLC to obtain N-Boc-1,3-difluoro-2-(S-methylsulfonimidoyl)benzene (4.5 g, 15.45 mmol, 24%) as a brown oil. ESI-MS (EI$^+$, m/z): 236.1 [M−55]$^+$.

Step 4: 1-(N-Boc-3-fluoro-2-(S-methylsulfonimidoyl) phenyl) piperazine

K$_2$CO$_3$ (994.8 mg, 7.2 mmol) was added to a solution of piperazine (341.5 mg, 3.96 mmol) and N-Boc-1,3-difluoro-2-(S-methylsulfonimidoyl)benzene (1050 mg, 3.0 mmol) in DMF (25 mL). The mixture was stirred at 110° C. for 1 h. After being cooled, the mixture was purified via preparative HPLC to obtain 1-(N-Boc-3-fluoro-2-(S-methylsulfonimidoyl)phenyl)piperazine (420 mg, 1.2 mmol, 32%) as a colorless oil.

Step 5: (R)-2-(4-(5-(4-(3-Fluoro-N-Boc-2-(S-methylsulfonimidoyl)phenyl)piperazine-1-carbonyl)-2,4-dimethylphenylamino)piperidin-1-yl)benzonitrile EDCI (96.18 mg, 503.58 umol), HOBt (68.04 mg, 503.58 umol) and DIPEA (108.47 mg, 839.30 umol, 146.58 uL) were added to a solution of (R)-1-(N-Boc-3-fluoro-2-(S-methylsulfonimidoyl)phenyl)piperazine (150.00 mg, 419.65 umol) and 5-[[1-(2-cyanophenyl)-4-piperidyl]amino]-2,4-dimethyl-benzoic acid (146.64 mg, 419.65 umol) in DMF (4.00 mL). The mixture was stirred at 25° C. for 1 h. Then the mixture was purified via preparative HPLC to obtain (R)-2-(4-(5-(4-(3-fluoro-N-Boc-2-(S-methylsulfonimidoyl) phenyl)piperazine-1-carbonyl)-2,4-dimethylphenylamino) piperidin-1-yl)benzonitrile (115 mg, 0.17 mmol, 39%) as a white solid. ESI-MS (EI$^+$, m/z): 689.3[M+1]$^+$.

Step 6: (R)-2-(4-(5-(4-(3-Fluoro-2-(S-methylsulfonimidoyl)phenyl)piperazine-1-carbonyl)-2,4-dimethylphenylamino)piperidin-1-yl)benzonitrile TFA (702.01 mg, 6.16 mmol) was added to a solution (R)-2-(4-(5-(4-(3-fluoro-N-Boc-2-(S-methylsulfonimidoyl) phenyl)piperazine-1-carbonyl)-2,4-dimethylphenylamino) piperidin-1-yl)benzonitrile (115.00 mg, 166.94 umol) in DCM (5.00 mL). The mixture was stirred at 25° C. for 1 h. Then the mixture was concentrated to obtain a residue. The residue was purified via preparative HPLC to obtain (R)-2-(4-(5-(4-(3-fluoro-2-(S-methylsulfonimidoyl)phenyl)piperazine-1-carbonyl)-2,4-dimethylphenylamino)piperidin-1-yl)benzonitrile I-89 (50 mg, 0.085 mmol, 50%) as a white solid. The stereochemistry was arbitrarily assigned. ESI-MS (EI$^+$, m/z): 589.3 [M+1]$^+$. $^1$H NMR (500 MHz, CDCl$_3$) δ 7.58-7.60 (d, J=7.7 Hz 1H), 7.46-7.54 (m, 2H), 7.14-7.17 (d, J=8.0 Hz, 1H), 7.01-7.08 (m, 3H), 6.94 (s, 1H), 6.44-6.50 (m, 1H), 4.94-5.20 (m, 2H), 2.62-3.63 (m, 16H), 2.14-2.26 (m, 8H), 1.70-1.80 (m, 2H).

Example 79: (S)-2-(4-(5-(4-(3-Fluoro-2-(S-methylsulfonimidoyl)phenyl)piperazine-1-carbonyl)-2,4-dimethylphenylamino)piperidin-1-yl) benzonitrile, I-88

I-88

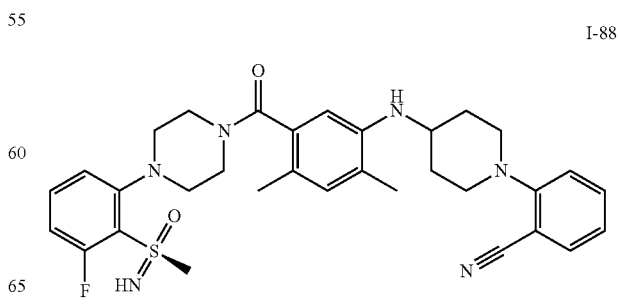

Synthetic Scheme:

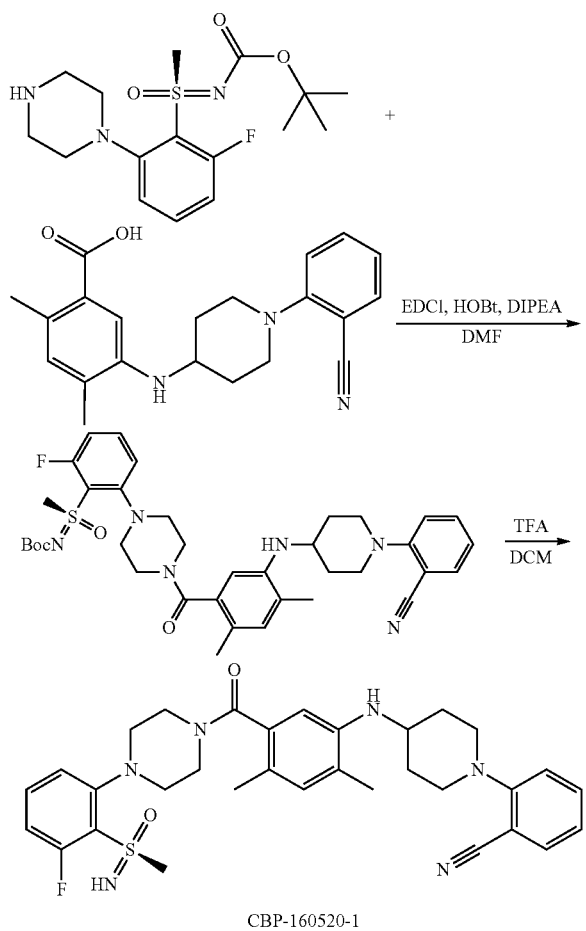

Procedures and Characterization:
The analysis method was following Method B and the separation method was following Method D.

Step 1: (S)-2-(4-(5-(4-(3-Fluoro-N-Boc-2-(S-methylsulfonimidoyl)phenyl)piperazine-1-carbonyl)-2,4-dimethylphenylamino)piperidin-1-yl)benzonitrile EDCI (96.18 mg, 503.58 umol), HOBt (68.04 mg, 503.58 umol) and DIPEA (108.47 mg, 839.30 umol, 146.58 uL) were added to a solution of (S)-1-(N-Boc-3-fluoro-2-(S-methylsulfonimidoyl)phenyl)piperazine (150.00 mg, 419.65 umol) and 5-[[1-(2-cyanophenyl)-4-piperidyl]amino]-2,4-dimethyl-benzoic acid (146.64 mg, 419.65 umol) in DMF (4.00 mL). The mixture was stirred at 25° C. for 1 h. Then the mixture was purified via preparative HPLC to obtain (S)-2-(4-(5-(4-(3-fluoro-N-Boc-2-(S-methylsulfonimidoyl)phenyl)piperazine-1-carbonyl)-2,4-dimethylphenylamino)piperidin-1-yl)benzonitrile (120 mg, 0.17 mmol, 41%) as a white solid. ESI-MS (EI⁺, m/z): 689.3 [M+1]⁺.

Step 2: (S)-2-(4-(5-(4-(3-Fluoro-2-(S-methylsulfonimidoyl)phenyl)piperazine-1-carbonyl)-2,4-dimethylphenylamino)piperidin-1-yl)benzonitrile TFA (732.54 mg, 6.42 mmol) was added to a solution of (S)-2-(4-(5-(4-(3-fluoro-N-Boc-2-(S-methylsulfonimidoyl)phenyl)piperazine-1-carbonyl)-2,4-dimethylphenylamino)piperidin-1-yl)benzonitrile (120.00 mg, 174.20 umol) in DCM (5.00 mL). The mixture was stirred at 25° C. for 1 h. Then the mixture was concentrated to obtain a residue. The residue was purified via preparative HPLC to obtain (S)-2-(4-(5-(4-(3-fluoro-2-(S-methylsulfonimidoyl)phenyl)piperazine-1-carbonyl)-2,4-dimethylphenylamino)piperidin-1-yl)benzonitrile I-88 (30 mg, 0.051 mmol, 29%) as a white solid. The stereochemistry was arbitrarily assigned. ESI-MS (EI⁺, m/z): 589.3 [M+1]⁺. ¹H NMR (500 MHz, CDCl₃) δ 7.58-7.60 (d, J=7.6 Hz, 1H), 7.46-7.53 (m, 2H), 7.15-7.17 (d, J=8.1 Hz, 1H), 7.02-7.08 (m, 3H), 6.94 (s, 1H), 6.43-6.54 (m, 1H), 4.86-5.21 (m, 2H), 2.60-3.64 (m, 16H), 2.14-2.26 (m, 8H), 1.68-1.80 (m, 2H).

Example 80: Synthesis of (S)-2-amino-5,5,5-trifluoro-4,4-dimethylpentanoic Acid and (R)-2-amino-5,5,5-trifluoro-4,4-dimethylpentanoic Acid, I-124

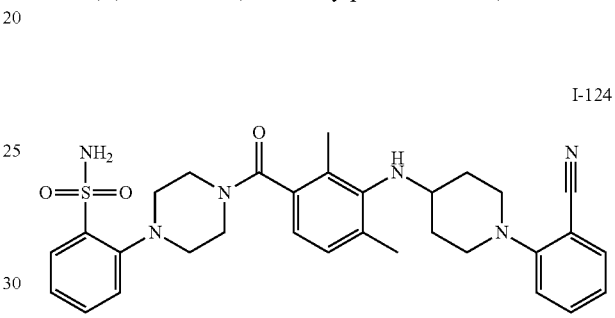

I-124

Synthetic Scheme:

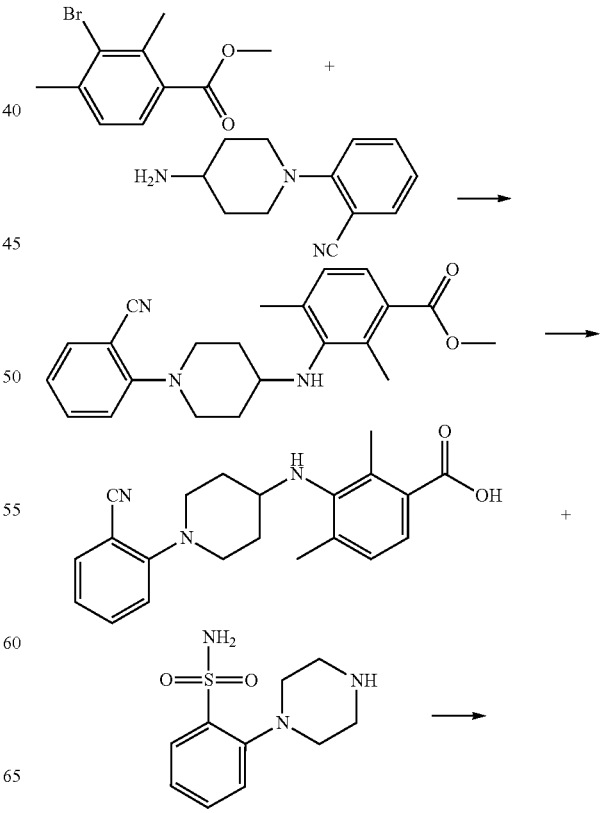

-continued

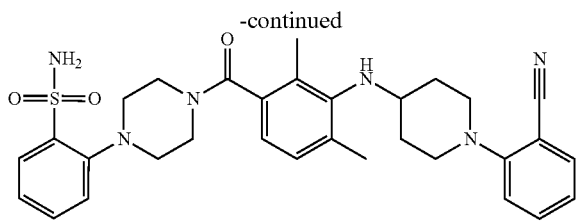

Procedures and Characterization:

The analysis method was following Method B and the separation method was following Method D.

Step 1: methyl 3-[[1-(2-cyanophenyl)-4-piperidyl]amino]-2, 4-dimethyl-benzoate

A mixture of methyl 3-bromo-2,4-dimethyl-benzoate (800 mg, 3.29 mmol), 2-(4-amino-1-piperidyl)benzonitrile (1.32 g, 6.58 mmol), BrettPhos (353.28 mg, 0.658 mmol), $Pd_2(dba)_3$ (301 mg, 0.329 mmol) and $Cs_2CO_3$ (2.14 g, 6.58 mmol) in toluene (60.00 mL) was heated to 100° C. for 24 h, the mixture was diluted with EtOAc (100 mL), washed with water (100 mL) and brine (100 mL), dried ($Na_2SO_4$), filtered and concentrated under vacuum and purified by chromatography (silica, PE/EA=5:1) to afford methyl 3-[[1-(2-cyanophenyl)-4-piperidyl]amino]-2,4-dimethyl-benzoate (500 mg, 605 umol, 18.40% yield, 44% purity) as a brown solid. ESI-MS (EI+, m/z): 364.0 [M+H]+.

Step 2: 3-[[1-(2-cyanophenyl)-4-piperidyl]amino]-2, 4-dimethyl-benzoic Acid

A solution of methyl 3-[[1-(2-cyanophenyl)-4-piperidyl]amino]-2,4-dimethyl-benzoate (450 mg, 1.24 mmol) and $LiOH.H_2O$ (416 mg, 9.92 mmol) in methanol (15.00 mL) and $H_2O$ (5.00 mL) was heated to 60° C. for 17 h, the solution was diluted with water (100 mL), extracted with DCM (50 mL×2), the organic phase was adjusted PH to 3 with 6M HCl, and then extracted with EtOAc (50 mL×2), dried ($Na_2SO_4$), filtered and concentrated under vacuum to afford 3-[[1-(2-cyanophenyl)-4-piperidyl]amino]-2,4-dimethyl-benzoic acid (220 mg, 629 umol, 50%, 2 steps) as a brown solid. ESI-MS (EI+, m/z): 350.0 [M+H]+. $^1$H-NMR (400 MHz, CDCl$_3$): δ 7.55-7.60 (m, 2H), 7.45-7.49 (m, 1H), 7.08 (d, J=8.0 Hz, 1H), 6.98-7.01 (m, 2H), 3.58 (d, J=12.0 Hz, 2H), 3.07-3.09 (m, 1H), 2.80 (t, J=11.2 Hz), 2.58 (s, 3H), 2.35 (s, 3H), 2.05-2.07 (m, 2H), 1.69-1.75 (m, 2H).

Step 3: 2-[4-[3-[[1-(2-cyanophenyl)-4-piperidyl]amino]-2,4-dimethyl-benzoyl]piperazin-1-yl]benzenesulfonamide Following the amide coupling HATU method to afford 2-[4-[3-[[1-(2-cyanophenyl)-4-piperidyl]amino]-2,4-dimethyl-benzoyl]piperazin-1-yl]benzenesulfonamide I-124 as a white solid. ESI-MS (EI–, m/z): 572.9 [M+H]+. 1H NMR (500 MHz, DMSO) δ 7.87 (dd, J=8.0 Hz, 1.5 Hz, 1H), 7.68 (dd, J=7.5, 1.5 Hz, 1H), 7.66-7.53 (m, 3H), 7.34 (t, J=7.5 Hz, 1H), 7.20-7.03 (m, 3H), 6.97 (m, 2H), 6.85 (m, 1H), 3.95 (m, 2H), 3.51 (d, J=12.0 Hz, 2H), 3.33 (d, J=6.5 Hz, 2H), 3.15-3.20 (m, 1H), 2.97-3.00 (m, 2H), 2.80-2.86 (m, 4H), 2.33 (s, 3H), 2.23 (s, 3H), 1.91-1.97 (m, 2H), 1.81-1.82 (m, 2H).

Example 81: 3-(4-(3-(1-(2-cyanophenyl)piperidin-4-ylamino)-2,4-dimethylbenzoyl)piperazin-1-yl)pyridine-2-sulfonamide, I-121

I-121

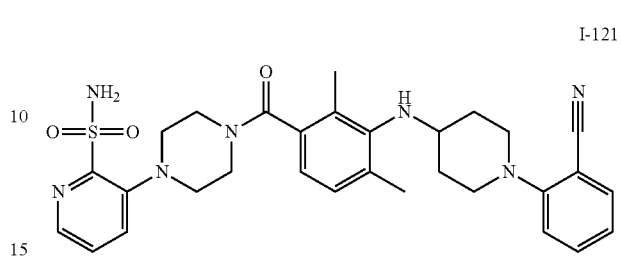

Synthetic Scheme:
Procedures and characterization:

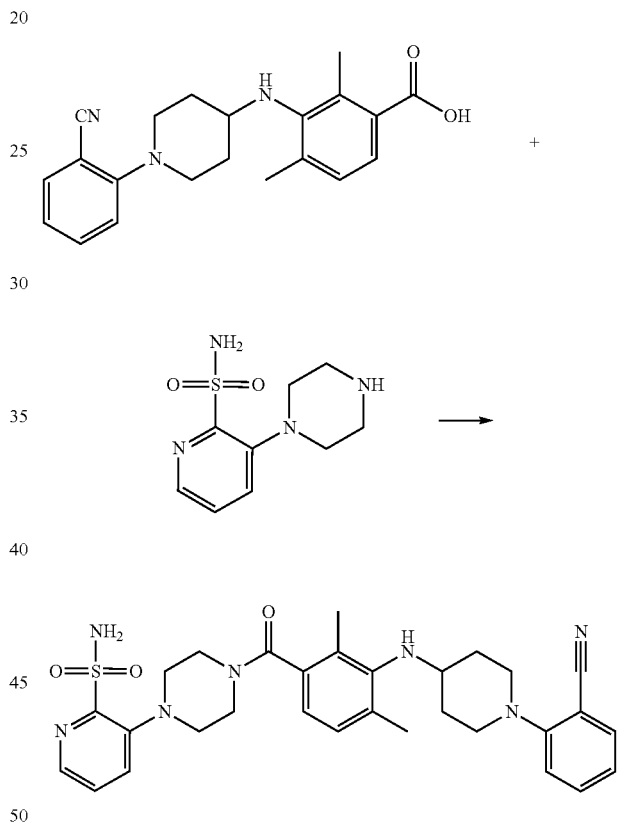

The analysis method was following Method B and the separation method was following Method D.

3-[4-[3-[[1-(2-cyanophenyl)-4-piperidyl] amino]-2, 4-dimethyl-benzoyl] piperazin-1-yl]pyridine-2-sulfonamide Following the amide coupling EDCI/HOBT method to afford 3-[4-[3-[[1-(2-cyanophenyl)-4-piperidyl]amino]-2,4-dimethyl-benzoyl]piperazin-1-yl]pyridine-2-sulfonamide I-121 as a white solid. ESI-MS (EI+, m/z): 574.3 [M+H]+. 1H NMR (400 MHz, DMSO) δ 8.38 (dd, J=4.4, 1.2 Hz, 1H), 7.92 (d, J=7.1 Hz, 1H), 7.74-7.46 (m, 4H), 7.05-7.20 (m, 5H), 6.86 (d, J=7.6 Hz, 1H), 3.75-3.90 (m, 2H), 3.50-3.53 (m, 2H), 3.09-3.29 (m, 5H), 2.83-2.96 (m, 4H), 2.34 (s, 3H), 2.23 (s, 3H), 1.81-2.09 (m, 4H).

301

Example 82: 2-(4-(3-(1-(2-cyanophenyl)piperidin-4-ylamino)-2,4-dimethylbenzoyl)piperazin-1-yl)pyridine-3-sulfonamide, I-120

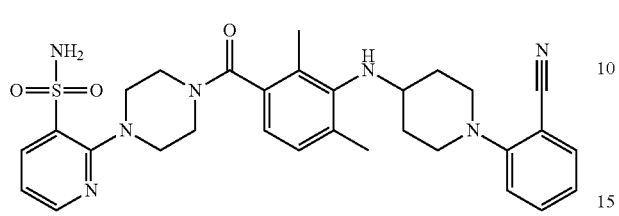

Synthetic Scheme:

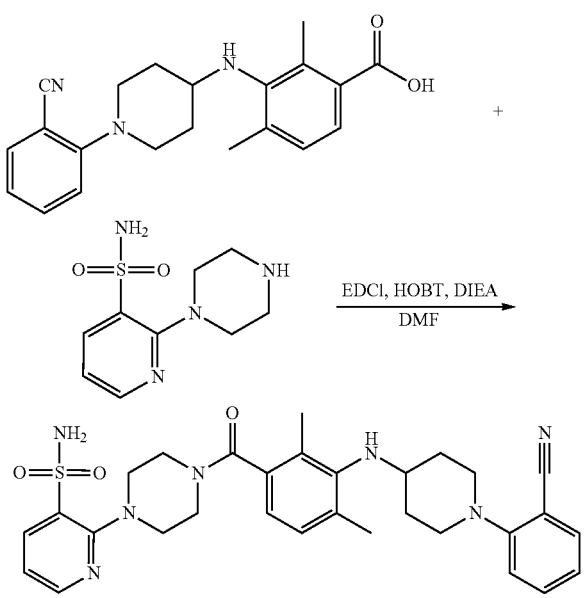

Procedures and Characterization:

The analysis method was following Method B and the separation method was following Method D.

2-[4-[3-[[1-(2-cyanophenyl)-4-piperidyl] amino]-2,4-dimethyl-benzoyl] piperazin-1-yl]pyridine-3-sulfonamide Following the amide coupling EDCI/HOBT method to afford 2-[4-[3-[[1-(2-cyanophenyl)-4-piperidyl]amino]-2,4-dimethyl-benzoyl]piperazin-1-yl]pyridine-3-sulfonamide I-120 as a white solid. ESI-MS (EI+, m/z): 574.3 [M+H]+.
$^1$H NMR (400 MHz, DMSO-$d_6$) δ 8.49 (dd, J=4.4, 1.6 Hz, 1H), 8.23 (dd, J=8.0 Hz, J=1.6 Hz, 1H), 7.69 (dd, J=8.0 Hz, J=1.6 Hz, 1H), 7.55-7.58 (m, 1H), 7.26-7.33 (m, 3H), 7.05-7.16 (m, 3H), 6.83 (d, J=7.6 Hz, 1H), 3.84-3.87 (m, 2H), 3.50-3.53 (m, 2H), 3.26-3.34 (m, 4H), 3.11-3.13 (m, 3H), 2.81-2.84 (m, 2H), 2.34 (s, 3H), 2.22 (s, 3H), 1.81-1.94 (m, 4H).

302

Example 83: (5-(1-(2-chlorophenyl) piperidin-4-ylamino)-2, 4-dimethylphenyl) (4-(6-methylpyridin-2-yl) piperazin-1-yl) Methanone, I-35

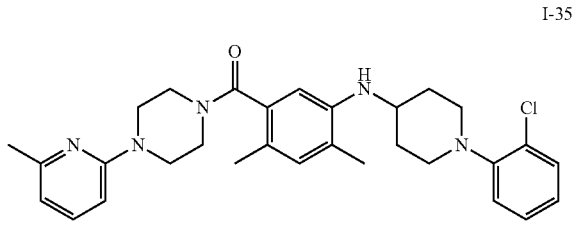 [SMILES: Cc1cccc(N2CCN(C(=O)c3cc(NC4CCN(c5ccccc5Cl)CC4)c(C)cc3C)CC2)n1]

Synthetic Scheme:

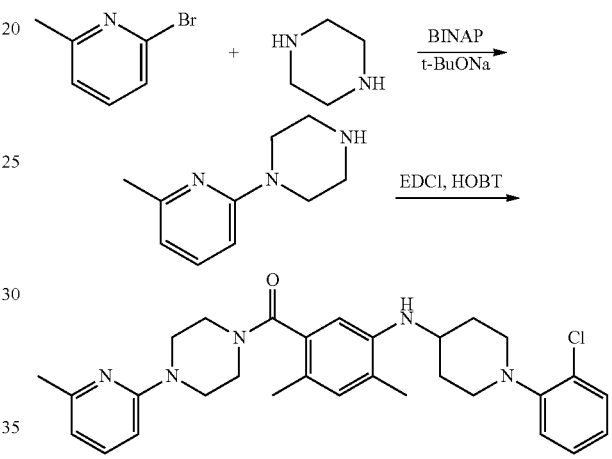

Procedures and Characterization:

The analysis method was following Method B and the separation method was following Method D.

Step 1: 1-(6-methylpyridin-2-yl)piperazine

To a solution of 2-bromo-6-methylpyridine (1.00 g, 5.81 mmol), piperazine (751.13 mg, 8.72 mmol) in toluene (20.00 mL) was added Pd$_2$(dba)$_3$ (266.01 mg, 290.50 umol), BINAP (180.87 mg, 290.50 umol), tBuONa (558.34 mg, 5.81 mmol). The mixture was stirred at 100° C. underN$_2$ for 17 h. The mixture was added water (20 mL), extracted with DCM (20 mL×3). The organic layer was dried and concentrated to give the crude. The crude was purified by SCG (PE: EA=10:1 to MeOH) to give the 1-(6-methylpyridin-2-yl) piperazine (500.00 mg, 2.82 mmol, 48.55% yield, 100% purity) as yellow oil.

Step 2: (5-(1-(2-chlorophenyl) piperidin-4-ylamino)-2, 4-dimethylphenyl) (4-(6-methylpyridin-2-yl) piperazin-1-yl) Methanone Following the amide coupling EDCI/HOBT method to obtain (5-(1-(2-chlorophenyl) piperidin-4-ylamino)-2, 4-dimethylphenyl) (4-(6-methylpyridin-2-yl) piperazin-1-yl) methanone I-35 as a white solid. ESI-MS (EI$^+$, m/z): 518.3 [M+H]$^+$.
$^1$H NMR (500 MHz, CDCl$_3$) δ 7.41-7.35 (m, 2H), 7.23-7.20 (m, 1H), 7.06 (d, J=7.0 Hz, 1H), 6.98-6.94 (m, 1H), 6.92 (s, 1H), 6.54 (d, J=7.5 Hz, 1H), 6.49 (s, 1H), 6.45 (d, J=8.5 Hz, 1H), 3.94-3.91 (m, 2H), 3.62 (t, J=5.5 Hz, 1H), 3.48-3.36 (m, 8H), 2.81-2.79 (m, 2H), 2.38 (s, 3H), 2.29-2.20 (m, 5H), 2.13 (s, 3H).

Example 84: 4-(5-{[1-(2-cyanophenyl)piperidin-4-yl]amino}-2,4-dimethylbenzoyl)-1-phenylpiperazine-2-carboxylic Acid, I-39

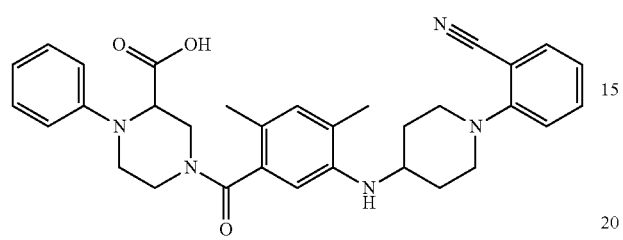

I-39

To a solution of 5-{[1-(2-cyanophenyl)piperidin-4-yl]amino}-2,4-dimethylbenzoic acid [Intermediate 1] (75 mg, 0.21 mmol) and HATU (85 mg, 0.22 mmol) in DMF (2 ml) was added DIPEA (200 µl, 1.12 mmol). The reaction mixture stirred at rt for 30 mins. 1-phenylpiperazine-2-carboxylic acid dihydrochloride (61 mg, 0.22 mmol) was added and the reaction mixture was stirred at rt for 5 h. $H_2O$ was added to the reaction mixture and left to stand for 15 min. The crude reaction mixture was purified by preparative HPLC [UV-Directed High pH prep method]. The fractions containing product were combined and concentrated in vacuo to afford the title compound I-39 as a pink solid (51 mg, 42%).

1H NMR (500 MHz, DMSO-d6) δ 7.68 (d, J=7.6 Hz, 1H), 7.58 (t, J=7.6 Hz, 1H), 7.22-7.12 (m, 3H), 7.06 (t, J=7.5 Hz, 1H), 6.92-6.78 (m, 3H), 6.78-6.62 (m, 1H), 6.42 (s, 1H), 5.05-3.62 (m, 4H), 3.62-3.47 (m, 5H), 3.18-2.73 (m, 5H), 2.18-1.97 (m, 8H), 1.85-1.55 (m, 2H). LCMS Method 6—Tr=3.27 min (ES+) (M+H)+ 538.3

Example 85: 4-(5-{[1-(2-cyanophenyl)piperidin-4-yl]amino}-2,4-dimethylbenzoyl)-N-methyl-1-phenylpiperazine-2-carboxamide, I-32

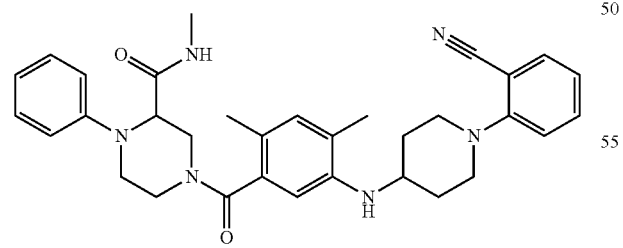

I-32

4-(5-{[1-(2-cyanophenyl)piperidin-4-yl]amino}-2,4-dimethylbenzoyl)-1-phenylpiperazine-2-carboxylic acid (50 mg, 0.09 mmol) and HATU (40 mg, 0.11 mmol) were dissolved in DMF (1 ml). DIPEA (50 µl, 0.28 mmol) was added and the reaction mixture was stirred for 30 min. methanamine hydrochloride (15 mg, 0.22 mmol) was added and the reaction mixture was sonicated for 20 min then left to stand overnight. The reaction mixture was purified by preparative HPLC [UV-Directed High pH prep method]. The fraction containing product was reduced in vacuo and dried in a vac oven over night to yield the title compound I-32 as a white solid (15 mg, 28%)

1H NMR (250 MHz, DMSO-d6; 353° K) δ 7.77-7.51 (m, 3H), 7.27-7.12 (m, 3H), 7.10-7.00 (m, 1H), 6.92-6.71 (m, 4H), 6.44 (s, 1H), 4.26 (d, J=7.9 Hz, 1H), 4.13 (s, 1H), 3.56 (d, J=14.1 Hz, 9H), 2.98 (s, 2H), 2.59 (d, J=4.6 Hz, 3H), 2.17-1.99 (m, 8H), 1.82-1.62 (m, 2H).

LCMS Method 6—Tr=4.81 min (ES+) (M+H)+ 551.2

Example 86: 4-(5-{[1-(2-cyanophenyl)piperidin-4-yl]amino}-2,4-dimethylbenzoyl)-1-phenylpiperazine-2-carboxamide, I-31

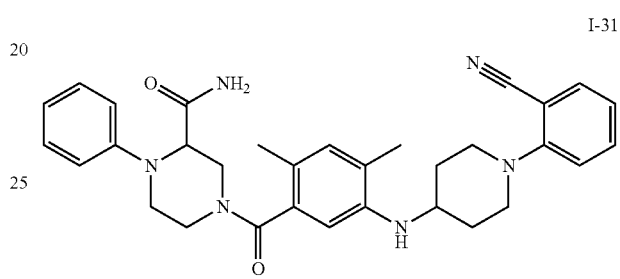

I-31

4-(5-{[1-(2-cyanophenyl)piperidin-4-yl]amino}-2,4-dimethylbenzoyl)-1-phenylpiperazine-2-carboxylic acid [Example 84] (50 mg, 0.09 mmol) and HATU (40 mg, 0.11 mmol) were dissolved in DMF (1 ml). DIPEA (50 µl, 0.28 mmol) was added and the reaction mixture was stirred for 30 min. Formic acid amine (20 mg, 0.32 mmol) was added and the reaction mixture was sonicated for 20 min then left to stand overnight. The reaction mixture was purified by preparative HPLC [UV-Directed High pH prep method]. The fraction containing product was reduced in vacuo and dried in a vac oven over night to yield the title compound I-31 as a white solid (21 mg, 40%)

1H NMR (250 MHz, DMSO-d6) δ 7.69-7.50 (m, 2H), 7.28-7.13 (m, 3H), 7.12-6.90 (m, 3H), 6.90-6.70 (m, 4H), 6.46 (s, 1H), 4.32-4.08 (m, 2H), 4.00-3.31 (m, 9H), 3.02-2.93 (m, 2H), 2.18-2.05 (m, 8H), 1.83-1.62 (m, 2H).

LCMS Method 6—Tr=4.67 min (ES+) (M+H)+ 537.2

Example 87: 2-[4-({2,4-Dimethyl-5-[4-(pyridazin-3-yl)piperazine-1-carbonyl]phenyl}amino)piperidin-1-yl]benzonitrile, I-70

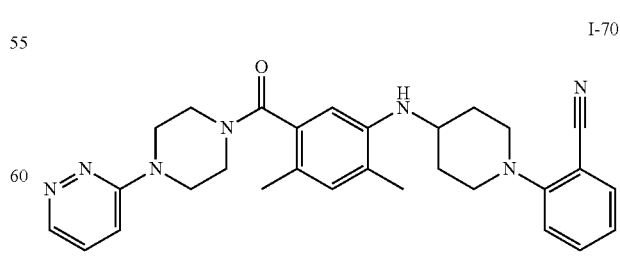

I-70

The title compound was prepared according to the general method employed in [Example 154] below, using 5-{[1-(2-cyanophenyl)piperidin-4-yl]amino}-2,4-dimethylbenzoic acid [Intermediate 1] (29.79 mg, 0.09 mmol) and 3-(piperazin-1-yl)pyridazine (14 mg, 0.09 mmol) to yield the title compound I-70 as an off-white powder (7.0 mg, 17%). 1H NMR (500 MHz, Chloroform-d) δ 8.63 (dd, J=4.5, 1.2 Hz, 1H), 7.56 (dd, J=7.7, 1.5 Hz, 1H), 7.50-7.45 (m, 1H), 7.26-7.21 (m, 1H), 7.06-6.98 (m, 2H), 6.95-6.92 (m, 2H), 6.48 (s, 1H), 4.03-3.90 (m, 2H), 3.76-3.40 (m, 10H), 3.03-2.91 (m, 2H), 2.30-2.17 (m, 5H), 2.14 (s, 3H), 1.82-1.64 (m, 2H).

LCMS Method 7—Tr=2.60 min (ES+) (M+H)+ 496.3

Example 88: 2-[(3S)-4-(5-{[1-(2-Cyanophenyl)piperidin-4-yl]amino}-2,4-dimethylbenzoyl)-3-methyl-piperazin-1-yl]-4,5-difluorobenzonitrile, I-69

I-69

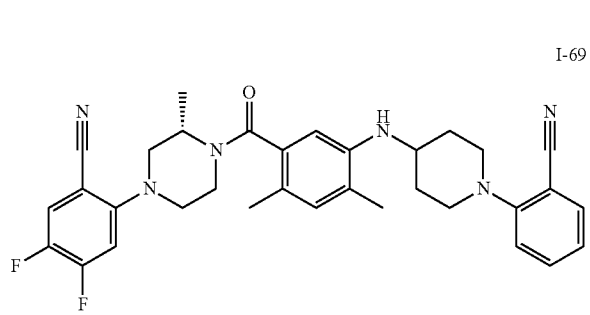 [SMILES: Cc1cc(C)c(C(=O)N2CCN(c3cc(F)c(F)cc3C#N)C[C@@H]2C)cc1NC1CCN(c2ccccc2C#N)CC1]

The title compound was prepared according to the generic method [Example 154] using 5-{[1-(2-cyanophenyl)piperidin-4-yl]amino}-2,4-dimethylbenzoic acid [Intermediate 1](28 mg, 0.08 mmol) and 4,5-difluoro-2-[(3S)-3-methyl-piperazin-1-yl]benzonitrile [Intermediate 7] (19 mg, 0.08 mmol) to yield a pale yellow solid I-69 (2.0 mg, 4%).

1H NMR (250 MHz, DMSO-d6) δ 7.96-7.83 (m, 1H), 7.67-7.52 (m, 2H), 7.27 (dd, J=12.7, 7.2 Hz, 1H), 7.17 (d, J=8.1 Hz, 1H), 7.05 (t, J=7.5 Hz, 1H), 6.90 (s, 1H), 6.45 (s, 1H), 4.29 (d, J=8.2 Hz, 1H), 3.62-3.45 (m, 5H), 3.44-3.21 (m, 6H), 2.15-2.02 (m, 9H), 1.82-1.62 (m, 2H), 1.38 (d, J=6.8 Hz, 3H).

LCMS Method 7—Tr=4.36 min (ES+) (M+H)+ 569.2

Example 89: 2-[4-({5-[4-(2-cyanophenyl)piperazine-1-carbonyl]-2,4-dimethylphenyl}(methyl)amino)piperidin-1-yl]benzonitrile, I-68

I-68

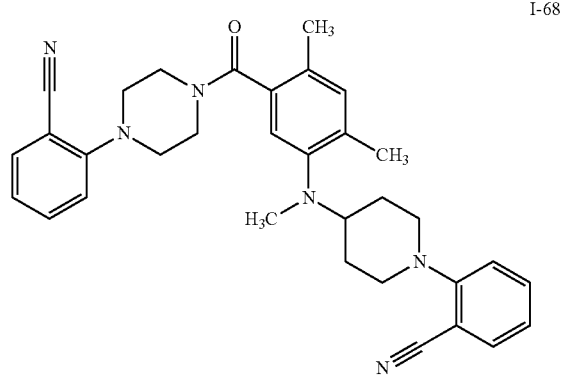 [SMILES: Cc1cc(C)c(N(C)C2CCN(c3ccccc3C#N)CC2)cc1C(=O)N1CCN(c2ccccc2C#N)CC1]

The title compound was synthesized from 5-{[1-(2-cyanophenyl)piperidin-4-yl](methyl)amino}-2,4-dimethylbenzoic acid [Intermediate 9] (35 mg, 0.096 mmol) and 2-(piperazin-1-yl)benzonitrile (18 mg, 0.096 mmol) using the method described below for example 154 to afford the title compound I-68 as a straw glass (10 mg, 19%).

1H NMR (500 MHz, Chloroform-d) δ 7.59 (dd, J=7.7, 1.6 Hz, 1H), 7.56-7.49 (m, 2H), 7.44 (td, J=7.9, 7.5, 1.7 Hz, 1H), 7.09-7.05 (m, 2H), 7.02 (d, J=8.2 Hz, 1H), 6.99-6.94 (m, 2H), 6.93 (s, 1H), 4.07-3.98 (m, 2H), 3.63-3.54 (m, 2H), 3.54-3.47 (m, 2H), 3.29-3.21 (m, 2H), 3.14-3.07 (m, 2H), 2.95-2.85 (m, 1H), 2.83-2.74 (m, 2H), 2.66 (s, 3H), 2.29 (s, 3H), 2.26 (s, 3H), 2.00-1.82 (m, 4H), 1.54 (s, 6H).

LCMS Method 6—Tr=4.68 min (ES+) (M+H)+ 533

Example 90: 2-(4-{[5-(4-{2-[imino(methyl)oxo-λ6-sulfanyl]phenyl}piperazine-1-carbonyl)-2,4-dimethylphenyl]amino}piperidin-1-yl)benzonitrile, I-62

I-62

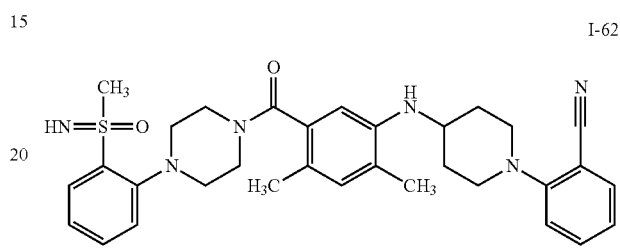

To a suspension of tert-butyl N-({2-[4-(5-{[1-(2-cyanophenyl)piperidin-4-yl]amino}-2,4-dimethylbenzoyl)piperazin-1-yl]phenyl}(methyl)oxo-λ-sulfanylidene)carbamate [Intermediate 13] (440 mg, 0.63 mmol) in DCM (4 mL) was added 4M HCl in dioxane (6 mL). The reaction mixture stirred overnight. The reaction mixture was concentrated in vacuo to afford a white solid. The white solid was then dissolved in DCM (10 mL) and sat. aq. NaHCO₃ (10 mL) and the mixture stirred at rt for 30 min. After 30 min, the organic phase was separated dried (MgSO₄), filtered and reduced in vacuo. The resulting residue was dissolved in acetonitrile/water (3 mL, 4:1) and freeze dried under vacuum to afford the title compound I-62 as off-white solid (340 mg, 90%).

1H NMR (500 MHz, Chloroform-d) δ 8.05 (dd, J=7.8, 1.4 Hz, 1H), 7.62-7.54 (m, 2H), 7.53-7.45 (m, 1H), 7.39-7.32 (m, 2H), 7.06-6.98 (m, 2H), 6.92 (s, 1H), 6.49 (s, 1H), 3.68-3.27 (m, 10H), 3.25-2.72 (m, 7H), 2.32-2.17 (m, 5H), 2.12 (s, 3H), 1.84-1.73 (m, 1H), 1.73-1.62 (m, 1H).

LCMS Method 6—Tr=4.45 min (ES+) (M+H)+ 571

Example 91: 2-(4-{[5-(4-{2-[(R or S)-imino(methyl)oxo-λ⁶-sulfanyl]phenyl}piperazine-1-carbonyl)-2,4-dimethylphenyl]amino}piperidin-1-yl)benzonitrile, I-50

Example 92: 2-(4-{[5-(4-{2-[(S or R)-imino(methyl)oxo-λ⁶-sulfanyl]phenyl}piperazine-1-carbonyl)-2,4-dimethylphenyl]amino}piperidin-1-yl)benzonitrile, I-49

I-49/I-50

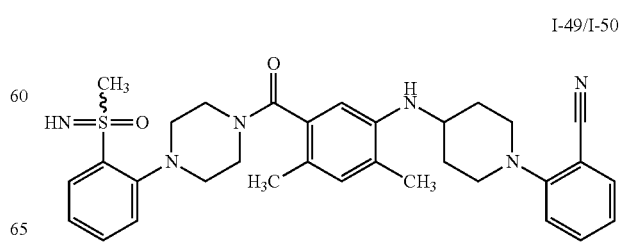

2-(4-{[5-(4-{2-[imino(methyl)oxo-λ⁶-sulfanyl]phenyl}piperazine-1-carbonyl)-2,4-dimethylphenyl]amino}piperidin-1-yl)benzonitrile [Example 90] was dissolved in 55 mg/mL in methanol and was then purified by chiral HPLC. Combined fractions of the first eluting peak 1 at 9.023 min and peak 2 at 11.235 min were then evaporated to near dryness using a rotary evaporator, transferred into final vessels with DCM, which was removed under a stream of nitrogen at 40° C. before being stored in a vacuum oven at 40° C. and 5 mbar for 16 h to afford yellow gums. The yellow gums were dissolved in 4:1 acetonitrile/water (2 ml) and lyophilized, followed by oven drying at 40° C. to obtain the title compounds as off white colored powders (116 mg, 42%).

Separation conditions:
Column Details Lux C4 (21.2 mm×250 mm, 5 um)
Column Temperature Ambient
Flow Rate 21 mL/min
Detector Wavelength 216 nm
Injection Volume 325 uL (18 mg)
Isocratic Conditions MeOH (0.1% v/v NH3)
Arbitrary Assignment of Stereochemistry Peak 1: 2-(4-{[5-(4-{2-[(R or S)-imino(methyl)oxo-λ⁶-sulfanyl]phenyl}piperazine-1-carbonyl)-2,4-dimethylphenyl]amino}piperidin-1-yl)benzonitrile 1H NMR (500 MHz, Chloroform-d) δ 8.05 (dd, J=7.8, 1.5 Hz, 1H), 7.62-7.54 (m, 2H), 7.52-7.47 (m, 1H), 7.39-7.33 (m, 2H), 7.06-6.98 (m, 2H), 6.92 (s, 1H), 6.49 (s, 1H), 3.68-3.23 (m, 10H), 3.24-2.41 (m, 7H), 2.34-2.19 (m, 5H), 2.12 (s, 3H), 1.86-1.73 (m, 1H), 1.73-1.65 (m, 1H).
LCMS Method 7—Tr=3.10 min (ES+) (M+H)⁺ 571
Arbitrary Assignment of Stereochemistry Peak 2: 2-(4-{[5-(4-{2-[(S or R)-imino(methyl)oxo-λ⁶-sulfanyl]phenyl}piperazine-1-carbonyl)-2,4-dimethylphenyl]amino}piperidin-1-yl)benzonitrile 1H NMR (500 MHz, Chloroform-d) δ 8.05 (dd, J=7.9, 1.5 Hz, 1H), 7.64-7.52 (m, 2H), 7.51-7.46 (m, 1H), 7.38-7.31 (m, 2H), 7.06-6.99 (m, 2H), 6.92 (s, 1H), 6.49 (s, 1H), 3.69-3.20 (m, 10H), 3.20-2.31 (m, 7H), 2.29-2.16 (m, 5H), 2.12 (s, 3H), 1.85-1.73 (m, 1H), 1.73-1.66 (m, 1H).
LCMS Method 7—Tr=3.10 min (ES+) (M+H)⁺ 571

Example 93: 2-[4-({5-[3R or S-(hydroxymethyl)-4-phenylpiperazine-1-carbonyl]-2,4-dimethylphenyl}amino)piperidin-1-yl]benzonitrile, I-41

Example 94: 2-[4-({5-[3S or R-(hydroxymethyl)-4-phenylpiperazine-1-carbonyl]-2,4-dimethylphenyl}amino)piperidin-1-yl]benzonitrile, I-40

I-40/I-41

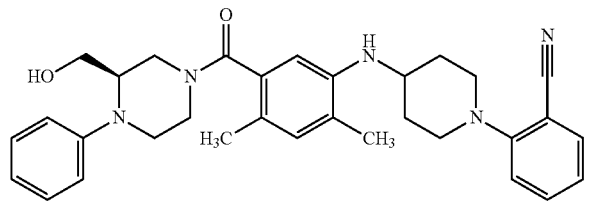

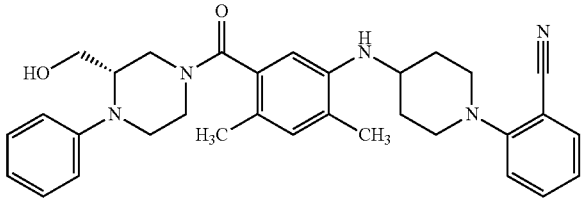

2-[4-({5-[3-(Hydroxymethyl)-4-phenylpiperazine-1-carbonyl]-2,4-dimethylphenyl}amino)piperidin-1-yl]benzonitrile [I-63] was dissolved to 40 mg/mL in methanol and was then purified by SFC. Combined fractions of each of peak 1 at 2.514 min and peak 2 at 3.447 min were then evaporated to near dryness using a rotary evaporator, transferred into final vessels with DCM, which was removed under a stream of nitrogen at 40° C. before being stored in a vacuum oven at 40° C. and 5 mbar for 16 h to afford I-40 and I-41 as clear oils. The oils were lyophilized overnight to give the title compounds as white solids.

Separation Conditions:
Column Details: CHIRALPAK® AS-H (20 mm×250 mm)
Column Temperature: 40° C.
Flow Rate: 50 ml/min
Detector Wavelength: 210 nm
Injection Volume: 200 μl (8 mg)
Isocratic Conditions: 30:70 MeOH:CO₂ (0.1% v/v NH₃)
The Stereochemistry was Arbitrarily Assigned.

2-[4-({5-[3R or S-(hydroxymethyl)-4-phenylpiperazine-1-carbonyl]-2,4-dimethylphenyl}amino)piperidin-1-yl]benzonitrile (53 mg, 24%)

Peak 1 at 2.514 min
¹H NMR (500 MHz, DMSO-d6) δ 7.68 (dd, J=7.7, 1.5 Hz, 1H), 7.61-7.55 (m, 1H), 7.23-7.15 (m, 3H), 7.06 (t, J=7.5 Hz, 1H), 6.92-6.83 (m, 3H), 6.73 (t, J=7.2 Hz, 1H), 6.41 (s, 1H), 4.78-4.49 (m, 2H), 4.49-4.05 (m, 1H), 3.91-3.41 (m, 6H), 3.40-3.32 (m, 3H), 3.30-3.08 (m, 2H), 2.96 (t, J=11.0 Hz, 3H), 2.09 (d, J=2.8 Hz, 3H), 2.07-1.99 (m, 4H), 1.77-1.62 (m, 2H). LCMS Method 7—Tr=3.73 min (ES+) (M+H)+ 524.2

2-[4-({5-[3S or R-(hydroxymethyl)-4-phenylpiperazine-1-carbonyl]-2,4-dimethylphenyl}amino)piperidin-1-yl]benzonitrile (55 mg, 24%)

Peak 2 at 3.447 min
¹H NMR (500 MHz, DMSO-d6) δ 7.68 (dd, J=7.7, 1.5 Hz, 1H), 7.61-7.55 (m, 1H), 7.23-7.14 (m, 3H), 7.06 (t, J=7.5 Hz, 1H), 6.92-6.82 (m, 3H), 6.73 (t, J=7.2 Hz, 1H), 6.41 (s, 1H), 4.79-4.50 (m, 2H), 4.49-4.09 (m, 1H), 3.71 (d, J=127.7 Hz, 6H), 3.41-3.32 (m, 3H), 3.24-2.87 (m, 4H), 2.14-2.00 (m, 8H), 1.76-1.62 (m, 2H). LCMS Method 7—Tr=3.73 min (ES+) (M+H)+ 524.2

Example 95: (4-{2,4-Dimethyl-5-[(1-phenylpyrrolidin-3-yl)amino]benzoyl}-1-phenylpiperazin-2-yl)methanol, I-73

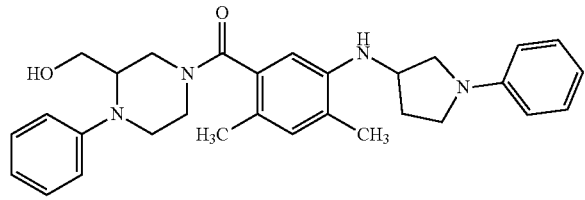

I-73

[4-(5-amino-2,4-dimethylbenzoyl)-1-phenylpiperazin-2-yl]methanol [Intermediate 34] (30 mg, 0.09 mmol) and 1-phenylpyrrolidin-3-one (21 mg, 0.13 mmol) were suspended in DCM (2 ml) and stirred at rt for 1 hr. Sodium triacetoxyborohydride (45 mg, 0.21 mmol) was added and the reaction was stirred for 16 h. Additional Sodium triacetoxyborohydride (45 mg, 0.21 mmol) and glacial acetic acid (1 ml) was added and the reaction stirred for 16 h. The reaction mixture was partitioned between DCM (4 ml) and water (5 ml). The aqueous phase was extracted with DCM (5 ml). The organics were combined and concentrated in vacuo. The resultant residue was purified by preparative HPLC [UV-Directed High pH prep method]. The fractions containing product were combined and concentrated in vacuo to yield the title compound I-73 as a white solid (5 mg, 12%). $^1$H NMR (500 MHz, Chloroform-d) δ 7.31-7.26 (m, 2H), 7.26-7.20 (m, 2H), 7.00-6.83 (m, 4H), 6.72 (t, J=7.2 Hz, 1H), 6.60 (s, 1H), 6.58 (s, 1H), 6.53 (s, 1H), 4.86-4.74 (m, 1H), 4.31-4.02 (m, 2H), 3.73-3.56 (m, 5H), 3.53-2.94 (m, 8H), 2.42-2.32 (m, 1H), 2.30-2.13 (m, 3H), 2.12-2.02 (m, 4H). LCMS Method 7—Tr=3.97 min (ES+) (M+H)+ 485.3

Example 96: 2-(4-{2,4-Dimethyl-5-[(1-phenylazepan-4-yl)amino]benzoyl}piperazin-1-yl)benzonitrile, I-78

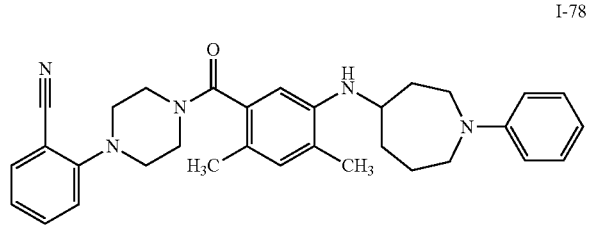 [SMILES: Cc1cc(C)c(C(=O)N2CCN(c3ccccc3C#N)CC2)cc1NC1CCCN(c2ccccc2)CC1]

I-78

The title compound was synthesized from 2-[4-(5-amino-2,4-dimethylbenzoyl)piperazin-1-yl]benzonitrile [Intermediate 38] (40 mg, 0.09 mmol) and 1-phenylazepan-4-one [Intermediate 39] (27 mg, 0.14 mmol) using the method described above for example 95 to afford the title compound I-78 as a white solid (6 mg, 12%). $^1$H NMR (500 MHz, Chloroform-d) δ 7.59 (d, J=7.5 Hz, 1H), 7.51 (s, 1H), 7.25-7.16 (m, 2H), 7.07 (t, J=7.5 Hz, 1H), 7.01 (d, J=7.9 Hz, 1H), 6.86 (s, 1H), 6.71 (d, J=8.2 Hz, 2H), 6.66 (s, 1H), 6.34 (s, 1H), 4.03 (s, 2H), 3.66-3.53 (m, 2H), 3.51-3.45 (m, 4H), 3.44-3.29 (m, 1H), 3.27-3.20 (m, 2H), 3.07 (s, 2H), 2.19 (s, 1H), 2.17 (s, 3H), 1.99-1.57 (m, 9H). LCMS Method 7—Tr=4.32 min (ES+) (M+H)+ 508.4

Example 97: 2-[4-(5-{[1-(4-cyanophenyl)azepan-4-yl]amino}-2,4-dimethylbenzoyl) piperazin-1-yl]benzonitrile, I-80

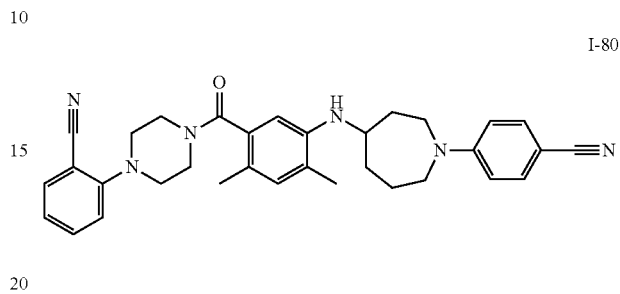

I-80

The title compound was synthesized from 2-[4-(5-amino-2,4-dimethylbenzoyl)piperazin-1-yl]benzonitrile [Intermediate 38] (40 mg, 0.09 mmol) and 1-phenylazepan-4-one [Intermediate 46] (27 mg, 0.14 mmol) using the method described above for example 95 to afford the title compound I-80 as a white solid (16 mg, 32%). $^1$H NMR (500 MHz, Chloroform-d) δ 7.59 (d, J=7.3 Hz, 1H), 7.52 (s, 1H), 7.46 (d, J=8.4 Hz, 2H), 7.07 (t, J=7.5 Hz, 1H), 7.01 (d, J=8.3 Hz, 1H), 6.88 (s, 1H), 6.68 (s, 2H), 6.33 (s, 1H), 4.02 (d, J=38.6 Hz, 2H), 3.70-3.32 (m, 8H), 3.30-3.19 (m, 2H), 3.12-3.04 (m, 2H), 2.28-2.20 (m, 1H), 2.18 (s, 3H), 2.04-1.91 (m, 5H), 1.89-1.75 (m, 2H), 1.68-1.60 (m, 1H). LCMS Method 7—Tr=4.05 min (ES+) (M+H)+ 533.4

Example 98: 2-[4-(5-{[1-(3-cyanophenyl)azepan-4-yl]amino}-2,4-dimethylbenzoyl) piperazin-1-yl]benzonitrile, I-81

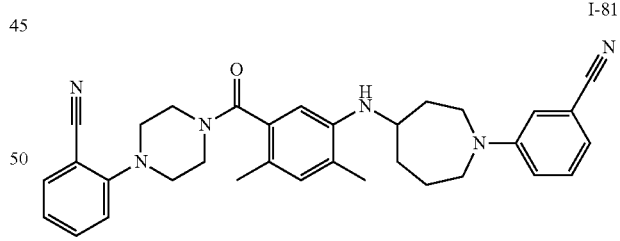

I-81

The title compound was synthesized from 2-[4-(5-amino-2,4-dimethylbenzoyl)piperazin-1-yl]benzonitrile [Intermediate 38] (40 mg, 0.09 mmol) and 1-phenylazepan-4-one [Intermediate 45] (27 mg, 0.14 mmol) using the method described above for example 95 to afford the title compound I-81 as a white solid (4 mg, 8%). $^1$H NMR (500 MHz, Chloroform-d) δ 7.59 (d, J=7.7 Hz, 1H), 7.52 (t, J=7.7 Hz, 1H), 7.28 (s, 1H), 7.25 (s, 1H), 7.07 (t, J=7.5 Hz, 1H), 7.01 (s, 1H), 6.94-6.84 (m, 4H), 6.34 (s, 1H), 4.12-3.94 (m, 2H), 3.65-3.16 (m, 11H), 3.12-3.04 (m, 2H), 2.27-2.20 (m, 1H), 2.18 (s, 3H), 1.99-1.94 (m, 4H), 1.88-1.77 (m, 2H). LCMS Method 7—Tr=4.20 min (ES+) (M+H)+ 533.4

Example 99: 2-[4-({3-[(3R or S)-3-(hydroxymethyl)-4-phenylpiperazine-1-carbonyl]-4-methyl phenyl}amino)piperidin-1-yl]benzonitrile, I-82

Example 100: 2-[4-({3-[(3S or R)-3-(hydroxymethyl)-4-phenylpiperazine-1-carbonyl]-4-methyl phenyl}amino)piperidin-1-yl]benzonitrile, I-83

Example 101: 2-[4-({5-[(3R or S)-3-(hydroxymethyl)-4-phenylpiperazine-1-carbonyl]-2-methylphenyl}amino)piperidin-1-yl]benzonitrile, I-84

Example 102: 2-[4-({5-[(3S or R)-3-(hydroxymethyl)-4-phenylpiperazine-1-carbonyl]-2-methylphenyl}amino)piperidin-1-yl]benzonitrile, I-85

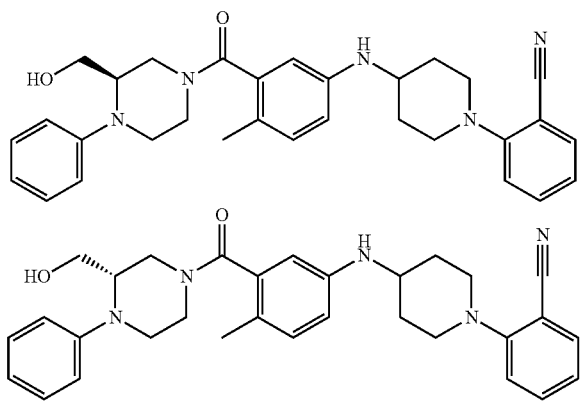

2-[4-({3-[3-(hydroxymethyl)-4-phenylpiperazine-1-carbonyl]-4-methylphenyl}amino)piperidin-1-yl]benzonitrile [Example 58] was dissolved to 38.75 mg/mL in methanol and was then purified by SFC. Combined fractions of the first eluting peak 1 at I-682.22 min and the second eluting peak 2 at 2.93 min were then evaporated to near dryness using a rotary evaporator, transferred into final vessels with DCM, which was removed under a stream of nitrogen at 40° C. before being stored in a vacuum oven at 40° C. and 5 mbar for 16 h to afford the products as white solids. Analysis was performed from concentrated fractions prior to final vessel transfer.

Separation conditions:

Column Details: CHIRALPAK® AS-H (20 mm×250 mm, 5 um)

Column Temperature: 40° C.

Flow Rate: 50 mL/min

BPR: 125 BarG

Detector Wavelength: 210 nm

Injection Volume: 400 uL (15.5 mg)

Isocratic Conditions: 40:60 MeOH:$CO_2$ (0.1% v/v $NH_3$)

The Stereochemistry was Arbitrarily Assigned:

Peak 1—2-[4-({3-[(3R or S)-3-(hydroxymethyl)-4-phenylpiperazine-1-carbonyl]-4-methyl phenyl}amino)piperidin-1-yl]benzonitrile HPLC Method A—Tr=2.594 mins Peak 2—2-[4-({3-[(3S or R)-3-(hydroxymethyl)-4-phenylpiperazine-1-carbonyl]-4-methyl phenyl}amino)piperidin-1-yl]benzonitrile HPLC Method A—Tr=2.596 mins 2-[4-({5-[3-(hydroxymethyl)-4-phenylpiperazine-1-carbonyl]-2-methylphenyl}amino)piperidin-1-yl]benzonitrile [Example 56] was dissolved to 10.3 mg/mL in methanol:DCM (3:1) and was then purified by SFC. Combined fractions of the first eluting peak 1 at 2.87 min and the second eluting peak 2 at 3.63 min were then evaporated to near dryness using a rotary evaporator, transferred into final vessels with DCM, which was removed under a stream of nitrogen at 40° C. before being stored in a vacuum oven at 40° C. and 5 mbar for 16 h to afford the products as a white solid. Analysis was performed from concentrated fractions prior to final vessel transfer.

Separation conditions:

Column Details: CHIRALPAK® AS-H (20 mm×250 mm, 5 um)

Column Temperature: 40° C.

Flow Rate: 50 mL/min

BPR: 125 BarG

Detector Wavelength: 210 nm

Injection Volume: 1500 uL (15.5 mg)

Isocratic Conditions: 40:60 MeOH:$CO_2$ (0.1% v/v $NH_3$)

The Stereochemistry was Arbitrarily Assigned.

Peak 1—2-[4-({5-[(3R or S)-3-(hydroxymethyl)-4-phenylpiperazine-1-carbonyl]-2-methylphenyl}amino)piperidin-1-yl]benzonitrile HPLC Method A—Tr=2.864 mins Peak 2—2-[4-({5-[(3S or R)-3-(hydroxymethyl)-4-phenylpiperazine-1-carbonyl]-2-methylphenyl}amino)piperidin-1-yl]benzonitrile HPLC Method A—Tr=2.865 mins Example 103: 2-[4-({5-[(3R or 3S)-4-(2-Cyanophenyl)-3-(hydroxymethyl)piperazine-1-carbonyl]-2,4-dimethylphenyl}amino)piperidin-1-yl]benzonitrile, I-133

Example 104: 2-[4-({5-[(3S or 3R)-4-(2-cyanophenyl)-3-(hydroxymethyl)piperazine-1-carbonyl]-2,4-dimethylphenyl}amino)piperidin-1-yl]benzonitrile, I-134

I-133/I-134

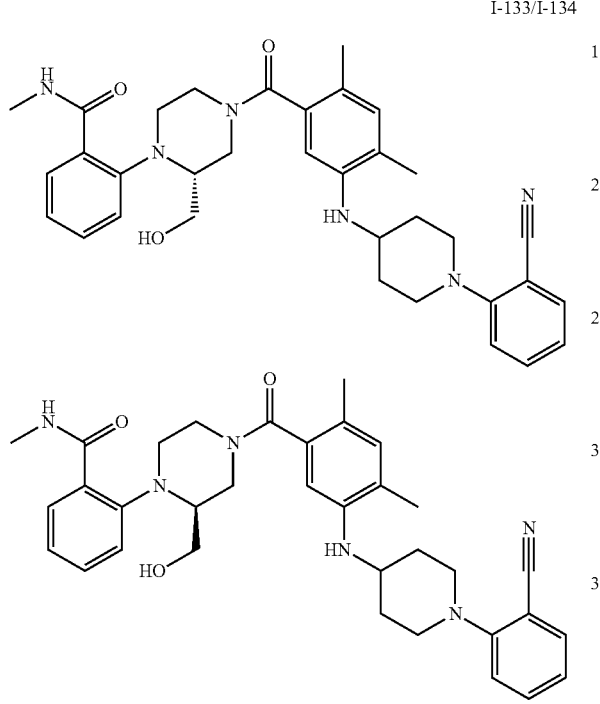

2-[4-(5-{[1-(2-cyanophenyl)piperidin-4-yl]amino}-2,4-dimethylbenzoyl)-2-(hydroxymethyl)piperazin-1-yl]-N-methylbenzamide [Example 60] (11 mg, 0.019 mmol) was dissolved to 35 mg/mL in methanol and was then purified by SFC. The first eluting peak and second eluting peak fractions were then evaporated to near dryness using a rotary evaporator, transferred into final vessels with DCM, which was removed under a stream of nitrogen at 40° C. before being stored in a vacuum oven at 40° C. and 5 mbar for 16 h. Peak 1 afford [Example 103] 2-[4-({5-[(3R or 3S)-4-(2-Cyanophenyl)-3-(hydroxymethyl)piperazine-1-carbonyl]-2,4-dimethylphenyl}amino)piperidin-1-yl]benzonitrile as a solid (3.9 mg). $^1$H NMR (500 MHz, Chloroform-d) δ 8.87-8.32 (m, 1H), 7.99 (s, 0.3H), 7.97-7.82 (m, 1H), 7.57 (dd, J=7.7, 1.3 Hz, 1H), 7.52-7.37 (m, 2H), 7.11-6.97 (m, 2H), 6.97-6.82 (m, 1H), 6.65-6.38 (m, 1H), 4.77-4.37 (m, 1H), 3.75-3.41 (m, 7H), 3.41-3.25 (s, 2H), 3.23-3.08 (m, 1H), 3.08-2.81 (m, 7H), 2.80-2.68 (m, 1H), 2.30-2.08 (m, 9H), 1.83-1.74 (s, 2H).
Chiral LCMS (35% IPA: 65% CO2 with CHIRALPAK® AS-H 25 cm column at 4 ml/min) Tr=7.15 min chiral purity 98% ee
And peak 2 [Example 104]—2-[4-({5-[(3S or 3R)-4-(2-cyanophenyl)-3-(hydroxymethyl)piperazine-1-carbonyl]-2,4-dimethylphenyl}amino)piperidin-1-yl]benzonitrile as solid (5.9 mg)$^1$H NMR (500 MHz, Chloroform-d) δ 8.92-8.43 (m, 1H), 8.00 (s, 1H), 7.97-7.85 (m, 1H), 7.61-7.53 (m, 1H), 7.52-7.42 (m, 2H), 7.25-7.23 (m, 1H), 7.06-6.99 (m, 2H), 6.95-6.90 (m, 1H), 6.65-6.37 (m, 1H), 4.66-4.34 (m, 1H), 3.76-3.40 (m, 7H), 3.40-3.26 (m, 2H), 3.13 (s, 1H), 3.07-2.91 (m, 7H), 2.78-2.72 (m, 1H), 2.38-2.09 (m, 9H), 1.82-1.64 (m, 2H). Chiral LCMS (Lux A1 (4.6 mm×250 mm, 5 um)—35% IPA: 65% CO$_2$ with CHIRALPAK® AS-H 25 cm column at 4 ml/min) Tr=11.60 min chiral purity 100% ee
Separation Conditions:
Column Details: CHIRALPAK® AS-H 25 cm column
Flow Rate: 15 ml/min
Isocratic Conditions: 30% IPA: 70% CO$_2$
The Stereochemistry was Arbitrarily Assigned Example 105: 2-[4-({5-[(3R or 3S)-4-(2-Cyanophenyl)-3-(hydroxymethyl)piperazine-1-carbonyl]-2,4-dimethylphenyl}amino)piperidin-1-yl]benzonitrile, I-77

Example 106: 2-[4-({5-[(3S or 3R)-4-(2-Cyanophenyl)-3-(hydroxymethyl)piperazine-1-carbonyl]-2,4-dimethylphenyl}amino)piperidin-1-yl]benzonitrile, I-79

I-77/I-79

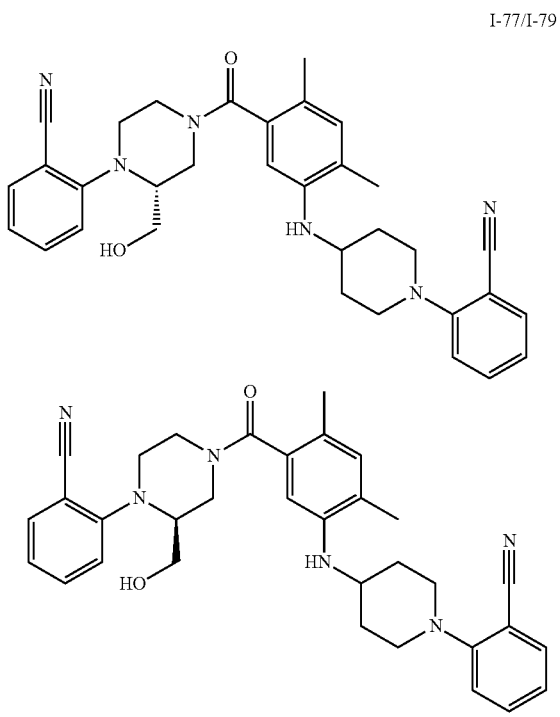

The racemic material was synthesized from tert-Butyl 4-(2-cyanophenyl)-3-(hydroxymethyl)piperazine-1-carboxylate [Intermediate 59] (60 mg, 0.17 mmol) the compound was treated with 4M HCl in dioxane (2 ml) for 2 h. The reaction mixture was reduced to afford 5-{[1-(2-cyanophenyl)piperidin-4-yl]amino}-2,4-dimethylbenzoic acid.
5-{[1-(2-Cyanophenyl)piperidin-4-yl]amino}-2,4-dimethylbenzoic acid from above and 5-{[1-(2-cyanophenyl)piperidin-4-yl]amino}-2,4-dimethylbenzoic acid [Intermediate 1] (27 mg, 0.14 mmol) coupled together using the method described above for example 1 to afford the racemic material (59 mg, 62%).

The racemic material was dissolved to 35 mg/mL in methanol and was then purified by SFC. The first eluting peak and second eluting peak fractions were then evaporated to near dryness using a rotary evaporator, transferred into final vessels with DCM, which was removed under a stream of nitrogen at 40° C. before being stored in a vacuum oven at 40° C. and 5 mbar for 16 h. Peak 1 afforded 2-[4-({5-[(3R or 3S)-4-(2-Cyanophenyl)-3-(hydroxymethyl)piperazine-1-carbonyl]-2,4-dimethylphenyl}amino)piperidin-1-yl]benzonitrile I-77 (15.1 mg)

$^1$H NMR—(500 MHz, Chloroform-d) δ 7.63-7.54 (m, 2H), 7.54-7.29 (m, 3H), 7.18-6.96 (m, 4H), 6.96-6.82 (m, 1H), 6.61-6.41 (m, 1H), 4.72-4.54 (s, 0.7H), 4.47-4.26 (m, 0.3H), 4.08-3.94 (m, 0.7H), 3.85-3.75 (m, 0.7H), 3.70-3.41 (m, 9H), 3.38-3.32 (m, 0.7H), 3.23-3.14 (m, 0.4H), 3.07-2.93 (m, 2.6H), 2.90-2.72 (m, 0.6H), 2.30-2.16 (m, 5H), 1.81-1.67 (m, 2.4H), 1.42-1.23 (m, 2H).

Chiral LCMS (35% IPA: 65% CO2 with CHIRALPAK® AS-H 25 cm column at 4 ml/min) Tr=3.69 min chiral purity 100% ee And peak 2 afforded 2-[4-({5-[(3R or 3S)-4-(2-Cyanophenyl)-3-(hydroxymethyl)piperazine-1-carbonyl]-2,4-dimethylphenyl}amino)piperidin-1-yl]benzonitrile I-79 (16.3 mg)

$^1$H NMR—(500 MHz, Chloroform-d) δ 7.62-7.54 (m, 2H), 7.53-7.28 (m, 3H), 7.18-6.99 (m, 4H), 6.97-6.90 (m, 1H), 6.61-6.41 (m, 1H), 4.71-4.55 (m, 0.7H), 4.47-4.27 (m, 0.3H), 4.09-3.93 (m, 0.7H), 3.85-3.75 (m, 0.7H), 3.70-3.41 (m, 9H), 3.38-3.32 (m, 0.7H), 3.23-3.14 (m, 0.4H), 3.07-2.93 (m, 2.6H), 2.90-2.72 (m, 0.6H), 2.31-2.17 (m, 5H), 1.86-1.67 (m, 2.4H), 1.41-1.26 (m, 2H).

Chiral LCMS (Lux A1 (4.6 mm×250 mm, 5 um)—35% IPA: 65% CO$_2$ with CHIRALPAK® AS-H 25 cm column at 4 ml/min) Tr=5.53 min chiral purity 99% ee Separation Conditions:
Column Details: CHIRALPAK® AS-H 25 cm column
Flow Rate: 15 ml/min
Isocratic Conditions: 30% IPA: 70% CO$_2$
The Stereochemistry was Arbitrarily Assigned Example 107: 2-[4-({5-[(3R or 3S)-3-(hydroxymethyl)-4-(pyridin-2-yl)piperazine-1-carbonyl]-2,4-dimethylphenyl}amino)piperidin-1-yl]benzonitrile, I-48

Example 108: 2-[4-({5-[(3S or 3R)-3-(hydroxymethyl)-4-(pyridin-2-yl)piperazine-1-carbonyl]-2,4-dimethylphenyl}amino)piperidin-1-yl]benzonitrile, I-38

I-38/I-48

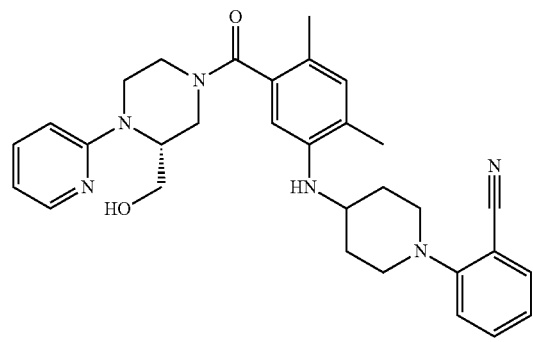

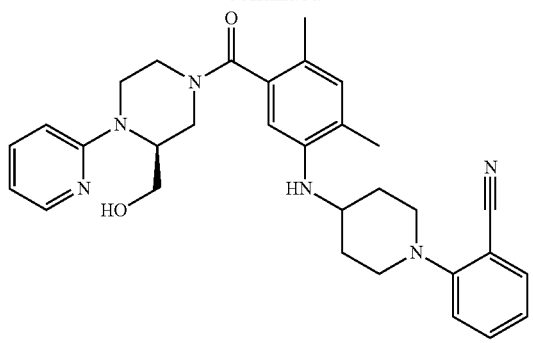

2-[4-({5-[3-(hydroxymethyl)-4-(pyridin-2-yl)piperazine-1-carbonyl]-2,4-dimethylphenyl}amino)piperidin-1-yl]benzonitrile [Example 49] was dissolved to 8 mg/mL in methanol and was then purified by HPLC. Combined fractions of each of first eluting peak at 5.53 mins and second eluting peak at 7.01 min were then evaporated to near dryness using a rotary evaporator, transferred into final vessels with DCM, which was removed under a stream of nitrogen at 40° C. before being stored in a vacuum oven at 40° C. and 5 mbar for 16 h to afford peak 1 I-48 and peak 2 I-38 as white solids. Analysis of I-48 and I-38 were performed with concentrated fractions prior to final vessel transfer.

Separation Conditions:
Column Details: Lux C1 (21.2 mm×250 mm, 5 um)
Column Temperature: Ambient
Flow Rate: 21 mL/min
Detector Wavelength: 220 nm
Injection Volume: 1500 uL (12 mg)
Isocratic Conditions: MeOH (0.1% v/v NH$_3$)
The Stereochemistry was Arbitrarily Assigned:

2-[4-({5-[(3R or 3S)-3-(hydroxymethyl)-4-(pyridin-2-yl)piperazine-1-carbonyl]-2,4-dimethylphenyl}amino)piperidin-1-yl]benzonitrile (4.3 mg)

Peak 1 at 5.53 min $^1$H NMR (500 MHz, Chloroform-d) δ 8.20-8.03 (m, 1H), 7.61-7.42 (m, 3H), 7.09-6.97 (m, 2H), 6.97-6.82 (m, 1H), 6.75-6.59 (m, 2H), 6.59-6.28 (m, 1H), 4.86-4.21 (m, 2H), 4.07-2.71 (m, 14H), 2.30-2.09 (m, 8H), 1.78-1.67 (m, 2H).

2-[4-({5-[(3S or 3R)-3-(hydroxymethyl)-4-(pyridin-2-yl)piperazine-1-carbonyl]-2,4-dimethylphenyl}amino)piperidin-1-yl]benzonitrile (3.0 mg)

Peak 2 at 7.01 min $^1$H NMR (500 MHz, Chloroform-d) δ 8.20-8.04 (m, 1H), 7.63-7.40 (m, 3H), 7.09-6.97 (m, 2H), 6.97-6.85 (m, 1H), 6.74-6.58 (m, 2H), 6.60-6.28 (m, 1H), 4.92-4.18 (m, 2H), 3.98-2.93 (m, 14H), 2.29-2.09 (m, 8H), 1.88-1.66 (m, 2H).

Example 109: 2-[4-(5-{[1-(2-Cyanophenyl)piperidin-4-yl]amino}-2,4-dimethylbenzoyl) piperazin-1-yl]-6-fluorobenzene-1-sulfonamide, I-24

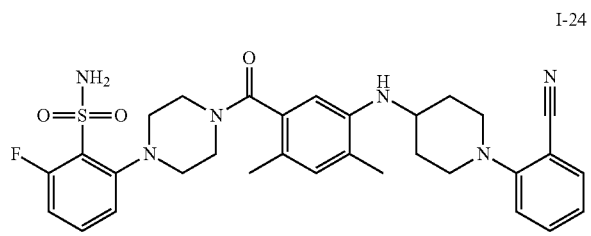 [SMILES: Cc1cc(C)c(C(=O)N2CCN(c3cccc(F)c3S(N)(=O)=O)CC2)cc1NC1CCN(c2ccccc2C#N)CC1]

I-24 tert-Butyl 4-(3-fluoro-2-sulfamoylphenyl)piperazine-1-carboxylate [Intermediate 62](39.5 mg, 0.11 mmol) was dissolved in 1,4-dioxane (0.6 ml) and 4M HCl in 1,4-dioxane and stirred for 2 h. The suspension was carefully blown down with dry nitrogen to yield 2-fluoro-6-(piperazin-1-yl)benzenesulfonamide dihydrochloride as a white crystalline solid.

5-{[1-(2-cyanophenyl)piperidin-4-yl]amino}-2,4-dimethylbenzoic acid [Intermediate 1] (34.9 mg, 0.1 mmol) and DIPEA (69.7 µl, 0.4 mmol) were dissolved in DCM (0.5 ml) under nitrogen atmosphere. The reaction mixture was cooled 0° C. and a solution of thionyl chloride (8.8 µl, 0.12 mmol) in DCM (0.5 ml) was added dropwise to the reaction mixture. The reaction mixture was warmed to rt and stirred for 1 h. The reaction mixture was reduced and redissolved in DCM (1 ml) and the process repeated. The residue was dissolved in DCM (1 ml) and 2-fluoro-6-(piperazin-1-yl)benzenesulfonamide dihydrochloride (0.11 mmol) was added and the reaction stirred for 1 h at rt. The reaction mixture was concentrated in vacuo to yield the crude product as a brown gum. The crude product was purified by preparative HPLC [Generic UV-Directed low pH prep method] to yield the title compound as a pale beige solid (13.3 mg, 22%). $^1$H NMR (500 MHz, Chloroform-d) δ 7.56 (dd, J=7.7, 1.6 Hz, 1H), 7.54-7.45 (m, 2H), 7.10 (d, J=8.1 Hz, 1H), 7.07-6.98 (m, 3H), 6.92 (s, 1H), 6.47 (s, 1H), 5.78 (s, 2H), 3.75-2.46 (m, 12H), 2.31-2.08 (m, 8H), 1.87-1.58 (m, 4H). LCMS Method 7—Tr=3.50 mins, (ES+) (M+H$^+$) 591.

Example 110: 2-{2-[4-(5-{[1-(2-cyanophenyl)piperidin-4-yl]amino}-2,4-dimethylbenzoyl) piperazin-1-yl]-6-fluorobenzenesulfonyl}-1,1,3,3-tetramethylguanidine, I-19

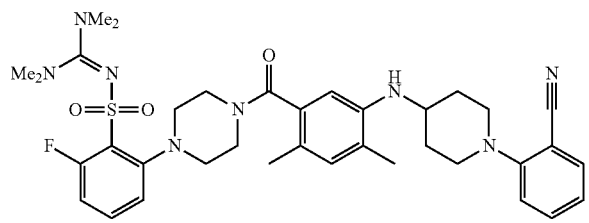

I-19 tert-Butyl 4-(3-fluoro-2-sulfamoylphenyl)piperazine-1-carboxylate [Intermediate 62](39.5 mg, 0.11 mmol) was dissolved in 1,4-dioxane (0.6 ml) and 4M HCl in 1,4-dioxane and stirred for 2 h. The suspension was carefully blown down with dry nitrogen to yield 2-fluoro-6-(piperazin-1-yl)benzenesulfonamide dihydrochloride as a white crystalline solid.

5-{[1-(2-Cyanophenyl)piperidin-4-yl]amino}-2,4-dimethylbenzoic acid [Intermediate 1] (30 mg, 0.086 mmol) in dry DMF (1.5 ml) under nitrogen was treated with 2-fluoro-6-(piperazin-1-yl)benzenesulfonamide hydrochloride (36.2 mg, 0.123 mmol) and HATU (56 mg, 0.147 mmol). DIPEA (85 µL, 0.491 mmol), was then added and the reaction mixture stirred at ambient temperature overnight. HPLC showed mass for the sulphonyl-guanidine product rather than the expected sulphonamide. The reaction was reduced in vacuo to yield pale red residual gum. The residue was dissolved in DCM and filtered, the filtrate was diluted with MBTE and the supernatant discarded. The resultant precipitate was dissolved in DCM and purified by flash column chromatography on silica gel (5 g) eluting with a gradient of 0% to 100% acetone in MBTE to yield the title compound I-19 as a pale pink solid (28.5 mg, 34%). $^1$H NMR (500 MHz, Chloroform-d) δ 7.56 (dd, J=7.7, 1.6 Hz, 1H), 7.52-7.45 (m, 1H), 7.42-7.28 (m, 1H), 7.05 (d, J=8.2 Hz, 1H), 7.00 (t, J=7.5 Hz, 1H), 6.97-6.63 (m, 2H), 6.90 (s, 1H), 6.50 (s, 1H), 3.79-3.14 (m, 8H), 3.13-2.49 (m, 4H), 2.95 (s, 12H), 2.34-1.91 (m, 8H), 1.85-1.62 (m, 3H). LCMS Method 6—Tr=4.79 min, (ES+) (M+H$^+$) 689

Example 111: 2-[4-({5-[4-(5-Fluoropyridin-2-yl)-3-oxopiperazine-1-carbonyl]-2,4-dimethylphenyl}amino)piperidin-1-yl]benzonitrile, I-72

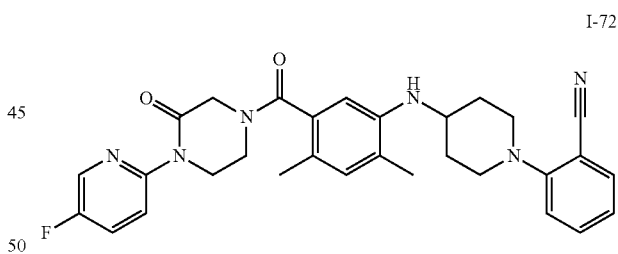

I-72

The title compound was synthesized from 5-{[1-(2-Cyanophenyl)piperidin-4-yl]amino}-2,4-dimethylbenzoic acid [Intermediate 1] (26 mg, 0.075 mmol) and tert-Butyl 4-(5-fluoropyridin-2-yl)-3-oxopiperazine-1-carboxylate [Intermediate 63] (29 mg, 0.1 mmol) using the method described above for example 109 to afford the title compound I-72 as a beige solid (7.8 mg, 20%). 1H NMR (500 MHz, Chloroform-d) δ 8.33-8.19 (m, 1H), 8.09-7.91 (m, 1H), 7.56 (dd, J=7.6, 1.5 Hz, 1H), 7.52-7.40 (m, 2H), 7.05-6.98 (m, 2H), 6.95 (d, J=7.6 Hz, 1H), 6.62-6.44 (m, 1H), 4.90-4.36 (m, 1H), 4.34-3.89 (m, 4H), 3.70-3.41 (m, 4H), 3.02-2.89 (m, 2H), 2.27-2.11 (m, 8H), 1.75 (s, 1H), 1.74 (s, 2H). LCMS Method 7—Tr=3.59 mins, (ES+) (M+H$^+$) 527.

Example 112: 2-[4-({5-[4-(2-Fluorophenyl)-3-(hydroxymethyl)piperazine-1-carbonyl]-2,4-dimethylphenyl}amino)piperidin-1-yl]benzonitrile, I-74

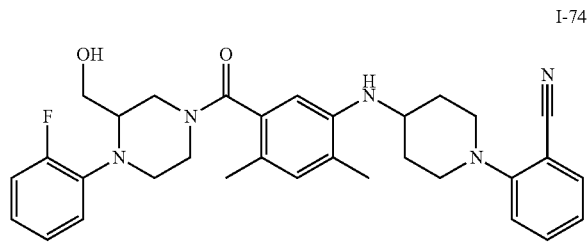 [SMILES: Cc1cc(C)c(C(=O)N2CCN(c3ccccc3F)C(CO)C2)cc1NC1CCN(c2ccccc2C#N)CC1]

The title compound was synthesized from 5-{[1-(2-Cyanophenyl)piperidin-4-yl]amino}-2,4-dimethylbenzoic acid [Intermediate 1] and tert-Butyl 4-(2-fluorophenyl)-3-(hydroxymethyl)piperazine-1-carboxylate [Intermediate 64] using the method described above for example 109 with the exception of the compound being purified by [Generic UV-Directed high pH prep method] which afford the title compound I-74 as a beige solid (40 mg, 75%). $^1$H NMR VT (250 MHz, DMSO-d6) δ 7.63 (dd, J=7.7, 1.5 Hz, 1H), 7.57 (ddd, J=9.0, 7.5, 1.6 Hz, 1H), 7.27-6.93 (m, 6H), 6.88 (s, 1H), 6.47 (s, 1H), 4.26 (d, J=7.9 Hz, 2H), 3.80-3.33 (m, 10H), 3.27-3.05 (m, 3H), 2.11 (d, J=3.5 Hz, 6H), 2.07 (s, 2H), 1.84-1.60 (m, 2H). LCMS Method 7—Tr=3.82 mins, (ES+) (M+H+) 542

Example 113: 2-[4-({5-[4-(3-Fluorophenyl)-3-(hydroxymethyl)piperazine-1-carbonyl]-2,4-dimethylphenyl}amino)piperidin-1-yl]benzonitrile, I-75

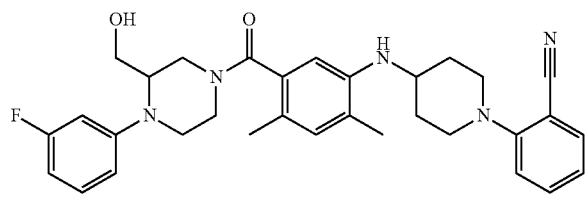

The title compound was synthesized from 5-{[1-(2-Cyanophenyl)piperidin-4-yl]amino}-2,4-dimethylbenzoic acid [Intermediate 1] and tert-Butyl 4-(3-fluorophenyl)-3-(hydroxymethyl)piperazine-1-carboxylate [Intermediate 65] using the method described above for example 112 to afford the title compound I-75 as a white solid (45.1 mg, 83%). $^1$H NMR VT (250 MHz, DMSO-d6) δ 7.63 (dd, J=7.7, 1.6 Hz, 1H), 7.56 (ddd, J=9.0, 7.4, 1.7 Hz, 1H), 7.27-7.11 (m, 2H), 7.04 (td, J=7.5, 1.0 Hz, 1H), 6.88 (s, 1H), 6.77-6.59 (m, 2H), 6.54-6.39 (m, 2H), 4.99-3.05 (m, 16H), 2.19-1.94 (m, 8H), 1.82-1.61 (m, 2H). LCMS Method 7—Tr=3.85 mins, (ES+) (M+H$^+$) 542.

Example 114: 2-[4-({5-[4-(4-fluorophenyl)-3-(hydroxymethyl)piperazine-1-carbonyl]-2,4-dimethylphenyl}amino)piperidin-1-yl]benzonitrile, I-76

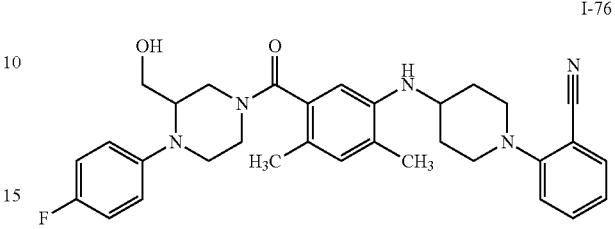

The title compound was synthesized from 5-{[1-(2-Cyanophenyl)piperidin-4-yl]amino}-2,4-dimethylbenzoic acid [Intermediate 1] and tert-Butyl 4-(4-fluorophenyl)-3-(hydroxymethyl)piperazine-1-carboxylate [Intermediate 66] using the method described above for example 112 to afford the title compound I-76 as a white solid (43.8 mg, 81%). $^1$H NMR VT (250 MHz, DMSO-d6) δ 7.69-7.50 (m, 2H), 7.17 (d, J=8.0 Hz, 1H), 7.11-6.85 (m, 6H), 6.45 (s, 1H), 4.42-4.19 (m, 2H), 3.89-3.19 (m, 11H), 3.07 (s, 2H), 2.14-2.03 (m, 8H), 1.81-1.62 (m, 2H). LCMS Method 7—Tr=3.76 mins (ES+) (M+H+) 542.

Example 115: 2-[4-({3-[3-(Aminomethyl)-4-phenylpiperazine-1-carbonyl]-2,4,6-trimethylphenyl}amino)piperidin-1-yl]benzonitrile; bis(formic Acid) Salt, I-135

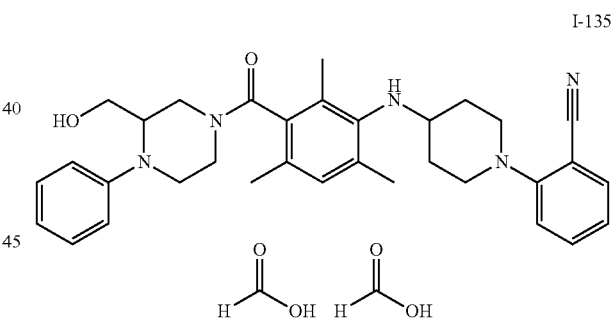

In a pressure tube, a stirred solution of 2-{4-[(3-{3-[(1,3-dioxo-2,3-dihydro-1H-isoindol-2-yl)methyl]-4-phenylpiperazine-1-carbonyl}-2,4,6-trimethylphenyl)amino]piperidin-1-yl}benzonitrile [Intermediate 117] (141 mg, 0.21 mmol) in EtOH (5 ml) was treated with hydrazine hydrate (1:1) (44 µl, 0.9 mmol). The tube was sealed and heated at 90° C. for 3 hours. The reaction mixture was concentrated in vacuo. The crude product was purified by preparative HPLC [Generic UV-Directed low pH prep method] to yield the title compound I-135 as a yellow solid (38 mg, 27%). Atropoisomerism observed. $^1$H NMR (250 MHz, DMSO-d6) δ 8.26 (s, 1H), 7.68 (d, J=7.6 Hz, 1H), 7.58 (t, J=7.9 Hz, 1H), 7.28-7.11 (m, 3H), 7.06 (t, J=7.5 Hz, 1H), 7.01-6.82 (m, 3H), 6.77 (t, J=6.9 Hz, 1H), 4.62-3.89 (m, 3H), 3.38 (s, 3H), 3.18 (s, 3H), 3.05-2.59 (m, 6H), 2.25 (s, 3H), 2.21-2.07 (m, 3H), 2.01 (d, J=6.8 Hz, 3H), 1.87 (s, 2H), 1.70 (d, J=10.8 Hz, 2H). LCMS Method 5—Tr=2.23, 2.34, 2.45, 2.60 min (ES+) (M+H$^+$) 537.3

Example 116: 2-[4-({3-[(3S)-4-(3,4-Difluorophenyl)-3-(hydroxymethyl)-5-oxopiperazine-1-carbonyl]-2,4,6-trimethylphenyl}amino)piperidin-1-yl]benzonitrile, I-136

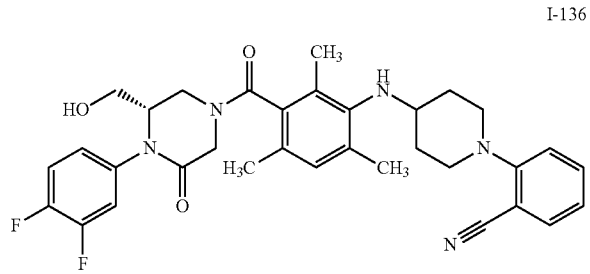 [SMILES: Cc1cc(C)c(C(=O)N2CC(=O)N(c3ccc(F)c(F)c3)[C@H](CO)C2)c(C)c1NC1CCN(c2ccccc2C#N)CC1]

I-136

To a solution of 3-{[1-(2-cyanophenyl)piperidin-4-yl]amino}-2,4,6-trimethylbenzoic acid hydrochloride [Intermediate 111] (50 mg, 0.13 mmol) and HATU (52 mg, 0.14 mmol) in DMF (3 ml) was added DiPEA (87 µl, 0.5 mmol). The reaction mixture stirred at ambient temperature for 30 mins. (6S)-1-(3,4-difluorophenyl)-6-(hydroxymethyl)piperazin-2-one (31 mg, 0.13 mmol) [Intermediate 128] was added and the reaction mixture was heat at 50° C. overnight. The crude reaction mixture was purified by preparative HPLC [UV-Directed Low pH prep method]. The fractions containing product were combined and concentrated in vacuo to afford the title compound I-136 as a white solid (23 mg, 31%). Atropisomerism observed. $^1$H NMR (500 MHz, DMSO-d6) δ 7.71-7.65 (m, 1H), 7.61-7.45 (m, 3H), 7.22 (t, J=8.9 Hz, 1H), 7.17-7.10 (m, 1H), 7.10-7.02 (m, 1H), 6.95-6.83 (m, 1H), 5.08-4.70 (m, 1H), 4.64-4.38 (m, 1H), 4.21-3.92 (m, 1H), 3.91-3.68 (m, 3H), 3.67-3.37 (m, 5H), 2.94 (s, 1H), 2.86-2.70 (m, 2H), 2.30-2.21 (m, 3H), 2.19-2.04 (m, 6H), 1.96-1.79 (m, 2H), 1.77-1.60 (m, 2H). LCMS Method 5—Tr=3.6, 3.10 min (ES+) (M+H$^+$) 589

Example 117: 2-[4-({3-[(3R)-3-(Aminomethyl)-4-phenylpiperazine-1-carbonyl]-2,4,6-trimethylphenyl}amino)piperidin-1-yl]benzonitrile, I-137

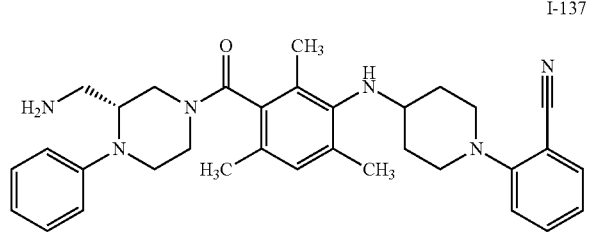 [SMILES: Cc1cc(C)c(C(=O)N2CCN(c3ccccc3)[C@H](CN)C2)c(C)c1NC1CCN(c2ccccc2C#N)CC1]

I-137

In a pressure tube, a stirred solution of 2-[4-({3-[(3S)-3-[(1,3-dioxo-2,3-dihydro-1H-isoindol-2-yl)methyl]-4-phenylpiperazine-1-carbonyl]-2,4,6-trimethylphenyl}amino)piperidin-1-yl]benzonitrile [Intermediate 115] (90%, 210 mg, 0.28 mmol) in EtOH (8 ml) was treated with hydrazine hydrate (1:1) (59 µl, 1.2 mmol). The tube was sealed and stirred at 90° C. for 3 hours. The reaction mixture was concentrated in vacuo. The residue was dissolved in EtOAc (20 ml) and washed with 1M aq. NaOH (20 ml). The aqueous phase was extracted with EtOAc (2×20 ml). The combined organics were dried over Na$_2$SO$_4$, filtered and concentrated in vacuo. The crude product was dissolved in the minimum volume of (1:1) MeOH/DCM and loaded onto an SCX-2 cartridge (5 g). The cartridge was sequentially washed with MeOH (10 ml), DCM, (10 ml), MeOH (10 ml), DCM (10 ml) and MeOH (10 ml). The product was eluted with 7M NH$_3$ in MeOH (30 ml). The resulting fractions were concentrated in vacuo to yield the title compound I-137 as a cream solid (114 mg, 74%). Atropisomerism observed. $^1$H NMR (500 MHz, DMSO-d6) δ 7.67 (dt, J=7.6, 2.3 Hz, 1H), 7.60-7.51 (m, 1H), 7.19 (t, J=7.8 Hz, 2H), 7.16-7.11 (m, 1H), 7.06 (t, J=7.5 Hz, 1H), 6.95-6.82 (m, 3H), 6.72 (q, J=7.0 Hz, 1H), 4.75-3.98 (m, 1H), 3.90-3.38 (m, 5H), 3.30-3.02 (m, 4H), 3.01-2.68 (m, 4H), 2.67-2.54 (m, 1H), 2.29-2.21 (m, 3H), 2.19-2.08 (m, 3H), 2.07-1.98 (m, 3H), 1.96-1.60 (m, 5H), 1.51 (s, 1H). LCMS Method 5—Tr=2.23, 2.35, 2.46, 2.61 min (ES+) (M+H$^+$) 537.3

Example 118: 5-Fluoro-2-[4-[3-[(3S)-3-(hydroxymethyl)-4-pyridazin-3-yl-piperazine-1-carbonyl]-2,4,6-trimethyl-anilino]-1-piperidyl]benzonitrile, I-141

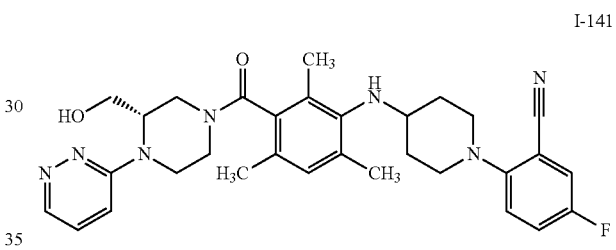

I-141

[(2S)-1-pyridazin-3-ylpiperazin-2-yl]MeOH [Intermediate 82] (73 mg, 0.38 mmol) and DiPEA (178 µl, 1.02 mmol) were suspended in DCM (1 ml) and MeCN (1.5 ml) with stirring. 3-{[1-(2-cyano-4-fluorophenyl)piperidin-4-yl]amino}-2,4,6-trimethylbenzoyl chloride hydrochloride [Intermediate 93] (149 mg, 0.34 mmol) was dissolved in DCM (2.0 ml) then the solution was slowly added to the reaction mixture. The reaction was stirred at ambient temperature for 4 hours. The reaction was partitioned between DCM (2 ml) and water (3 ml) then the organics were separated and concentrated in vacuo. The residue obtained was purified via flash column chromatography using a gradient of 0% to 100% EtOAc in heptane followed by a gradient of 0% to 100% MeOH in EtOAc. The fractions containing product were combined and concentrated in vacuo. The resultant residue was purified by preparative HPLC [UV-Directed High pH prep method]. The fractions containing product were combined and reduced in vacuo. The resultant residue purified further by preparative HPLC [UV-Directed Low pH prep method]. The fractions containing product were combined and reduced in vacuo to yield the title compound I-141 as a white powdery solid (28.9 mg, 15%). Atropisomerism observed. $^1$H NMR (500 MHz, DMSO-d6) δ 8.53 (dd, J=7.9, 4.4 Hz, 1H), 7.69 (dd, J=8.4, 3.1 Hz, 1H), 7.47 (t, J=8.8 Hz, 1H), 7.40-7.34 (m, 1H), 7.19 (dq, J=9.8, 5.8, 5.1 Hz, 2H), 6.90-6.82 (m, 1H), 4.80 (d, J=98.3 Hz, 1H), 4.63-4.42 (m, 1H), 4.23 (d, J=13.1 Hz, 2H), 3.80-3.65 (m, 1H), 3.57 (s, 1H), 3.50-3.35 (m, 4H), 3.21 (d, J=10.7 Hz, 1H), 3.15-3.01 (m, 1H), 2.82 (d, J=43.9 Hz, 1H), 2.46 (s, 1H), 2.23 (d, J=3.8 Hz, 3H), 2.19-2.09 (m, 3H), 1.98 (dd, J=18.1, 12.1 Hz, 3H), 1.86 (s, 2H), 1.68 (s, 2H). LCMS Method 4—Tr=3.14, 3.22, 3.25, 3.30 min (ES+) (M+H⁺) 558.2. LCMS Method 5—Tr=2.19, 2.24, 2.28, 2.35 min (ES+) (M+H⁺) 558.2.

Example 119: [(3S)-4-(5-Fluoro-2-pyridyl)-3-(hydroxymethyl)piperazin-1-yl]-[3-[[1-(5-fluoro-2-pyridyl)-4-piperidyl]amino]-2,4,6-trimethyl-phenyl]methanone, I-146

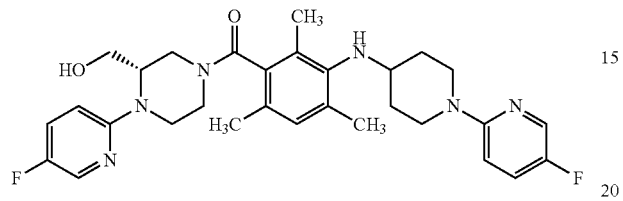

I-146

[(2S)-1-(5-fluoro-2-pyridyl)piperazin-2-yl]MeOH (16 mg, 0.08 mmol) [Intermediate 124] and DiPEA (38 µl, 0.22 mmol) were dissolved in DCM (1 ml). 3-[[1-(5-Fluoro-2-pyridyl)-4-piperidyl]amino]-2,4,6-trimethylbenzoyl chloride hydrochloride [Intermediate 92] (30 mg, 0.07 mmol) was added and the reaction was stirred at ambient temperature for 18 hours. The reaction was partitioned between DCM (2 ml) and sat. aq. NaHCO₃ (2 ml), the organics were separated and concentrated in vacuo. The resultant residue was purified via flash column chromatography using a gradient of 0% to 100% EtOAc in heptane followed by a gradient of 0% to 100% MeOH in EtOAc. The fractions containing product were combined and concentrated in vacuo to afford the title compound I-146 as a pale yellow glassy solid (18.3 mg, 46%). Atropisomerism observed.

¹H NMR (500 MHz, DMSO-d6) δ 8.08-8.03 (m, 2H), 7.47 (ddt, J=20.7, 8.4, 4.4 Hz, 2H), 6.86 (dd, J=9.3, 3.1 Hz, 1H), 6.80 (td, J=10.1, 9.4, 3.8 Hz, 2H), 4.86-4.53 (m, 2H), 4.30 (d, J=28.0 Hz, 1H), 4.18 (d, J=12.5 Hz, 2H), 4.03 (d, J=4.6 Hz, 1H), 3.96 (d, J=10.4 Hz, 1H), 3.65-3.55 (m, 1H), 3.50 (d, J=33.5 Hz, 1H), 3.46-3.33 (m, 2H), 3.21 (dd, J=29.2, 11.7 Hz, 2H), 2.96 (d, J=9.9 Hz, 1H), 2.84-2.71 (m, 2H), 2.19 (d, J=5.3 Hz, 3H), 2.14-2.08 (m, 3H), 1.96 (d, J=14.9 Hz, 3H), 1.76 (d, J=12.7 Hz, 2H), 1.43 (d, J=12.1 Hz, 2H). LCMS Method 5—Tr=2.58, 2.72, 2.88, 2.96 min (ES+) (M+H⁺) 551.2.

Example 120: [(2S)-4-(3-{[1-(5-Fluoropyridin-2-yl)piperidin-4-yl]amino}-2,4,6-trimethylbenzoyl)-1-(pyridin-2-yl)piperazin-2-yl]methanol, I-147

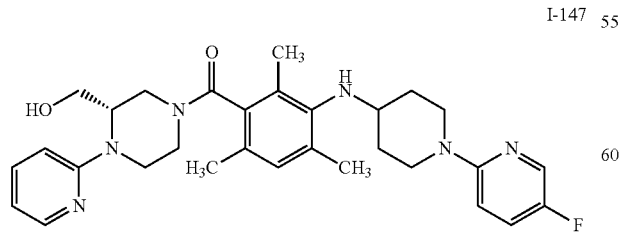

I-147

Prepared analogously to [Example 119] from 3-{[1-(5-fluoropyridin-2-yl)piperidin-4-yl]amino}-2,4,6-trimethyl-benzoyl chloride hydrochloride [Intermediate 92] and [(2S)-1-(pyridin-2-yl)piperazin-2-yl]methanol [Intermediate 122] to yield the title compound I-147 as a white solid (13 mg, 23%). Atropisomerism observed. ¹H NMR (500 MHz, Chloroform-d) δ 8.15-8.08 (m, 1H), 8.04 (t, J=2.6 Hz, 1H), 7.51 (td, J=16.0, 8.7 Hz, 1H), 7.25-7.20 (m, 1H), 6.92-6.84 (m, 1H), 6.71-6.59 (m, 3H), 4.77 (dd, J=13.6, 7.9 Hz, 1H), 4.66 (s, 1H), 4.17 (d, J=9.0 Hz, 2H), 3.95-3.77 (m, 3H), 3.73-3.56 (m, 1H), 3.55-3.45 (m, 1H), 3.44-3.34 (m, 2H), 3.30-3.04 (m, 3H), 2.81 (q, J=14.1, 13.6 Hz, 2H), 2.29-2.20 (m, 6H), 2.14-2.08 (m, 3H), 2.05-1.93 (m, 2H), 1.50-1.36 (m, 2H). LCMS Method 5—Tr=1.69, 1.78, 1.82, 1.90 min (ES+) (M+H⁺) 533.

Example 121: [(3S)-4-(5-Fluoro-2-pyridyl)-3-(hydroxymethyl)piperazin-1-yl]-[2,4,6-trimethyl-3-[(1-pyrazin-2-yl-4-piperidyl)amino]phenyl]methanone, I-148

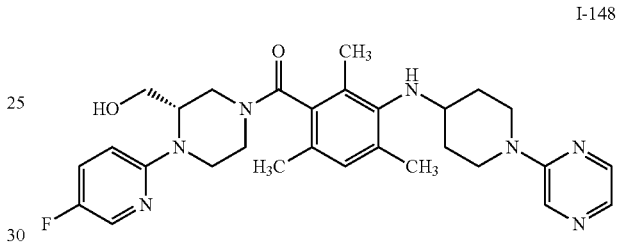

I-148

Prepared analogously to [Example 119] from 2,4,6-trimethyl-3-{[1-(pyrazin-2-yl)piperidin-4-yl]amino}benzoyl chloride hydrochloride [Intermediate 91] (30 mg, 0.08 mmol) and [(2S)-1-(5-fluoro-2-pyridyl)piperazin-2-yl]MeOH (17.63 mg, 0.08 mmol) [Intermediate 124] to yield the title compound I-148 as a pale yellow glassy solid (17.3 mg, 42%). Atropisomerism observed. ¹H NMR (500 MHz, DMSO-d6) δ 8.31 (d, J=7.5 Hz, 1H), 8.06 (dd, J=7.9, 3.4 Hz, 2H), 7.77 (dd, J=2.5, 1.4 Hz, 1H), 7.55-7.48 (m, 1H), 6.88-6.78 (m, 2H), 4.87-4.53 (m, 2H), 4.33 (d, J=12.6 Hz, 2H), 4.18-3.92 (m, 2H), 3.68-3.46 (m, 2H), 3.41 (d, J=38.0 Hz, 2H), 3.26-3.15 (m, 2H), 3.01 (d, J=35.3 Hz, 2H), 2.85 (d, J=30.2 Hz, 2H), 2.20 (d, J=5.4 Hz, 3H), 2.15-2.09 (m, 3H), 1.97 (d, J=14.7 Hz, 3H), 1.80 (d, J=13.1 Hz, 2H), 1.45 (d, J=11.9 Hz, 2H). LCMS Method 5—Tr=2.26, 2.43, 2.54, 2.64 min (ES+) (M+H⁺) 534.2.

Example 122: [(2S)-1-(5-Fluoropyridin-2-yl)-4-(2,4,6-trimethyl-3-{[1-(pyrimidin-2-yl) piperidin-4-yl]amino}benzoyl)piperazin-2-yl]methanol, I-151

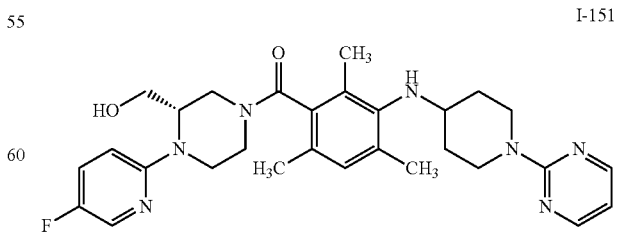

I-151

2,4,6-Trimethyl-3-{[1-(pyrimidin-2-yl)piperidin-4-yl]amino}benzoic acid [Intermediate 113] (38 mg, 0.11 mmol) was dissolved in toluene (3 ml) under nitrogen atmosphere.

SOCl$_2$ (33 µl, 0.45 mmol) was added followed by DMF (1 drop). The reaction mixture was heated for at 70° C. for 1 hour. The reaction mixture was concentrated and the resultant residue was azeotroped with DCM (2×) to yield the acid chloride intermediate. The acid chloride intermediate was dissolved in DCM (3 ml). DiPEA (58 µl, 0.33 mmol) and [(2S)-1-(5-fluoropyridin-2-yl)piperazin-2-yl]methanol [Intermediate 124] (26 mg, 0.12 mmol) were added and the reaction mixture was stirred under an atmosphere of nitrogen at ambient temperature overnight. The reaction mixture was partitioned between sat. aq. NaHCO$_3$ (5 ml) and DCM. The aqueous phase was extracted with DCM (2×3 ml). The organics were combined and concentrated to yield the crude product. The crude product was purified by preparative HPLC [UV-Directed High pH prep method]. The product containing fractions were combined and reduced in vacuo to yield the title compound I-151 as a brown solid (5 mg, 7% yield). Atropisomerism observed. $^1$H NMR (250 MHz, Chloroform-d) δ 8.38-8.20 (m, 2H), 8.00 (t, J=3.4 Hz, 1H), 7.36-7.20 (m, 1H), 6.88 (d, J=6.9 Hz, 1H), 6.73-6.54 (m, 1H), 6.47 (t, J=4.7 Hz, 1H), 4.78 (t, J=10.6 Hz, 3H), 4.64-4.41 (m, 1H), 4.40-4.18 (m, 1H), 4.01-3.71 (m, 3H), 3.64-3.36 (m, 3H), 3.29-3.04 (m, 3H), 2.96-2.79 (m, 2H), 2.29-2.21 (m, 6H), 2.14-2.08 (m, 3H), 2.04-1.95 (m, 2H), 1.46-1.30 (m, 2H). LCMS Method 5—Tr=2.30, 2.46, 2.60, 2.69 min (ES+) (M+H$^+$) 534.

Example 123: (2S)-1-Phenyl-4-(2,4,6-trimethyl-3-{[1-(pyridazin-3-yl)piperidin-4-yl]amino}benzoyl)piperazine-2-carboxamide, I-164

I-164

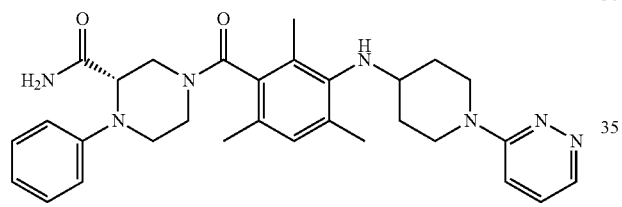

Prepared analogously to [Example 119] 2,4,6-trimethyl-3-{[1-(pyridazin-3-yl)piperidin-4-yl]amino}benzoyl chloride hydrochloride [Intermediate 105] (50 mg, 0.126 mmol) and (2S)-1-Phenylpiperazine-2-carboxamide [Intermediate 73] (27 mg, 0.129 mmol) to yield the title compound I-164 as a white solid (23 mg, 33%). Atropisomerism observed. $^1$H NMR (500 MHz, DMSO-d6) δ 8.53-8.45 (m, 1H), 7.59-7.41 (m, 1H), 7.37-7.29 (m, 1H), 7.28-7.11 (m, 4H), 6.86-6.69 (m, 4H), 4.80-3.90 (m, 4H), 3.76-3.35 (m, 5H), 3.28-2.80 (m, 4H), 2.25-2.18 (m, 3H), 2.08-1.99 (m, 6H), 1.88-1.75 (m, 2H), 1.52-1.38 (m, 2H). LCMS Method 5—Tr=1.55, 1.75, 1.85, 1.94 min (ES+) (M+H+) 528.3.

Example 124: [(3S)-3-(Hydroxymethyl)-4-phenyl-piperazin-1-yl]-[2,4,6-trimethyl-3-[(1-pyrimidin-4-yl-4-piperidyl)amino]phenyl]methanone, I-166

I-166

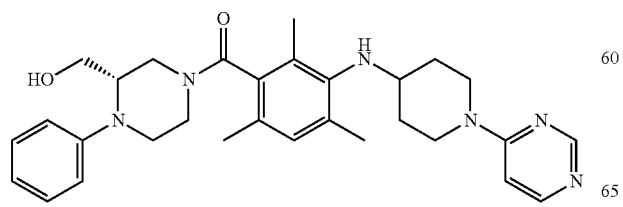

[(3 S)-3-(hydroxymethyl)-4-phenyl-piperazin-1-yl]-[2,4,6-trimethyl-3-(4-piperidylamino)phenyl]methanone [Intermediate 109] (25 mg, 0.06 mmol), 4-chloropyrimidine hydrochloride (10 mg, 0.07 mmol) and Cs$_2$CO$_3$ (19 mg, 0.06 mmol) were suspended in toluene (0.5 ml) in a pressure tube. The reaction was sealed and heated at 100° C. for 16 hours. The reaction mixture was concentrated in vacuo, and the resulting oil was partitioned between water (1 ml) and EtOAc (1 ml). The organic layer was separated, washed with brine (1 ml), dried over Na$_2$SO$_4$ and concentrated in vacuo to yield the crude product as an oil. The crude product was purified via preparative HPLC [UV-directed High pH prep method]. The product containing fractions were combined and concentrated in vacuo to give the title compound I-166 as a white solid (6 mg, 20%). Atropisomerism observed. $^1$H NMR (500 MHz, Chloroform-d) δ 8.60-8.57 (m, 1H), 8.21-8.15 (m, 1H), 7.32-7.27 (m, 2H), 6.99-6.85 (m, 4H), 6.54-6.49 (m, 1H), 4.78-3.99 (m, 4H), 3.78-3.55 (m, 3H), 3.54-3.35 (m, 3H), 3.32-3.22 (m, 2H), 3.21-3.02 (m, 2H), 2.93-2.81 (m, 2H), 2.29-2.22 (m, 6H), 2.15 (s, 3H), 2.03 (d, J=24.4 Hz, 2H), 1.37 (s, 2H). LCMS Method 5—Tr 1.71, 1.94, 1.9, 2.06 min (ES$^+$) (M+H$^+$) 515.

Example 125: Synthesis of 3-(4-(3-(1-(2-cyanophenyl)piperidin-4-ylamino)-2,4,6 trimethylbenzoyl)piperazin-1-yl)pyrazine-2-sulfonamide, I-167

I-167

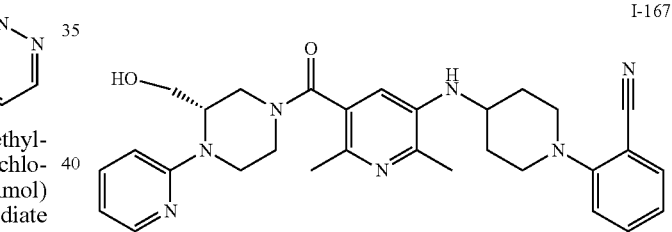

Synthetic Scheme:

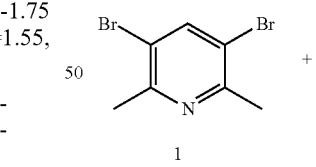

1

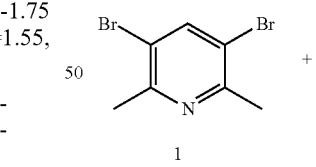

+

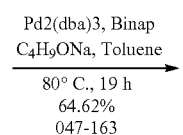

Pd2(dba)3, Binap
C$_4$H$_9$ONa, Toluene
⟶
80° C., 19 h
64.62%
047-163

2

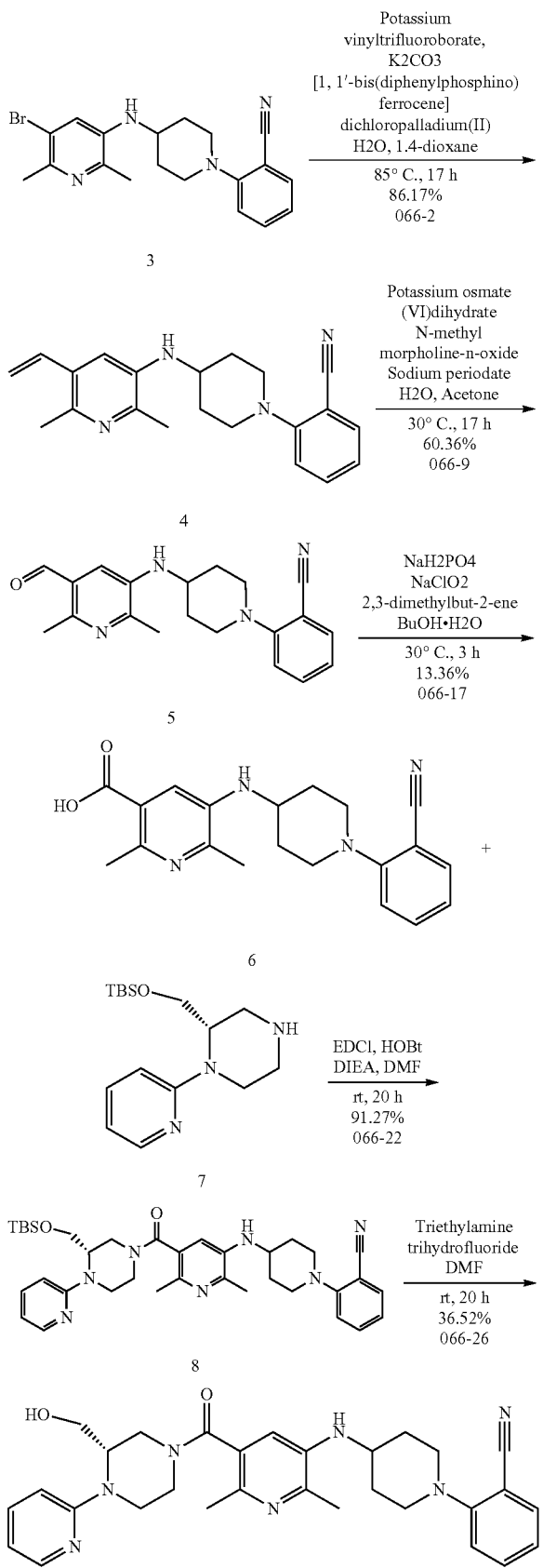

Procedures and Characterization:

Step 1: 2-[4-[(5-bromo-2,6-dimethyl-3-pyridyl)methyl]-1-piperidyl]benzonitrile

To a solution of 3,5-dibromo-2,6-dimethyl-pyridine (2.40 g, 9.06 mmol), 2-(4-amino-1-piperidyl)benzonitrile (1.22 g, 6.04 mmol), $C_4H_9ONa$ (1.16 g, 12.08 mmol), and Binap (752.07 mg, 1.21 mmol) in toluene (60.00 mL) was added $Pd_2(dba)_3$ (553.01 mg, 603.91 umol) under $N_2(g)$, and the mixture was stirred at 85° C. for 18 h. The mixture was filtrated, concentrated and purified by flash column with eluting with PE: EA from 95:5 to 60:40 to get 2-[4-[(5-bromo-2,6-dimethyl-3-pyridyl)methyl]-1-piperidyl]benzonitrile (1.50 g, 3.90 mmol, 64.62% yield) as light yellow solid. MS (EI+, m/z): 385.1 [M+H]+. $^1$H NMR (500 MHz, $CDCl_3$) δ 7.58 (dd, J=7.7, 1.4 Hz, 1H), 7.52-7.46 (m, 1H), 7.07-6.99 (m, 3H), 3.58 (d, J=12.6 Hz, 2H), 3.39 (t, J=8.4 Hz, 1H), 3.05-2.96 (m, 2H), 2.52 (s, 3H), 2.33 (s, 3H), 2.23 (d, J=11.9 Hz, 2H), 1.75 (d, J=10.7 Hz, 2H).

Step 2: 2-[4-[(2,6-dimethyl-5-vinyl-3-pyridyl)amino]-1-piperidyl]benzonitrile

A mixture of 2-[4-[(5-bromo-2,6-dimethyl-3-pyridyl)amino]-1-piperidyl]benzonitrile (1.48 g, 3.84 mmol), Potassium vinyltrifluoroborate (771.55 mg, 5.76 mmol), $K_2CO_3$ (1.06 g, 7.68 mmol), [1,1′-bis(diphenylphosphino)ferrocene]dichloropalladium(II) (280.97 mg, 384.00 umol) in $H_2O$ (22.00 mL) and 1,4-dioxane (90.00 mL) was stirred at 80° C. for 17 h under $N_2(g)$. The mixture was filtered, the filtrate was washed with water and extracted with EtOAc (50 mL*2). The org. layer was dried by $Na_2SO_4$, concentrated and purified by SGC to give 2-[4-[(2,6-dimethyl-5-vinyl-3-pyridyl)amino]-1-piperidyl]benzonitrile (1.10 g, 3.31 mmol, 86.17% yield) as yellow liquid. MS (EI+, m/z): 333.3[M+H]+. $^1$H NMR (500 MHz, $CDCl_3$) δ 7.57 (dd, J=7.7, 1.5 Hz, 1H), 7.53-7.41 (m, 1H), 7.12-6.93 (m, 3H), 6.88 (dd, J=17.4, 10.9 Hz, 1H), 5.59 (dd, J=17.4, 1.0 Hz, 1H), 5.32 (dd, J=11.0, 1.0 Hz, 1H), 3.55 (dd, J=31.9, 8.4 Hz, 3H), 3.10-2.93 (m, 2H), 2.45 (s, 3H), 2.38 (s, 3H), 2.25 (d, J=11.7 Hz, 2H), 1.84-1.71 (m, 2H).

Step 3: 2-[4-[(5-formyl-2,6-dimethyl-3-pyridyl)amino]-1-piperidyl]benzonitrile

A mixture of 2-[4-[(2,6-dimethyl-5-vinyl-3-pyridyl)amino]-1-piperidyl]benzonitrile (1.07 g, 3.22 mmol), Potassium osmate (VI) dihydrate (59.22 mg, 161.00 umol), N-methyl morpholine-n-oxide (1.13 g, 9.66 mmol) in Acetone (25.00 mL) was added Sodium periodate (1.38 g, 6.44 mmol) in $H_2O$ (25.00 mL), and the mixture was stirred at 30° C. for 17 h. LC-MS showed the desired product. The mixture was filtered with celite, concentrated and purified by flash column eluting with DCM/CH3OH from 99:1 to 9:1 to get product 2-[4-[(5-formyl-2,6-dimethyl-3-pyridyl)amino]-1-piperidyl]benzonitrile (650.00 mg, 1.94 mmol, 60.36% yield) as yellow solid. MS (ESI+, m/z): 335.2 [M+H]+. $^1$H NMR (500 MHz, $CDCl_3$) δ 10.27 (s, 1H), 7.51 (dd, J=7.6, 1.5 Hz, 1H), 7.43 (dt, J=15.9, 4.4 Hz, 1H), 7.21 (s, 1H), 6.97 (dd, J=15.2, 7.9 Hz, 2H), 3.58-3.37 (m, 3H), 2.94 (t, J=10.7 Hz, 2H), 2.68 (s, 3H), 2.38 (s, 3H), 2.18 (d, J=12.4 Hz, 2H), 1.69 (td, J=13.4, 3.6 Hz, 2H).

Step 4: 5-[[1-(2-cyanophenyl)-4-piperidyl]amino]-2,6-dimethyl-pyridine-3-carboxylic Acid To a solution of 2-[4-[(5-formyl-2,6-dimethyl-3-pyridyl)amino]-1-piperidyl]benzonitrile (200.00 mg, 598.07 umol)

in BuOH (20.00 mL) and H₂O (10.00 mL) was added NaH₂PO₄ (358.78 mg, 2.99 mmol), NaClO₂ (108.18 mg, 1.20 mmol), 2,3-dimethylbut-2-ene (402.67 mg, 4.78 mmol). the mixture was stirred at room temperature for 3 h. After reaction, H₂O (30 mL) and EtOAc (30 mL) was added and separated the organic phase, then the aqueous was further extracted with EtOAc (2*30 mL) and combine the organic phase, washed with brine (30 mL), dried with anhydrous Na₂SO₄, filtered and purified by flash column to get 5-[[1-(2-cyanophenyl)-4-piperidyl]amino]-2,6-dimethyl-pyridine-3-carboxylic acid (28.00 mg, 79.91 umol, 13.36% yield). MS (EI⁺, m/z): 351.0 [M+H]⁺. ¹H NMR (500 MHz, MeOD-d₄) δ 7.63 (s, 1H), 7.51 (d, J=7.6 Hz, 1H), 7.47 (t, J=7.9 Hz, 1H), 7.10 (d, J=8.3 Hz, 1H), 6.97 (t, J=7.5 Hz, 1H), 3.50 (d, J=10.2 Hz, 3H), 2.92 (t, J=11.6 Hz, 2H), 2.58 (s, 3H), 2.40 (s, 3H), 2.09 (d, J=14.2 Hz, 2H), 1.74 (d, J=8.9 Hz, 2H).

Step 5: (S)-2-(4-(5-(3-((tert-butyldimethylsilyloxy)methyl)-4-(pyridin-2-yl)piperazine-1-carbonyl)-2,6-dimethylpyridin-3-ylamino)piperidin-1-yl)benzonitrile At r.t, a solution of 5-[[1-(2-cyanophenyl)-4-piperidyl]amino]-2,6-dimethyl-pyridine-3-carboxylic acid (48.00 mg, 136.98 umol), HOBT (27.76 mg, 205.47 umol), EDCI (39.39 mg, 205.47 umol), DIPEA (44.26 mg, 342.45 umol, 59.81 uL) in DMF (5.00 mL) was stirred for 1 h, then added tert-butyl-dimethyl-[[(2S)-1-(2-pyridyl)piperazin-2-yl]methoxy]silane (42.12 mg, 136.98 umol) and continued to stir for 20 h. LC-MS showed well. the mixture was added water (20 mL) and extracted with EtOAc (30 mL*2), combined organic phase and concentrated to get (S)-2-(4-(5-(3-(((tert-butyldimethylsilyloxy)methyl)-4-(pyridin-2-yl)piperazine-1-carbonyl)-2,6-dimethylpyridin-3-ylamino)piperidin-1-yl)benzonitrile (80.00 mg, 125.02 umol, 91.27% yield). MS (EI⁺, m/z): 640.3 [M+H]⁺.

Step 6: (S)-2-(4-(5-(3-(hydroxymethyl)-4-(pyridin-2-yl)piperazine-1-carbonyl)-2,6-dimethylpyridin-3-ylamino)piperidin-1-yl)benzonitrile To a solution of (S)-2-(4-(5-(3-(((tert-butyldimethylsilyloxy)methyl)-4-(pyridin-2-yl)piperazine-1-carbonyl)-2,6-dimethylpyridin-3-ylamino)piperidin-1-yl)benzonitrile (80.00 mg, 125.02 umol) was added Triethylamine trihydrofluoride (80.62 mg, 500.08 umol) and stirred for 18 h at r.t. LC-MS showed it worked well, the was purified via preparative HPLC to get (S)-2-(4-(5-(3-(hydroxymethyl)-4-(pyridin-2-yl)piperazine-1-carbonyl)-2,6-dimethylpyridin-3-ylamino)piperidin-1-yl)benzonitrile (24.00 mg, 45.66 umol, 36.52% yield). MS (EI⁺, m/z): 526.3 [M+H]⁺. ¹H NMR (500 MHz, MeOD-d₄) δ 7.99 (s, 1H), 7.56-7.37 (m, 3H), 7.08 (d, J=8.3 Hz, 1H), 6.95 (t, J=7.5 Hz, 1H), 6.86 (d, J=39.8 Hz, 1H), 6.72 (t, J=9.4 Hz, 1H), 6.57 (dd, J=6.9, 5.1 Hz, 1H), 4.40 (dd, J=142.3, 72.3 Hz, 2H), 3.97 (d, J=6.6 Hz, 1H), 3.68 (d, J=12.8 Hz, 1H), 3.61-3.22 (m, 8H), 2.90 (t, J=10.7 Hz, 2H), 2.27 (t, J=24.5 Hz, 6H), 2.11-1.99 (m, 2H), 1.70 (d, J=11.3 Hz, 2H)

Example 126: Synthesis of (S)-2-(4-(3-(3-(hydroxymethyl)-4-(3,4,5-trifluorophenyl)piperazine-1-carbonyl)-2,4,6-trimethylphenylamino)piperidin-1-yl)benzonitrile, I-168

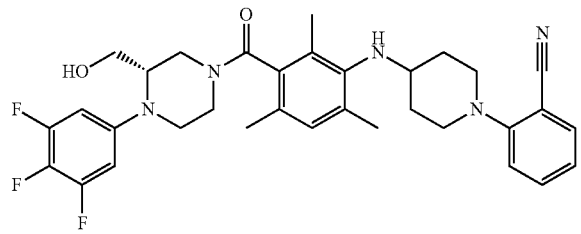

I-168

Synthetic Scheme:

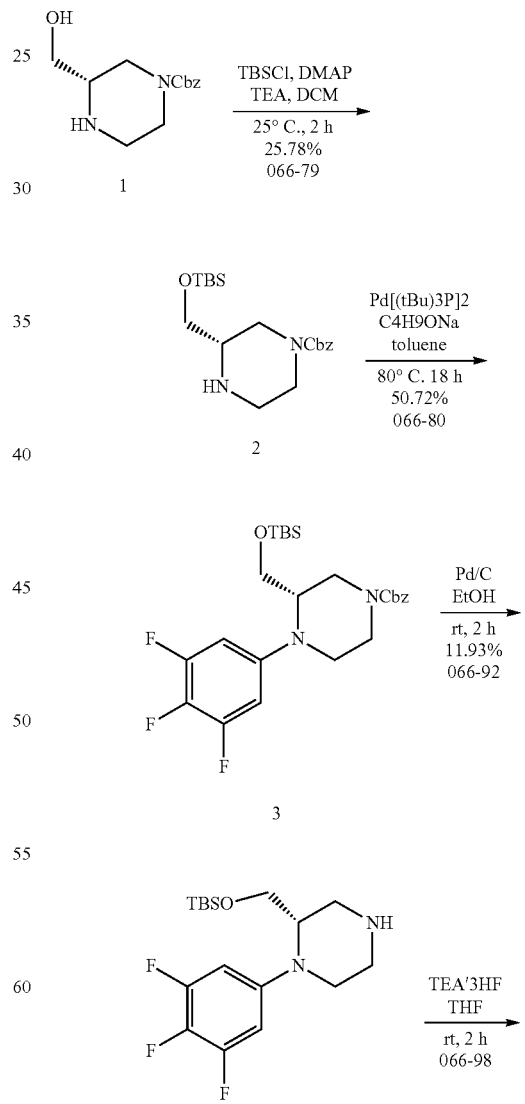

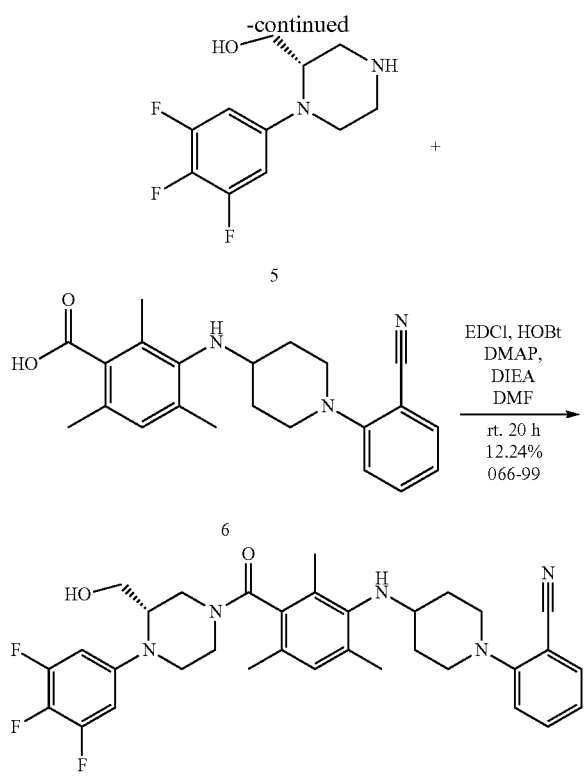

Procedures and Characterization:

Step 1: benzyl (3S)-3-[[tert-butyl(dimethyl)silyl]oxymethyl]piperazine-1-carboxylate A mixture of benzyl (3S)-3-(hydroxymethyl)piperazine-1-carboxylate (1.00 g, 4.00 mmol), TBSCl (658.04 mg, 7.99 mmol), DMAP (97.62 mg, 799.07 umol), and TEA (2.77 g, 19.98 mmol, 3.82 uL, 73% purity) in DCM (10.00 mL) was stirred at 25° C. for 2 h. The mixture was washed with 2N NaOH(aq) (40 mL*2) and water (30 mL), dried with Na$_2$SO$_4$, concentrated and purified by SGC to get benzyl (3S)-3-[[tert-butyl(dimethyl)silyl]oxymethyl]piperazine-1-carboxylate (376.00 mg, 1.03 mmol, 25.78% yield). MS (EI$^+$, m/z): 365.4 [M+H]$^+$. Step 2: benzyl (3S)-3-[[tert-butyl(dimethyl)silyl]oxymethyl]-4-(3,4,5-trifluorophenyl)piperazine-1-carboxylate:

To a solution of 5-bromo-1,2,3-trifluoro-benzene (240.00 mg, 1.14 mmol), benzyl (3S)-3-[[tert-butyl(dimethyl)silyl]oxymethyl]piperazine-1-carboxylate (377.81 mg, 1.04 mmol), Sodium tert-butoxide (199.19 mg, 2.07 mmol) in toluene (8.00 mL) was added Pd[(tBu)3P]2 (79.44 mg, 155.45 umol) under N$_2$(g), then the mixture was stirred at 80° C. for 18 h. The mixture was filtered with celite, concentrated and purified by SGC (PE:EA=7:3) to get benzyl (3S)-3-[[tert-butyl(dimethyl)silyl]oxymethyl]-4-(3,4,5-trifluorophenyl)piperazine-1-carboxylate (260.00 mg, 525.66 umol, 50.72% yield). MS (EI$^+$, m/z): 495.3 [M+H]$^+$.

Step 3: (S)-2-((tert-butyldimethylsilyloxy)methyl)-1-(3,4,5-trifluorophenyl)piperazine To a mixture of benzyl 3-[[tert-butyl(dimethyl)silyl]oxymethyl]-4-(3,4,5-trifluorophenyl)piperazine-1-carboxylate (230 mg, 465.00 umol) in EtOH (10 mL) was added Pd/C (14.85 mg, 139.50 umol), and the mixture was kept stirring at 32° C. for 2 h under H$_2$ atmosphere. LC-MS showed well, the crude was filtered and purified by SGC to get (S)-2-((tert-butyldimethylsilyloxy)methyl)-1-(3,4,5-trifluorophenyl)piperazine (20 mg, 55.48 umol, 11.93% yield). MS (ESI$^+$, m/z): 361.3 [M+H]$^+$.

Step 4: (S)-(1-(3,4,5-trifluorophenyl)piperazin-2-yl)methanol

To a solution of (S)-2-((tert-butyldimethylsilyloxy)methyl)-1-(3,4,5-trifluorophenyl)piperazine (100 mg, 277.40 umol) in THF (2.00 mL) was added 3TEA·HF (223.60 mg, 1.39 mmol) and kept stirred at 25° C. for 2 h. LC-MS showed the deisred product, adjusted the pH about 8 and used to the next step without further purification. MS (EI$^+$, m/z): 247.3 [M+H]$^+$.

Step 5: 2-[4-[3-[(3S)-3-(hydroxymethyl)-4-(3,4,5 trifluorophenyl)piperazine-1-carbonyl]-2,4,6-trimethyl-anilino]-1-piperidyl]benzonitrile The mixture of 3-[[1-(2-cyanophenyl)-4-piperidyl]amino]-2,4,6-trimethyl-benzoic acid (100.37 mg, 276.16 umol), EDCI (52.94 mg, 276.16 umol), HOBt (93.29 mg, 690.40 umol). DMAP (3.37 mg, 27.62 umol) and DIPEA (178.46 mg, 1.38 mmol, 240.51 uL) in DMF (3 mL) was stirred for 1 h, then added [(2S)-1-(3,4,5-trifluorophenyl)piperazin-2-yl]methanol (68.00 mg, 276.16 umol) and kept stirring overnight. the crude was purified via preparative HPLC to get 2-[4-[3-[(3S)-3-(hydroxymethyl)-4-(3,4,5 trifluorophenyl)piperazine-1-carbonyl]-2,4,6-trimethyl-anilino]-1-piperidyl]benzonitrile (20 mg, 33.80 umol, 12.24% yield) as a white solid. MS (EI$^+$, m/z): 592.1 [M+H]$^+$. $^1$H NMR (400 MHz, MeOD-d$_4$) δ 7.61 (d, J=7.7 Hz, 1H), 7.56 (t, J=8.0 Hz, 1H), 7.17 (d, J=8.3 Hz, 1H), 7.07 (t, J=7.6 Hz, 1H), 6.96 (t, J=7.7 Hz, 1H), 6.70 (d, J=11.3 Hz, 2H), 4.84-4.66 (m, 2H), 3.57 (dt, J=67.9, 45.7 Hz, 8H), 3.12 (d, J=28.8 Hz, 3H), 2.85 (s, 2H), 2.38-2.09 (m, 9H), 2.00 (s, 2H), 1.76 (s, 2H).

Example 127: 2-(4-(5-(((3R,4S)-1-(2-cyanophenyl)-3-methylpiperidin-4-yl)amino)-2,4-dimethylbenzoyl)piperazin-1-yl)benzenesulfonamide, I-169

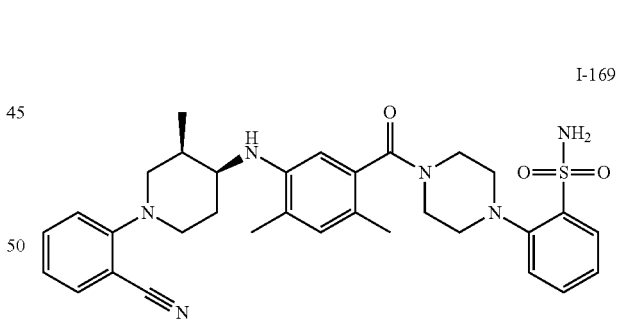

Synthetic Scheme:

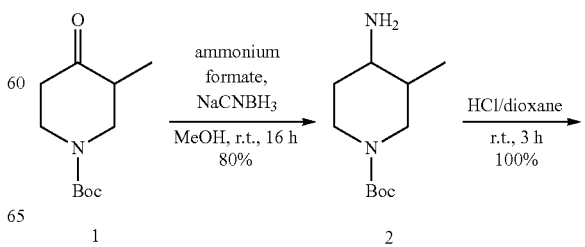

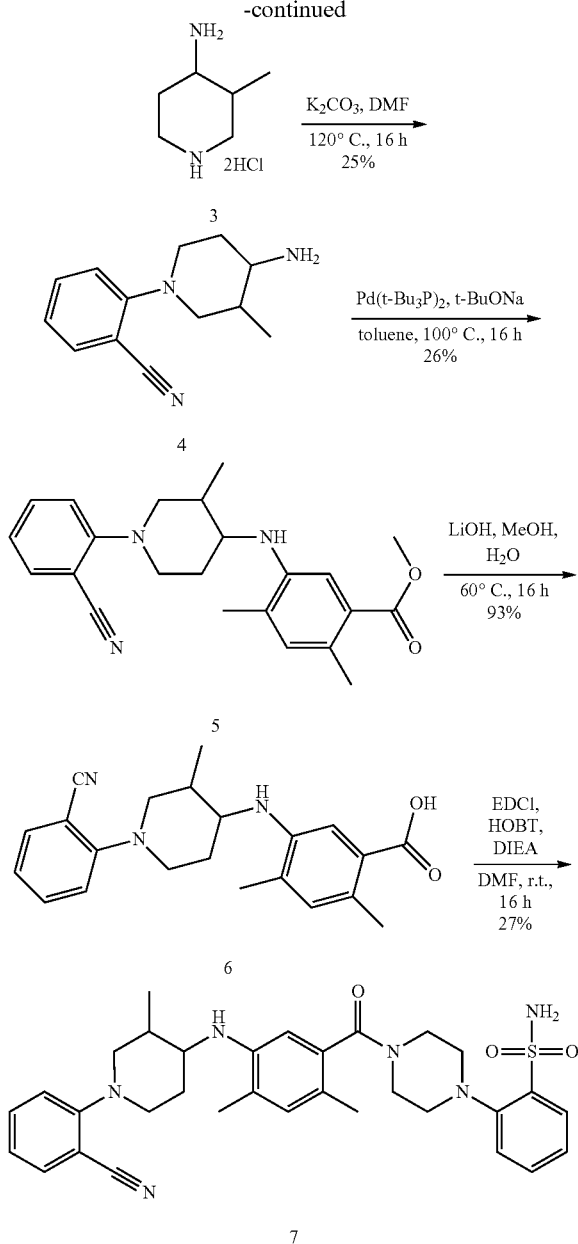

Procedures and Characterization:

Step 1: tert-butyl 4-amino-3-methylpiperidine-1-carboxylate

To a solution of tert-butyl 3-methyl-4-oxo-piperidine-1-carboxylate (10.00 g, 46.89 mmol) ammonium formate (17.74 g, 281.34 mmol) and molecular sieves (2.00 g) in MeOH (100.00 mL) was added NaCNBH$_3$ (3.54 g, 56.27 mmol). The mixture was stirred at 30° C. for 16 hour. It was purified by SGC to afford tert-butyl 4-amino-3-methyl-piperidine-1-carboxylate (8.12 g, 37.89 mmol, 80%) as product. ESI-MS (EI$^+$, m/z): 159.3 [M−56+H]$^+$.

Step 2: 3-methylpiperidin-4-amine Hydrochloride Salt tert-butyl 4-amino-3-methyl-piperidine-1-carboxylate (12.18 g, 56.83 mmol) was dissolved in HCl (4M,dioxane) (60.00 mL). It was stirred at 30° C. for 3 hour, concentrated to afford 3-methylpiperidin-4-amine (11.04 g, 58.98 mmol, 100%, 2HCl) as a white solid. ESI-MS (EI$^+$, m/z): 115.2 [M+H]$^+$.

Step 3: 2-(4-amino-3-methylpiperidin-1-yl)benzonitrile

To a solution of 2-fluorobenzonitrile (10.65 g, 87.92 mmol) and 3-methylpiperidin-4-amine (10.04 g, 87.92 mmol) in DMF (100.00 mL) was added Potassium carbonate (46.18 g, 334.10 mmol), it was stirred at 120° C. for 16 hour. It was diluted with water and extracted with DCM, the organic layer was washed with water, dried over anhydrous Na$_2$SO$_4$, concentrated and purified by SGC to afford 2-(4-amino-3-methyl-1-piperidyl)benzonitrile (4.80 g, 22.30 mmol, 25%) as a yellow oil. ESI-MS (EI$^+$, m/z): 216.3 [M+H]$^+$.

Step 4: methyl 5-((1-(2-cyanophenyl)-3-methylpiperidin-4-yl)amino)-2,4-dimethylbenzoate 2-(4-amino-3-methyl-1-piperidyl)benzonitrile (350.00 mg, 1.63 mmol), methyl 5-bromo-2,4-dimethyl-benzoate (515.13 mg, 2.12 mmol), Pd(t-Bu$_3$P)$_2$ (166.60 mg, 326.00 umol), t-BuONa (447.92 mg, 4.89 mmol) were dissolved in toluene (10.00 mL) and the mixture was stirred at 100° C. for 16 hour. The mixture was cooled to rt and quenched with 1M HCl, extracted with EA, the organic layer was concentrated to purified via preparative HPLC (acid) to give methyl 5-[[1-(2-cyanophenyl)-3-methyl-4-piperidyl]amino]-2,4-dimethyl-benzoate (160.00 mg, 423.86 umol, 26%) as a red oil. ESI-MS (EI$^+$, m/z): 378.3 [M+H]$^+$.

Step 5: 5-((1-(2-cyanophenyl)-3-methylpiperidin-4-yl)amino)-2,4-dimethylbenzoic Acid Methyl 5-[[(3R,4S)-1-(2-cyanophenyl)-3-methyl-4-piperidyl]amino]-2,4-dimethyl-benzoate (100.00 mg, 264.91 umol) dissolved in MeOH (10.00 mL) and H$_2$O (3.00 mL) was added LiOH.H$_2$O (88.93 mg, 2.12 mmol). The mixture was stirred at 60° C. for 16 hour. The mixture was concentrated and acidified with 1M HCl and extracted with EA. The combined organic layer were washed with brine, dried (Na$_2$SO$_4$), filtered and concentrated to give crude 5-[[(3R,4S)-1-(2-cyanophenyl)-3-methyl-4-piperidyl]amino]-2,4-dimethyl-benzoic acid (90.00 mg, 247.63 umol, 93%) as a yellow oil. ESI-MS (EI$^+$, m/z): 364.3 [M+H]$^+$.

Step 6: 2-(4-(5-(((3R,4S)-1-(2-cyanophenyl)-3-methylpiperidin-4-yl)amino)-2,4-dimethylbenzoyl)piperazin-1-yl)benzenesulfonamide 5-[[(3R,4S)-1-(2-cyanophenyl)-3-methyl-4-piperidyl]amino]-2,4-dimethyl-benzoic acid (90.00 mg, 247.63 umol) and 2-piperazin-1-ylbenzenesulfonamide (68.78 mg, 247.63 umol, HCl) was dissolved in DMF (5.00 mL). Then EDCI (73.17 mg, 371.45 umol), HOBT (40.15 mg, 297.16 umol), DIEA (96.01 mg, 742.89 umol, 129.74 uL) were added to the above solution. The mixture was stirred at 40° C. for 16 hour. The mixture was purified via preparative HPLC to give 2-[4-[5-[[(3R,4S)-1-(2-cyanophenyl)-3-methyl-4-piperidyl]amino]-2,4-dimethyl-benzoyl]piperazin-1-yl]benzenesulfonamide (40.20 mg, 68.51 umol, 27%) as a white solid. ESI-MS (EI$^+$, m/z): 587.3 [M+H]$^+$. $^1$H NMR (500 MHz, CDCl$_3$) δ 8.04-8.02 (dd, J=8.0, 1.5 Hz, 1H), 7.62-7.55 (m, 2H), 7.50-7.47 (m, 1H), 7.37-7.33 (m, 2H), 7.04-6.99 (m, 2H), 6.91 (s, 1H), 6.45 (s, 1H), 5.54 (s, 2H), 3.60-3.50 (m, 4H), 3.12-2.92 (m, 8H), 2.68-2.64 (t, J=11.5 Hz, 4H), 2.29 (m, 1H), 2.20 (s, 3H), 2.12 (s, 3H), 1.99-1.97 (m, 1H), 1.56 (m, 1H), 1.10-1.05 (dd, J=23, 6.0 Hz, 3H).

Example 128: 2-(4-(5-(((3R,4R)-1-(2-cyanophenyl)-3-methylpiperidin-4-yl)amino)-2,4-dimethylbenzoyl)piperazin-1-yl)benzenesulfonamide, I-170

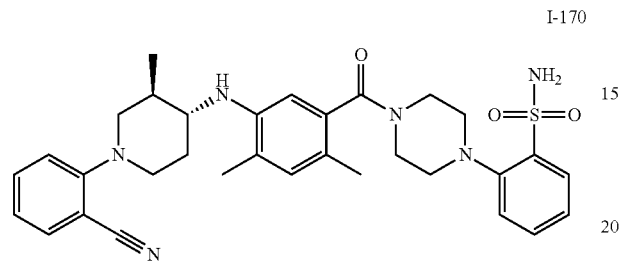

I-170

5-[[(3R,4R)-1-(2-cyanophenyl)-3-methyl-4-piperidyl]amino]-2,4-dimethyl-benzoic acid (60.00 mg, 165.08 umol) and 2-piperazin-1-ylbenzenesulfonamide (45.86 mg, 165.08 umol, HCl) was dissolved in DMF (5.00 mL). Then EDCI (48.78 mg, 247.62 umol), HOBT (26.77 mg, 198.10 umol), DIEA (64.00 mg, 495.24 umol, 86.49 uL) were added to the above solution. The mixture was stirred at 40° C. for 16 hour. The mixture was purified via preparative HPLC to give 2-[4-[5-[[(3R,4R)-1-(2-cyanophenyl)-3-methyl-4-piperidyl]amino]-2,4-dimethyl-benzoyl]piperazin-1-yl]benzenesulfonamide (29.60 mg, 50.45 umol, 30%) as a white solid. ESI-MS (EI+, m/z): 587.3 [M+H]+. 1H NMR (500 MHz, CDCl3) δ 8.04-8.02 (dd, J=8.0, 1.5 Hz, 1H), 7.62-7.55 (m, 2H), 7.50-7.47 (m, 1H), 7.37-7.33 (m, 2H), 7.04-6.99 (m, 2H), 6.91 (s, 1H), 6.45 (s, 1H), 5.54 (s, 2H), 3.65 (m, 1H), 3.51 (m, 4H), 3.26-3.05 (m, 7H), 2.40 (m, 1H), 2.20 (s, 3H), 2.14 (s, 3H), 2.02 (m, 1H), 1.94-1.91 (m, 1H), 1.56 (m, 1H), 1.15-1.05 (dd, J=46.5, 6.5 Hz, 3H).

Example 129: 2-(4-(5-(((3S,4R)-1-(2-cyanophenyl)-3-methylpiperidin-4-yl)amino)-2,4-dimethylbenzoyl)piperazin-1-yl)benzenesulfonamide, I-171

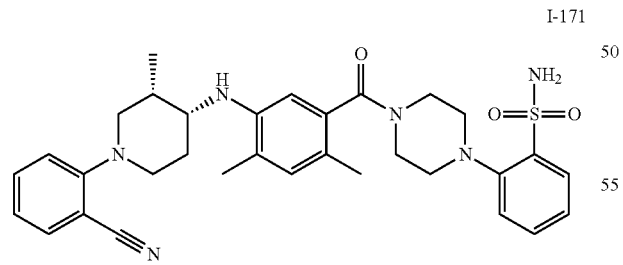

I-171

5-[[(3 S,4R)-1-(2-cyanophenyl)-3-methyl-4-piperidyl]amino]-2,4-dimethyl-benzoic acid (90.00 mg, 247.63 umol) and 2-piperazin-1-ylbenzenesulfonamide (68.78 mg, 247.63 umol, HCl) was dissolved in DMF (5.00 mL). Then EDCI (73.17 mg, 371.45 umol), HOBT (40.15 mg, 297.16 umol), DIEA (96.01 mg, 742.89 umol, 129.74 uL) were added to the above solution. The mixture was stirred at 30° C. for 16 hour. The mixture was purified via preparative HPLC to give 2-[4-[5-[[(3 S,4R)-1-(2-cyanophenyl)-3-methyl-4-piperidyl]amino]-2,4-dimethyl-benzoyl]piperazin-1-yl]benzenesulfonamide (84.80 mg, 144.52 umol, 58%) as a white solid. ESI-MS (EI+, m/z): 587.3 [M+H]+. 1H NMR (500 MHz, CDCl3) δ 8.03-8.01 (dd, J=8.0, 1.5 Hz, 1H), 7.62-7.55 (m, 2H), 7.50-7.47 (m, 1H), 7.37-7.33 (m, 2H), 7.04-6.99 (m, 2H), 6.91 (s, 1H), 6.45 (s, 1H), 5.54 (s, 2H), 3.60-3.50 (m, 4H), 3.12-2.92 (m, 8H), 2.68-2.64 (t, J=11.5 Hz, 4H), 2.29 (m, 1H), 2.20 (s, 3H), 2.12 (s, 3H), 1.99-1.97 (m, 1H), 1.58 (m, 1H), 1.10-1.05 (dd, J=21.5, 6.0 Hz, 3H).

Example 130: 3-(4-(5-((1-(2-cyanophenyl)piperidin-4-yl)amino)-2-methyl-4-(trifluoromethyl)benzoyl)piperazin-1-yl)pyridine-2-sulfonamide, I-172

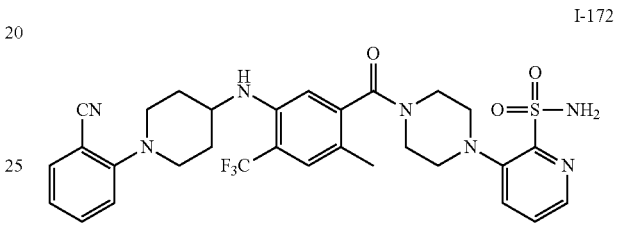

I-172

Synthetic Scheme:

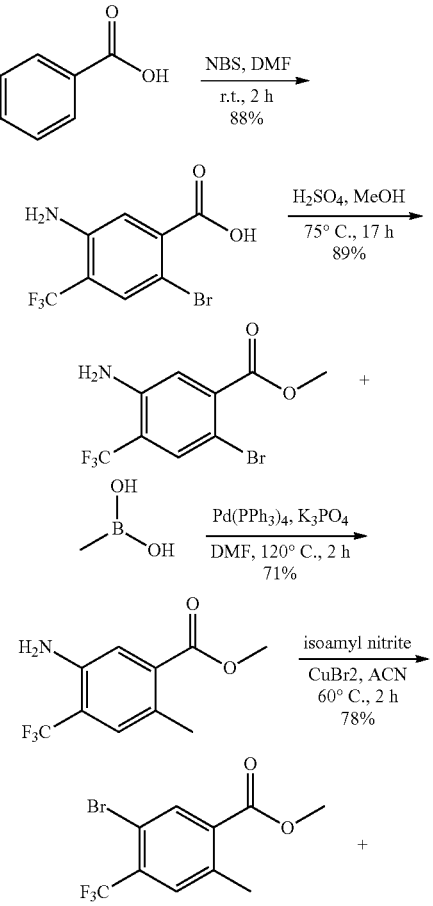

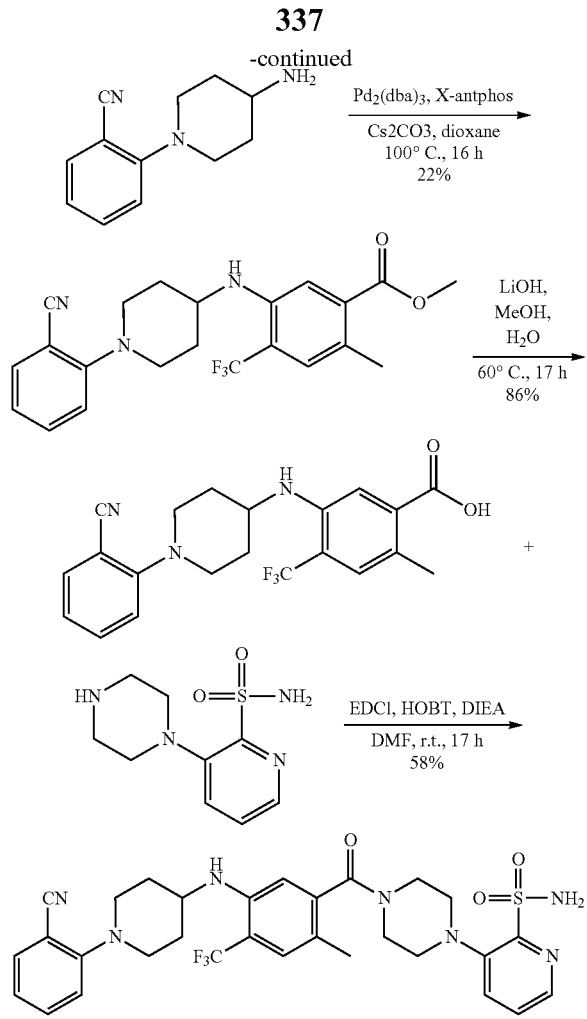

Procedures and Characterization:

Step 1: 2,4,5-trifluorobenzenesulfonamide

To a solution of 3-amino-4-(trifluoromethyl)benzoic acid (10.00 g, 48.75 mmol) in DMF (20.00 mL) was added NBS (8.68 g, 48.75 mmol), after 10-20° C. for 2 hour, the solution was poured into ice-water (100 mL), extracted with EA (50 mL×2), the solution was washed with water (100 mL×2) and brine (100 mL), dried ($Na_2SO_4$) and concentrated to afford 5-amino-2-bromo-4-(trifluoromethyl)benzoic acid (12.30 g, 43.31 mmol, 88%) as a brown solid. ESI-MS (EI+, m/z): 285.8 [M+H]+.

Step 2: methyl 5-amino-2-bromo-4-(trifluoromethyl)benzoate

To a solution of 5-amino-2-bromo-4-(trifluoromethyl)benzoic acid (10.00 g, 35.21 mmol) in Methanol (100.00 mL) was added $H_2SO_4$ (7.00 mL), the solution was heated to 75° C. for 17 hour, the solution was poured into ice-water (100 mL), extracted with EA (50 mL×2), the organic phase was washed with sat. $NAHCO_3$ solution (50 mL) and brine (50 mL), dried ($Na_2SO_4$) and concentrated to afford methyl 5-amino-2-bromo-4-(trifluoromethyl)benzoate (9.40 g, 31.54 mmol, 89%) as a brown solid. ESI-MS (EI+, m/z): 297.8 [M+H]+.

Step 3: methyl 5-amino-2-methyl-4-(trifluoromethyl)benzoate

A mixture of methyl 5-amino-2-bromo-4-(trifluoromethyl)benzoate (2.00 g, 6.71 mmol), methylboronic acid (2.01 g, 33.55 mmol) and $K_3PO_4$ (4.27 g, 20.13 mmol) in DMF (20.00 mL) was irradiated in the microwave at 120° C. for 2 hour, the solution was diluted with water (100 mL), extracted with EA (50 mL×2), the organic phase was washed with water (100 mL) and brine (100 mL), dried ($Na_2SO_4$), concentrated and purified by chromatography (silica, PE/EA=15:1) to afford methyl 5-amino-2-methyl-4-(trifluoromethyl)benzoate (1.30 g, 4.79 mmol, 71.4%) as a brown solid. ESI-MS (EI+, m/z): 234.0 [M+H]+.

Step 4: methyl 5-bromo-2-methyl-4-(trifluoromethyl)benzoate

To a mixture of methyl 5-amino-2-methyl-4-(trifluoromethyl)benzoate (1.00 g, 4.29 mmol) and $CuBr_2$ (1.92 g, 8.58 mmol) in ACN (40.00 mL) was added Isoamyl nitrite (753.57 mg, 6.44 mmol), the solution was heated to 60° C. for 2 hour, the solution was diluted with water (100 mL), extracted with EtOAc (50 mL×2), washed with water (50 mL) and brine (50 mL), dried ($Na_2SO_4$), concentrated in vacuo to afford methyl 5-bromo-2-methyl-4-(trifluoromethyl)benzoate (1.00 g, 3.37 mmol, 78%) as a brown liquid.

Step 5: methyl 5-((1-(2-cyanophenyl)piperidin-4-yl)amino)-2-methyl-4-(trifluoromethyl)benzoate methyl 5-bromo-2-methyl-4-(trifluoromethyl)benzoate (750.00 mg, 2.52 mmol), 2-(4-amino-1-piperidyl)benzonitrile (659.36 mg, 3.28 mmol), xantphos (145.81 mg, 252.00 umol), $Pd_2(dba)_3$ (230.83 mg, 252.00 umol), $Cs_2CO_3$ (2.46 g, 7.56 mmol) were dissolved in dioxane (50.00 mL) and the mixture was stirred at 100° C. for 16 hour. LCMS showed our desired product. The mixture was cooled to rt, filtered and the filtrate was concentrated. The residue was extracted between water and EA, the combined organic layer was concentrated. The residue was purified via preparative HPLC to give methyl 5-[[1-(2-cyanophenyl)-4-piperidyl]amino]-2-methyl-4-(trifluoromethyl)benzoate (240.00 mg, 574.96 umol, 22%) as a yellow solid. ESI-MS (EI+, m/z): 418.2 [M+H]+.

Step 6: 5-((1-(2-cyanophenyl)piperidin-4-yl)amino)-2-methyl-4-(trifluoromethyl)benzoic Acid methyl 5-[[1-(2-cyanophenyl)-4-piperidyl]amino]-2-methyl-4-(trifluoromethyl)benzoate (240.00 mg, 574.96 umol) dissolved in MeOH (10.00 mL) and $H_2O$ (3.00 mL) was added $LiOH.H_2O$ (193.00 mg, 4.60 mmol). The mixture was stirred at 60° C. for 17 hour. The mixture was concentrated and acidified with 1M HCl and extracted with EA. The organic layer was washed with brine, dried over $MgSO_4$, filtered and concentrated to give crude 5-[[1-(2-cyanophenyl)-4-piperidyl]amino]-2-methyl-4-(trifluoromethyl)benzoic acid (200.00 mg, 495.79 umol, 86%) as a yellow solid. ESI-MS (EI+, m/z): 404.2 [M+H]+.

Step 7: 3-(4-(5-((1-(2-cyanophenyl)piperidin-4-yl)amino)-2-methyl-4-(trifluoromethyl)benzoyl)piperazin-1-yl)pyridine-2-sulfonamide 5-[[1-(2-cyanophenyl)-4-piperidyl]amino]-2-methyl-4-(trifluoromethyl)benzoic acid (50.00 mg, 123.95 umol), 3-piperazin-1-ylpyridine-2-sulfonamide (51.83 mg, 185.93 umol, HCl), EDCI (36.63 mg, 185.93 umol), HOBT (20.10 mg, 148.74 umol), DIEA (48.06 mg, 371.85 umol, 64.95 uL) were dissolved in DMF (3.00 mL) and the mixture was stirred at 30° C. for 17 hour. The mixture was filtered and purified via preparative HPLC to give 3-[4-[5-[[1-(2-cyanophenyl)-4-piperidyl]amino]-2-methyl-4-(trifluoromethyl)benzoyl]piperazin-1-yl]pyridine-2-sulfonamide (45.60 mg, 72.65 umol, 58%) as a white solid. ESI-MS (EI$^+$, m/z): 628.3 [M+H]$^+$. $^1$H NMR (500 MHz, CDCl$_3$) δ 8.38-8.37 (m, 1H), 7.68-7.66 (dd, J=8.0, 1.0 Hz, 1H), 7.58-7.56 (dd, J=7.5, 1.5 Hz, 1H), 7.52-7.47 (m, 2H), 7.30 (s, 1H), 7.05-7.00 (m, 2H), 6.60 (s, 1H), 5.22 (s, 2H), 4.26-4.25 (d, J=6.0 Hz, 1H), 4.12 (m, 1H), 3.97-3.95 (m, 1H), 3.58-3.55 (m, 2H), 3.50-3.47 (m, 3H), 3.23-3.17 (m, 2H), 3.09-2.98 (m, 4H), 2.23-2.19 (m, 5H), 1.81-1.74 (m, 2H).

Example 131: 2-(4-(5-((1-(2-cyanophenyl)piperidin-4-yl)amino)-2-methyl-4-vinylbenzoyl)piperazin-1-yl)benzenesulfonamide, I-173

Synthetic Scheme:

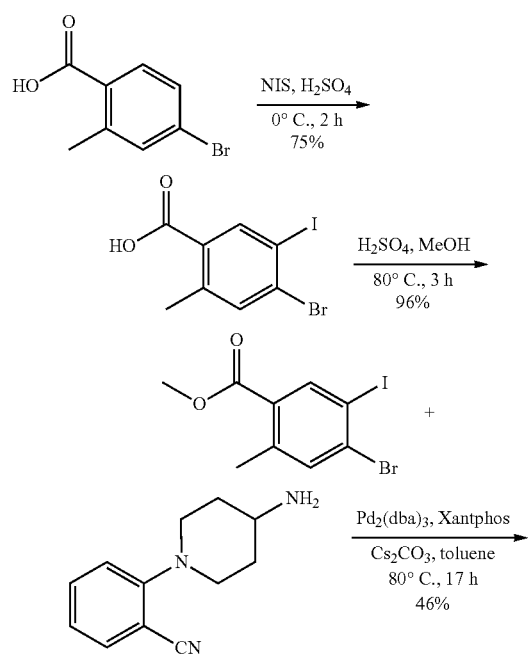

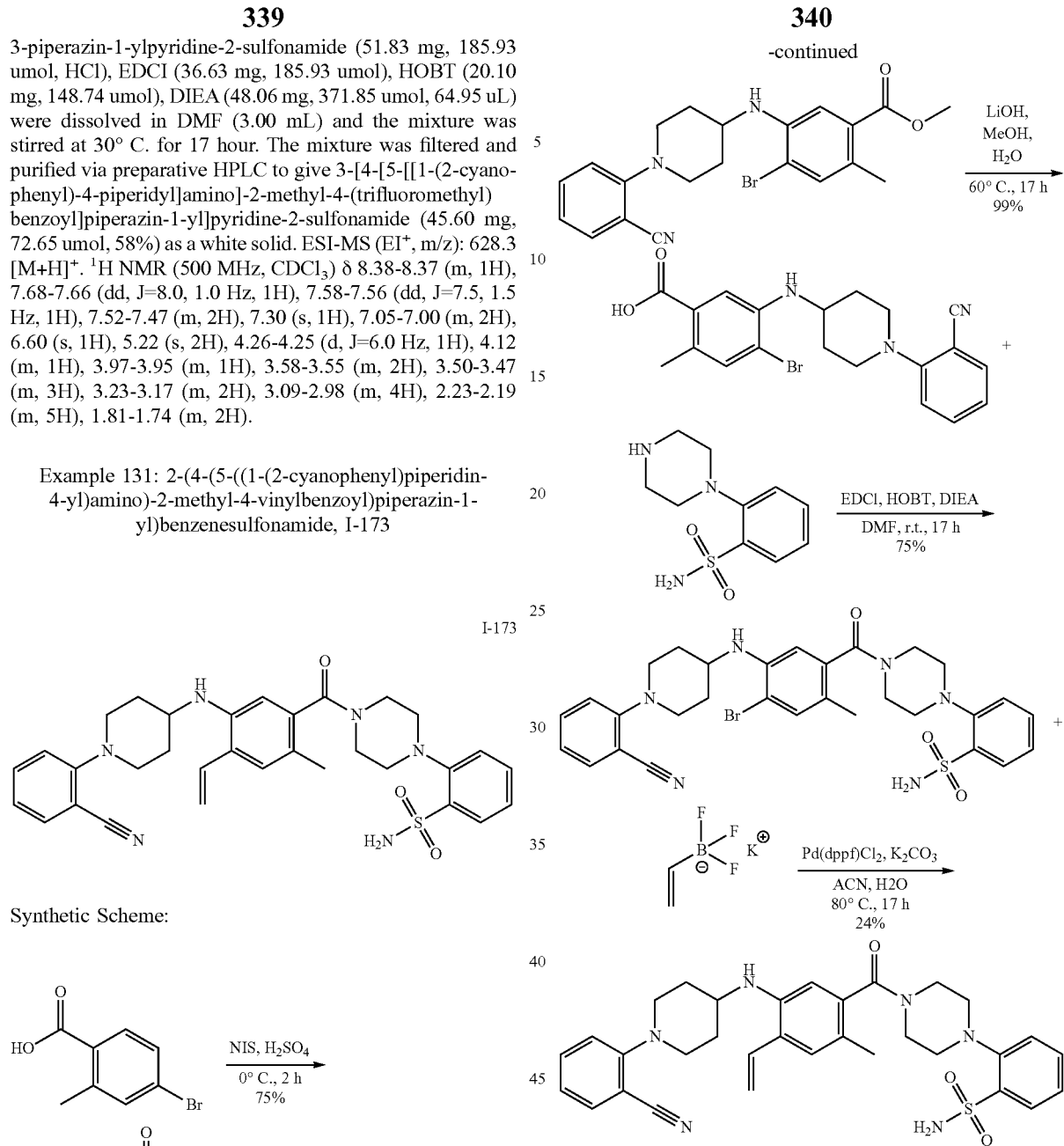

Procedures and Characterization:

Step 1: 4-bromo-5-iodo-2-methylbenzoic Acid

N-Iodosuccinimide (11.51 g, 51.15 mmol) is added in portions to an ice-cold solution of sulphuric acid (110.37 g, 1.13 mol, 59.98 mL). The resulting mixture was stirred at that temperature for 40 min, then 4-bromo-2-methyl-benzoic acid (10.00 g, 46.50 mmol) dissolved in 60 ml of sulphuric acid is added while the temperature maintains at 0-5° C. The mixture was stirred for 1 h, then the mixture poured on crushed ice and the resulting precipitate was washed with water ten times, heptane three times, dried in vacuo to afford 4-bromo-5-iodo-2-methyl-benzoic acid (12.00 g, 35.20 mmol, 75%) as a white solid.

Step 2: methyl 4-bromo-5-iodo-2-methylbenzoate

To a solution of 4-bromo-5-iodo-2-methyl-benzoic acid (10.00 g, 29.33 mmol) in MeOH (100.00 mL) was added H₂SO₄ (18.41 g, 187.71 mmol, 10.01 mL) at rt, then the reaction mixture was stirred at 80° C. for 3 hour. Cooled to rt, removed the solvent, extracted with EA (200 mL*3) and water (50 mL*2), dried, concentrated to afford methyl 4-bromo-5-iodo-2-methyl-benzoate (10.00 g, 28.17 mmol, 96%) as a pale white solid. ESI-MS (EI⁺, m/z): 356.8 [M+2]⁺.

Step 3: methyl 4-bromo-5-((1-(2-cyanophenyl)piperidin-4-yl)amino)-2-methylbenzoate methyl 4-bromo-5-iodo-2-methyl-benzoate (3.00 g, 8.45 mmol), 2-(4-amino-1-piperidyl)benzonitrile (2.04 g, 10.14 mmol), Cs₂CO₃ (5.51 g, 16.90 mmol), Pd₂(dba)₃ (154.83 mg, 169.00 umol), xantphos (195.73 mg, 338.00 umol) were dissolved in toluene (40.00 mL). Then the mixture was stirred at 80° C. for 17 hour. The mixture was cooled to rt and filtered. To the filtrate was added water (50 mL) and the resulting mixture was extracted with EA (30 mL×3). The combined organic layer was washed with water, brine, dried (Na₂SO₄), filtered and the filtrate was concentrated. The reside was purified by SGC (PE/EA=10) to give methyl 4-bromo-5-[[1-(2-cyanophenyl)-4-piperidyl]amino]-2-methyl-benzoate (1.70 g, 3.97 mmol, 46%) as a yellow solid. ESI-MS (EI⁺, m/z): 428.1 [M+H]⁺.

Step 4: 4-bromo-5-((1-(2-cyanophenyl)piperidin-4-yl)amino)-2-methylbenzoic Acid methyl 4-bromo-5-[[1-(2-cyanophenyl)-4-piperidyl]amino]-2-methyl-benzoate (300.00 mg, 700.41 umol), LiOH.H₂O (235.13 mg, 5.60 mmol) were dissolved in MeOH (10.00 mL) and H₂O (3.00 mL). Then the mixture was stirred at 60° C. for 17 hour. The solvent was removed and to the residue was added water (50 mL) and the resulting mixture was extracted with EA (30 mL×3). The combined organic layer was washed with water, brine, dried (Na₂SO₄), filtered and the filtrate was concentrated to give 4-bromo-5-[[1-(2-cyanophenyl)-4-piperidyl]amino]-2-methyl-benzoic acid (290.00 mg, 699.99 umol, 99%) as a yellow solid. ESI-MS (EI⁺, m/z): 416.1 [M+2]⁺.

Step 5: 2-(4-(4-bromo-5-((1-(2-cyanophenyl)piperidin-4-yl)amino)-2-methylbenzoyl)piperazin-1-yl)benzenesulfonamide 4-bromo-5-[[1-(2-cyanophenyl)-4-piperidyl]amino]-2-methyl-benzoic acid (290.00 mg, 699.98 umol), 2-piperazin-1-ylbenzenesulfonamide (291.65 mg, 1.05 mmol, HCl), HOBT (94.58 mg, 699.98 umol), EDCI (134.19 mg, 699.98 umol), DIEA (452.33 mg, 3.50 mmol, 611.26 uL) were dissolved in DMF (5.00 mL). Then the mixture was stirred at 30° C. for 17 hour. Water (50 mL) was added and the resulting mixture was filtered, the solid was dried to give 2-[4-[4-bromo-5-[[1-(2-cyanophenyl)-4-piperidyl]amino]-2-methyl-benzoyl]piperazin-1-yl]benzenesulfonamide (420.00 mg, 526.98 umol, 75%) as a brown oil. ESI-MS (EI⁺, m/z): 637.2 [M+H]⁺.

Step 6: 2-(4-(5-((1-(2-cyanophenyl)piperidin-4-yl)amino)-2-methyl-4-vinylbenzoyl)piperazin-1-yl)benzenesulfonamide 2-[4-[4-bromo-5-[[1-(2-cyanophenyl)-4-piperidyl]amino]-2-methyl-benzoyl]piperazin-1-yl]benzenesulfonamide (440.00 mg, 690.10 umol), Vinyltrifluoroboric acid potassium (184.88 mg, 1.38 mmol), K₂CO₃ (286.14 mg, 2.07 mmol), Pd(dppf)Cl₂ (16.91 mg, 20.70 umol) were dissolved in ACN (10.00 mL) and H₂O (4.00 mL). Then the mixture was stirred at 80° C. for 17 hour. The mixture was filtered and the filtrate was purified via preparative HPLC to give 2-[4-[5-[[1-(2-cyanophenyl)-4-piperidyl]amino]-2-methyl-4-vinyl-benzoyl]piperazin-1-yl]benzenesulfonamide (100.00 mg, 171.02 umol, 24%) as a yellow solid. ESI-MS (EI⁺, m/z): 585.3 [M+H]⁺. ¹H NMR (500 MHz, CDCl₃) δ 8.03 (m, 1H), 7.62-7.55 (m, 2H), 7.50-7.47 (m, 1H), 7.39-7.33 (m, 2H), 7.10 (s, 1H), 7.04-6.99 (m, 2H), 6.72-6.66 (m, 1H), 6.51 (s, 1H), 5.63-5.59 (dd, J=12, 1.0 Hz, 1H), 5.52 (s, 1H), 4.26-4.25 (dd, J=10.5, 1.0 Hz, 1H), 3.71-3.47 (m, 6H), 3.17-2.95 (m, 6H), 2.23 (m, 5H), 1.78-1.58 (m, 2H).

Example 132: 2-(4-(5-((1-(2-cyanophenyl)piperidin-4-yl)amino)-2,4-dimethylbenzoyl)piperazin-1-yl)-3,5-difluorobenzenesulfonamide, I-174

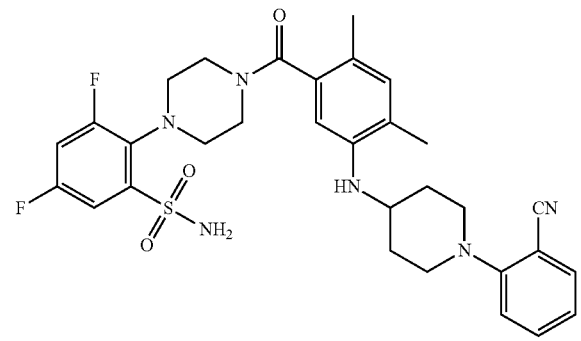

I-174

Synthetic Scheme:

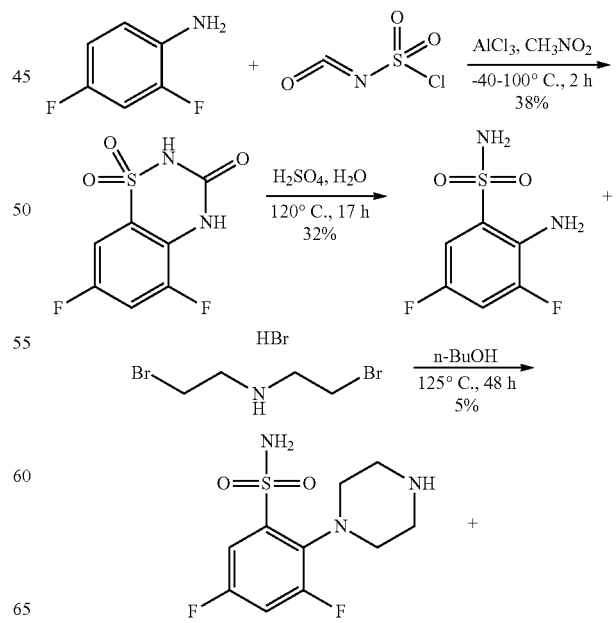

343
-continued

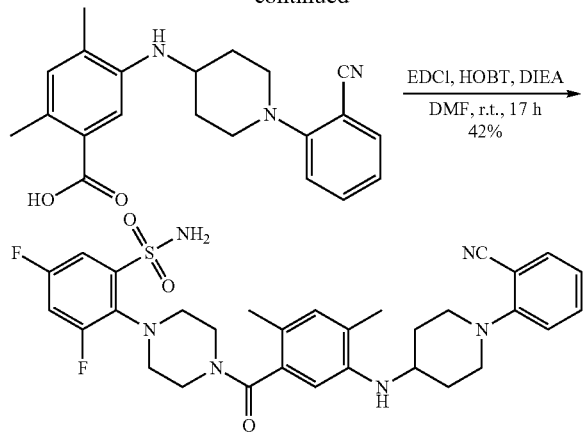

Procedures and Characterization:

Step 1: 5,7-difluoro-2H-benzo[e][1,2,4]thiadiazin-3(4H)-one 1,1-dioxide

To a solution of N-(oxomethylene)sulfamoyl chloride (6.36 g, 44.92 mmol, 3.90 mL) in CH₃NO₂ (50 mL) was added 2,4-difluoroaniline (5 g, 38.73 mmol, 3.94 mL) at −42° C., and the mixture was stirred at −42° C. for 1 hour. Then AlCl₃ (6.45 g, 48.41 mmol) was added and the mixture was stirred at 100° C. for 1 hour. The mixture was poured onto ice-water, and stirred for 10 min, extracted with EA (400 mL), the organic layer was washed with brine, dried over Na₂SO₄, filtered and concentrated. The residue was suspended in aqueous sodium bicarbonate (10 g/200 mL of water). The suspension was heated until most of the precipitate dissolved, treated with charcoal and filtered. The pH of the filtrate was adjusted to pH-1 using 6 M hydrochloric acid and extracted with EA (400 mL), the organic layer was washed with brine, dried over Na₂SO₄, filtered and concentrated to give crude 5,7-difluoro-2H-benzo[e][1,2,4]thiadiazin-3(4H)-one (3.5 g, 14.95 mmol, 38%) as a yellow solid.

Step 2: 2-amino-3,5-difluorobenzenesulfonamide 5,7-difluoro-2H-benzo[e][1,2,4]thiadiazin-3(4H)-one (3.5 g, 14.95 mmol) was added to aqueous Sulfuric Acid (10 mL) and water (10 mL). The resulting mixture was stirred at 120° C. for 17 hour until a clear solution was obtained. The reaction mixture was cooled to 0° C., and the pH was adjusted to pH-7 using aqueous sodium hydroxide (30 percent w/v) and extracted with EtOAc (500 mL×2). The combined organic layers were dried (Na₂SO₄), filtered and concentrated in vacuo. The residue was purified by chromatography (silica, ethyl acetate/petroleum ether=1/1) to afford 2-amino-3,5-difluoro-benzenesulfonamide (1 g, 4.80 mmol, 32%) as a yellow solid. ESI-MS (EI⁺, m/z): 209.1 [M+H]⁺.

Step 3: 2-amino-3,5-3,5-difluoro-2-(piperazin-1-yl)benzenesulfonamide

To a solution of 2-amino-3,5-difluoro-benzenesulfonamide (1.2 g, 5.76 mmol) in n-BuOH (20 mL) was added 2-bromo-N-(2-bromoethyl)ethanamine (3.8 g, 12.19 mmol, HBr), then the mixture was stirred at 125° C. for 48 hour. The solvent was concentrated, the residue was adjusted pH-8 with aq.NaOH (3M). Then mixture was concentrated. Then DMF (10 mL) was added and purified via preparative

344

HPLC to give crude 3,5-difluoro-2-piperazin-1-yl-benzenesulfonamide (120 mg, 333.22 umol, 5%, 77% purity) as a white solid. ESI-MS (EI⁺, m/z): 278.2 [M+H]⁺.

Step 4: 2-(4-(5-((1-(2-cyanophenyl)piperidin-4-yl)amino)-2,4-dimethylbenzoyl)piperazin-1-yl)-3,5-difluorobenzenesulfonamide 3,5-difluoro-2-piperazin-1-yl-benzenesulfonamide (98 mg, 353.42 umol), 5-[[1-(2-cyanophenyl)-4-piperidyl]amino]-2,4-dimethyl-benzoic acid (148.19 mg, 424.10 umol), EDCI (101.63 mg, 530.13 umol), HOBT (62.08 mg, 459.45 umol), DIEA (274.06 mg, 2.12 mmol, 369.36 uL) were dissolved in DMF (5 mL). Then the mixture was stirred at 25° C. for 17 hour. The mixture was filtered and the filtrate was purified via preparative HPLC to give 2-[4-[5-[[1-(2-cyanophenyl)-4-piperidyl]amino]-2,4-dimethyl-benzoyl]piperazin-1-yl]-3,5-difluoro-benzenesulfonamide (91.2 mg, 149.83 umol, 42%) as a white solid. ESI-MS (EI⁺, m/z): 609.1 [M+H]⁺. ¹H NMR (500 MHz, CDCl₃) δ 7.57-7.56 (d, J=7.5 Hz, 2H), 7.51-7.48 (t, 1H), 7.08-7.00 (m, 3H), 6.93-6.90 (d, J=11 Hz, 1H), 6.55-6.41 (d, J=18 Hz, 1H), 5.50 (s, 2H), 4.92-4.90 (m, 1H), 3.63-3.39 (m, 6H), 3.29-3.25 (m, 1H), 3.17-3.13 (m, 2H), 3.02-2.96 (m, 4H), 2.25-2.11 (m, 8H), 1.77-1.59 (m, 2H).

Example 133: (R)-(3-(4-(3-((1-(3-chloropyridin-2-yl)piperidin-4-yl)amino)-2,4,6-trimethylbenzoyl)piperazin-1-yl)pyridin-2-yl)(imino)(methyl)-λ⁶-sulfanone trifluoroacetate salt, I-175

I-175

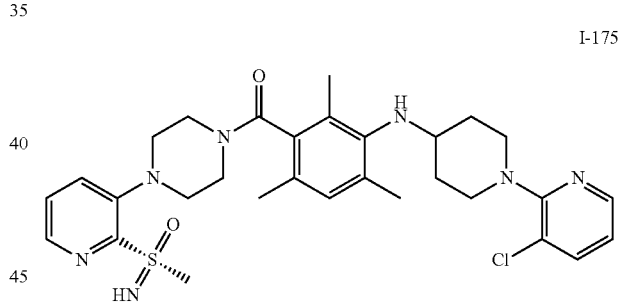

Synthetic Scheme:

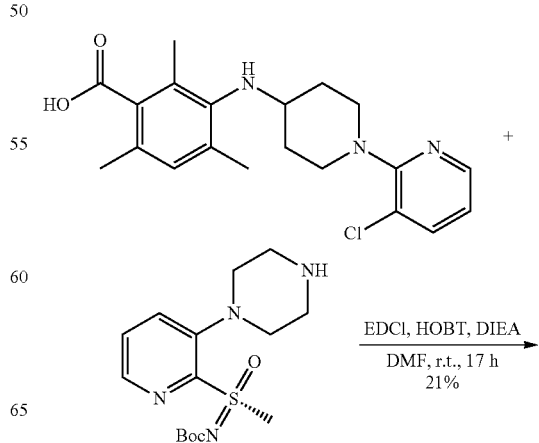

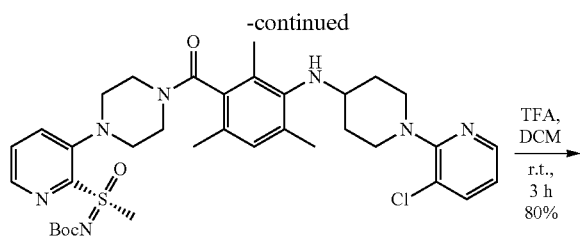

Procedures and Characterization:

Step 1: (R)-(3-(4-(3-((1-(3-chloropyridin-2-yl)piperidin-4-yl)amino)-2,4,6-trimethylbenzoyl)piperazin-1-yl)pyridin-2-yl)(imino)(methyl)-λ6-sulfanone 3-[[1-(3-chloro-2-pyridyl)-4-piperidyl]amino]-2,4,6-trimethyl-benzoic acid (50.00 mg, 133.73 umol), tert-butyl (R)-(methyl(oxo)(3-(piperazin-1-yl)pyridin-2-yl)-λ$^6$-sulfanylidene)carbamate (45.53 mg, 133.73 umol), HOBT (36.14 mg, 267.46 umol), EDCI (51.27 mg, 267.46 umol), DIEA (86.42 mg, 668.65 umol, 116.78 uL) were dissolved in DMF (5.00 mL). Then the mixture was stirred at 27° C. for 17 hour. The mixture was filtered and the filtrate was purified via preparative HPLC to give tert-butyl N-[[3-[4-[3-[[1-(3-chloro-2-pyridyl)-4-piperidyl]amino]-2,4,6-trimethyl-benzoyl]piperazin-1-yl]-2-pyridyl]-methyl-oxo-$1^{6}$-sulfanylidene]carbamate (20.00 mg, 28.72 umol, 21%) as a white solid. ESI-MS (EI$^+$, m/z): 696.3 [M+H]$^+$.

Step 2: (R)-(3-(4-(3-((1-(3-chloropyridin-2-yl)piperidin-4-yl)amino)-2,4,6-trimethylbenzoyl)piperazin-1-yl)pyridin-2-yl)(imino)(methyl)-16-sulfanone Trifluoroacetate Salt tert-butyl N-[[3-[4-[3-[[1-(3-chloro-2-pyridyl)-4-piperidyl]amino]-2,4,6-trimethyl-benzoyl]piperazin-1-yl]-2-pyridyl]-methyl-oxo-$1^{6}$-sulfanylidene]carbamate (20.00 mg, 28.72 umol) was dissolved in TFA (1.00 mL) and DCM (5.00 mL). The mixture was stirred at 25° C. for 3 hour. The solvent was removed and the residue was purified via preparative HPLC to give [3-[[1-(3-chloro-2-pyridyl)-4-piperidyl]amino]-2,4,6-trimethyl-phenyl]-[4-[2-(methylsulfonimidoyl)-3-pyridyl]piperazin-1-yl]methanone (16.40 mg, 23.09 umol, 80%, TFA) as a white solid. ESI-MS (EI$^+$, m/z): 596.2 [M+H]$^+$. $^1$H-NMR (500 MHz, CD$_3$OD) δ 8.58 (m, 1H), 8.23-8.17 (m, 2H), 7.83-7.76 (m, 2H), 7.24 (s, 1H), 7.01-6.99 (m, 1H), 4.11 (m, 2H), 4.04-3.94 (m, 2H), 3.81 (s, 3H), 3.62 (m, 1H), 3.48 (m, 2H), 3.29-3.26 (m, 2H), 3.12-3.07 (m, 2H), 2.95-2.89 (m, 2H), 2.51 (s, 3H), 2.42 (s, 3H), 2.33 (s, 3H), 2.16-2.05 (m, 5H).

Example 134: (3-(4-(3-((1-(3-chloropyridin-2-yl)piperidin-4-yl)amino)-2,4,6-trimethylbenzoyl)piperazin-1-yl)pyridin-2-yl)(imino)(methyl)-16-sulfanone Trifluoroacetate Salt, I-176

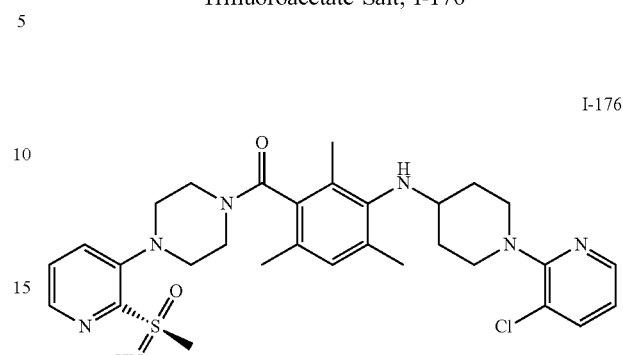

I-176

Synthetic Scheme:

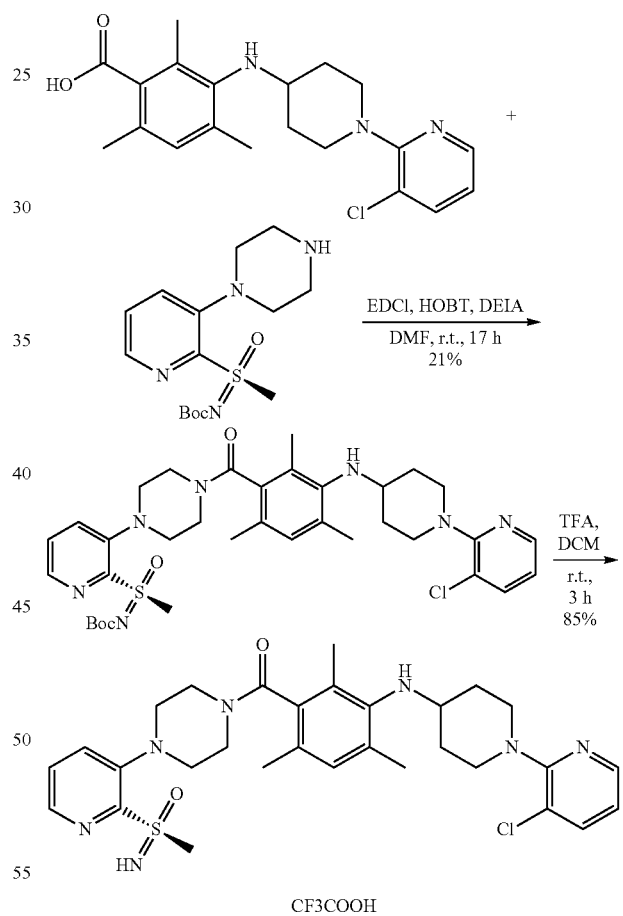

Procedures and Characterization:

Step 1: tert-butyl ((3-(4-(3-((1-(3-chloropyridin-2-yl)piperidin-4-yl)amino)-2,4,6-trimethylbenzoyl)piperazin-1-yl)pyridin-2-yl)(methyl)(oxo)-16-sulfanylidene)carbamate 3-[[1-(3-chloro-2-pyridyl)-4-piperidyl]amino]-2,4,6-trimethyl-benzoic acid (50.00 mg, 133.73 umol), tert-butyl (S)-(methyl(oxo)(3-(piperazin-1-yl)pyridin-2-yl)-λ⁶-sulfanylidene)carbamate (68.29 mg, 200.59 umol), HOBT (36.14 mg, 267.46 umol), EDCI (51.27 mg, 267.46 umol), DIEA (86.42 mg, 668.65 umol, 116.78 uL) were dissolved in DMF (5.00 mL). Then the mixture was stirred at 27° C. for 17 hour. The mixture was filtered and the filtrate was purified via preparative HPLC to give tert-butyl ((3-(4-(3-((1-(3-chloropyridin-2-yl)piperidin-4-yl)amino)-2,4,6-trimethylbenzoyl)piperazin-1-yl)pyridin-2-yl)(methyl)(oxo)-λ⁶-sulfanylidene)carbamate (20.00 mg, 28.72 umol, 21%) as a white solid. ESI-MS (EI⁺, m/z): 696.3 [M+H]⁺.

Step 2: (3-(4-(3-((1-(3-chloropyridin-2-yl)piperidin-4-yl)amino)-2,4,6-trimethylbenzoyl)piperazin-1-yl)pyridin-2-yl)(imino)(methyl)-16-sulfanone trifluoroacetate Salt tert-butyl((3-(4-(3-((1-(3-chloropyridin-2-yl)piperidin-4-yl)amino)-2,4,6-trimethylbenzoyl)piperazin-1-yl)pyridin-2-yl)(methyl)(oxo)-λ⁶-sulfanylidene)carbamate (25.00 mg, 35.90 umol) was dissolved in TFA (1.00 mL) and DCM (5.00 mL). The mixture was stirred at 25° C. for 3 hour. The solvent was removed and the residue was purified via preparative HPLC to give [3-[[1-(3-chloro-2-pyridyl)-4-piperidyl]amino]-2,4,6-trimethyl-phenyl]-[4-[2-(methylsulfonimidoyl)-3-pyridyl]piperazin-1-yl]methanone (21.70 mg, 30.55 umol, 85%, TFA) as a white solid. ESI-MS (EI⁺, m/z): 596.2 [M+H]⁺. ¹H-NMR (500 MHz, MeOD) δ 8.56 (m, 1H), 8.20-8.17 (m, 2H), 7.81-7.76 (m, 2H), 7.23 (s, 1H), 7.02-6.99 (m, 1H), 4.21-3.94 (m, 4H), 3.78-3.75 (m, 3H), 3.62 (m, 1H), 3.48 (m, 2H), 3.29-3.26 (m, 2H), 3.14-3.05 (m, 2H), 2.95-2.90 (m, 2H), 2.51 (s, 3H), 2.42 (s, 3H), 2.33 (s, 3H), 2.18-2.04 (m, 5H).

Example 135: (S)-2-(4-((5-(3-(hydroxymethyl)-4-(1,3,4-oxadiazol-2-yl)piperazine-1-carbonyl)-2,4-dimethylphenyl)amino)piperidin-1-yl)benzonitrile, I-177

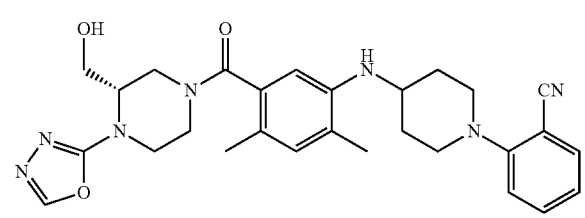 [SMILES: Cc1cc(C)c(C(=O)N2CCN(c3nnco3)[C@H](CO)C2)cc1NC1CCN(c2ccccc2C#N)CC1]

I-177

Synthetic Scheme:

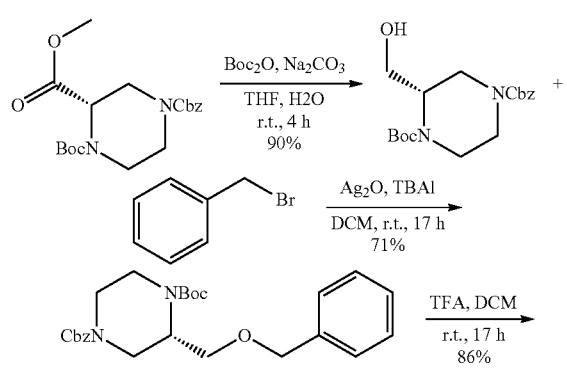

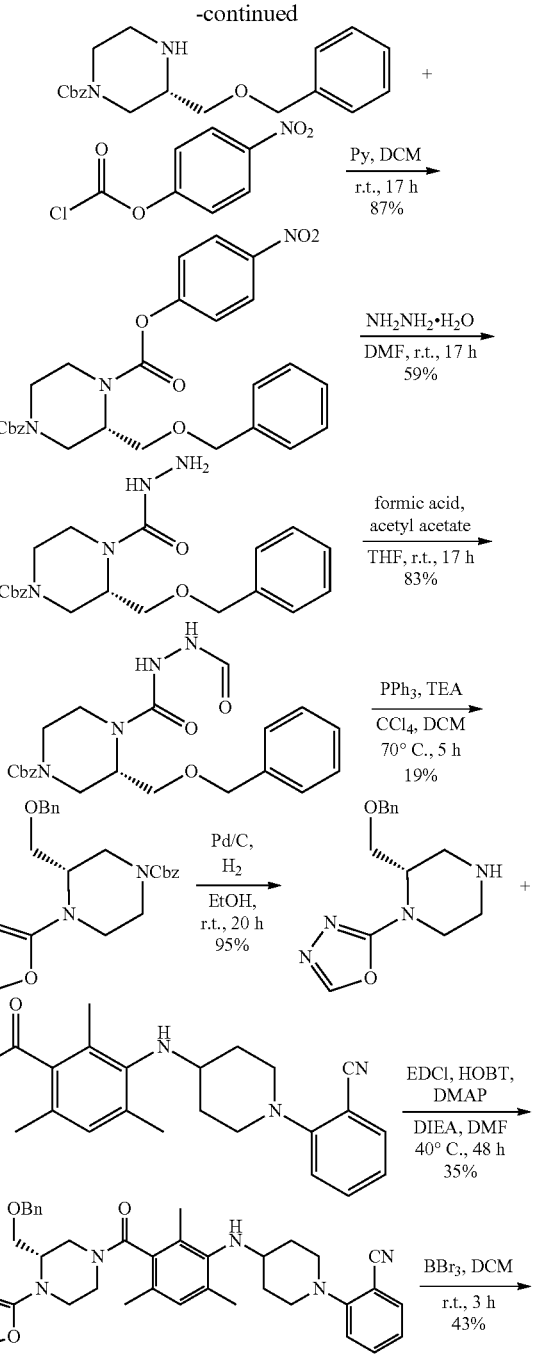

Procedures and Characterization:

Step 1: 4-benzyl 1-(tert-butyl) (S)-2-(hydroxymethyl)piperazine-1,4-dicarboxylate benzyl (3S)-3-(hydroxymethyl)piperazine-1-carboxylate (3.00 g, 11.99 mmol), di-tert-butyl dicarbonate (5.23 g, 23.98 mmol), Na$_2$CO$_3$ (5.08 g, 47.96 mmol) were dissolved in THF (20.00 mL) and H$_2$O (10.00 mL). Then the mixture was stirred at 30° C. for 4 hour. EA (100 mL) was added to the reaction and extracted with EA, the organic layer was dried (Na$_2$SO$_4$), filtered and the filtrate was concentrated. The residue was purified by SGC (PE/EA=1) to give 4-benzyl 1-tert-butyl (2S)-2-(hydroxymethyl)piperazine-1,4-dicarboxylate (3.80 g, 10.84 mmol, 90%) as a colorless oil. ESI-MS (EI$^+$, m/z): 251.4 [M−100+H]$^+$.

Step 2: 4-benzyl 1-(tert-butyl) (S)-2-((benzyloxy)methyl)piperazine-1,4-dicarboxylate 4-benzyl 1-tert-butyl (2S)-2-(hydroxymethyl)piperazine-1,4-dicarboxylate (2.80 g, 7.99 mmol), (bromomethyl)benzene (2.05 g, 11.99 mmol), TBAI (1.48 g, 4.00 mmol) were dissolved in DCM (20.00 mL). Then Ag$_2$O (2.22 g, 9.59 mmol, 311.22 uL) was added. The mixture was stirred at rt for 17 hour. Filtered and the filtrate was concentrated, the residue was purified by SGC (PE/EA=5) to give 4-benzyl 1-tert-butyl (2S)-2-(benzyloxymethyl)piperazine-1,4-dicarboxylate (2.50 g, 5.67 mmol, 71%) as a colorless oil. ESI-MS (EI$^+$, m/z): 463.3 [M+Na]$^+$.

Step 3: benzyl (S)-3-((benzyloxy)methyl)piperazine-1-carboxylate 4-benzyl 1-(tert-butyl) (S)-2-((benzyloxy)methyl)piperazine-1,4-dicarboxylate (2.80 g, 7.99 mmol was dissolved in DCM (10.00 mL) and TFA (8.00 mL), the mixture was stirred at rt for 17 hour. The solvent was concentrated and the residue was poured onto ice water, then adjusted pH~8 with sat.NaHCO$_3$. The mixture was extracted with DCM (100 mL), the organic layer was washed with water, brine, dried (Na$_2$SO$_4$) and filtered to concentrate to give crude benzyl (3S)-3-(benzyloxymethyl)piperazine-1-carboxylate (2.20 g, 6.46 mmol, 86%) as a yellow oil. ESI-MS (EI$^+$, m/z): 341.2 [M+H].

Step 4: 4-benzyl 1-(4-nitrophenyl) (S)-2-((benzyloxy)methyl)piperazine-1,4-dicarboxylate benzyl (3S)-3-(benzyloxymethyl)piperazine-1-carboxylate (2.30 g, 6.76 mmol), (4-nitrophenyl) carbonochloridate (2.72 g, 13.51 mmol), pyridine (2.67 g, 33.78 mmol, 2.73 mL) was dissolved in DCM (30.00 mL). The mixture was stirred at 30° C. for 17 hour. Water was added and extracted with DCM (50 mL), the organic layer was concentrated. The residue was purified by SGC (PE/EA=5) to give 4-benzyl 1-(4-nitrophenyl) (2S)-2-(benzyloxymethyl)piperazine-1,4-dicarboxylate (3.00 g, 5.93 mmol, 87%) as a yellow oil. ESI-MS (EI$^+$, m/z): 506.2 [M+H]$^+$.

Step 5: benzyl (S)-3-((benzyloxy)methyl)-4-(hydrazinecarbonyl)piperazine-1-carboxylate 4-benzyl 1-(4-nitrophenyl) (2S)-2-(benzyloxymethyl)piperazine-1,4-dicarboxylate (3.00 g, 5.93 mmol), Hydrazine hydrate (1.11 g, 17.80 mmol) were dissolved in DMF (10.00 mL). Then the mixture was stirred at 25° C. for 17 hour. The mixture was added water (50 mL) and extracted with EA (30 mL×3). The combined organic layer was washed with water, brine, dried (Na$_2$SO$_4$), filtered and the filtrate was concentrated. The reside was purified by Prep-TLC (DCM/MeOH=10) to give benzyl (3S)-3-(benzyloxymethyl)-4-(hydrazinecarbonyl)piperazine-1-carboxylate (2.00 g, 3.51 mmol, 59%, 70% purity) as a yellow oil. ESI-MS (EI$^+$, m/z): 399.3 [M+H]$^+$.

Step 6: benzyl (S)-3-((benzyloxy)methyl)-4-(2-formylhydrazine-1-carbonyl)piperazine-1-carboxylate Formic acid (8.24 g, 178.99 mmol, 6.75 mL), acetyl acetate (12.13 g, 118.88 mmol, 1.00 mL) were mixed and stirred at 60° C. for 3 hour, then the mixture was cooled to rt, and 1.5 mL this mixture was added to a solution of benzyl (3S)-3-(benzyloxymethyl)-4-(hydrazinecarbonyl)piperazine-1-carboxylate (1.80 g, 4.52 mmol) in THF (20.00 mL). The mixture was stirred at 25° C. for 17 hour. The mixture was added water (50 mL) and extracted with EA (30 mL×3). The combined organic layer was washed with water, brine, dried (Na$_2$SO$_4$), filtered and the filtrate was concentrated. The reside was purified by SGC (DCM/MeOH=15) to give benzyl (3S)-3-(benzyloxymethyl)-4-(formamidocarbamoyl)piperazine-1-carboxylate (1.60 g, 3.75 mmol, 83%) as a yellow oil. ESI-MS (EI$^+$, m/z): 427.3 [M+H]$^+$.

Step 7: benzyl (S)-3-((benzyloxy)methyl)-4-(1,3,4-oxadiazol-2-yl)piperazine-1-carboxylate benzyl (3 S)-3-(benzyloxymethyl)-4-(formamidocarbamoyl)piperazine-1-carboxylate (1.60 g, 3.75 mmol), PPh$_3$ (1.97 g, 7.50 mmol), TEA (1.14 g, 11.25 mmol, 1.56 mL) were dissolved in CCl$_4$ (10.00 mL) and DCM (10.00 mL). Then the mixture was stirred at 70° C. for 5 hour. The mixture was filtered and the filtrate was purified via preparative HPLC to give benzyl (3S)-3-(benzyloxymethyl)-4-(1,3,4-oxadiazol-2-yl)piperazine-1-carboxylate (600.00 mg, 734.48 umol, 19%, 50% purity) as a white solid. ESI-MS (EI$^+$, m/z): 409.3 [M+H]$^+$.

Step 8: (S)-2-(2-((benzyloxy)methyl)piperazin-1-yl)-1,3,4-oxadiazole benzyl (3S)-3-(benzyloxymethyl)-4-(1,3,4-oxadiazol-2-yl)piperazine-1-carboxylate (600.00 mg, 1.47 mmol), Pd/C (500.00 mg, 411.60 umol, 10% purity) were dissolved in EtOH (20.00 mL). Then the mixture was stirred at 25° C. for 24 hour under H$_2$. The mixture was filtered and concentrated to give crude 2-[(2S)-2-(benzyloxymethyl)piperazin-1-yl]-1,3,4-oxadiazole (430.00 mg, 1.41 mmol, 95%, 90% purity) as a colorless oil. ESI-MS (EI$^+$, m/z): 275.3 [M+H]$^+$.

Step 9: (S)-2-(4-((3-(3-((benzyloxy)methyl)-4-(1,3,4-oxadiazol-2-yl)piperazine-1-carbonyl)-2,4,6-trimethylphenyl)amino)piperidin-1-yl)benzonitrile 2-[(2S)-2-(benzyloxymethyl)piperazin-1-yl]-1,3,4-oxadiazole (330.00 mg, 1.20 mmol), 3-[[1-(2-cyanophenyl)-4-piperidyl]amino]-2,4,6-trimethyl-benzoic acid (654.21 mg, 1.80 mmol), HOBT (324.29 mg, 2.40 mmol), EDCI (459.60 mg, 2.40 mmol), DIEA (1.24 g, 9.60 mmol, 1.68 mL), DMAP (14.66 mg, 120.00 umol) were dissolved in DMF (10.00 mL). Then the mixture was stirred at 40° C. for 48 hour. The mixture was cooled to rt added water (50 mL) and extracted with EA (30 mL×3). The combined organic layer was washed with water, brine, dried (Na$_2$SO$_4$), filtered and the filtrate was concentrated. The reside was purified by SGC (DCM/MeOH=50) to give 2-[4-[3-[(3 S)-3-(benzyloxymethyl)-4-(1,3,4-oxadiazol-2-yl)piperazine-1-carbonyl]-2,4,6-trimethyl-anilino]-1-piperidyl]benzonitrile (340.00 mg, 427.91 umol, 35%, 78% purity) as a yellow solid. ESI-MS (EI⁺, m/z): 620.3 [M+H]⁺.

Step 10: (S)-2-(4-((5-(3-(hydroxymethyl)-4-(1,3,4-oxadiazol-2-yl)piperazine-1-carbonyl)-2,4-dimethyl-phenyl)amino)piperidin-1-yl)benzonitril 2-[4-[3-[(3S)-3-(benzyloxymethyl)-4-(1,3,4-oxadiazol-2-yl)piperazine-1-carbonyl]-2,4,6-trimethyl-anilino]-1-piperidyl]benzonitrile (250.00 mg, 403.39 umol), BBr₃ (2.95 g, 2.00 mmol, 2.00 mL, 17% purity) were dissolved in DCM (5.00 mL). The mixture was stirred at 20° C. for 3 hour. MeOH (5 mL) was added and DCM (10 mL×3) was added and washed with aq.NaHCO3. The organic layer was concentrated. The residue was purified via preparative HPLC to get 2-[4-[3-[(3S)-3-(hydroxymethyl)-4-(1,3,4-oxadiazol-2-yl)piperazine-1-carbonyl]-2,4,6-trimethyl-anilino]-1-piperidyl]benzonitrile (92.00 mg, 173.71 umol, 43%) as a white solid. ESI-MS (EI⁺, m/z): 530.3 [M+H]⁺. ¹H NMR (500 MHz, CDCl₃) δ 7.95 (s, 1H), 7.55-7.45 (m, 2H), 7.00-6.97 (m, 2H), 6.89-6.85 (m, 1H), 4.84-4.81 (m, 1H), 4.25 (m, 1H), 3.92-3.72 (m, 4H), 3.57-3.40 (m, 4H), 3.40-2.74 (m, 7H), 2.27-2.20 (m, 6H), 2.12-2.09 (m, 3H), 2.03-2.00 (m, 2H), 1.71-1.67 (m, 2H).

Example 136: 2-(4-(3-(((3R,4S)-1-(2-cyanophenyl)-3-methylpiperidin-4-yl)amino)-2,4,6-trimethylbenzoyl)piperazin-1-yl)pyridine-3-sulfonamide, I-178

I-178

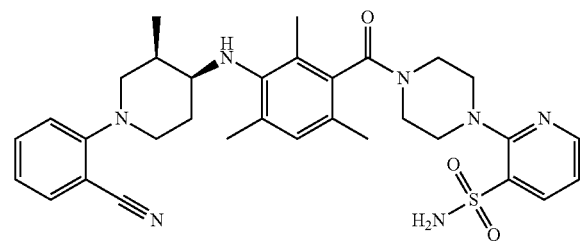

Synthetic Scheme:

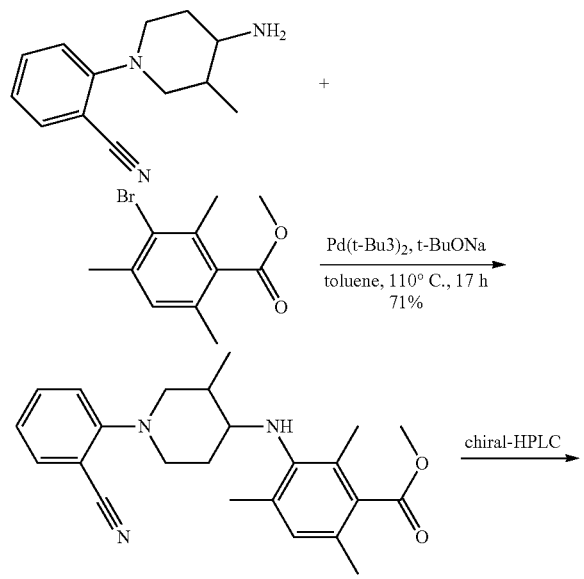

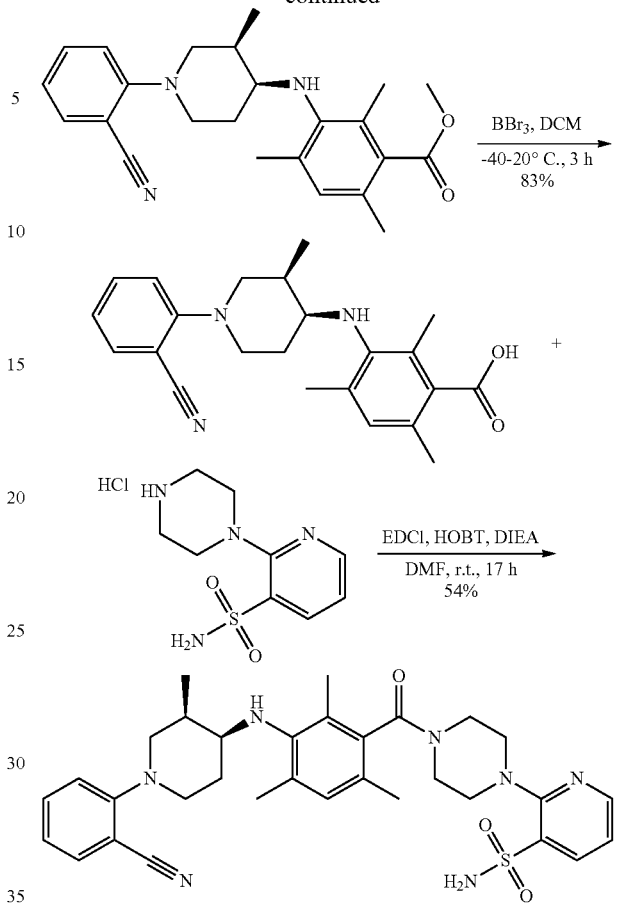

Procedures and Characterization:

Step 1: methyl 3-((1-(2-cyanophenyl)-3-methylpiperidin-4-yl)amino)-2,4,6-trimethylbenzoate 2-(4-amino-3-methyl-1-piperidyl)benzonitrile (4.60 g, 21.37 mmol) methyl 3-bromo-2,4,6-trimethyl-benzoate (6.59 g, 25.64 mmol), Pd(t-Bu₃P)₂ (1.09 g, 2.14 mmol), t-BuONa (5.87 g, 64.11 mmol) was dissolved in toluene (150.00 mL) and the mixture was stirred at 110° C. for 17 hour. The mixture was cooled to rt and filtered. The filtrate was concentrated and the residue was purified by SGC (PE/EA=10) to give methyl 3-[[1-(2-cyanophenyl)-3-methyl-4-piperidyl]amino]-2,4,6-trimethyl-benzoate (6.00 g, 15.33 mmol, 71%) as a red oil. ESI-MS (EI⁺, m/z): 392.3 [M+H]⁺.

Step 2: methyl 3-(((3R,4S)-1-(2-cyanophenyl)-3-methylpiperidin-4-yl)amino)-2,4,6-trimethylbenzoate methyl 3-[[(3R,4S)-1-(2-cyanophenyl)-3-methyl-4-piperidyl]amino]-2,4,6-trimethyl-benzoate (1.50 g, 3.83 mmol), BBr₃ (28.22 g, 19.15 mmol, 19.00 mL, 17% purity) were dissolved in DCM (10.00 mL). Then the mixture was stirred at −40-20° C. for 3 hour. The solvent was removed and the residue was added water (50 mL) and extracted with DCM (30 mL×3). The combined organic layer was washed with water, brine, dried (Na₂SO₄), filtered and the filtrate was concentrated to give 3-[[(3R,4S)-1-(2-cyanophenyl)-3- methyl-4-piperidyl]amino]-2,4,6-trimethyl-benzoic acid (1.20 g, 3.18 mmol, 83%) as a red solid. ESI-MS (EI+, m/z): 378.3 [M+H]+.

Step 3: 2-(4-(3-(((3R,4S)-1-(2-cyanophenyl)-3-methylpiperidin-4-yl)amino)-2,4,6-trimethylbenzoyl)piperazin-1-yl)pyridine-3-sulfonamide 3-[[(3R,4S)-1-(2-cyanophenyl)-3-methyl-4-piperidyl]amino]-2,4,6-trimethyl-benzoic acid (150.00 mg, 397.37 umol), 2-piperazin-1-ylpyridine-3-sulfonamide (166.16 mg, 596.06 umol, HCl), HOBT (107.39 mg, 794.74 umol), EDCI (152.35 mg, 794.74 umol), DIEA (308.14 mg, 2.38 mmol, 416.41 uL) were dissolved in DMF (3.00 mL). Then the mixture was stirred at 20° C. for 17 hour. The mixture was filtered and the filtrate was purified via preparative HPLC to give 2-[4-[3-[[(3R,4S)-1-(2-cyanophenyl)-3-methyl-4-piperidyl]amino]-2,4,6-trimethyl-benzoyl]piperazin-1-yl]pyridine-3-sulfonamide (131.00 mg, 217.69 umol, 54%) as a white solid. ESI-MS (EI+, m/z): 602.3 [M+H]+. 1H NMR (500 MHz, CDCl3) δ 8.56-8.54 (m, 1H), 8.28-8.26 (m, 1H), 7.54-7.52 (d, J=8.0 Hz, 1H), 7.47-7.24 (m, 1H), 7.27-7.24 (m, 1H), 6.99-6.96 (m, 2H), 6.85 (d, J=2.5 Hz, 1H), 5.65 (s, 2H), 4.04-3.99 (m, 2H), 3.58-3.46 (m, 2H), 3.39-3.31 (m, 4H), 3.15-3.10 (m, 2H), 2.80-2.54 (m, 4H), 2.27-2.17 (m, 9H), 1.87-1.76 (m, 2H), 1.62-1.51 (m, 1H), 1.22-1.17 (dd, J=16, 6.5 Hz, 3H).

Example 137: 2-(4-(3-(((3S,4R)-1-(2-cyanophenyl)-3-methylpiperidin-4-yl)amino)-2,4,6-trimethylbenzoyl)piperazin-1-yl)pyridine-3-sulfonamide I-179

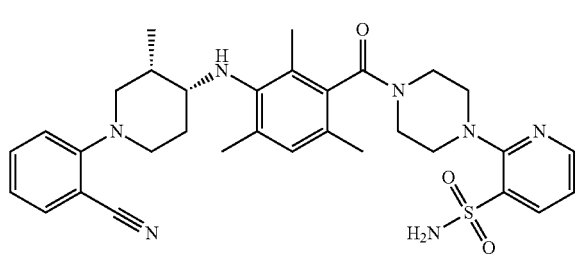

I-179

Synthetic Scheme:

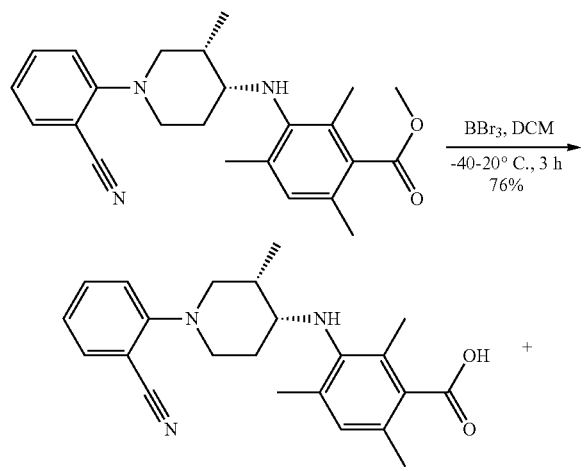

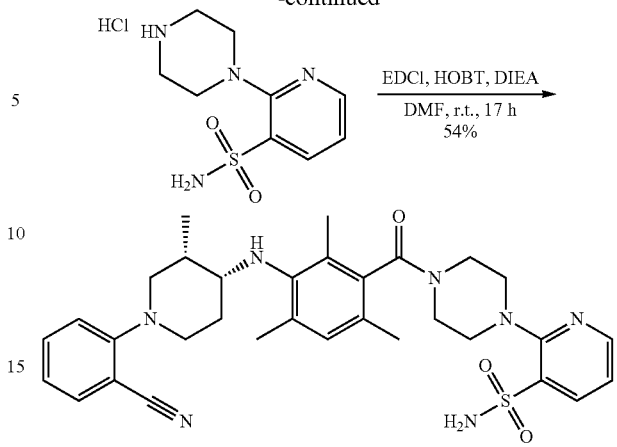

Procedures and Characterization:

Step 1: 3-(((3S,4R)-1-(2-cyanophenyl)-3-methylpiperidin-4-yl)amino)-2,4,6-trimethylbenzoic Acid methyl 3-[[(3 S,4R)-1-(2-cyanophenyl)-3-methyl-4-piperidyl]amino]-2,4,6-trimethyl-benzoate (300.00 mg, 766.28 umol), BBr3 (2.94 g, 2.00 mmol, 2.00 mL, 17% purity) were dissolved in DCM (5.00 mL). Then the mixture was stirred at −40-20 OC for 3 hour. The solvent was evaporated and to the residue was added water (50 mL) and the resulting mixture was extracted with DCM (30 mL×3). The combined organic layers were washed with water, brine, dried (Na2SO4), filtered and the filtrate was concentrated to give 3-[[(3S,4R)-1-(2-cyanophenyl)-3-methyl-4-piperidyl]amino]-2,4,6-trimethyl-benzoic acid (220.00 mg, 582.81 umol, 76%) as a white solid. ESI-MS (EI+, m/z): 278.3 [M+H]+.

Step 2: 2-(4-(3-(((3S,4R)-1-(2-cyanophenyl)-3-methylpiperidin-4-yl)amino)-2,4,6-trimethylbenzoyl)piperazin-1-yl)pyridine-3-sulfonamide 3-[[(3R,4S)-1-(2-cyanophenyl)-3-methyl-4-piperidyl]amino]-2,4,6-trimethyl-benzoic acid (150.00 mg, 397.37 umol), 2-piperazin-1-yl pyridine3-[[(3S,4R)-1-(2-cyanophenyl)-3-methyl-4-piperidyl]amino]-2,4,6-trimethyl-benzoic acid (220.00 mg, 582.81 umol), 2-piperazin-1-ylpyridine-3-sulfonamide (243.70 mg, 874.21 umol, HCl), HOBT (157.50 mg, 1.17 mmol), EDCI (223.45 mg, 1.17 mmol), DIEA (451.94 mg, 3.50 mmol, 610.73 uL) were dissolved in DMF (5.00 mL). Then the mixture was stirred at 20° C. for 17 hour. The mixture was filtered and the filtrate was purified via preparative HPLC to give 2-[4-[3-[[(3S,4R)-1-(2-cyanophenyl)-3-methyl-4-piperidyl]amino]-2,4,6-trimethyl-benzoyl]piperazin-1-yl]pyridine-3-sulfonamide (192.10 mg, 319.23 umol, 54%) as a white solid. ESI-MS (EI+, m/z): 602.3 [M+H]+. 1H NMR (500 MHz, CDCl3) δ 8.56-8.54 (m, 1H), 8.28-8.26 (m, 1H), 7.54-7.52 (d, J=8.0 Hz, 1H), 7.47-7.44 (m, 1H), 7.27-7.24 (m, 1H), 6.99-6.96 (m, 2H), 6.85 (d, J=2.5 Hz, 1H), 5.58 (s, 2H), 4.07-3.99 (m, 2H), 3.58-3.46 (m, 2H), 3.39-3.31 (m, 4H), 3.15-3.10 (m, 2H), 2.80-2.54 (m, 4H), 2.27-2.17 (m, 9H), 1.87-1.76 (m, 2H), 1.62-1.51 (m, 1H), 1.22-1.17 (dd, J=16, 6.5 Hz, 3H).

Example 138: 2-(4-(3-(((3R,4R)-1-(2-cyanophenyl)-3-methylpiperidin-4-yl)amino)-2,4,6-trimethylbenzoyl)piperazin-1-yl)pyridine-3-sulfonamide, I-180

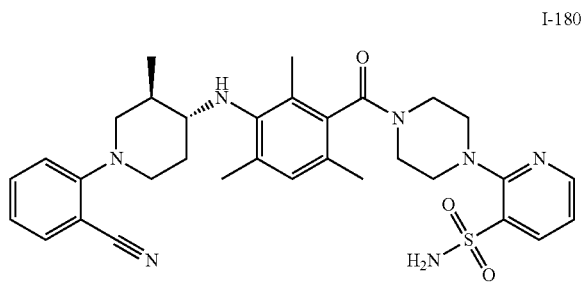 [SMILES: Cc1cc(C)c(C(=O)N2CCN(c3ncccc3S(N)(=O)=O)CC2)c(C)c1N[C@@H]1CCN(c2ccccc2C#N)C[C@H]1C]

Synthetic Scheme:

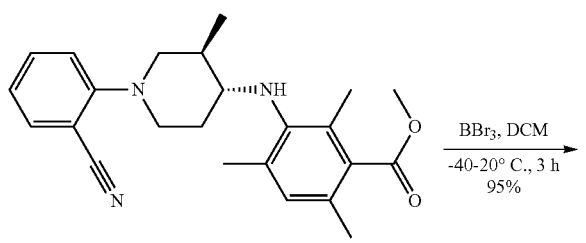

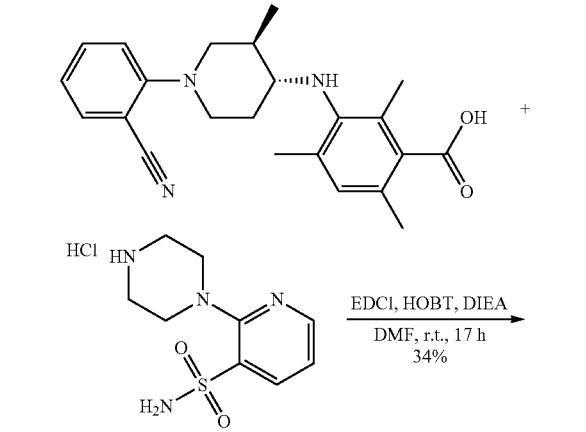

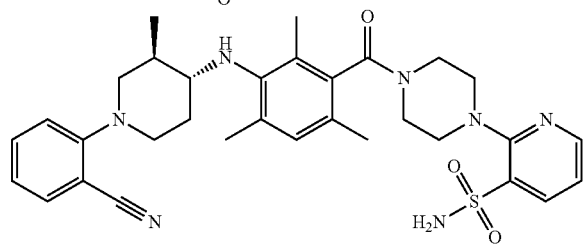

Procedures and Characterization:

Step 1: 3-(((3R,4R)-1-(2-cyanophenyl)-3-methylpiperidin-4-yl)amino)-2,4,6-trimethylbenzoic Acid methyl 3-[[(3R,4R)-1-(2-cyanophenyl)-3-methyl-4-piperidyl]amino]-2,4,6-trimethyl-benzoate (500.00 mg, 1.28 mmol), BBr$_3$ (9.43 g, 6.40 mmol, 5.00 mL, 17% purity) were dissolved in DCM (5.00 mL). Then the mixture was stirred at −40-20° C. for 3 hour. The solvent was evaporated and to the residue was added water (50 mL) and extracted with DCM (30 mL×3). The combined organic layer was washed with water, brine, dried (Na$_2$SO$_4$), filtered and the filtrate was concentrated to give 3-[[(3R,4R)-1-(2-cyanophenyl)-3-methyl-4-piperidyl]amino]-2,4,6-trimethyl-benzoic acid (460.00 mg, 1.22 mmol, 95%) as a red solid. ESI-MS (EI$^+$, m/z): 278.3 [M+H]$^+$.

Step 2: 2-(4-(3-(((3R,4R)-1-(2-cyanophenyl)-3-methylpiperidin-4-yl)amino)-2,4,6-trimethylbenzoyl)piperazin-1-yl)pyridine-3-sulfonamide 3-[[(3R,4R)-1-(2-cyanophenyl)-3-methyl-4-piperidyl]amino]-2,4,6-trimethyl-benzoic acid (150.00 mg, 397.37 umol), 2-piperazin-1-ylpyridine-3-sulfonamide (166.16 mg, 596.06 umol, HCl), HOBT (107.39 mg, 794.74 umol), EDCI (152.35 mg, 794.74 umol), DIEA (308.14 mg, 2.38 mmol, 0.42 uL) were dissolved in DMF (5.00 mL). Then the mixture was stirred at 20° C. for 17 hour. The mixture was filtered and the filtrate was purified via preparative HPLC to give 2-[4-[3-[[(3R,4R)-1-(2-cyanophenyl)-3-methyl-4-piperidyl]amino]-2,4,6-trimethyl-benzoyl]piperazin-1-yl]pyridine-3-sulfonamide (82.30 mg, 136.77 umol, 34%) as a white solid. ESI-MS (EI$^+$, m/z): 602.3 [M+H]$^+$. $^1$H NMR (500 MHz, CDCl$_3$) δ 8.57-8.55 (m, 1H), 8.30-8.28 (m, 1H), 7.55-7.53 (m, 1H), 7.47-7.44 (m, 1H), 7.28-7.26 (m, 1H), 7.00-6.97 (m, 2H), 6.86 (s, 1H), 5.56 (s, 2H), 4.05-4.01 (m, 2H), 3.46-3.32 (m, 6H), 3.19-2.99 (m, 5H), 3.32-3.22 (m, 1H), 2.27-2.18 (m, 10H), 1.89 (m, 1H), 1.68-1.66 (m, 1H), 1.30-1.25 (dd, J=16, 7.0 Hz, 3H).

Example 139: 2-(4-(3-(((3S,4S)-1-(2-cyanophenyl)-3-methylpiperidin-4-yl)amino)-2,4,6-trimethylbenzoyl)piperazin-1-yl)pyridine-3-sulfonamide, I-181

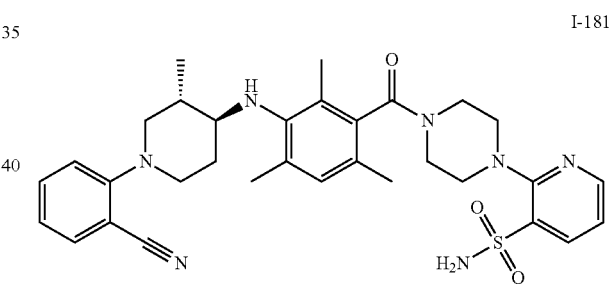

Synthetic Scheme:

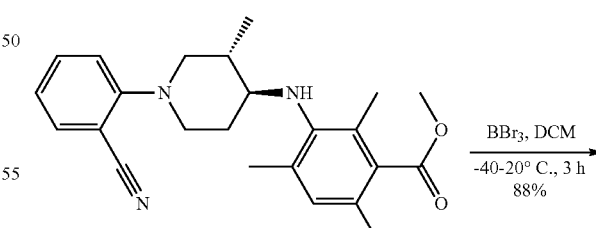

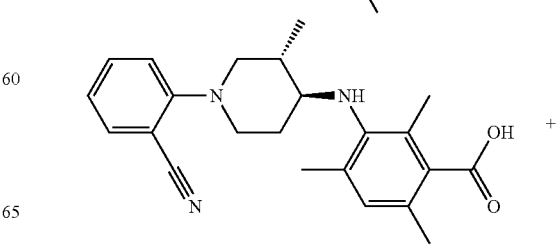

Example 140: (S)-2-(4-(3-((1-(2-cyano-4-fluorophenyl)piperidin-4-yl)amino)-2,4,6-trimethylbenzoyl)-3-methylpiperazin-1-yl)-6-fluorobenzenesulfonamide, I-182

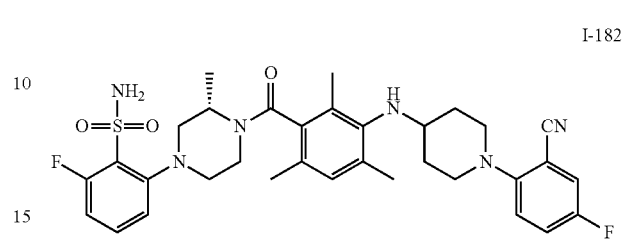

I-182

Synthetic Scheme:

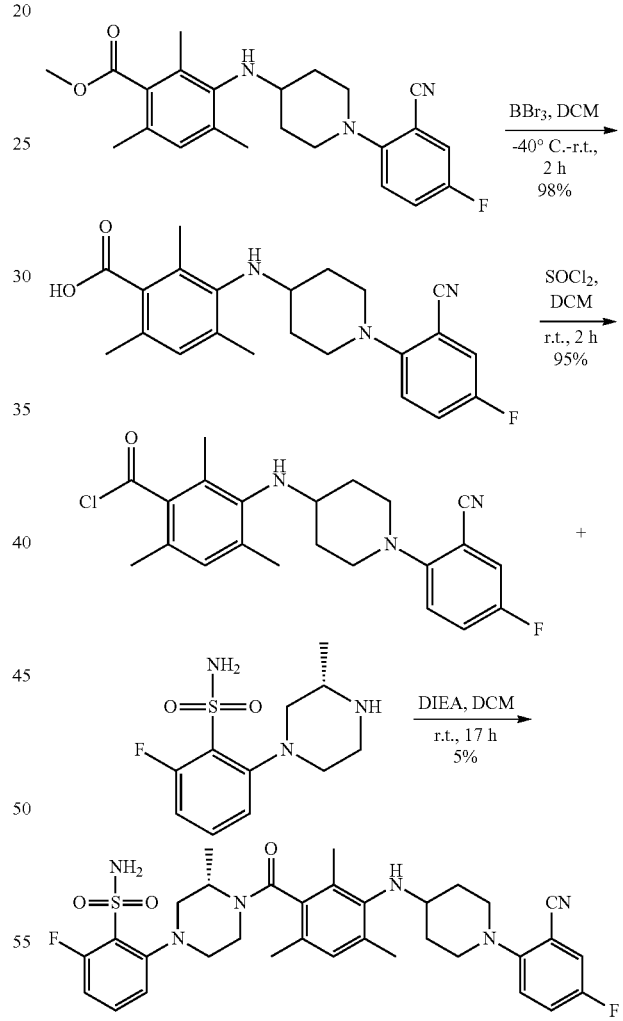

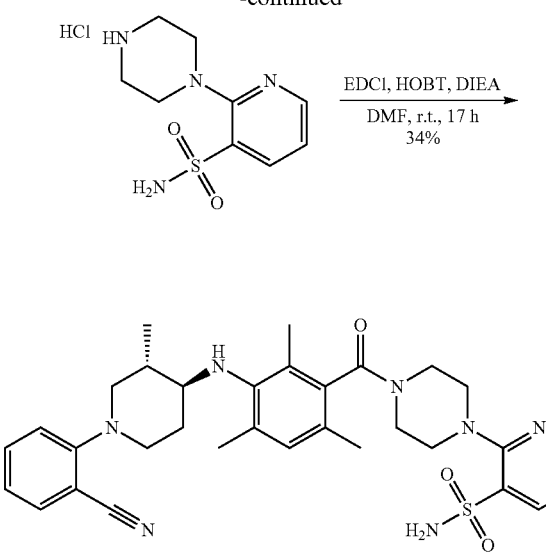

Procedures and Characterization:

Step 1: 3-(((3S,4S)-1-(2-cyanophenyl)-3-methylpiperidin-4-yl)amino)-2,4,6-trimethylbenzoic Acid methyl 3-[[(3 S,4S)-1-(2-cyanophenyl)-3-methyl-4-piperidyl]amino]-2,4,6-trimethyl-benzoate (550.00 mg, 1.40 mmol), BBr$_3$ (6.23 g, 4.23 mmol, 6.00 mL, 17% purity) were dissolved in DCM (5.00 mL). Then the mixture was stirred at −40-20° C. for 3 hour. The solvent was evaporated and the residue was added water (50 mL) and extracted with DCM (30 mL×3). The combined organic layer was washed with water, brine, dried (Na$_2$SO$_4$), filtered and the filtrate was concentrated to give 3-[[(3S,4S)-1-(2-cyanophenyl)-3-methyl-4-piperidyl]amino]-2,4,6-trimethyl-benzoic acid (470.00 mg, 1.25 mmol, 88%) as a red solid. ESI-MS (EI$^+$, m/z): 278.3 [M+H]$^+$.

Step 2: 2-(4-(3-(((3S,4S)-1-(2-cyanophenyl)-3-methylpiperidin-4-yl)amino)-2,4,6-trimethylbenzoyl)piperazin-1-yl)pyridine-3-sulfonamide 3-[[(3 S,4S)-1-(2-cyanophenyl)-3-methyl-4-piperidyl]amino]-2,4,6-trimethyl-benzoic acid (150.00 mg, 397.37 umol), 2-piperazin-1-ylpyridine-3-sulfonamide (166.16 mg, 596.06 umol, HCl), HOBT (107.39 mg, 794.74 umol), EDCI (152.35 mg, 794.74 umol), DIEA (308.14 mg, 2.38 mmol, 0.42 uL) were dissolved in DMF (5.00 mL). Then the mixture was stirred at 20° C. for 17 hour. The mixture was filtered and the filtrate was purified via preparative HPLC to give 2-[4-[3-[[(3S,4S)-1-(2-cyanophenyl)-3-methyl-4-piperidyl]amino]-2,4,6-trimethyl-benzoyl]piperazin-1-yl]pyridine-3-sulfonamide (82.30 mg, 136.77 umol, 34%) as a white solid. ESI-MS (EI$^+$, m/z): 602.3 [M+H]$^+$. $^1$H NMR (500 MHz, CDCl$_3$) δ 8.56-8.54 (m, 1H), 8.28-8.26 (m, 1H), 7.55-7.53 (m, 1H), 7.45-7.44 (m, 1H), 7.27-7.25 (m, 1H), 7.00-6.97 (m, 2H), 6.85 (s, 1H), 5.66 (s, 2H), 4.05-4.01 (m, 2H), 3.46-3.32 (m, 6H), 3.19-2.99 (m, 5H), 3.32-3.22 (m, 1H), 2.27-2.18 (m, 10H), 1.89 (m, 1H), 1.68-1.66 (m, 1H), 1.29-1.25 (dd, J=15.5, 8.0 Hz, 3H).

Procedures and Characterization:

Step 1: 3-((1-(2-cyano-4-fluorophenyl)piperidin-4-yl)amino)-2,4,6-trimethylbenzoic Acid A mixture of methyl 3-[[1-(2-cyano-4-fluoro-phenyl)-4-piperidyl]amino]-2,4,6-trimethyl-benzoate (20 g, 50.57 mmol) in DCM (40 mL) was cooled down to −40° C., BBr$_3$ (41.05 g, 163.87 mmol, 15.79 mL) was added into it, the resulting mixture was kept stirring at 10° C. for 2 hour. The mixture was quenched with ice-water, dissolved in water (50 mL), adjusted pH-5 with $Na_2CO_3$, extracted with DCM (1.5 L*2), the organic layer was washed with water (500 mL), brine, dried over $Na_2SO_4$, filtrated and concentrated by vacuo to give product 3-[[1-(2-cyano-4-fluoro-phenyl)-4-piperidyl]amino]-2,4,6-trimethyl-benzoic acid (19 g, 49.81 mmol, 98%) was yellow solid. ESI-MS (EI+, m/z): 382.1 [M+H]+.

Step 2: 3-((1-(2-cyano-4-fluorophenyl)piperidin-4-yl)amino)-2,4,6-trimethylbenzoyl Chloride A mixture of 3-[[1-(2-cyano-4-fluoro-phenyl)-4-piperidyl]amino]-2,4,6-trimethyl-benzoic acid (200 mg, 524.33 umol) in DCM (5 mL) was added $SOCl_2$ (0.5 mL), then stirred at 20° C. for 2 hour. The mixture was concentrated to obtain 3-[[1-(2-cyano-4-fluoro-phenyl)-4-piperidyl]amino]-2,4,6-trimethyl-benzoyl chloride (200 mg, 500.14 umol, 95%) as yellow solid, which was used in the next step without further purification.

Step 3: (S)-2-(4-(3-((1-(2-cyano-4-fluorophenyl)piperidin-4-yl)amino)-2,4,6-trimethylbenzoyl)-3-methylpiperazin-1-yl)-6-fluorobenzenesulfonamide 2-fluoro-6-[(3S)-3-methylpiperazin-1-yl]benzenesulfonamide (140 mg, 512.21 umol), 3-[[1-(2-cyano-4-fluoro-phenyl)-4-piperidyl]amino]-2,4,6-trimethyl-benzoyl chloride (204.83 mg, 512.21 umol), DIEA (330.99 mg, 2.56 mmol, 446.08 uL) were dissolved in DCM (5 mL). Then the mixture was stirred at 20° C. for 17 hour. The mixture was purified via preparative HPLC to give 2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-benzenesulfonamide (17.6 mg, 27.64 umol, 5%) as a white solid. ESI-MS (EI+, m/z): 637.1 [M+H]+. 1H NMR (400 MHz, $CDCl_3$) δ 7.56-7.44 (m, 1H), 7.30-7.16 (m, 1H), 7.09-6.96 (m, 3H), 6.91-6.85 (m, 1H), 5.76-5.72 (m, 2H), 5.21-4.82 (m, 1H), 3.78-3.52 (m, 1H), 3.47-3.17 (m, 5H), 3.03-2.57 (m, 5H), 2.29-2.22 (m, 7H), 2.21-1.96 (m, 5H), 1.75-1.58 (m, 3H), 1.52-1.48 (m, 2H), 1.36-1.32 (m, 1H).

Example 141: (S)-(2,4-dimethyl-5-(1-(2-(trifluoromethoxy)phenyl)piperidin-4-ylamino)phenyl)(3-(hydroxymethyl)-4-(pyridin-2-yl)piperazin-1-yl)methanone, I-183

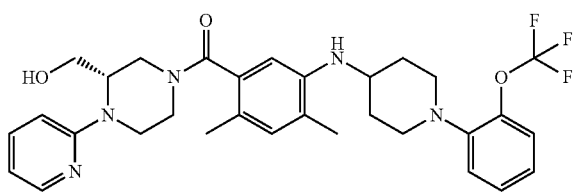

Synthetic Scheme:

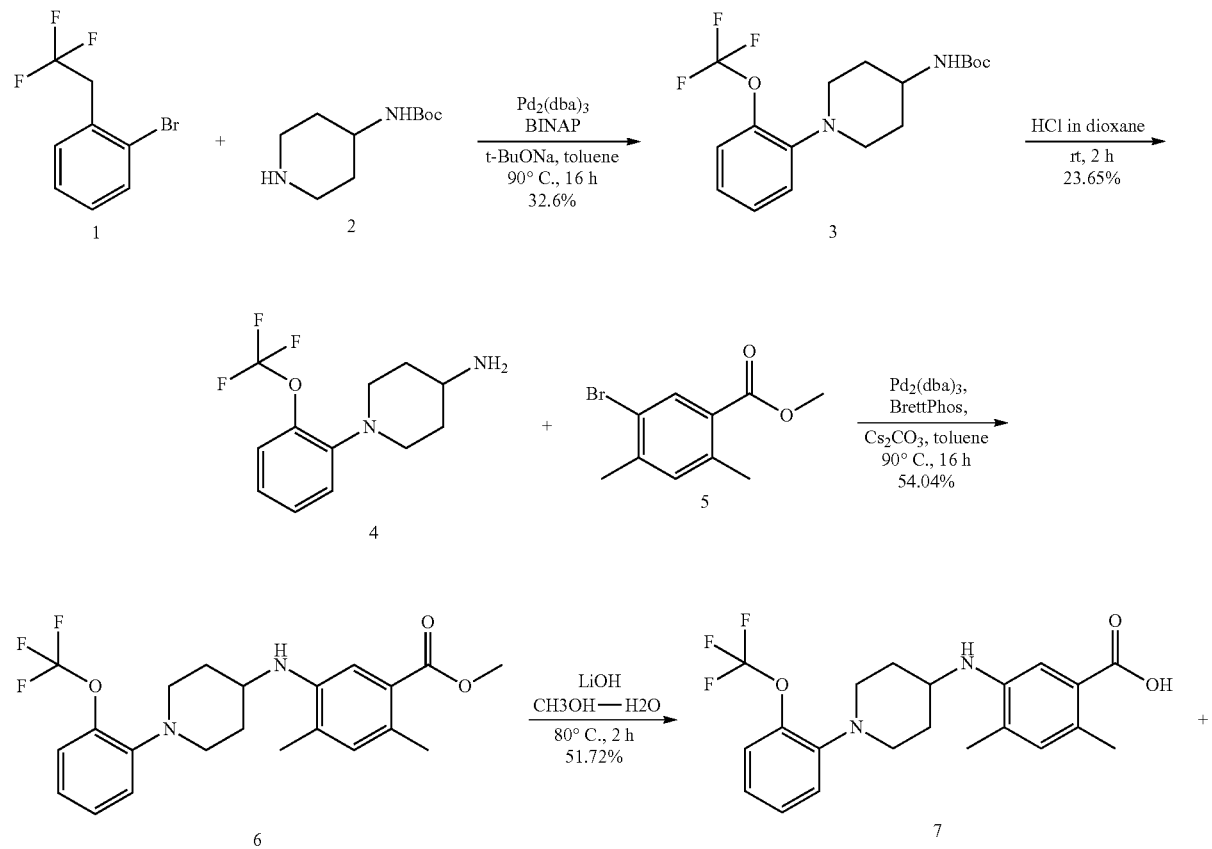

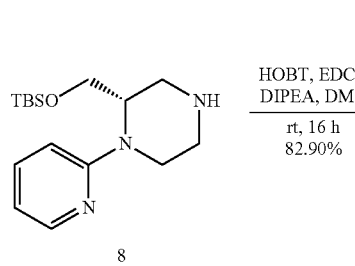
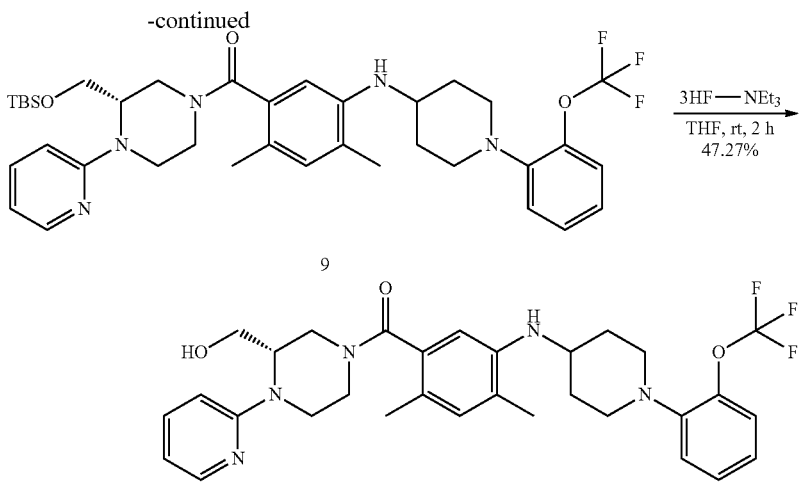

Procedures and Characterization:

Step 1: tert-butyl 1-(2-(trifluoromethoxy)phenyl)piperidin-4-ylcarbamate

A mixture of 1-bromo-2-(trifluoromethoxy)benzene (2.40 g, 9.96 mmol), tert-butyl N-(4-piperidyl)carbamate (1.99 g, 9.96 mmol), Pd$_2$(dba)$_3$ (546 mg, 597 umol), BINAP (744 mg, 1.20 mmol), t-BuONa (6.47 g, 69 mmol) in toluene (50 mL) was stirred at 90° C. for 16 h. Cooled to rt, filtered and concentrated, eluted with EtOAc (50 mL), washed with H$_2$O (100 mL), then extracted with EtOAc (100 mL×3), washed with brine (50 mL×2), dried, concentrated to afford methyl 5-formyl-2,4-dimethylbenzoate (1.6 g, 32.6%) as brown gum. ESI-MS (EI+, m/z): 361 [M+H]$^+$.

Step 2: 1-(2-(trifluoromethoxy)phenyl)piperidin-4-amine

A mixture of tert-butyl N-[1-[2-(trifluoromethoxy)phenyl]-4-piperidyl]carbamate (1.6 g, 4.44 mmol) in HCl in dioxane (4 M, 28 mmol, 7 mL) was stirred at 25° C. for 2 h. The mixture was cooled to rt, quenched with water (50 mL), extracted with EtOAc (100 mL×3), the pH was adjusted to 8-9, extracted with CH$_2$Cl2/CH$_3$OH=10/1 (50 mL×3), dried and concentrated to obtain 1-[2-(trifluoromethoxy)phenyl]piperidin-4-amine (273 mg, 23.65%). ESI-MS (EI+, m/z): 261 [M+H]$^+$. $^1$H NMR (400 MHz, DMSO-d6) δ 7.32-7.21 (m, 2H), 7.13 (dd, J=8.0, 1.3 Hz, 1H), 7.06-6.99 (m, 1H), 3.25 (d, J=12.1 Hz, 2H), 2.68 (d, J=10.5 Hz, 4H), 1.80 (d, J=10.9 Hz, 2H), 1.36 (m, 2H).

Step 3: methyl 2,4-dimethyl-5-(1-(2-trifluoromethoxyphenyl)piperidin-4-yl-amino)benzoate 1-[2-(trifluoromethoxy)phenyl]piperidin-4-amine (276 mg, 1.06 mmol), methyl 5-bromo-2,4-dimethyl-benzoate (257 mg, 1.06 mmol), Pd$_2$(dba)$_3$ (58 mg, 63 umol), BrettPhos (79 mg, 127 umol), Cs$_2$CO$_3$ (482 mg, 1.48 mmol) in toluene (10 mL) was stirred at 90° C. for 16 h. The mixture was filtered through celite, H$_2$O (50 mL) was added, then extracted with EtOAc (50 mL×3), combined the organic layers, concentrated to give a residue which was purified by flash column (PE/EA=7/3) to afford methyl 2,4-dimethyl-5-(1-(2-(trifluoromethoxy)phenyl)piperidin-4-ylamino)benzoate (242 mg, 54.04%) as a pale white solid. ESI-MS (EI+, m/z): 423 [M+H]$^+$.

Step 4: 2,4-dimethyl-5-(1-(2-(trifluoromethoxy)phenyl)piperidin-4-ylamino)benzoic Acid 2,4-dimethyl-5-[[1-[2-(trifluoromethoxy)phenyl]-4-piperidyl]amino]benzoate (200 mg, 473 umol) in CH$_3$OH (2 mL) was added LiOH—H$_2$O (198 mg, 4.73 mmol), then the mixture was stirred at 50° C. for 2 h. The solvent was removed and quenched with H$_2$O (10 mL), the pH adjusted to 5~6, extracted with EtOAc (50 mL×3), concentrated and the crude product was purified via silica gel chromatography eluting with PE/EA from 20/1 to 10/1 to obtain 2,4-dimethyl-5-[[1-[2-(trifluoro methoxy)phenyl]-4-piperidyl]amino]benzoic acid (100 mg, 51.72%) as white solid. ESI-MS (EI+, m/z): 409 [M+H]$^+$. $^1$H NMR (500 MHz, CDCl$_3$) δ 7.38 (s, 1H), 7.24-7.17 (m, 2H), 7.05 (dd, J=8.0, 1.3 Hz, 1H), 7.01-6.96 (m, 2H), 3.61-3.50 (m, 1H), 3.41 (d, J=12.2 Hz, 2H), 2.88 (dd, J=16.6, 6.4 Hz, 2H), 2.53 (s, 3H), 2.22 (d, J=10.8 Hz, 2H), 2.17 (s, 3H), 1.65 (t, J=13.9, 3.6 Hz, 2H).

Step 5: (S)-(3-((tert-butyldimethylsilyloxy)methyl)-4-(pyridin-2-yl)piperazin-1-yl)(2,4-dimethyl-5-(1-(2-(trifluoromethoxy)phenyl)piperidin-4-ylamino)phenyl)methanone A mixture of 2,4-dimethyl-5-[[1-[2-(trifluoromethoxy)phenyl]-4-piperidyl]amino]benzoic acid (60 mg, 146 umol), tert-butyl-dimethyl-[2-[(2R)-1-(2-pyridyl)piperazin-2-yl]ethoxy] silane (47 mg, 146 umol), HOBT (29 mg, 220 umol), EDCI (43 mg, 220 umol), DIPEA (47 mg, 367 umol) in DMF (3 mL) was stirred at 25° C. for 16 h. The mixture was washed with H$_2$O (20 mL), extracted with EtOAc (50 mL×3), dried and concentrated to obtain [(3S)-3-[[tert-butyl(dimethyl)silyl]oxymethyl]-4-(2-pyridyl)piperazin-1-yl]-[2,4-dimethyl-5-[[1-[2-(trifluoromethoxy) phenyl]-4-piperidyl]amino]phenyl]methanone (85 mg, 82.90%) as white solid. ESI-MS (EI+, m/z): 698 [M+H]$^+$.

Step 6: (S)-(2,4-dimethyl-5-(1-(2-(trifluoromethoxy)phenyl)piperidin-4-ylamino)phenyl)(3-(hydroxymethyl)-4-(pyridin-2-yl)piperazin-1-yl)methanone

[(3 S)-3-[[tert-butyl(dimethyl)silyl]oxymethyl]-4-(2-pyridyl)piperazin-1-yl]-[2,4-dimethyl-5-[[1-[2-(trifluoromethoxy)phenyl]-4-piperidyl]amino]phenyl]methanone (86 mg, 123 umol), 3HF-TEA (246 umol, 500 uL) in THF (2 mL) was stirred at 25° C. for 2 h. Further purification by preparative HPLC provided [2,4-dimethyl-5-[[1-[2-(trifluoromethoxy)phenyl]-4-piperidyl]amino]phenyl]-[(3S)-3-(hydroxymethyl)-4-(2-pyridyl)piperazin-1-yl]methanone (34 mg, 47.27%) as a white solid. ESI-MS (EI+, m/z): 584 [M+H]+. $^1$H NMR (500 MHz, MeOD) δ 8.10 (d, J=3.8 Hz, 1H), 7.62-7.53 (m, 1H), 7.28 (t, J=7.7 Hz, 1H), 7.22 (d, J=8.1 Hz, 1H), 7.17 (d, J=8.0 Hz, 1H), 7.04 (t, J=7.2 Hz, 1H), 6.97 (s, 1H), 6.88-6.81 (m, 1H), 6.72-6.66 (m, 1H), 6.65-6.45 (m, 1H), 4.66 (d, J=97.2 Hz, 1H), 4.50-3.98 (m, 2H), 3.59 (m, 8H), 3.14 (s, 1H), 2.86 (d, J=10.7 Hz, 2H), 2.31-2.06 (m, 8H), 1.71 (d, J=9.7 Hz, 2H)

Example 142: (S)-(5-(1-(2-(difluoromethoxy)phenyl)piperid in-4-ylamino)-2,4-dimethylphenyl)(3-(hydroxymethyl)-4-(pyridin-2-yl)piperazin-1-yl) methanone, I-184

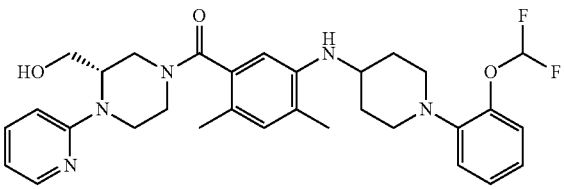

Synthetic Scheme:

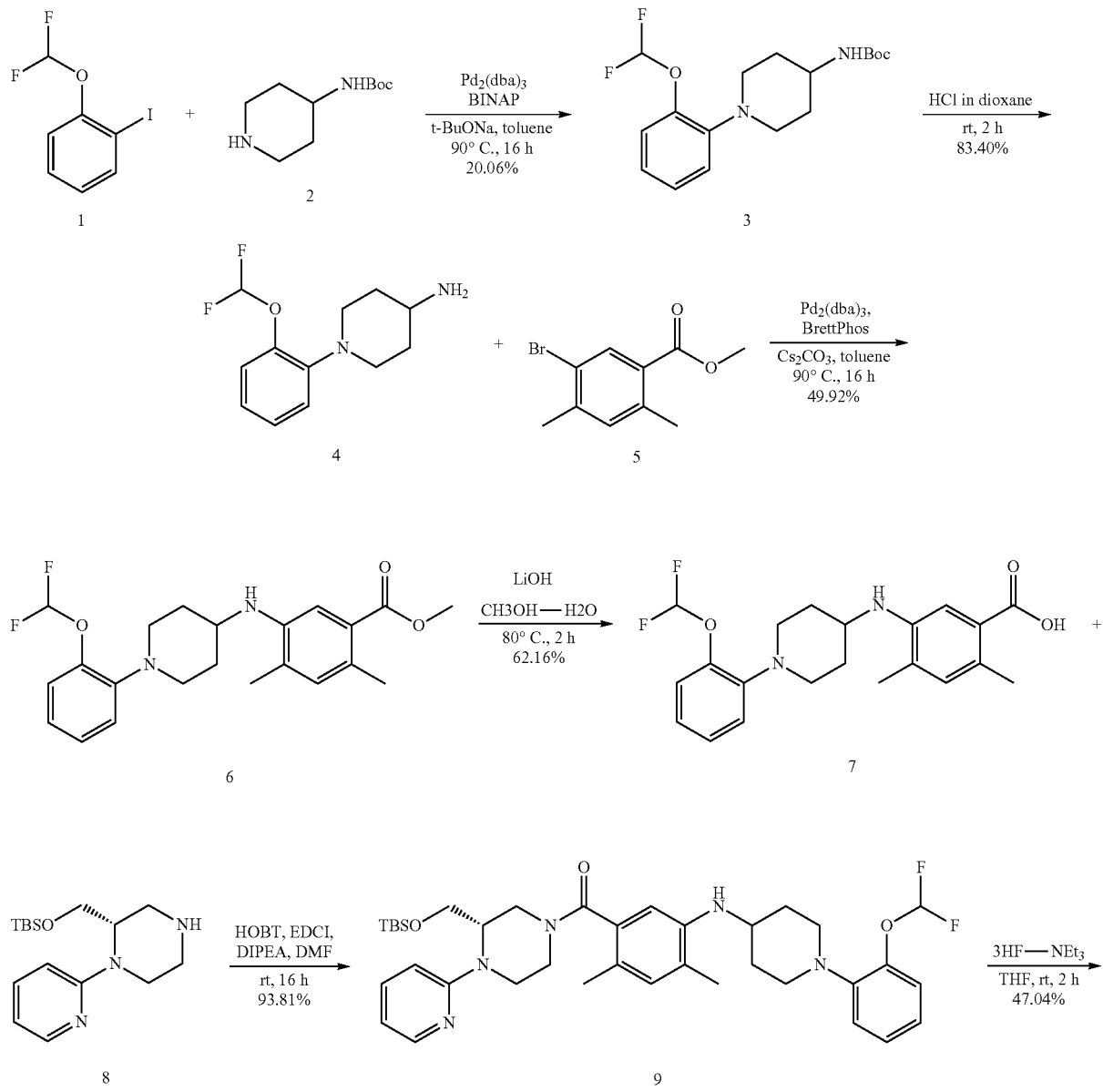

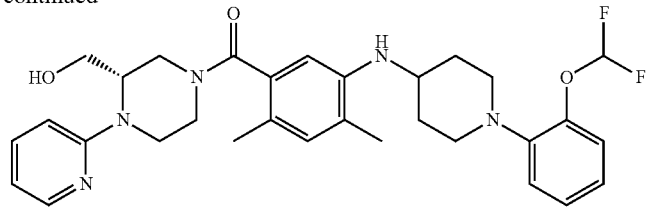

Procedures and Characterization:

Step 1: tert-butyl 1-(2-(difluoromethoxy)phenyl) piperidin-4-ylcarbamate 1-(difluoromethoxy)-2-iodo-benzene (2.7 g, 9.99 mmol), tert-butyl N-(4-piperidyl) carbamate (2 g, 9.99 mmol), Pd$_2$(dba)$_3$ (540 mg, 600 umol), BINAP (740 mg, 1.19 mmol), t-BuONa (1.91 g, 20 mmol) in toluene (50 mL) was stirred at 90° C. for 16 h. The mixture was cooled to rt, quenched with H$_2$O (100 mL), then extracted with EtOAc (50 mL×3), washed with brine (50 mL×3), dried, concentrated and purified via silica gel chromatography eluting with PE/EA from 20/1 to 1/1 to afford methyl tert-butyl 1-(2-(difluoromethoxy)phenyl)piperidin-4-ylcarbamate (686 mg, 20.06%) as brown solid. MS (EI+, m/z): 343 [M+H]$^+$.

Step 2: 1-(2-(difluoromethoxy)phenyl)piperidin-4-amine

A mixture of tert-butyl N-[1-[2-(difluoromethoxy)phenyl]-4-piperidyl]carbamate (500 mg, 1.46 mmol) in HCl in dioxane (4M, 20 mmol, 5 mL) was stirred at 25° C. for 2 h then quenched with water (50 mL), extracted with EtOAc (50 mL×3), adjusted the pH to 8-9, extracted with CH$_2$Cl$_2$/CH$_3$OH=10/1 (50 mL×3), dried and concentrated to obtain 1-[2-(trifluoromethoxy)phenyl]piperidin-4-amine (295 mg, 83.40%). ESI-MS (EI+, m/z): 243 [M+H]$^+$. $^1$H NMR (500 MHz, CDCl$_3$) δ 7.20-7.14 (m, 1H), 7.10 (d, J=7.1 Hz, 1H), 7.04-6.95 (m, 2H), 6.61 (t, J=76.1 Hz, 1H), 3.39 (d, J=12.1 Hz, 2H), 2.81 (d, J=10.3 Hz, 1H), 2.69 (dd, J=16.8, 6.6 Hz, 2H), 1.93 (d, J=12.0 Hz, 2H), 1.54-1.46 (m, 3H).

Step 3: methyl 5-(1-(2-(difluoromethoxy)phenyl)piperidin-4-ylamino)-2,4-dimethylbenzoate 1-[2-(difluoromethoxy)phenyl]piperidin-4-amine (240 mg, 990 umol), methyl 5-bromo-2,4-dimethyl-benzoate (240 mg, 990 umol), Pd$_2$(dba)$_3$ (54 mg, 59 umol), BrettPhos (73 mg, 118 umol), Cs$_2$CO$_3$ (450 mg, 1 mmol) in toluene (5 mL) was stirred at 90° C. for 16 h. The mixture was filtered by celite, the filtrate was concentrated and was purified via silica gel chromatography eluting with PE/EA from 50/1 to 20/1 to obtain methyl 5-[[1-[2-(difluoromethoxy)phenyl]-4-piperidyl]amino]-2,4-dimethyl-benzoate (200 mg, 49.92%) as white solid. ESI-MS (EI+, m/z): 405 [M+H]$^+$.

Step 4: 5-(1-(2-(difluoromethoxy)phenyl)piperidin-4-ylamino)-2,4-dimethylbenzoic Acid To methyl 5-[[1-[2-(difluoromethoxy)phenyl]-4-piperidyl]amino]-2,4-dimethyl-benzoate (200 mg, 494 umol) in CH$_3$OH (5 mL) was added LiOH—H$_2$O (207 mg, 4 mmol), then the mixture was stirred at 50° C. for 3 h. The pH was adjusted to 5-6, then extracted with EtOAc (50 mL×3), washed with brine (50 mL), dried over Na$_2$SO$_4$ and concentrated to obtain 5-[[1-[2-(difluoromethoxy)phenyl]-4-piperidyl]amino]-2,4-dimethyl-benzoic acid (120 mg, 62.16%) as yellow solid. ESI-MS (EI+, m/z): 391 [M+H]$^+$. $^1$H NMR (500 MHz, CDCl$_3$) δ 7.37 (s, 1H), 7.19 (td, J=7.8, 1.5 Hz, 1H), 7.12 (d, J=7.0 Hz, 1H), 7.07-6.96 (m, 3H), 6.62 (t, J=75.8 Hz, 1H), 3.60-3.51 (m, 1H), 3.43 (d, J=12.2 Hz, 2H), 2.87 (t, J=10.6 Hz, 2H), 2.53 (s, 3H), 2.24 (d, J=12.2 Hz, 2H), 2.18 (s, 3H), 1.64 (t, J=13.8, 3.6 Hz, 2H).

Step 5: (S)-(3-((tert-butyldimethylsilyloxy)methyl)-4-(pyridin-2-yl)piperazin-1-yl)(5-(1-(2-(difluoromethoxy)phenyl)piperidin-4-ylamino)-2,4-dimethylphenyl)methanone A mixture of 5-[[1-[2-(difluoromethoxy)phenyl]-4-piperidyl]amino]-2,4-dimethyl-benzoic acid (60 mg, 153 umol), tert-butyl-dimethyl-[(2R)-1-(2-pyridyl)piperazin-2-yl]oxysilane (45 mg, 153 umol), HOBT (31 mg, 230 umol), EDCI (45 mg, 230 umol), DIPEA (49 mg, 384 umol) in DMF (3 mL) was stirred at 25° C. for 16 h. The reaction mixture was quenched with H$_2$O (10 mL), extracted with EtOAc (50 mL×3), dried and concentrated to obtain (S)-(3-((tert-butyldimethylsilyloxy)methyl)-4-(pyridin-2-yl)piperazin-1-yl)(5-(1-(2-(difluoromethoxy) phenyl)piperidin-4-ylamino)-2,4-dimethylphenyl)methanone (96 mg, 93.81%) as white solid. ESI-MS (EI+, m/z): 666 [M+H]$^+$.

Step 6: (S)-(5-(1-(2-(difluoromethoxy)phenyl)piperidin-4-ylamino)-2,4-dimethylphenyl)(3-(hydroxymethyl)-4-(pyridin-2-yl)piperazin-1-yl)methanone

[(3S)-3-[[tert-butyl(dimethyl)silyl]oxymethyl]-4-(2-pyridyl)piperazin-1-yl]-[5-[[1-[2-(difluoromethoxy)phenyl]-4-piperidyl]amino]-2,4-dimethyl-phenyl]methanone (92 mg, 135 umol), 3HF-TEA (270 umol, 500 uL) in THF (2 mL) was stirred at 25° C. for 2 h. The mixture was then purifies by preparative HPLC to obtain [5-[[1-[2-(difluoromethoxy)phenyl]-4-piperidyl]amino]-2,4-dimethyl-phenyl]-[(3S)-3-(hydroxymethyl)-4-(2-pyridyl)piperazin-1-yl] methanone (36 mg, 47.04%) as white solid. ESI-MS (EI+, m/z): 566 [M+H]$^+$. $^1$H NMR (500 MHz, MeOD) δ 8.10 (d, J=3.9 Hz, 1H), 7.58 (t, J=7.6 Hz, 1H), 7.21 (t, J=7.4 Hz, 1H), 7.15 (d, J=7.7 Hz, 1H), 7.10 (d, J=7.7 Hz, 1H), 7.02 (t, J=7.4 Hz, 1H), 6.97 (d, J=10.0 Hz, 1H), 6.86 (dd, J=8.5, 5.1 Hz, 1H), 6.68 (dd, J=14.5, 9.1 Hz, 1H), 6.63-6.45 (m, 1H), 4.66 (d, J=92.3 Hz, 1H), 4.36 (d, J=56.0 Hz, 1H), 4.09 (dd, J=58.9, 13.0 Hz, 1H), 3.85-3.39 (m, 8H), 3.13 (d, J=14.9 Hz, 1H), 2.87 (d, J=31.9 Hz, 2H), 2.31-2.04 (m, 8H), 1.72 (d, J=10.4 Hz, 2H).

Example 143: 3-(4-(3-(1-(3-chloropyridin-2-yl)piperidin-4-ylamino)-2,4,6-trimethyl benzoyl)piperazin-1-yl)pyridine-2-sulfonamide, I-185

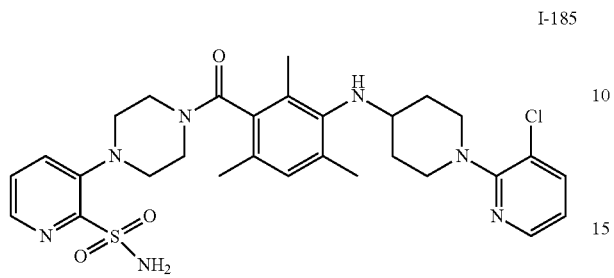

I-185

Synthetic Scheme:

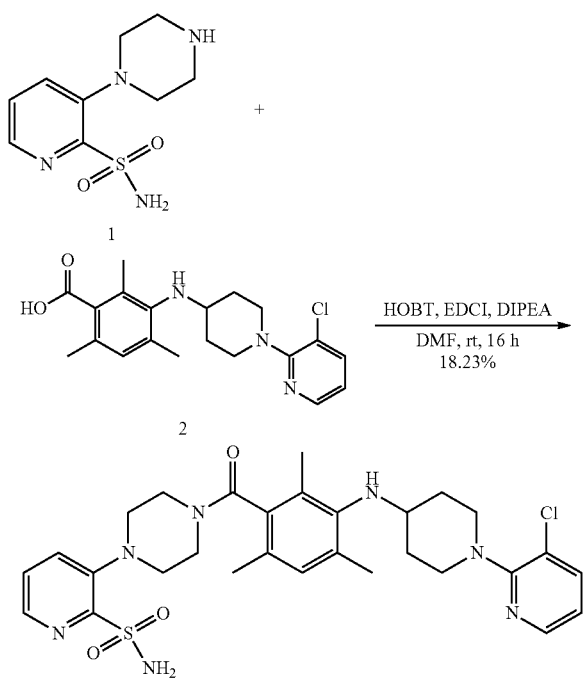

Procedures and Characterization:

Step 1: 3-(4-(3-(1-(3-chloropyridin-2-yl)piperidin-4-ylamino)-2,4,6-trimethylbenzoyl) piperazin-1-yl)pyridine-2-sulfonamide A mixture of 3-[[1-(3-chloro-2-pyridyl)-4-piperidyl]amino]-2,4,6-trimethyl-benzoic acid (92 mg, 247 umol), HOBT (50 mg, 371 umol), EDCI (73 mg, 371 umol), DIPEA (80 mg, 619 umol, 108 uL) in DMF (3 mL) was stirred at 25° C. for 1 h, then 3-piperazin-1-ylpyridine-2-sulfonamide (60 mg, 247 umol) was added and stirred at 25° C. for another 16 h. The mixture was quenched with $H_2O$ (6 mL), extracted with EtOAc (50 mL×3) and the crude product was purified by Pre-HPLC to obtain 3-[4-[3-[[1-(3-chloro-2-pyridyl)-4-piperidyl]amino]-2,4,6-trimethyl-benzoyl]piperazin-1-yl]pyridine-2-sulfonamide (27 mg, 18.23%) as white solid. MS (EI+, m/z): 599 [M+H]$^+$. $^1$H NMR (500 MHz, DMSO-d6) δ 8.37 (d, J=4.5 Hz, 1H), 8.19 (d, J=4.7 Hz, 1H), 7.92 (d, J=8.2 Hz, 1H), 7.77 (d, J=7.7 Hz, 1H), 7.61 (dd, J=8.1, 4.5 Hz, 1H), 7.20 (s, 2H), 6.96 (dd, J=7.7, 4.7 Hz, 1H), 6.86 (s, 1H), 3.84 (d, J=19.5 Hz, 2H), 3.71 (d, J=12.0 Hz, 3H), 3.24 (s, 2H), 3.09 (dd, J=17.2, 9.2 Hz, 2H), 2.92 (s, 3H), 2.77 (dd, J=19.6, 11.6 Hz, 2H), 2.23 (s, 3H), 2.11 (d, J=14.8 Hz, 6H), 1.84 (s, 2H), 1.63 (dd, J=23.5, 12.0 Hz, 2H).

Example 144: 2-(4-(3-(1-(3-chloropyridin-2-yl)piperidin-4-ylamino)-2,4,6-trimethylbenzoyl)piperazin-1-yl)pyridine-3-sulfonamide, I-186

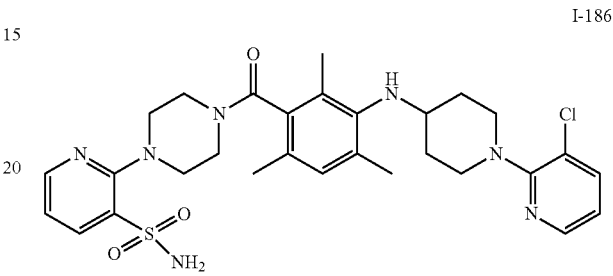

I-186

Synthetic Scheme:

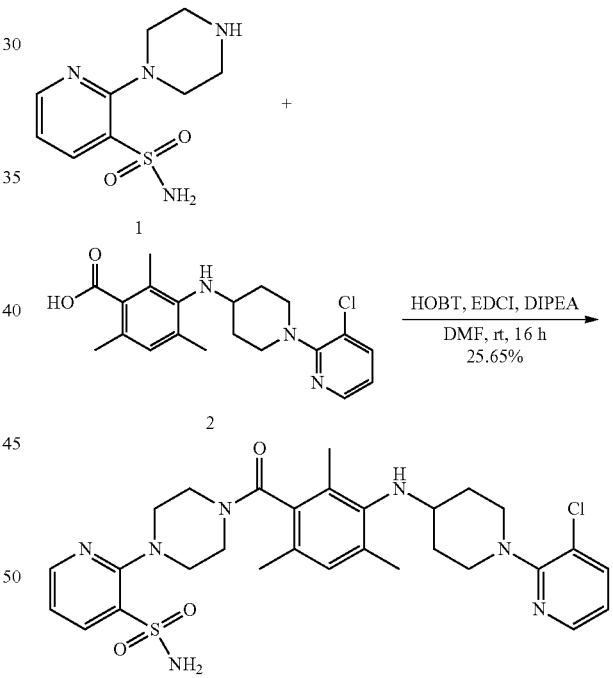

Procedures and Characterization:

Step 1: 2-(4-(3-(1-(3-chloropyridin-2-yl)piperidin-4-ylamino)-2,4,6-trimethylbenzoyl) piperazin-1-yl)pyridine-3-sulfonamide 3-[[1-(3-chloro-2-pyridyl)-4-piperidyl]amino]-2,4,6-trimethyl-benzoic acid (92 mg, 247 umol), HOBT (50 mg, 371 umol), EDCI (73 mg, 371 umol), DIPEA (80 mg, 619 umol, 108 uL) in DMF (3 mL) was stirred at 25° C. for 1 h, then 2-piperazin-1-ylpyridine-3-sulfonamide (60 mg, 247 umol) was added and stirred at 25° C. for another 16 h. The mixture was quenched with H$_2$O (6 mL), extracted with EtOAc (50 mL×3) and the crude product was purified via preparative HPLC to obtain 2-[4-[3-[[1-(3-chloro-2-pyridyl)-4-piperidyl]amino]-2,4,6-trimethyl-benzoyl piperazin-1-yl]pyridine-3-sulfonamide (38 mg, 25.65%) as white solid. MS (EI+, m/z): 599 [M+H]$^+$. $^1$H NMR (500 MHz, DMSO-d6) δ 8.50 (dd, J=4.7, 1.6 Hz, 1H), 8.23 (dd, J=7.8, 1.6 Hz, 1H), 8.20-8.17 (m, 1H), 7.77 (d, J=7.7 Hz, 1H), 7.32 (s, 2H), 7.29 (dd, J=7.8, 4.8 Hz, 1H), 6.96 (dd, J=7.7, 4.7 Hz, 1H), 6.86 (s, 1H), 3.90 (d, J=18.1 Hz, 2H), 3.71 (d, J=12.1 Hz, 3H), 3.24 (d, J=4.5 Hz, 4H), 3.10 (s, 2H), 2.93 (s, 1H), 2.76 (dd, J=20.2, 11.0 Hz, 2H), 2.23 (s, 3H), 2.10 (d, J=16.2 Hz, 6H), 1.85 (s, 2H), 1.73-1.57 (m, 2H).

Example 145: 2-(4-(5-(1-(2-cyano-4,6-difluorophenyl)piperidin-4-ylamino)-2,4-dimethylbenzoyl)piperazin-1-yl)-6-fluorobenzenesulfonamide, I-187

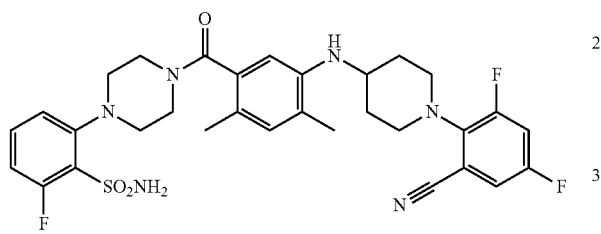

I-187

Synthetic Scheme:

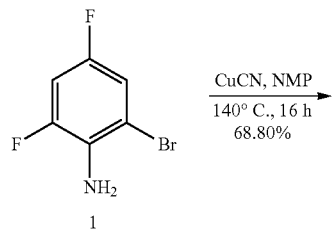

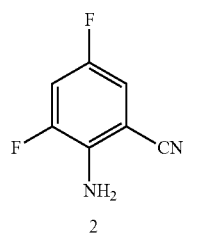

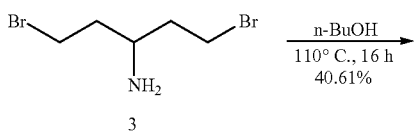

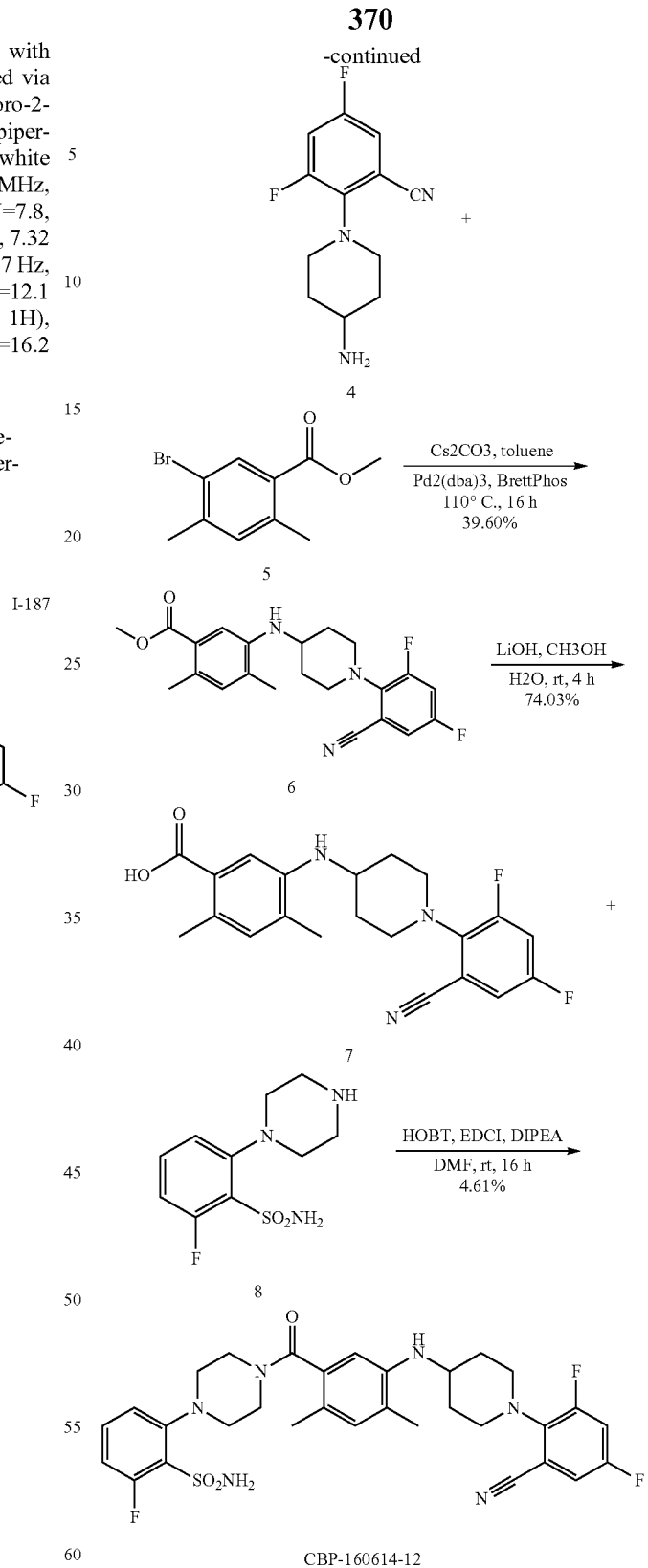

Procedures and Characterization:

Step 1: 2-amino-3,5-difluorobenzonitrile

A mixture of 2-bromo-4,6-difluoro-aniline (2 g, 9 mmol), CuCN (2.34 g, 25 mmol) in NMP (5 mL) was stirred at 140°

C. for 16 h. The reaction was monitored by TLC (PE/EA=30/1), then eluted with EtOAc (50 mL×3), a solution of FeCl₃ in HCl was added and extracted. This was then purified by SGC eluting with PE/EA from 30/1 to obtain 2-amino-3,5-difluoro-benzonitrile (1.02 g, 68.80%) as yellow solid. $^1$H NMR (400 MHz, CDCl₃) δ 7.02 (m, 1H), 6.95 (m, 1H), 4.38 (s, 2H).

Step 2: 2-(4-aminopiperidin-1-yl)-3,5-difluorobenzonitrile 2-amino-3,5-difluoro-benzonitrile (800 mg, 5.19 mmol), 1,5-dibromopentan-3-amine (2.54 g, 7.79 mmol) in n-BuOH (3 mL) was stirred at 120° C. for 16 h. This was then purified by SGC (DCM/MeOH=20/1) to obtain 2-(4-amino-1-piperidyl)-3,5-difluoro-benzonitrile (500 mg, 40.61%) as yellow solid. ESI-MS (EI+, m/z): 238 [M+H]⁺.

Step 3: methyl 5-(1-(2-cyano-4,6-difluorophenyl)piperidin-4-ylamino)-2,4-dimethylbenzoate A solution of 2-(4-amino-1-piperidyl)-3,5-difluoro-benzonitrile (120 mg, 505 umol), methyl 5-bromo-2,4-dimethyl-benzoate (122 mg, 505 umol), Pd₂(dba)₃ (27 mg, 30 umol), BrettPhos (37 mg, 60 umol), Cs₂CO₃ (230 mg, 708 umol) in toluene (5 mL) was stirred at 100° C. for 16 h. Filtered and concentrated, the crude product was purified via silica gel chromatography to obtain methyl 5-[[1-(2-cyano-4,6-difluoro-phenyl)-4-piperidyl]amino]-2,4-dimethyl-benzoate (80 mg, 39.60%) as yellow solid. ESI-MS (EI+, m/z): 400 [M+H]⁺.

Step 4: 5-(1-(2-cyano-4,6-difluorophenyl)piperidin-4-ylamino)-2,4-dimethylbenzoic Acid A solution of methyl 5-[[1-(2-cyano-4,6-difluoro-phenyl)-4-piperidyl]amino]-2,4-dimethyl-benzoate (70 mg, 175 umol), LiOH (33 mg, 1.4 mmol) in CH₃OH (5 mL) and H₂O (3 mL) was stirred at 25° C. for 4 h then extracted with DCM (20 mL), adjusted to pH5-6, extracted with DCM/CH₃OH (50 mL×3), dried and concentrated to obtain the 5-[[1-(2-cyano-4,6-difluoro-phenyl)-4-piperidyl]amino]-2,4-dimethyl-benzoic acid (50 mg, 74.03%). ESI-MS (EI+, m/z): 386 [M+H]⁺.

Step 5: 2-(4-(5-(1-(2-cyano-4,6-difluorophenyl)piperidin-4-ylamino)-2,4-dimethylbenzoyl) piperazin-1-yl)-6-fluorobenzenesulfonamide 5-[[1-(2-cyano-4,6-difluoro-phenyl)-4-piperidyl]amino]-2,4-dimethyl-benzoic acid (40 mg, 103 umol), 2-fluoro-6-piperazin-1-yl-benzenesulfonamide (34 mg, 134 umol), HOBT (21 mg, 155 umol), EDC (29 mg, 155 umol), DIPEA (33 mg, 259 umol) in DMF (3 mL) was stirred at 25° C. for 16 h. The resulting material was purified via preparative HPLC to obtain 2-[4-[5-[[1-(2-cyano-4,6-difluoro-phenyl)-4-piperidyl]amino]-2,4-dimethyl-benzoyl]piperazin-1-yl]-6-fluoro-benzenesulfonamide (3 mg, 4.61%). ESI-MS (EI+, m/z): 627 [M+H]⁺. $^1$H NMR (400 MHz, MeOD) δ 7.58 (dd, J=14.2, 8.2 Hz, 1H), 7.42-7.24 (m, 1H), 7.15-7.02 (m, 1H), 6.97 (s, 1H), 6.57 (s, 1H), 3.54 (dd, J=12.1, 7.8 Hz, 1H), 3.36 (s, 1H), 3.22-2.86 (m, 1H), 2.26-1.98 (m, 2H), 1.73 (d, J=7.4 Hz, 1H), 1.32 (s, 1H).

Example 146: (S)-2-(4-(3-(1-(2-cyanophenyl)piperidin-4-ylamino)-2,4,6-trimethyl benzoyl)-3-methylpiperazin-1-yl)pyridine-3-sulfonamide, I-188

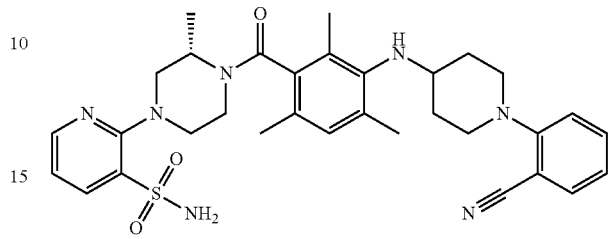

I-188

Synthetic Scheme:

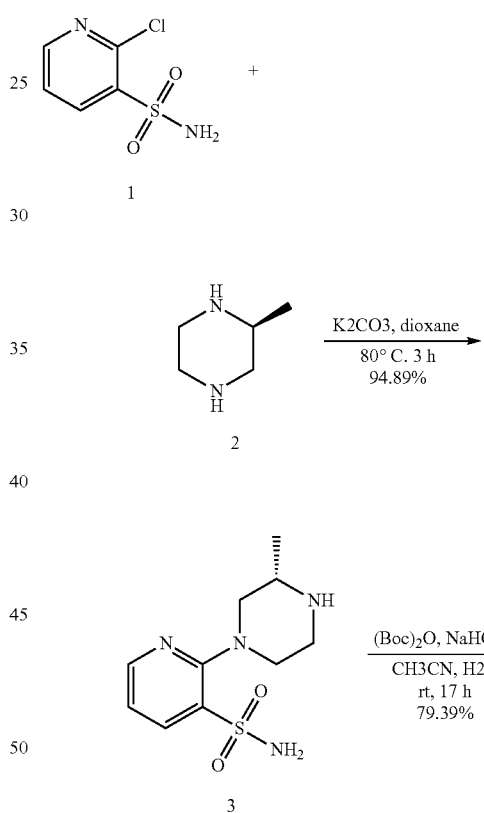

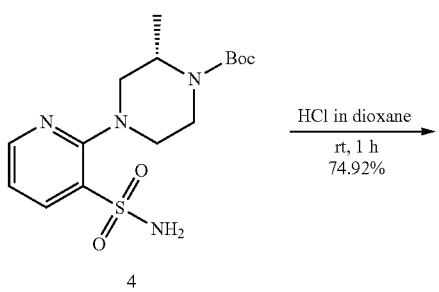

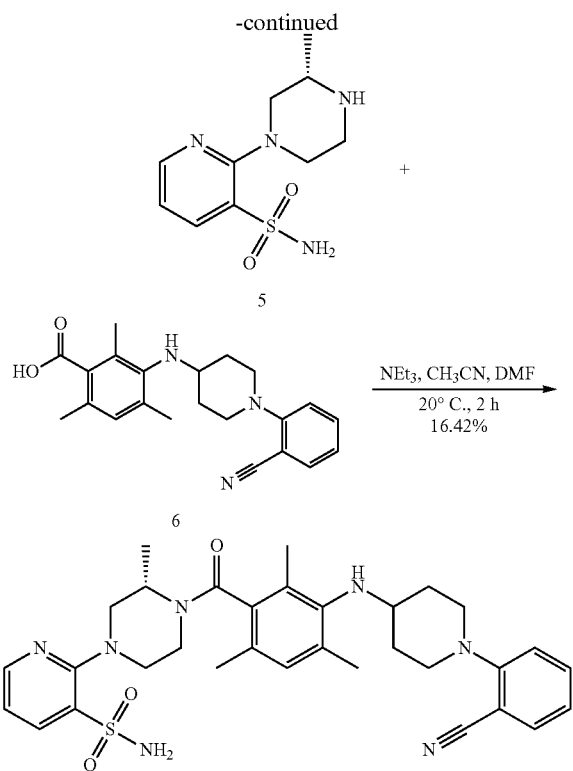

Procedures and Characterization:

Step 1: (S)-2-(3-methylpiperazin-1-yl)pyridine-3-sulfonamide

To a mixture of (S)-2-methylpiperazine (7.99 g, 79.74 mmol), K₂CO₃ (8.25 g, 59 mmol) in dioxane (5 mL) was added 2-chloropyridine-3-sulfonamide (3.84 g, 19.94 mmol) in three portions every 30 min at 80° C., then stirred at 80° C. for 30 min. The reaction mixture was concentrated and washed with CH₃CN (50 mL×3) to obtain the crude product 2-[(3S)-3-methylpiperazin-1-yl]pyridine-3-sulfonamide (4.85 g, 94.89%) as yellow solid and used in the next step without further purification. MS (EI+, m/z): 257 [M+H]⁺.

Step 2: (S)-tert-butyl 2-methyl-4-(3-sulfamoylpyridin-2-yl)piperazine-1-carboxylate To a mixture of 2-[(3S)-3-methylpiperazin-1-yl]pyridine-3-sulfonamide (4.8 g, 18.73 mmol) in CH₃CN (70 mL) was added a solution of tert-butoxycarbonyl tert-butyl carbonate (16.35 g, 74.91 mmol) in H₂O (50 mL), then the mixture stirred at 25° C. for 17 h. The reaction mixture was concentrated and extracted with EtOAc (50 mL×3), dried and concentrated. The crude product was purified via silica gel chromatography eluting with PE/EA from 20/1 to 50/1 to obtain tert-butyl (2S)-2-methyl-4-(3-sulfamoyl-2-pyridyl)piperazine-1-carboxylate (5.3 g, 79.39%) as off-white solid. MS (EI+, m/z): 357 [M+H]⁺.

Step 3: (S)-2-(3-methylpiperazin-1-yl)pyridine-3-sulfonamide

A solution of tert-butyl (2S)-2-methyl-4-(3-sulfamoyl-2-pyridyl)piperazine-1-carboxylate (5.20 g, 14.59 mmol) in HCl in dioxane (4 M, 72.94 mmol, 19 mL) was stirred at 25° C. for 1 h. The reaction mixture was filtered, the crude product was washed with Et₂O (50 mL×3) and CH₃CN (50 mL×3), dried to obtain 2-[(3S)-3-methylpiperazin-1-yl]pyridine-3-sulfonamide (3.20 g, 74.92%) as white solid. MS (EI+, m/z): 257 [M+H]⁺. ¹H NMR (400 MHz, DMSO-d6) δ 9.97 (d, J=9.3 Hz, 1H), 9.47 (d, J=7.9 Hz, 1H), 8.84 (s, 2H), 8.52 (dd, J=4.8, 1.8 Hz, 1H), 8.28 (dd, J=7.8, 1.8 Hz, 1H), 7.74-7.41 (m, 1H), 7.34 (dd, J=7.8, 4.8 Hz, 1H), 3.58 (t, J=11.1 Hz, 3H), 3.41-3.20 (m, 3H), 3.13-2.99 (m, 1H), 1.29 (d, J=6.5 Hz, 3H).

Step 4: (S)-2-(4-(3-(1-(2-cyanophenyl)piperidin-4-ylamino)-2,4,6-trimethylbenzoyl)-3-methylpiperazin-1-yl)pyridine-3-sulfonamide To a solution of 3-[[1-(2-cyanophenyl)-4-piperidyl]amino]-2,4,6-trimethyl-benzoic acid (297 mg, 819 umol) in DCM (5 mL) was added SOCl₂ (0.5 mL) and the mixture stirred at 20° C. for 2 h. The mixture was concentrated to obtain 3-[[1-(2-cyanophenyl)-4-piperidyl]amino]-2,4,6-trimethyl-benzoyl chloride (260 mg, 99.67%) as a yellow solid which was used directly. A CH₃CN solution (5 mL) containing (S)-2-(3-methylpiperazin-1-yl)pyridine-3-sulfonamide (160 mg, 546 umol), TEA (105 mg, 1.04 umol) was added in 3-[[1-(2-cyanophenyl)-4-piperidyl]amino]-2,4,6-trimethyl-benzoyl chloride (250 mg, 655 umol), then the mixture was stirred at 20° C. for 2 h, quenched with water (30 mL), extracted with EtOAc (50 mL×3), dried and concentrated. The crude product was purified via silica gel chromatography eluting with DCM/MeOH from 50/1 to 30/1 to obtain 2-[(3S)-4-[3-[[1-(2-cyanophenyl)-4-piperidyl]amino]-2,4,6-trimethyl-benzoyl]-3-methyl-piperazin-1-yl]pyridine-3-sulfonamide (54 mg, 16.42%) as yellow solid. MS (EI+, m/z): 602 [M+H]⁺. ¹H NMR (500 MHz, MeOD) δ 8.41-8.36 (m, 1H), 8.24-8.18 (m, 1H), 7.49 (d, J=7.6 Hz, 1H), 7.46-7.39 (m, 1H), 7.15 (m, 1H), 7.05 (d, J=8.2 Hz, 1H), 6.94 (dd, J=8.6, 6.5 Hz, 1H), 6.85 (dd, J=12.5, 5.7 Hz, 1H), 4.94 (s, 1H), 3.71-3.31 (m, 6H), 3.16-3.02 (m, 2H), 3.01-2.82 (m, 2H), 2.81-2.67 (m, 2H), 2.26-2.01 (m, 9H), 1.90 (s, 2H), 1.66 (d, J=8.2 Hz, 2H), 1.40 (t, J=6.4 Hz, 2H), 1.25 (d, J=6.7 Hz, 1H).

Example 147: 2-(4-(3-((S)-4-(3-fluoro-2-((S)—S-methylsulfonimidoyl)phenyl)-2-methylpiperazine-1-carbonyl)-2,4,6-trimethylphenylamino)piperidin-1-yl)benzonitrile, I-189

I-189

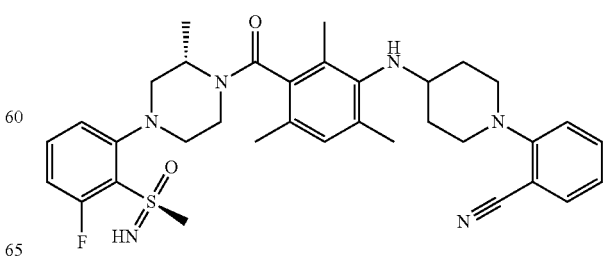

Synthetic Scheme:

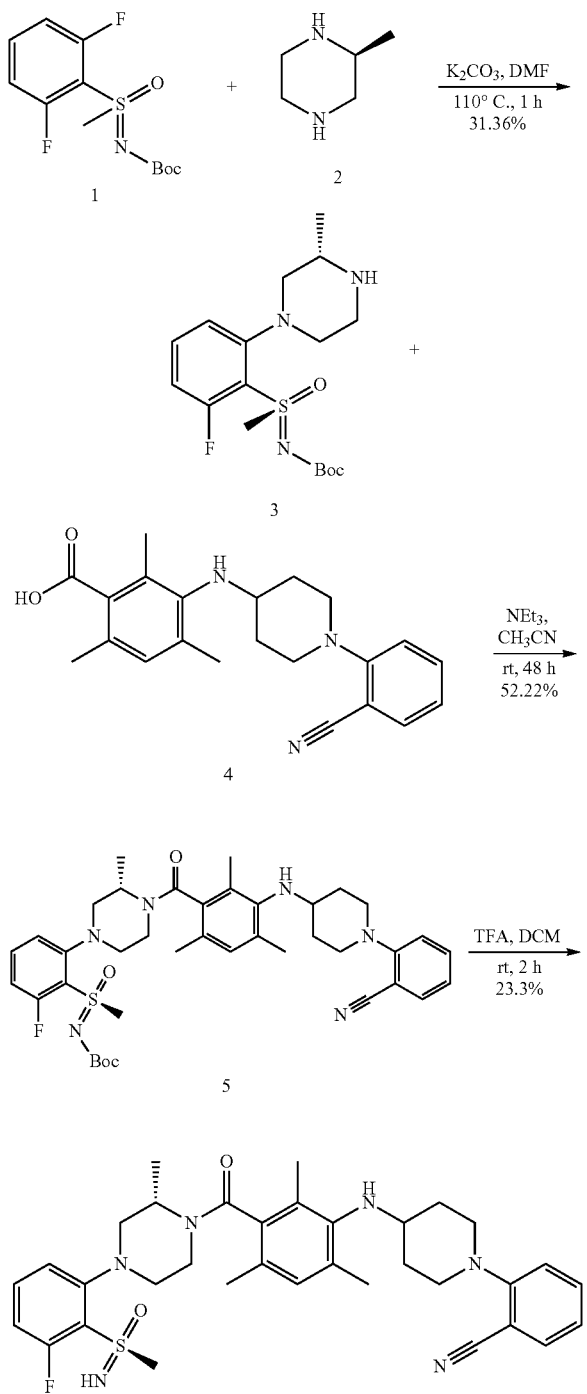

Procedures and Characterization:

Step 1: tert-butyl N-[[2-fluoro-6-[(3S)-3-methylpiperazin-1-yl]phenyl]-(S)-methyl-6-sulfanylidene] carbamate A mixture of tert-butyl N-[(2,6-difluorophenyl)-methyl-6-sulfanylidene]carbamate (2.10 g, 7.21 mmol), (2S)-2-methylpiperazine (722 mg, 7.21 mmol), K₂CO₃ (1.99 g, 14.42 mmol) and DMF (2 mL) was stirred at 110° C. for 1 h. The reaction mixture was quenched with water (50 mL), extracted with EtOAc (50 mL×3), dried and concentrated. The crude product was purified via silica gel chromatography eluting with DCM/MeOH from 40/1 to 10/1 to obtain total product 2.1 g, further purification was carried on chiral-HPLC to obtain tert-butyl N-[[2-fluoro-6-[(3S)-3-methylpiperazin-1-yl]phenyl]-methyl-6-sulfanylidene]carbamate (840 mg, 31.36%) as colorless gum. MS (EI+, m/z): 372 [M+H]⁺.

Step 2: N-[[2-[(3S)-4-[3-[[1-(2-cyanophenyl)-4-piperidyl]amino]-2,4,6-trimethyl-benzoyl]-3-methyl-piperazin-1-yl]-6-fluoro-phenyl]-(S)-methyl-oxo-6-sulfanylidene]carbamate To a solution of 3-[[1-(2-cyanophenyl)-4-piperidyl]amino]-2,4,6-trimethyl-benzoic acid (297 mg, 819 umol) in DCM (5 mL) was added SOCl₂ (0.5 mL) and stirred at 20° C. for 2 h. The mixture was concentrated to obtain 3-[[1-(2-cyanophenyl)-4-piperidyl]amino]-2,4,6-trimethyl-benzoyl chloride (260 mg, 680 umol, 99.67%) as a yellow solid, which used in the next step without further purification. To a mixture of tert-butyl N-[[2-fluoro-6-[(3S)-3-methylpiperazin-1-yl]phenyl]-methyl-6-sulfanylidene]carbamate (258 mg, 694 umol) and TEA (84 mg, 833 umol) in CH₃CN (5 mL) was added in 3-[[1-(2-cyanophenyl)-4-piperidyl]amino]-2,4,6-trimethyl-benzoyl chloride (260 mg, 680 umol), then the mixture was stirred at 20° C. for 48 h, quenched with water (30 mL), extracted with EtOAc (50 mL×3), dried and concentrated, the crude product was purified via silica gel chromatography eluting with PE/EA from 6/1 to 3/1 to obtain tert-butyl N-[[2-[(3S)-4-[3-[[1-(2-cyanophenyl)-4-piperidyl]amino]-2,4,6-trimethyl-benzoyl]-3-methyl-piperazin-1-yl]-6-fluoro-phenyl]-methyl-oxo-6-sulfanylidene]carbamate (260 mg, 52.22%) as colorless gum. MS (EI+, m/z): 717 [M+H]⁺.

Step 3: 2-(4-(3-((S)-4-(3-fluoro-2-((S)—S-methyl-sulfonimidoyl)phenyl)-2-methylpiperazine-1-carbonyl)-2,4,6-trimethylphenylamino)piperidin-1-yl)benzonitrile To a solution of tert-butyl N-[[2-[(3S)-4-[3-[[1-(2-cyanophenyl)-4-piperidyl]amino]-2,4,6-trimethyl-benzoyl]-3-methyl-piperazin-1-yl]-6-fluoro-phenyl]-methyl-6-sulfanylidene]carbamate (240 mg, 334 umol) in DCM (7 mL) was added TFA (3 mL), then the mixture was stirred at 20° C. for 2 h, concentrated and adjusted to pH 7~8 with NEt₃ (3 mL), concentrated and purified by preparative HPLC to obtain 2-[4-[3-[(2S)-4-[3-fluoro-2-(methylsulfonimidoyl)phenyl]-2-methyl-piperazine-1-carbonyl]-2,4,6-trimethyl-anilino]-1-piperidyl]benzonitrile (48 mg, 23.3%) as white solid. MS (EI+, m/z): 617 [M+H]⁺. ¹H NMR (500 MHz, MeOD) δ 7.63 (dd, J=18.4, 8.0 Hz, 2H), 7.56 (t, J=7.9 Hz, 1H), 7.38 (dd, J=15.5, 8.1 Hz, 1H), 7.18 (t, J=9.7 Hz, 2H), 7.07 (t, J=7.5 Hz, 1H), 6.97 (d, J=16.7 Hz, 1H), 5.11 (s, 1H), 3.88-3.44 (m, 7H), 3.31-3.01 (m, 4H), 2.81 (dd, J=56.4, 44.4 Hz, 3H), 2.38-2.29 (m, 4H), 2.29-2.17 (m, 5H), 2.02 (d, J=11.0 Hz, 2H), 1.78 (d, J=12.1 Hz, 2H), 1.56 (d, J=6.9 Hz, 2H), 1.40 (d, J=6.8 Hz, 1H).

Example 148: 2-(4-(3-((S)-4-(3-fluoro-2-((R)—S-methylsulfonimidoyl)phenyl)-2-methylpiperazine-1-carbonyl)-2,4,6-trimethylphenylamino)piperidin-1-yl)benzonitrile, I-190

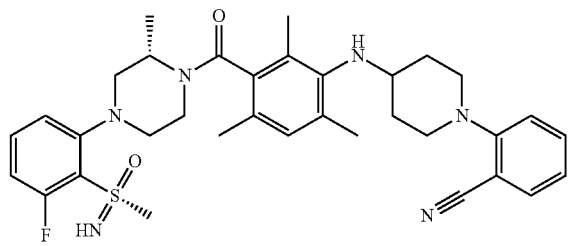

I-190

Synthetic Scheme:

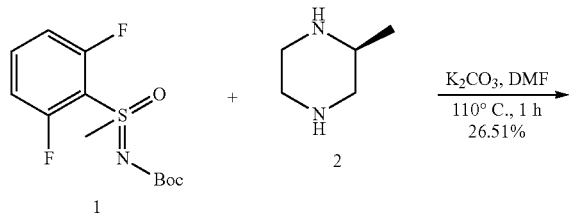

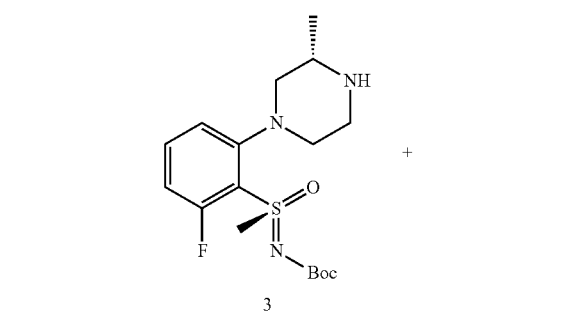

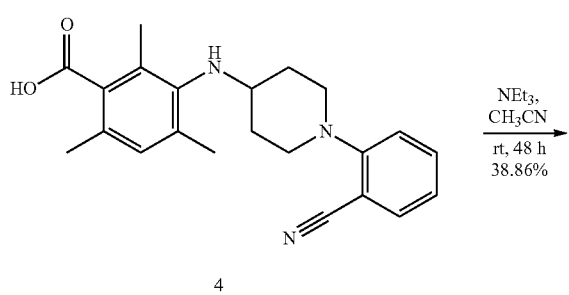

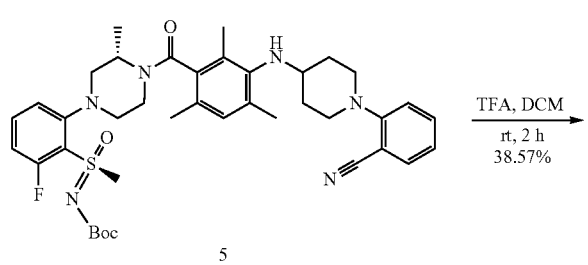

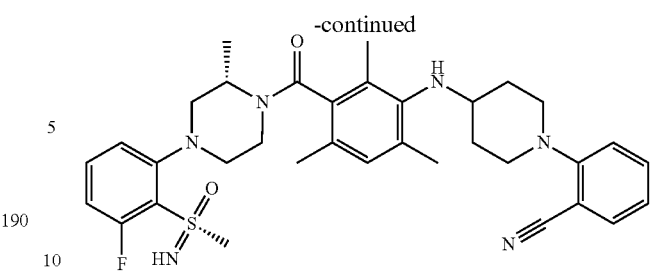

Procedures and Characterization:

Step 1: tert-butyl N-[[2-fluoro-6-[(3S)-3-methylpiperazin-1-yl]phenyl]-(R)-methyl-6-sulfanylidene] Carbamate A mixture of tert-butyl N-[(2,6-difluorophenyl)-methyl-6-sulfanylidene]carbamate (2.10 g, 7.21 mmol), (2S)-2-methylpiperazine (722 mg, 7.21 mmol), K$_2$CO$_3$ (1.99 g, 14.42 mmol) in DMF (2 mL) was stirred at 110° C. for 1 h. The reaction mixture was quenched with water (50 mL), extracted with EtOAc (50 mL×3), dried and concentrated, the crude product was purified via silica gel chromatography eluting with DCM/MeOH from 40/1 to 10/1 to obtain total product 2.1 g, further purification was carried out via chiral-HPLC to obtain tert-butyl N-[[2-fluoro-6-[(3S)-3-methylpiperazin-1-yl]phenyl]-(R)-methyl-6-sulfanylidene] carbamate (710 mg, 26.51%) as colorless gum. MS (EI+, m/z): 372 [M+H]$^+$. $^1$H NMR (500 MHz, CDCl$_3$) δ 7.48 (m, 1H), 7.09 (dd, J=8.1, 3.7 Hz, 1H), 6.99-6.90 (m, 1H), 3.51 (d, J=17.8 Hz, 1H), 3.21-2.71 (m, 2H), 2.37 (dt, J=41.8, 10.4 Hz, 1H), 1.36 (s, 3H), 1.02 (d, J=6.3 Hz, 1H).

Step 2: N-[[2-[(3S)-4-[3-[[1-(2-cyanophenyl)-4-piperidyl]amino]-2,4,6-trimethyl-benzoyl]-3-methyl-piperazin-1-yl]-6-fluoro-phenyl]-(R)-methyl-oxo-6-sulfanylidene]carbamate To a solution of 3-[[1-(2-cyanophenyl)-4-piperidyl]amino]-2,4,6-trimethyl-benzoic acid (400 mg, 1.1 mmol) in DCM (10 mL) was added SOCl$_2$ (0.2 mL), then the mixture stirred at 20° C. for 2 h. The mixture was concentrated to obtain 3-[[1-(2-cyanophenyl)-4-piperidyl]amino]-2,4,6-trimethyl-benzoyl chloride (420 mg, 90.44%) as yellow solid, which was used in the next step without further purification. To a solution of tert-butyl N-[[2-fluoro-6-[(3S)-3-methylpiperazin-1-yl]phenyl]-(R)-methyl-6-sulfanylidene]carbamate (320 mg, 861 umol), NEt$_3$ (104 mg, 1.03 mmol) in CH$_3$CN (5 mL) was added 3-[[1-(2-cyanophenyl)-4-piperidyl]amino]-2,4,6-trimethyl-benzoyl chloride (394 mg, 1.03 mmol), then the reaction mixture was stirred at 30° C. for 48 h. Quenched with water (30 mL), extracted with EtOAc (50 mL×3), dried and concentrated, the crude product was purified via silica gel chromatography eluting with DCM/CH$_3$OH from 30/1 to 10/1 to obtain tert-butyl N-[[2-[(3S)-4-[3-[[1-(2-cyanophenyl)-4-piperidyl]amino]-2,4,6-trimethyl-benzo yl]-3-methyl-piperazin-1-yl]-6-fluoro-phenyl]-(R)-methyl-6-sulfanylidene]carbamate (240 mg, 38.86%) as yellow solid. MS (EI+, m/z): 717 [M+H]$^+$.

Step 3: 2-(4-(3-((S)-4-(3-fluoro-2-((R)—S-methylsulfonimidoyl)phenyl)-2-methylpiperazine-1-carbonyl)-2,4,6-trimethylphenylamino)piperidin-1-yl)benzonitrile To a solution of tert-butyl N-[[2-[(3S)-4-[3-[[1-(2-cyanophenyl)-4-piperidyl]amino]-2,4,6-trimethyl-benzoyl]-3- methyl-piperazin-1-yl]-6-fluoro-phenyl]-(R)-methyl-6-sulfanylidene]carbamate (220 mg, 306 umol) in DCM (7 mL) was added TFA (3 mL), then the mixture was stirred at 20° C. for 2 h. Concentrated and adjusted the pH to 7-8 with NEt₃ (3 mL), concentrated and purified by Pre-HPLC to obtain 2-[4-[3-[(2S)-4-[3-fluoro-2-(methylsulfonimidoyl)phenyl]-2-methyl-piperazine-1-carbonyl]-2,4,6-trimethyl-anilino]-1-piperidyl]benzonitrile (73 mg, 38.57%) as white solid. MS (EI+, m/z): 617 [M+H]⁺. ¹H NMR (500 MHz, MeOD) δ 7.67-7.58 (m, 1H), 7.57-7.51 (m, 1H), 7.34 (dd, J=10.9, 5.9 Hz, 1H), 7.15 (dd, J=16.8, 8.6 Hz, 1H), 7.06 (td, J=7.5, 2.6 Hz, 1H), 6.97 (dd, J=15.8, 5.0 Hz, 1H), 5.07 (s, 1H), 2.37-2.14 (m, 1H), 2.07-1.95 (m, 1H), 1.78 (dd, J=23.2, 11.5 Hz, 1H), 1.55 (t, J=6.5 Hz, 1H), 1.39 (dt, J=38.8, 19.4 Hz, 1H).

Example 149: 5-fluoro-2-(4-(3-((2S)-4-(3-fluoro-2-(S-methylsulfonimidoyl)phenyl)-2-methylpiperazine-1-carbonyl)-2,4,6-trimethylphenylamino)piperidin-1-yl)benzonitrile, I-191

I-191

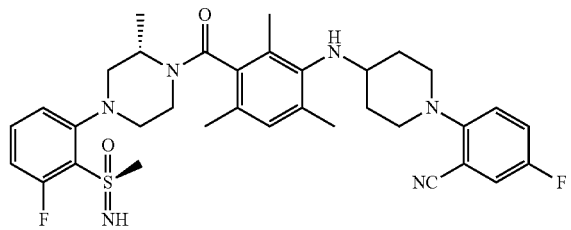

Synthetic Scheme:

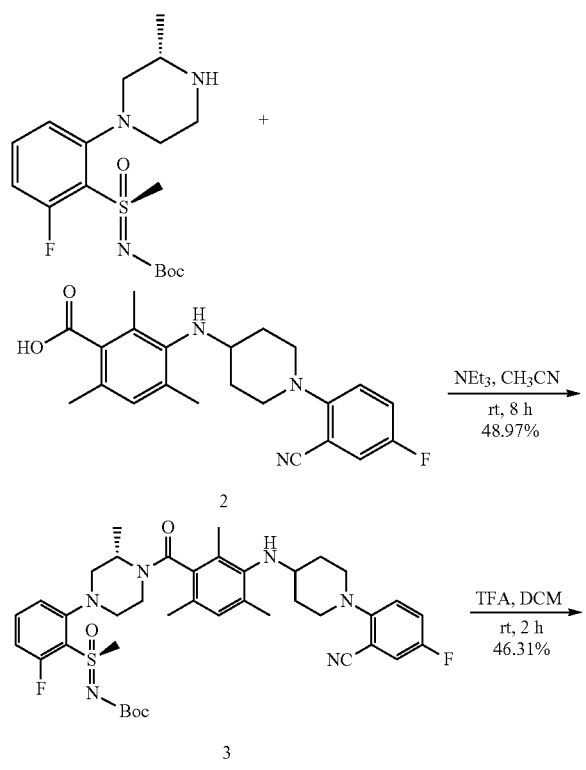

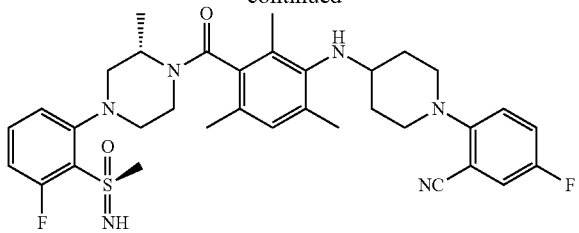

Procedures and Characterization:

Step 1: tert-butyl N-[[2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene]carbamate To a solution of 3-[[1-(2-cyano-4-fluoro-phenyl)-4-piperidyl]amino]-2,4,6-trimethyl-benzoic acid (500 mg, 1.31 mmol) in DCM (20 mL) was added SOCl₂ (311 mg, 2.62 mmol), then the mixture was stirred at 20° C. for 1 h. The mixture was concentrated, the crude product 3-[[1-(2-cyano-4-fluoro-phenyl)-4-piperidyl]amino]-2,4,6-trimethyl-benzoyl chloride (520 mg, 1.30 mmol, 99.20%) was used in the next step without further purification. A mixture of tert-butyl N-[[2-fluoro-6-[(3 S)-3-methylpiperazin-1-yl]phenyl]-(S)-methyl-6-sulfanylidene]carbamate (268 mg, 722 umol) in CH₃CN (20 mL) was added TEA (87 mg, 866 umol), and 3-[[1-(2-cyano-4-fluoro-phenyl)-4-piperidyl]amino]-2,4,6-trimethyl-benzoyl chloride (520 mg, 1.30 mmol), then the mixture stirred at 20° C. for 8 h. Quenched with water (30 mL), extracted with EtOAc (50 mL×3), dried and concentrated, the crude product was purified via silica gel chromatography eluting with DCM/CH₃OH from 50/1 to 30/1 to obtain tert-butyl N-[[2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene]carbamate (260 mg, 48.97%) as yellow solid. MS (EI+, m/z): 735 [M+H]⁺.

Step 2: 5-fluoro-2-(4-(3-((2S)-4-(3-fluoro-2-(S-methylsulfonimidoyl)phenyl)-2-methyl piperazine-1-carbonyl)-2,4,6-trimethylphenylamino)piperidin-1-yl)benzonitrile To a solution of tert-butyl N-[[2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene]carbamate (240 mg, 326 umol) in DCM (10 mL) was added in TFA (10 mL), the mixture was stirred at 20° C. for 2 h. Concentrated and eluted with CH₃CN (3 mL), then adjusted the pH to 7~8 with NEt₃, removed the solvent and sent to pre-HPLC to obtain 5-fluoro-2-[4-[3-[(2S)-4-[3-fluoro-2-(methylsulfonimidoyl)phenyl]-2-methyl-piperazine-1-carbonyl]-2,4,6-trimethyl-anilino]-1-piperidyl]benzonitrile (96 mg, 46.31%) as white solid. MS (EI+, m/z): 635 [M+H]⁺. ¹H NMR (500 MHz, MeOD) δ 7.63 (dd, J=14.5, 8.2 Hz, 1H), 7.48-7.29 (m, 3H), 7.23-7.15 (m, 2H), 6.97 (d, J=16.7 Hz, 1H), 5.11 (m, 1H), 3.85-3.40 (m, 7H), 3.29-3.01 (m, 4H), 2.91-2.58 (m, 3H), 2.37-2.15 (m, 9H), 2.07-1.96 (m, 2H), 1.78 (q, J=11.7 Hz, 2H), 1.56 (d, J=6.9 Hz, 2H), 1.39 (d, J=6.8 Hz, 1H).

Example 150: 2-(4-(3-((2S)-4-(3-fluoro-2-(S-methylsulfonimidoyl)phenyl)-2-methylpiperazine-1-carbonyl)-2,4,6-trimethylphenylamino)piperidin-1-yl)benzonitrile, I-192

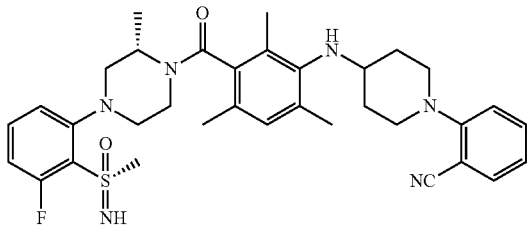

I-192

Synthetic Scheme:

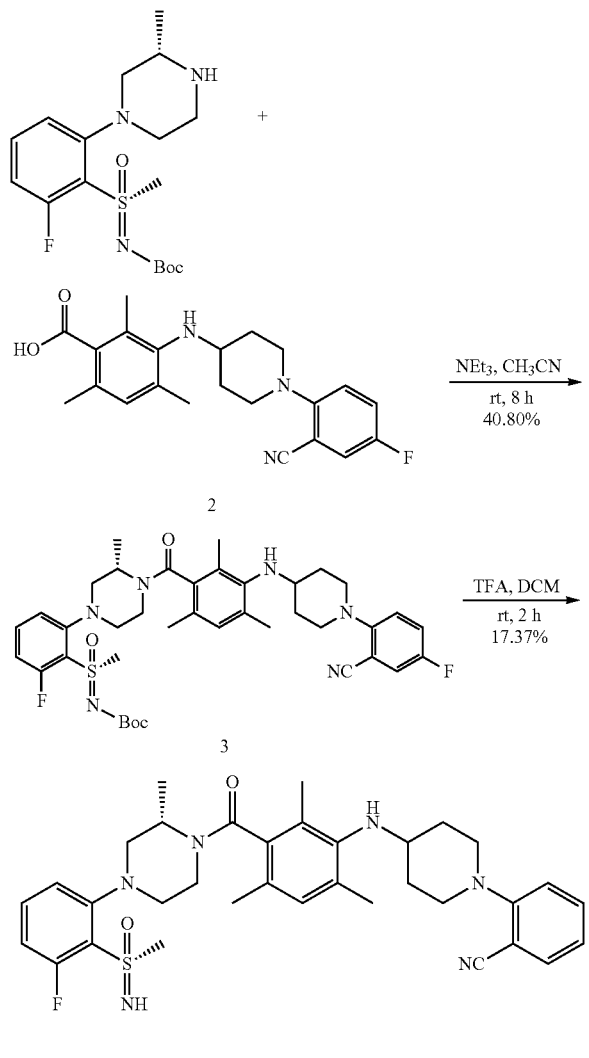

Procedures and Characterization:

Step 1: tert-butyl N-[[2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene]carbamate To a solution of 3-[[1-(2-cyano-4-fluoro-phenyl)-4-piperidyl]amino]-2,4,6-trimethyl-benzoic acid (500 mg, 1.31 mmol) in DCM (20 mL) was added SOCl$_2$ (311 mg, 2.62 mmol), then the mixture was stirred at 20° C. for 1 h. Concentrated, the crude product 3-[[1-(2-cyano-4-fluoro-phenyl)-4-piperidyl]amino]-2,4,6-trimethyl-benzoyl chloride (520 mg, 99.20%) was used in the next step without further purification. Tert-butyl N-[[2-fluoro-6-[(3S)-3-methyl-piperazin-1-yl]phenyl]-(S)-methyl-6-sulfanylidene]carbamate (309 mg, 833 umol) in CH$_3$CN (20 mL) was added in 3-[[1-(2-cyano-4-fluoro-phenyl)-4-piperidyl]amino]-2,4,6-trimethyl-benzoyl chloride (500 mg, 1.25 mmol) and NEt$_3$ (126 mg, 1.25 mmol), then the mixture was stirred at 20° C. for 16 h. Quenched with water (30 mL), extracted with EtOAc (50 mL×3), dried and concentrated, the crude product was purified via silica gel chromatography eluting with DCM/CH$_3$OH from 50/1 to 30/1 to obtain tert-butyl N-[[2-[(3S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene]carbamate (250 mg, 40.81%) as white solid. MS (EI+, m/z): 735 [M+H]$^+$.

Step 2: 5-fluoro-2-(4-(3-((2S)-4-(3-fluoro-2-(S-methylsulfonimidoyl)phenyl)-2-methyl piperazine-1-carbonyl)-2,4,6-trimethylphenylamino)piperidin-1-yl)benzonitrile To tert-butyl N-[[2-[(3 S)-4-[3-[[1-(2-cyano-4-fluoro-phenyl)-4-piperidyl]amino]-2,4,6-trimethyl-benzoyl]-3-methyl-piperazin-1-yl]-6-fluoro-phenyl]-(S)-methyl-6-sulfanylidene] carbamate (200 mg, 272 umol) in DCM (10 mL) was added TFA (10 mL), then the mixture was stirred at 20° C. for 2 h then purified via preparative HPLC to obtain 5-fluoro-2-[4-[3-[(2S)-4-[3-fluoro-2-(methylsulfonimidoyl)phenyl]-2-methyl-piperazine-1-carbonyl]-2,4,6-trimethyl-anilino]-1-piperidyl]benzonitrile (30 mg, 17.37%) as white solid. MS (EI+, m/z): 635 [M+H]$^+$. $^1$H NMR (500 MHz, MeOD) δ 7.62 (dd, J=14.6, 8.2 Hz, 1H), 7.43 (dd, J=7.5, 3.8 Hz, 1H), 7.34 (dd, J=8.2, 5.5 Hz, 2H), 7.18 (m, 2H), 6.97 (dd, J=15.7, 4.7 Hz, 1H), 5.08 (s, 1H), 3.69 (dd, J=35.5, 22.8 Hz, 1H), 3.46 (dd, J=21.9, 6.8 Hz, 5H), 3.17 (m, 4H), 2.85 (m, 3H), 2.43-2.10 (m, 9H), 2.00 (t, J=15.7 Hz, 2H), 1.86-1.72 (m, 2H), 1.55 (t, J=6.5 Hz, 2H), 1.40 (m, 1H).

Example 151: (S)-2-(4-(3-(1-(2-cyano-4-fluorophenyl)piperidin-4-ylamino)-2,4,6-trimethylbenzoyl)-3-methylpiperazin-1-yl)pyridine-3-sulfonamide, I-193

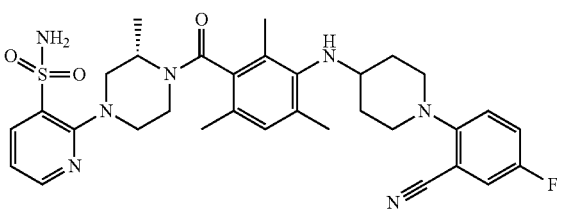

I-193

Synthetic Scheme:

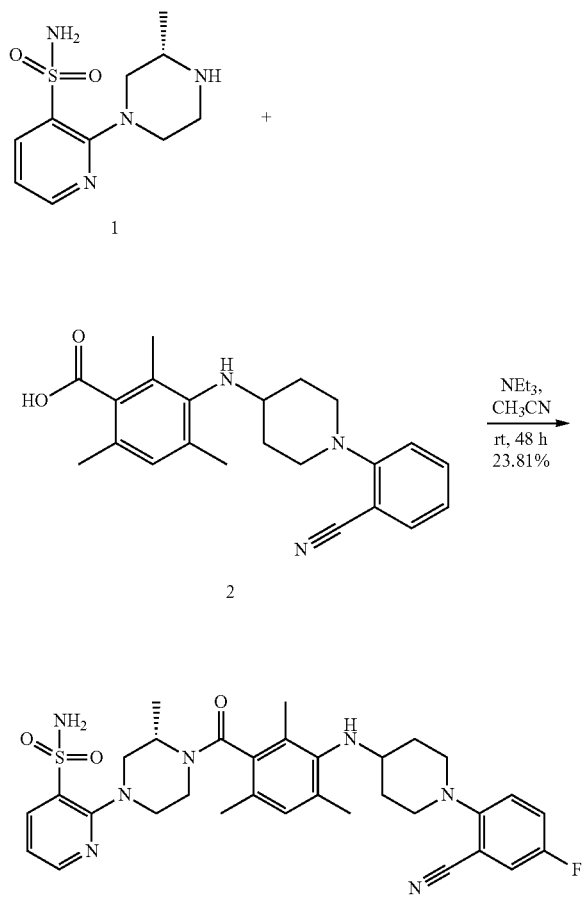

Procedures and Characterization:

Step 1: (S)-2-(4-(3-(1-(2-cyano-4-fluorophenyl)piperidin-4-ylamino)-2,4,6-trimethylbenzoyl-3-methyl-piperazin-1-yl)pyridine-3-sulfonamide To a solution of 3-[[1-(2-cyano-4-fluoro-phenyl)-4-piperidyl]amino]-2,4,6-trimethyl-benzoic acid (200 mg, 524 umol) in DCM (5 mL) was added SOCl$_2$ (0.5 mL) then the mixture stirred at 20° C. for 2 h. The mixture was concentrated to obtain 3-[[1-(2-cyano-4-fluoro-phenyl)-4-piperidyl]amino]-2,4,6-trimethyl-benzoyl chloride (209 mg, 99.68%) as yellow solid which was used in the next step without further purification. 2-[(3S)-3-methylpiperazin-1-yl]pyridine-3-sulfonamide (127 mg, 433 umol), NEt$_3$ (87.79 mg, 867 umol) in CH$_3$CN (5 mL) was added to 3-[[1-(2-cyano-4-fluoro-phenyl)-4-piperidyl]amino]-2,4,6-trimethyl-benzoyl chloride (208 mg, 520 umol) in CH$_3$CN (5 mL) then the mixture was stirred at 20° C. for 16 h then quenched with water (3 mL). The mixture was purified via preparative HPLC to obtain 2-[(3S)-4-[3-[[1-(2-cyano-4-fluoro-phenyl)-4-piperidyl]amino]-2,4,6-trimethyl-benzoyl]-3-methyl-piperazin-1-yl]pyridine-3-sulfonamide (64 mg, 23.81%) as a white solid. MS (EI+, m/z): 620. [M+H]$^+$. $^1$H NMR (500 MHz, MeOD) δ 8.51 (t, J=4.7, 1.5 Hz, 1H), 8.33 (t, J=7.8, 1.8 Hz, 1H), 7.43 (t, J=8.0, 3.1 Hz, 1H), 7.34 (m, 1H), 7.28 (m, 1H), 7.24-7.16 (m, 1H), 6.97 (dd, J=12.4, 5.8 Hz, 1H), 5.05 (m, 1H), 3.82-3.60 (m, 2H), 3.58-3.38 (m, 3H), 3.28-3.15 (m, 2H), 3.14-2.97 (m, 2H), 2.85-2.71 (m, 2H), 2.37-2.10 (m, 9H), 2.02 (s, 2H), 1.86-1.71 (m, 2H), 1.59-1.46 (m, 2H), 1.37 (dd, J=6.8, 1.8 Hz, 1H).

Example 152: (R)-2-(4-(3-(3-(aminomethyl)-4-(pyridazin-3-yl)piperazine-1-carbonyl)-2,4,6-trimethylphenylamino)piperidin-1-yl)benzonitrile, I-194

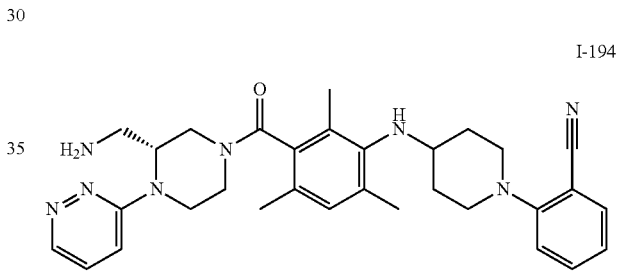

Synthetic Scheme:

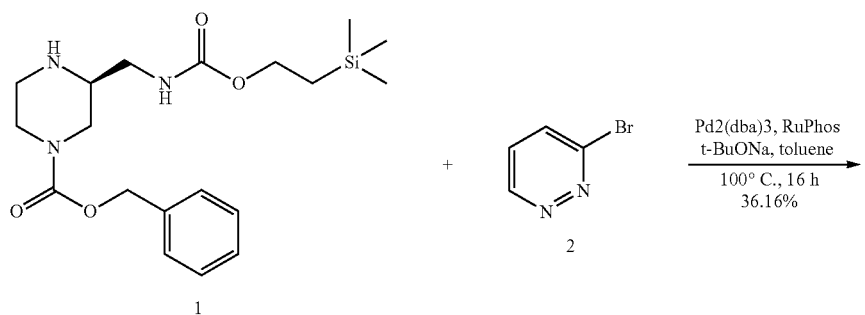

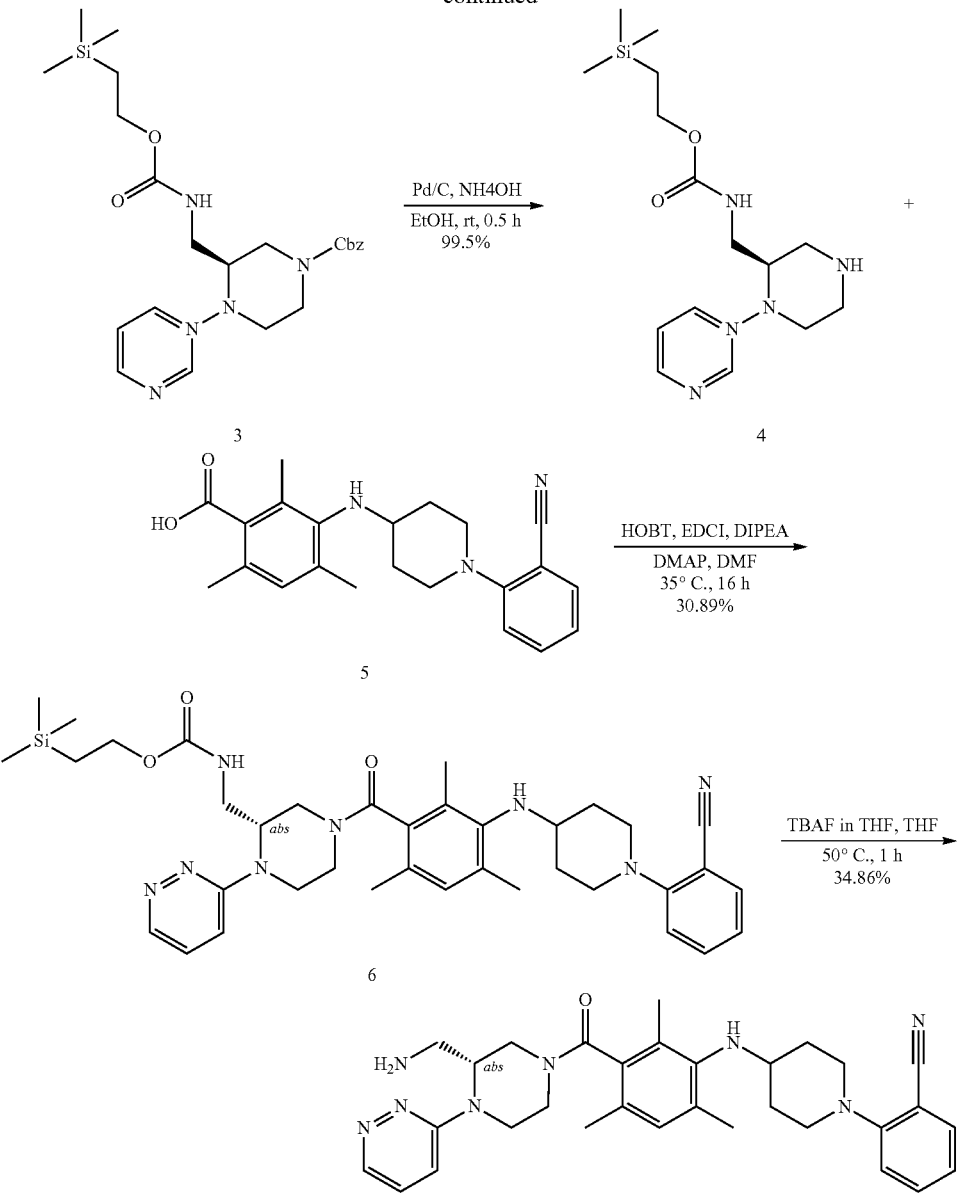

Procedures and Characterization:

Step 1: (S)-benzyl 4-(pyridazin-3-yl)-3-(((2-(trimethylsilyl)ethoxy)carbonylamino)methyl) piperazine-1-carboxylate A mixture of benzyl (3S)-3-[(2-trimethylsilylethoxycarbonylamino)methyl]piperazine-1-carboxylate (600 mg, 1.52 mmol), 3-bromopyridazine (484 mg, 3.05 mmol), Pd₂(dba)₃ (139 mg, 152 umol), t-BuONa (293 mg, 3.05 mmol) in toluene (20 mL) was stirred at 100° C. for 16 h. Filtered and concentrated, the crude product was purified via silica gel chromatography eluting with PE/EA from 100/1 to 1/100 to obtain benzyl (3S)-4-pyridazin-3-yl-3-[(2-trimethylsilylethoxycarbonyl-amino)methyl]piperazine-1-carboxylate (260 mg, 36.16%) as yellow gum. MS (EI+, m/z): 472 [M+H]⁺.

Step 2: (R)-2-(trimethylsilyl)ethyl (1-(pyridazin-3-yl)piperazin-2-yl)methylcarbamate benzyl (3S)-4-pyridazin-3-yl-3-[(2-trimethylsilylethoxycarbonylamino)methyl]piperazine-1-carboxylate (250 mg, 530 umol), Pd/C (100 mg, 823 umol), NH₄OH (0.2 mL) in EtOH (5 mL) was stirred at 20° C. for 0.5 h. The mixture was filtered and concentrated to obtain (R)-2-(trimethylsilyl)ethyl (1-(pyridazin-3-yl)piperazin-2-yl)methylcarbamate (178 mg, 99.5%) as yellow solid. MS (EI+, m/z): 338 [M+H]⁺.

Step 3: (R)-2-(trimethylsilyl)ethyl (4-(3-(1-(2-cyanophenyl)piperidin-4-ylamino)-2,4,6-trimethylbenzoyl)-1-(pyridazin-3-yl)piperazin-2-yl)methylcarbamate 3-[[1-(2-cyanophenyl)-4-piperidyl]amino]-2,4,6-trimethyl-benzoic acid (103 mg, 284 umol), HOBT (41 mg, 308 umol), EDCI (54 mg, 284 umol), DIPEA (153 mg, 1.1 mmol), DMAP (2 mg, 23 umol) in DMF (10 mL) was stirred at rt for 1 h, 2-trimethylsilylethyl N-[[(2S)-1-pyridazin-3-ylpiperazin-2-yl]methyl]carbamate (80 mg, 237 umol) was added in and stirred at 35° C. for 16 h. Quenched by H₂O (10 mL), extracted with EtOAc (50 mL×3), dried and concentrated, was purified via preparative HPLC to obtain 2-trimethylsilylethyl N-[[(2R)-4-[3-[[1-(2-cyanophenyl)-4-piperidyl]amino]-2,4,6-trimethyl-benzoyl]-1-pyridazin-3-yl-piperazin-2-yl]methyl]carbamate (50 mg, 30.89%) as white solid. MS (EI+, m/z): 683 [M+H]+.

Step 4: (R)-2-(4-(3-(3-(aminomethyl)-4-(pyridazin-3-yl)piperazine-1-carbonyl)-2,4,6-trimethylphenylamino)piperidin-1-yl)benzonitrile 2-trimethylsilylethyl N-[[(2R)-4-[3-[[1-(2-cyanophenyl)-4-piperidyl]amino]-2,4,6-trimethyl-benzoyl]-1-pyridazin-3-yl-piperazin-2-yl]methyl]carbamate (40 mg, 58 umol) in THF (3 mL) was added in TBAF in THF (78 mg, 0.3 mmol), then the mixture was stirred at 50° C. for 1 h. Quenched with H₂O (30 mL), extracted with EtOAc (50 mL×3), adjusted the pH to 8-9, extracted with EtOAc (50 mL×3), washed with H₂O (50 mL×3), dried and concentrated, was purified via preparative HPLC to obtain 2-[4-[3-[(3R)-3-(aminomethyl)-4-pyridazin-3-yl-piperazine-1-carbonyl]-2,4,6-trimethyl-anilino]-1-piperidyl]benzonitrile (11 mg, 34.86%) as white solid. MS (EI+, m/z): 539 [M+H]+. ¹H NMR (500 MHz, CDCl₃) δ 8.60 (d, J=4.4 Hz, 1H), 7.56 (d, J=6.6 Hz, 1H), 7.47 (t, J=7.9 Hz, 1H), 7.24 (dd, J=9.3, 4.5 Hz, 1H), 7.04-6.83 (m, 4H), 5.01-4.62 (m, 1H), 4.44 (s, 1H), 4.25 (m, 1H), 3.59 (t, J=17.9 Hz, 3H), 3.48-3.10 (m, 3H), 3.10-2.70 (m, 5H), 2.35-2.22 (m, 6H), 2.09 (t, J=40.7, 8.2 Hz, 5H), 1.69 (d, J=11.4 Hz, 2H).

Example 153: (R)-2-(4-(3-(3-(aminomethyl)-4-(pyridazin-3-yl)piperazine-1-carbonyl)-2,4,6-trimethylphenylamino)piperidin-1-yl)-5-fluorobenzonitrile, I-195

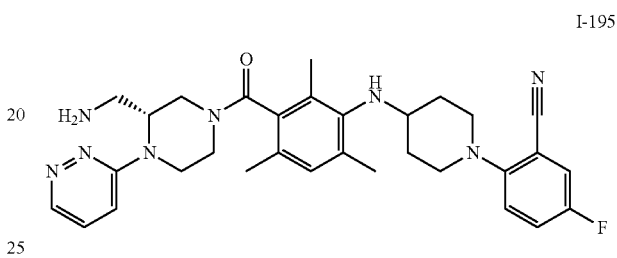

Synthetic Scheme:

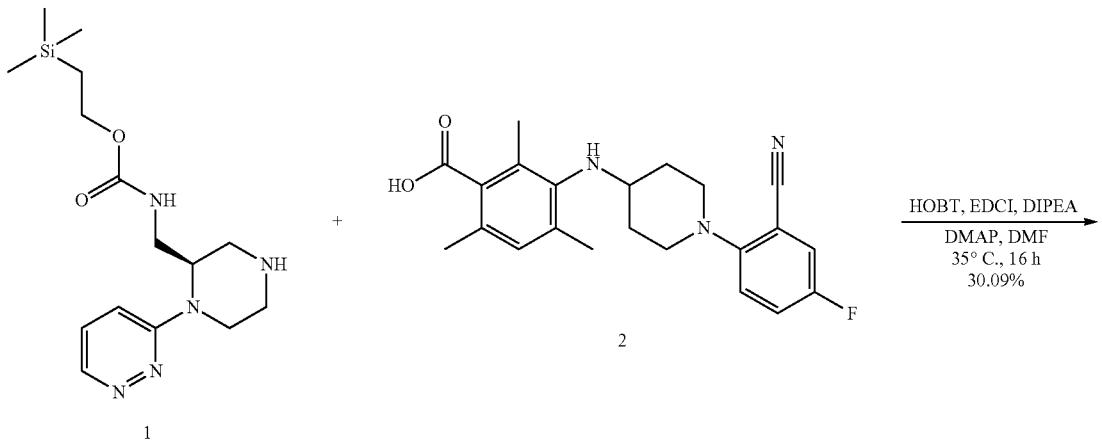

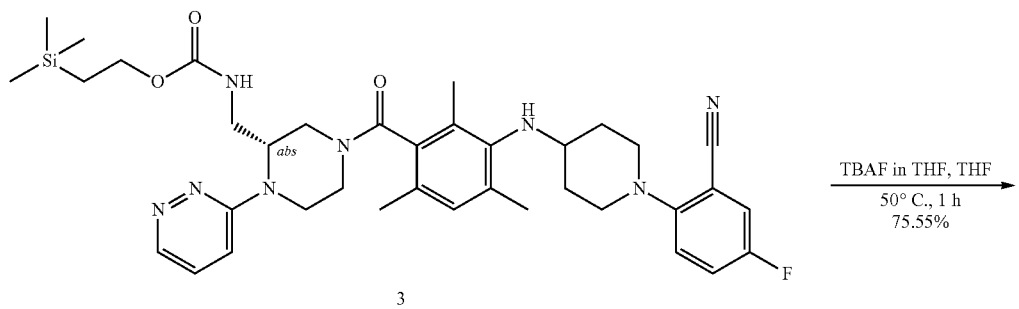

-continued

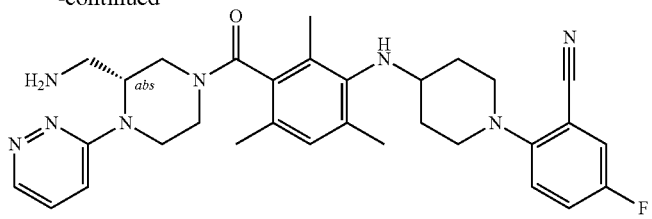

Procedures and Characterization:

Step 1: (R)-2-(trimethylsilyl)ethyl (4-(3-(1-(2-cyano-4-fluorophenyl)piperidin-4-ylamino)-2,4,6-trimethylbenzoyl)-1-(pyridazin-3-yl)piperazin-2-yl)methylcarbamate A mixture of 3-[[1-(2-cyano-4-fluoro-phenyl)-4-piperidyl]amino]-2,4,6-trimethyl-benzoic acid (108 mg, 284 umol), HOBT (41 mg, 308 umol), EDCI (54 mg, 284 umol), DIPEA (153 mg, 1.19 mmol), DMAP (2 mg, 23 umol) in DMF (10 mL) was stirred at rt for 1 h, 2-trimethylsilylethyl N-[[(2S)-1-pyridazin-3-ylpiperazin-2-yl]methyl]carbamate (80 mg, 237 umol) was added in and stirred at 35° C. for 16 h. The reaction was quenched with H₂O (10 mL), extracted with EtOAc (50 mL×3), dried and concentrated and purified via preparative HPLC to obtain (R)-2-(trimethylsilyl)ethyl (4-(3-(1-(2-cyano-4-fluorophenyl)piperidin-4-ylamino)-2,4,6-trimethylbenzoyl)-1-(pyridazin-3-yl)piperazin-2-yl)methylcarbamate (50 mg, 30.09%) as a white solid. MS (EI+, m/z): 701 [M+H]$^+$.

Step 2: (R)-2-(4-(3-(3-(aminomethyl)-4-(pyridazin-3-yl)piperazine-1-carbonyl)-2,4,6-trimethylphenylamino)piperidin-1-yl)-5-fluorobenzonitrile 2-trimethylsilylethyl N-[[(2R)-4-[3-[[1-(2-cyano-4-fluoro-phenyl)-4-piperidyl]amino-2,4,6-trimethyl-benzoyl]-1-pyridazin-3-yl-piperazin-2-yl]methyl]carbamate (50 mg, 71 umol) in THF (3 mL) was added to TBAF in THF (18 mg, 71 umol), then the mixture was stirred at 50° C. for 1 h. The mixture was quenched with water (30 mL), extracted with EtOAc (50 mL×3), adjusted the pH to 8~9, extracted with EtOAc (50 mL×3), washed with H₂O (50 mL×3), dried and concentrated and purified via preparative HPLC to obtain 2-[4-[3-[(3R)-3-(amino methyl)-4-pyridazin-3-yl-piperazine-1-carbonyl]-2,4,6-trimethyl-anilino]-1-piperidyl]-5-fluoro-benzonitrile (30 mg, 75.55%) as white solid. MS (EI+, m/z): 557 [M+H]+. $^1$H NMR (500 MHz, CDCl₃) δ 8.61-8.57 (m, 1H), 7.21-7.12 (m, 3H), 7.07-6.85 (m, 3H), 5.03-4.57 (m, 1H), 4.43 (s, 1H), 4.25 (dd, J=56.2, 13.0 Hz, 1H), 3.67-3.29 (m, 4H), 3.28-2.88 (m, 5H), 2.85-2.65 (m, 2H), 2.34-2.18 (m, 6H), 2.08 (t, J=43.3, 8.2 Hz, 5H), 1.69 (dd, J=23.8, 11.9 Hz, 2H).

Amide Coupling Using HATU: Generic Method

Example 154: 2-[4-({5-[4-(2-Cyanophenyl)piperazine-1-carbonyl]-2,4-dimethylphenyl}amino)piperidin-1-yl]benzonitrile, I-71

I-71

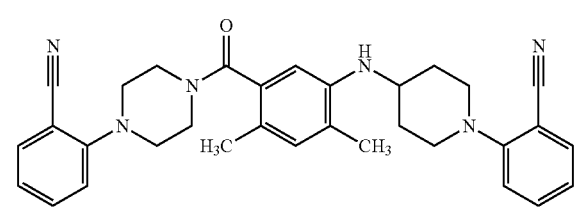

To a suspension of 5-{[1-(2-cyanophenyl)piperidin-4-yl]amino}-2,4-dimethylbenzoic acid [Intermediate 1] (30 mg, 0.085 mmol) and HATU (36 mg, 0.094 mmol) in DMF (1 ml) was added DIPEA (46 μl, 0.256 mmol) and the resultant solution was stirred at rt for 1 h. 2-(Piperazin-1-yl)benzonitrile (16 mg, 0.085 mmol) was then added and the reaction was stirred at rt for 18 h. The reaction was purified by preparative HPLC (Generic UV-Directed High pH prep method). The fractions containing product were lyophilized to afford the title compound I-71 as a white solid (13 mg, 29%). $^1$H NMR (500 MHz, Chloroform-d) δ 7.63-7.53 (m, 2H), 7.53-7.46 (m, 2H), 7.09-6.98 (m, 4H), 6.92 (s, 1H), 6.48 (s, 1H), 4.14-3.93 (m, 2H), 3.67-3.58 (m, 1H), 3.57-3.45 (m, 4H), 3.45-3.31 (m, 1H), 3.32-3.19 (m, 2H), 3.14-3.06 (m, 2H), 3.03-2.90 (m, 2H), 2.30-2.18 (m, 5H), 2.13 (s, 3H), 1.84-1.73 (m, 1H), 1.72-1.63 (m, 1H). LCMS Method 7—Tr=4.09 min (ES+) (M+H)+ 519

Additional, nonlimiting examples of the general HATU coupling method are exemplified in Table 13 below. Intermediate Acid (1 eq) and HATU (1.1-1.4 eq) were dissolved in DMF. DiPEA (3-5 eq) was added and the reaction mixture stirred at ambient temperature for 30 mins. Intermediate Amine (1.0 eq) was added and the reaction mixture was heat at 30-50° C. overnight. The crude reaction mixture was purified by preparative HPLC using either [UV-Directed Low pH prep method] or [UV-Directed High pH prep method]. The fractions containing product were combined and concentrated in vacuo to afford the title compound. Where atropisomers were observed multiple retention times are quoted.

TABLE 13

| Example | Structure | Int. Acid/ Amine | NMR Data | m/z | RT (min) | LCMS | IUPAC Name |
|---|---|---|---|---|---|---|---|
| 1-136 | 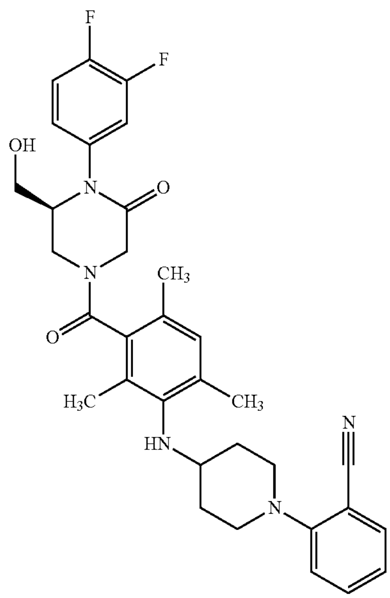 [SMILES: Cc1cc(C)c(C(=O)N2CC(=O)N(c3ccc(F)c(F)c3)[C@H](CO)C2)c(C)c1NC1CCN(c2ccccc2C#N)CC1] | 111/128 | 1H NMR (500 MHz, DMSO-d6) δ 7.71 - 7.65 (m, 1H), 7.61-7.45 (m, 3H), 7.22 (t, J = 8.9 Hz, 1H), 7.17-7.10 (m, 1H), 7.10-7.02 (m, 1H), 6.95-6.83 (m, 1H), 5.08-4.70 (m, 1H), 4.64-4.38 (m, 1H), 4.21-3.92 (m, 1H), 3.91-3.68 (m, 3H), 3.67-3.37 (m, 5H), 2.94 (s, 1H), 2.86-2.70 (m, 2H), 2.30-2.21 (m, 3H), 2.19-2.04 (m, 6H), 1.96-1.79 (m, 2H), 1.77-1.60 (m, 2H). | 589 | 3.6, 3.10 | Method 5 | 2-[4-({3-[(3S)-4-(3,4-difluoro-phenyl)-3-(hydroxy methyl)-5-oxopiperazine-1-carbonyl]-2,4,6-trimethyl phenyl} amino) piperidin-1-yl]benzonitrile |
| 1-138 | 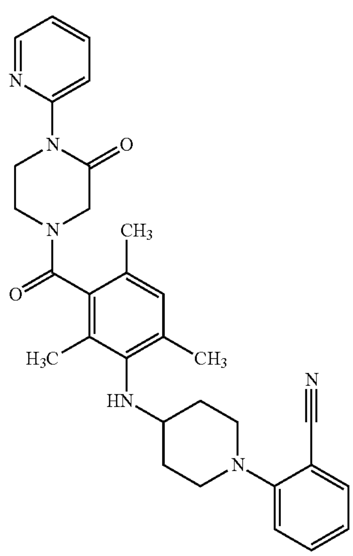 [SMILES: Cc1cc(C)c(C(=O)N2CCN(c3ccccn3)C(=O)C2)c(C)c1NC1CCN(c2ccccc2C#N)CC1] | 111/ Commercial | 1H NMR (500 MHz, Chloroform-d) δ 8.47-8.37 (m, 1H), 7.96 (dd, J = 59.3, 8.3 Hz, 1H), 7.75-7.70 (m, 1H), 7.58-7.53 (m, 1H), 7.51-7.43 (m, 1H), 7.17-7.10 (m, 1H), 7.03 -6.96 (m, 2H), 6.90 (d, J = 5.9 Hz, 1H), 4.66-4.63 (m, 1H), 4.28-4.23 (m, 1H), 4.21-4.10 (m, 1H), 4.10- 4.03 (m, 1H), 4.02-3.98 (m, 1H), 3.63-3.54 (m, 2H), 3.54-3.48 (m, 1H), 3.12-2.97 (m, 1H), 2.86-2.69 (m, 2H), 2.31-2.26 (m, 3H), 2.23-2.16 (m, 6H), 2.14-2.07 (m, 1H), 2.06-2.00 (m, 1H), 1.79-1.68 (m, 3H). | 523 | 4.63 | Method 4 | 2-[4-({2,4,6-trimethyl-3-[3-oxo-4-(pyridin-2-yl)piperazine-1-carbonyl] phenyl} amino) piperidin-1-yl] benzonitrile |

TABLE 13-continued

| Example | Structure | Int. Acid/Amine | NMR Data | m/z | RT (min) LCMS | Method | IUPAC Name |
|---|---|---|---|---|---|---|---|
| 1-139 | 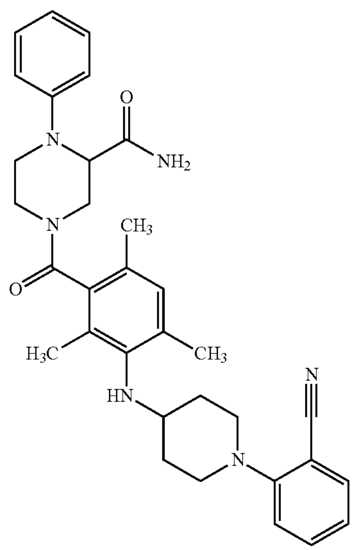 [SMILES: Cc1cc(C)c(C(=O)N2CCN(c3ccccc3)C(C(N)=O)C2)c(C)c1NC1CCN(c2ccccc2C#N)CC1] | 111/50 | 1H NMR (250 MHz, DMSO-d6) δ 7.69-7.48 (m, 2H), 7.28-6.90 (m, 6H), 6.89-6.68 (m, 4H), 4.74-4.27 (m, 1H), 4.13-3.93 (m, 1H), 3.76-3.24 (m, 8H), 2.90-2.75 (m, 2H), 2.26 (s, 3H), 2.17-1.98 (m, 6H), 1.98-1.84 (m, 2H), 1.79-1.54 (m, 3H). | 552 | 4.55, 4.68, 4.79 | Method 6 | 4-(3-{[1-(2-cyanophenyl)piperidin-4-yl]amino}-2,4,6-trimethylbenzoyl)-1-phenylpiperazine-2-carboxamide |
| 1-140 | 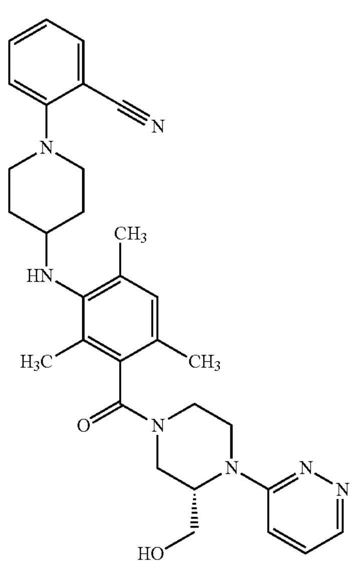 [SMILES: Cc1cc(C)c(C(=O)N2CCN(c3cccnn3)[C@H](CO)C2)c(C)c1NC1CCN(c2ccccc2C#N)CC1] | 111/82 | 1H NMR (500 MHz, DMSO-d6) δ 8.55-8.51 (m, 1H), 7.67 (d, J = 7.7 Hz, 1H), 7.59-7.55 (m, 1H), 7.41-7.35 (m, 1H), 7.23-7.12 (m, 2H), 7.05 (t, J = 7.5 Hz, 1H), 6.91-6.82 (m, 1H), 4.97-4.16 (m, 4H), 3.79-3.66 (m, 1H), 3.63-3.39 (m, 4H), 3.29-2.70 (m, 7H), 2.26 -2.22 (m, 3H), 2.19- 1.99 (m, 5H), 1.96-1.77 (m, 3H), 1.75-1.58 (m, 2H) | 540 | 2.09, 2.14, 2.18, 2.24 | Method 5 | 2-[4-({3-[(3S)-3-(hydroxymethyl)-4-(pyridazin-3-yl)piperazine-1-carbonyl]-2,4,6-trimethylphenyl}amino)piperidin-1-yl]benzonitrile |

TABLE 13-continued

| Example | Structure | Int. Acid/ Amine | NMR Data | m/z | RT (min) | LCMS | IUPAC Name |
|---|---|---|---|---|---|---|---|
| 1-142 | 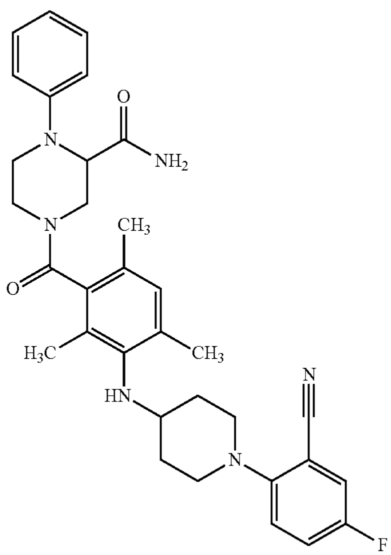 [SMILES: Cc1cc(C)c(C(=O)N2CCN(c3ccccc3)C(C(N)=O)C2)c(C)c1NC1CCN(c2ccc(F)cc2C#N)CC1] | 100/50 | 1H NMR (500 MHz, Chloroform-d) δ 7.34-7.28 (m, 2H), 7.28-7.24 (m, 2H), 7.23-7.16 (m, 1H), 7.03-6.82 (m, 5H), 6.55 (s, 1H), 6.40 (s, 1H), 5.64-5.48 (m, 1H), 4.76-4.65 (m, 0.5H), 4.33-4.29 (m, 0.5H), 4.25-4.06 (m, 0.5H), 3.97-3.73 (m, 2H), 3.68-3.61 (m, 0.5H), 3.60-3.24 (m, 5H), 3.11-2.91 (m, 1H), 2.85-2.66 (m, 2H), 2.26 (s, 3H), 2.22-1.90 (m, 9H), 1.76-1.61 (m, 2H). | 570 | 4.64, 4.76, 4.87 | Method 6 | 4-(3-{[1-(2-cyano-4-fluorophenyl)piperidin-4-yl]amino}-2,4,6-trimethylbenzoyl)-1-phenylpiperazine-2-carboxamide |
| 1-143 | 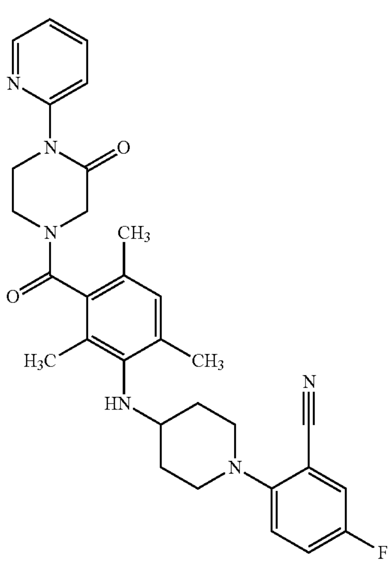 [SMILES: Cc1cc(C)c(C(=O)N2CCN(c3ccccn3)C(=O)C2)c(C)c1NC1CCN(c2ccc(F)cc2C#N)CC1] | 100/ Commercial | 1H NMR (500 MHz, Chloroform-d) δ 8.48-8.36 (m, 1H), 7.95 (d, 1H), 7.76-7.69 (m, 1H), 7.28-7.26 (m, 0H), 7.26-7.25 (m, 1H), 7.23-7.09 (m, 2H), 7.01-6.95 (m, 1H), 6.89 (d, J = 4.0 Hz, 1H), 4.64 (d, J = 3.9 Hz, 1H), 4.28-4.23 (m, 1H), 4.18-4.10 (m, 1H), 4.09-4.03 (m, 1H), 4.00 (d, J = 4.4 Hz, 1H), 3.53-3.40 (m, 3H), 3.05-2.94 (m, 1H), 2.82-2.67 (m, 2H), 2.28 (d, J = 3.7 Hz, 3H), 2.26-2.13 (m, 7H), 2.12-1.97 (m, 3H), 1.77-1.62 (m, 2H). | 560 | 4.73 | Method 6 | 5-fluoro-2-[4-({2,4,6-trimethyl-3-[3-oxo-4-(pyridin-2-yl)piperazine-1-carbonyl]phenyl}amino)piperidin-1-yl]benzonitrile |

TABLE 13-continued

| Example | Structure | Int. Acid/Amine | NMR Data | m/z | RT (min) LCMS | IUPAC Name |
|---|---|---|---|---|---|---|
| 1-144 | 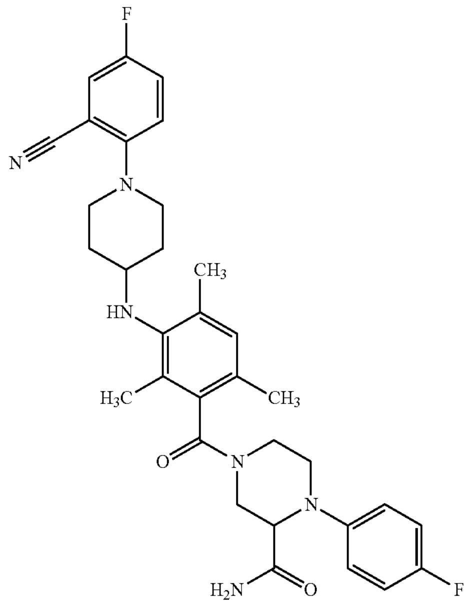 [SMILES: Cc1cc(C)c(C(=O)N2CCN(c3ccc(F)cc3)C(C(N)=O)C2)c(C)c1NC1CCN(c2ccc(F)cc2C#N)CC1] | 100/86 | 1H NMR (500 MHz, Chloroform-d) δ 7.26-7.24 (m, 1H), 7.22-7.16 (m, 1H), 7.04-6.95 (m, 3H), 6.93-6.83 (m, 3H), 6.49-6.26 (m, 1H), 5.51-5.31 (m, 1H), 4.48-4.00 (m, 2H), 3.85-3.52 (m, 3H), 3.46 (s, 2H), 3.40-3.26 (m, 2H), 3.16-2.87 (m, 2H), 2.84-2.67 (m, 2H), 2.26 (s, 3H), 2.21-2.12 (m, 6H), 2.11-1.95 (m, 2H), 1.77-1.61 (m, 2H) | 587 | 3.10, 3.14, 3.30, 3.38 Method 5 | 4-(3-{[1-(2-cyano-4-fluorophenyl)piperidin-4-yl]amino}-2,4,6-trimethylbenzoyl)-1-(4-fluorophenyl)piperazine-2-carboxamide |
| 1-145 | 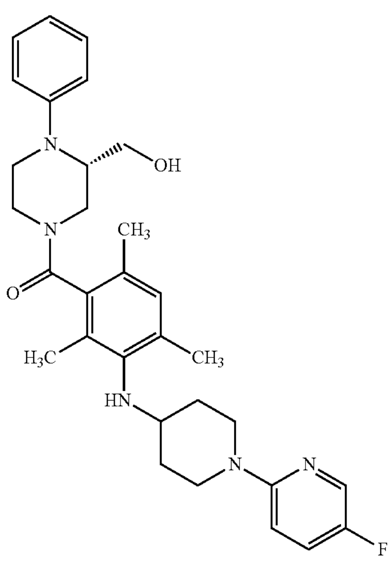 [SMILES: Cc1cc(C)c(C(=O)N2CCN(c3ccccc3)[C@H](CO)C2)c(C)c1NC1CCN(c2ccc(F)cn2)CC1] | 70/119 | 1H NMR (500 MHz, Chloroform-d) δ 8.08-8.03 (m, 1H), 7.34-7.23 (m, 3H), 7.01-6.88 (m, 4H), 6.65 (dd, J = 9.3, 3.0 Hz, 1H), 4.83-4.02 (m, 4H), 3.80-3.38 (m, 5H), 3.35-3.24 (m, 2H), 3.19-3.03 (m, 2H), 2.89-2.57 (m, 3H), 2.31-2.24 (m, 6H), 2.18 (d, J = 3.3 Hz, 3H), 2.02 (d, J = 9.8 Hz, 2H), 1.50-1.38 (m, 2H). | 532 | 2.77, 2.91, 3.12, 3.19 Method 5 | [(2S)-4-(3-{[1-(5-fluoropyridin-2-yl)piperidin-4-yl]amino}-2,4,6-trimethylbenzoyl)-1-phenylpiperazin-2-yl]MeOH |

TABLE 13-continued

| Example | Structure | Int. Acid/ Amine | NMR Data | m/z | RT (min) | LCMS | IUPAC Name |
|---|---|---|---|---|---|---|---|
| 1-149 | 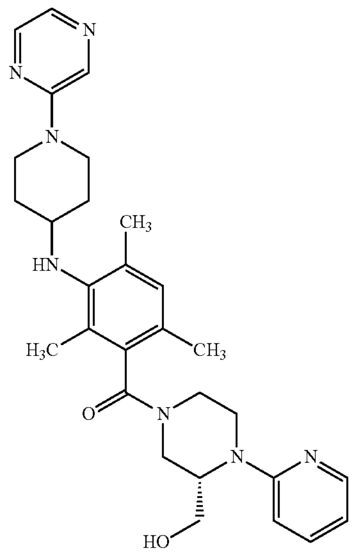 [SMILES: Cc1cc(C)c(C(=O)N2CCN(c3ccccn3)[C@H](CO)C2)c(C)c1NC1CCN(c2cnccn2)CC1] | 101/122 | 1H NMR (500 MHz, DMSO-d6) 8.31 (d, J = 8.1 Hz, 1H), 8.08 (t, J = 4.9 Hz, 1H), 8.05 (d, J = 1.4 Hz, 1H), 7.77 (d, J = 2.4 Hz, 1H), 7.56- 7.49 (m, 1H), 6.88-6.81 (m, 1H), 6.76 (dd, J = 8.4, 3.4 Hz, 1H), 6.62 (dd, J = 6.9, 5.0 Hz, 1H), 4.92-4.20 (m, 3H), 4.08 (dd, J = 26.4, 10.8 Hz, 1H), 3.69-3.37 (m, 6H), 3.26-3.10 (m, 3H), 3.10-2.78 (m, 3H), 2.20 (d, J = 5.2 Hz, 3H), 2.17-2.09 (m, 3H), 1.97 (d, J = 16.6 Hz, 3H), 1.91-1.72 (m, 2H), 1.52-1.31 (m, 2H). | 516 | 2.79, 2.97, 3.02, 3.11 | Method 6 | [(2S)-1-(pyridin-2-yl)-4-(2,4,6-trimethyl-3-{[1-(pyrazin-2-yl)piperidin-4-yl]amino} benzoyl) piperazin-2-yl]MeOH |
| 1-150 | 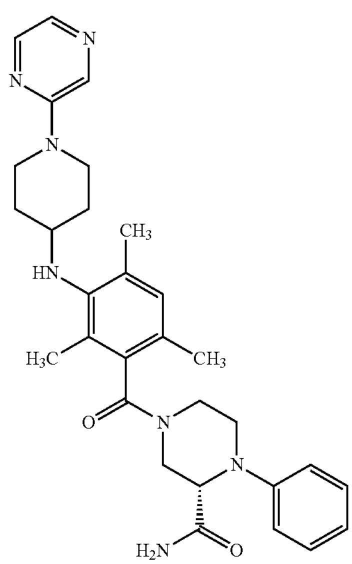 [SMILES: Cc1cc(C)c(C(=O)N2CCN(c3ccccc3)[C@H](C(N)=O)C2)c(C)c1NC1CCN(c2cnccn2)CC1] | 101/20 | 1H NMR (500 MHz, DMSO-d6) δ 8.34-8.30 (m, 1H), 8.08-8.03 (m, 1H), 7.80-7.76 (m, 1H), 7.50 (dd, J = 47.5, 5.8 Hz, 1H), 7.24-7.11 (m, 3H), 6.87-6.69 (m, 4H), 4.79-3.87 (m, 4H), 3.72-3.39 (m, 5H), 3.27-2.96 (m, 2H), 2.94-2.82 (m, 2H), 2.24-2.17 (m, 3H), 2.09-1.98 (m, 6H), 1.88-1.73 (m, 2H), 1.51-1.37 (m, 2H) | 528 | 2.21, 2.36, 2.43, 2.56 | Method 5 | (2S)-1-phenyl-4-(2,4,6-trimethyl-3-{[1-(pyrazin-2-yl) piperidin-4-yl]amino} benzo yl)piperazine-2-carboxamide |

TABLE 13-continued

| Example | Structure | Int. Acid/Amine | NMR Data | m/z | RT (min) LCMS | Method | IUPAC Name |
|---|---|---|---|---|---|---|---|
| 1-152 | 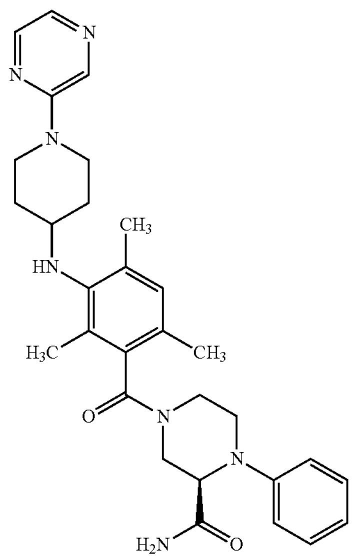 [SMILES: Cc1cc(C)c(C(=O)N2CCN(c3ccccc3)[C@@H](C(N)=O)C2)c(C)c1NC1CCN(c2cnccn2)CC1] | 101/73 | 1H NMR (500 MHz, DMSO-d6) δ 8.32 (s, 1H), 8.08-8.03 (m, 1H), 7.80-7.75 (m, 1H), 7.50 (dd, J = 47.4, 5.9 Hz, 1H), 7.24 - 7.12 (m, 3H), 6.86-6.69 (m, 4H), 4.79-4.27 (m, 3H), 4.16-3.90 (m, 1H), 3.75-3.38 (m, 5H), 3.28-2.81 (m, 4H), 2.25-2.17 (m, 3H), 2.10-1.96 (m, 6H), 1.88-1.73 (m, 2H), 1.53-1.35 (m, 2H) | 528 | 2.22, 2.36, 2.44, 2.56 | Method 5 | (2R)-1-phenyl-4-(2,4,6-trimethyl-3-{[1-(pyrazin-2-yl]amino}benzoyl)piperazine-2-carboxamide |
| 1-153 | 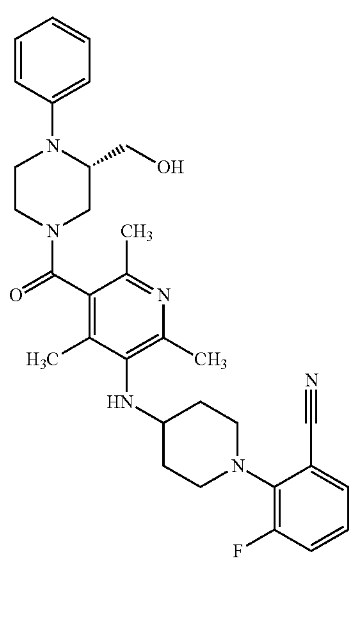 [SMILES: Cc1nc(C)c(C(=O)N2CCN(c3ccccc3)[C@H](CO)C2)c(C)c1NC1CCN(c2c(F)cccc2C#N)CC1] | 132/119 | 1H NMR (250 MHz, DMSO-d6) δ 7.58-7.36 (m, 2H), 7.30-7.07 (m, 3H), 6.91 (d, J = 7.2 Hz, 2H), 6.84-6.67 (m, 1H), 4.73-3.98 (m, 2H), 3.95-3.19 (m, 12H), 2.46 (s, 3H), 2.36-2.01 (m, 6H), 2.00-1.55 (m, 4H). | 557 | 4.52 | Method 4 | 3-fluoro-2-[4-({5-[(3S)-3-(hydroxymethyl)-4-phenyl-piperazine-1-carbonyl]-2,4,6-trimethyl-pyridin-3-yl}amino)piperidin-1-yl]benzonitrile |

TABLE 13-continued

| Example | Structure | Int. Acid/ Amine | NMR Data | m/z | RT (min) | LCMS | IUPAC Name |
|---|---|---|---|---|---|---|---|
| 1-154 | 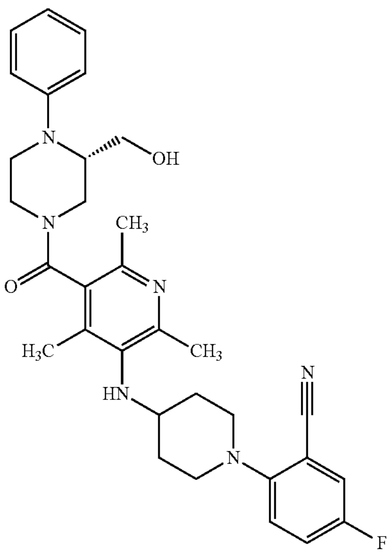 [SMILES: Cc1nc(C)c(C(=O)N2CCN(c3ccccc3)[C@H](CO)C2)c(C)c1NC1CCN(c2ccc(F)cc2C#N)CC1] | 134/119 | 1H NMR (250 MHz, DMSO-d6) δ 7.56 (dd, J = 8.3, 2.9 Hz, 1H), 7.49-7.34 (m, 1H), 7.30-7.11 (m, 3H), 6.92 (d, J = 7.0 Hz, 2H), 6.84-6.67 (m, 1H), 4.70-3.99 (m, 2H), 3.97-3.29 (m, 10H), 2.95-2.68 (m, 3H), 2.46 (s, 3H), 2.38-2.03 (m, 6H), 2.02-1.57 (m, 4H). | 557 | 4.47 | Method 4 | 5-fluoro-2-[4-({5-[(3S)-3-(hydroxymethyl)-4-phenylpiperazine-1-carbonyl]-2,4,6-trimethylpyridin-3-yl}amino)piperidin-1-yl]benzonitrile |
| 1-155 | 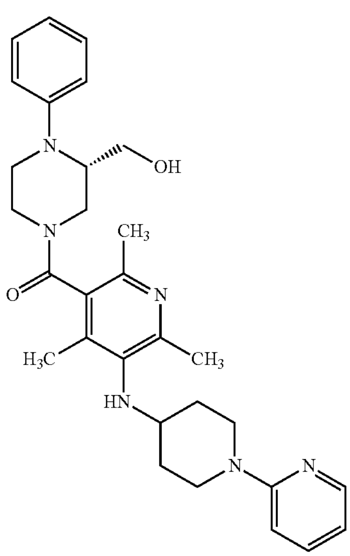 [SMILES: Cc1nc(C)c(C(=O)N2CCN(c3ccccc3)[C@H](CO)C2)c(C)c1NC1CCN(c2ccccn2)CC1] | 136/119 | 1H NMR (250 MHz, DMSO-d6) δ 8.14-8.04 (m, 1H), 7.56-7.41 (m, 1H), 7.29-7.13 (m, 2H), 6.98-6.85 (m, 2H), 6.83-6.70 (m, 2H), 6.64-6.50 (m, 1H), 4.58-4.41 (m, 1H), 4.39-4.00 (m, 3H), 3.92-3.30 (m, 7H), 3.28-2.76 (m, 4H), 2.46-2.42 (m, 3H), 2.34-2.03 (m, 6H), 1.90-1.76 (m, 2H), 1.59-1.38 (m, 2H). | 515 | 4.02 | Method 4 | [(2S)-1-phenyl-4-(2,4,6-trimethyl-5-{[1-(pyridin-2-yl)piperidin-4-yl]amino}pyridine-3-carbonyl)piperazin-2-yl]MeOH |

TABLE 13-continued

| Example | Structure | Int. Acid/ Amine | NMR Data | m/z | RT (min) | LCMS | IUPAC Name |
|---|---|---|---|---|---|---|---|
| 1-156 | 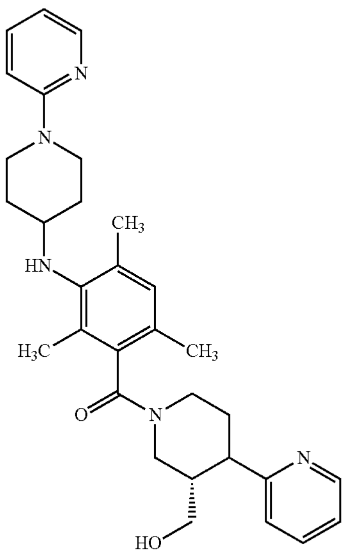 [SMILES: Cc1cc(C)c(C(=O)N2CCC(c3ccccn3)[C@H](CO)C2)c(C)c1NC1CCN(c2ccccn2)CC1] | 141/122 | 1H NMR (500 MHz, DMSO-d6) δ 8.13-8.04 (m, 2H), 7.57-7.44 (m, 2H), 6.90-6.73 (m, 3H), 6.67-6.53 (m, 2H), 4.90-4.35 (m, 2H), 4.33-4.01 (m, 4H), 3.65- 3.37 (m, 3H), 3.28-3.10 (m, 3H), 3.10-2.91 (m, 2H), 2.85-2.70 (m, 2H), 2.20 (d, J = 5.2 Hz, 3H), 2.17-2.09 (m, 3H), 1.97 (d, J = 16.6 Hz, 3H), 1.88-1.70 (m, 2H), 1.40 (dq, J = 25.2, 12.1 Hz, 2H). | 515 | 1.02, 1.15, 1.18, 1.24 | Method 5 | [(2S)-1-(pyridin-2-yl)-4-(2,4,6-trimethyl-3-{[1-(pyridin-2-yl)piperidin-4-yl]amino}benzoyl)piperazin-2-yl]MeOH |
| 1-157 | 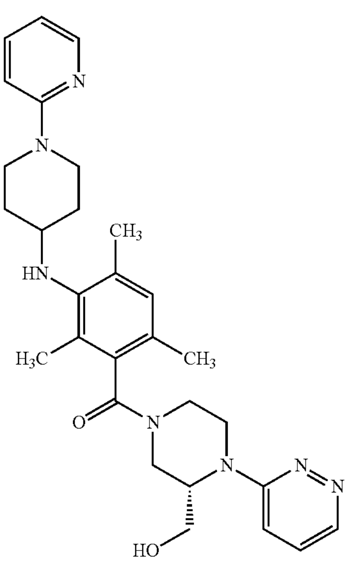 [SMILES: Cc1cc(C)c(C(=O)N2CCN(c3cccnn3)[C@H](CO)C2)c(C)c1NC1CCN(c2ccccn2)CC1] | 141/82 | 1H NMR (500 MHz, DMSO-d6) δ 8.53 (ddd, J = 7.1, 4.4, 1.0 Hz, 1H), 8.13-8.05 (m, 1H), 7.53-7.45 (m, 1H), 7.37 (ddd, J = 9.4, 6.1, 4.5 Hz, 1H), 7.28-7.13 (m, 1H), 6.88-6.77 (m, 2H), 6.64-6.54 (m, 1H), 4.81 (d, J = 88.6 Hz, 1H), 4.64-4.42 (m, 1H), 4.24 (dt, J = 19.8, 15.0 Hz, 4H), 3.69-3.52 (m, 2H), 3.51-3.37 (m, 2H), 3.26-2.91 (m, 4H), 2.79 (q, J = 11.6, 10.9 Hz, 2H), 2.21 (s, 3H), 2.17-2.06 (m, 3H), 1.97 (d, J = 19.0 Hz, 3H), 1.78 (d, J = 11.6 Hz, 2H), 1.43 (q, J = 12.0 Hz, 2H). | 516 | 1.04, 1.13, 1.19, 1.23 | Method 5 | [(2S)-1-(pyridazin-3-yl)-4-(2,4,6-trimethyl-3-{[1-(pyridin-2-yl)piperidin-4-yl]amino}benzoyl)piperazin-2-yl]MeOH |

TABLE 13-continued

| Example | Structure | Int. Acid/Amine | NMR Data | m/z | RT (min) | LCMS | IUPAC Name |
|---|---|---|---|---|---|---|---|
| 1-158 | 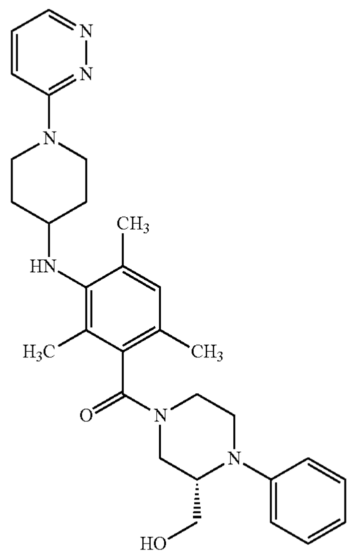 [SMILES: Cc1cc(C)c(C(=O)N2CCN(c3ccccc3)[C@H](CO)C2)c(C)c1NC1CCN(c2cccnn2)CC1] | 102/119 | 1H NMR (500 MHz, DMSO-d6) δ 8.50 (ddd, J = 4.2, 2.8, 1.2 Hz, 1H), 7.34 (ddd, J = 9.3, 4.3, 3.1 Hz, 1H), 7.28-7.23 (m, 1H), 7.22-7.16 (m, 2H), 6.92-6.81 (m, 3H), 6.74 (q, J = 7.1 Hz, 1H), 4.86-4.03 (m, 4H), 3.89-3.63 (m, 1H), 3.63-3.52 (m, 1H), 3.51-3.33 (m, 3H), 3.29-3.17 (m, 2H), 3.16-2.98 (m, 2H), 2.96-2.79 (m, 3H), 2.21 (d, J = 8.2 Hz, 3H), 2.17-2.06 (m, 3H), 2.05-1.97 (m, 3H), 1.91-1.73 (m, 2H), 1.53-1.33 (m, 2H). | 515 | 1.72, 1.94, 1.97, 2.07 | Method 5 | [(2S)-1-phenyl-4-(2,4,6-trimethyl-3-{[1-(pyridazin-3-yl)piperidin-4-yl]amino}benzoyl)piperazin-2-yl]MeOH |
| 1-159 | 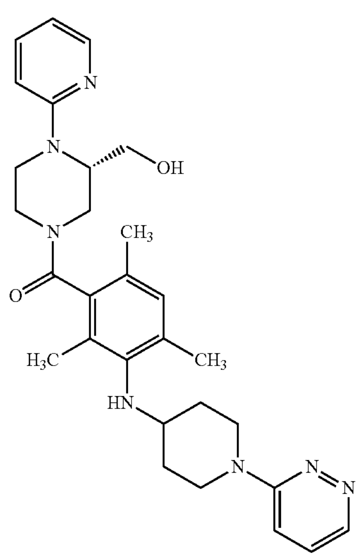 [SMILES: Cc1cc(C)c(C(=O)N2CCN(c3ccccn3)[C@H](CO)C2)c(C)c1NC1CCN(c2cccnn2)CC1] | 102/122 | 1H NMR (500 MHz, Chloroform-d) δ 8.62-8.54 (m, 1H), 8.20-8.08 (m, 1H), 7.61-7.44 (m, 1H), 7.24-7.15 (m, 1H), 7.00-6.85 (m, 2H), 6.75-6.63 (m, 2H), 4.86-4.62 (m, 1H), 4.52-4.16 (m, 3H), 3.99-3.75 (m, 3H), 3.75-3.35 (m, 4H), 3.35-3.11 (m, 3H), 3.05-2.86 (m, 2H), 2.34-2.20 (m, 6H), 2.17-2.10 (m, 3H), 2.10-1.96 (m, 2H), 1.54-1.39 (m, 2H) | 516 | 1.00, 1.12, 1.16, 1.22 | Method 5 | [(2S)-1-(pyridin-2-yl)-4-(2,4,6-trimethyl-3-{[1-(pyridazin-3-yl)piperidin-4-yl]amino}benzoyl)piperazin-2-yl]MeOH |

TABLE 13-continued

| Example | Structure | Int. Acid/Amine | NMR Data | m/z | RT (min) | LCMS | IUPAC Name |
|---|---|---|---|---|---|---|---|
| 1-160 | 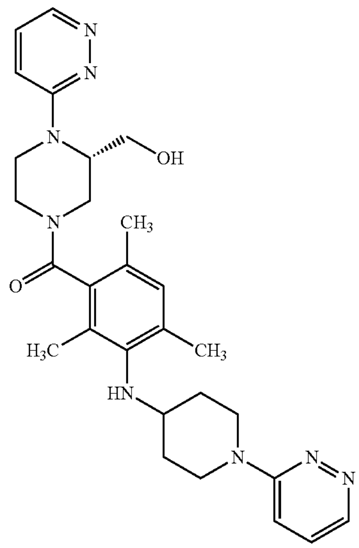 [SMILES: Cc1cc(C)c(C(=O)N2CCN(c3cccnn3)[C@H](CO)C2)c(C)c1NC1CCN(c2cccnn2)CC1] | 102/82 | 1H NMR (500 MHz, DMSO-d6) δ 8.49 (d, J = 4.4 Hz, 1H), 8.13-8.03 (m, 1H), 7.58-7.48 (m, 1H), 7.34 (dd, J = 9.3, 4.4 Hz, 1H), 7.28-7.21 (m, 1H), 6.89-6.81 (m, 1H), 6.81-6.74 (m, 1H), 6.65-6.58 (m, 1H), 5.04-4.52 (m, 2H), 4.45-4.20 (m, 3H), 4.18-3.95 (m, 2H), 3.30-2.79 (m, 8H), 2.20 (d, J = 5.0 Hz, 3H), 2.18-2.08 (m, 3H), 2.02-1.93 (m, 3H), 1.91-1.71 (m, 2H), 1.55-1.33 (m, 2H).). | 517 | 1.45 | Method 4 | [(2S)-1-(pyridazin-3-yl)-4-(2,4,6-trimethyl-3-{[1-(pyridazin-3-yl)piperidin-4-yl]amino}benzoyl)piperazin-2-yl]MeOH |
| 1-161 | 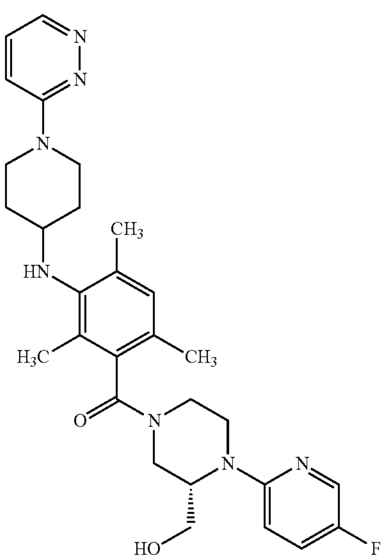 [SMILES: Cc1cc(C)c(C(=O)N2CCN(c3ccc(F)cn3)[C@H](CO)C2)c(C)c1NC1CCN(c2cccnn2)CC1] | 102/12 | 1H NMR (500 MHz, Chloroform-d) δ 8.66-8.48 (m, 1H), 8.00 (dd, J = 6.1, 3.0 Hz, 1H), 7.34-7.27 (m, 1H), 7.20 (dd, J=9.3, 4.5 Hz, 1H), 6.99-6.78 (m, 2H), 6.64 (td, J = 10.3, 9.3, 3.0 Hz, 1H), 4.85-4.50 (m, 1H), 4.48-4.21 (m, 3H), 3.91-3.75 (m, 2H), 3.65-3.30 (m, 3H), 3.28-3.03 (m, 3H), 3.03-2.84 (m, 2H), 2.30-2.21 (m, 7H), 2.12-2.09 (m, 3H), 2.09-1.99 (m, 3H), 1.50-1.38 (m, 2H). | 534 | 1.58, 1.80, 1.83, 1.94 | Method 5 | [(2S)-1-(5-fluoropyridin-2-yl)-4-(2,4,6-trimethyl-3-{[1-(pyridazin-3-yl)piperidin-4-yl]amino}benzoyl)piperazin-2-yl]MeOH |

TABLE 13-continued

| Example | Structure | Int. Acid/Amine | NMR Data | m/z | RT (min) | LCMS | IUPAC Name |
|---|---|---|---|---|---|---|---|
| 1-162 | 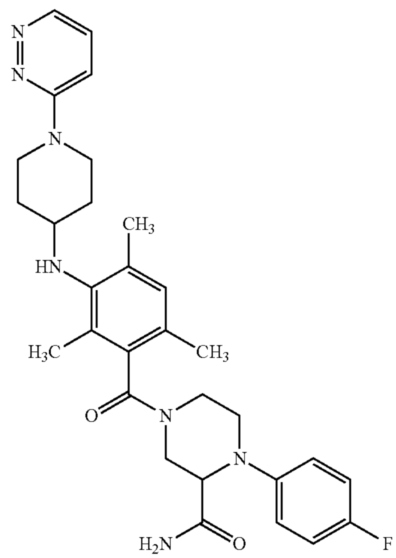 [SMILES: Cc1cc(C)c(C(=O)N2CCN(c3ccc(F)cc3)C(C(N)=O)C2)c(C)c1NC1CCN(c2cccnn2)CC1] | 102/86 | 1H NMR (500 MHz, Chloroform-d) δ 8.55 (t, J = 4.8 Hz, 1H), 7.21-7.15 (m, 1H), 7.03-6.96 (m, 2H), 6.93-6.83 (m, 4H), 6.53-6.32 (m, 1H), 5.64-5.44 (m, 1H), 4.50-3.97 (m, 4H), 3.85-3.09 (m, 6H), 3.02-2.84 (m, 2H), 2.24 (s, 3H), 2.19-2.12 (m, 6H), 2.12-1.93 (m, 3H), 1.51-1.36 (m, 2H) | 546 | 1.62, 1.81, 1.89, 2.00 | Method 5 | 1-(4-fluorophenyl)-4-(2,4,6-trimethyl-3-{[1-(pyridazin-3-yl)piperidin-4-yl]amino}benzoyl)piperazine-2-carboxamide |
| 1-163 | 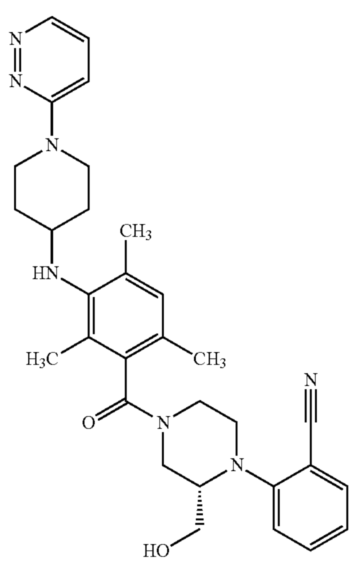 [SMILES: Cc1cc(C)c(C(=O)N2CCN(c3ccccc3C#N)[C@H](CO)C2)c(C)c1NC1CCN(c2cccnn2)CC1] | 102/90 | 1H NMR (500 MHz, DMSO-d6) δ 8.53-8.49 (m, 1H), 7.73-7.67 (m, 1H), 7.65-7.55 (m, 1H), 7.37-7.31 (m, 1H), 7.25 (q, J = 9.0, 8.2 Hz, 2H), 7.19-7.07 (m, 1H), 6.90-6.83 (m, 1H), 4.63 (d, J = 113.9 Hz, 1H), 4.43-4.20 (m, 3H), 4.02-3.37 (m, 4H), 3.29-3.13 (m, 3H), 3.13-2.96 (m, 2H), 2.96-2.80 (m, 2H), 2.22 (d, J = 5.5 Hz, 3H), 2.17-2.09 (m, 3H), 2.09-2.04 (m, 4H), 1.81 (s, 2H), 1.54-1.35 (m, 2H). | 540 | 2.77, 2.90, 2.94, 3.07 | Method 6 | 2-[(2S)-2-(hydroxymethyl)-4-(2,4,6-trimethyl-3-{[1-(pyridazin-3-yl)piperidin-4-yl]amino}benzoyl)piperazin-1-yl]benzonitrile |

TABLE 13-continued

| Example | Structure | Int. Acid/ Amine | NMR Data | m/z | RT (min) | LCMS | IUPAC Name |
|---|---|---|---|---|---|---|---|
| 1-165 | 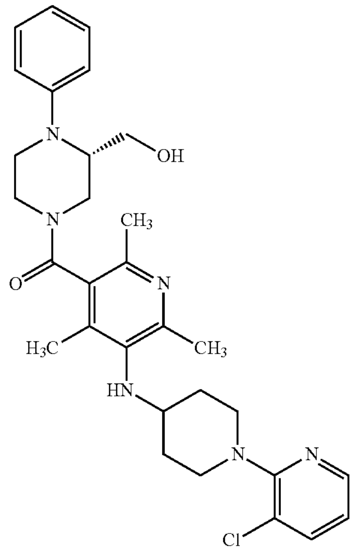 [SMILES: Cc1nc(C)c(C(=O)N2CCN(c3ccccc3)[C@H](CO)C2)c(C)c1NC1CCN(c2ncccc2Cl)CC1] | 138/119 | 1H NMR (500 MHz, DMSO-d6) δ 8.23-8.14 (m, 1H), 7.81-7.73 (m, 1H), 7.27-7.13 (m, 2H), 7.01-6.93 (m, 1H), 6.93-6.86 (m, 2H), 6.80- 6.66 (m, 1H), 4.80 (s, 1H), 4.65-4.23 (m, 1H), 4.20-3.79 (m, 2H), 3.79-3.41 (m, 5H), 3.26-2.88 (m, 4H), 2.88-2.67 (m, 2H), 2.47-2.38 (m, 3H), 2.31-2.02 (m, 6H), 1.95-1.75 (m, 2H), 1.75-1.51 (m, 2H). | 550 | 2.22, 2.30, 2.32, 2.36 | Method 5 | [(2S)-4-(5-{[1-(3-chloropyridin-2-yl)piperidin-4-yl]amino}-2,4,6-trimethyl-pyridine-3-carbonyl)-1-phenyl-piperazin-2-yl]MeOH |

Example 155: AlphaLISA Ultra pS6K1 Assay

Assay Protocol:
1. Seed MCF-7 cells in Corning 3701 plate and incubate for 20-24 hour. 12,000-16,000 cells will be seeded in 36 μL medium per well.
2. Change the culture medium with fresh medium and incubate for another 2 hours.
3. Add 12 μL (4×) compounds into the cell plate by HAMILTON. Final DMSO concentration is 0.5%. Incubate for 2 hours.
4. Aspirate 38 μL by HAMILTON, 10 μL rest per well.
5. Add 10 μL 2× lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 ul lysate to assay plate (Optiplate-384).
7. Add 5 ul acceptor beads into assay plate and incubation for 2 hours
8. Add 5 ul donor beads and incubation for 2 hours
9. Count the plate by EnSpire Multimode Plate Reader

TABLE 14

| Key Reagents/Supplies | | | |
|---|---|---|---|
| Reagents/materials | Vendor | Cat. No. | Lot. No. |
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| Rapamycin | SELLECK | S1039 | 08 |
| OptiPlate-384, White Opaque 384-well MicroPlate | PerkinElmer | 6007299 | 8210-14501 |
| AlphaLISA SureFire Ultra p-p70 S6 Kinase (Thr389) Assay Kit | PerkinElmer | ALSU-PP70-A10K | U0381 |

Example 156: AlphaLISA Ultra pAKT Assay

Assay Protocol:
1. MCF-7 cells in Corning 3701 plate and incubate for 20-24 hour. 16,000-20,000 cells will be seeded in 36 μL medium per well.
2. Change the culture medium with fresh medium and incubate for another 2 hours.
3. Add 12 μL (4×) compounds into the cell plate by HAMILTON. Final DMSO concentration is 0.5%. Incubate for 2 hours.
4. Aspirate 38 μL by HAMILTON, 10 μL rest per well.
5. Add 10 μL 2× lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 ul lysate to assay plate (Optiplate-384).
7. Add 5 ul acceptor beads into assay plate and incubation for 2 hours
8. Add 5 ul donor beads and incubation for 2 hours
9. Count the plate by EnSpire Multimode Plate Reader

TABLE 15

Key Reagents/Supplies

| Reagents/materials | Vendor | Cat. No. | Lot. No. |
|---|---|---|---|
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| Rapamycin | SELLECK | S1039 | 08 |
| OptiPlate-384, White Opaque 384- well MicroPlate | PerkinElmer | 6007299 | 8210-14501 |
| AlphaLISA SureFire Ultra p-Akt 1/2/3 (Ser473) Assay Kits | PerkinElmer | ALSU-PAKT-B10K | U0329 |

Example 157: Radioactive Glucose Uptake in MCF-7 Cells

Assay Protocol
1. Seed approximately 12,000 MCF-7 cells cultured without insulin per well in 96-well plates (BIOCOAT, #356690) and let the cells sit in hood for 30 min. (Cell culture medium: DMEM+10% FBS).
2. Put the cell culture plates in TC incubator (5% $CO_2$, 37° C.) and incubate overnight.
3. Take out the cell plates and wash with prewarmed KRH buffer (37° C.) three times using BioTek plate washer. (KRH buffer preparation: 136 mM NaCl, 4.7 mM KCl, 1.25 mM MgCl2, 1.2 mM $CaCl_2$, 20 mM HEPES, 0.1 mg/ml sodium pyruvate, 0.1% BSA, pH 7.4).
4. Compound preparation and treatment:
   a) Add 12 ul compound stock in 100% DMSO to the first column of Echo LDV plate
   b) Serially dilute the compound solution in 100% DMSO (4 uL+8 uL DMSO) using Bravo for 9 doses
   c) Dispense 350 nL compounds using Echo to the working plate.
   d) i) Without compound preincubation condition, dispense 116 uL KRH buffer containing tritiated 2-deoxy-D-glucose (3H-2DG) and 2-deoxy-D-glucose (2DG) to the working plate and mix.
   ii) With compound preincubation condition, dispense 110 uL KRH buffer only to the working plates and mix
   e) Keep the compound working plate at 37° C. incubator until use
5. Discard the KRH buffer (cells were kept in KRH buffer for 10-15 min before 2-DG addition) and transfer 100 uL compound working solution out to the cell culture plate using Bravo. Incubate for 20 mins at 37° C. (2DG final at 0.2 mM, 3H-2DG at 10 uCi/mL).
6. Add prewarmed 50 uL KRH buffer (37° C.) containing 60 mM cold 2DG to the wells to stop the 2DG uptake using Multidrop combi
7. Wash the cells with prewarmed PBS three times using BioTek plate washer
8. Add 50 uL lysis buffer (0.1 M NaOH) into the assay plate to lyse the cells using Bravo and shake at 800 rpm for 30 min.
9. Mix and transfer 20 uL lysate to a new white plate (Corning, #3610) and add 200 uL MicroScint-20 using Bravo
10. Shake the plate at 1000 rpm for 30 min and count in a MicroBeta plate reader.

Example 158: ATP/Rotenone Assay

Assay Protocol
Day 1: Plate cells in Corning 96-Well Clear Bottom Black Polystyrene Microplates (corning 3340) in Glucose-free DMEM+10% dFBS
   80 uL/well
   25,000 cells/well for 293T
   10,000 cells/well for MCF7
Day 2:
Glucose DR to Establish Glucose EC50
1. 1 h pre-treat with 10 uM Rotenone
   add 10 uL if 9× (90 uM) rotenone to each well (freshly made 10 mM stock diluted 1:11 Ix in glucose-free DMEM.
2. Stimulate with glucose for 15 min
   Make glucose DR at 10× concentration in glucose-free DMEM
   Add 10 uL per well and incubate at 37° C. for 15 min
3. Reconstitute and Measure
   Remove plate, immediately add 100 uL of reconstituted Celltiter-Glo reagent (Promega; G7570) per well
   Shake plate covered for 10 min at room temperature
   Let plate sit for 2-5 min, read luminescence
   Calculate EC50 for glucose (usually ~1 mM for 293T cells and ~0.25 mM for MCF-7 cells).
Determine Compound IC50s
1. 1 h pre-treat Rotenone/compound solution
   Make 9× (90 uM) rotenone: 10 mM stock of Rotenone fresh—dilute 1:111× in Glucose-free DMEM).
   Make compound dilution series in DMSO then dilute 1:111 in 90 uM rotenone in glucose-free media
   Add 10 uL of 9× rotenone/compound solutions per well
2. Stimulate with glucose for 15 min
   Make glucose DR at 10× concentration in glucose-free DMEM
   Add 10 uL per well and incubate at 37° C. for 15 min
3. Reconstitute and Measure
   Remove plate, immediately add 100 uL of reconstituted Celltiter-Glo reagent (Promega; G7570) per well
   Shake plate covered for 10 min at room temperature
   Let plate sit for 2-5 min, read luminescence
   Calculate IC50 for compounds Table 16 shows the inhibitory activity ($IC_{50}$) of selected compounds of this invention in the pS6K1, pAKT, and glucose uptake assays. The compound numbers correspond to the compound numbers in Table 1. Compounds having an activity designated as "A" provided inhibitory activity ($IC_{50}$) of 0.01-1 µM; compounds designated as "B" provided inhibitory activity ($IC_{50}$) of 1-3 µM; compounds designated as "C" provided inhibitory activity ($IC_{50}$) of 3-5 µM; compounds designated as "D" provided inhibitory activity ($IC_{50}$) of 5-10 µM and compounds designated as "E" provided inhibitory activity ($IC_{50}$) of >10 µM. "NA" stands for "not assayed."

TABLE 16

Assay Data for Exemplary Compounds

| Compound Number | pS6K1 in MCF7: IC$_{50}$ (μM) | pAKT in MCF7: IC$_{50}$ (μM) | Glucose uptake in MCF7: IC$_{50}$ (μM) |
|---|---|---|---|
| I-1 | A | E | A |
| I-2 | A | E | A |
| I-3 | A | E | A |
| I-4 | B | E | E |
| I-5 | B | E | NA |
| I-6 | E | E | E |
| I-7 | B | E | NA |
| I-8 | E | E | NA |
| I-9 | B | E | NA |
| I-10 | B | E | NA |
| I-11 | C | E | NA |
| I-12 | E | E | E |
| I-13 | C | E | NA |
| I-14 | A | E | A |
| I-15 | A | E | A |
| I-16 | A | E | NA |
| I-17 | B | E | NA |
| I-18 | B | E | NA |
| I-19 | B | E | NA |
| I-20 | B | E | NA |
| I-21 | C | E | NA |
| I-22 | C | E | C |
| I-23 | B | E | NA |
| I-24 | A | E | A |
| I-25 | A | E | A |
| I-26 | A | E | A |
| I-27 | B | E | NA |
| I-28 | B | E | NA |
| I-29 | A | E | NA |
| I-30 | A | E | NA |
| I-31 | A | E | NA |
| I-32 | B | E | NA |
| I-33 | D | E | NA |
| I-34 | B | E | NA |
| I-35 | C | E | NA |
| I-36 | D | E | NA |
| I-37 | B | E | NA |
| I-38 | C | E | NA |
| I-39 | E | E | NA |
| I-40 | A | E | NA |
| I-41 | B | E | NA |
| I-42 | A | E | NA |
| I-43 | A | E | A |
| I-44 | A | E | A |
| I-45 | A | E | A |
| I-46 | B | E | NA |
| I-47 | B | E | NA |
| I-48 | A | E | A |
| I-49 | A | E | A |
| I-50 | B | E | NA |
| I-51 | B | E | NA |
| I-52 | E | E | NA |
| I-53 | A | E | NA |
| I-54 | B | E | NA |
| I-55 | B | E | NA |
| I-56 | B | E | NA |
| I-57 | B | E | NA |
| I-58 | A | E | NA |
| I-59 | C | E | NA |
| I-60 | B | E | A |
| I-61 | A | E | A |
| I-62 | A | E | NA |
| I-63 | A | E | NA |
| I-64 | A | E | NA |
| I-65 | A | E | NA |
| I-66 | A | E | NA |
| I-67 | A | E | NA |
| I-68 | A | E | NA |
| I-69 | A | E | NA |
| I-70 | C | E | NA |
| I-71 | A | E | NA |
| I-72 | C | E | NA |
| I-73 | C | E | NA |
| I-74 | A | E | NA |
| I-75 | A | E | A |
| I-76 | A | E | NA |
| I-77 | A | E | NA |
| I-78 | E | E | NA |
| I-79 | A | E | A |
| I-80 | B | E | NA |
| I-81 | E | E | NA |
| I-82 | C | E | NA |
| I-83 | A | E | NA |
| I-84 | B | E | NA |
| I-85 | A | E | NA |
| I-86 | E | E | NA |
| I-87 | B | E | NA |
| I-88 | A | E | A |
| I-89 | A | E | NA |
| I-90 | C | E | NA |
| I-91 | D | E | B |
| I-92 | B | E | NA |
| I-93 | B | E | NA |
| I-94 | B | E | NA |
| I-95 | E | E | NA |
| I-96 | C | E | NA |
| I-97 | E | E | NA |
| I-98 | D | E | NA |
| I-99 | B | E | NA |
| I-100 | A | E | A |
| I-101 | B | E | NA |
| I-102 | A | E | A |
| I-103 | B | E | NA |
| I-104 | A | E | NA |
| I-105 | B | E | NA |
| I-106 | A | E | A |
| I-107 | C | E | NA |
| I-108 | B | E | NA |
| I-109 | C | E | NA |
| I-110 | A | E | NA |
| I-111 | A | E | A |
| I-112 | B | E | NA |
| I-113 | C | E | NA |
| I-114 | E | E | NA |
| I-115 | B | E | NA |
| I-116 | B | E | NA |
| I-117 | A | E | NA |
| I-118 | B | E | NA |
| I-119 | E | E | NA |
| I-120 | A | E | NA |
| I-121 | A | E | A |
| I-122 | A | E | NA |
| I-123 | B | E | NA |
| I-124 | A | E | NA |
| I-125 | E | E | NA |
| I-126 | A | E | NA |
| I-127 | C | E | NA |
| I-128 | A | E | A |
| I-129 | B | E | NA |
| I-130 | C | E | C |
| I-131 | E | E | NA |
| I-132 | B | E | NA |
| I-133 | B | E | NA |
| I-134 | B | E | NA |
| I-135 | A | E | NA |
| I-136 | A | E | NA |
| I-137 | A | E | NA |
| I-138 | A | E | A |
| I-139 | A | E | NA |
| I-140 | A | E | NA |
| I-141 | A | E | A |
| I-142 | A | E | NA |
| I-143 | A | E | NA |
| I-144 | A | E | NA |
| I-145 | A | E | NA |
| I-146 | A | A | NA |
| I-147 | A | E | NA |
| I-148 | A | E | NA |

TABLE 16-continued

Assay Data for Exemplary Compounds

| Compound Number | pS6K1 in MCF7: IC$_{50}$ (μM) | pAKT in MCF7: IC$_{50}$ (μM) | Glucose uptake in MCF7: IC$_{50}$ (μM) |
|---|---|---|---|
| I-149 | A | E | NA |
| I-150 | A | E | NA |
| I-151 | A | E | NA |
| I-152 | E | E | NA |
| I-153 | A | E | NA |
| I-154 | B | E | NA |
| I-155 | B | E | NA |
| I-156 | A | E | NA |
| I-157 | A | E | NA |
| I-158 | A | E | NA |
| I-159 | A | E | A |
| I-160 | B | E | NA |
| I-161 | A | E | NA |
| I-162 | A | E | NA |
| I-163 | A | E | NA |
| I-164 | A | E | NA |
| I-165 | A | E | NA |
| I-166 | B | E | E |
| I-167 | B | E | NA |
| I-168 | A | E | NA |
| I-169 | B | E | NA |
| I-170 | A | E | NA |
| I-171 | A | E | A |
| I-172 | C | E | NA |
| I-173 | B | E | NA |
| I-174 | A | E | NA |
| I-175 | A | E | NA |
| I-176 | A | E | A |
| I-177 | B | E | NA |
| I-178 | A | E | NA |
| I-179 | A | E | NA |
| I-180 | A | E | NA |
| I-181 | A | E | NA |
| I-182 | A | E | A |
| I-183 | A | E | NA |
| I-184 | A | E | NA |
| I-185 | A | E | NA |
| I-186 | A | E | NA |
| I-187 | E | E | NA |
| I-188 | B | E | NA |
| I-189 | A | E | NA |
| I-190 | A | E | NA |
| I-191 | A | E | A |
| I-192 | A | E | A |
| I-193 | B | E | NA |
| I-194 | A | E | A |
| I-195 | B | E | C |

We claim:

1. A compound of Formula I:

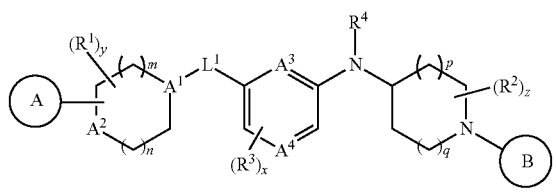

or a pharmaceutically acceptable salt thereof, wherein:
$A^1$ is N or CH;
$A^2$ is N(Ring A);
$A^3$ is C(R') or N;
$A^4$ is CH or N;
R' is H, $C_{1-6}$ aliphatic, or halogen;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
each of m, n, p, q, and x is independently 0, 1, or 2;
each of y and z is independently 0, 1, 2, 3 or 4;
each of $R^1$ and $R^2$ is independently R, or:
two $R^1$ groups are optionally taken together to form =O;
two $R^2$ groups are optionally taken together to form =O;
two $R^1$ groups are optionally taken together to form a covalent bond or a bivalent $C_{1-4}$ alkylene chain; or
two $R^2$ groups are optionally taken together to form a covalent bond or a bivalent $C_{1-4}$ alkylene chain;
an $R^1$ group and Ring A are optionally taken together with their intervening atoms to form a 5-8 membered fused ring having 0-2 heteroatoms independently selected from nitrogen, oxygen or sulfur; or
an $R^2$ group and Ring B are optionally taken together with their intervening atoms to form a 5-8 membered fused ring having 0-2 heteroatoms independently selected from nitrogen, oxygen or sulfur;
each of $R^3$ is independently R, halogen, —OR, —CN, or
two $R^3$ groups are optionally taken together with their intervening atoms to form a 5-8 membered partially unsaturated or aryl fused ring having 0-2 heteroatoms independently selected from nitrogen, oxygen, or sulfur;
$R^4$ is hydrogen or an optionally substituted $C_{1-6}$ aliphatic group;
Ring A is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur;
Ring B is an optionally substituted ring selected from 6-membered aryl containing 0-2 nitrogen atoms, 5-membered heteroaryl with 1-4 heteroatoms independently selected from nitrogen, oxygen or sulfur, or 8-10 membered bicyclic aryl or heteroaryl with 1-4 heteroatoms independently selected from nitrogen, oxygen or sulfur; and
$L^1$ is a covalent bond or a $C_1$-3 bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, or —S(O)$_2$—.

2. The compound according to claim 1, wherein $A^1$ is N.
3. The compound according to claim 2, wherein m is 1 and n is 1.
4. The compound according to claim 2, wherein $A^3$ is C(R').
5. The compound according to claim 2, wherein $A^4$ is CH.
6. The compound according to claim 2, wherein p is 1 and q is independently 0, 1, or 2.

7. The compound according to claim 2, wherein each of $R^1$ and $R^2$ is independently R, or: two $R^1$ groups are optionally taken together to form =O; two $R^2$ groups are optionally taken together to form =O; two $R^1$ groups are optionally taken together to form a covalent bond or a bivalent $C_{1-4}$ alkylene chain; or two $R^2$ groups are optionally taken together to form a covalent bond or a bivalent $C_{1-4}$ alkylene chain.

8. The compound according to claim 7, wherein $R^1$ is

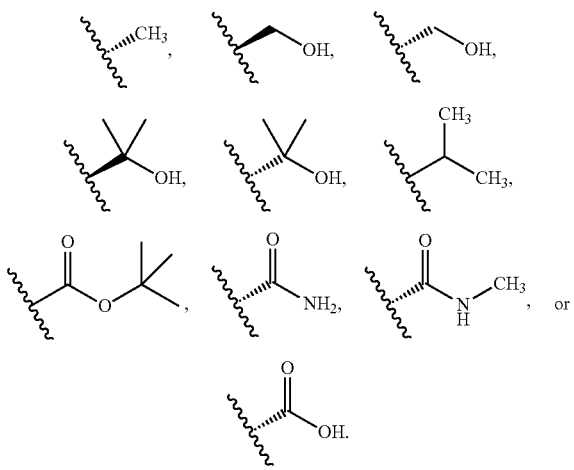

9. The compound according to claim 7, wherein $R^2$ is hydrogen or methyl.

10. The compound according to claim 2, wherein, each of $R^3$ is independently R, halogen, —OR, or —CN.

11. The compound according to claim 2, wherein Ring A is 1

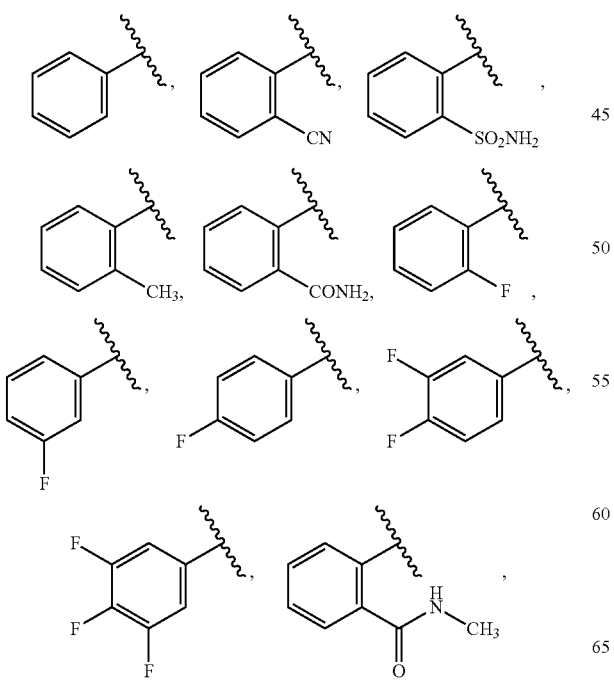

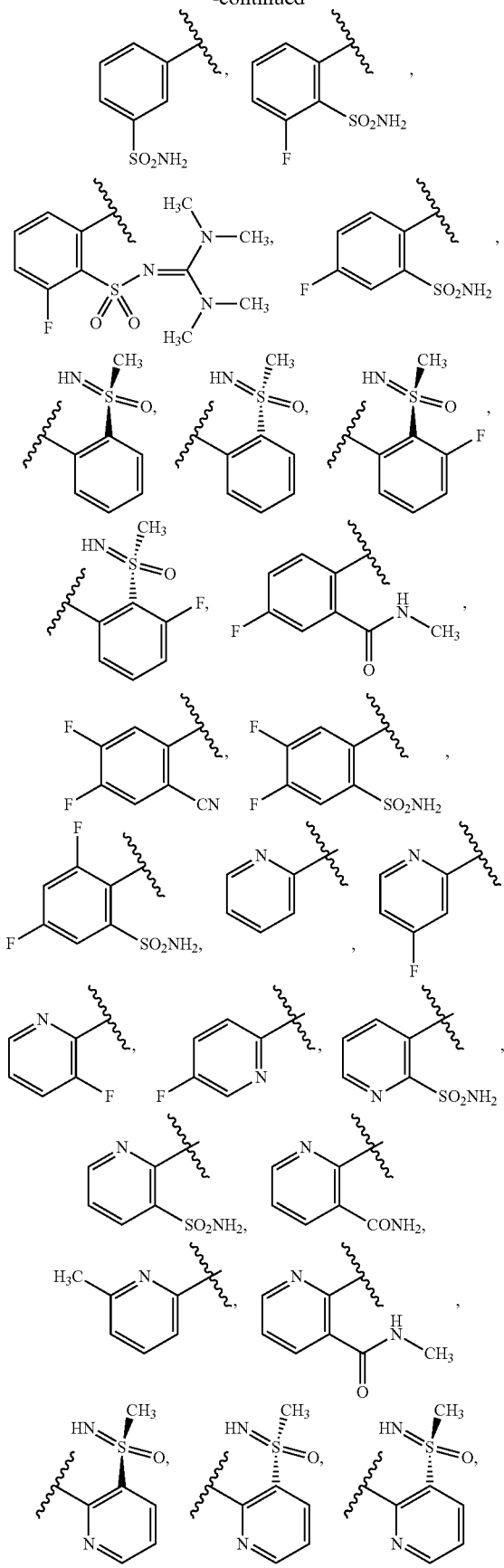

-continued

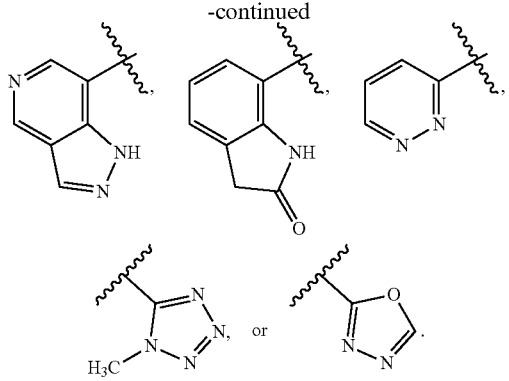

12. The compound according to claim 2, wherein Ring B is an optionally substituted ring selected from 6-membered aryl containing 0-2 nitrogen atoms.

13. The compound according to claim 12, wherein Ring B is

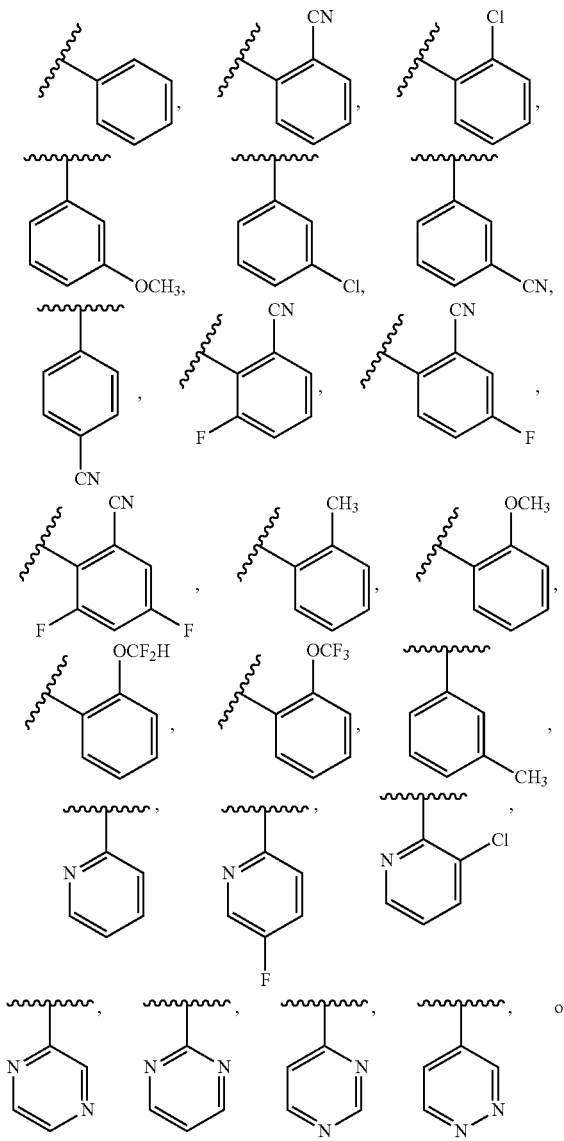

-continued

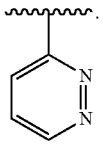

14. The compound according to claim 2, wherein $L^1$ is a covalent bond or a $C_{1-3}$ bivalent straight or branched saturated or unsaturated hydrocarbon chain wherein 1-2 methylene units of the chain are independently and optionally replaced with —C(O)—, —C(S)—, —C(R)$_2$—, —CH(R)—, —C(F)$_2$—, —N(R)—, or —S(O)$_2$—.

15. The compound according to claim 1, wherein said compound is of Formula II:

II

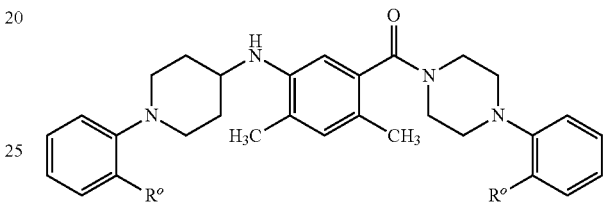

or a pharmaceutically acceptable salt thereof,
wherein each R° is a monovalent substituent independently selected from: halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$,
wherein each R$^\bullet$ is unsubstituted or, where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

16. The compound according to claim 1, wherein the compound is selected from:

I-1

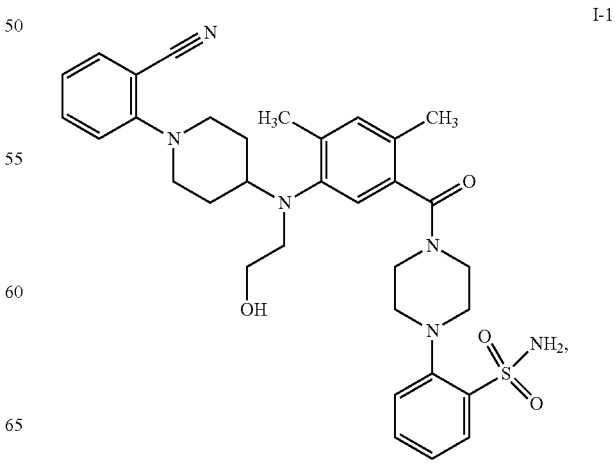

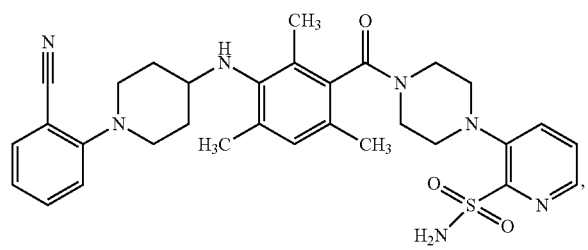
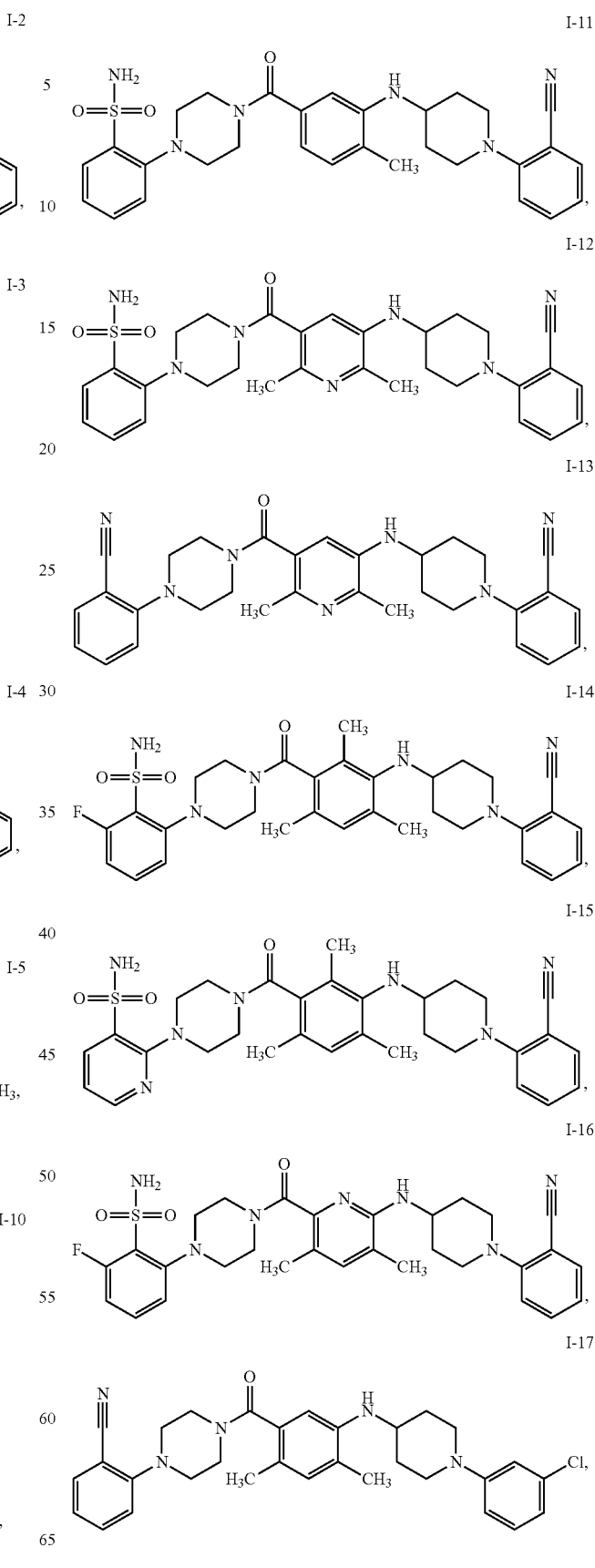

I-18
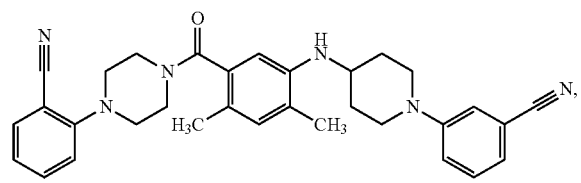
I-19
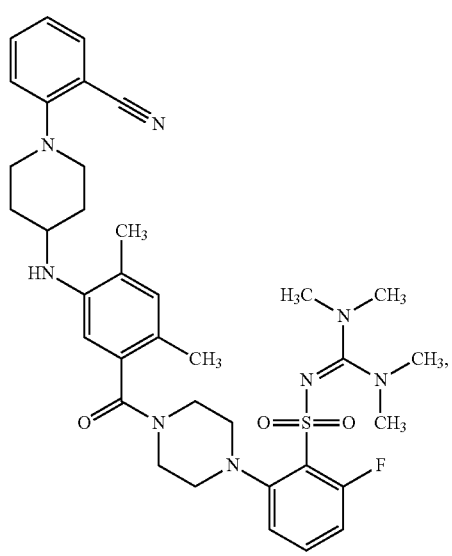
I-20
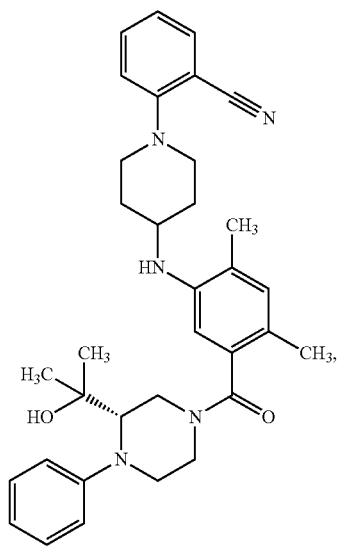
I-21
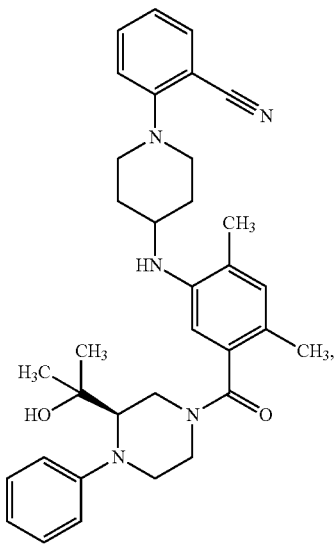
I-22
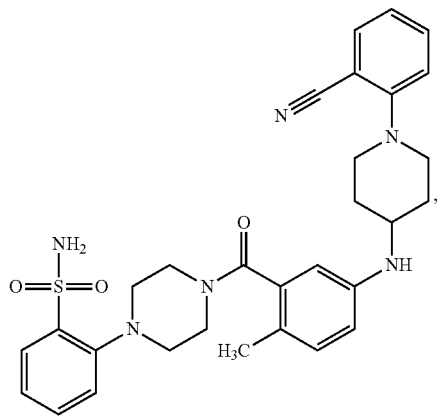
I-23
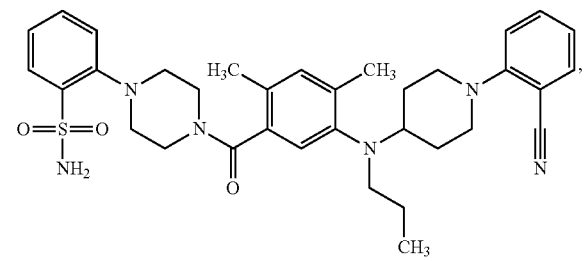

-continued
I-24
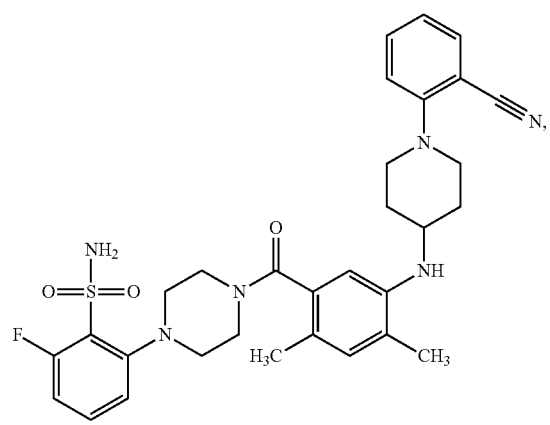
I-25
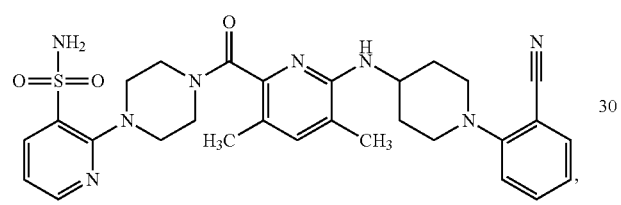
I-26
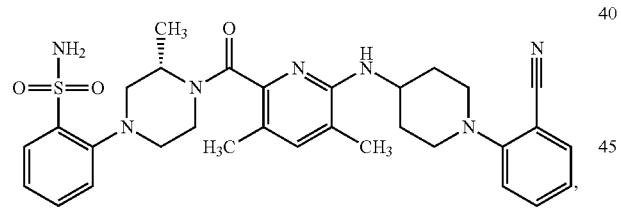
I-27
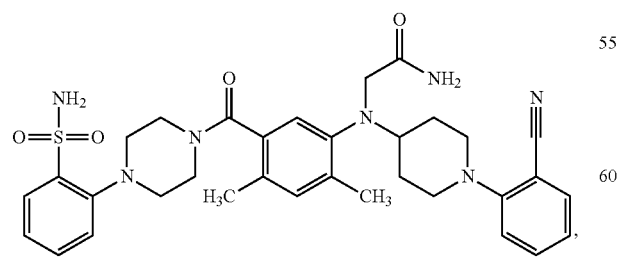
-continued
I-28
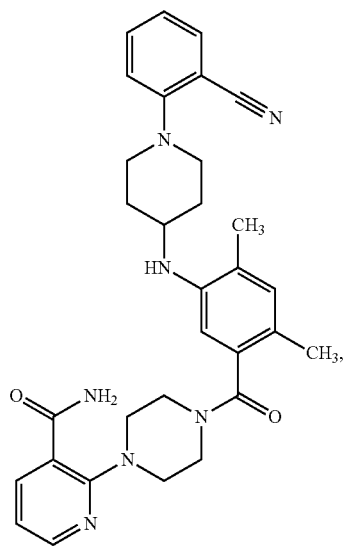
I-29
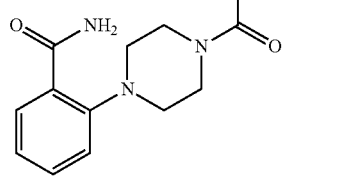
I-30
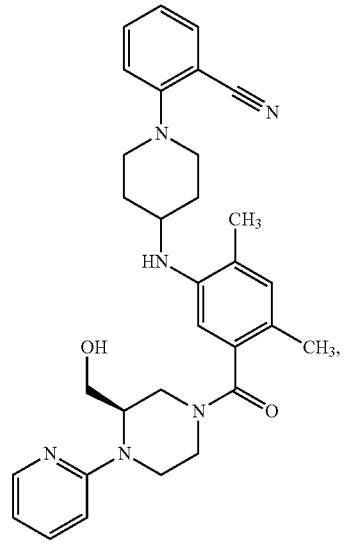

I-31
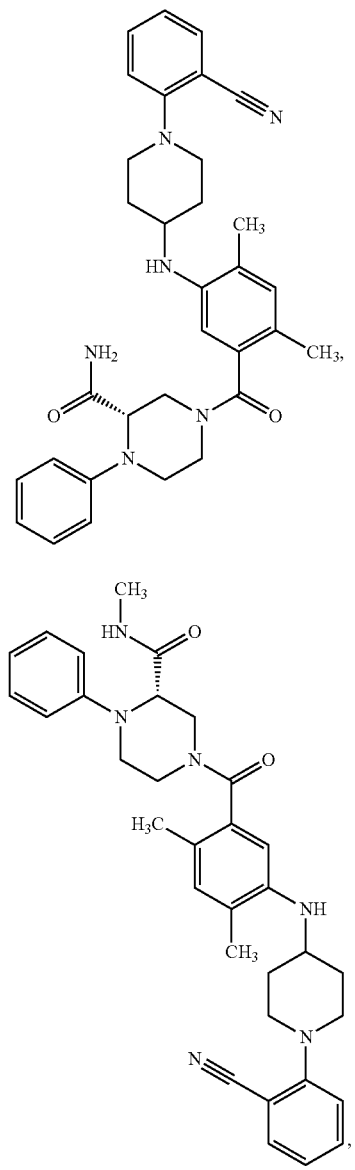
I-35
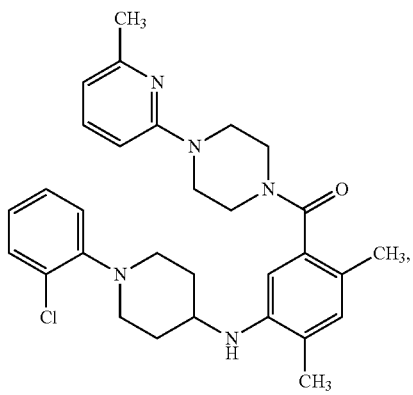
I-36
I-37
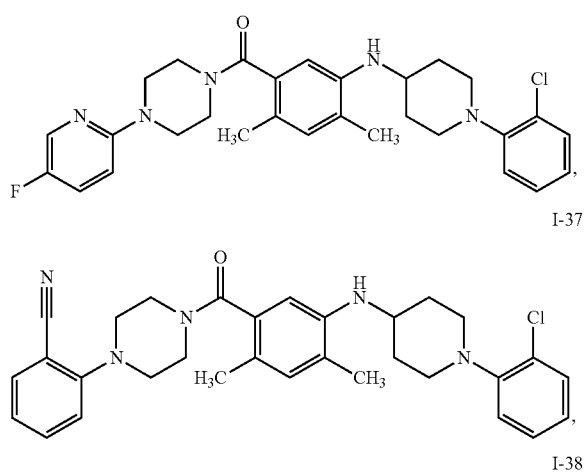
I-32
I-38
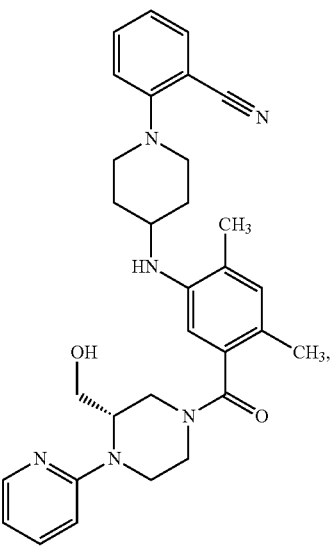
I-33
I-39
I-34
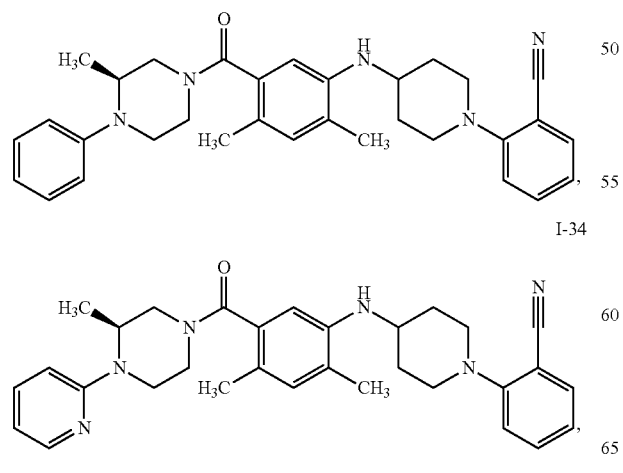

I-40
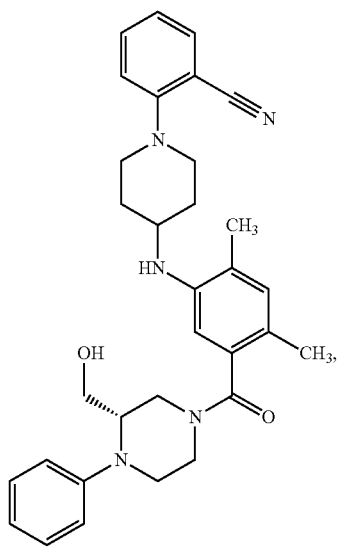
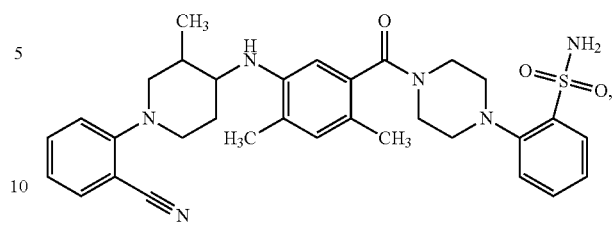
I-43
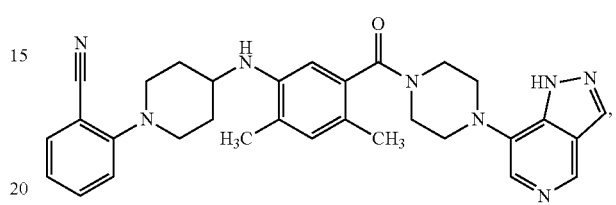
I-44
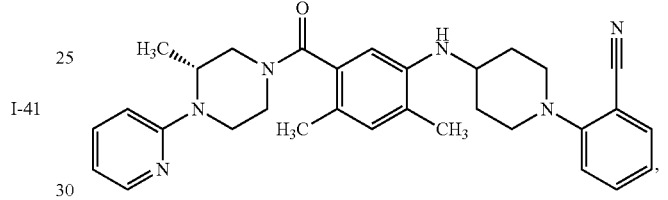
I-45
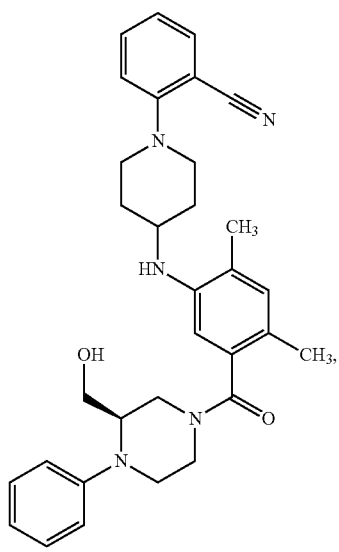
I-41
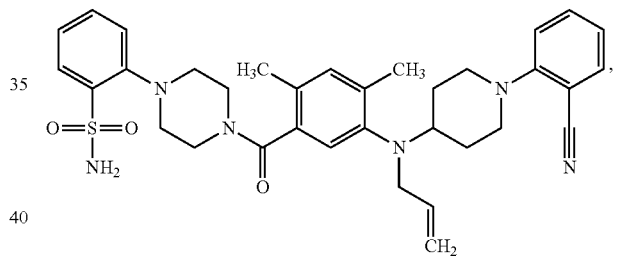
I-46
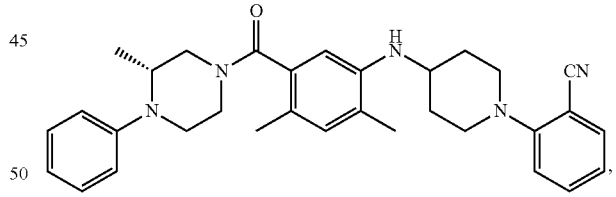
I-47
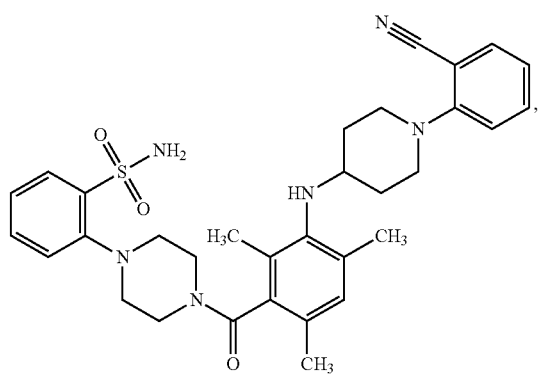
I-42
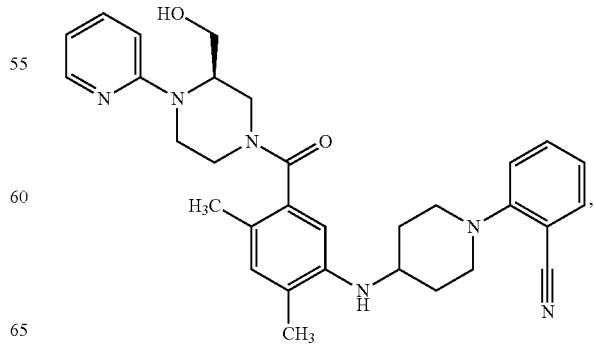
I-48

I-49
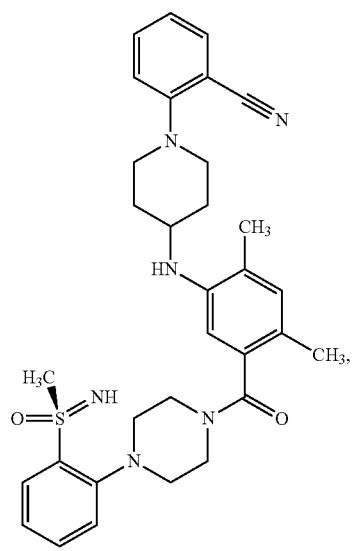
I-50
I-51
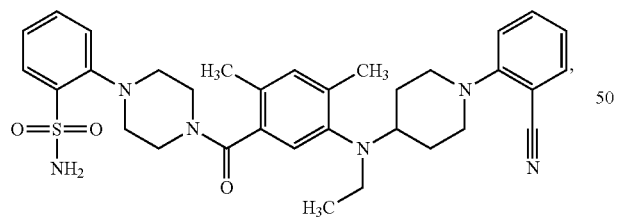
I-52
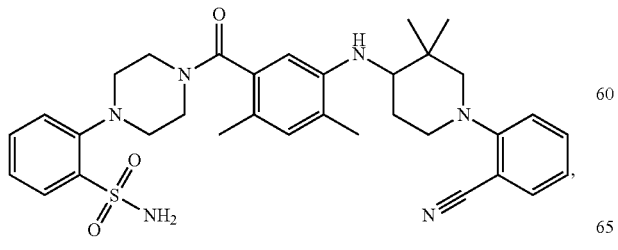
I-53
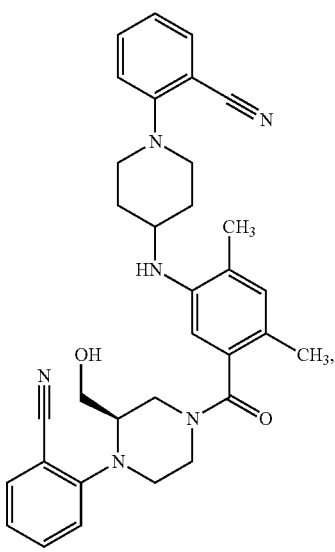
I-54
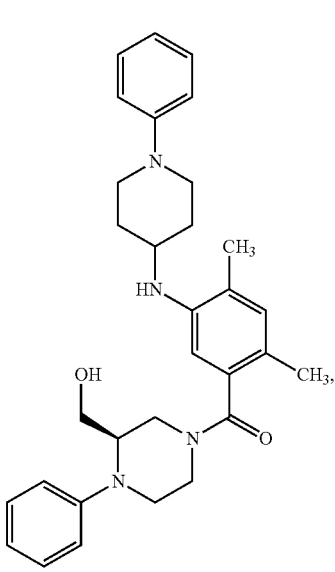
I-55
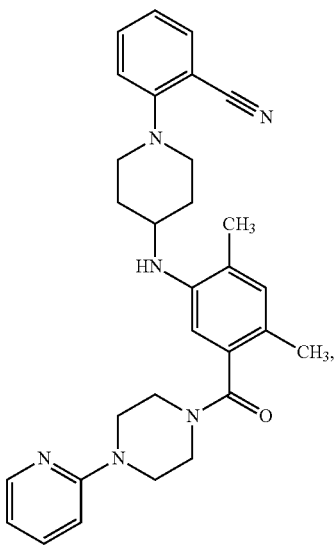

I-56
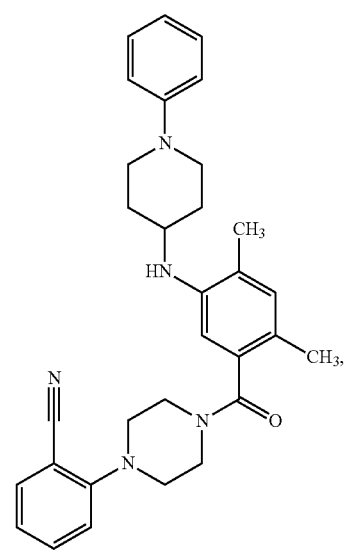
I-57
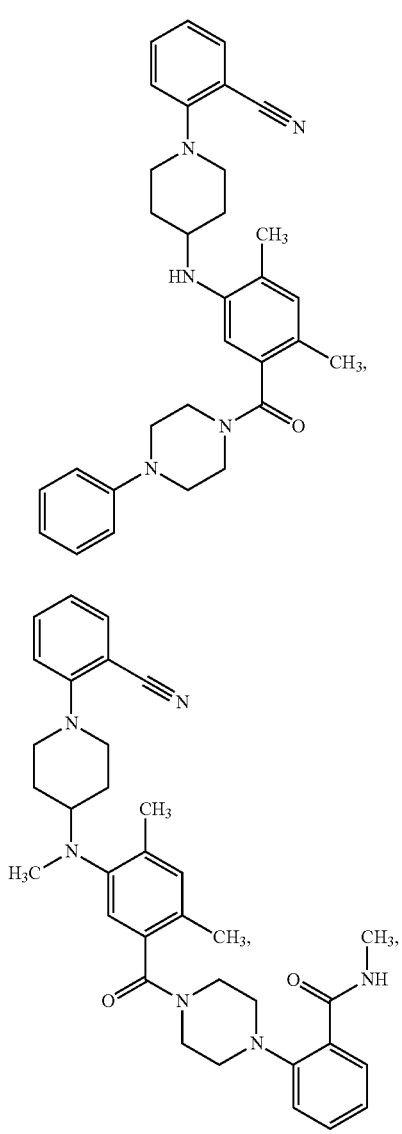
I-58
I-59
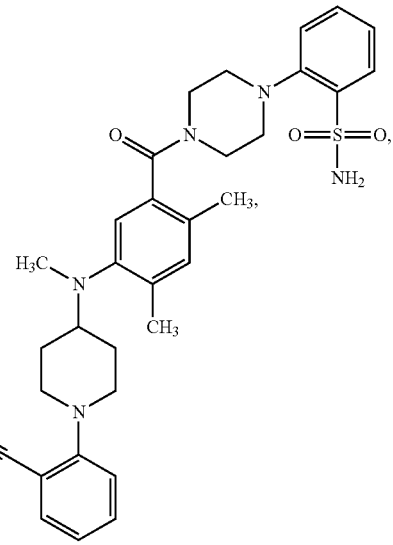
I-60
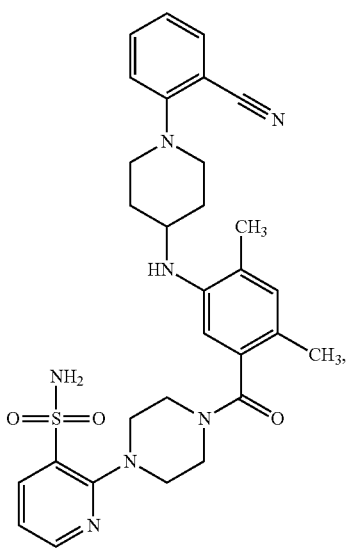
I-61
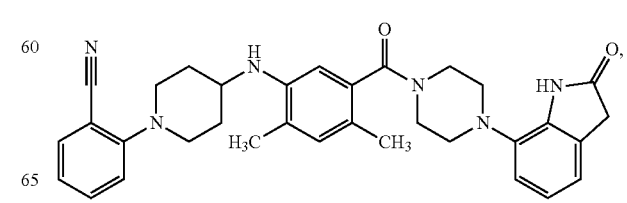

I-62
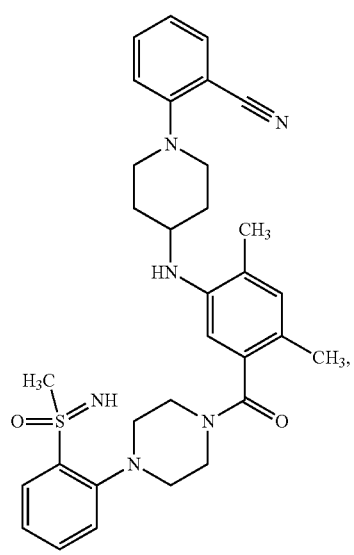
I-65
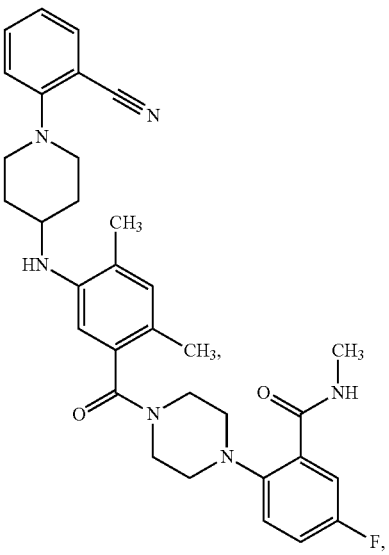
I-63
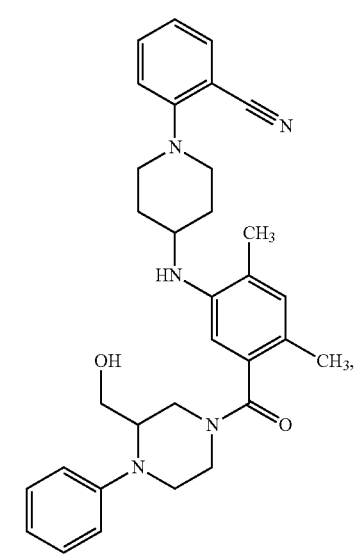
I-66
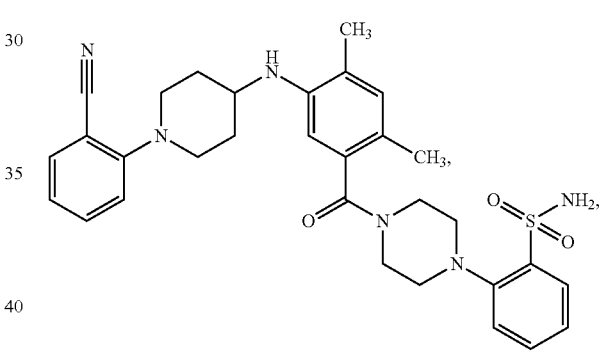
I-64
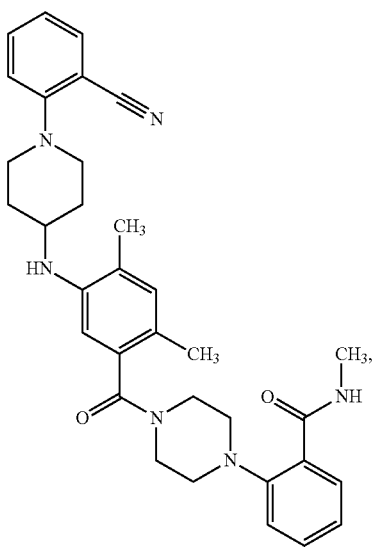
I-67
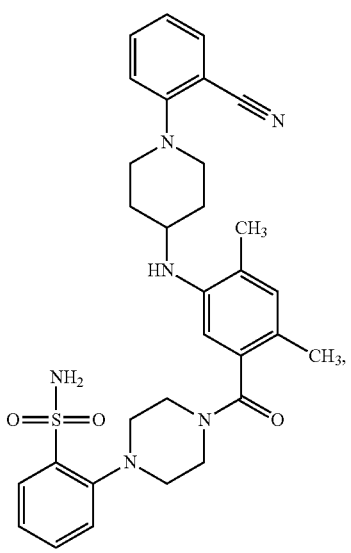

I-68
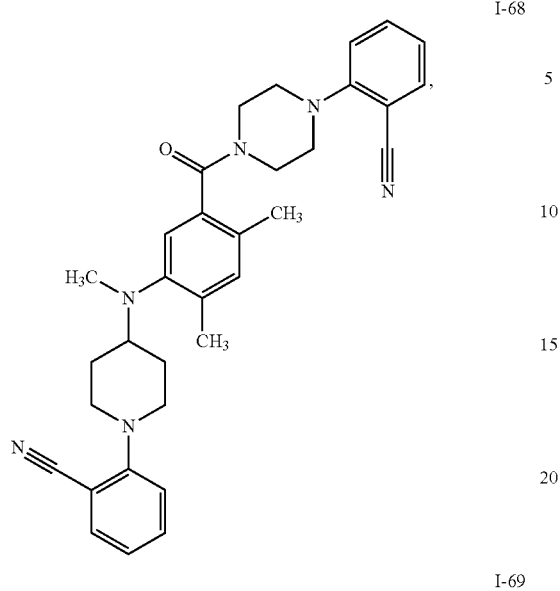
I-72
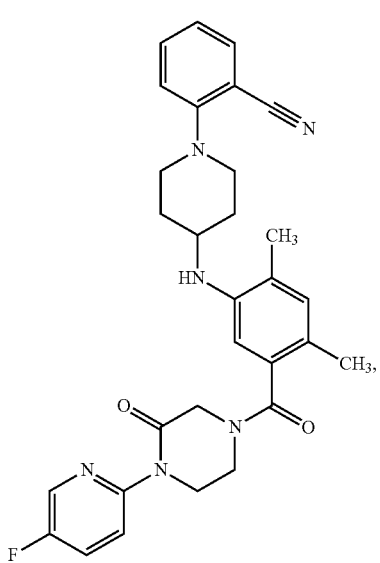
I-69
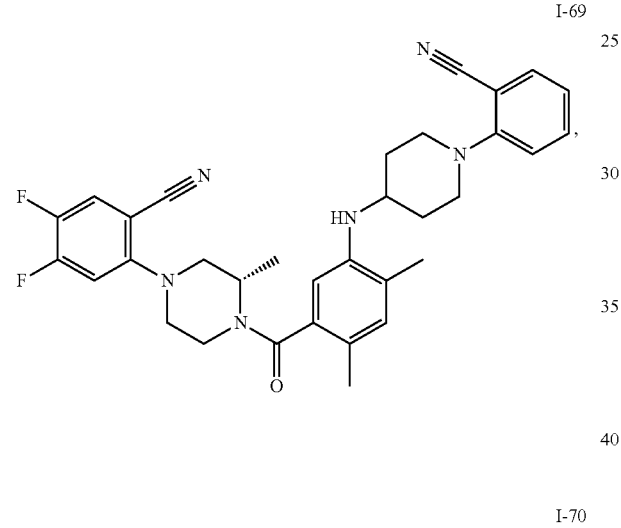
I-73
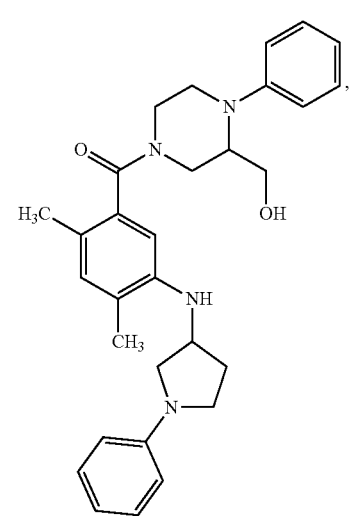
I-70
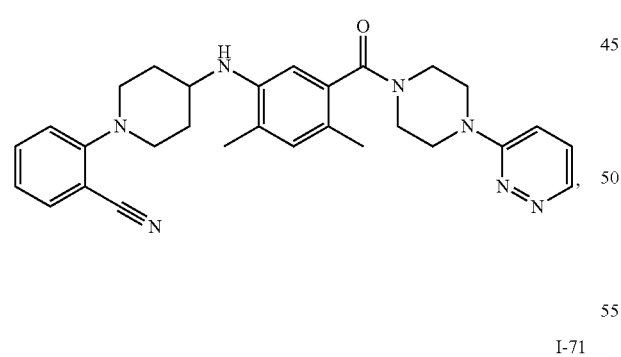
I-74
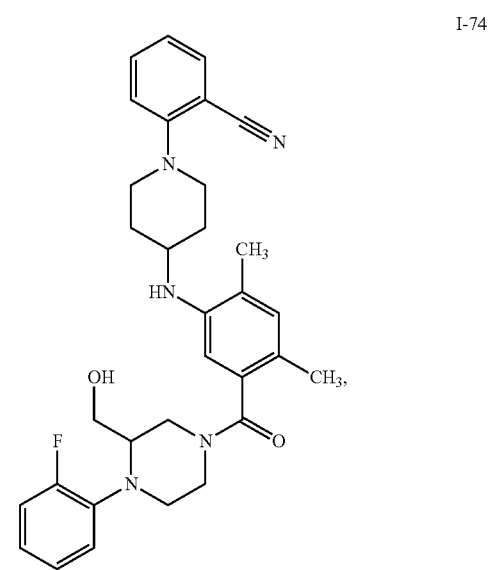
I-71
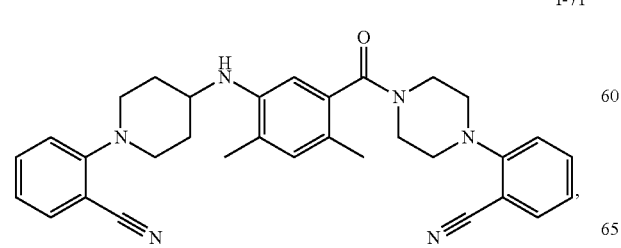

I-75
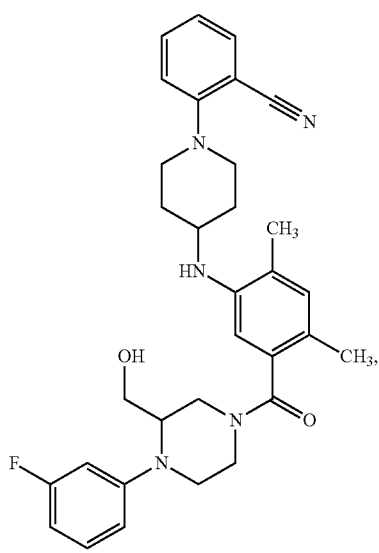
I-76
I-77
I-78
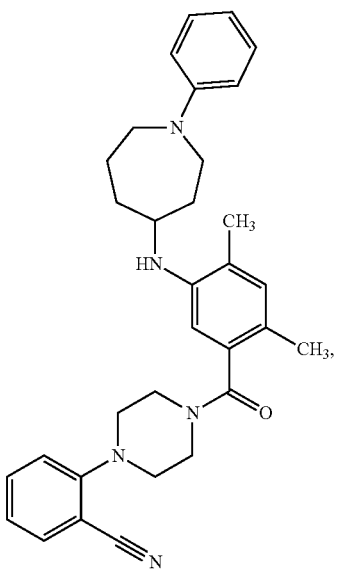
I-79
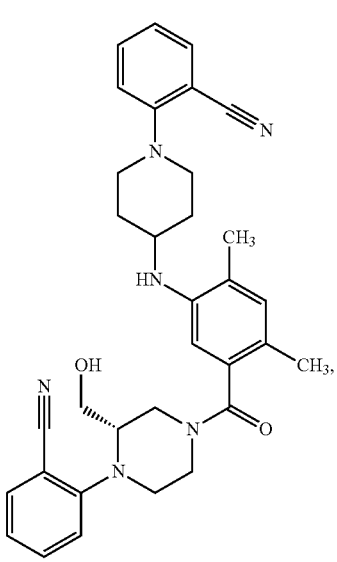

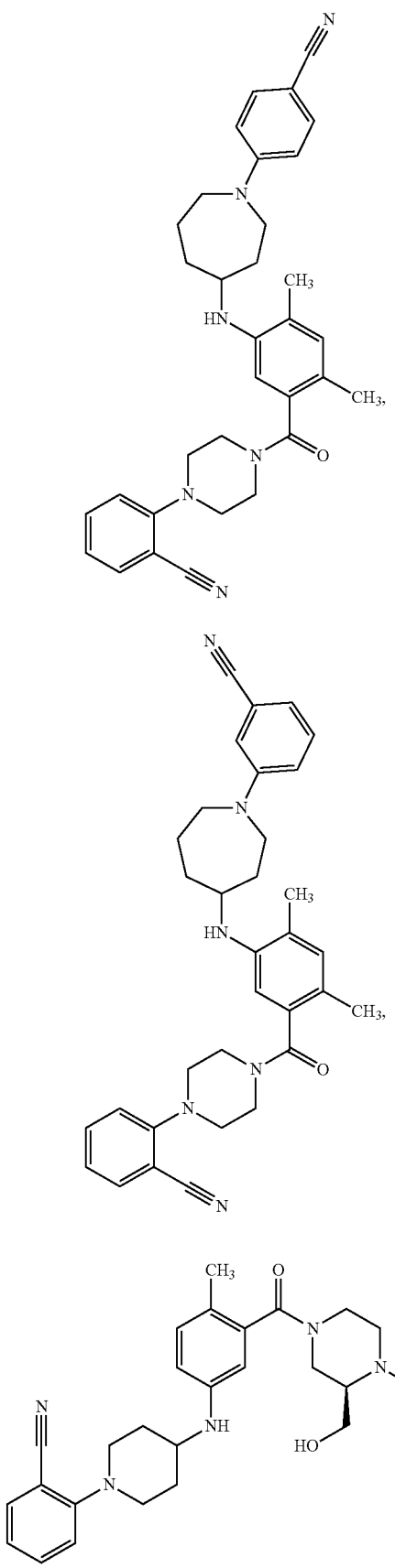
I-80
I-81
I-82
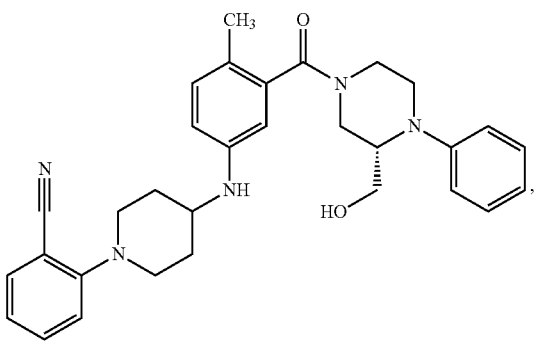
I-83
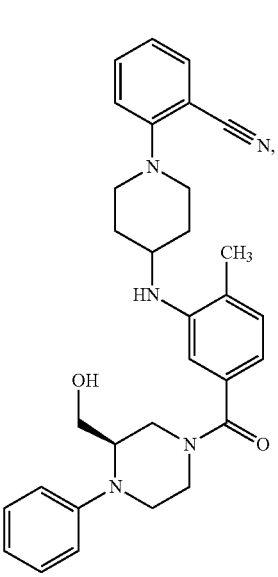
I-84
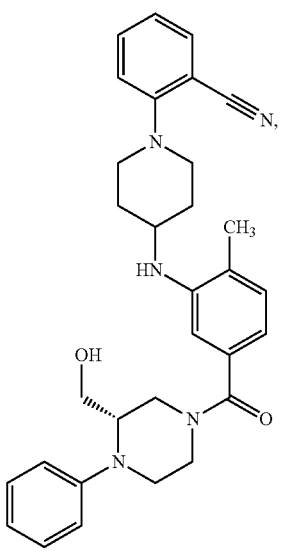
I-85

I-86
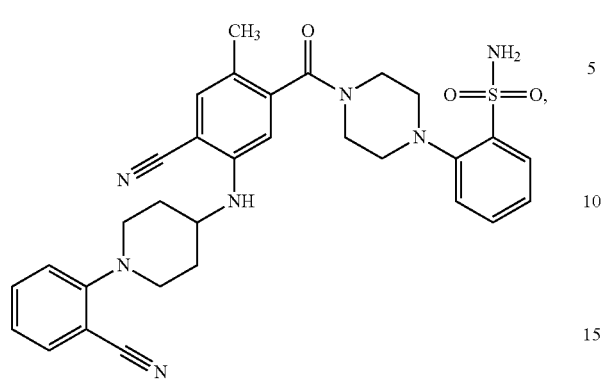
I-89
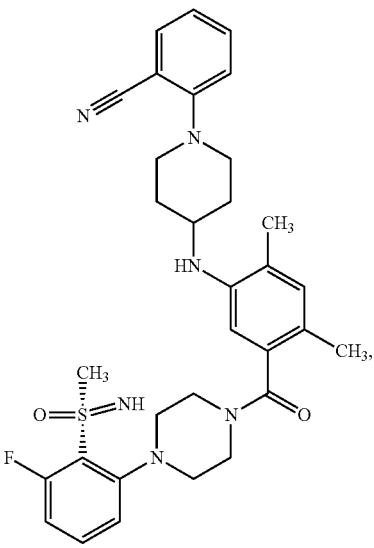
I-87
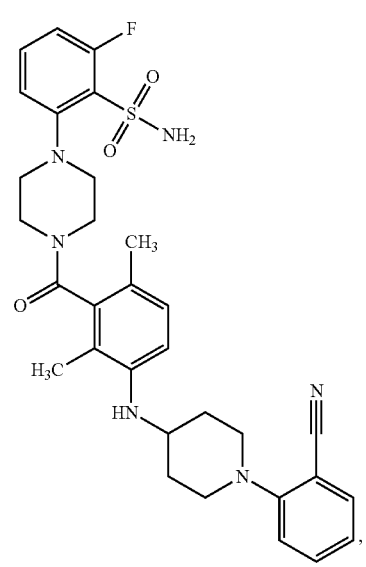
I-90
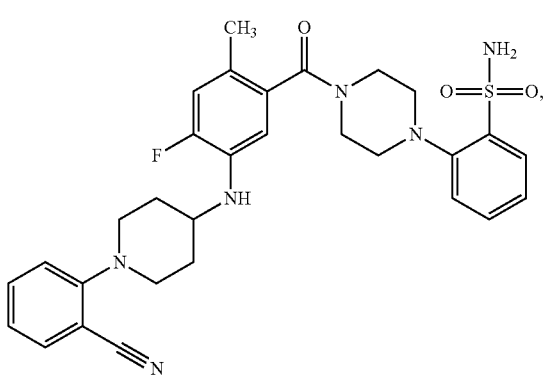
I-88
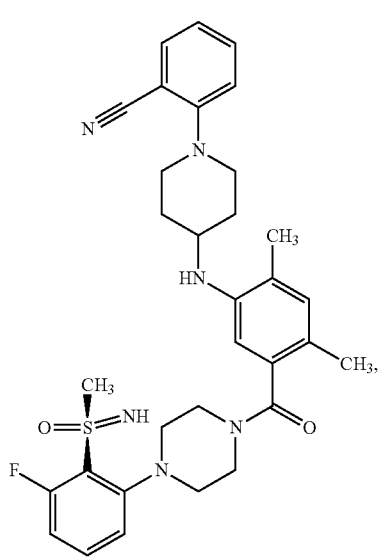
I-91
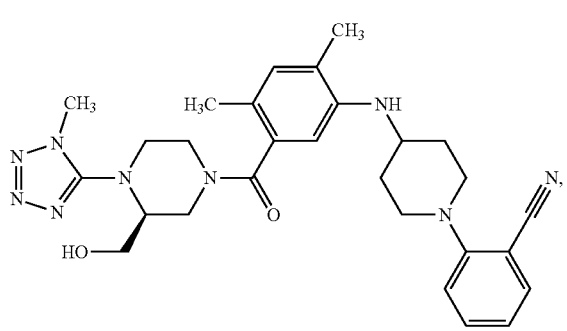

I-92
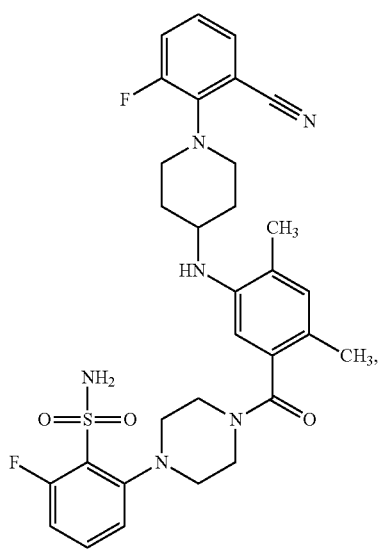
I-93
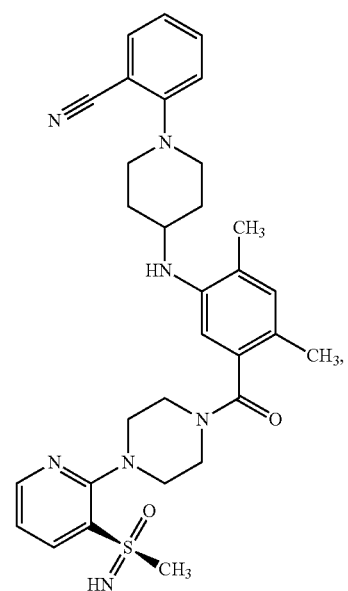
I-94
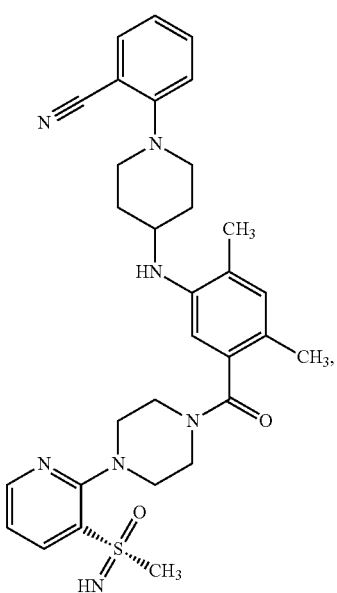
I-97
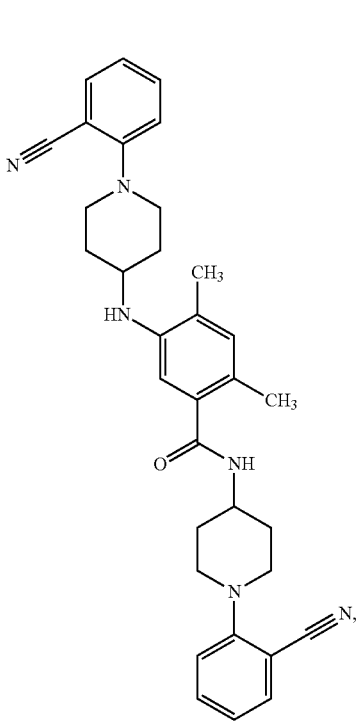

I-99
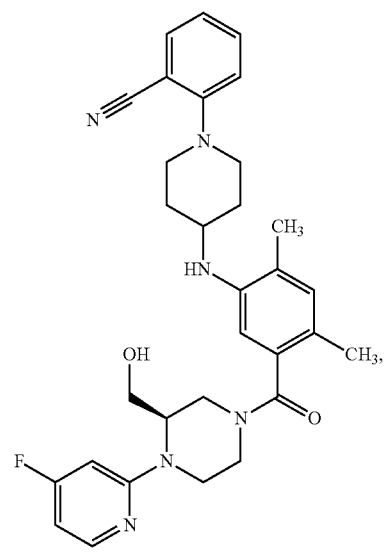
I-100
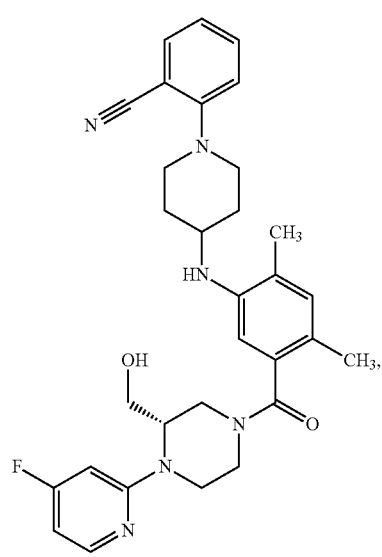
I-101
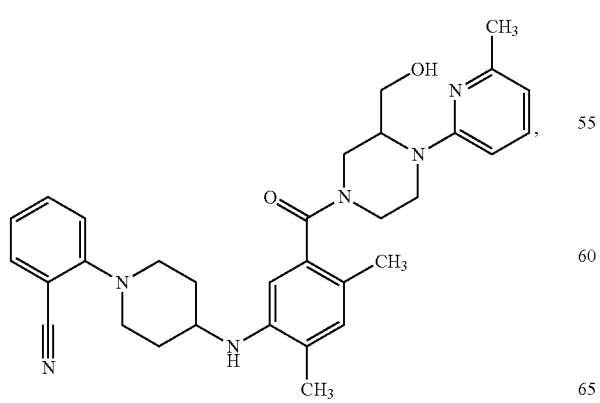
I-102
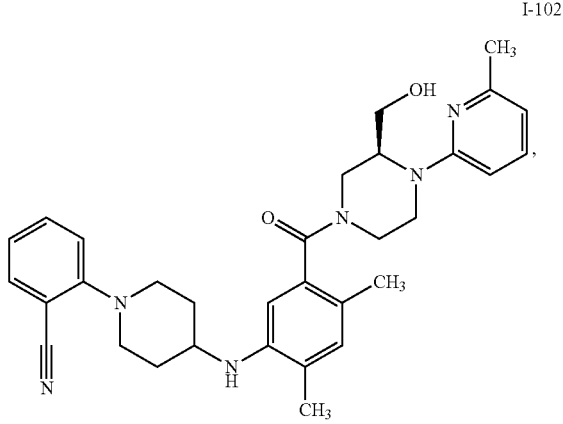
I-103
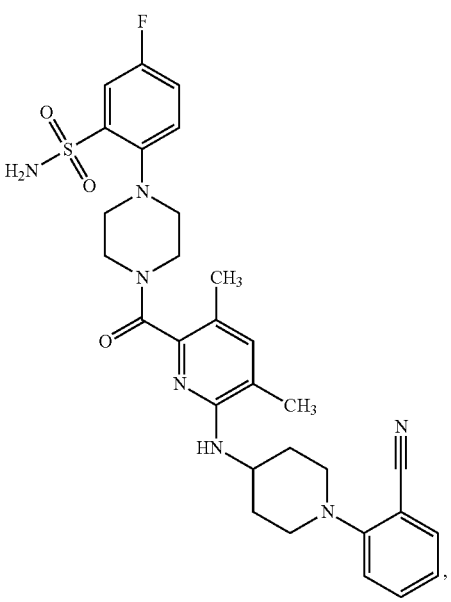
I-104
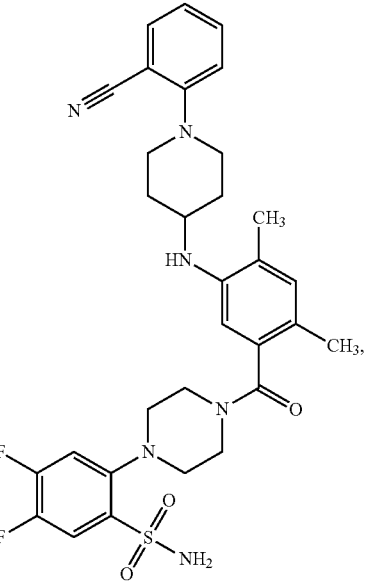

I-105
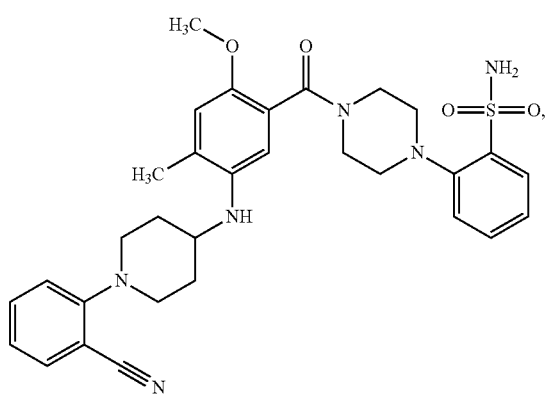
I-108
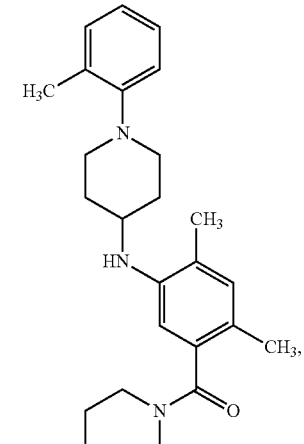
I-106
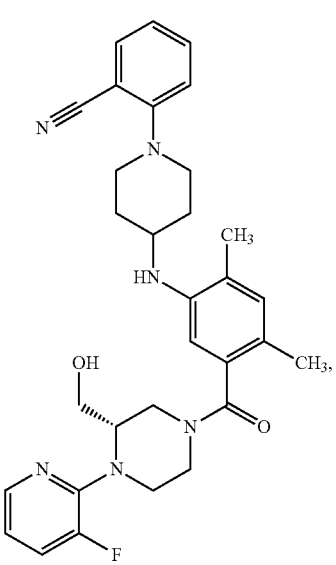
I-109
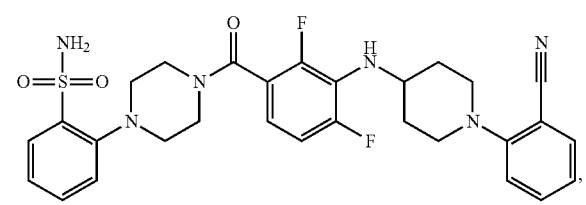
I-107
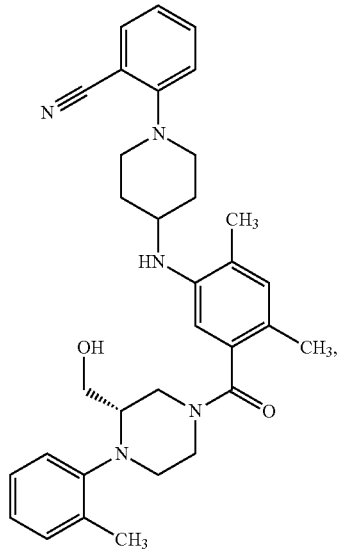
I-110
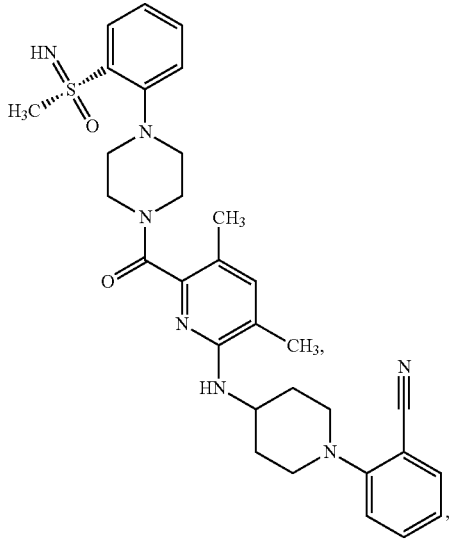

I-111
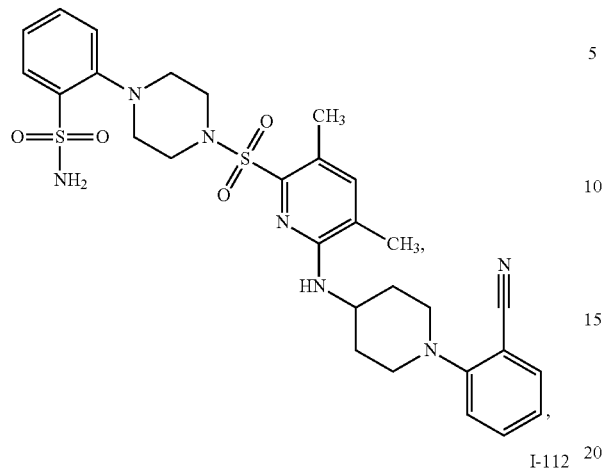
I-112
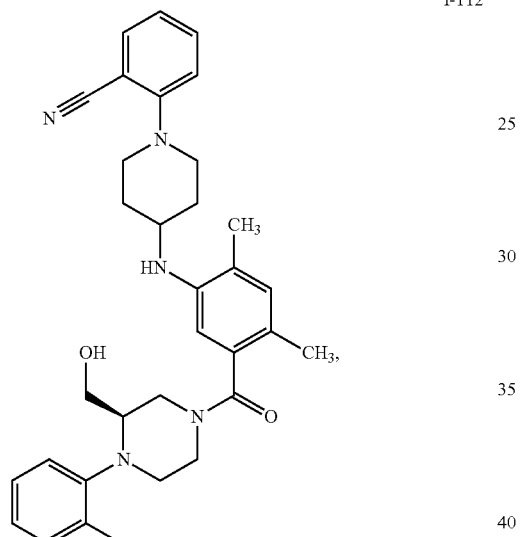
I-113
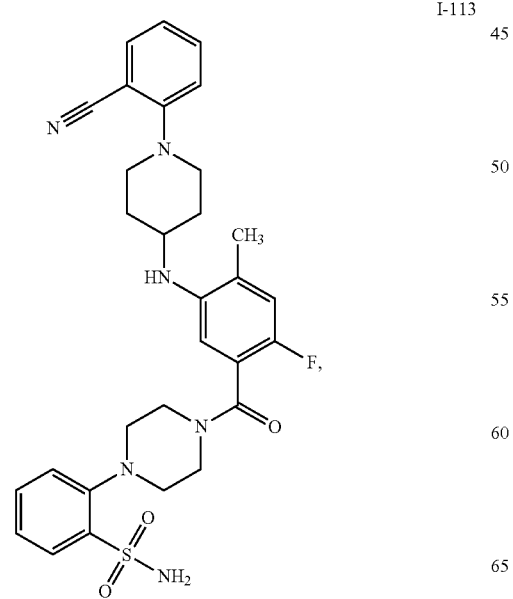
I-115
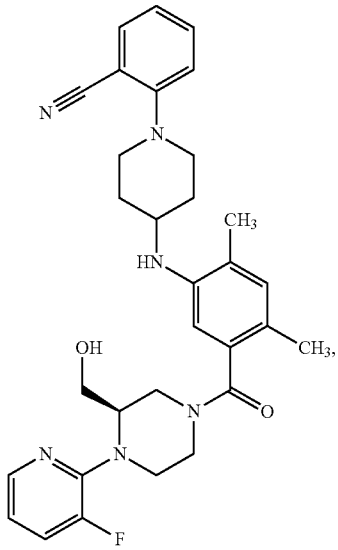
I-116
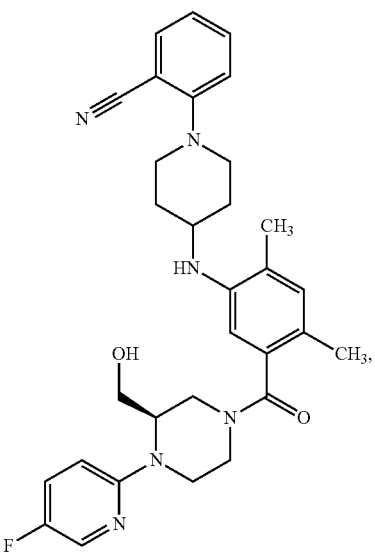
I-117
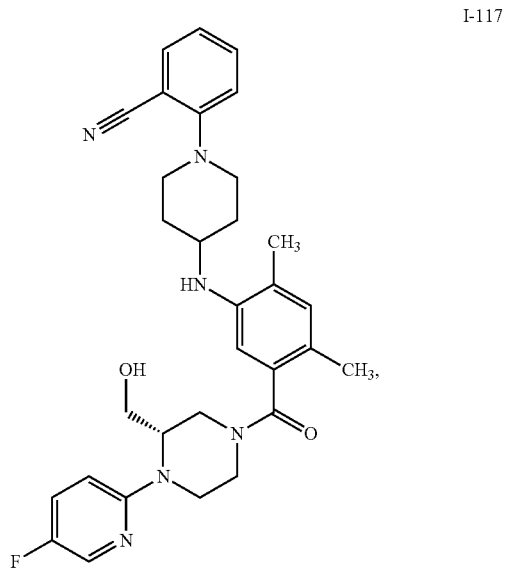

-continued
I-118
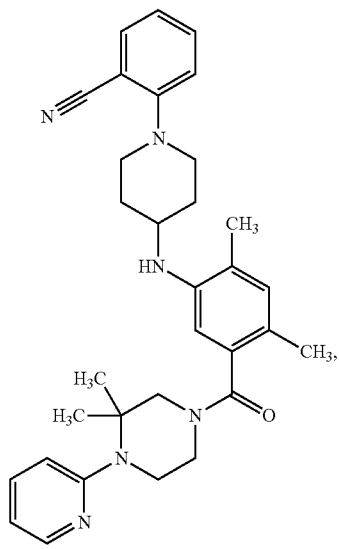
I-119
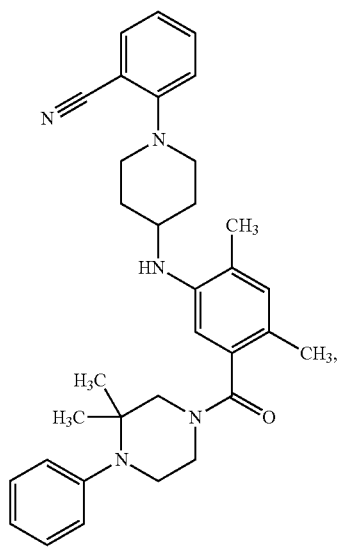
-continued
I-120
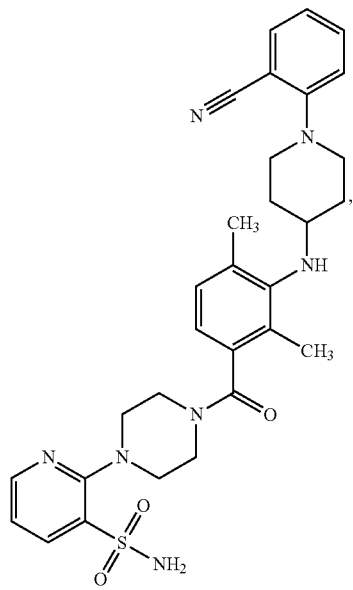
I-121
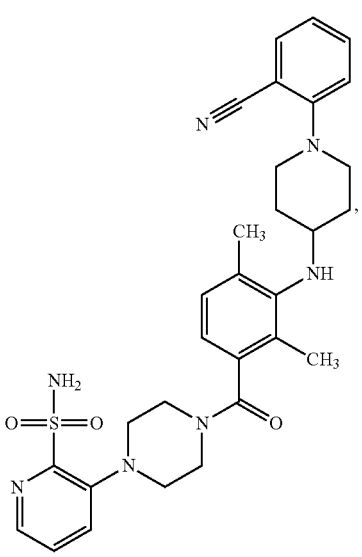
I-122
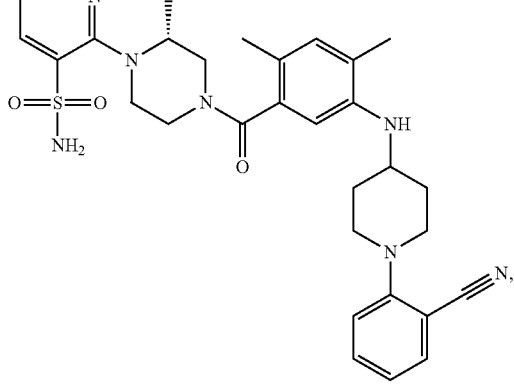

I-123
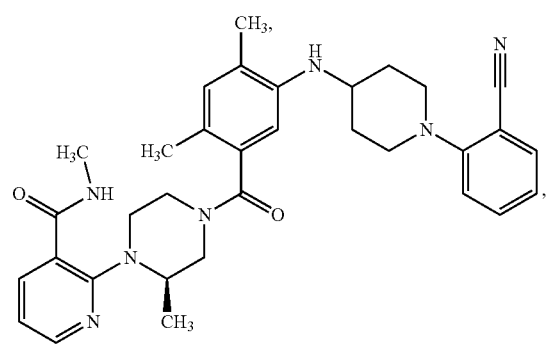
I-126
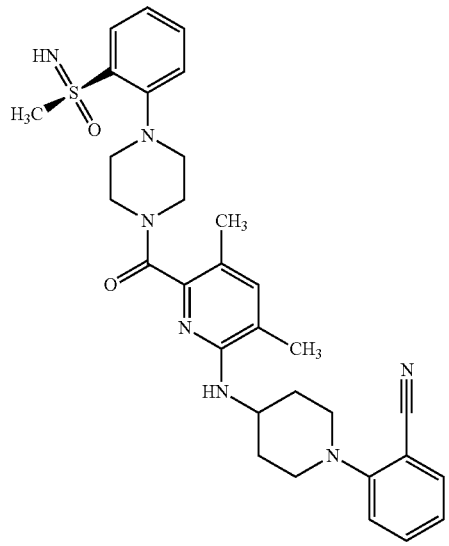
I-124
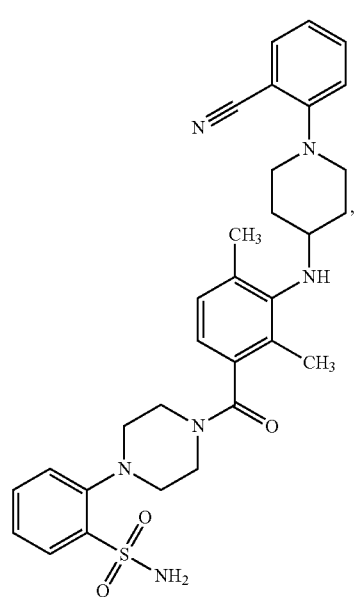
I-127
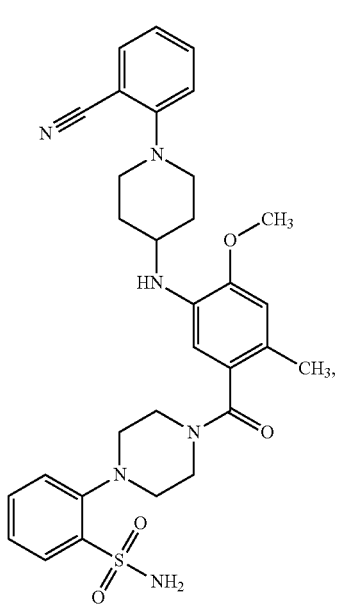
I-125
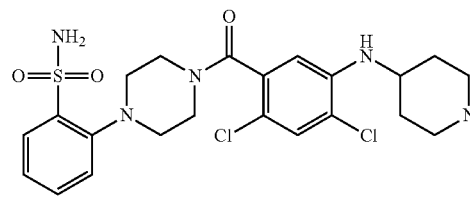
I-128
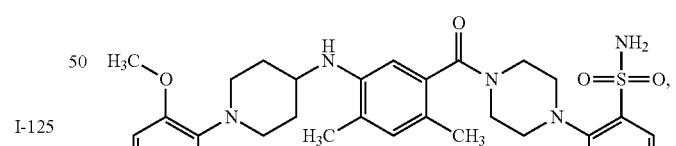
I-129
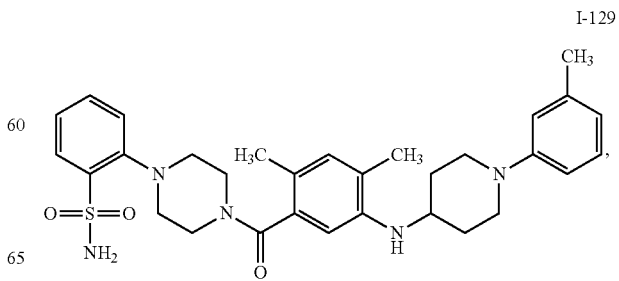

I-130
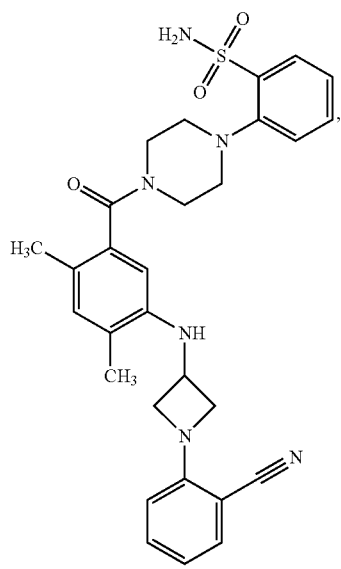
I-131
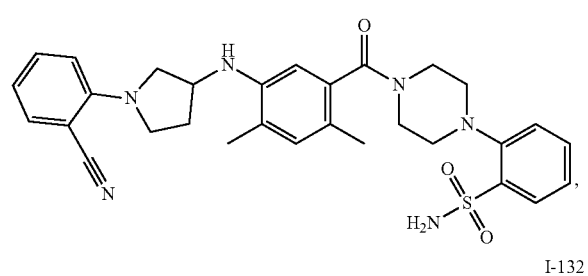
I-132
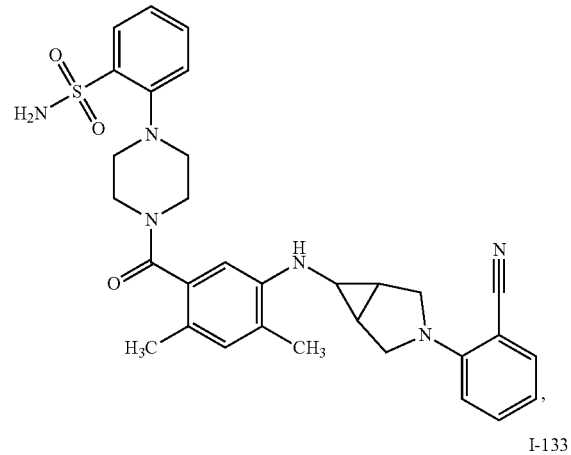
I-133
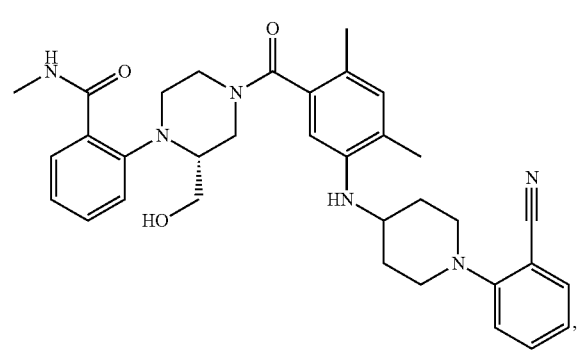
I-134
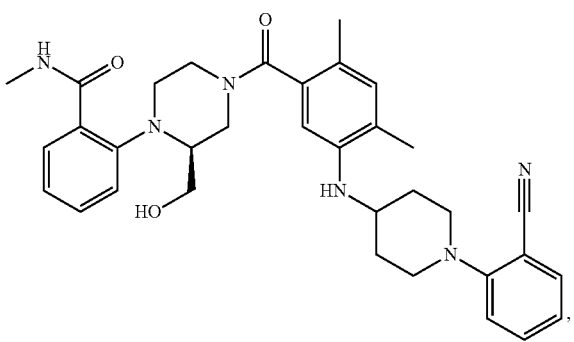
I-135
I-136
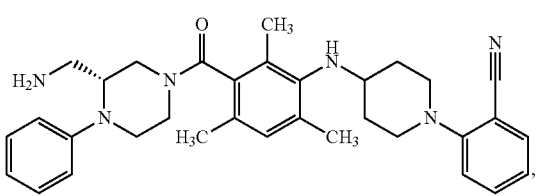
I-137
I-138
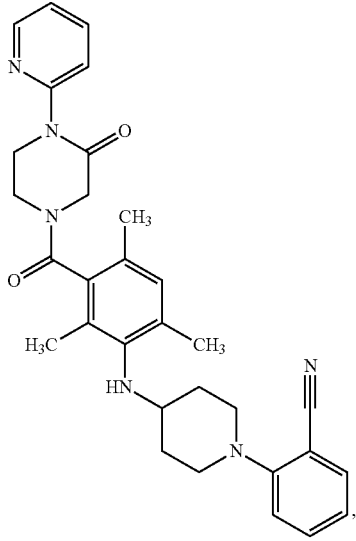

I-139
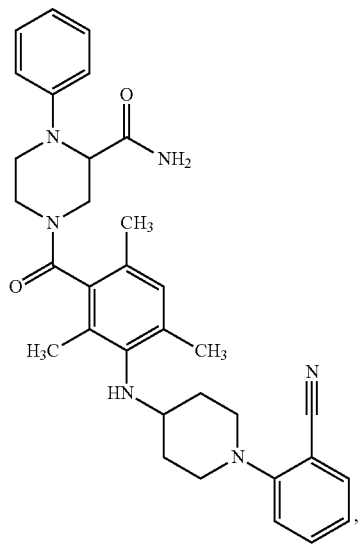
I-142
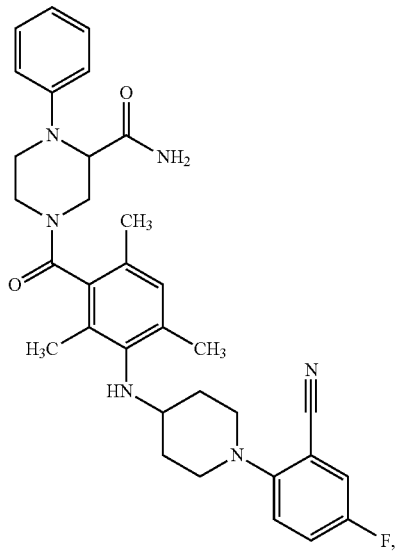
I-140
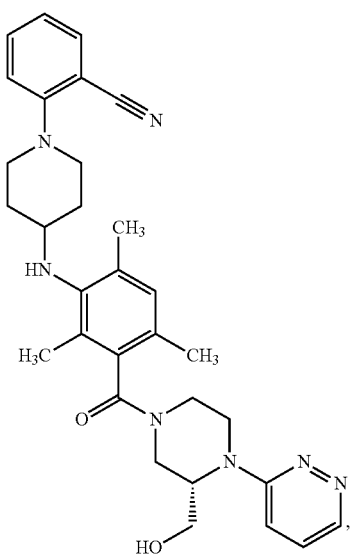
I-143
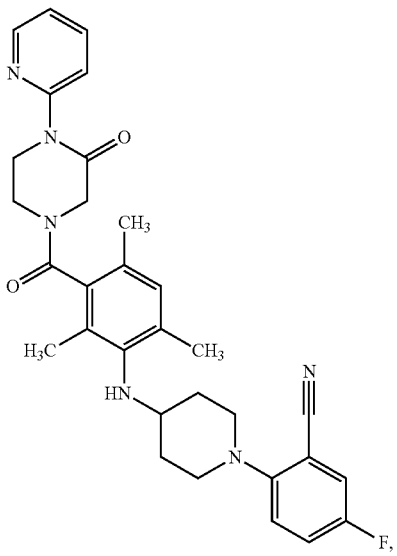
I-141
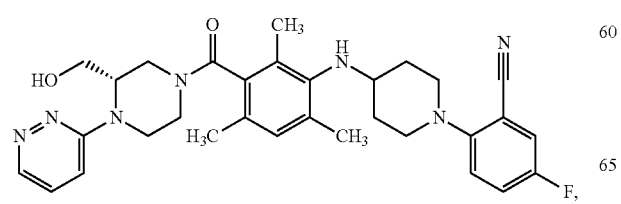

I-144
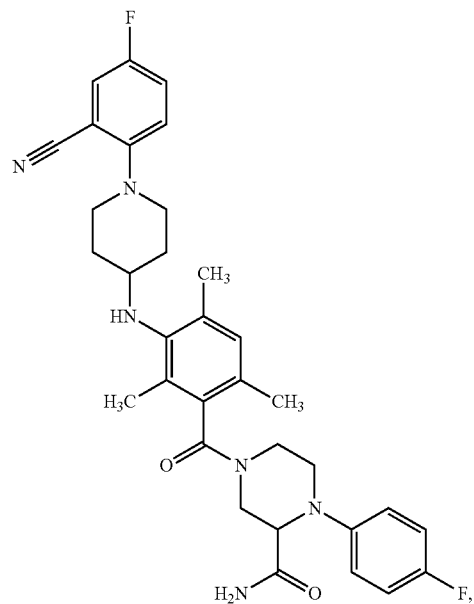
I-145
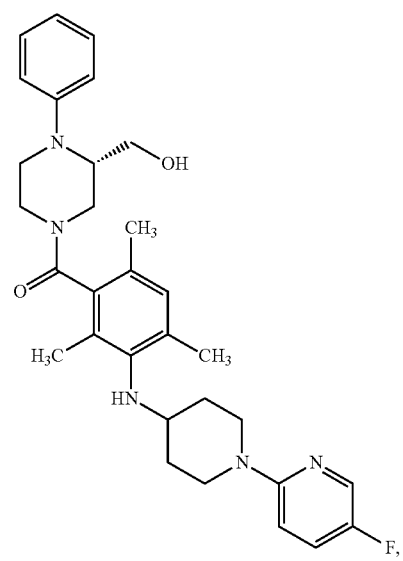
I-146
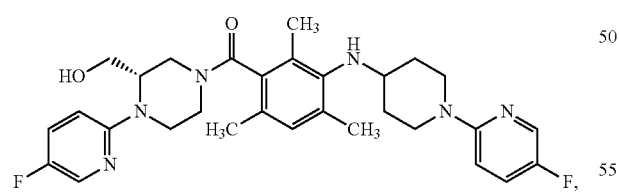
I-147
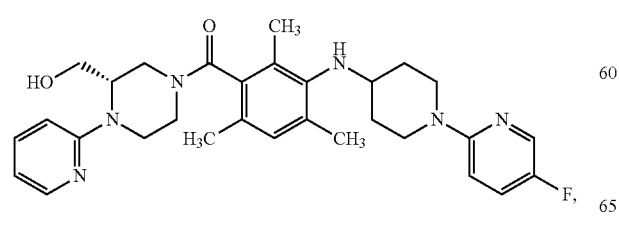
I-148
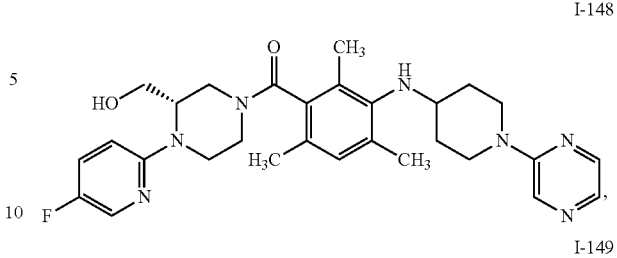
I-149
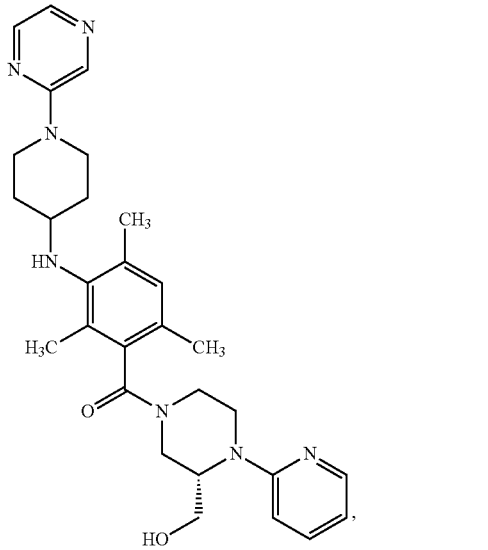
I-150
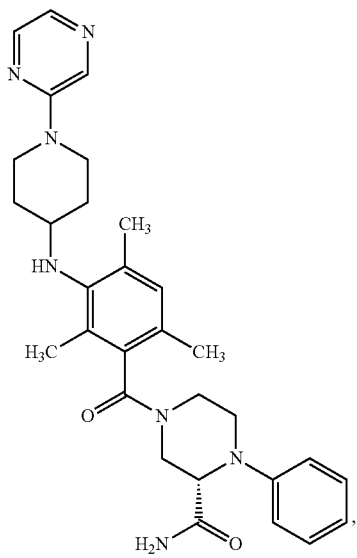
I-151
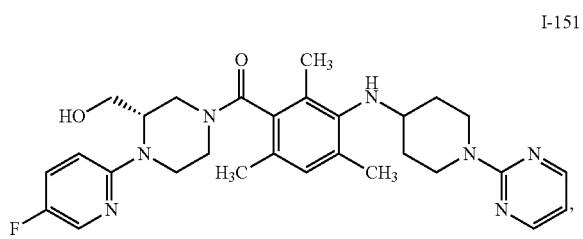

I-152
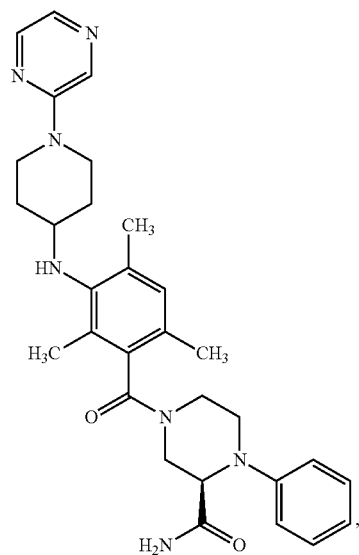
I-153
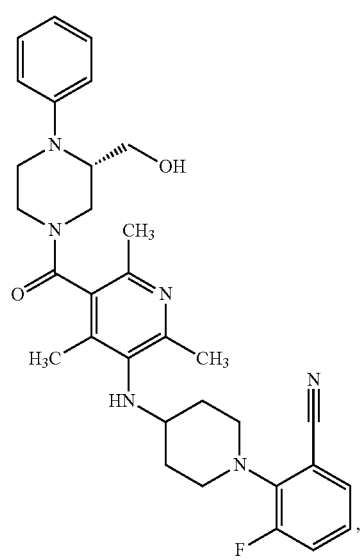
I-154
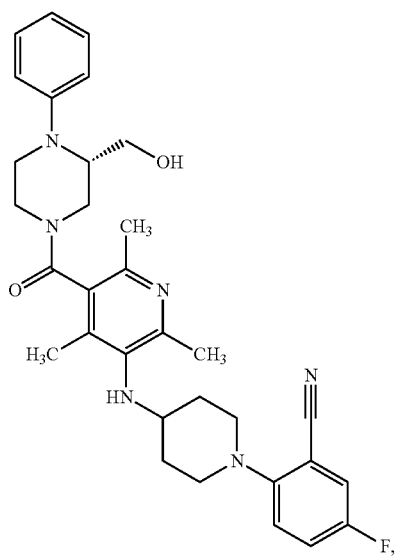
I-155
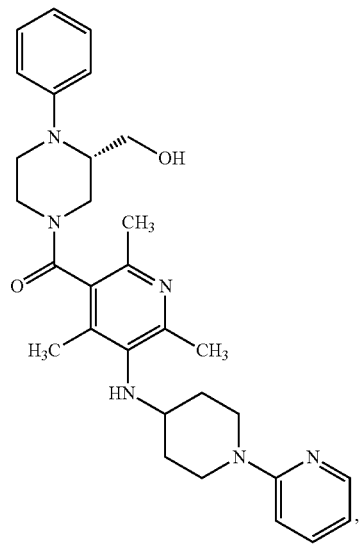
I-156
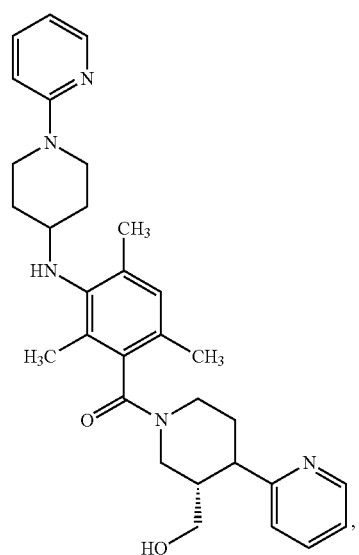
I-157
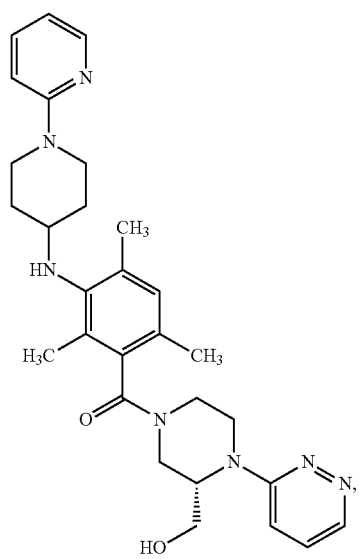

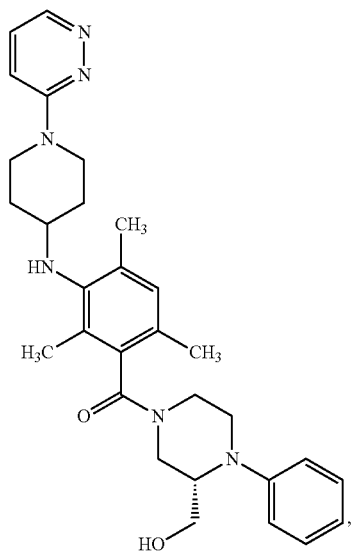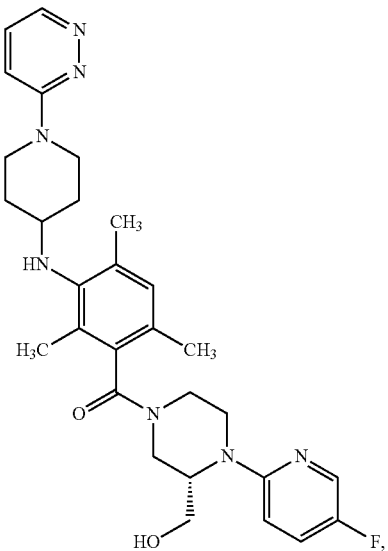

I-164
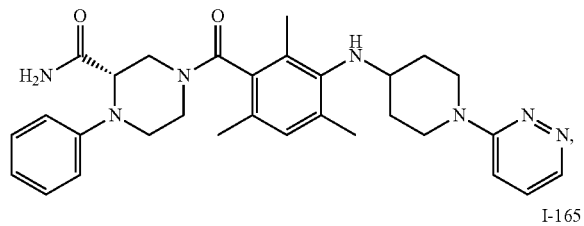
I-165
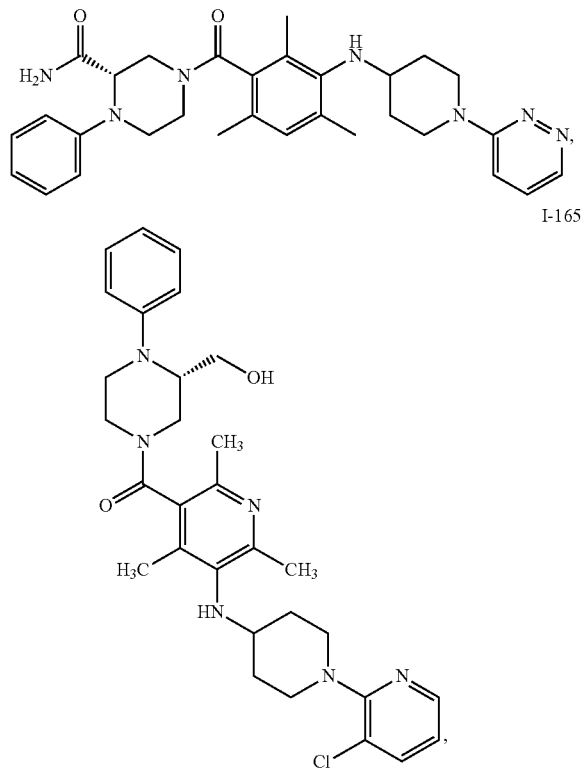
I-166
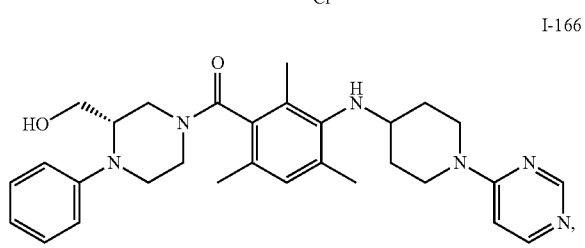
I-167
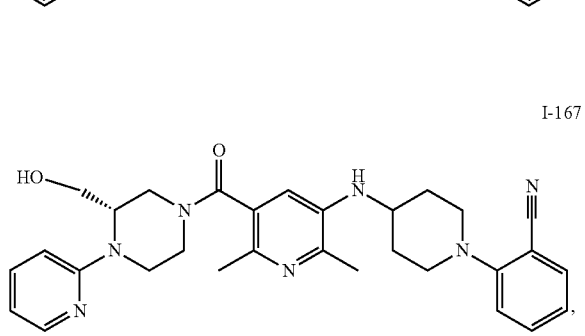
I-168
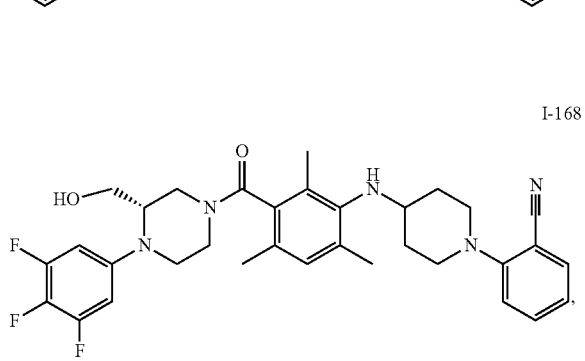
I-169
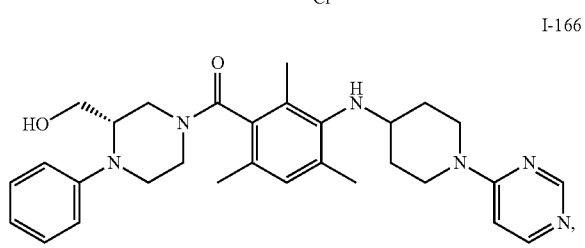
I-170
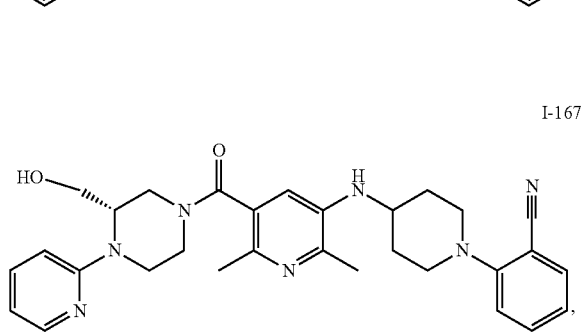
I-171
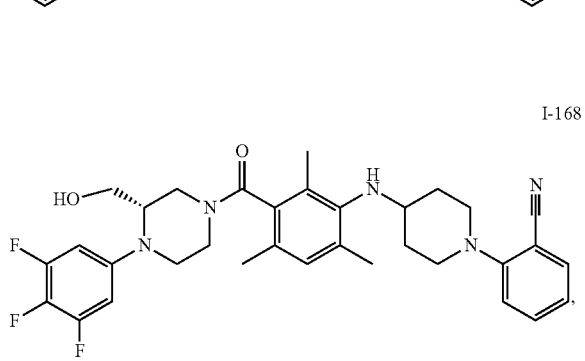
I-172
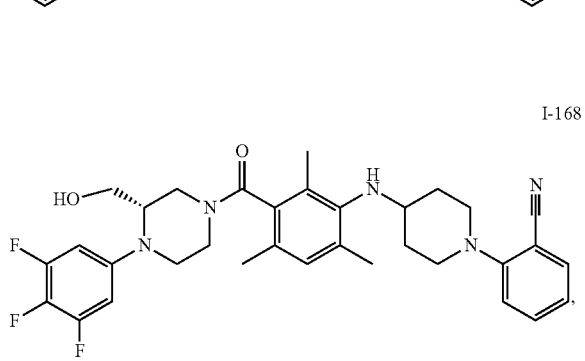
I-173
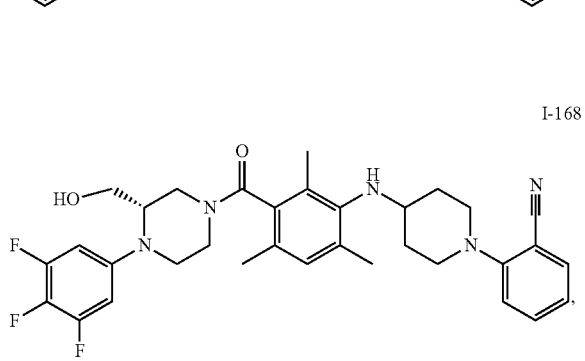
I-174
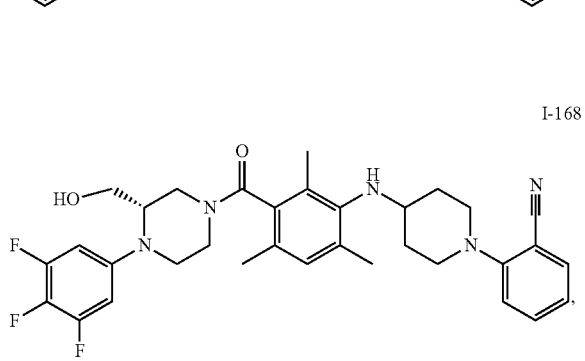

473
-continued
I-175
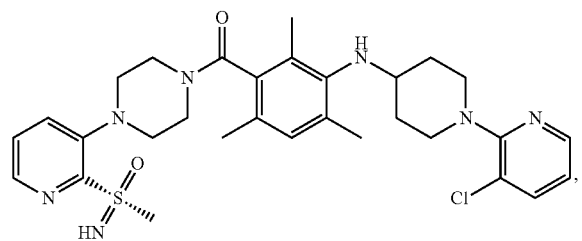
I-176
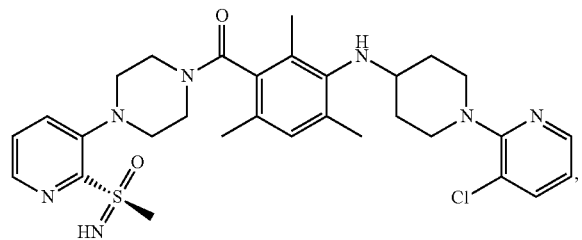
I-177
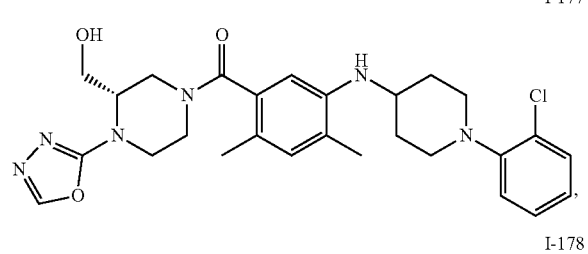
I-178
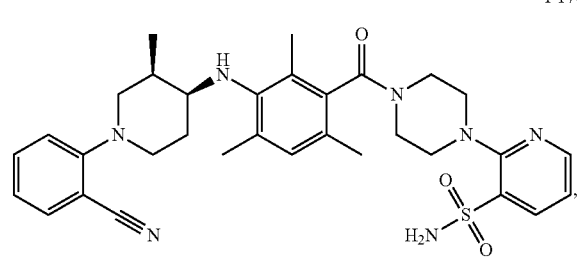
I-179
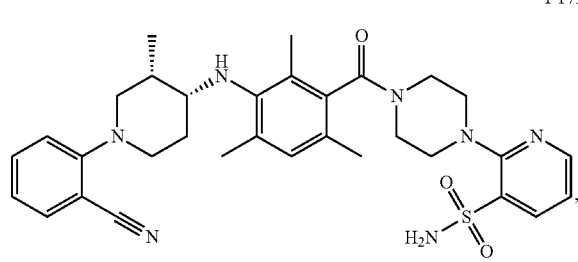
I-180
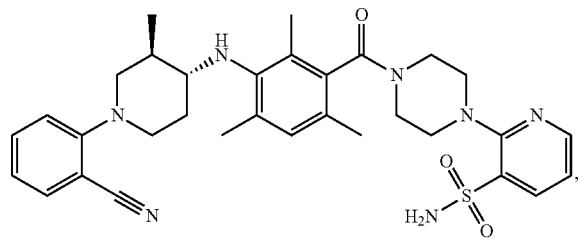
474
-continued
I-181
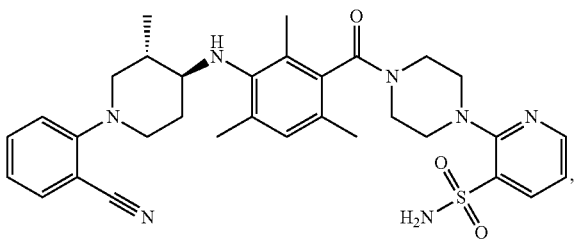
I-182
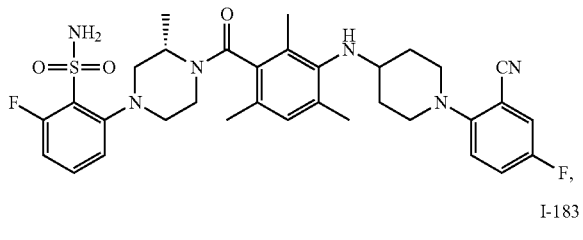
I-183
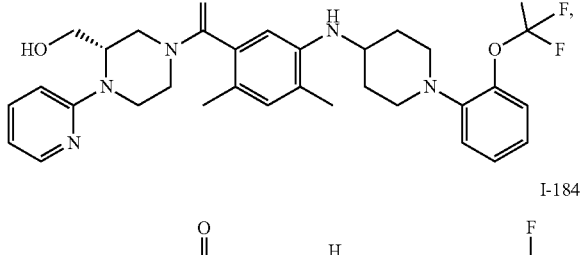
I-184
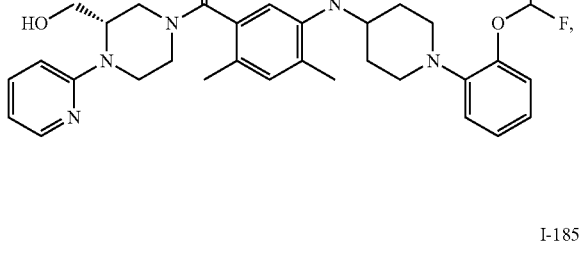
I-185
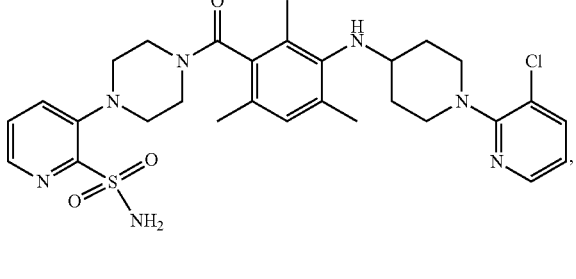
I-186
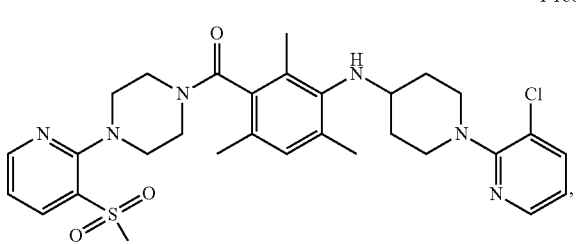

I-187
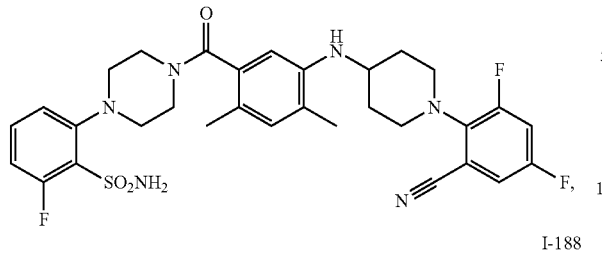
I-192
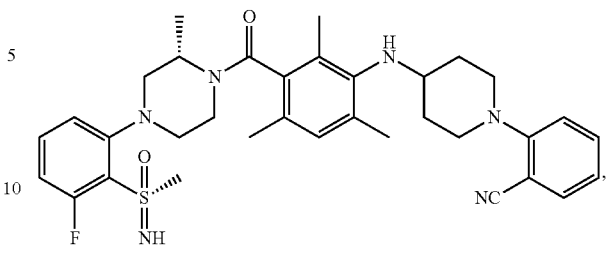
I-188
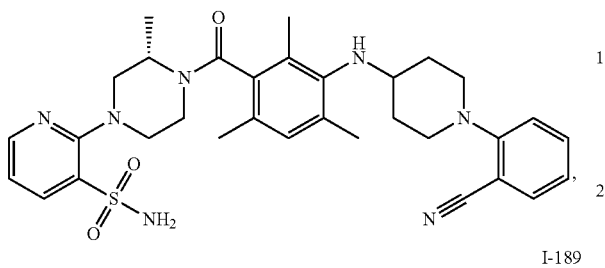
I-193
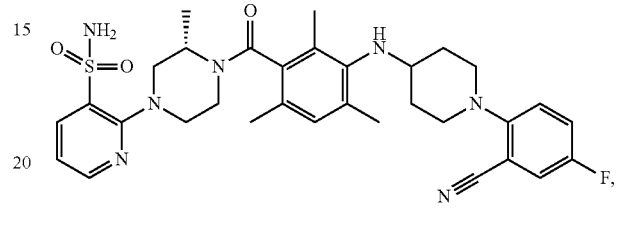
I-189
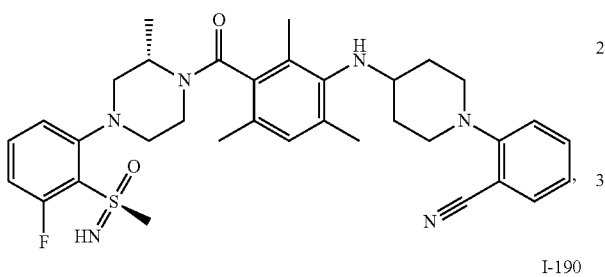
I-194
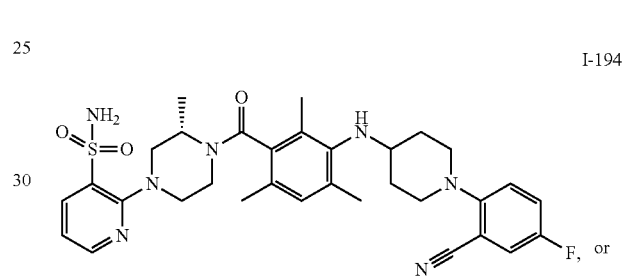
I-190
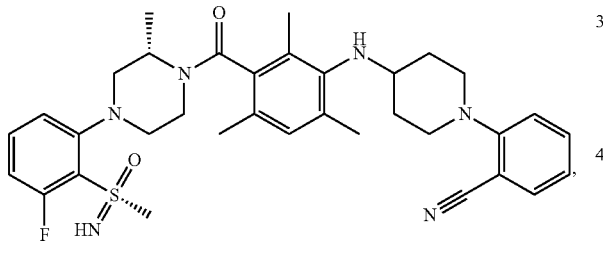
I-195
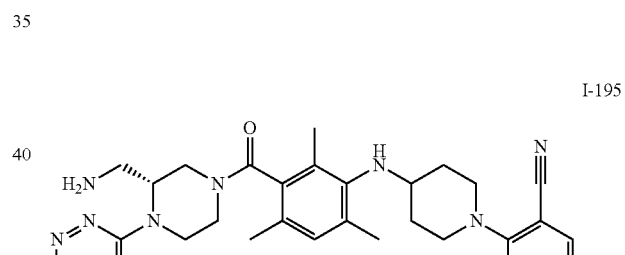
I-191
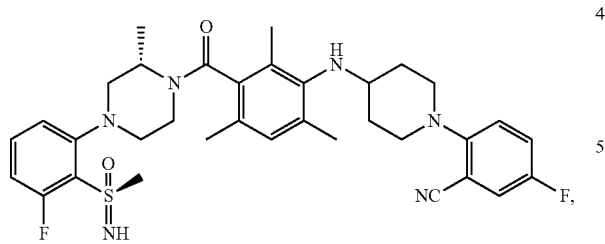
or pharmaceutically acceptable salts thereof.
17. A pharmaceutical composition comprising a compound according to claim 1, or a pharmaceutically acceptable salt thereof, and a pharmaceutically acceptable adjuvant, carrier, or vehicle.
* * * * *